US012760040B2

(12) United States Patent
Macor et al.

(10) Patent No.: US 12,760,040 B2
(45) Date of Patent: Oct. 13, 2026

(54) ORGANIC ELECTROLUMINESCENT MATERIALS AND DEVICES

(71) Applicant: UNIVERSAL DISPLAY CORPORATION, Ewing, NJ (US)

(72) Inventors: Joseph A. Macor, Morrisville, PA (US); Geza Szigethy, Newtown, PA (US); Sean Michael Ryno, Yardley, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 1045 days.

(21) Appl. No.: 17/937,801

(22) Filed: Oct. 4, 2022

(65) Prior Publication Data

US 2023/0287011 A1 Sep. 14, 2023

Related U.S. Application Data

(60) Provisional application No. 63/263,766, filed on Nov. 9, 2021.

(51) Int. Cl.

| | |
|---|---|
| ***H01L 51/50*** | (2006.01) |
| ***C07D 519/00*** | (2006.01) |
| ***C07F 5/02*** | (2006.01) |
| *H10K 50/81* | (2023.01) |
| *H10K 50/82* | (2023.01) |
| *H10K 85/30* | (2023.01) |

(52) U.S. Cl.

CPC ............ *C07F 5/027* (2013.01); *C07D 519/00* (2013.01); *H10K 50/81* (2023.02); *H10K 50/82* (2023.02); *H10K 85/322* (2023.02)

(58) Field of Classification Search

None

See application file for complete search history.

(56) References Cited

U.S. PATENT DOCUMENTS 4,769,292 A 9/1988 Tang et al.
5,061,569 A 10/1991 VanSlyke et al.
5,247,190 A 9/1993 Friend et al.

(Continued)

FOREIGN PATENT DOCUMENTS

CN 1696137 A 11/2005
CN 102702075 A 10/2012

(Continued)

OTHER PUBLICATIONS

Ming Yan, et al., Tetrahedron 2015, 71, 1425-30 and Atzrodt et al., Angew. Chem. Int. Ed. (Reviews) 2007, 46, 7744-65.

(Continued)

*Primary Examiner* — Gregory D Clark

(74) *Attorney, Agent, or Firm* — LNK Law, PLLC

(57) ABSTRACT

Provided are organometallic compounds comprising a first ligand $L_A$ which comprises at least two rings which are bridged by a two-atom linker comprising two structures which are independently selected from the group consisting of CR, CRR', SiRR', GeRR', BR, BRR', N, NR, O, and S. Also provided are formulations comprising these organometallic compounds. Further provided are organic light emitting devices (OLEDs) and related consumer products that utilize these organometallic compounds.

20 Claims, 2 Drawing Sheets

(56) References Cited

U.S. PATENT DOCUMENTS

| | | | |
|---|---|---|---|
| 5,639,914 | A | 6/1997 | Tomiyama et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,413,656 | B1 | 7/2002 | Thompson |
| 6,468,819 | B1 | 10/2002 | Kim et al. |
| 6,517,957 | B1 | 2/2003 | Senoo et al. |
| 6,653,654 | B1 | 11/2003 | Che |
| 6,656,612 | B2 | 12/2003 | Okada et al. |
| 6,670,645 | B2 | 12/2003 | Grushin et al. |
| 6,687,266 | B1 | 2/2004 | Ma et al. |
| 6,699,599 | B2 | 3/2004 | Li et al. |
| 6,835,469 | B2 | 12/2004 | Kwong et al. |
| 6,916,554 | B2 | 7/2005 | Ma et al. |
| 6,921,915 | B2 | 7/2005 | Takiguchi et al. |
| 7,154,114 | B2 | 12/2006 | Brooks et al. |
| 7,279,704 | B2 | 10/2007 | Walters et al. |
| 7,332,232 | B2 | 2/2008 | Ma et al. |
| 7,345,301 | B2 | 3/2008 | Gerhard et al. |
| 7,378,162 | B2 | 5/2008 | Jeong et al. |
| 7,431,968 | B1 | 10/2008 | Shtein et al. |
| 7,534,505 | B2 | 5/2009 | Lin et al. |
| 7,605,277 | B2 | 10/2009 | Kai et al. |
| 7,675,228 | B2 | 3/2010 | Ionkin et al. |
| 7,728,137 | B2 | 6/2010 | Stossel et al. |
| 7,740,957 | B2 | 6/2010 | Kim et al. |
| 7,749,615 | B2 | 7/2010 | Fukumatsu et al. |
| 7,759,489 | B2 | 7/2010 | Watanabe et al. |
| 7,846,763 | B2 | 12/2010 | Bold et al. |
| 7,951,947 | B2 | 5/2011 | Igarashi et al. |
| 7,968,146 | B2 | 6/2011 | Wagner et al. |
| 7,993,760 | B2 | 8/2011 | Komori et al. |
| 8,044,222 | B2 | 10/2011 | Yabunouchi et al. |
| 8,062,769 | B2 | 11/2011 | Kai et al. |
| 8,067,099 | B2 | 11/2011 | Watanabe et al. |
| 8,129,083 | B2 | 3/2012 | Yabunouchi et al. |
| 8,222,637 | B2 | 7/2012 | Kawamura et al. |
| 8,231,983 | B2 | 7/2012 | Sugita et al. |
| 8,258,297 | B2 | 9/2012 | Molt et al. |
| 8,263,770 | B2 | 9/2012 | Mat-Suo et al. |
| 8,288,013 | B2 | 10/2012 | Morishita |
| 8,372,527 | B2 | 2/2013 | Morishita et al. |
| 8,373,159 | B2 | 2/2013 | Langer et al. |
| 8,383,828 | B2 | 2/2013 | Molt et al. |
| 8,415,031 | B2 | 4/2013 | Xia et al. |
| 8,557,400 | B2 | 10/2013 | Xia et al. |
| 8,574,725 | B2 | 11/2013 | Nishimura et al. |
| 8,592,586 | B2 | 11/2013 | Molt et al. |
| 8,597,798 | B2 | 12/2013 | Parham et al. |
| 8,608,986 | B2 | 12/2013 | Akino et al. |
| 8,614,010 | B2 | 12/2013 | Yabunouchi |
| 8,703,304 | B2 | 4/2014 | Yabunouchi et al. |
| 8,759,819 | B2 | 6/2014 | Nishimura et al. |
| 8,871,361 | B2 | 10/2014 | Xia et al. |
| 9,093,652 | B2 | 7/2015 | Jung et al. |
| 9,169,282 | B2 | 10/2015 | Stoessel et al. |
| 9,181,289 | B2 | 11/2015 | Stoessel et al. |
| 9,196,842 | B2 | 11/2015 | Kato et al. |
| 9,296,944 | B2 | 3/2016 | Toshihiro et al. |
| 9,466,803 | B1 | 10/2016 | Park et al. |
| 9,472,762 | B2 | 10/2016 | Murer et al. |
| 9,490,432 | B2 | 11/2016 | Zeika et al. |
| 9,564,595 | B2 | 2/2017 | Kato et al. |
| 9,595,681 | B2 | 3/2017 | Mujica-Fernaud et al. |
| 9,604,972 | B2 | 3/2017 | Yoshida et al. |
| 9,634,255 | B2 | 4/2017 | Kato et al. |
| 9,799,835 | B2 | 10/2017 | Kim et al. |
| 9,837,622 | B2 | 12/2017 | Stoessel et al. |
| 9,882,142 | B2 | 1/2018 | Mujica-Fernaud et al. |
| 9,882,149 | B2 | 1/2018 | Kim et al. |
| 9,978,975 | B2 | 5/2018 | Kambe et al. |
| 10,008,672 | B2 | 6/2018 | Stoessel et al. |
| 10,103,340 | B2 | 10/2018 | Stoessel et al. |
| 10,347,850 | B2 | 7/2019 | Ono et al. |
| 10,385,263 | B2 | 8/2019 | Fuchs et al. |
| 10,522,768 | B2 | 12/2019 | Egen et al. |
| 2001/0019782 | A1 | 9/2001 | Igarashi et al. |
| 2002/0034656 | A1 | 3/2002 | Thompson et al. |
| 2002/0158242 | A1 | 10/2002 | Son et al. |
| 2003/0068526 | A1 | 4/2003 | Kamatani et al. |
| 2003/0072964 | A1 | 4/2003 | Kwong et al. |
| 2003/0138657 | A1 | 7/2003 | Li et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0174116 | A1 | 9/2004 | Lu et al. |
| 2005/0123751 | A1 | 6/2005 | Tsutsui et al. |
| 2005/0123788 | A1 | 6/2005 | Huo et al. |
| 2005/0123791 | A1 | 6/2005 | Deaton et al. |
| 2005/0139810 | A1 | 6/2005 | Kuehl et al. |
| 2005/0238919 | A1 | 10/2005 | Ogasawara |
| 2005/0244673 | A1 | 11/2005 | Satoh et al. |
| 2005/0260449 | A1 | 11/2005 | Walters et al. |
| 2006/0008670 | A1 | 1/2006 | Lin et al. |
| 2006/0065890 | A1 | 3/2006 | Stossel et al. |
| 2006/0127696 | A1 | 6/2006 | Stossel et al. |
| 2006/0134459 | A1 | 6/2006 | Huo et al. |
| 2006/0134462 | A1 | 6/2006 | Yeh et al. |
| 2006/0182993 | A1 | 8/2006 | Ogata et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0280965 | A1 | 12/2006 | Kwong et al. |
| 2007/0018155 | A1 | 1/2007 | Bae et al. |
| 2007/0034863 | A1 | 2/2007 | Fortte et al. |
| 2007/0087321 | A1 | 4/2007 | Pribenszky et al. |
| 2007/0103060 | A1 | 5/2007 | Itoh et al. |
| 2007/0104977 | A1 | 5/2007 | Arakane et al. |
| 2007/0104979 | A1 | 5/2007 | Kim et al. |
| 2007/0104980 | A1 | 5/2007 | Kim et al. |
| 2007/0111026 | A1 | 5/2007 | Deaton et al. |
| 2007/0138437 | A1 | 6/2007 | Haga et al. |
| 2007/0145888 | A1 | 6/2007 | Yabonouchi et al. |
| 2007/0160905 | A1 | 7/2007 | Morishita et al. |
| 2007/0181874 | A1 | 8/2007 | Prakash et al. |
| 2007/0190359 | A1 | 8/2007 | Knowles et al. |
| 2007/0224450 | A1 | 9/2007 | Kim et al. |
| 2007/0231600 | A1 | 10/2007 | Kamatani et al. |
| 2007/0252140 | A1 | 11/2007 | Limmert et al. |
| 2007/0278936 | A1 | 12/2007 | Herron et al. |
| 2007/0278938 | A1 | 12/2007 | Yabunouchi et al. |
| 2008/0005851 | A1 | 1/2008 | Perez-Prat Vinuesa et al. |
| 2008/0014464 | A1 | 1/2008 | Kawamura et al. |
| 2008/0018237 | A1 | 1/2008 | Yamamoto et al. |
| 2008/0020237 | A1 | 1/2008 | Ren et al. |
| 2008/0091025 | A1 | 4/2008 | Morishita et al. |
| 2008/0106190 | A1 | 5/2008 | Yabunouchi et al. |
| 2008/0107919 | A1 | 5/2008 | Hwang et al. |
| 2008/0124572 | A1 | 5/2008 | Mizuki et al. |
| 2008/0145707 | A1 | 6/2008 | Yabunouchi et al. |
| 2008/0161567 | A1 | 7/2008 | Stoessel et al. |
| 2008/0210930 | A1 | 9/2008 | Kamatani et al. |
| 2008/0220265 | A1 | 9/2008 | Xia et al. |
| 2008/0233410 | A1 | 9/2008 | Mashima et al. |
| 2008/0233434 | A1 | 9/2008 | Kawamura et al. |
| 2008/0261076 | A1 | 10/2008 | Kwong et al. |
| 2008/0297033 | A1 | 12/2008 | Knowles et al. |
| 2008/0303417 | A1 | 12/2008 | Yabunouchi et al. |
| 2009/0017330 | A1 | 1/2009 | Toshihiro et al. |
| 2009/0030202 | A1 | 1/2009 | Toshihiro et al. |
| 2009/0039776 | A1 | 2/2009 | Yamada et al. |
| 2009/0066235 | A1 | 3/2009 | Yabunouchi et al. |
| 2009/0085476 | A1 | 4/2009 | Park et al. |
| 2009/0091253 | A1 | 4/2009 | Yasukawa et al. |
| 2009/0101870 | A1 | 4/2009 | Prakash et al. |

(56) References Cited

U.S. PATENT DOCUMENTS

| | | | |
|---|---|---|---|
| 2009/0104472 | A1 | 4/2009 | Je et al. |
| 2009/0108737 | A1 | 4/2009 | Kwong et al. |
| 2009/0115316 | A1 | 5/2009 | Zheng et al. |
| 2009/0115320 | A1 | 5/2009 | Kawamura et al. |
| 2009/0115322 | A1 | 5/2009 | Walters et al. |
| 2009/0140637 | A1 | 6/2009 | Hosokawa et al. |
| 2009/0167161 | A1 | 7/2009 | Yabunouchi et al. |
| 2009/0167162 | A1 | 7/2009 | Chun et al. |
| 2009/0167167 | A1 | 7/2009 | Aoyama et al. |
| 2009/0179554 | A1 | 7/2009 | Kuma et al. |
| 2009/0179555 | A1 | 7/2009 | Kim et al. |
| 2009/0218940 | A1 | 9/2009 | Okajima et al. |
| 2009/0302743 | A1 | 12/2009 | Kato et al. |
| 2009/0309488 | A1 | 12/2009 | Kato et al. |
| 2010/0012931 | A1 | 1/2010 | Kato et al. |
| 2010/0084966 | A1 | 4/2010 | Shinya et al. |
| 2010/0090591 | A1 | 4/2010 | Alleyne et al. |
| 2010/0102716 | A1 | 4/2010 | Kim et al. |
| 2010/0105902 | A1 | 4/2010 | Inoue et al. |
| 2010/0108990 | A1 | 5/2010 | Hosokawa et al. |
| 2010/0148663 | A1 | 6/2010 | Tsai et al. |
| 2010/0187984 | A1 | 7/2010 | Chun et al. |
| 2010/0219397 | A1 | 9/2010 | Watanabe et al. |
| 2010/0244004 | A1 | 9/2010 | Xia et al. |
| 2010/0270916 | A1 | 10/2010 | Xia et al. |
| 2010/0288362 | A1 | 11/2010 | Hatwar et al. |
| 2010/0295032 | A1 | 11/2010 | Kwong et al. |
| 2011/0007385 | A1 | 1/2011 | Yamanashi et al. |
| 2011/0037057 | A1 | 2/2011 | LeCloux et al. |
| 2011/0057559 | A1 | 3/2011 | Xia et al. |
| 2011/0108822 | A1 | 5/2011 | Parham et al. |
| 2011/0156017 | A1 | 6/2011 | Lee et al. |
| 2011/0163302 | A1 | 7/2011 | Lin et al. |
| 2011/0204333 | A1 | 8/2011 | Xia et al. |
| 2011/0210320 | A1 | 9/2011 | Shin et al. |
| 2011/0215710 | A1 | 9/2011 | Xia et al. |
| 2011/0227049 | A1 | 9/2011 | Xia et al. |
| 2011/0240968 | A1 | 10/2011 | Kim et al. |
| 2011/0278551 | A1 | 11/2011 | Yabunouchi et al. |
| 2011/0285275 | A1 | 11/2011 | Huang et al. |
| 2012/0075273 | A1 | 3/2012 | Shigemoto et al. |
| 2012/0126221 | A1 | 5/2012 | Tetsu et al. |
| 2012/0146012 | A1 | 6/2012 | Limmert et al. |
| 2012/0193612 | A1 | 8/2012 | Chun et al. |
| 2012/0205642 | A1 | 8/2012 | Yokoyama et al. |
| 2012/0205645 | A1 | 8/2012 | Fuchs et al. |
| 2012/0214993 | A1 | 8/2012 | Aihara et al. |
| 2012/0292601 | A1 | 11/2012 | Kottas et al. |
| 2012/0319091 | A1 | 12/2012 | Kato |
| 2013/0009543 | A1 | 1/2013 | Hiroshi et al. |
| 2013/0033172 | A1 | 2/2013 | Huang et al. |
| 2013/0105787 | A1 | 5/2013 | Daisaku et al. |
| 2013/0146848 | A1 | 6/2013 | Ma et al. |
| 2013/0165653 | A1 | 6/2013 | Inoue et al. |
| 2013/0175519 | A1 | 7/2013 | Naoki et al. |
| 2013/0181190 | A1 | 7/2013 | Ma et al. |
| 2013/0241401 | A1 | 9/2013 | Kwong et al. |
| 2013/0248830 | A1 | 9/2013 | Welsh et al. |
| 2013/0334521 | A1 | 12/2013 | Lee et al. |
| 2014/0001446 | A1 | 1/2014 | Mizuki et al. |
| 2014/0014925 | A1 | 1/2014 | Jung et al. |
| 2014/0014927 | A1 | 1/2014 | Kim et al. |
| 2014/0034914 | A1 | 2/2014 | Takada et al. |
| 2014/0103305 | A1 | 4/2014 | Ma et al. |
| 2014/0117329 | A1 | 5/2014 | Lee et al. |
| 2014/0183503 | A1 | 7/2014 | Hiroshi et al. |
| 2014/0183517 | A1 | 7/2014 | Huh et al. |
| 2014/0191225 | A1 | 7/2014 | Inoue et al. |
| 2014/0225088 | A1 | 8/2014 | Hwang et al. |
| 2014/0246656 | A1 | 9/2014 | Inoue et al. |
| 2014/0284580 | A1 | 9/2014 | Balaganesan et al. |
| 2015/0060804 | A1 | 3/2015 | Kanitz et al. |
| 2015/0123047 | A1 | 5/2015 | Maltenberger et al. |
| 2015/0171348 | A1 | 6/2015 | Stoessel et al. |
| 2015/0221874 | A1 | 8/2015 | Kim et al. |
| 2015/0228899 | A1 | 8/2015 | Tomoki et al. |
| 2015/0263294 | A1 | 9/2015 | Kim et al. |
| 2015/0280136 | A1 | 10/2015 | Ryu et al. |
| 2016/0163995 | A1 | 6/2016 | Kang et al. |
| 2016/0233424 | A1* | 8/2016 | Kwong ................ C07D 495/04 |
| 2017/0263869 | A1 | 9/2017 | Tada et al. |
| 2019/0081248 | A1 | 3/2019 | Lin et al. |

FOREIGN PATENT DOCUMENTS

| | | | |
|---|---|---|---|
| CN | 103508940 | A | 1/2014 |
| CN | 103694277 | A | 4/2014 |
| DE | 102012005215 | B3 | 4/2013 |
| EP | 0650955 | A1 | 5/1995 |
| EP | 1238981 | A2 | 9/2002 |
| EP | 1239526 | A2 | 9/2002 |
| EP | 1244155 | A2 | 9/2002 |
| EP | 01602648 | A1 | 12/2005 |
| EP | 1617493 | A2 | 1/2006 |
| EP | 1624500 | A1 | 2/2006 |
| EP | 1642951 | A2 | 4/2006 |
| EP | 1647554 | A2 | 4/2006 |
| EP | 1698613 | A1 | 9/2006 |
| EP | 1725079 | A1 | 11/2006 |
| EP | 01734038 | A1 | 12/2006 |
| EP | 1806334 | A1 | 7/2007 |
| EP | 1841834 | A1 | 10/2007 |
| EP | 1930964 | A1 | 6/2008 |
| EP | 01956007 | A1 | 8/2008 |
| EP | 1961743 | A | 8/2008 |
| EP | 1968131 | A1 | 9/2008 |
| EP | 1972613 | A1 | 9/2008 |
| EP | 1997799 | A1 | 12/2008 |
| EP | 2011790 | A1 | 1/2009 |
| EP | 2020694 | A1 | 2/2009 |
| EP | 2034538 | A1 | 3/2009 |
| EP | 1841834 | B1 | 5/2009 |
| EP | 2055700 | A1 | 5/2009 |
| EP | 2055701 | A1 | 5/2009 |
| EP | 2062907 | A2 | 5/2009 |
| EP | 2085382 | A1 | 8/2009 |
| EP | 2660300 | A2 | 11/2013 |
| EP | 2684932 | A1 | 1/2014 |
| EP | 2730583 | A1 | 5/2014 |
| EP | 2757608 | A1 | 7/2014 |
| JP | 2004022334 | A | 1/2004 |
| JP | 2005112765 | A | 4/2005 |
| JP | 2005149918 | A | 6/2005 |
| JP | 2005268199 | A | 9/2005 |
| JP | 2007073529 | A | 3/2007 |
| JP | 2007091719 | A | 4/2007 |
| JP | 2007254297 | A | 10/2007 |
| JP | 2008021687 | A | 1/2008 |
| JP | 4478555 | B2 | 3/2010 |
| JP | 2012074444 | A | 4/2012 |
| JP | 2013110263 | A | 6/2013 |
| JP | 2014009196 | A | 1/2014 |
| KR | 0117693 | | 4/1998 |
| KR | 20100079458 | A | 7/2010 |
| KR | 20110077173 | A | 7/2011 |
| KR | 20110088898 | A | 8/2011 |
| KR | 20120032054 | A | 4/2012 |
| KR | 20120088644 | A | 8/2012 |
| KR | 20120129733 | A | 11/2012 |
| KR | 20130043460 | A | 4/2013 |
| KR | 20130077473 | A | 7/2013 |
| KR | 20130108183 | | 10/2013 |
| KR | 20130115564 | A | 10/2013 |
| TW | 201139402 | A | 1/2011 |
| TW | 201329200 | A1 | 7/2013 |
| TW | 201332980 | A | 8/2013 |
| WO | 2001039234 | A2 | 5/2001 |
| WO | 2002015645 | A1 | 2/2002 |
| WO | 2003040257 | A1 | 5/2003 |
| WO | 2003060956 | A1 | 7/2003 |
| WO | 2004093207 | A2 | 10/2004 |
| WO | 2005014551 | A1 | 2/2005 |
| WO | 2005019373 | A2 | 3/2005 |
| WO | 2005075451 | A1 | 8/2005 |

(56) References Cited

FOREIGN PATENT DOCUMENTS

| | | | |
|---|---|---|---|
| WO | 2005089025 | A1 | 9/2005 |
| WO | 2006056418 | A2 | 6/2006 |
| WO | 2006072002 | A2 | 7/2006 |
| WO | 2006081780 | A1 | 8/2006 |
| WO | 2006081973 | A1 | 8/2006 |
| WO | 2006095951 | A1 | 9/2006 |
| WO | 2006114966 | A1 | 11/2006 |
| WO | 2006121811 | A1 | 11/2006 |
| WO | 2007018067 | A1 | 2/2007 |
| WO | 2007063754 | A1 | 6/2007 |
| WO | 2007108362 | A1 | 9/2007 |
| WO | 2007111263 | A1 | 10/2007 |
| WO | 2007115970 | A1 | 10/2007 |
| WO | 2007115981 | A1 | 10/2007 |
| WO | 2007125714 | A1 | 11/2007 |
| WO | 2008023550 | A1 | 2/2008 |
| WO | 2008023759 | A1 | 2/2008 |
| WO | 2008035571 | A1 | 3/2008 |
| WO | 2008054584 | A1 | 5/2008 |
| WO | 2008056746 | A1 | 5/2008 |
| WO | 2008057394 | A1 | 5/2008 |
| WO | 2008078800 | A1 | 7/2008 |
| WO | 2008096609 | A1 | 8/2008 |
| WO | 2008101842 | A | 8/2008 |
| WO | 2009000673 | A2 | 12/2008 |
| WO | 2009003455 | A1 | 1/2009 |
| WO | 2009003898 | A1 | 1/2009 |
| WO | 2009008277 | A1 | 1/2009 |
| WO | 2009011327 | A1 | 1/2009 |
| WO | 2009021126 | A2 | 2/2009 |
| WO | 2009050281 | A1 | 4/2009 |
| WO | 2009063833 | A1 | 5/2009 |
| WO | 2009066778 | A1 | 5/2009 |
| WO | 2009066779 | A1 | 5/2009 |
| WO | 2009086028 | A2 | 7/2009 |
| WO | 2009100991 | A1 | 8/2009 |
| WO | 2009145016 | A1 | 12/2009 |
| WO | 2009148269 | A1 | 12/2009 |
| WO | 2010011390 | A2 | 1/2010 |
| WO | 2010028151 | A1 | 3/2010 |
| WO | 2010054731 | A1 | 5/2010 |
| WO | 2010056066 | A1 | 5/2010 |
| WO | 2010061824 | A1 | 6/2010 |
| WO | 2010067894 | A1 | 6/2010 |
| WO | 2010072300 | A1 | 7/2010 |
| WO | 2010086089 | A1 | 8/2010 |
| WO | 2010107244 | A2 | 9/2010 |
| WO | 2010118029 | A1 | 10/2010 |
| WO | 2011044988 | A1 | 4/2011 |
| WO | 2011051404 | A1 | 5/2011 |
| WO | 2011074770 | A1 | 6/2011 |
| WO | 2011074770 | A2 | 6/2011 |
| WO | 2011075644 | A2 | 6/2011 |
| WO | 2011081423 | A2 | 7/2011 |
| WO | 2011081431 | A2 | 7/2011 |
| WO | 2011086863 | A1 | 7/2011 |
| WO | 2011105373 | A1 | 9/2011 |
| WO | 2011107491 | A1 | 9/2011 |
| WO | 2012020327 | A1 | 2/2012 |
| WO | 2012128298 | A1 | 9/2012 |
| WO | 2012133644 | A1 | 10/2012 |
| WO | 2012133649 | A1 | 10/2012 |
| WO | 2012163471 | A1 | 12/2012 |
| WO | 2012177006 | A2 | 12/2012 |
| WO | 2013018530 | A1 | 2/2013 |
| WO | 2013024872 | A1 | 2/2013 |
| WO | 2013035275 | A1 | 3/2013 |
| WO | 2013039073 | A1 | 3/2013 |
| WO | 2013079217 | A1 | 6/2013 |
| WO | 2013081315 | A1 | 6/2013 |
| WO | 2013087142 | A1 | 6/2013 |
| WO | 2013094620 | A1 | 6/2013 |
| WO | 2013107487 | A1 | 7/2013 |
| WO | 2013118812 | A1 | 8/2013 |
| WO | 2013120577 | A1 | 8/2013 |
| WO | 2013145667 | A1 | 10/2013 |
| WO | 2013157367 | A1 | 10/2013 |
| WO | 2013174471 | A1 | 11/2013 |
| WO | 2013175747 | A1 | 11/2013 |
| WO | 2013180376 | A1 | 12/2013 |
| WO | 2013191404 | A1 | 12/2013 |
| WO | 2014002873 | A1 | 1/2014 |
| WO | 2014007565 | A1 | 1/2014 |
| WO | 2014008982 | A1 | 1/2014 |
| WO | 2014009310 | A1 | 1/2014 |
| WO | 2014015935 | A2 | 1/2014 |
| WO | 2014015937 | A1 | 1/2014 |
| WO | 2014023377 | A2 | 2/2014 |
| WO | 2014024131 | A1 | 2/2014 |
| WO | 2014030872 | A2 | 2/2014 |
| WO | 2014030921 | A1 | 2/2014 |
| WO | 2014031977 | A1 | 2/2014 |
| WO | 2014034791 | A1 | 3/2014 |
| WO | 2014038456 | A1 | 3/2014 |
| WO | 2014104499 | A1 | 7/2014 |
| WO | 2014104514 | A1 | 7/2014 |
| WO | 2014104535 | A1 | 7/2014 |
| WO | 2014112450 | A1 | 7/2014 |
| WO | 2014142472 | A1 | 9/2014 |
| WO | 2014157018 | A1 | 10/2014 |

OTHER PUBLICATIONS

Baldo et al., "Highly Efficient Phosphorescent Emission from Organic Electroluminescent Devices," Nature, vol. 395, 151-154, 1998.

Baldo et al., "Very high-efficiency green organic light-emitting devices based on electrophosphorescence," Appl. Phys. Lett., vol. 75, No. 3, 4-6 (1999).

Atzrodt et al., Angew. Chem. Int. Ed. (Reviews) 2007, 46, 7744-65.

Fink, R.; Heischkel, Y.; Thelakkat, M.; Schmidt, H.-W. Chem. Mater. 1998, 10, 3620-3625.

Pommerehne, J.; Vestweber, H.; Guss, W.; Mahrt, R. F.; Bassler, H.; Porsch, M.; Daub, J. Adv. Mater. 1995, 7, 551.

Hong et al., Chem. Mater. 2016, 28, 5791-98, 5792-93.

Tavasli et al., J. Mater. Chem. 2012, 22, 6419-29, 6422.

Morello, G.R., J. Mol. Model. 2017, 23:174.

* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Application No. 63/263,766, filed on Nov. 9, 2021, the entire contents of which are incorporated herein by reference.

FIELD

The present disclosure generally relates to organometallic compounds and formulations and their various uses including as emitters in devices such as organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

In one aspect, the present disclosure provides a compound comprising a first ligand $L_A$ of Formula I:

Formula I

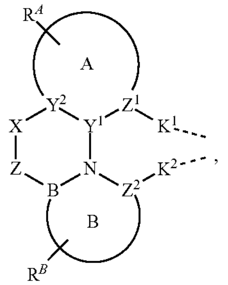

wherein ring A is a 5-membered or 6-membered carbocyclic or heterocyclic ring;

wherein ring B is a 5-membered or 6-membered heterocyclic ring;

wherein $K^1$ and $K^2$ are each independently selected from the group consisting of a direct bond, O, and S;

wherein at least one of $K^1$ and $K^2$ is a direct bond;

wherein $Z^1$ and $Z^2$ are each independently C or N;

wherein $Z^1$ is C if $K^1$ is O or S;

wherein $Z^2$ is C if $K^2$ is O or S;

wherein $Y^1$ and $Y^2$ are each independently selected from the group consisting of C, N, and B;

wherein X and Z are each independently selected from the group consisting of CR, CRR', SiRR', GeRR', BR, BRR', N, NR, O, and S;

wherein $R^A$ and $R^B$ each independently represent mono to the maximum allowable substitution, or no substitution;

wherein each R, R', $R^A$ and $R^B$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, germyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof;

wherein $L_A$ is coordinated to a metal M through the indicated dashed lines;

wherein M may be coordinated to other ligands;

wherein $L_A$ may be joined with other ligands to comprise a tridentate, tetradentate, pentadentate, or hexadentate ligand; and wherein any two R, R', $R^A$ and $R^B$ may be joined or fused to form a ring.

In another aspect, the present disclosure provides a formulation of a compound as described herein.

In yet another aspect, the present disclosure provides an OLED having an organic layer comprising a compound as described herein.

In yet another aspect, the present disclosure provides a consumer product comprising an OLED with an organic layer comprising a compound as described herein.

DETAILED DESCRIPTION

A. Terminology

Figure 1:
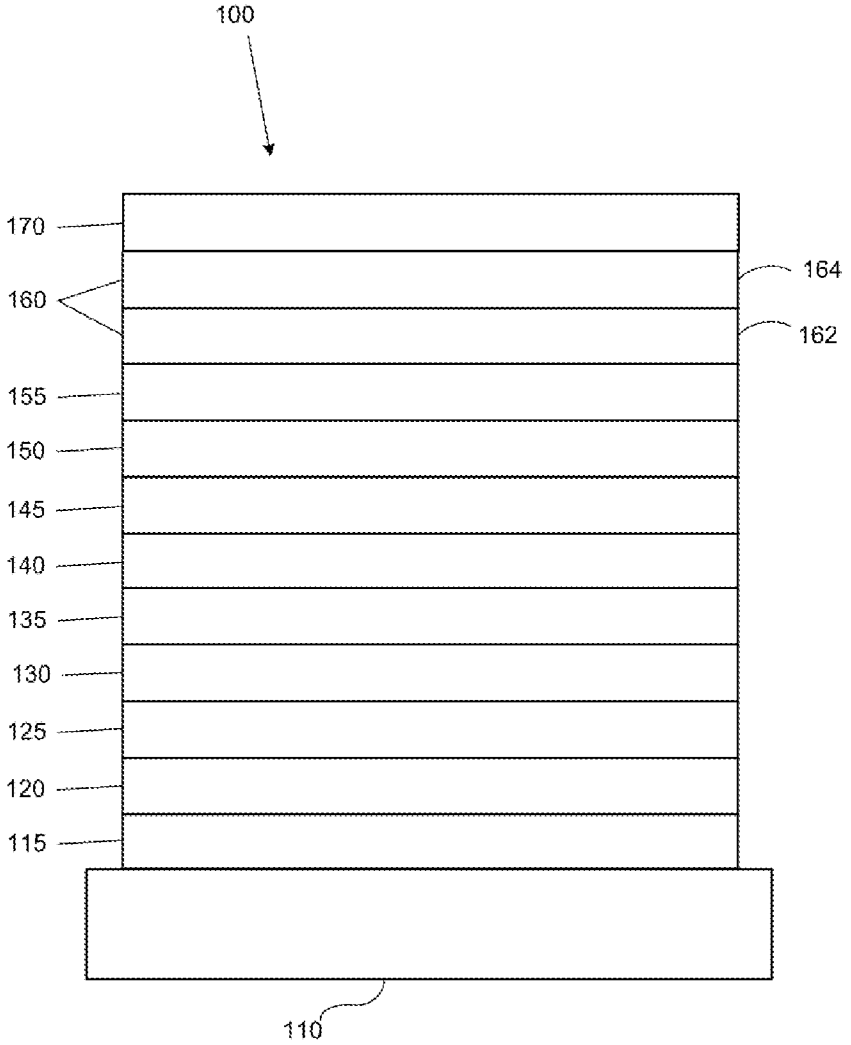
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level.

Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical ($C(O)—R_s$).

The term "ester" refers to a substituted oxycarbonyl ($—O—C(O)—R_s$ or $—C(O)—O—R_s$) radical.

The term "ether" refers to an $—OR_s$ radical.

The terms "sulfanyl" or "thio-ether" are used interchangeably and refer to a $—SR_s$ radical.

The term "selenyl" refers to a $—SeR_s$ radical.

The term "sulfinyl" refers to a $—S(O)—R_s$ radical.

The term "sulfonyl" refers to a $—SO_2—R_s$ radical.

The term "phosphino" refers to a $—P(R_s)_3$ radical, wherein each $R_s$ can be same or different.

The term "silyl" refers to a $—Si(R_s)_3$ radical, wherein each $R_s$ can be same or different.

The term "germyl" refers to a $—Ge(R_s)_3$ radical, wherein each $R_s$ can be same or different.

The term "boryl" refers to a $—B(R_s)_2$ radical or its Lewis adduct $—B(R_s)_3$ radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo [3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group may be optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group may be optionally substituted.

The term "alkynyl" refers to and includes both straight and branched chain alkyne radicals. Alkynyl groups are essentially alkyl groups that include at least one carbon-carbon triple bond in the alkyl chain. Preferred alkynyl groups are those containing two to fifteen carbon atoms. Additionally, the alkynyl group may be optionally substituted.

The terms "aralkyl" or "arylalkyl" are used interchangeably and refer to an alkyl group that is substituted with an aryl group. Additionally, the aralkyl group may be optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, germyl, boryl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, boryl, selenyl, and combinations thereof.

In some instances, the preferred general substituents are selected from the group consisting of deuterium, fluorine, alkyl, cycloalkyl, heteroalkyl, alkoxy, aryloxy, amino, silyl, boryl, germyl, alkenyl, cycloalkenyl, heteroalkenyl, aryl, heteroaryl, nitrile, isonitrile, sulfanyl, and combinations thereof.

In some instances, the more preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the most preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (*Reviews*) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

B. The Compounds of the Present Disclosure

In one aspect, the present disclosure provides a compound comprising a first ligand $L_A$ of Formula I:

Formula I

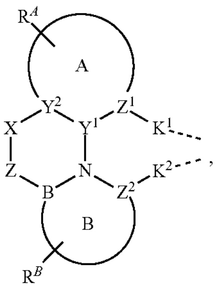

wherein ring A is a 5-membered or 6-membered carbocyclic or heterocyclic ring;

wherein ring B is a 5-membered or 6-membered heterocyclic ring;

wherein $K^1$ and $K^2$ are each independently selected from the group consisting of a direct bond, O, and S;

wherein at least one of $K^1$ and $K^2$ is a direct bond;

wherein $Z^1$ and $Z^2$ are each independently C or N;

wherein $Z^1$ is C if $K^1$ is O or S;

wherein $Z^2$ is C if $K^2$ is O or S;

wherein $Y^1$ and $Y^2$ are each independently selected from the group consisting of C, N, and B;

wherein X and Z are each independently selected from the group consisting of CR, CRR', SiRR', GeRR', BR, BRR', N, NR, O, and S;

wherein $R^A$ and $R^B$ each independently represent mono to the maximum allowable substitution, or no substitution;

wherein each R, R', $R^A$ and $R^B$ is independently a hydrogen or a substituent selected from the group of general substituents as described herein;

wherein $L_A$ is coordinated to a metal M through the indicated dashed lines;

wherein M may be coordinated to other ligands;

wherein $L_A$ may be joined with other ligands to comprise a tridentate, tetradentate, pentadentate, or hexadentate ligand; and wherein any two R, R', $R^A$ and $R^B$ may be joined or fused to form a ring.

In further embodiments, each R, R', $R^A$ and $R^B$ is independently a hydrogen or a substituent selected from the group consisting of preferred general substituents as described herein.

In further embodiments, ring A is a five-membered ring.

In further embodiments, ring A is a six-membered ring.

In further embodiments, ring A is a heterocyclic ring.

In further embodiments, ring A is a five-membered heterocyclic ring.

In further embodiments, ring A is an aromatic ring.

In further embodiments, ring A is a five-membered heterocyclic aromatic ring.

In further embodiments, ring A contains at least one nitrogen atom.

In further embodiments, ring A contains at least two nitrogen atoms.

In further embodiments, ring A contains exactly two nitrogen atoms.

In further embodiments, ring B is a six-membered ring.

In further embodiments, ring B is an aromatic six-membered ring.

In further embodiments, $K^1$ and $K^2$ are both direct bonds.

In further embodiments, $Z^1$ is N.

In further embodiments, $Z^1$ is C.

In further embodiments, $Z^2$ is C.

In further embodiments, $Z^1$ is N and $Z^2$ is C.

In further embodiments, X is C.

In further embodiments, X is B.

In further embodiments, Z is C.

In further embodiments, X is C and Z is C.

In further embodiments, $Y^1$ is C.

In further embodiments, $Y^1$ is N.

In further embodiments, $Y^2$ is C.

In further embodiments, $Y^2$ is N.

In further embodiments, exactly one of X, Z, $Y^1$, and $Y^2$ is N.

In further embodiments, a further ring is fused to X and Z.

In further embodiments, a further ring which is an aromatic ring is fused to X and Z.

In further embodiments, the ligand $L_A$ is selected from the group consisting of

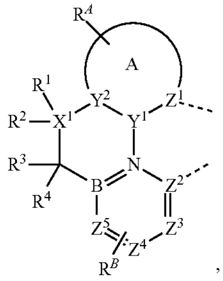

,

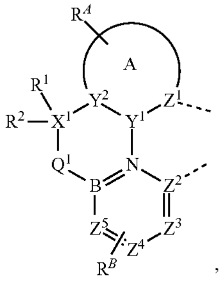

, and

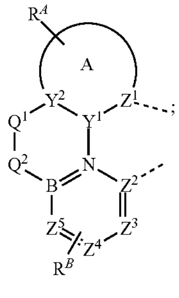

wherein ring

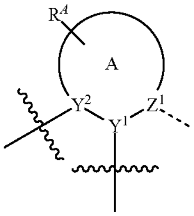

is selected from the list consisting of:

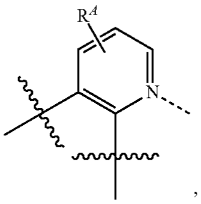

,

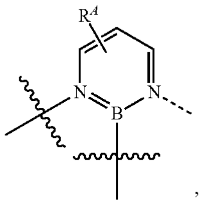

,

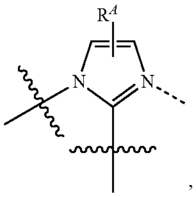

,

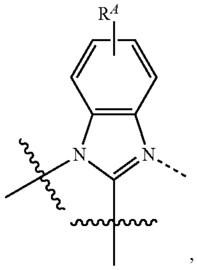

,

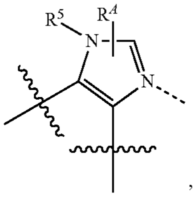

,

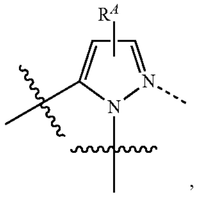

,

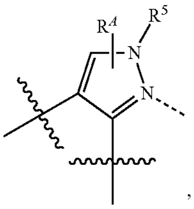

, and

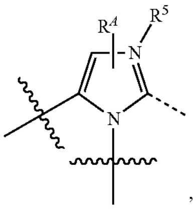

, wherein $Z^1$ through $Z^5$ are each independently C or N; $R^A$ and $R^B$ each independently represent zero, mono, or up to the maximum allowed number of substitutions to its associated ring; each of $R^1$, $R^2$, $R^3$, $R^4$, and $R^5$ is independently a hydrogen or a substituent selected from the group consisting of the general substituents defined herein; Y and $Y^2$ are each independently C, N, or B; $X^1$ and $X^2$ are each independently C or Si; and $Q^1$ and $Q^2$ are each independently O, S, NR, CR, or BR; wherein any two adjacent substituents may be joined or fused to form a ring.

In further embodiments, the ligand $L_A$ is selected from the group consisting of:

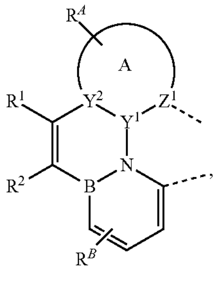

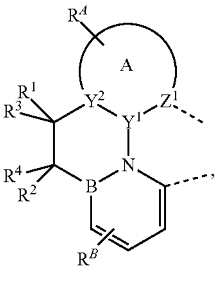

-continued

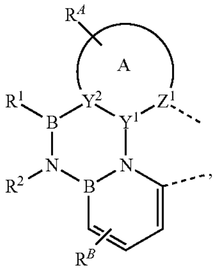

, and

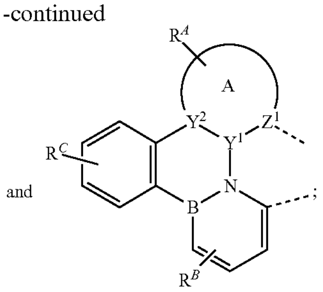

;

wherein ring

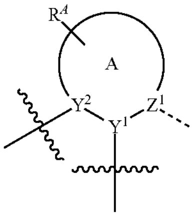

is selected from the list consisting of:

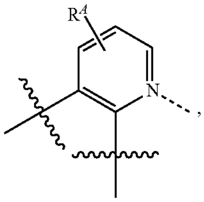

,

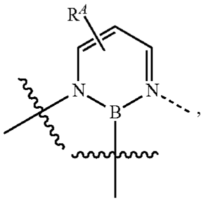

,

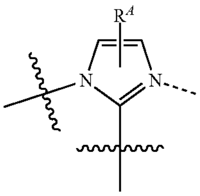

,

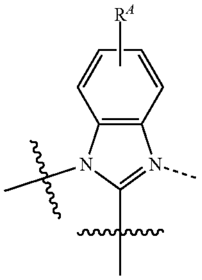

,

-continued

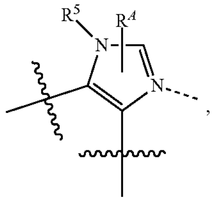

,

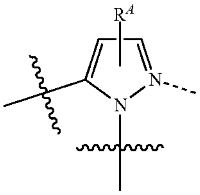

,

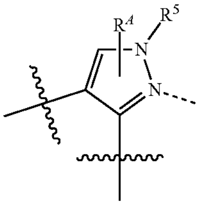

, and

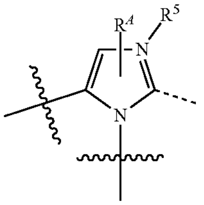

, wherein $Z^1$ is C or N; $R^A$ and $R^B$ each independently represent zero, mono, or up to the maximum allowed number of substitutions to its associated ring; each of $R^1$, $R^2$, $R^3$, $R^4$, and $R^5$ is independently a hydrogen or a substituent selected from the group consisting of the general substituents defined herein; $Y^1$ and $Y^2$ are each independently C, N, or B; $X^1$ and $X^2$ are each independently C or Si; and $Q^1$ and $Q^2$ are each independently O, S, NR, CR, or BR.

In further embodiments, the ligand $L_A$ is selected from the group consisting of structures as defined in the following table:

| $L_A$ | Structure of $L_A$ | $L_A$ | Structure of $L_A$ |
|---|---|---|---|
| For $L_A$1-(Rl)(Rm)(Rn), $L_A$1-(R1)(R1)(R1) to $L_A$1-(R134)(R134)(R134) have the structure, | 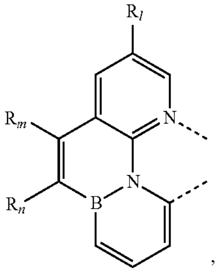 , | For $L_A$21-(Rl)(Rm)(Rn)(Ro), $L_A$21-(R1)(R1)(R1)(R1) to $L_A$21-(R134)(R134)(R134)(R134) have the structure, | 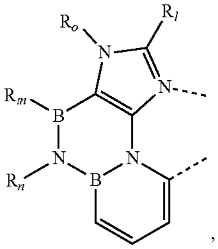 , |

-continued

| $L_A$ | Structure of $L_A$ | $L_A$ | Structure of $L_A$ |
|---|---|---|---|
| For $L_A$2-(Rl)(Rm)(Rn), $L_A$2-(R1)(R1)(R1) to $L_A$2-(R134)(R134)(R134) have the structure, | 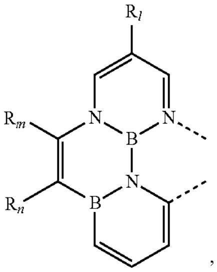, | For $L_A$22-(Rl)(Rm)(Rn), $L_A$22-(R1)(R1)(Rl) to $L_A$22-(R134)(R134)(R134) have the structure, | 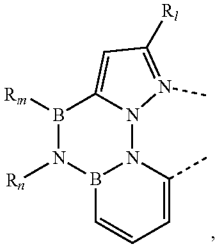, |
| For $L_A$3-(Rl)(Rm)(Rn), $L_A$3-(R1)(R1)(R1) to $L_A$3-(R134)(R134)(R134) have the structure, | 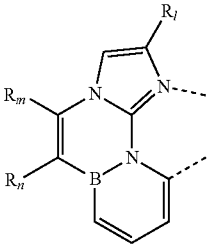, | For $L_A$23-(Rl)(Rm)(Rn), $L_A$23-(R1)(R1)(R1) to $L_A$23-(R134)(R134)(R134) have the structure, | 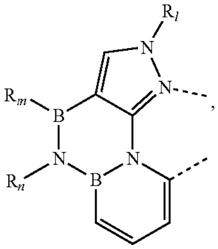, |
| For $L_A$4-(Rm)(Rn), $L_A$4-(R1)(R1) to $L_A$4-(R134)(R134) have the structure, | 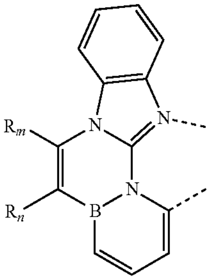, | For $L_A$24-(Rl)(Rm)(Rn), $L_A$24-(R1)(R1)(R1) to $L_A$24-(R134)(R134)(R134) have the structure, | 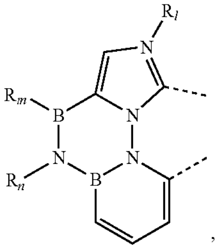, |
| For $L_A$5-(Rl)(Rm)(Rn)(Ro), $L_A$5-(R1)(R1)(R1)(R1) to $L_A$5-(R134)(R134)(R134)(R134) have the structure, | 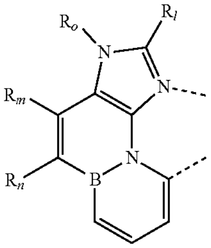, | For $L_A$25-(Rl)(Rm)(Rn), $L_A$25-(R1)(R1)(R1) to $L_A$25-(R134)(R134)(R134) have the structure, | 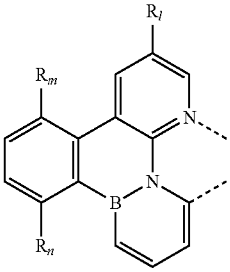, |
| For $L_A$6-(Rl)(Rm)(Rn), $L_A$6-(R1)(R1)(R1) to $L_A$6-(R134)(R134)(R134) have the structure, | 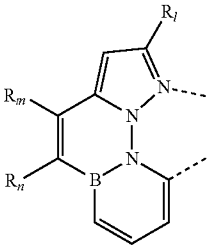, | For $L_A$26-(Rl)(Rm)(Rn), $L_A$26-(R1)(R1)(R1) to $L_A$26-(R134)(R134)(R134) have the structure, | 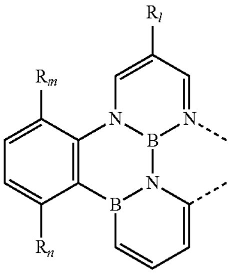, |

-continued

| $L_A$ | Structure of $L_A$ | $L_A$ | Structure of $L_A$ |
|---|---|---|---|
| For $L_A$7-(Rl)(Rm)(Rn), $L_A$7-(R1)(R1)(R1) to $L_A$7-(R134)(R134)(R134) have the structure, | 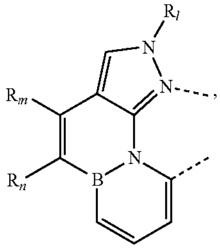 | For $L_A$27-(Rl)(Rm)(Rn)(Ro), $L_A$27-(R1)(R1)(R1)(R1) to $L_A$27-(R134)(R134)(R134)(R134) have the structure, | 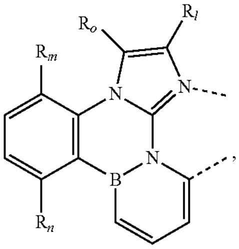 |
| For $L_A$8-(Rl)(Rm)(Rn), $L_A$8-(R1)(R1)(R1) to $L_A$8-(R134)(R134)(R134) have the structure, | 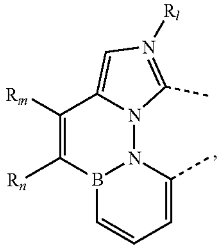 | For $L_A$28-(Rl)(Rm), $L_A$28-(R1)(R1) to $L_A$28-(R134)(R134) have the structure, | 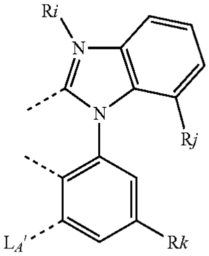 |
| For $L_A$9-(Rl)(Lz), $L_A$9-(R1)(LI) to $L_A$9-(R134)(L5) have the structure, | 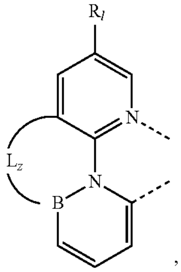 | For $L_A$29-(Rl)(Rm)(Rn)(Ro), $L_A$29-(R1)(R1)(R1)(R1) to $L_A$29-(R134)(R134)(R134)(R134) have the structure, | 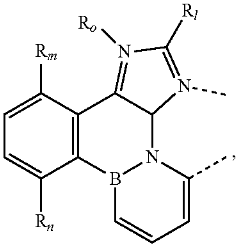 |
| For $L_A$10-(Rl)(Lz), $L_A$10-(R1)(L1) to $L_A$10-(R134)(L5) have the structure, | 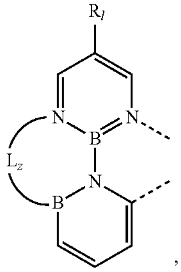 | For $L_A$30-(Rl)(Rm)(Rn), $L_A$30-(R1)(R1)(R1) to $L_A$30-(R134)(R134)(R134) have the structure, | 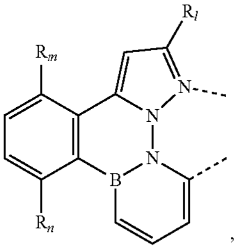 |
| For $L_A$11-(Rl)(Lz), $L_A$11-(R1)(L1) to $L_A$11-(R134)(L5) have the structure, | 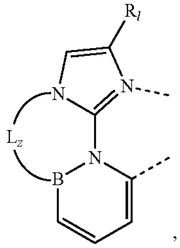 | For $L_A$31-(Rl)(Rm)(Rn), $L_A$31-(R1)(R1)(R1) to $L_A$31-(R134)(R134)(R134) have the structure, | 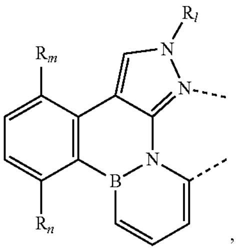 |

-continued

| $L_A$ | Structure of $L_A$ | $L_A$ | Structure of $L_A$ |
|---|---|---|---|
| For $L_A$12-(Lz), $L_A$12-(L1) to $L_A$12-(L5) have the structure, | 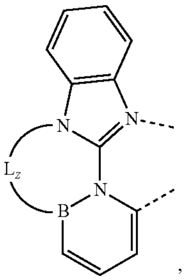 , | For $L_A$32-(Rl)(Rm)(Rn), $L_A$32-(R1)(R1)(R1) to $L_A$32-(R134)(R134)(R134) have the structure, | 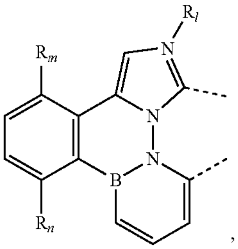 , |
| For $L_A$13-(Rl)(Ro)(Lz), $L_A$13-(R1)(R1)(L1) to $L_A$13-(R134)(R134)(L5) have the structure, | 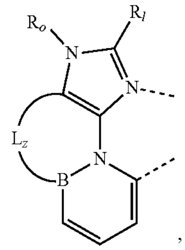 , | For $L_A$33-(Rl)(Rm)(Rn), $L_A$33-(R1)(R1)(R1) to $L_A$33-(R134)(R134)(R134) have the structure, | 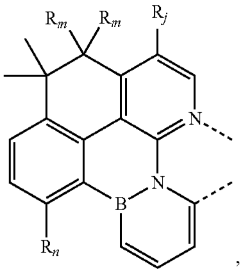 , |
| For $L_A$14-(Rl)(Lz), $L_A$14-(R1)(L1) to $L_A$14-(R134)(L5) have the structure, | 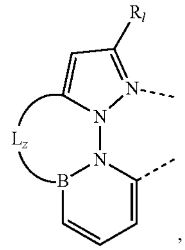 , | For $L_A$34-(Rl)(Rm)(Rn), $L_A$34-(R1)(R1)(R1) to $L_A$34-(R134)(R134)(R134) have the structure, | 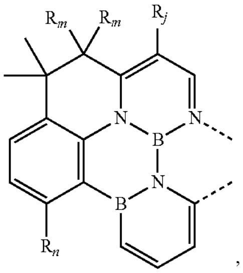 , |
| For $L_A$15-(Rl)(Lz), $L_A$15-(R1)(LI) to $L_A$15-(R134)(L5) have the structure, | 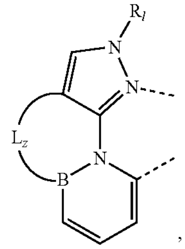 , | For $L_A$35-(Rl)(Rm)(Rn), $L_A$35-(R1)(R1)(R1) to $L_A$35-(R134)(R134)(R134) have the structure, | 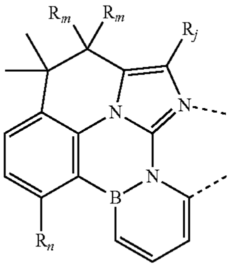 , |
| For $L_A$16-(Rl)(Lz), $L_A$16-(R1)(LI) to $L_A$16-(R134)(L5) have the structure, | 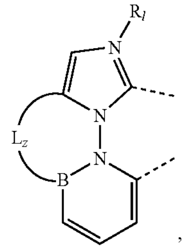 , | For $L_A$36-(Rl)(Rm)(Rn), $L_A$36-(R1)(R1)(R1) to $L_A$36-(R134)(R134)(R134) have the structure, | 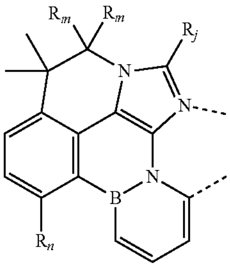 , |

-continued

| $L_A$ | Structure of $L_A$ | $L_A$ | Structure of $L_A$ |
| --- | --- | --- | --- |
| For $L_A$17-(Rl)(Rm)(Rn), $L_A$17-(R1)(R1)(R1) to $L_A$17-(R134)(R134)(R134) have the structure, | 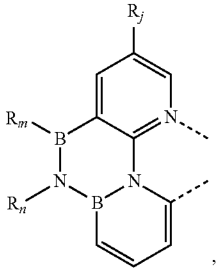 , | For $L_A$37-(Rl)(Rm)(Rn), $L_A$37-(R1)(R1)(R1) to $L_A$37-(R134)(R134)(R134) have the structure, | 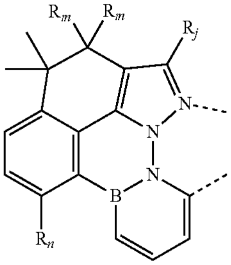 , |
| For $L_A$18-(Rl)(Rm)(Rn), $L_A$18-(R1)(R1)(R1) to $L_A$18-(R134)(R134)(R134) have the structure, | 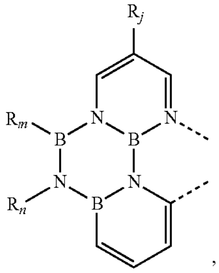 , | For $L_A$38-(Rl)(Rm)(Rn), $L_A$38-(R1)(R1)(R1) to $L_A$38-(R134)(R134)(R134) have the structure, | 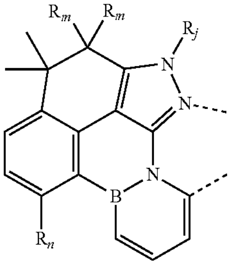 , |
| For $L_A$19-(Rl)(Rm)(Rn), $L_A$19-(R1)(R1)(R1) to $L_A$19-(R134)(R134)(R134) have the structure, | 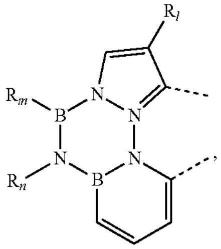 | For $L_A$39-(Rl)(Rm)(Rn), $L_A$39-(R1)(R1)(R1) to $L_A$30-(R134)(R134)(R134) have the structure, | 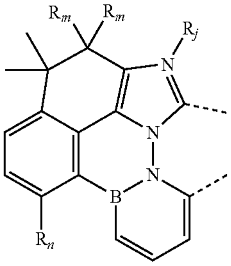 , |
| For $L_A$20-(Rm)(Rn), $L_A$20-(R1)(R1) to $L_A$20-(R134)(R134) have the structure, | 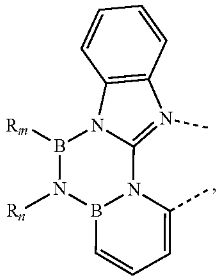 | | |

wherein R1 to R134 have the following structures as defined as follows:

R1

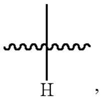 ,

R2

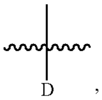 ,

-continued

R3

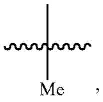 ,

R4

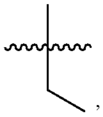 ,

R5

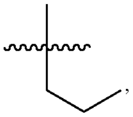 ,

-continued
R6
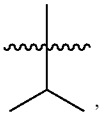
,
R7
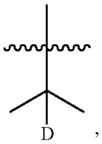
,
R8
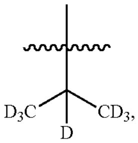
R9
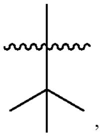
,
R10
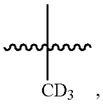
,
R11
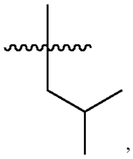
,
R12
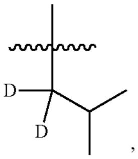
,
R13
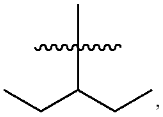
,
R14
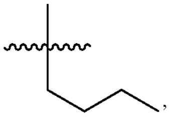
,
R15
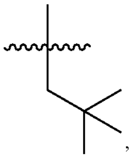
,
-continued
R16
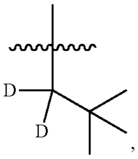
,
R17
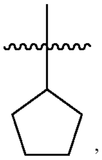
,
R18
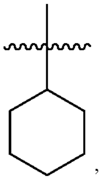
,
R19
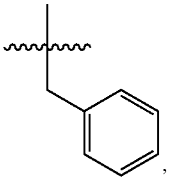
,
R20
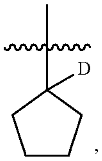
,
R21
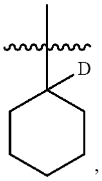
,
R22
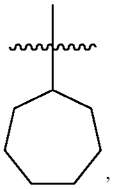
,
R23
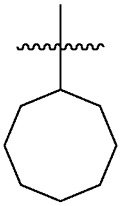
, -continued
R24
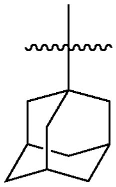
,
R25
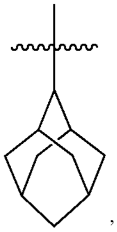
,
R26
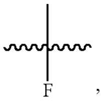
,
R27
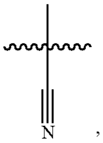
,
R28
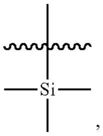
,
R29
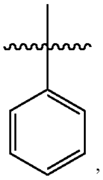
,
R30
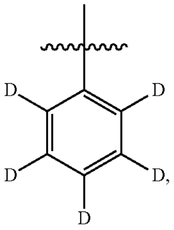
R31
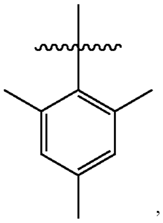
,
-continued
R32
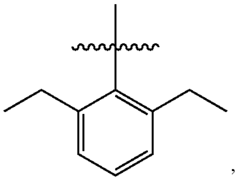
,
R33
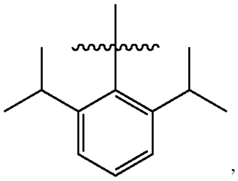
,
R34
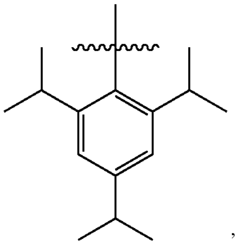
,
R35
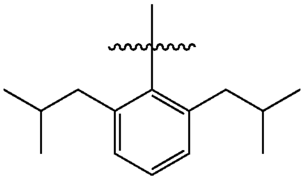
,
R36
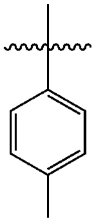
,
R37
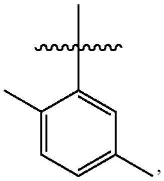
R38
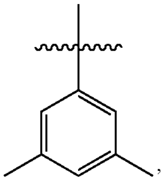
R39
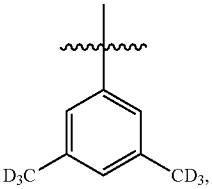

-continued
R40
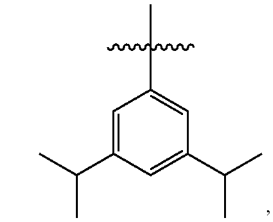
,
R41
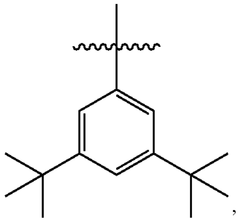
,
R42
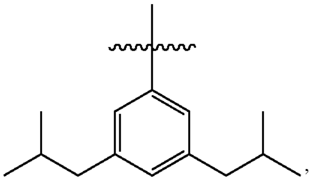
,
R43
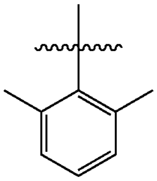
,
R44
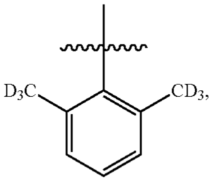
R45
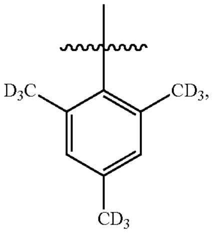
R46
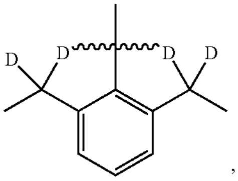
,
-continued
R47
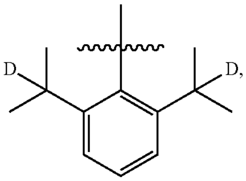
R48
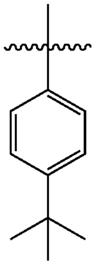
,
R49
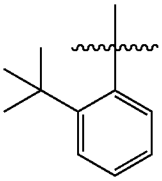
,
R50
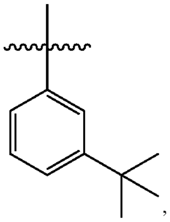
,
R51
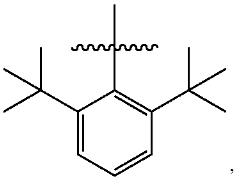
,
R52
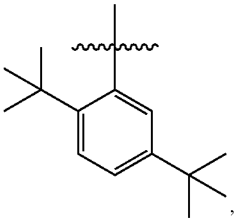
,
R53
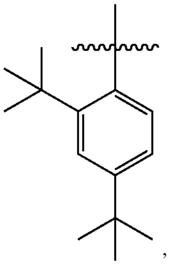
, -continued
R54
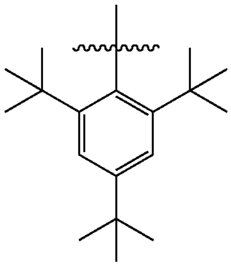
,
R55
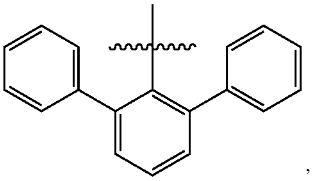
,
R56
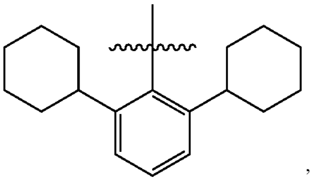
,
R57
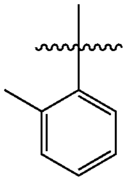
,
R58
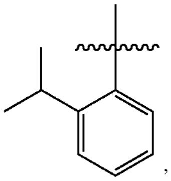
,
R59
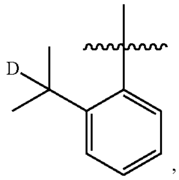
,
R60
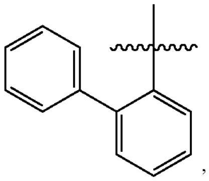
,
R61
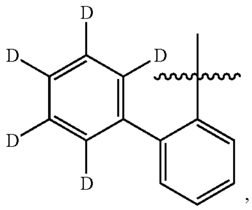
,
-continued
R62
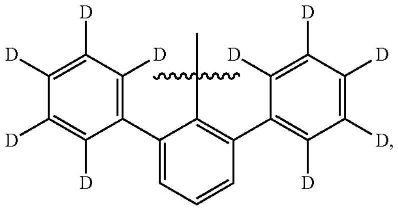
R63
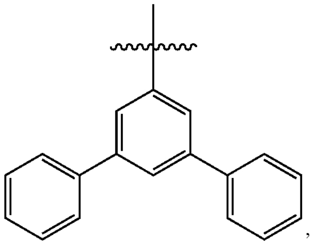
,
R64
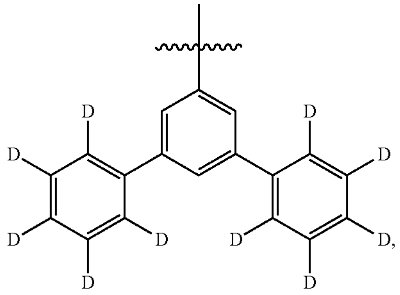
R65
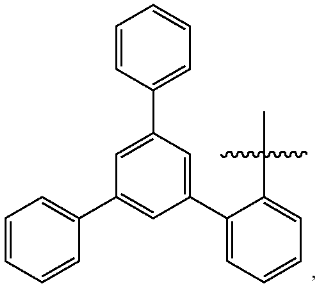
,
R66
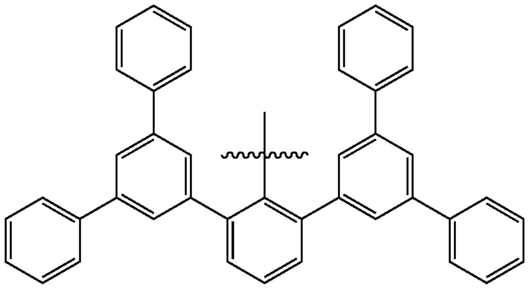
,
R67
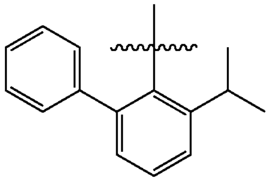
, -continued
R68
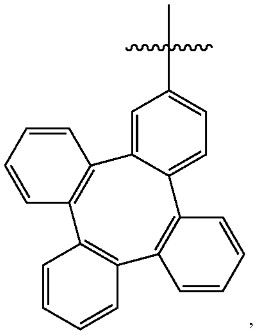
,
R69
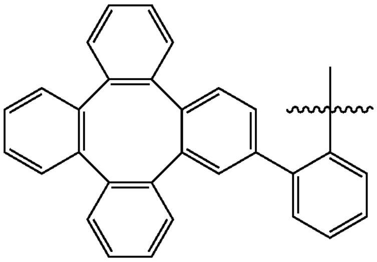
,
R70
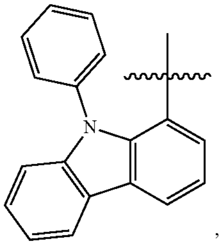
,
R71
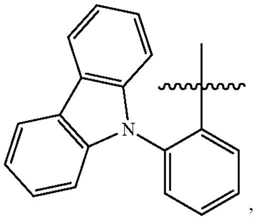
,
R72
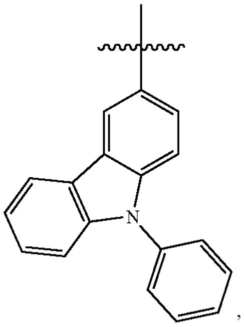
,
R73
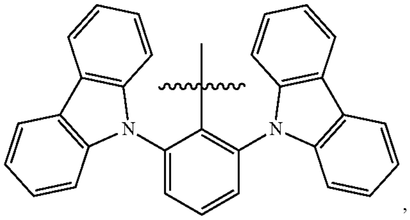
,
-continued
R74
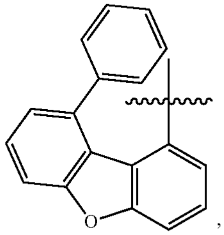
,
R75
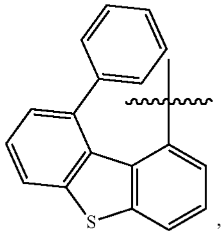
,
R76
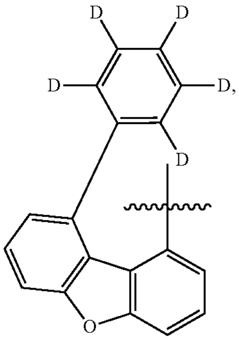
R77
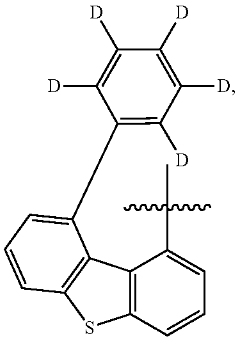
R78
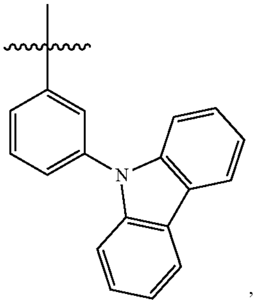
, -continued
R79
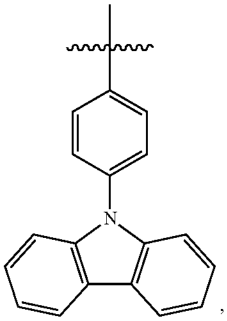
,
R80
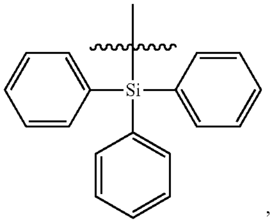
,
R81
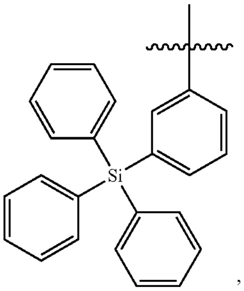
,
R82
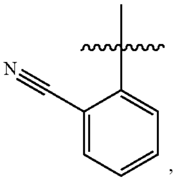
,
R83
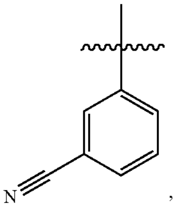
,
R84
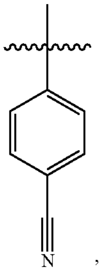
,
-continued
R85
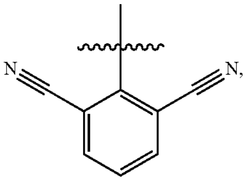
R86
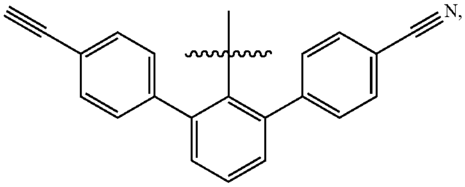
R87
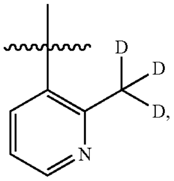
R88
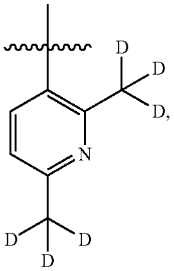
R89
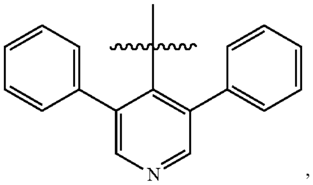
,
R90
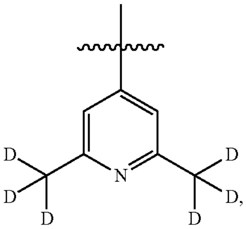
R91
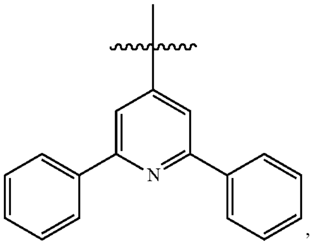
, -continued
R92
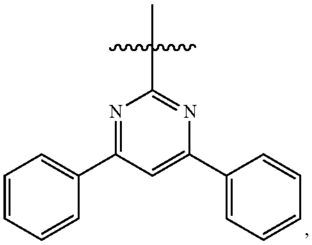
,
R93
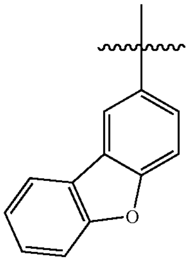
,
R94
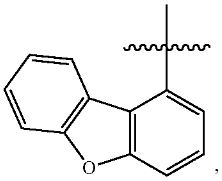
,
R95
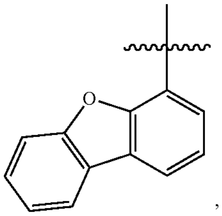
,
R96
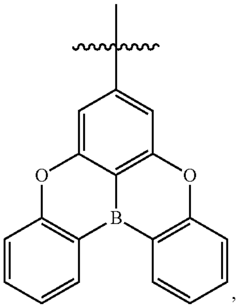
,
R97
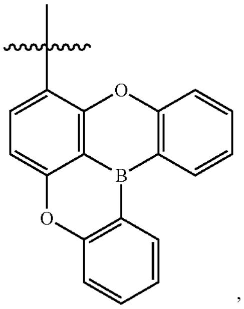
,
-continued
R98
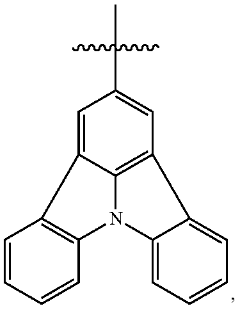
,
R99
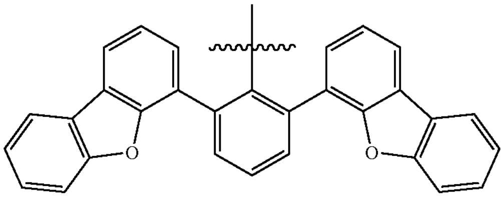
,
R100
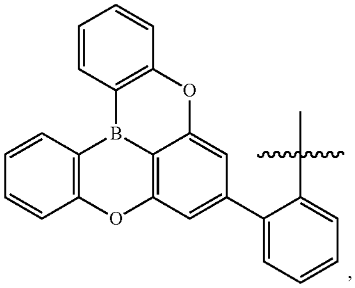
,
R101
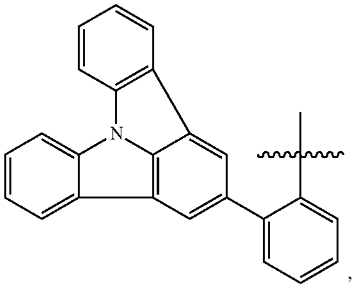
,
R102
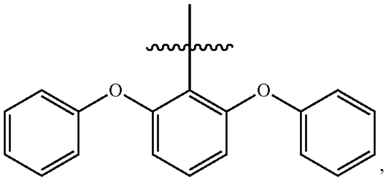
,
R103
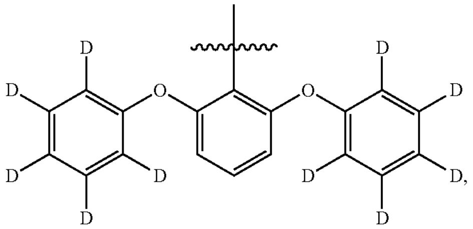

-continued
R104
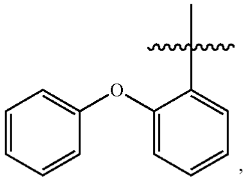
,
R105
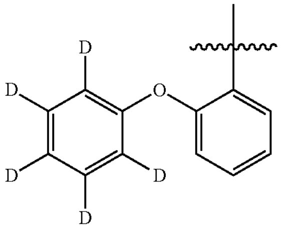
,
R106
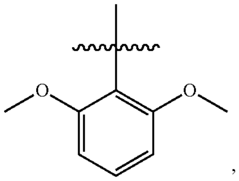
,
R107
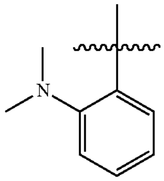
,
R108
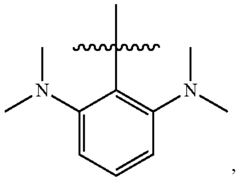
,
R109
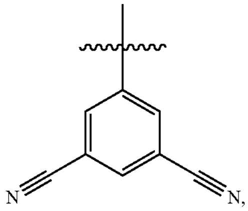
,
R110
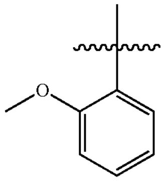
,
R111
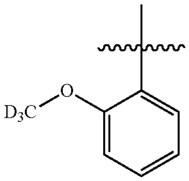
,
-continued
R112
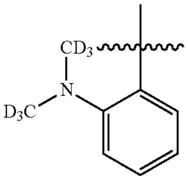
,
R113
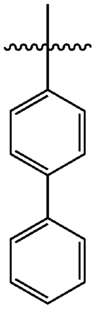
,
R114
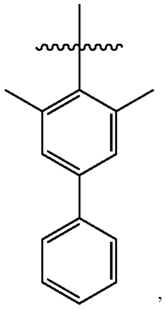
,
R115
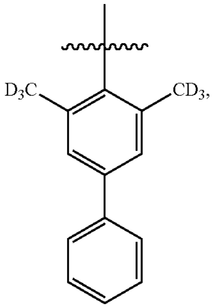
,
R116
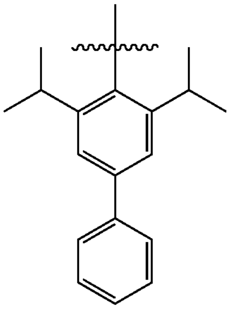
, -continued
R117
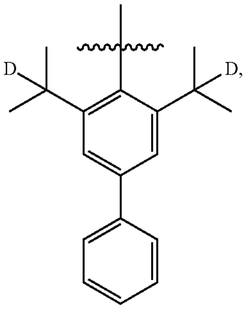
R118
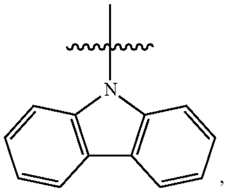
,
R119
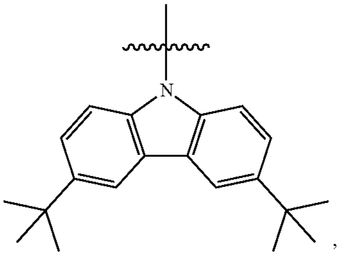
,
R120
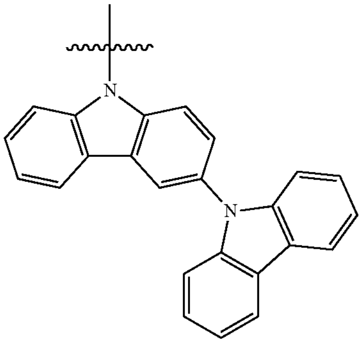
,
R121
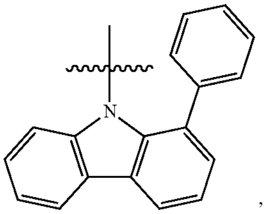
,
R122
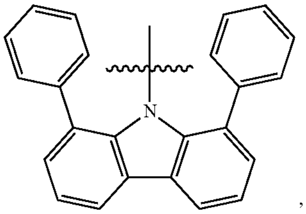
,
-continued
R123
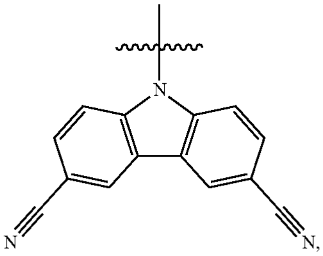
R124
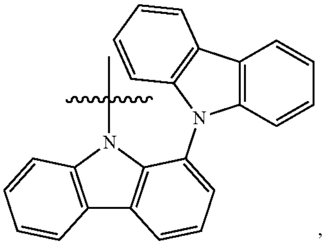
,
R125
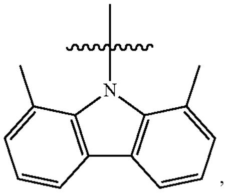
,
R126
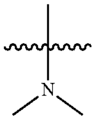
,
R127
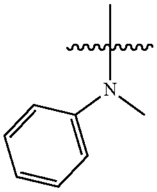
,
R128
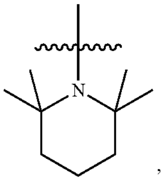
,
R129
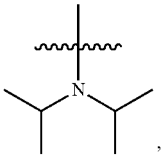
,
R130
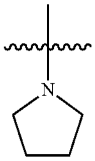
, -continued

R131

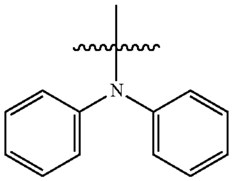,

R132

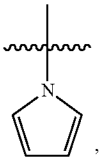,

R133

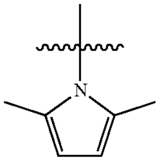, and

R134

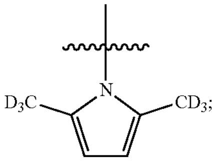

wherein $L_1$ through $L_5$ have the following structures:

L1

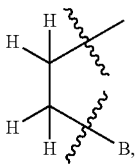

L2

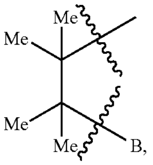

L3

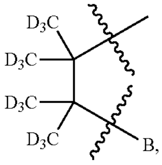

L4

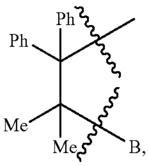 and

-continued

L5

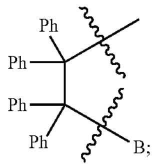

In further embodiments, the compound has a formula of $M(L_A)_p(L_B)_q(L_C)_r$ wherein $L_B$ and $L_C$ are each a bidentate ligand; and wherein p is 1, 2, or 3; q is 0, 1, or 2; r is 0, 1, or 2; and p+q+r is the oxidation state of the metal M.

In further embodiments, the compound has a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$; and wherein $L_A$, $L_B$, and $L_C$ are different from each other.

In further embodiments, $L_B$ is a substituted or unsubstituted phenylpyridine, and $L_C$ is a substituted or unsubstituted acetylacetonate.

In further embodiments, the compound has a formula of $Pt(L_A)(L_B)$; and wherein $L_A$ and $L_B$ can be same or different.

In further embodiments, $L_A$ and $L_B$ are connected to form a tetradentate ligand.

In further embodiments, $L_B$ and $L_C$ are each independently selected from the group consisting of structures as defined as follows:

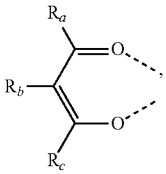,

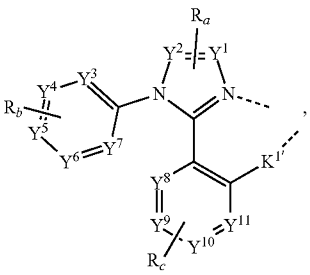,

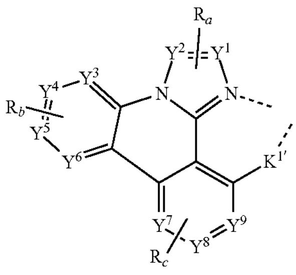,

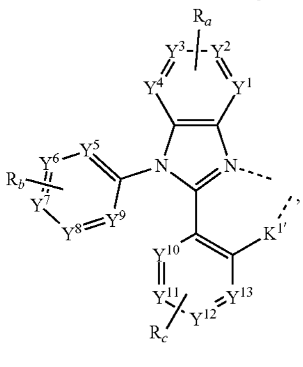,

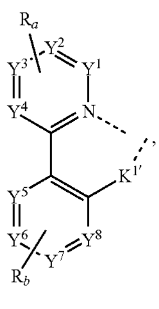

-continued
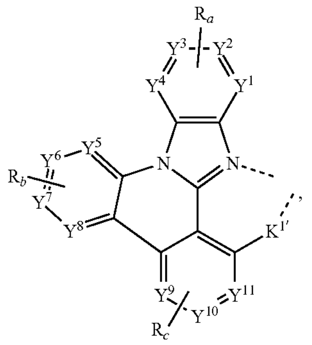
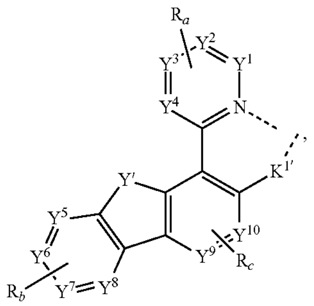
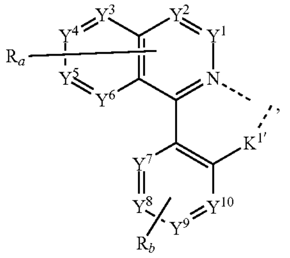
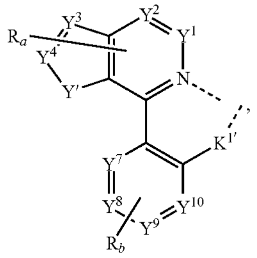
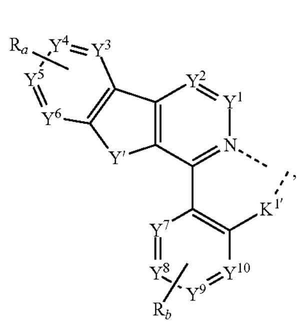
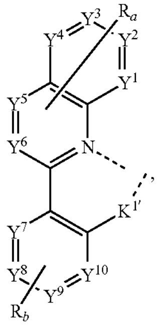
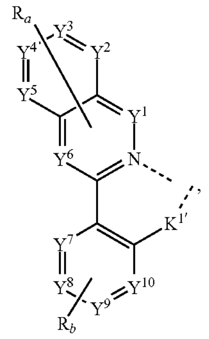
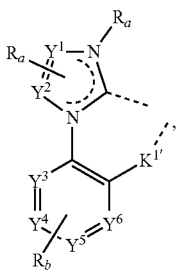
-continued
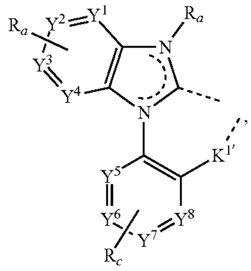
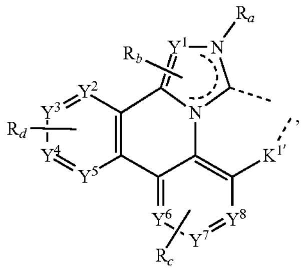
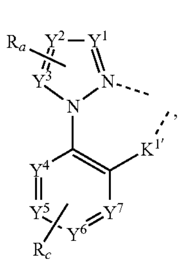
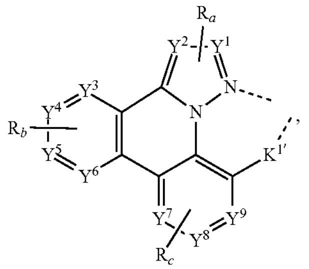
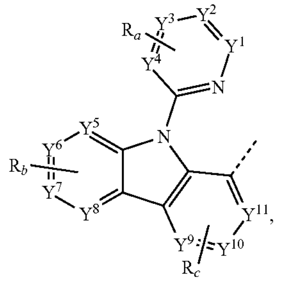
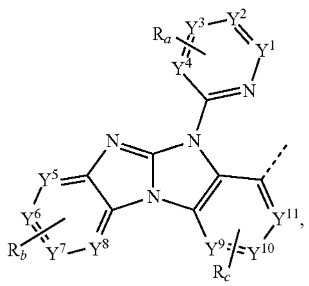
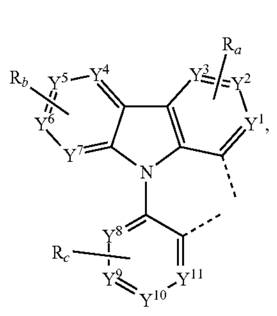
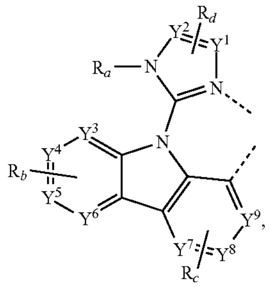

-continued
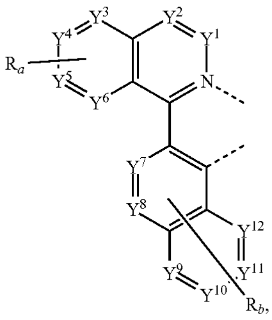
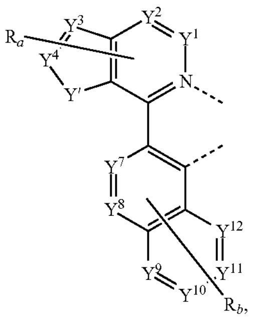
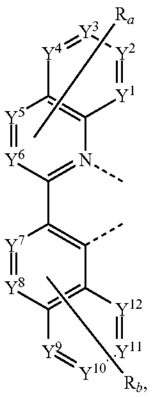
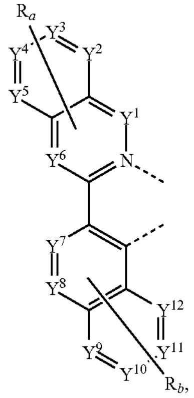
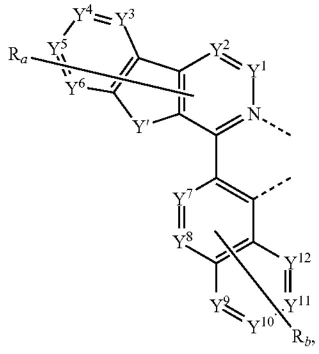
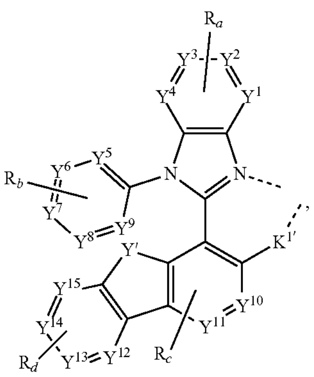
-continued
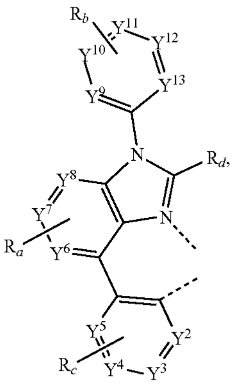
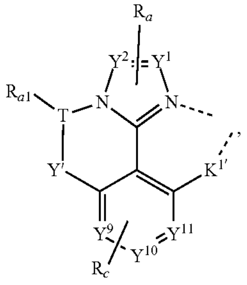
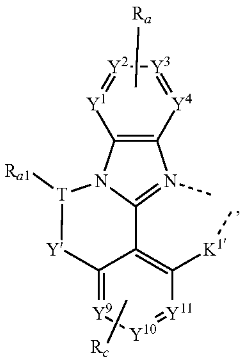
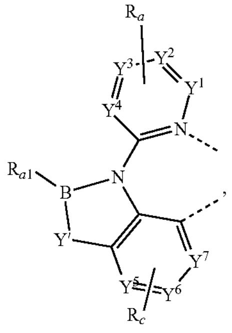
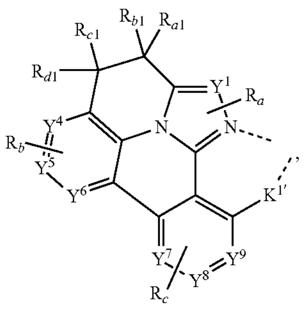
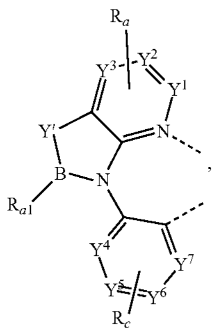
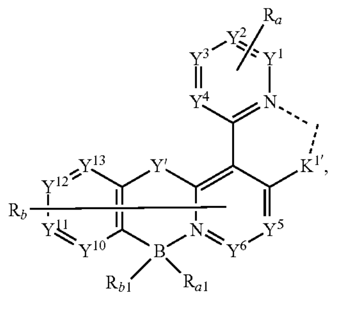
and -continued

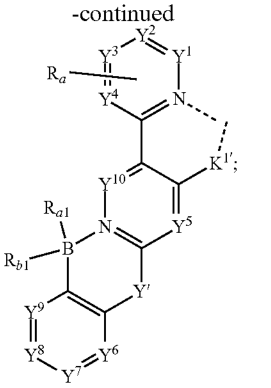

wherein:

T is selected from the group consisting of B, Al, Ga, and In;

wherein $K^{1'}$ is a direct bond or is selected from the group consisting of $NR_e$, $PR_e$, O, S, and Se;

each of $Y^1$ to $Y^{13}$ is independently selected from the group consisting of carbon and nitrogen;

Y' is selected from the group consisting of $BR_e$, $NR_e$, $PR_e$, O, S, Se, C═O, C═S, C═Se, $C═NR_e$, $C═CR_eR_f$, S═O, $SO_2$, $P(O)R_e$, $CR_eR_f$, $SiR_eR_f$, and $GeR_eR_f$;

$R_e$ and $R_f$ can be fused or joined to form a ring;

each $R_a$, $R_b$, $R_c$, and $R_d$ independently represent zero, mono, or up to a maximum allowed number of substitutions to its associated ring;

each of $R_{a1}$, $R_{b1}$, $R_{c1}$, $R_{do}$, $R_a$, $R_b$, $R_c$, $R_d$, $R_e$ and $R_f$ is independently a hydrogen or a substituent selected from the group consisting of deuterium, halide, alkyl, cycloalkyl, heteroalkyl, arylalkyl, alkoxy, aryloxy, amino, silyl, germyl, boryl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, selenyl, and combinations thereof; the general substituents defined herein; and any two adjacent $R_a$, $R_b$, $R_c$, $R_d$, $R_e$ and $R_f$ can be fused or joined to form a ring or form a multidentate ligand.

In further embodiments, $L_B$ and $L_C$ are each independently selected from the group consisting of structures as defined as follows:

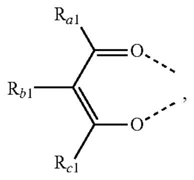

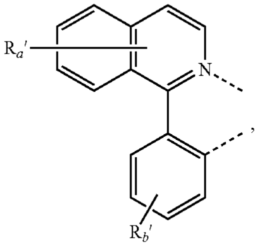

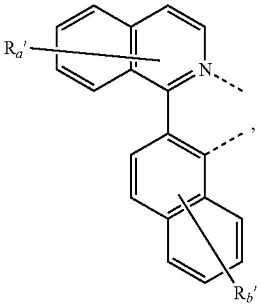

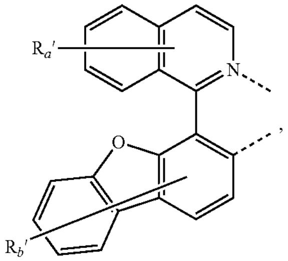

-continued

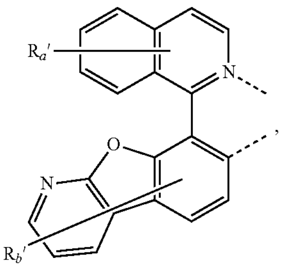

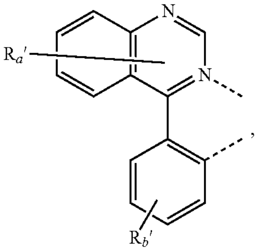

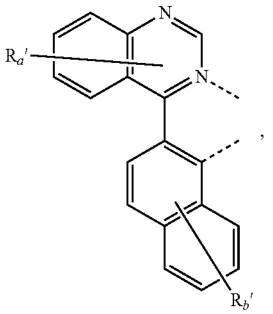

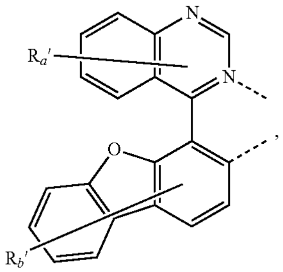

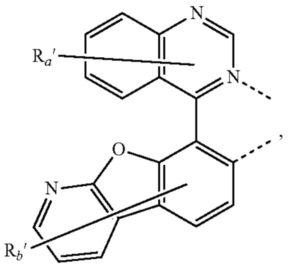

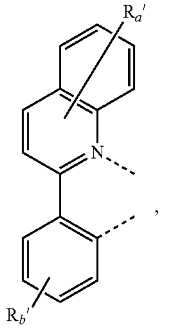

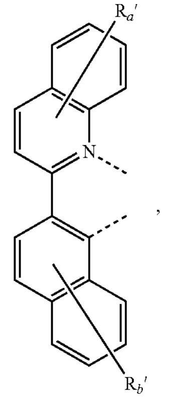

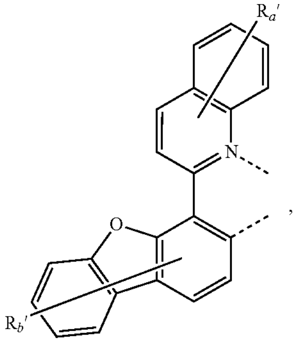

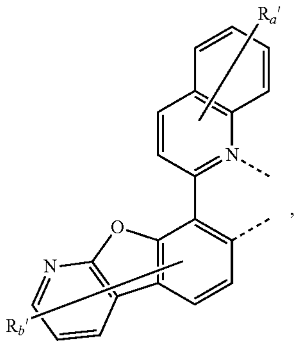

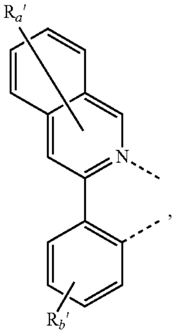

-continued
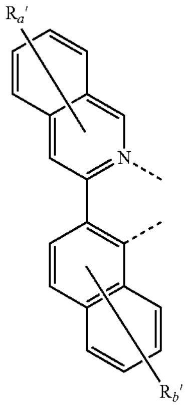
,
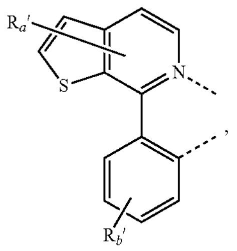
,
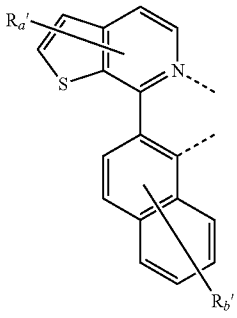
,
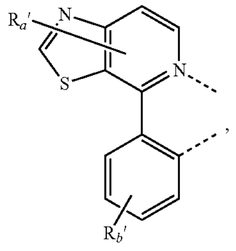
,
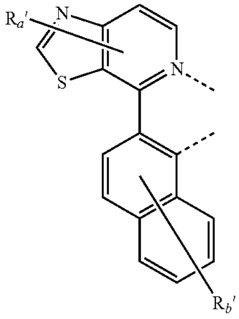
,
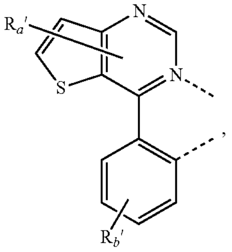
,
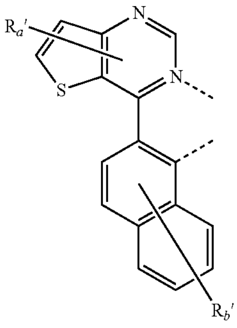
,
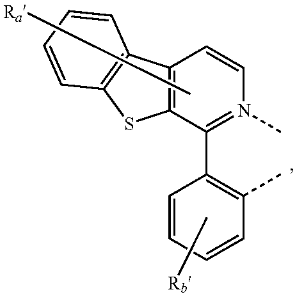
,
-continued
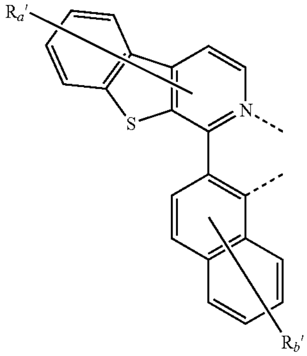
,
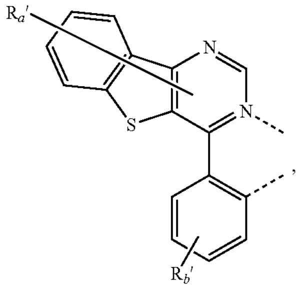
,
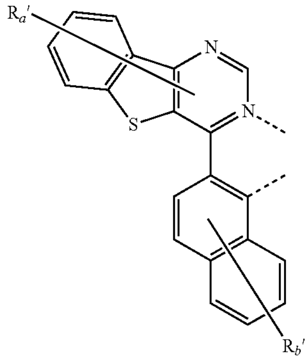
,
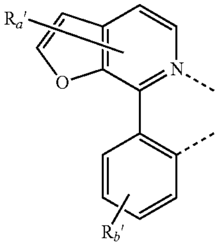
,
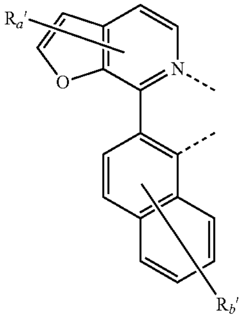
,
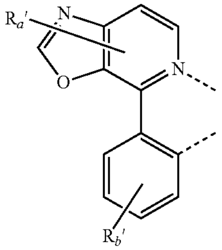
,
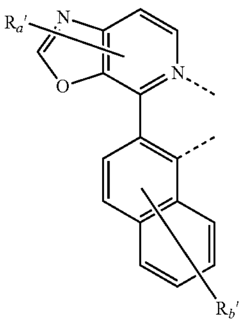
,
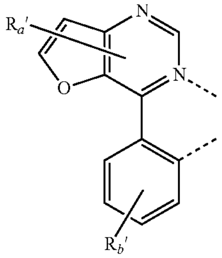
, -continued
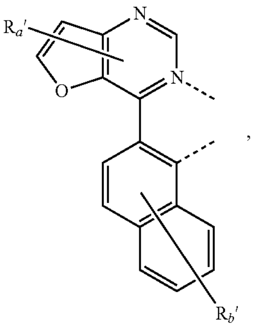
,
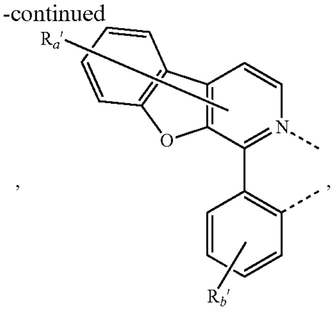
,
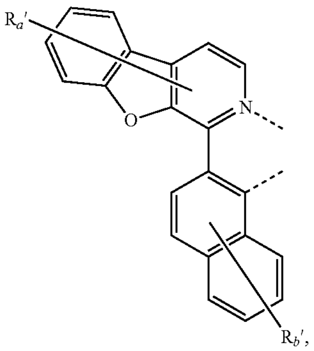
,
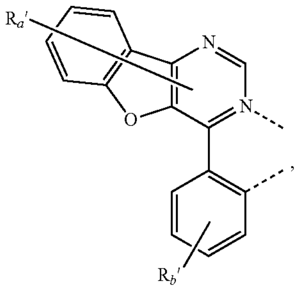
,
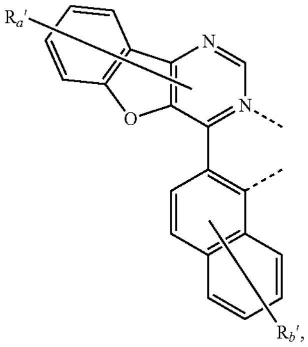
,
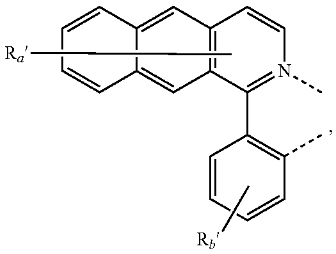
,
-continued
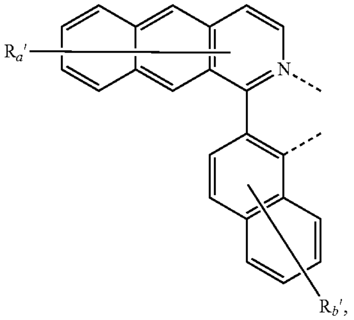
,
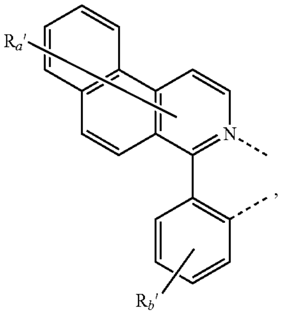
,
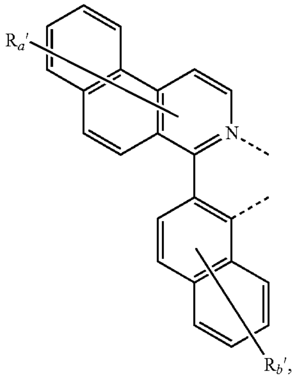
,
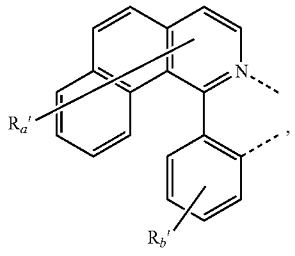
,
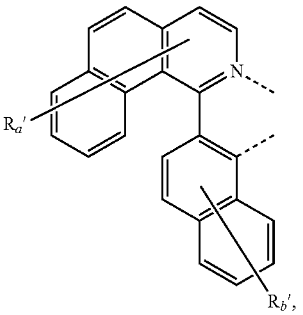
, -continued
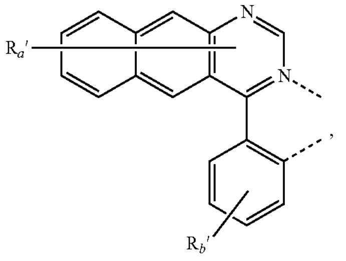
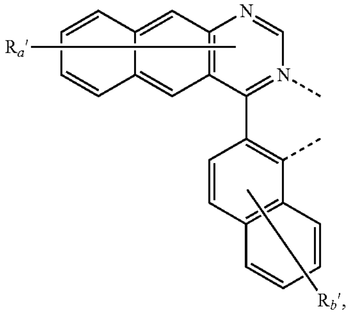
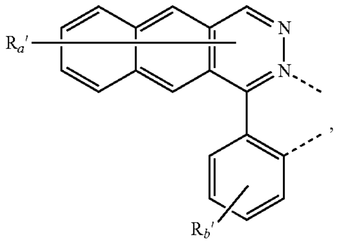
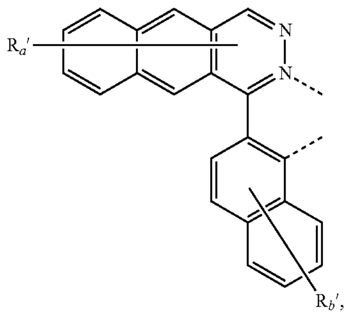
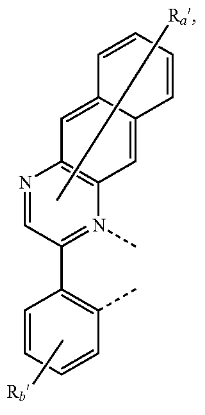
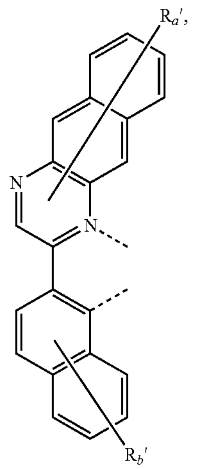
-continued
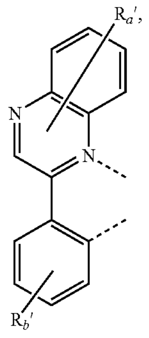
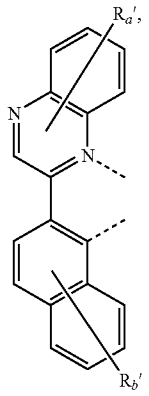
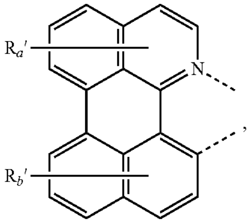
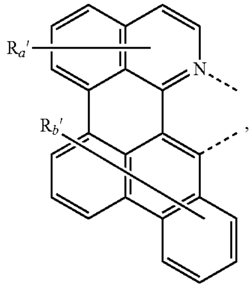
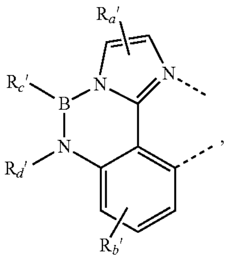
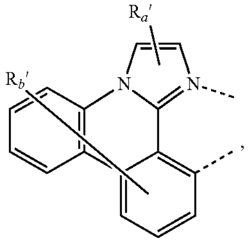
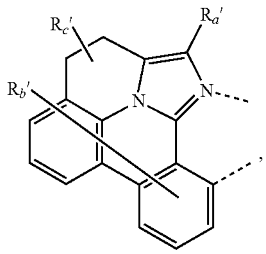
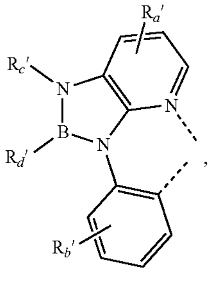
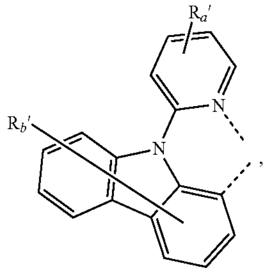
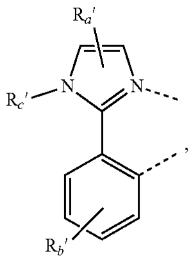

-continued
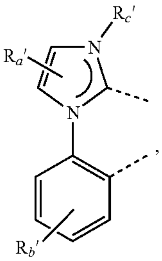
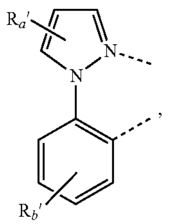
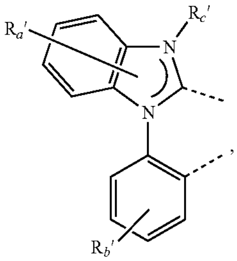
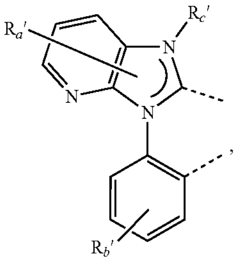
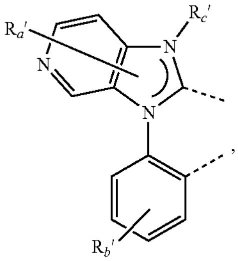
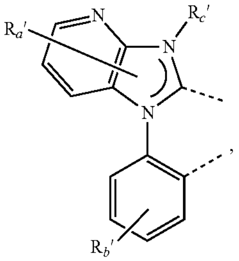
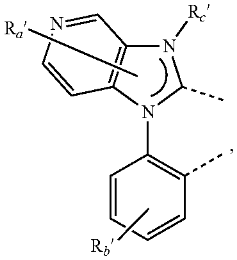
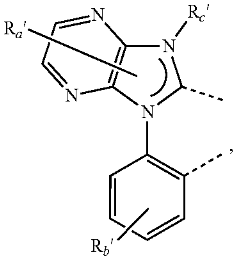
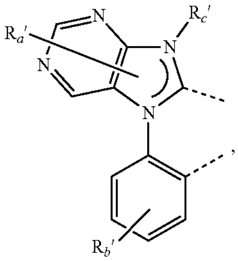
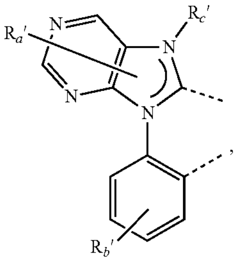
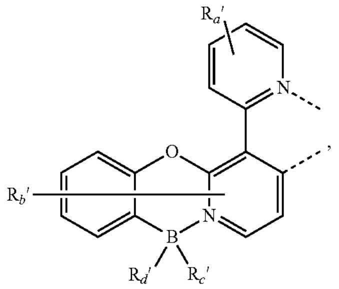
-continued
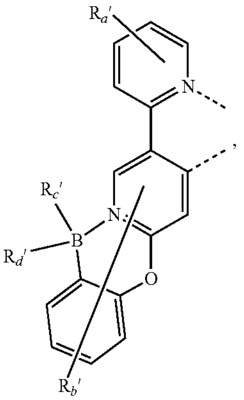
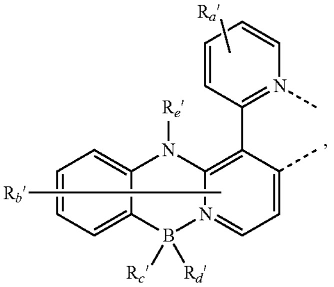
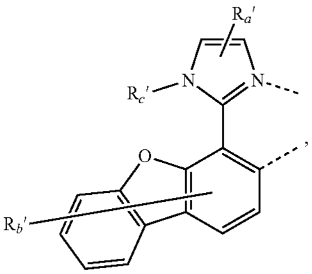
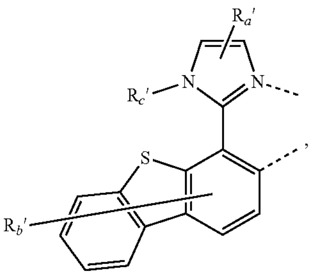
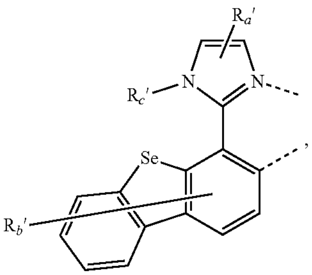

-continued
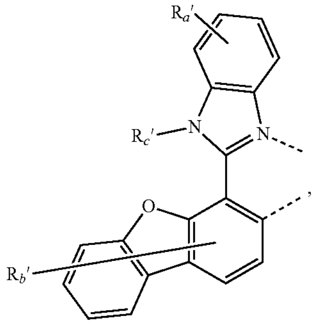
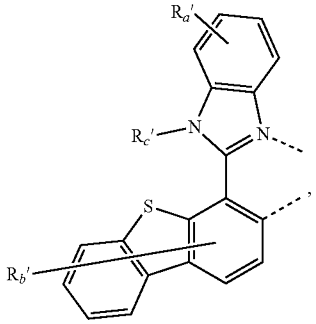
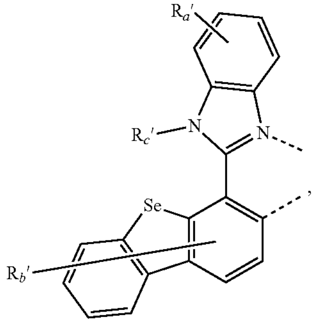
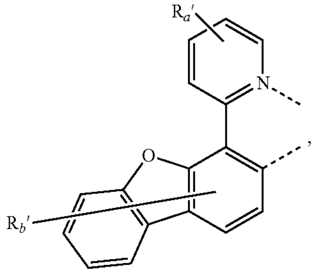
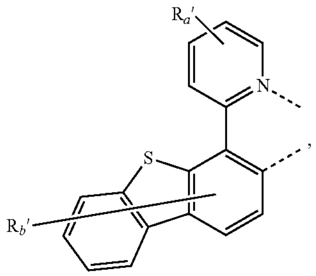
-continued
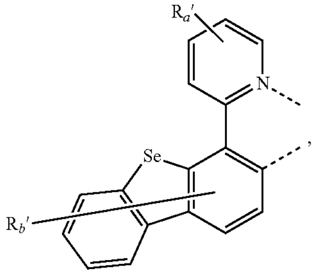
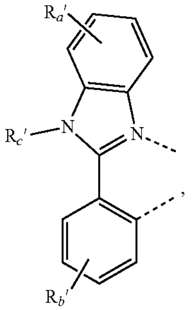
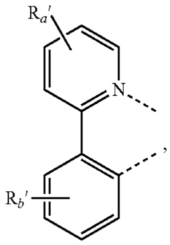
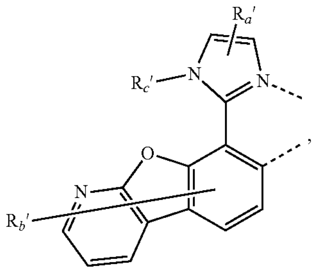
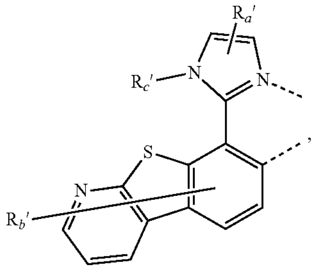
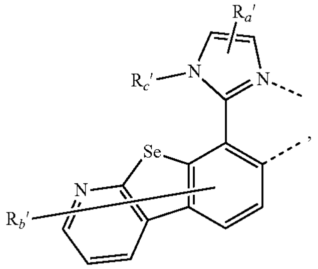
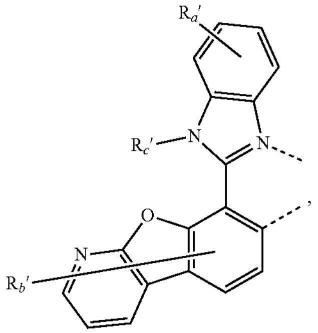

-continued
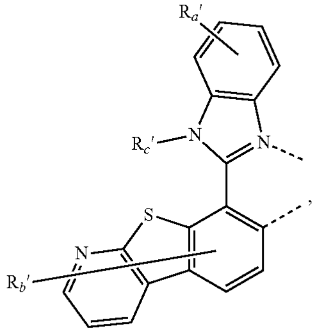
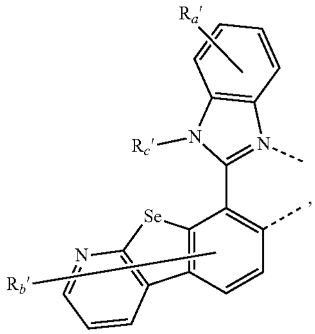
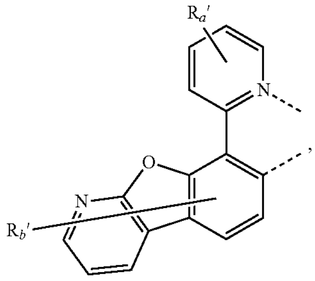
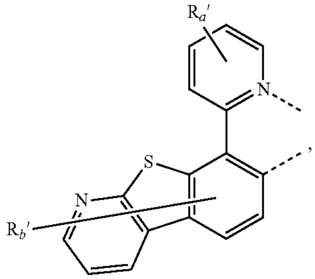
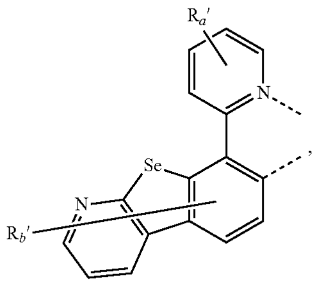
-continued
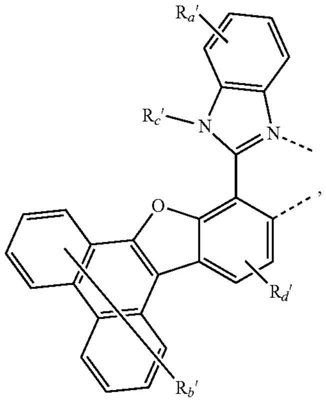
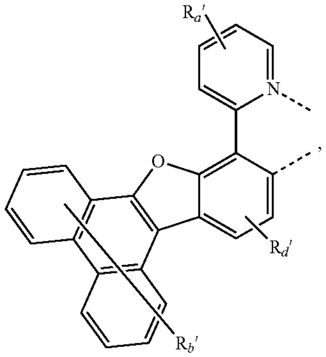
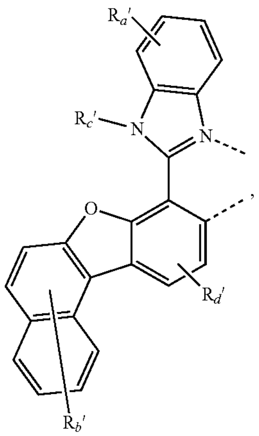
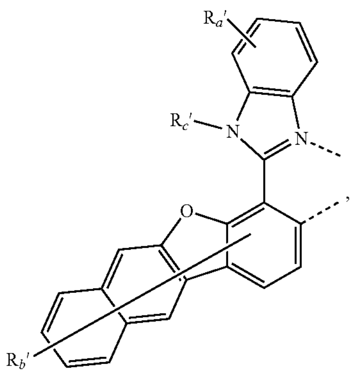

-continued
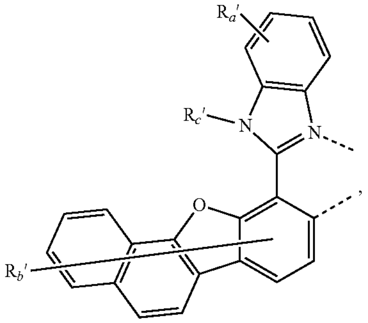
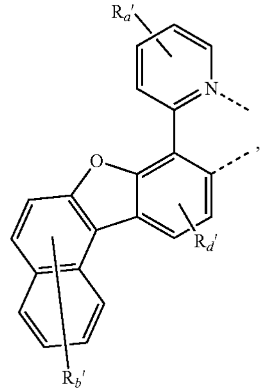
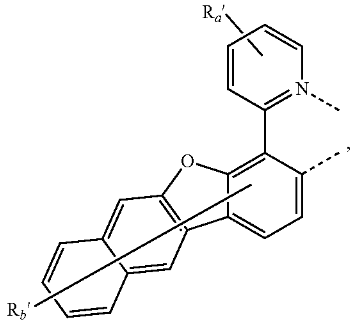
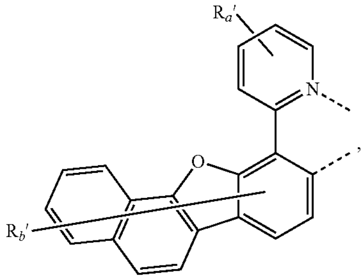
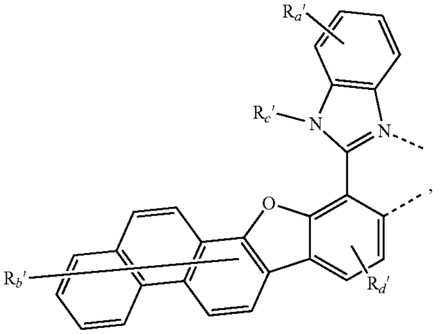
-continued
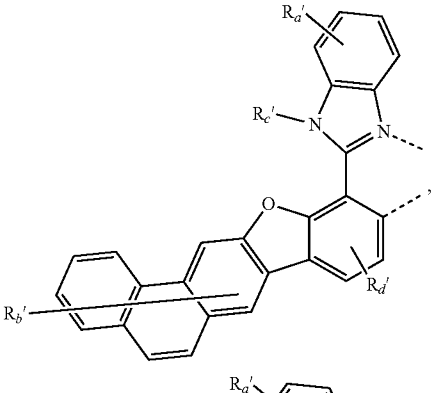
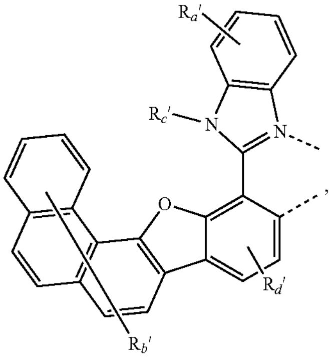
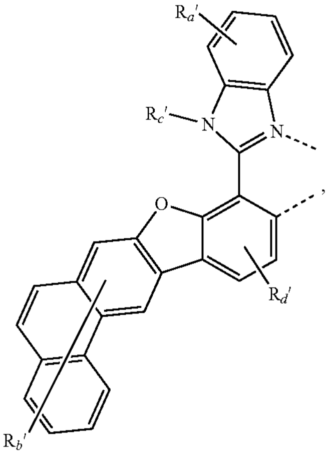
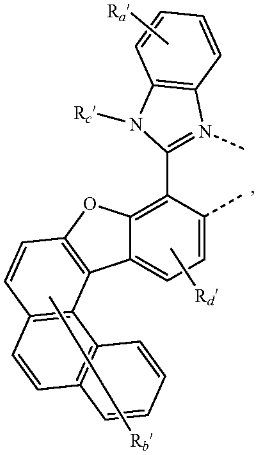

-continued
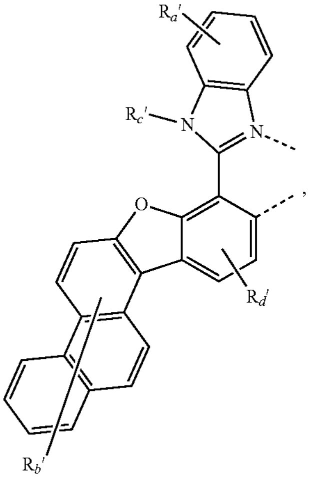
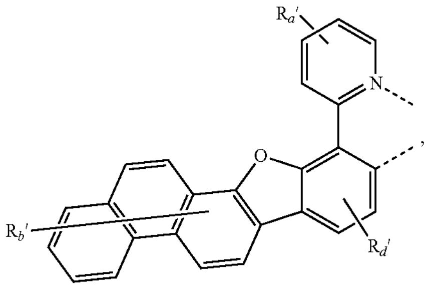
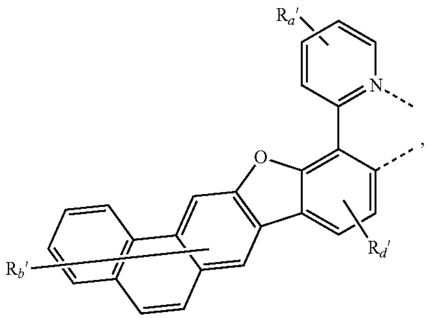
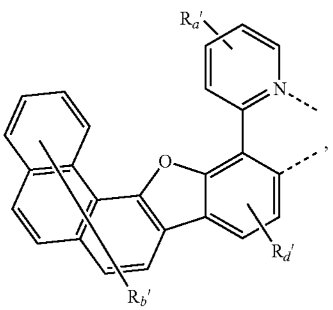
-continued
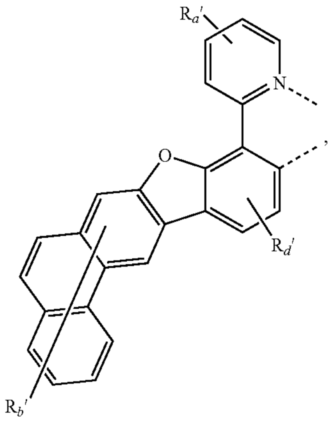
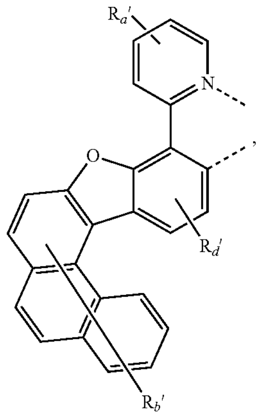
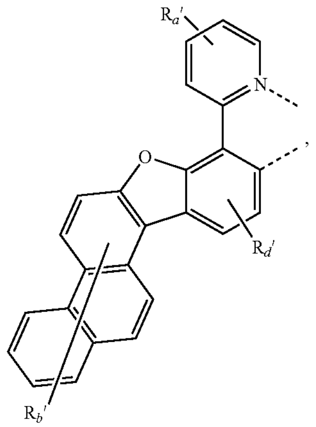
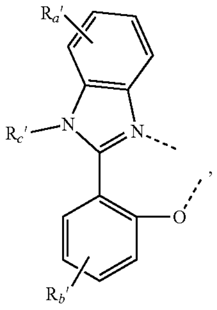
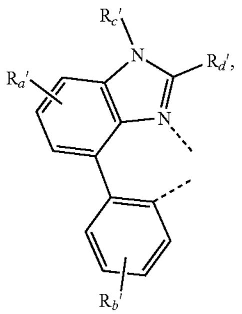
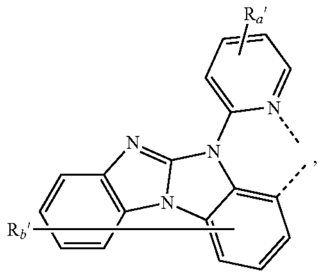

-continued

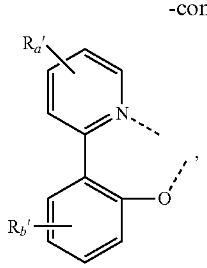

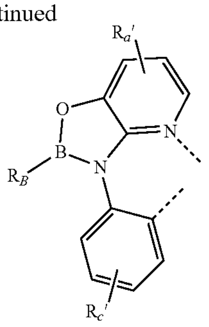

,

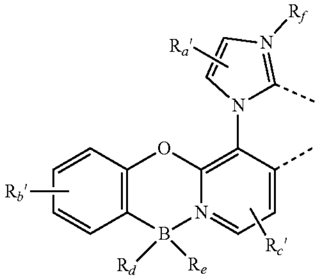

, and

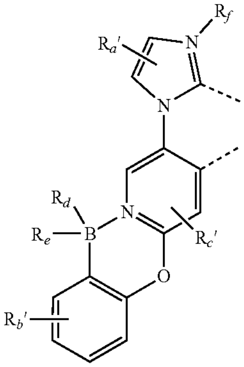

;

wherein $R_a'$, $R_b'$, $R_c'$, $R_d'$, and $R_e'$ each independently represent zero, mono, or up to a maximum allowed substitution to its associated ring;

wherein $R_a'$, $R_b'$, $R_c'$, $R_d'$, and $R_e'$ is each independently hydrogen or a substituent selected from the group consisting of deuterium, halide, alkyl, cycloalkyl, heteroalkyl, arylalkyl, alkoxy, aryloxy, amino, silyl, germyl, boryl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, selenyl, and combinations thereof; and wherein two adjacent substituents of $R_a'$, $R_b'$, $R_c'$, $R_d'$, and $R_e'$ can be fused or joined to form a ring or form a multidentate ligand.

In further embodiments, $L_A$ can be selected from $L_{Ai}$, wherein i is an integer from 1 to 39; and $L_B$ can be selected from $L_{Bk}$, wherein k is an integer from 1 to 561, wherein:

when the compound has formula $Ir(L_{Ai})_3$, the compound is selected from the group consisting of $Ir(L_{A1})_3$ to $Ir(L_{A39})_3$;

when the compound has formula $Ir(L_{Ai})(L_{Bk})_2$, the compound is selected from the group consisting of $Ir(L_{A1})(L_{B1})_2$ to $Ir(L_{A39})(L_{B561})_2$;

when the compound has formula $Ir(L_{Ai})_2(L_{Bk})$, the compound is selected from the group consisting of $Ir(L_{A1})_2(L_{B1})$ to $Ir(L_{A39})_2(L_{B561})$;

when the compound has formula $Ir(L_{Ai})_2(L_{Cj-I})$, the compound is selected from the group consisting of $Ir(L_{A1})_2(L_{C1-I})$ to $Ir(L_{A39})_2$ $(L_{C1416-I})$; and when the compound has formula $Ir(L_{Ai})_2(L_{Cj-II})$, the compound is selected from the group consisting of $Ir(L_{A1})_2(L_{C1-II})$ to $Ir(L_{A39})_2$ $(L_{C1416-II})$;

wherein the structures of each $L_{Ai}$ is defined as above;

wherein each $L_{Bk}$ has the structure defined as follows:

$L_{B1}$

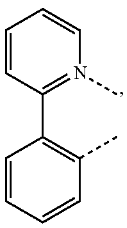

$L_{B2}$

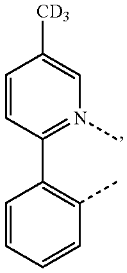

$L_{B3}$

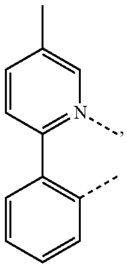

$L_{B4}$

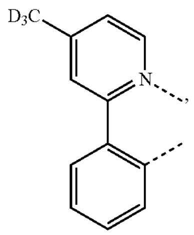

$L_{B5}$

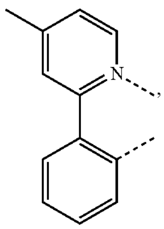

-continued
L$_{B6}$
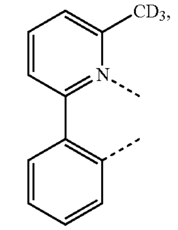
L$_{B7}$
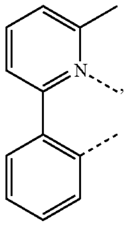
L$_{B8}$
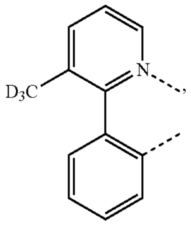
L$_{B9}$
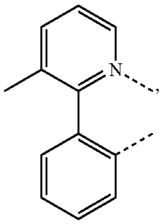
L$_{B10}$
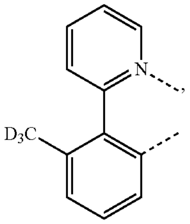
L$_{B11}$
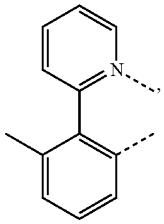
-continued
L$_{B12}$
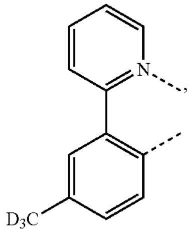
L$_{B13}$
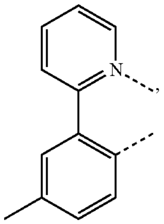
L$_{B14}$
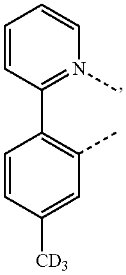
L$_{B15}$
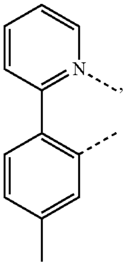
L$_{B16}$
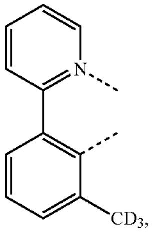
L$_{B17}$
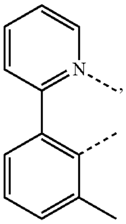

-continued
$L_{B18}$
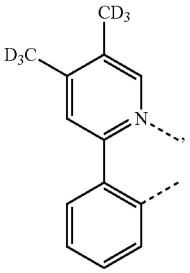
$L_{B19}$
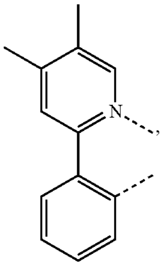
$L_{B20}$
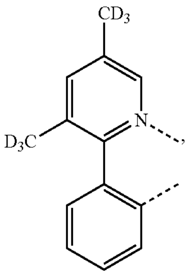
$L_{B21}$
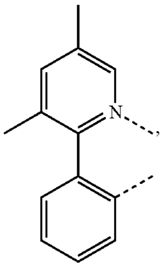
$L_{B22}$
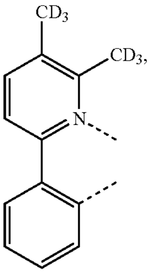
-continued
$L_{B23}$
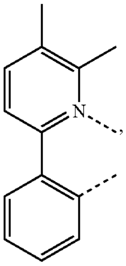
$L_{B24}$
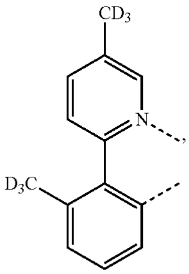
$L_{B25}$
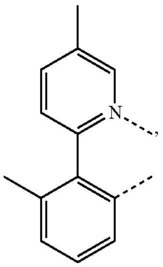
$L_{B26}$
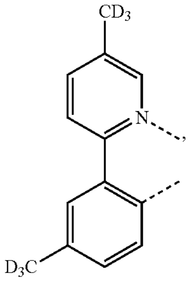
$L_{B27}$
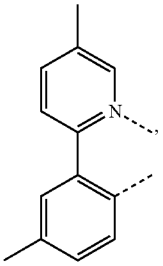

-continued
$L_{B28}$
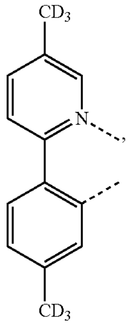
$L_{B29}$
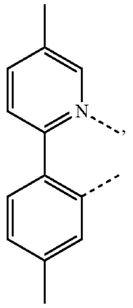
$L_{B30}$
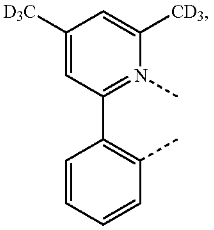
$L_{B31}$
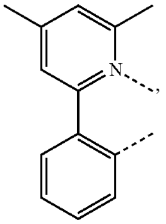
$L_{B32}$
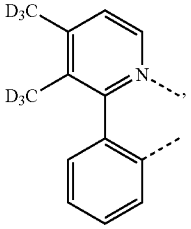
$L_{B33}$
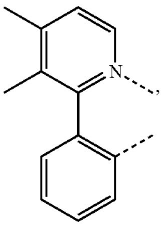
-continued
$L_{B34}$
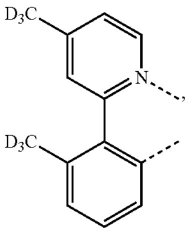
$L_{B35}$
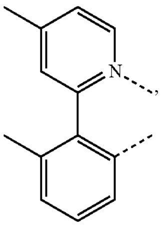
$L_{B36}$
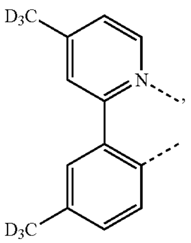
$L_{B37}$
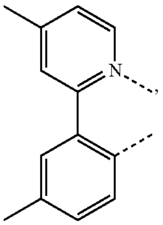
$L_{B38}$
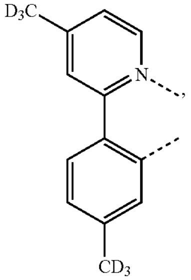
$L_{B39}$
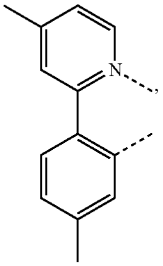

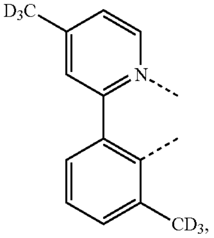
$L_{B40}$
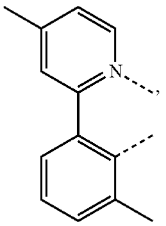
$L_{B41}$
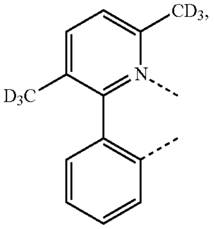
$L_{B42}$
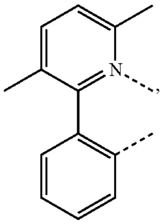
$L_{B43}$
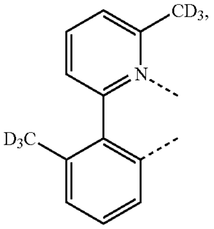
$L_{B44}$
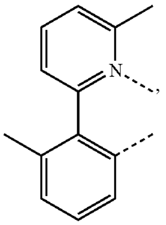
$L_{B45}$
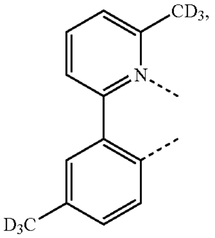
$L_{B46}$
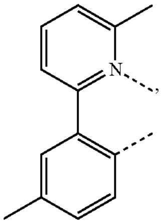
$L_{B47}$
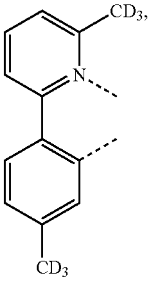
$L_{B48}$
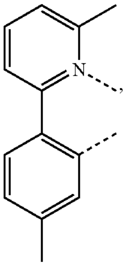
$L_{B49}$
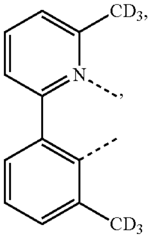
$L_{B50}$
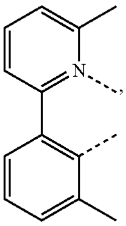
$L_{B51}$ -continued
$L_{B52}$
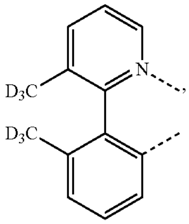
$L_{B53}$
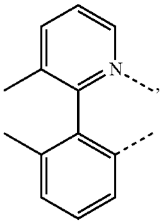
$L_{B54}$
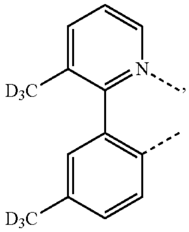
$L_{B55}$
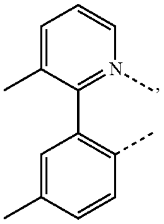
$L_{B56}$
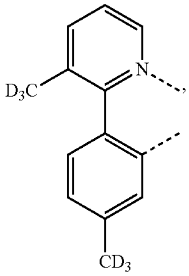
$L_{B57}$
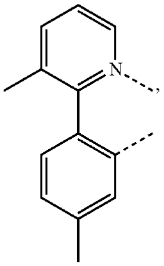
-continued
$L_{B58}$
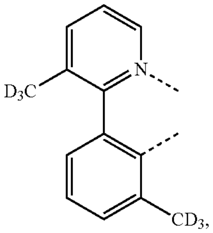
$L_{B59}$
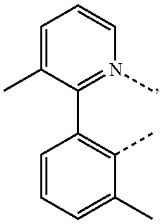
$L_{B60}$
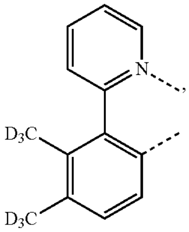
$L_{B61}$
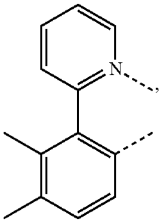
$L_{B62}$
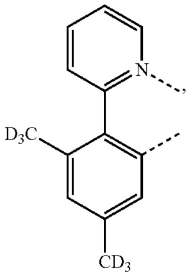
$L_{B63}$
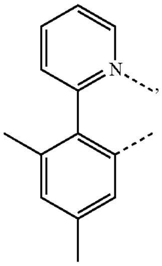

-continued
$L_{B64}$
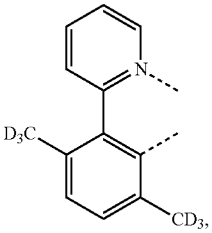
$L_{B65}$
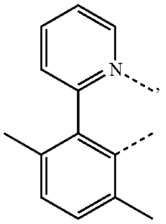
$L_{B66}$
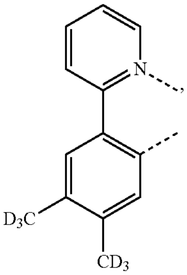
$L_{B67}$
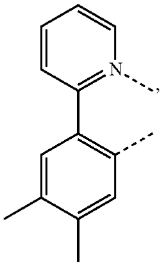
$L_{B68}$
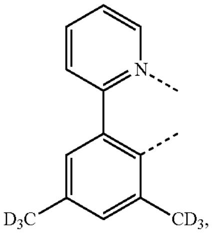
$L_{B69}$
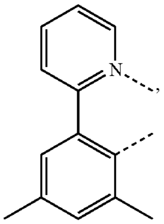
-continued
$L_{B70}$
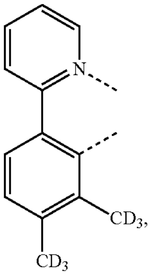
$L_{B71}$
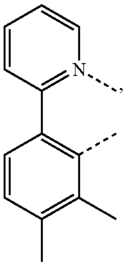
$L_{B72}$
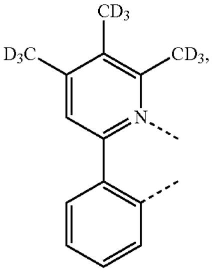
$L_{B73}$
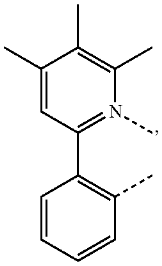
$L_{B74}$
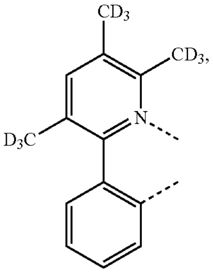

-continued
$L_{B75}$
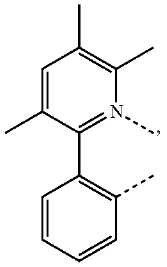
$L_{B76}$
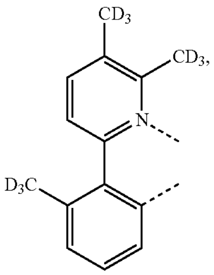
$L_{B77}$
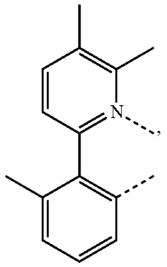
$L_{B78}$
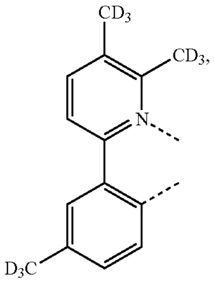
$L_{B79}$
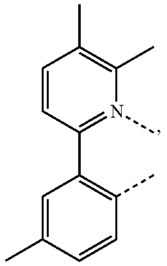
-continued
$L_{B80}$
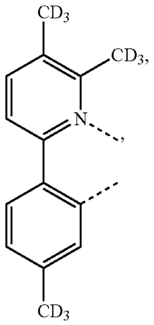
$L_{B81}$
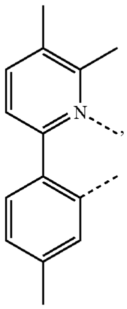
$L_{B82}$
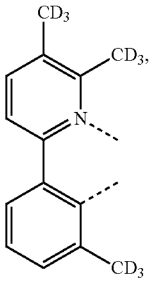
$L_{B83}$
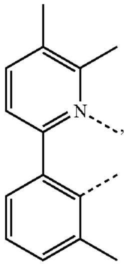
$L_{B84}$
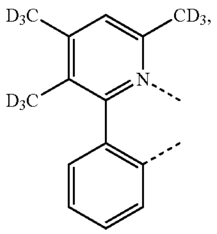

-continued
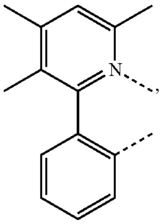
$L_{B85}$
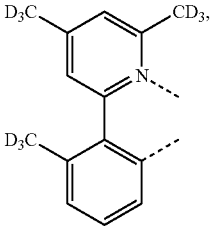
$L_{B86}$
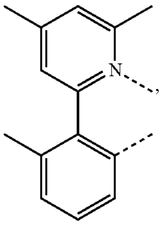
$L_{B87}$
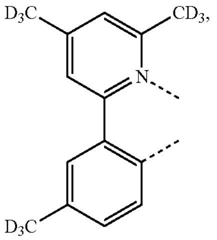
$L_{B88}$
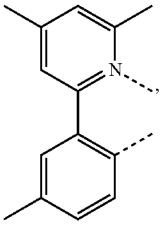
$L_{B89}$
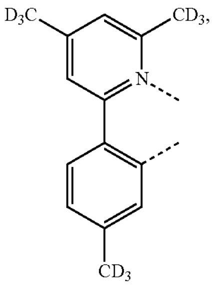
$L_{B90}$
-continued
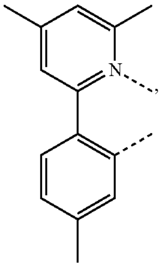
$L_{B91}$
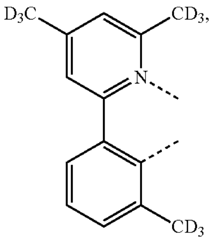
$L_{B92}$
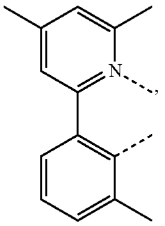
$L_{B93}$
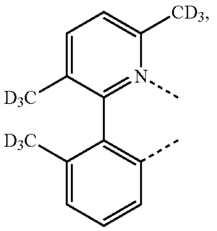
$L_{B94}$
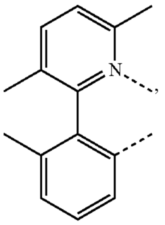
$L_{B95}$
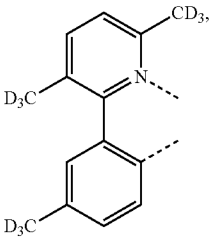
$L_{B96}$ -continued
$L_{B97}$
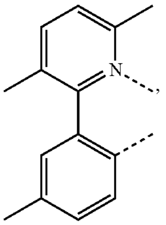
$L_{B98}$
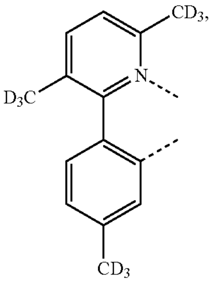
$L_{B99}$
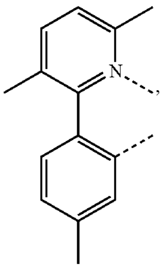
$L_{B100}$
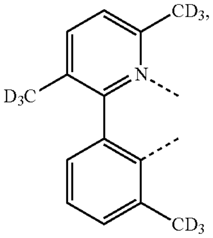
$L_{B101}$
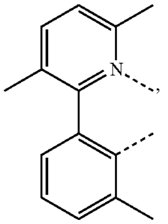
$L_{B102}$
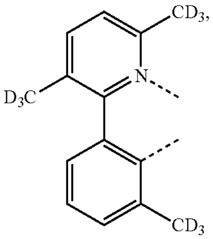
-continued
$L_{B103}$
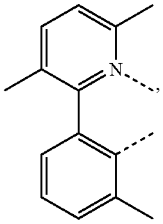
$L_{B104}$
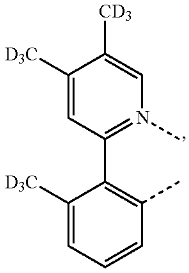
$L_{B105}$
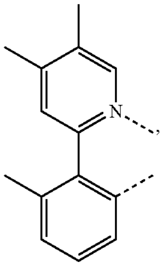
$L_{B106}$
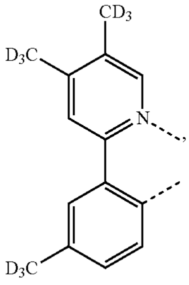
$L_{B107}$
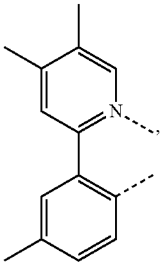

-continued
$L_{B108}$
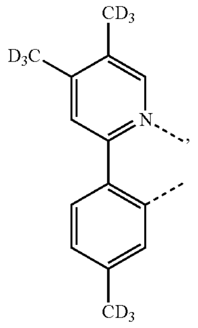
$L_{B109}$
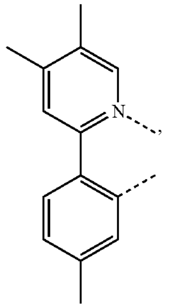
$L_{B110}$
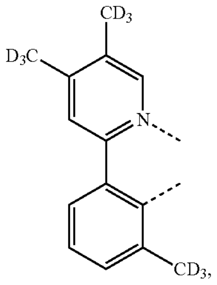
$L_{B111}$
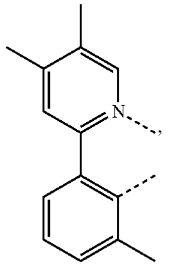
$L_{B112}$
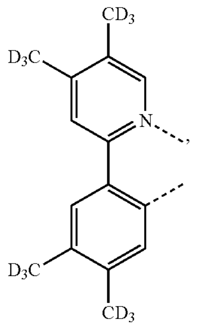
-continued
$L_{B113}$
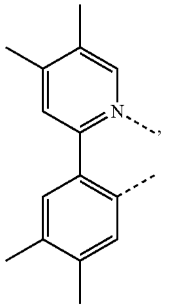
$L_{B114}$
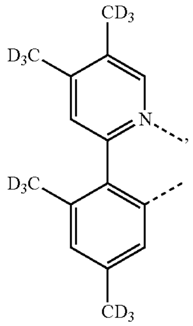
$L_{B115}$
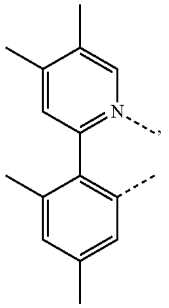
$L_{B116}$
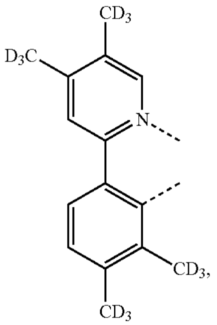
$L_{B117}$
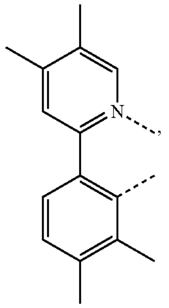

-continued
L$_{B118}$
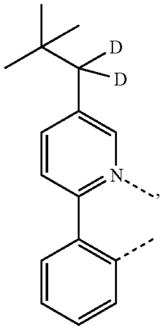
L$_{B119}$
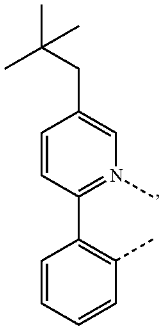
L$_{B120}$
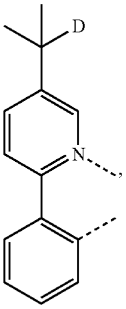
L$_{B121}$
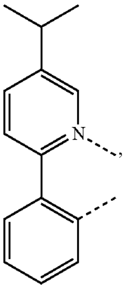
L$_{B122}$
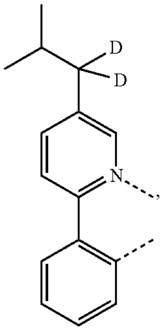
-continued
L$_{B123}$
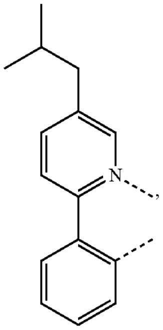
L$_{B124}$
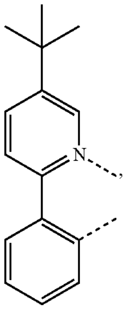
L$_{B125}$
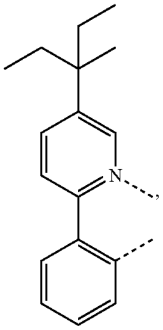
L$_{B126}$
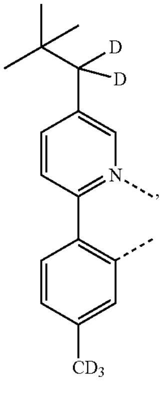

-continued
$L_{B127}$
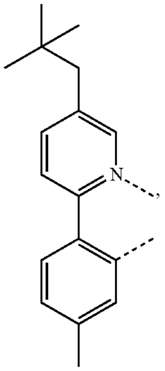
$L_{B128}$
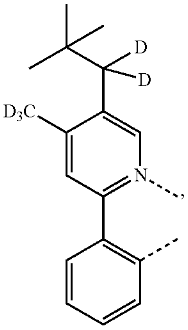
$L_{B129}$
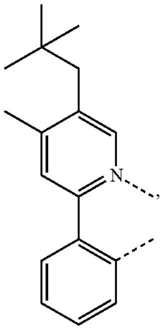
$L_{B130}$
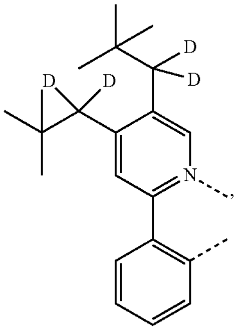
-continued
$L_{B131}$
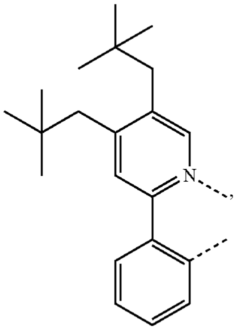
$L_{B132}$
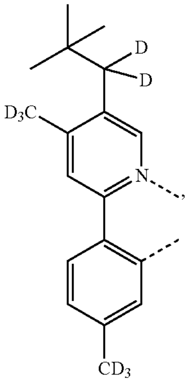
$L_{B133}$
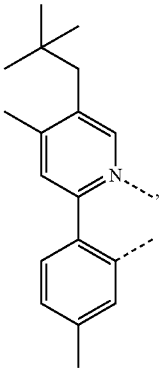
$L_{B134}$
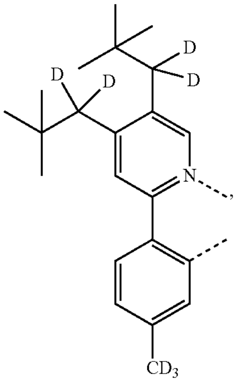

-continued
$L_{B135}$
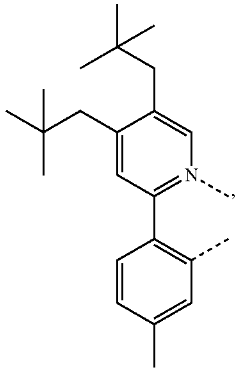
$L_{B136}$
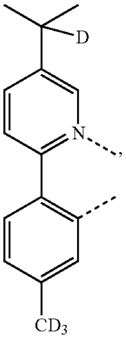
$L_{B137}$
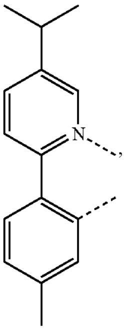
$L_{B138}$
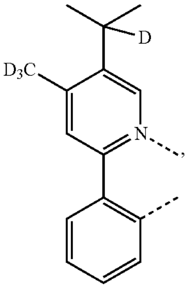
-continued
$L_{B139}$
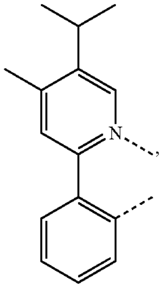
$L_{B140}$
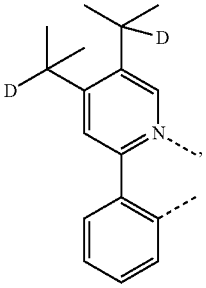
$L_{B141}$
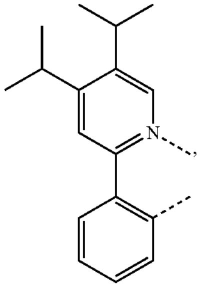
$L_{B142}$
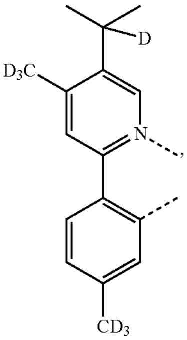
$L_{B143}$
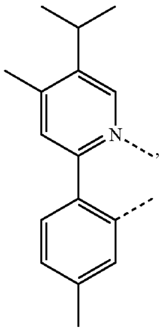

-continued
$L_{B144}$
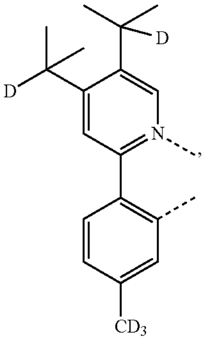
$L_{B145}$
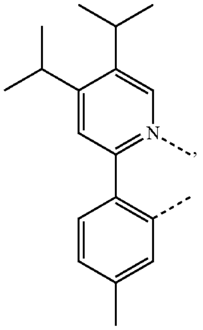
$L_{B146}$
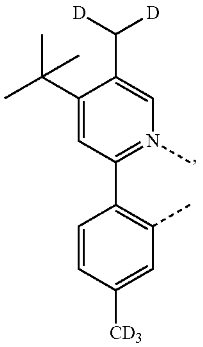
$L_{B147}$
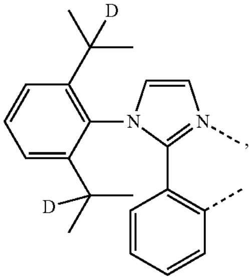
$L_{B148}$
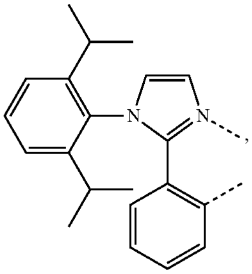
-continued
$L_{B149}$
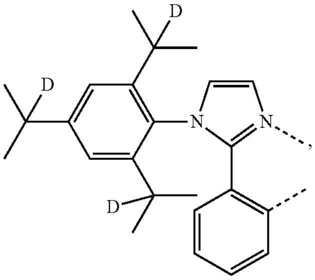
$L_{B150}$
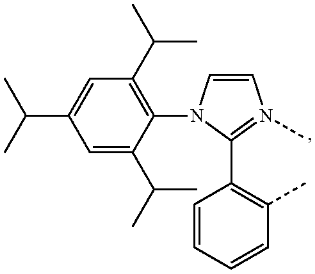
$L_{B151}$
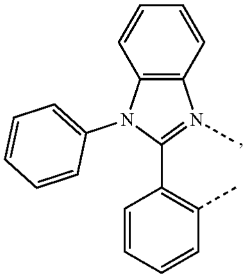
$L_{B152}$
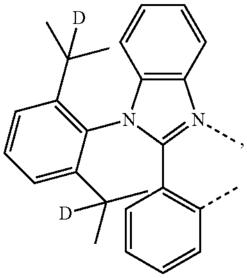
$L_{B153}$
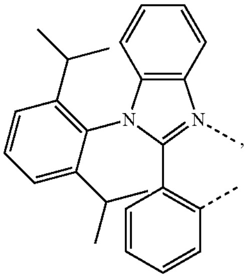

-continued
L$_{B154}$
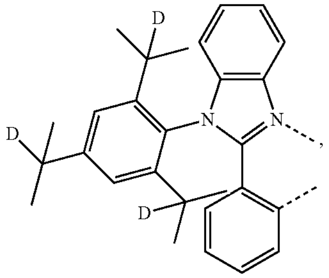
L$_{B155}$
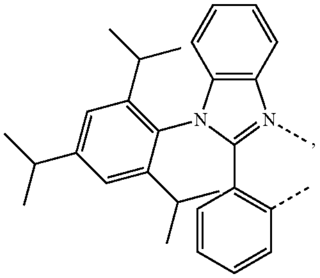
L$_{B156}$
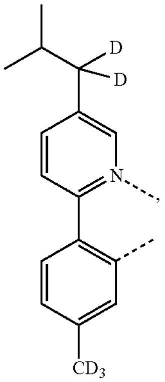
L$_{B157}$
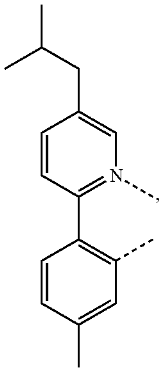
-continued
L$_{B158}$
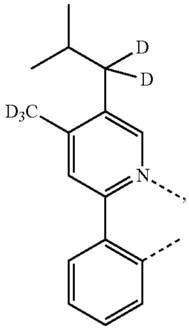
L$_{B159}$
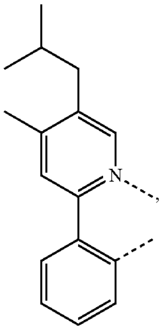
L$_{B160}$
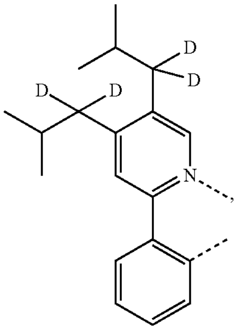
L$_{B161}$
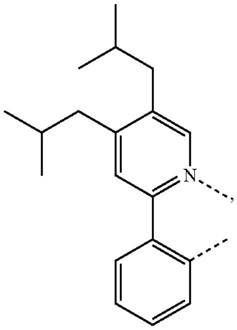

-continued
$L_{B162}$
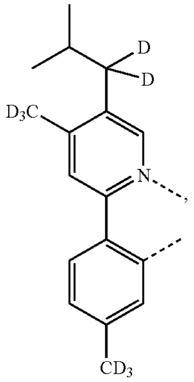
$L_{B163}$
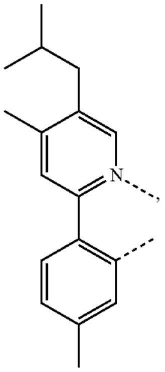
$L_{B164}$
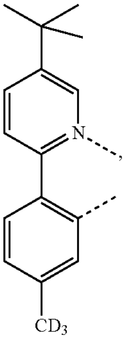
$L_{B165}$
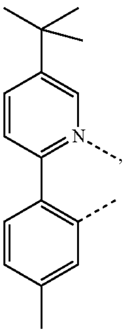
-continued
$L_{B166}$
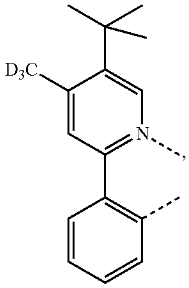
$L_{B167}$
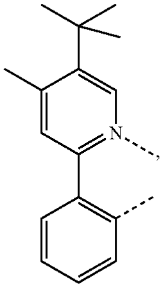
$L_{B168}$
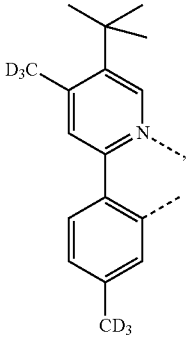
$L_{B169}$
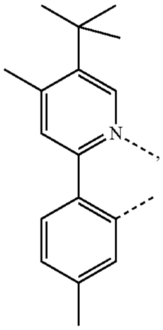

-continued
$L_{B170}$
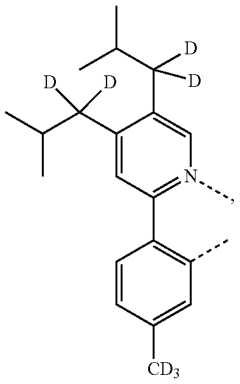
$L_{B171}$
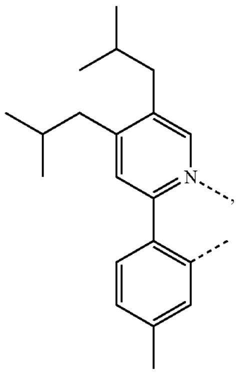
$L_{B172}$
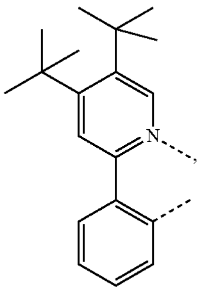
$L_{B173}$
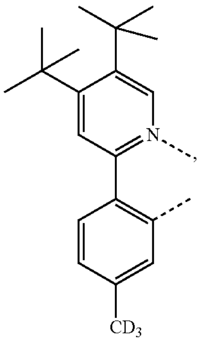
-continued
$L_{B174}$
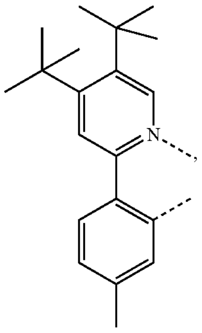
$L_{B175}$
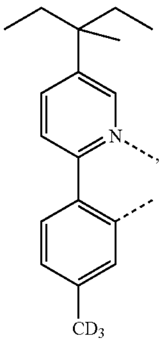
$L_{B176}$
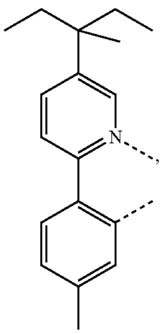
$L_{B177}$
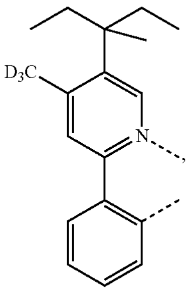
$L_{B178}$
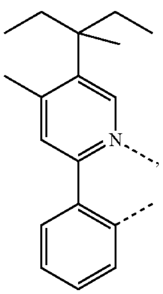

-continued
$L_{B179}$
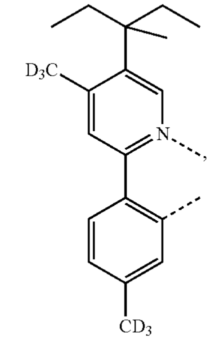
$L_{B180}$
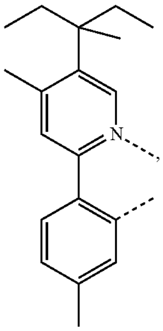
$L_{B181}$
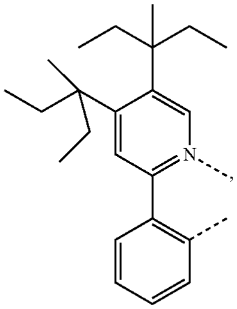
$L_{B182}$
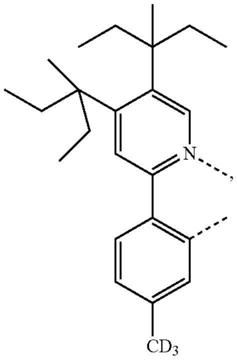
-continued
$L_{B183}$
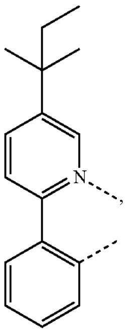
$L_{B184}$
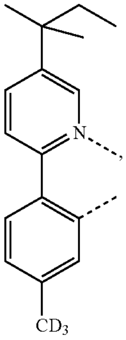
$L_{B185}$
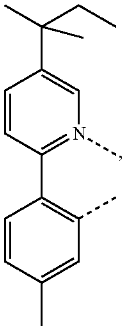
$L_{B186}$
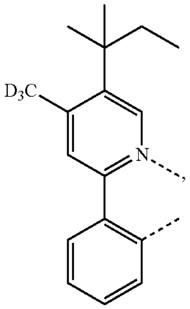

$L_{B187}$
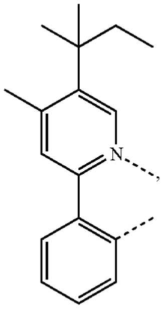
$L_{B188}$
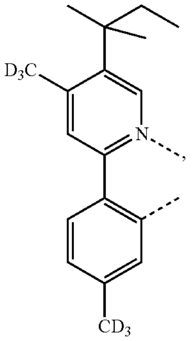
$L_{B189}$
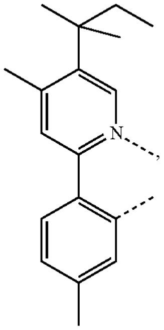
$L_{B190}$
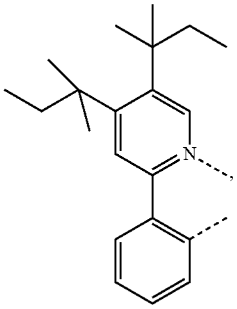
$L_{B191}$
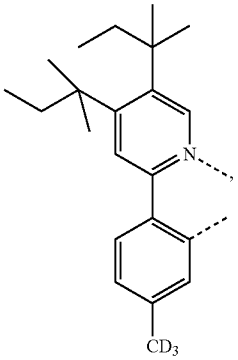
$L_{B192}$
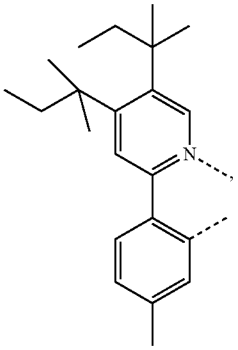
$L_{B193}$
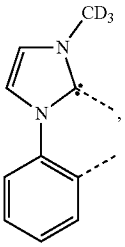
$L_{B194}$
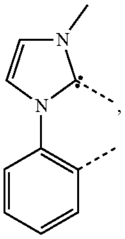
$L_{B195}$
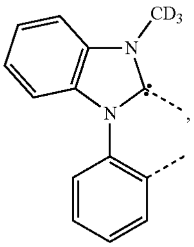

-continued
$L_{B196}$
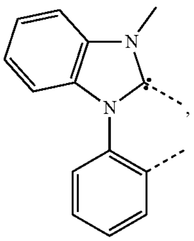
$L_{B197}$
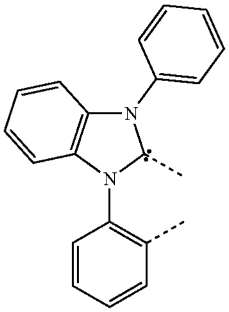
$L_{B198}$
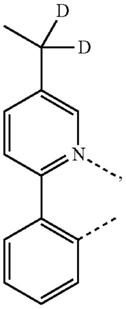
$L_{B199}$
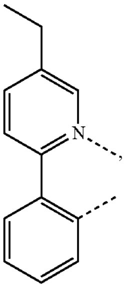
$L_{B200}$
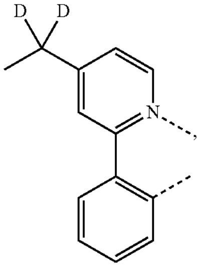
-continued
$L_{B201}$
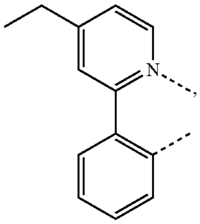
$L_{B202}$
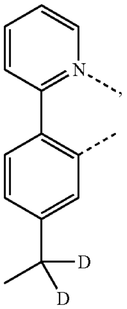
$L_{B203}$
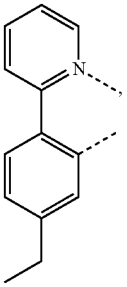
$L_{B204}$
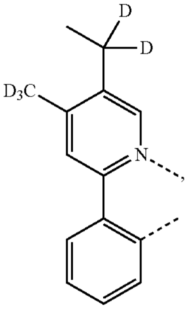
$L_{B205}$
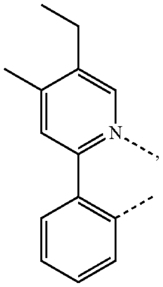

-continued
$L_{B206}$
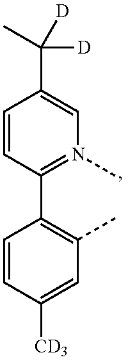
$L_{B207}$
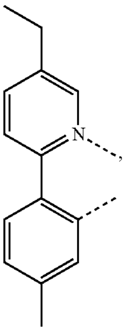
$L_{B208}$
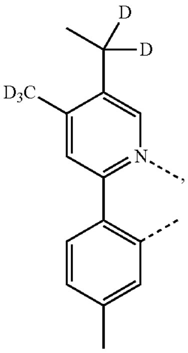
$L_{B209}$
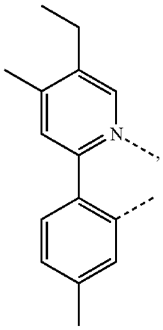
-continued
$L_{B210}$
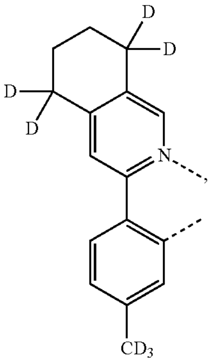
$L_{B211}$
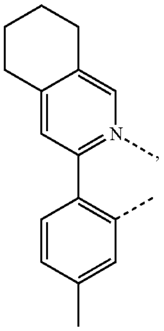
$L_{B212}$
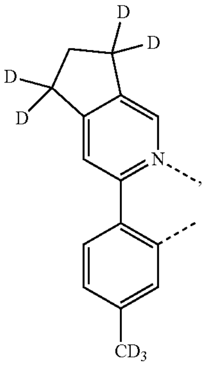
$L_{B213}$
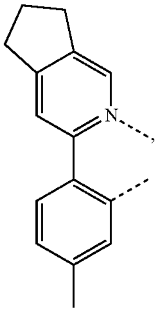

-continued
$L_{B214}$
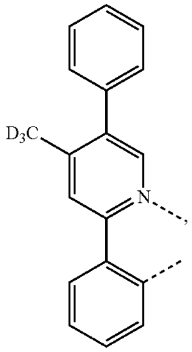
$L_{B215}$
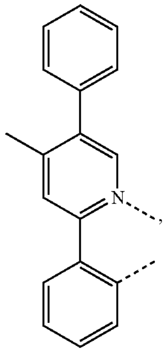
$L_{B216}$
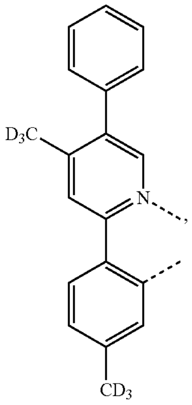
$L_{B217}$
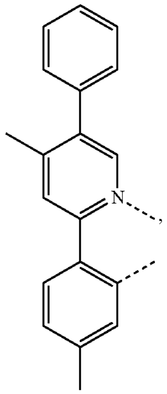
-continued
$L_{B218}$
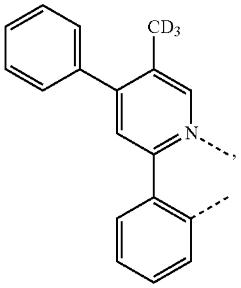
$L_{B219}$
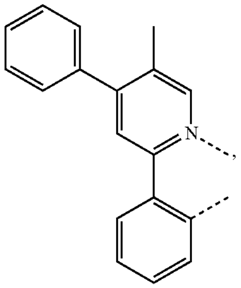
$L_{B220}$
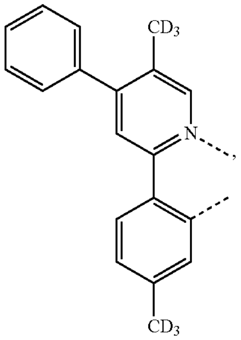
$L_{B221}$
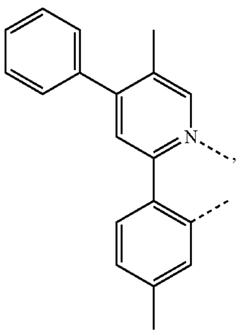

$L_{B222}$
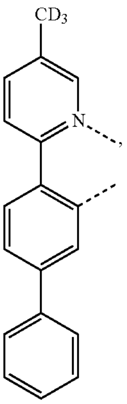
$L_{B223}$
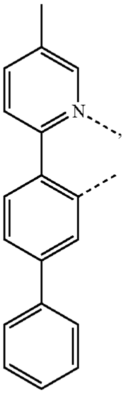
$L_{B224}$
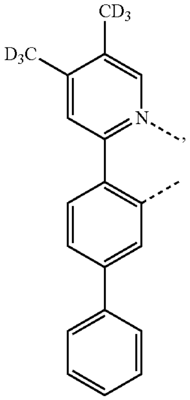
$L_{B225}$
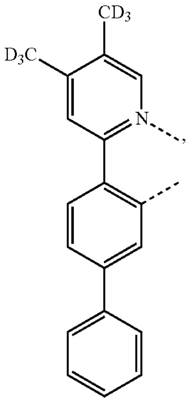
$L_{B226}$
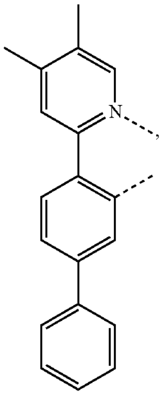
$L_{B227}$
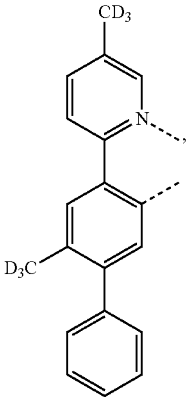
$L_{B228}$
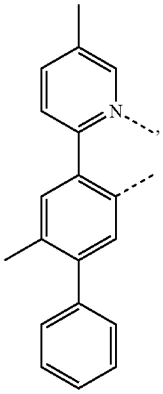
$L_{B229}$
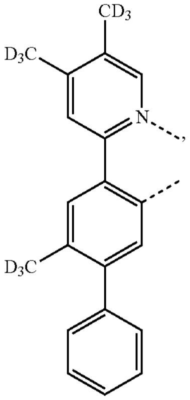

-continued
$L_{B230}$
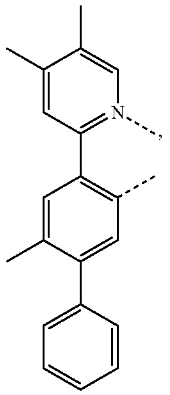
$L_{B231}$
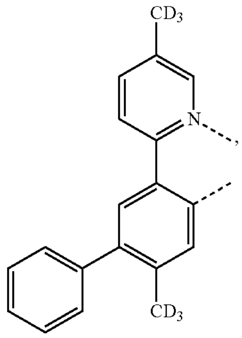
$L_{B232}$
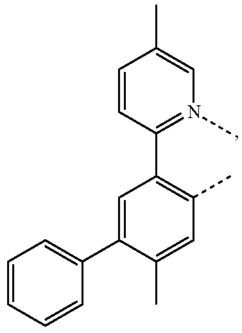
$L_{B233}$
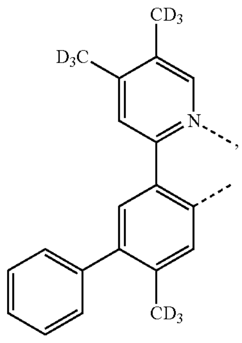
-continued
$L_{B234}$
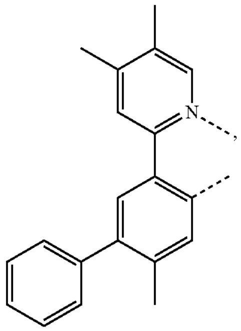
$L_{B235}$
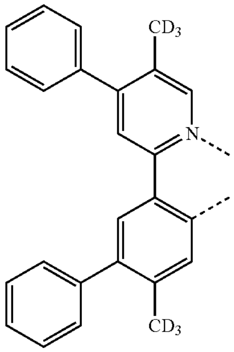
$L_{B236}$
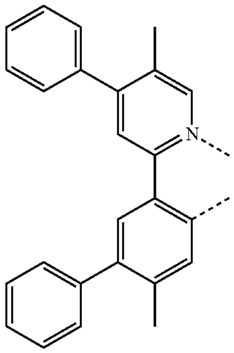
$L_{B237}$
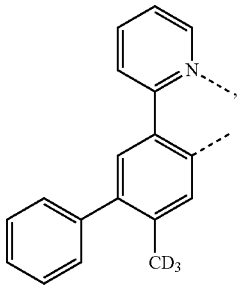
$L_{B238}$
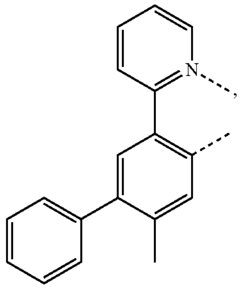

-continued
$L_{B239}$
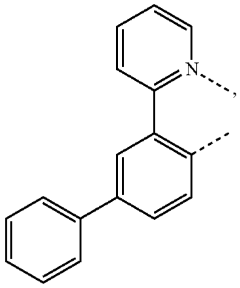
$L_{B240}$
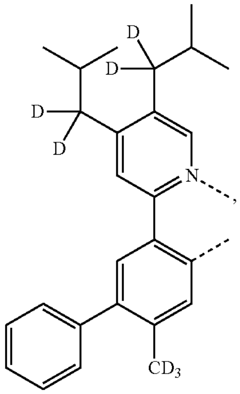
$L_{B241}$
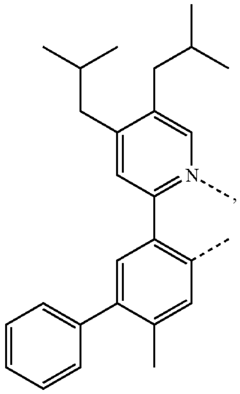
$L_{B242}$
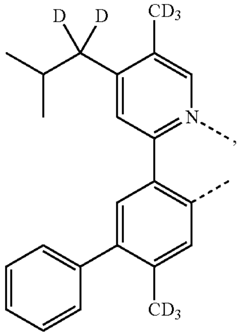
-continued
$L_{B243}$
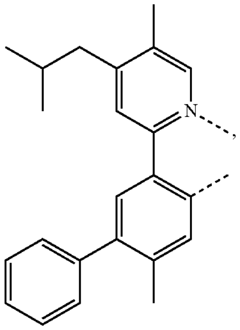
$L_{B244}$
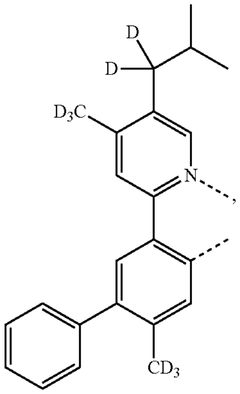
$L_{B245}$
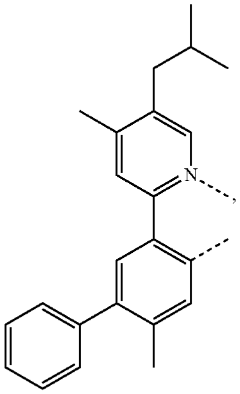
$L_{B246}$
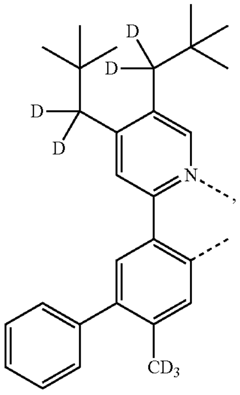

-continued
$L_{B247}$
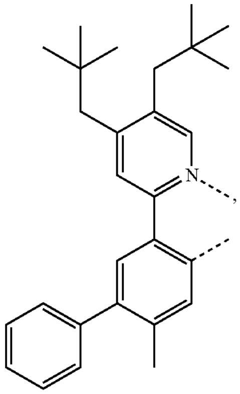
$L_{B248}$
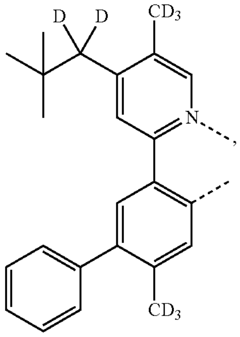
$L_{B249}$
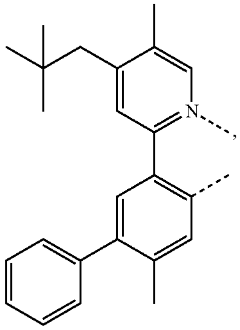
$L_{B250}$
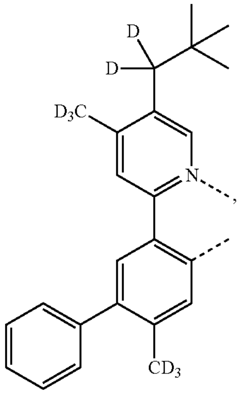
-continued
$L_{B251}$
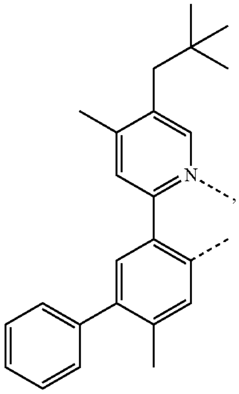
$L_{B252}$
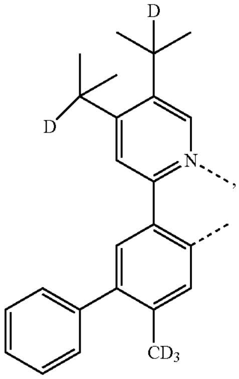
$L_{B253}$
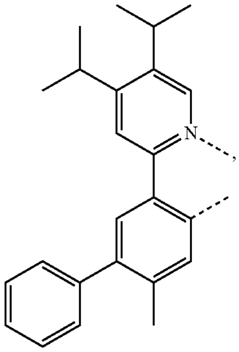
$L_{B254}$
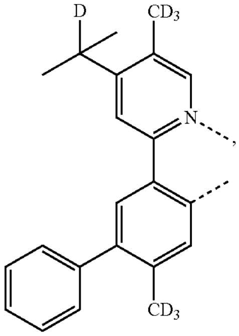

L$_{B255}$
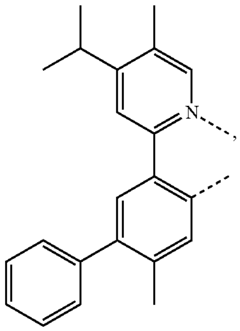
L$_{B256}$
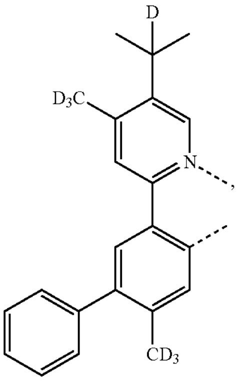
L$_{B257}$
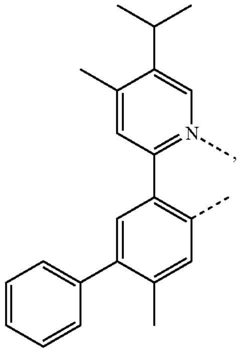
L$_{B258}$
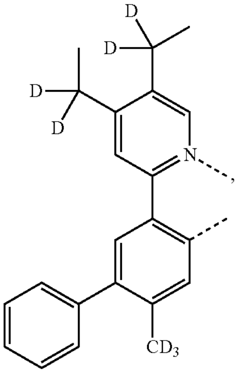
L$_{B259}$
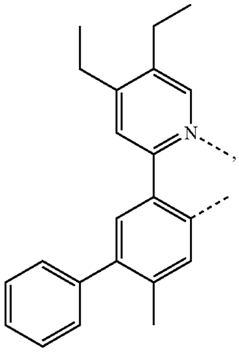
L$_{B260}$
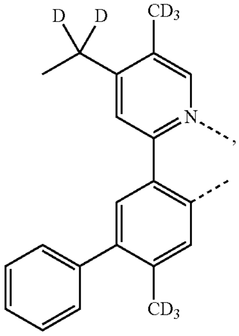
L$_{B261}$
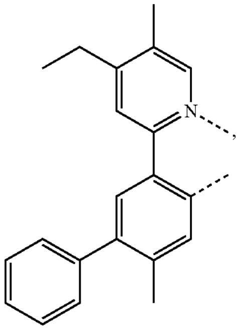
L$_{B262}$
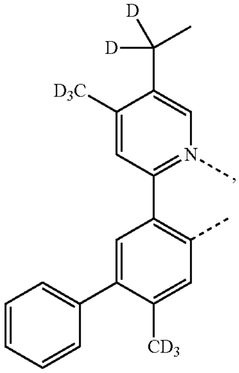

-continued
L$_{B263}$
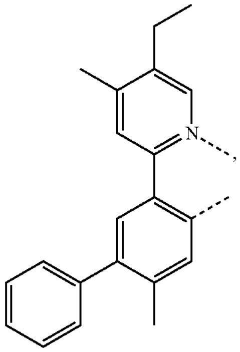
L$_{B264}$
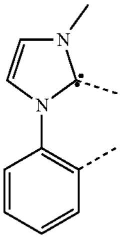
L$_{B265}$
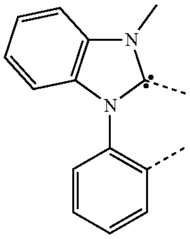
L$_{B266}$
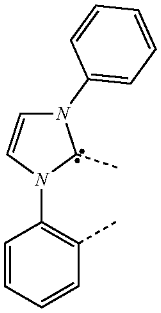
L$_{B267}$
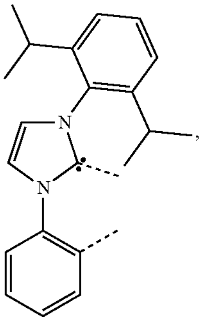
-continued
L$_{B268}$
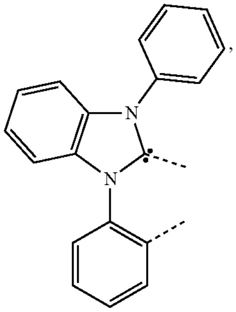
L$_{B269}$
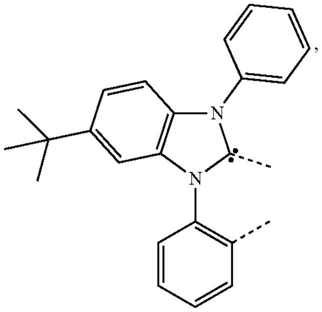
L$_{B270}$
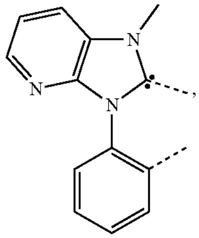
L$_{B271}$
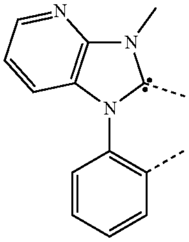
L$_{B272}$
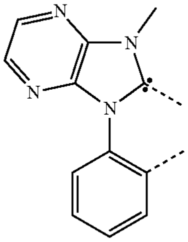

$L_{B273}$
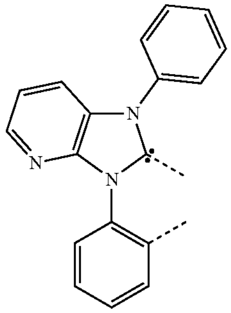
$L_{B274}$
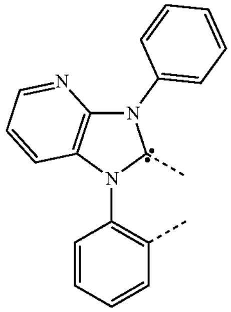
$L_{B275}$
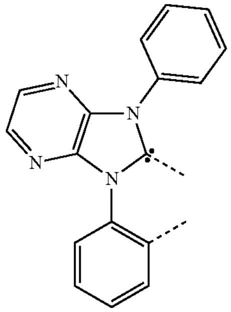
$L_{B276}$
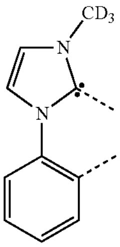
$L_{B277}$
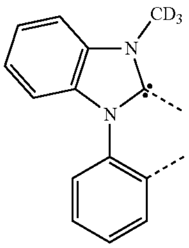
$L_{B278}$
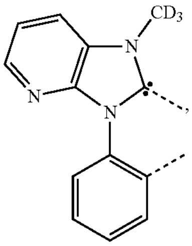
$L_{B279}$
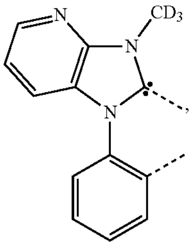
$L_{B280}$
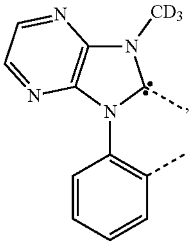
$L_{B281}$
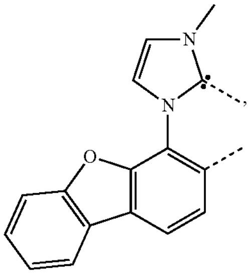
$L_{B282}$
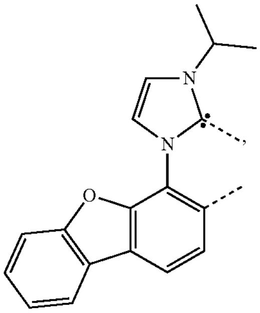

-continued
$L_{B283}$
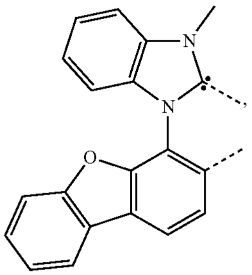
$L_{B284}$
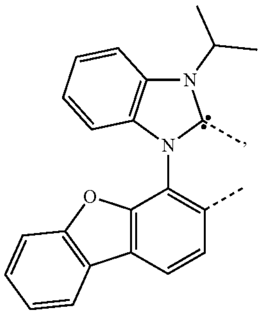
$L_{B285}$
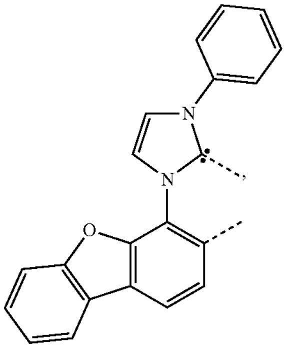
$L_{B286}$
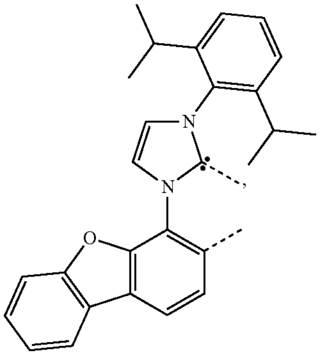
-continued
$L_{B287}$
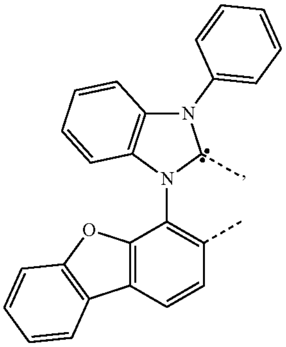
$L_{B288}$
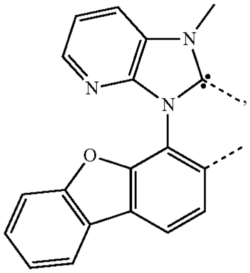
$L_{B289}$
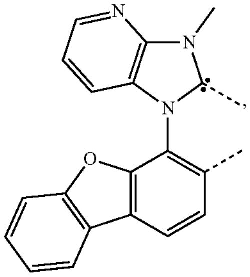
$L_{B290}$
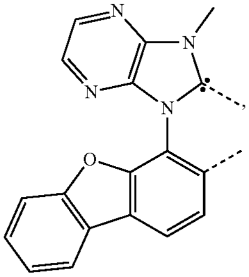
$L_{B291}$
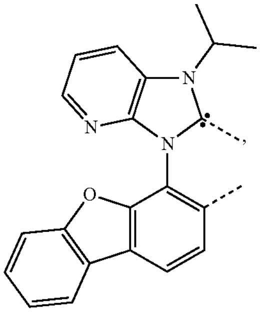

-continued
$L_{B292}$
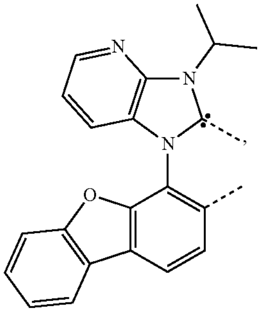
$L_{B293}$
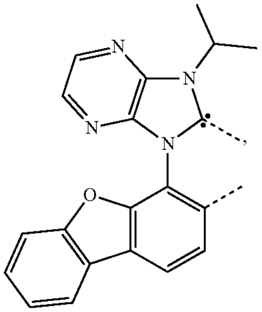
$L_{B294}$
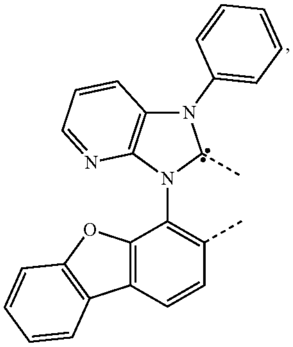
$L_{B295}$
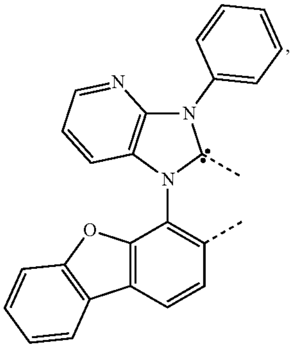
-continued
$L_{B296}$
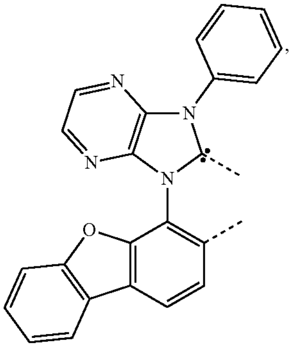
$L_{B297}$
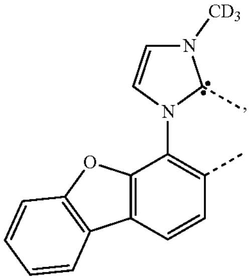
$L_{B298}$
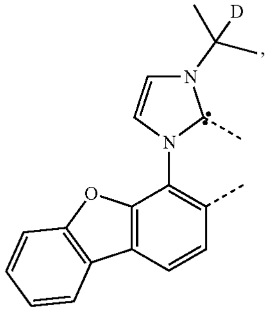
$L_{B299}$
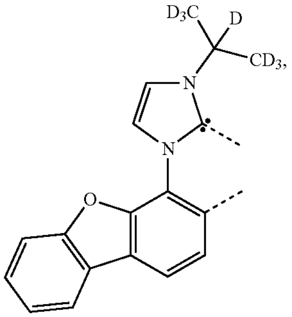
$L_{B300}$
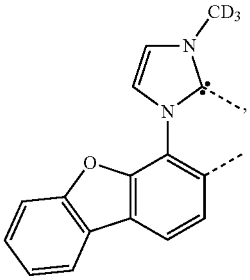

-continued
$L_{B301}$
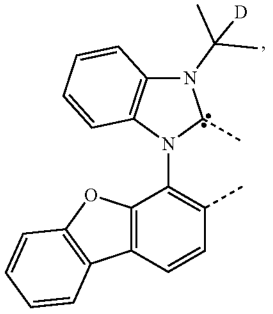
$L_{B302}$
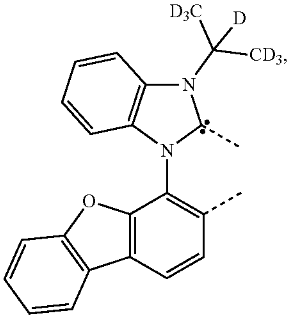
$L_{B303}$
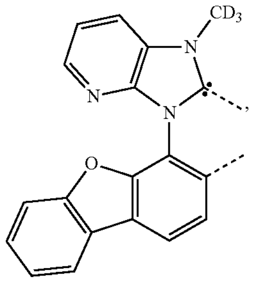
$L_{B304}$
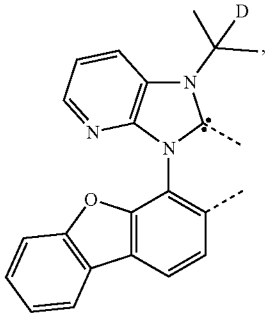
$L_{B305}$
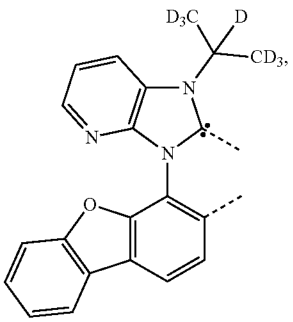
-continued
$L_{B306}$
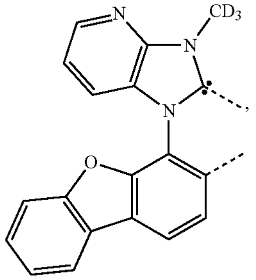
$L_{B307}$
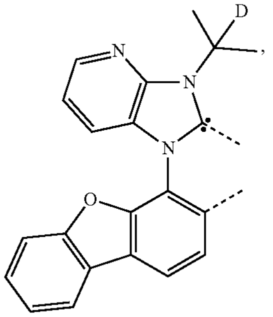
$L_{B308}$
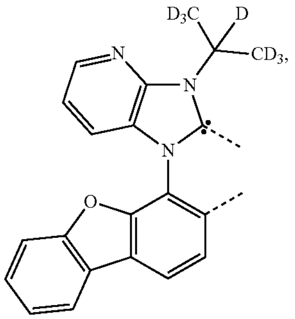
$L_{B309}$
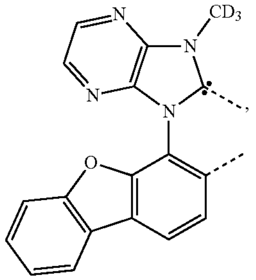
$L_{B310}$
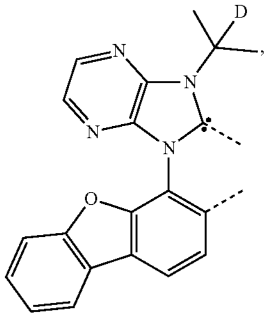

-continued
L$_{B311}$
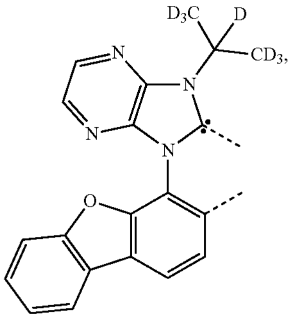
L$_{B312}$
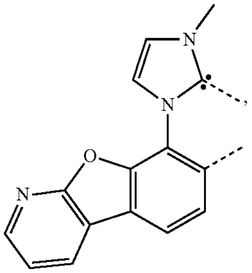
L$_{B313}$
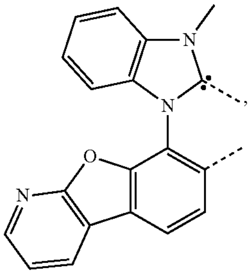
L$_{B314}$
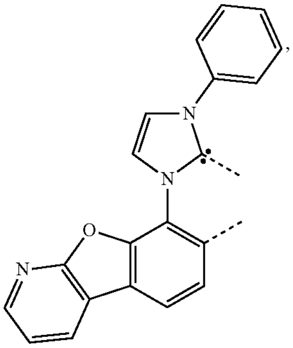
L$_{B315}$
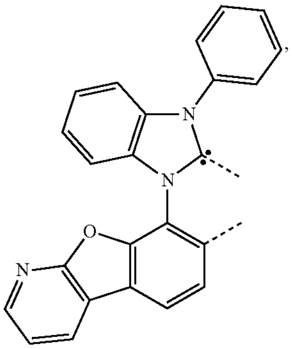
-continued
L$_{B316}$
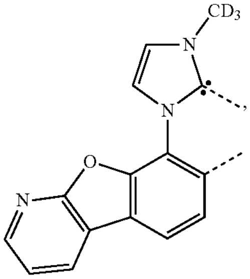
L$_{B317}$
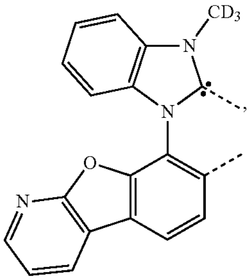
L$_{B318}$
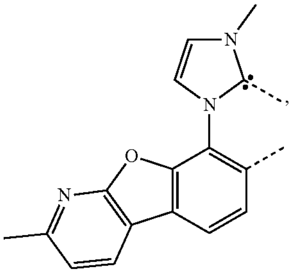
L$_{B319}$
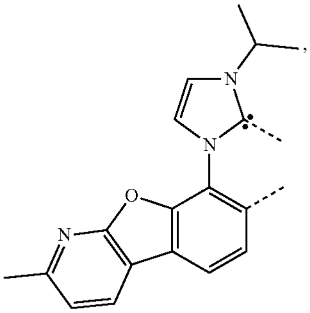
L$_{B320}$
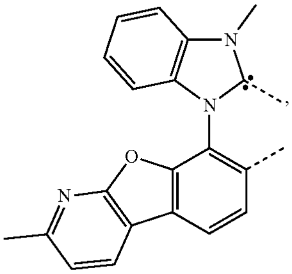

-continued
$L_{B321}$
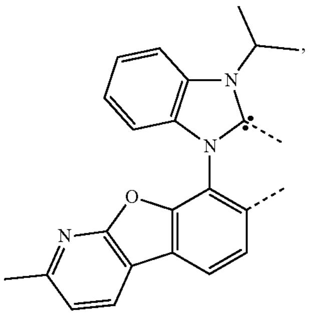
$L_{B323}$
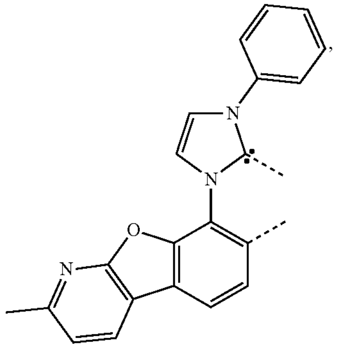
$L_{B324}$
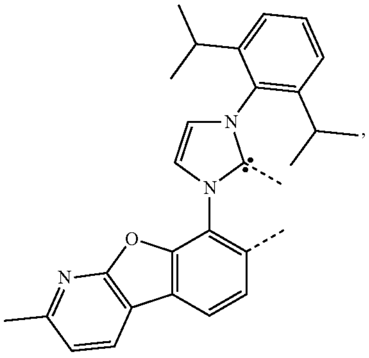
$L_{B325}$
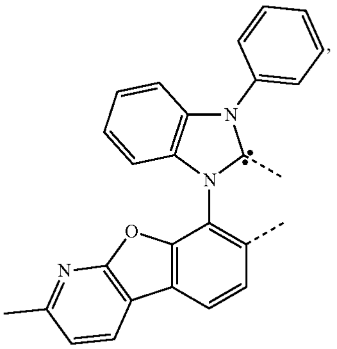
-continued
$L_{B326}$
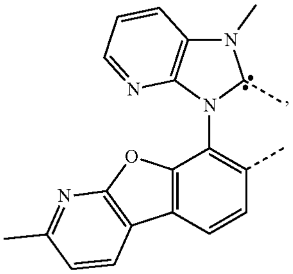
$L_{B327}$
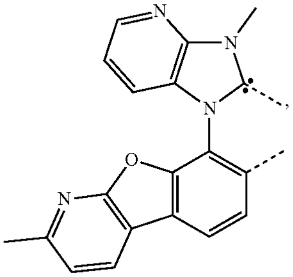
$L_{B328}$
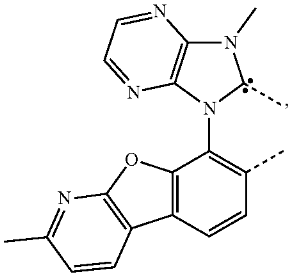
$L_{B329}$
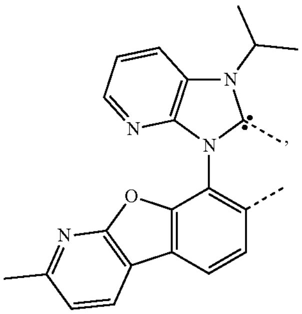
$L_{B330}$
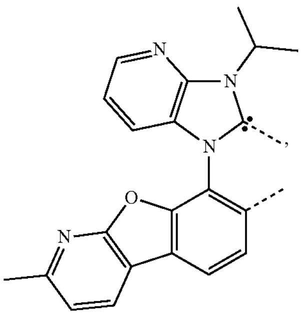

-continued
$L_{B331}$
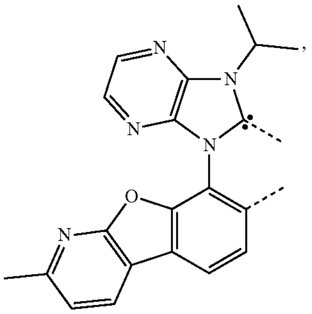
$L_{B332}$
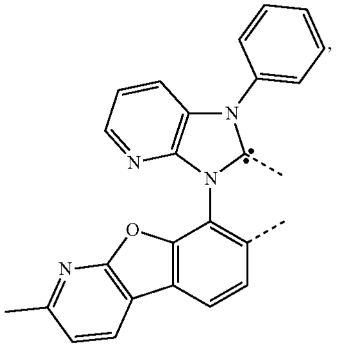
$L_{B333}$
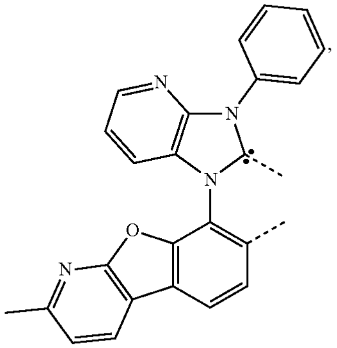
$L_{B334}$
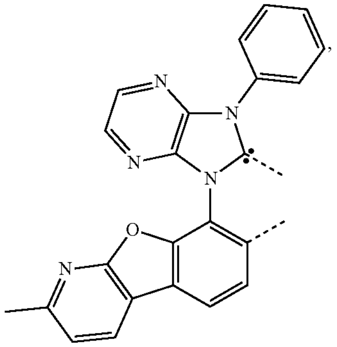
-continued
$L_{B335}$
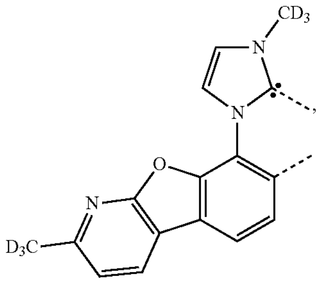
$L_{B336}$
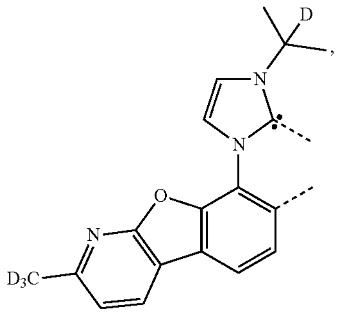
$L_{B337}$
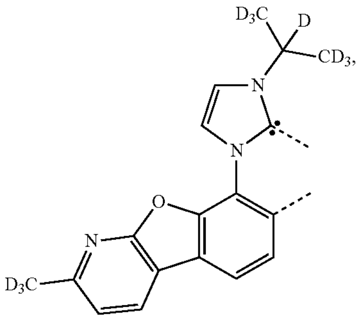
$L_{B338}$
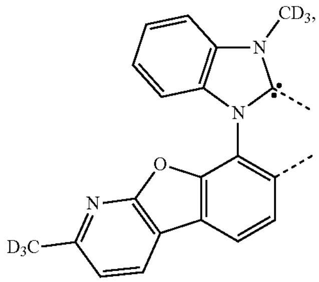
$L_{B339}$
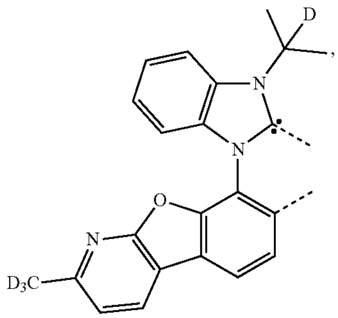

-continued
$L_{B340}$
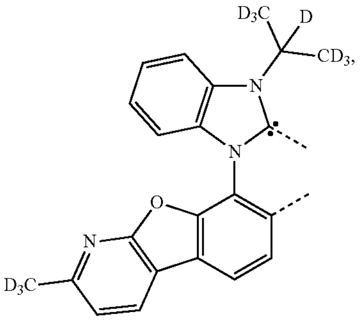
$L_{B341}$
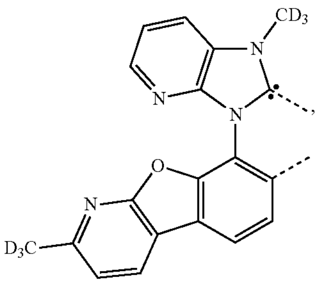
$L_{B342}$
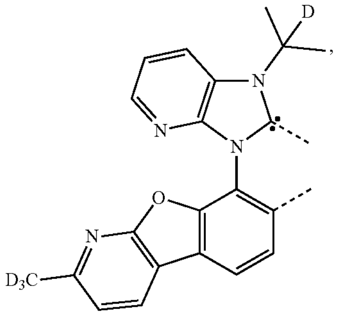
$L_{B343}$
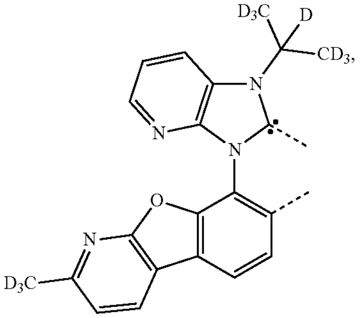
$L_{B344}$
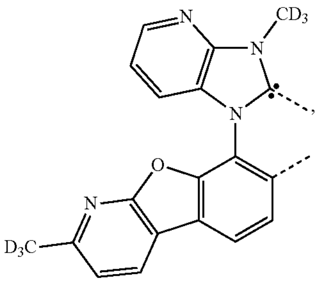
-continued
$L_{B345}$
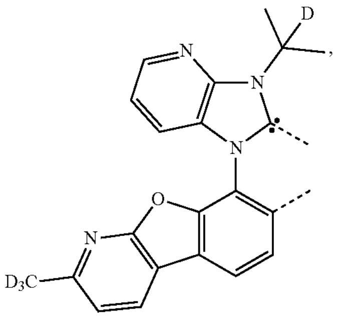
$L_{B346}$
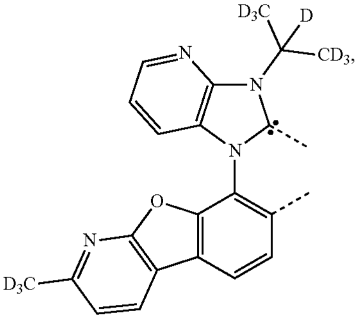
$L_{B347}$
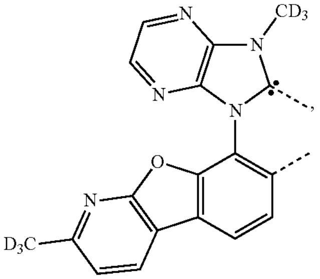
$L_{B348}$
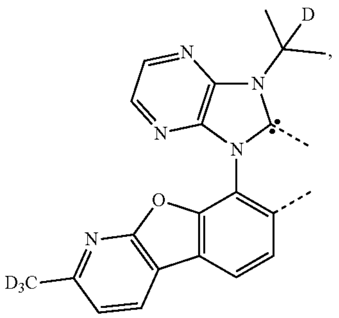
$L_{B349}$
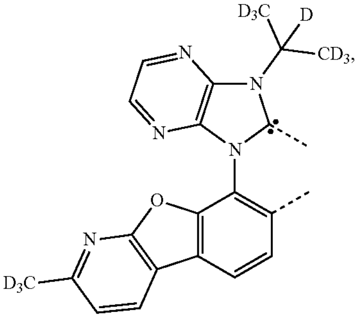

-continued
$L_{B350}$
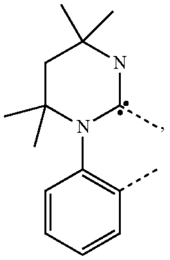
$L_{B351}$
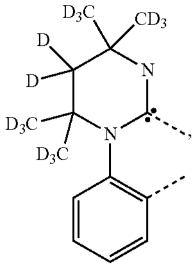
$L_{B352}$
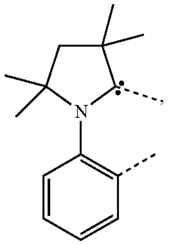
$L_{B353}$
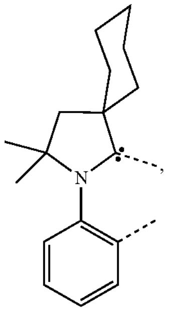
$L_{B354}$
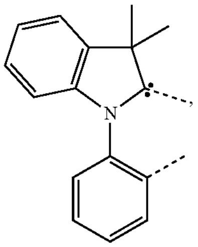
-continued
$L_{B355}$
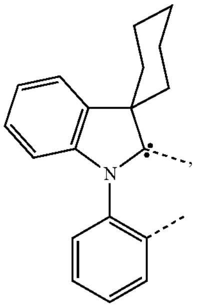
$L_{B356}$
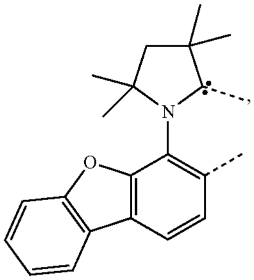
$L_{B357}$
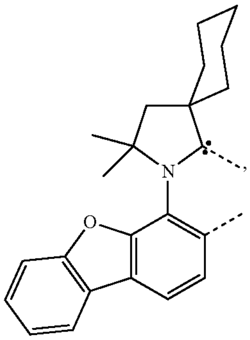
$L_{B358}$
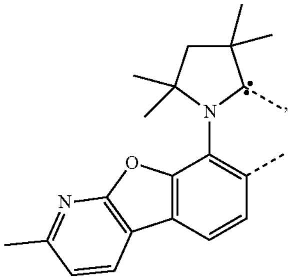
$L_{B359}$
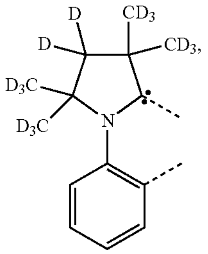

-continued
$L_{B360}$
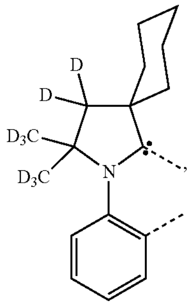
$L_{B361}$
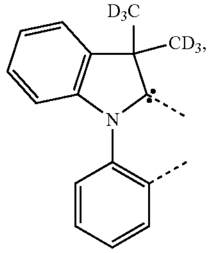
$L_{B362}$
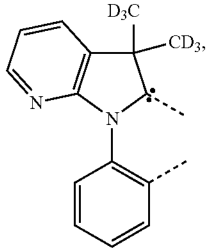
$L_{B363}$
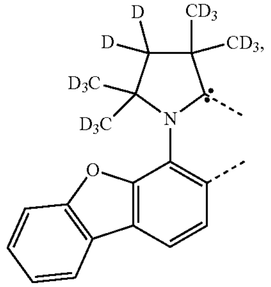
$L_{B364}$
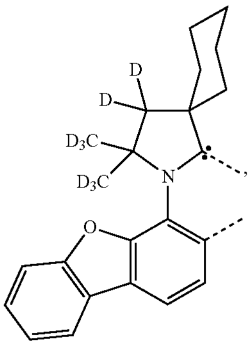
$L_{B365}$
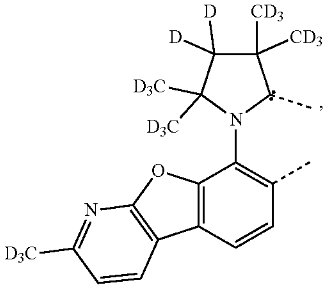
$L_{B366}$
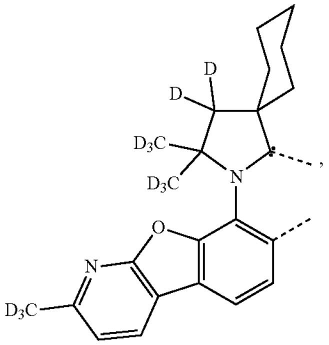
$L_{B367}$
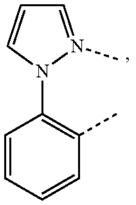
$L_{B368}$
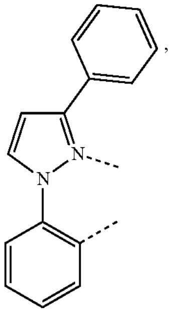
$L_{B369}$
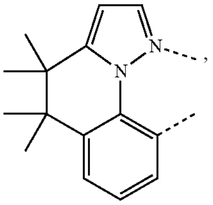

-continued
$L_{B370}$
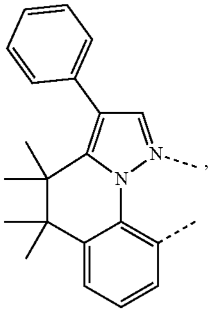
$L_{B371}$
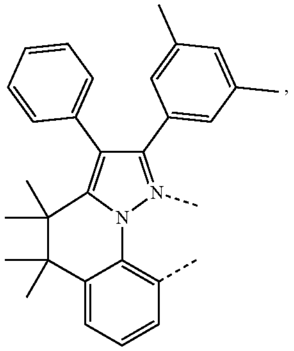
$L_{B372}$
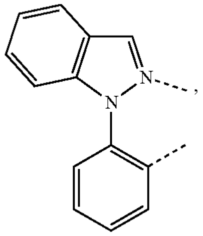
$L_{B373}$
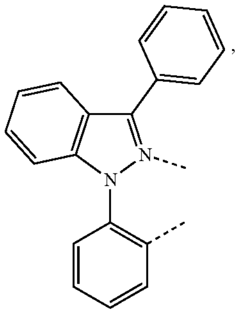
$L_{B374}$
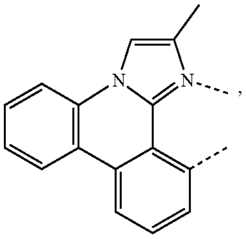
-continued
$L_{B375}$
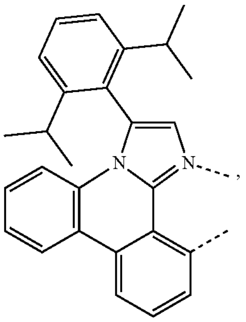
$L_{B376}$
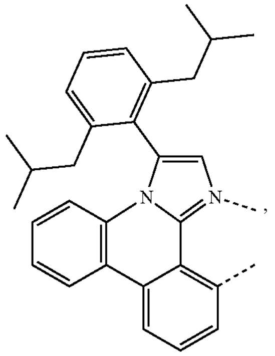
$L_{B377}$
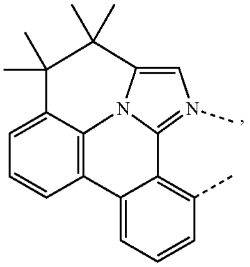
$L_{B378}$
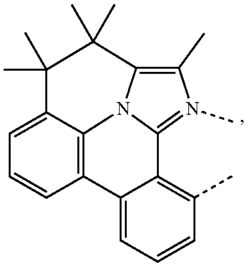
$L_{B379}$
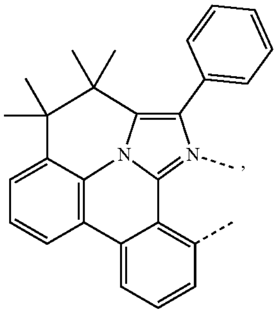

-continued
$L_{B380}$
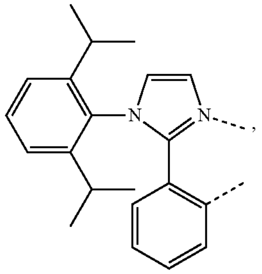
$L_{B381}$
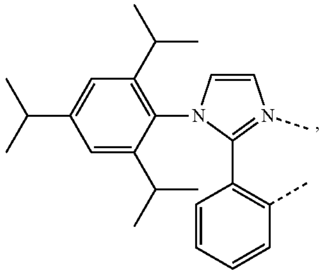
$L_{B382}$
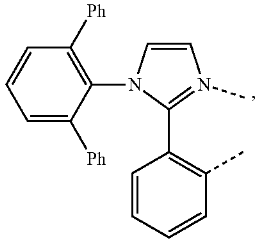
$L_{B383}$
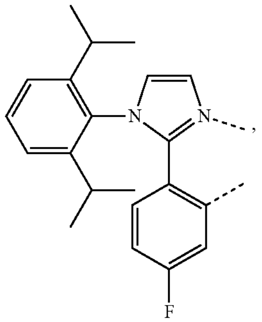
$L_{B384}$
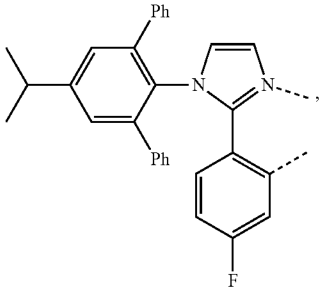
-continued
$L_{B385}$
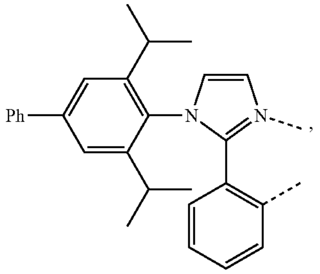
$L_{B386}$
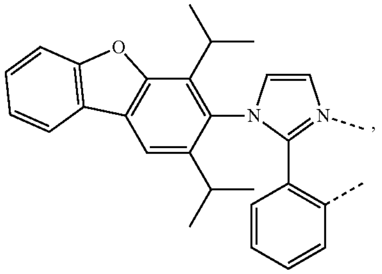
$L_{B387}$
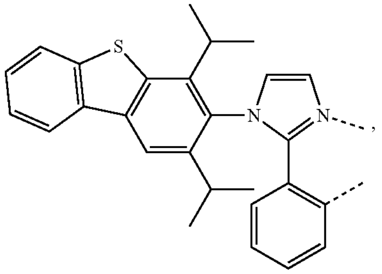
$L_{B388}$
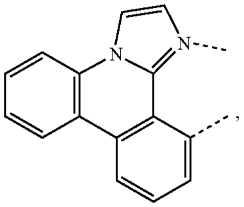
$L_{B389}$
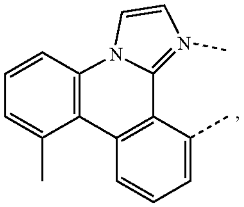
$L_{B390}$
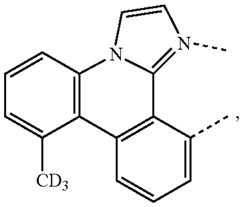

-continued
$L_{B391}$
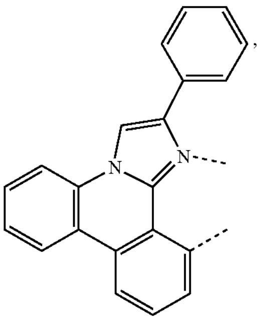
$L_{B392}$
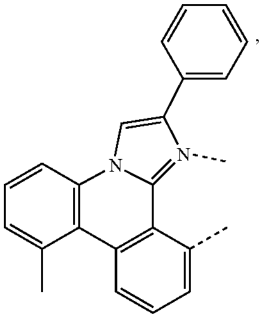
$L_{B393}$
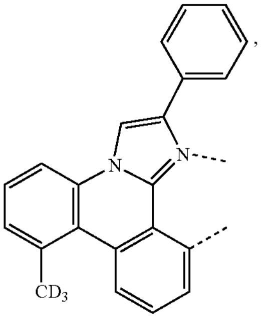
$L_{B394}$
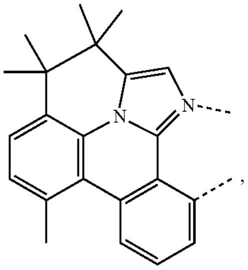
$L_{B395}$
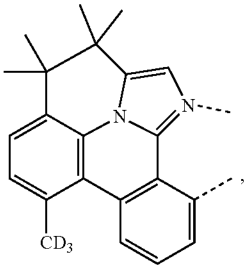
-continued
$L_{B396}$
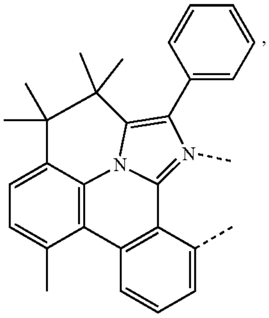
$L_{B397}$
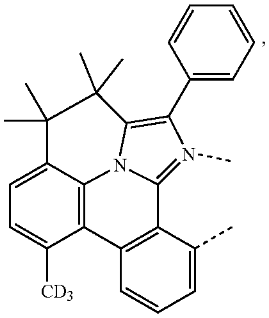
$L_{B398}$
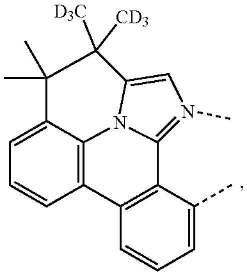
$L_{B399}$
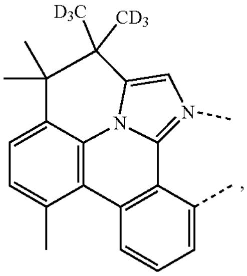
$L_{B400}$
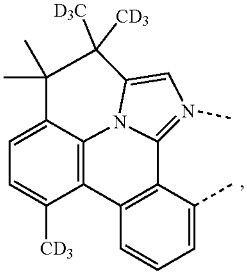

$L_{B401}$
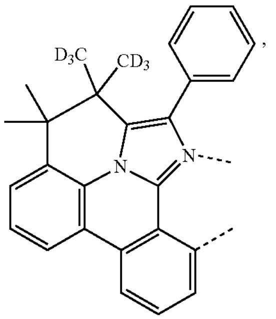
$L_{B402}$
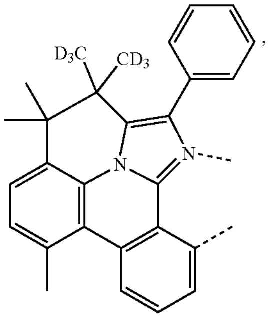
$L_{B403}$
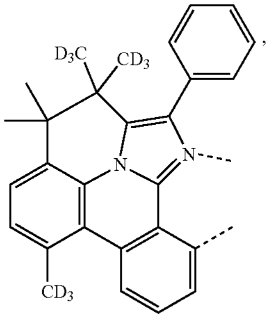
$L_{B404}$
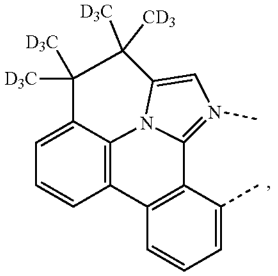
$L_{B405}$
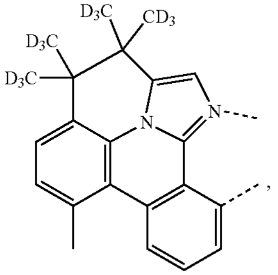
$L_{B406}$
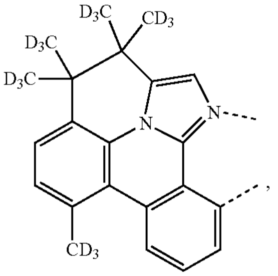
$L_{B407}$
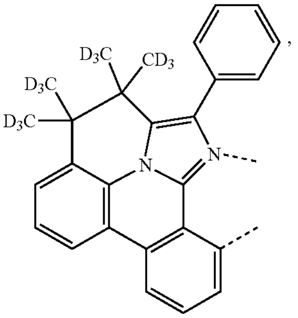
$L_{B408}$
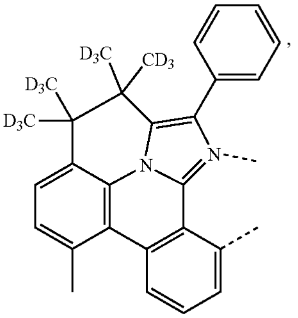
$L_{B409}$
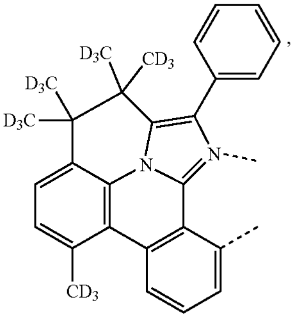
$L_{B410}$
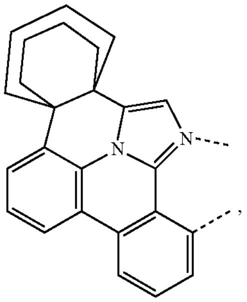

-continued
$L_{B411}$
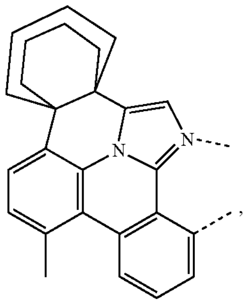
,
$L_{B412}$
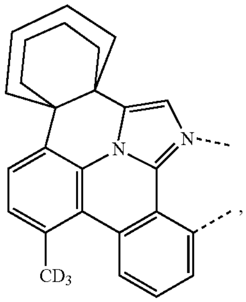
,
$L_{B413}$
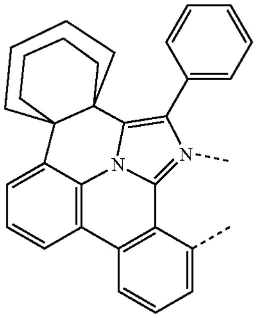
,
$L_{B414}$
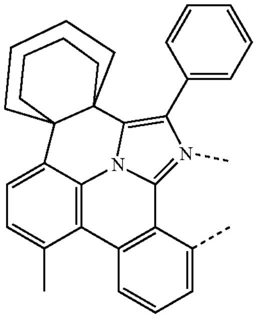
,
$L_{B415}$
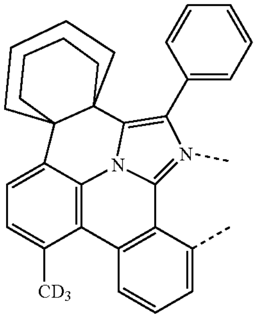
,
-continued
$L_{B416}$
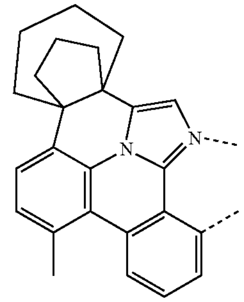
,
$L_{B417}$
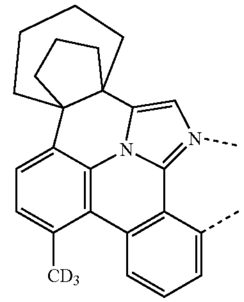
,
$L_{B418}$
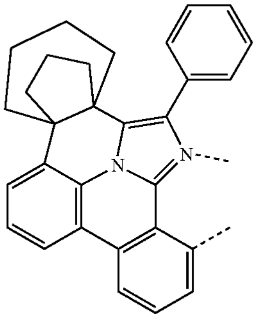
,
$L_{B419}$
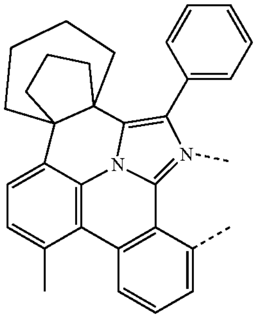
,
$L_{B420}$
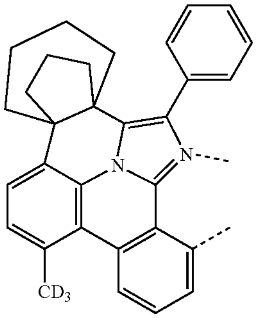
, -continued
$L_{B421}$
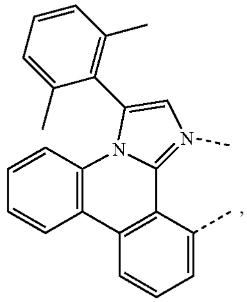
$L_{B422}$
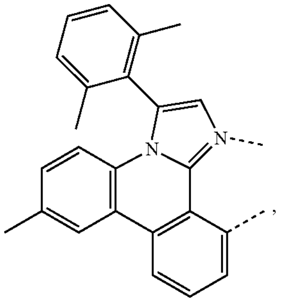
$L_{B435}$
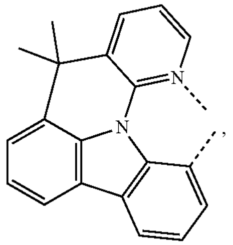
$L_{B443}$
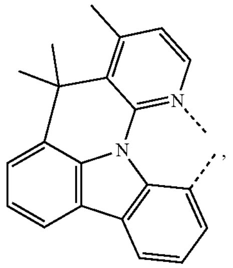
$L_{B425}$
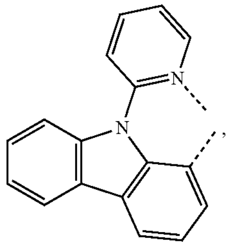
-continued
$L_{B426}$
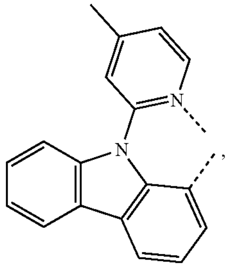
$L_{B427}$
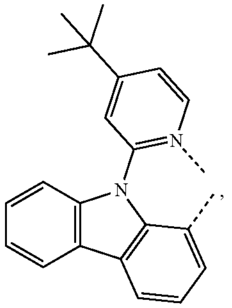
$L_{B428}$
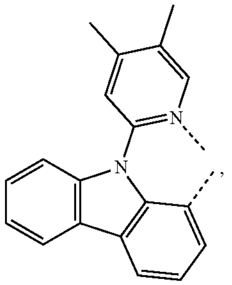
$L_{B429}$
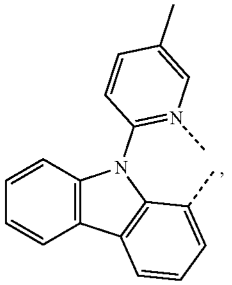
$L_{B430}$
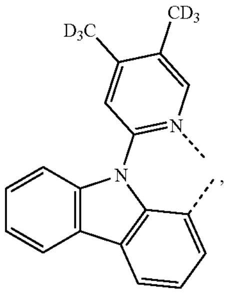

-continued
$L_{B431}$
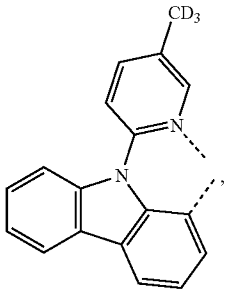
$L_{B432}$
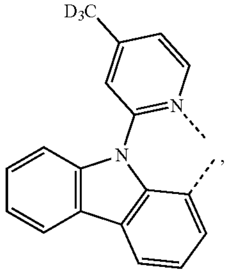
$L_{B433}$
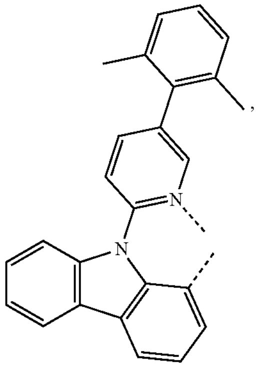
$L_{B434}$
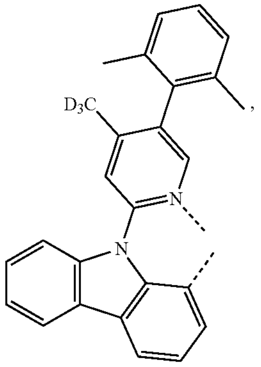
-continued
$L_{B423}$
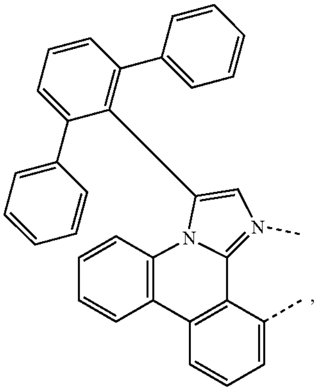
$L_{B436}$
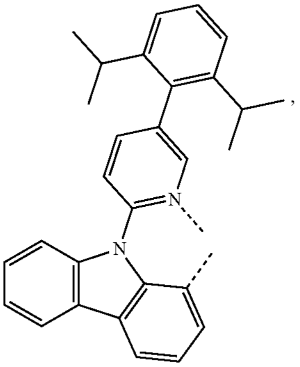
$L_{B437}$
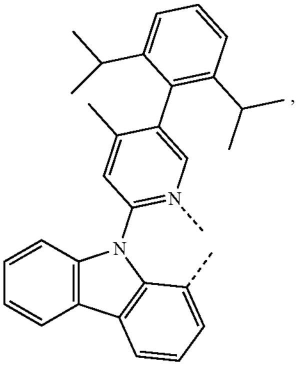
$L_{B438}$
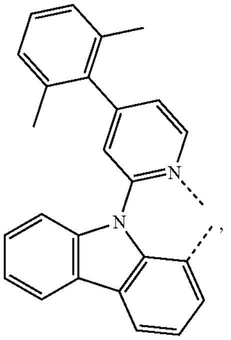

-continued
$L_{B439}$
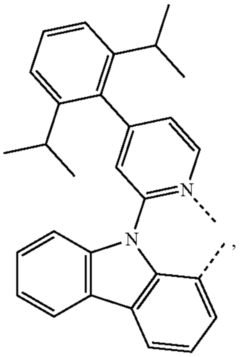
$L_{B440}$
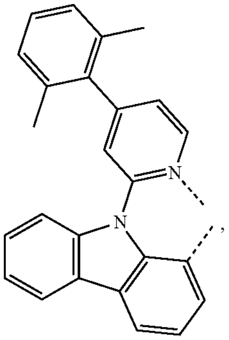
$L_{B441}$
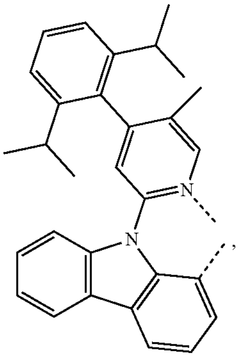
$L_{B442}$
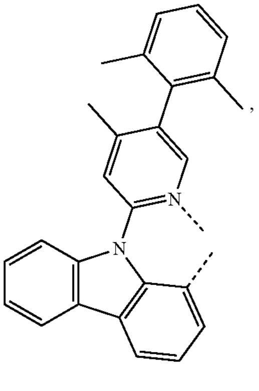
-continued
$L_{B424}$
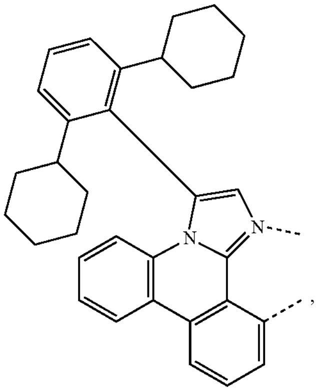
$L_{B444}$
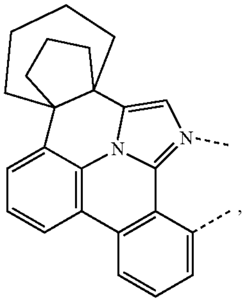
$L_{B445}$
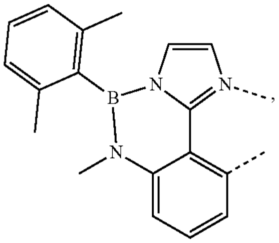
$L_{B446}$
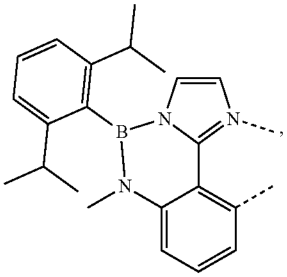
$L_{B447}$
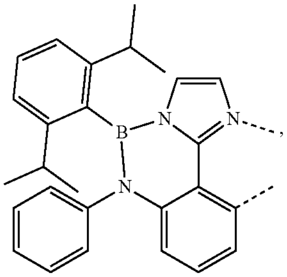

-continued
$L_{B448}$
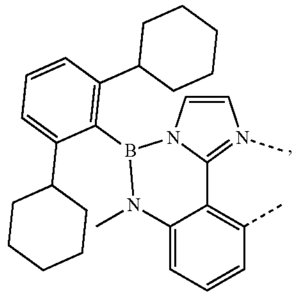
$L_{B449}$
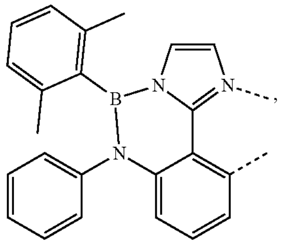
$L_{B450}$
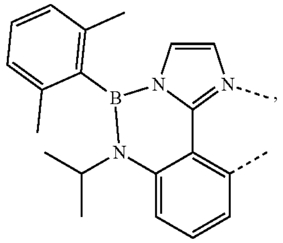
$L_{B452}$
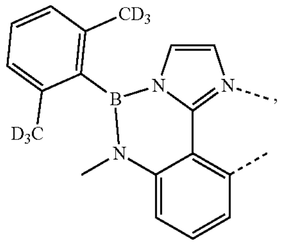
$L_{B454}$
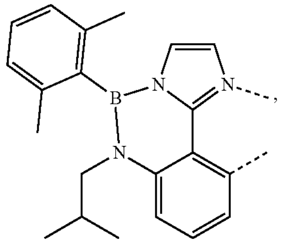
$L_{B456}$
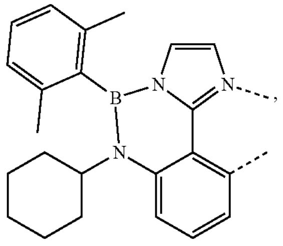
-continued
$L_{B453}$
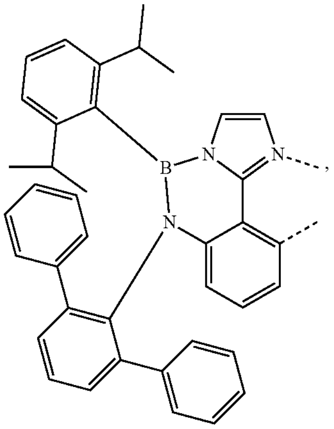
$L_{B455}$
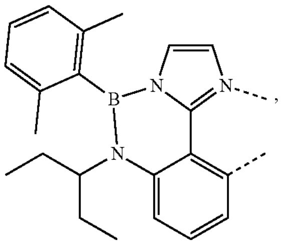
$L_{B451}$
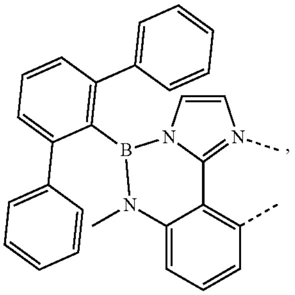
$L_{B457}$
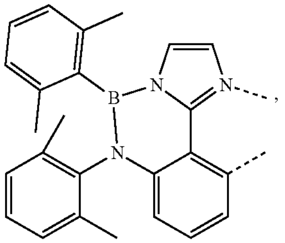
$L_{B458}$
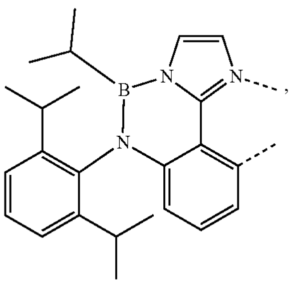

-continued
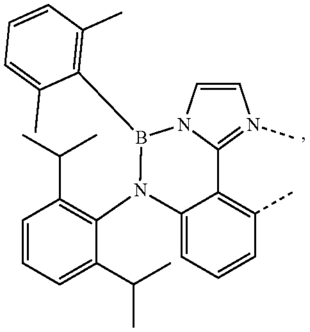
$L_{B459}$
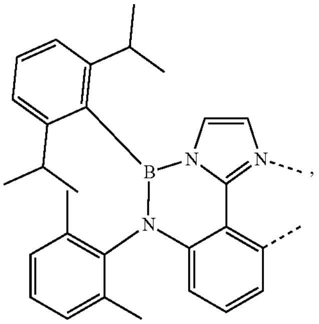
$L_{B460}$
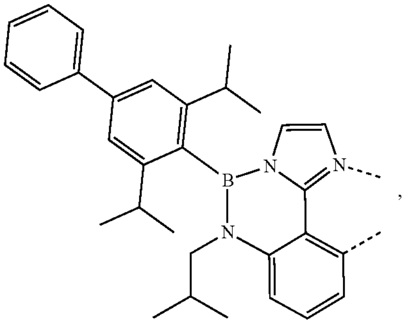
$L_{B461}$
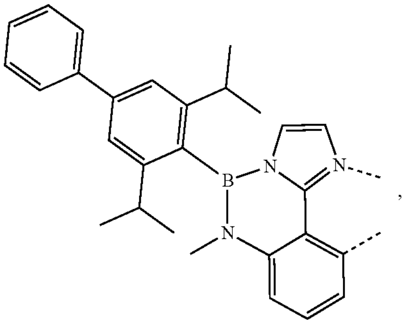
$L_{B462}$
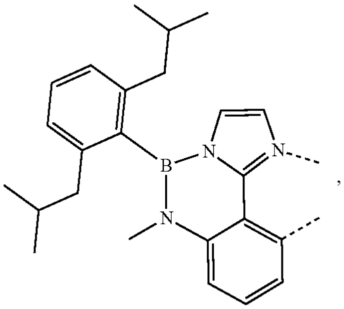
$L_{B463}$
-continued
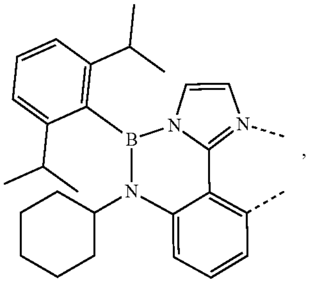
$L_{B464}$
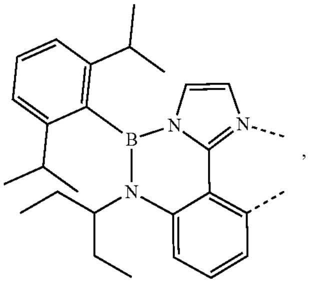
$L_{B465}$
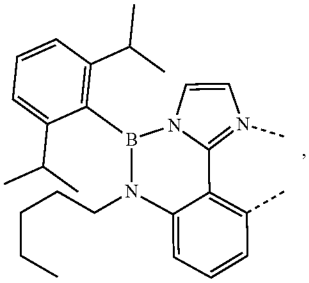
$L_{B466}$
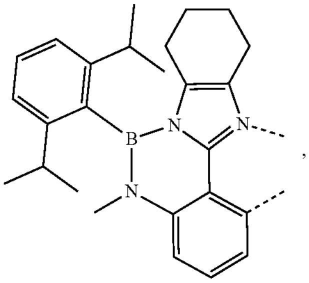
$L_{B467}$
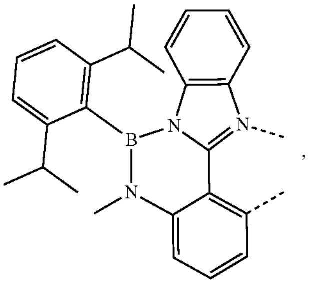
$L_{B468}$ -continued
$L_{B469}$
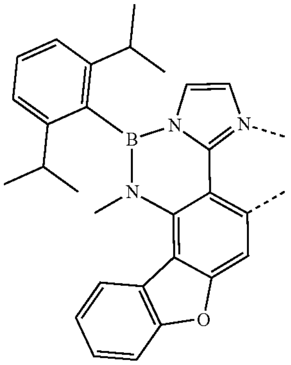
,
$L_{B470}$
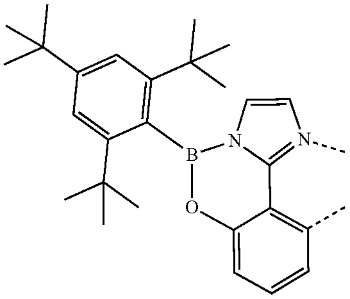
,
$L_{B471}$
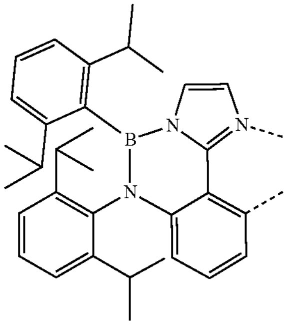
,
$L_{B472}$
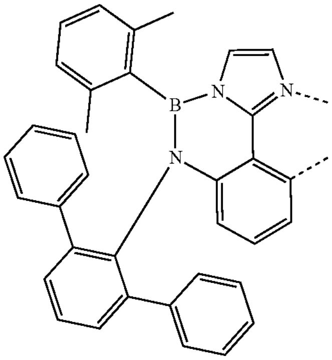
,
$L_{B473}$
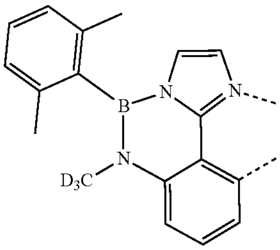
,
-continued
$L_{B474}$
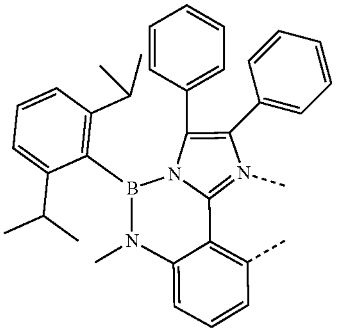
,
$L_{B475}$
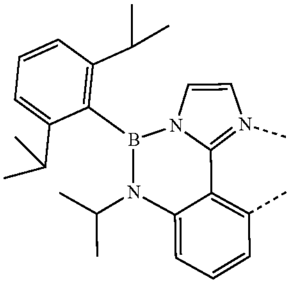
,
$L_{B476}$
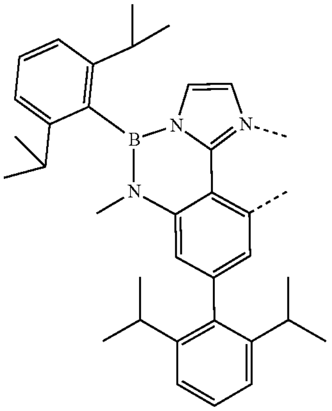
,
$L_{B477}$
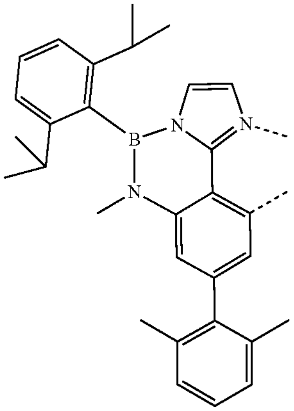
, -continued
$L_{B478}$
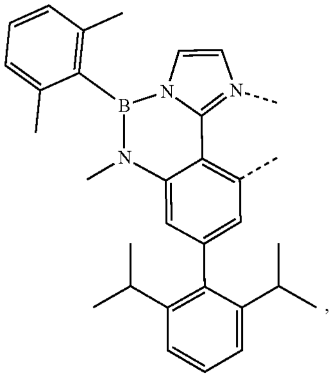
$L_{B479}$
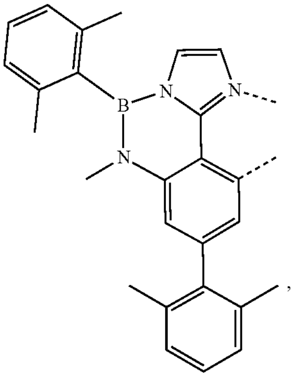
$L_{B480}$
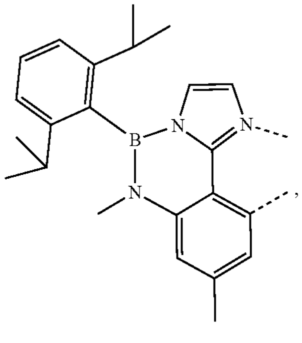
$L_{B481}$
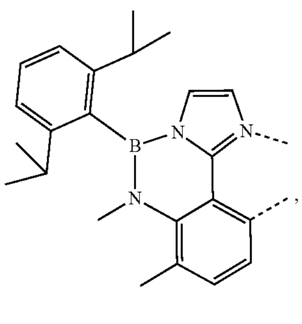
-continued
$L_{B482}$
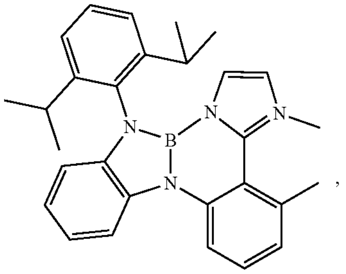
and
$L_{B483}$
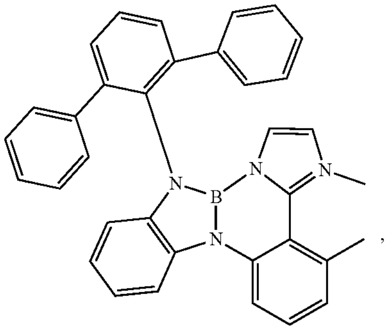
$L_{B484}$
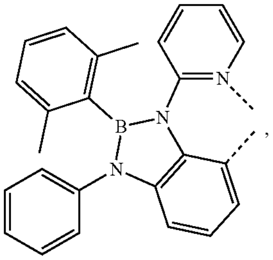
$L_{B485}$
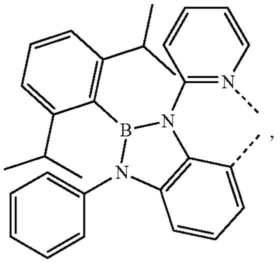
$L_{B486}$
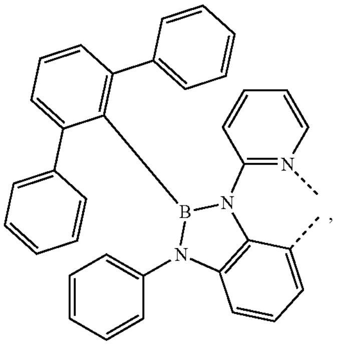

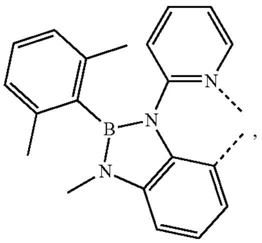
$L_{B487}$
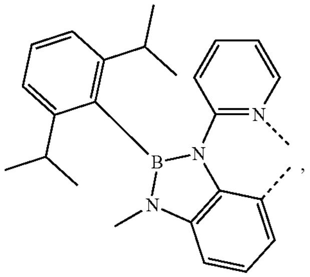
$L_{B488}$
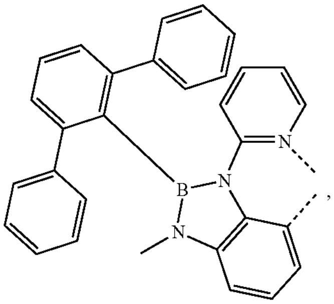
$L_{B489}$
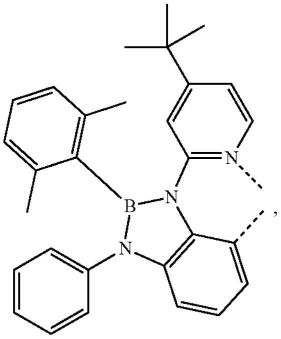
$L_{B490}$
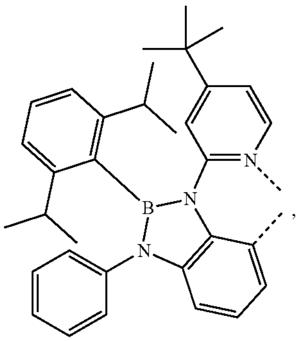
$L_{B491}$
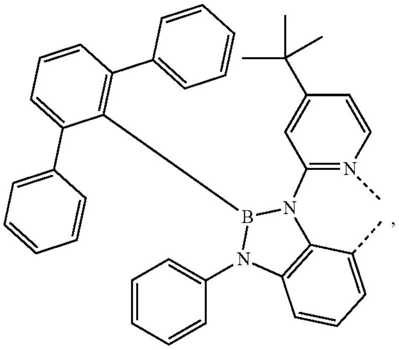
$L_{B492}$
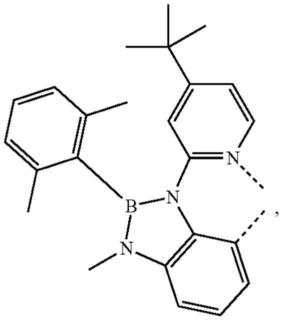
$L_{B493}$
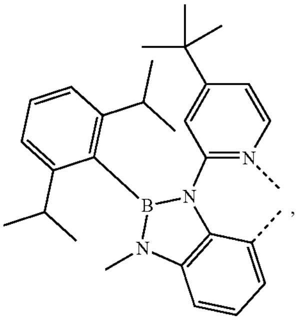
$L_{B494}$
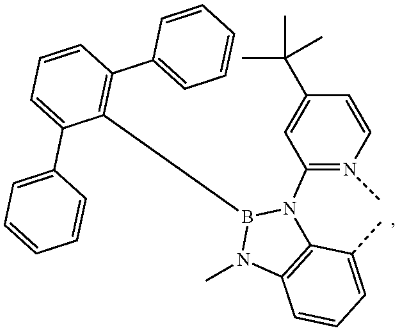
$L_{B495}$ -continued
$L_{B496}$
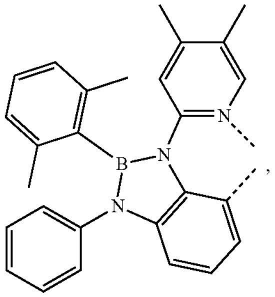
$L_{B497}$
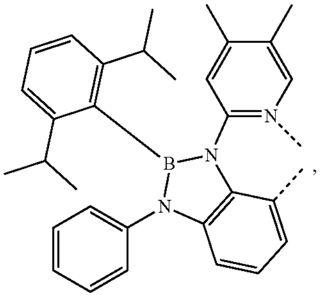
$L_{B498}$
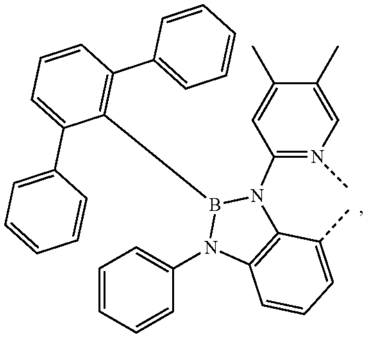
$L_{B499}$
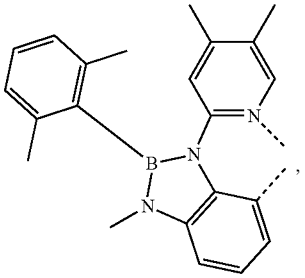
$L_{B500}$
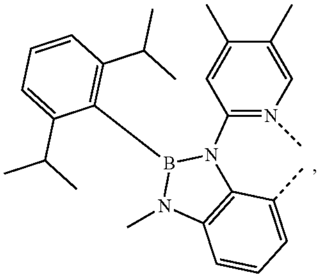
$L_{B501}$
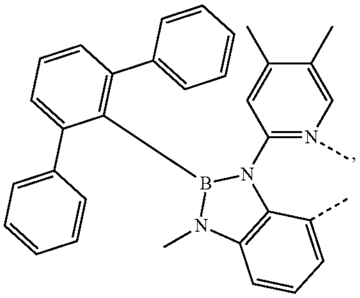
$L_{B502}$
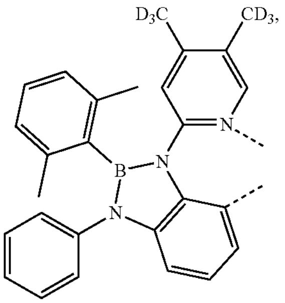
$L_{B503}$
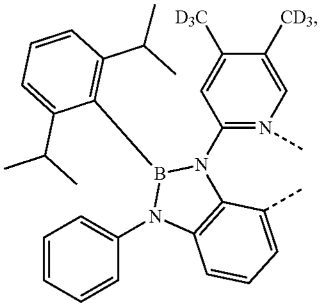
$L_{B504}$
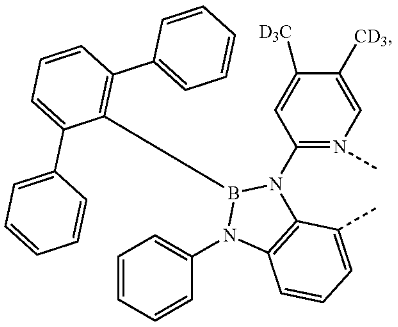
$L_{B505}$
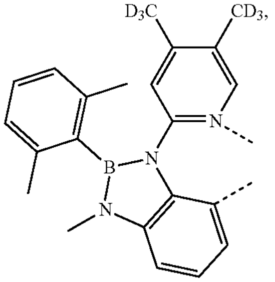

-continued
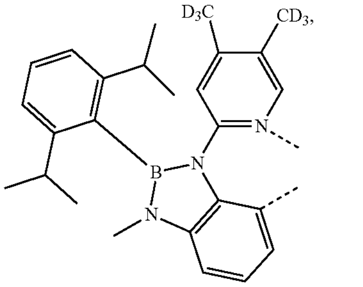
$L_{B506}$
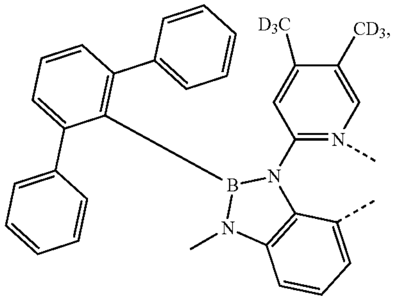
$L_{B507}$
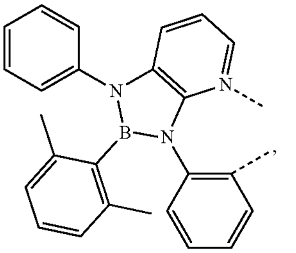
$L_{B508}$
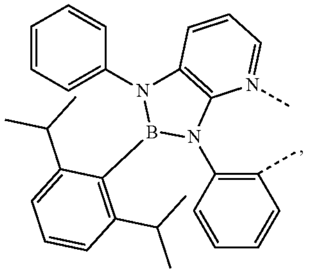
$L_{B509}$
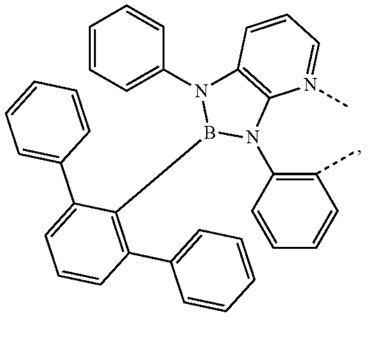
$L_{B510}$
-continued
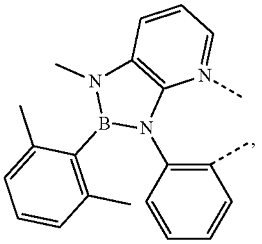
$L_{B511}$
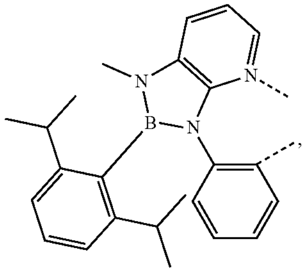
$L_{B512}$
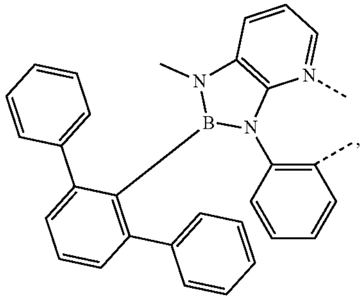
$L_{B513}$
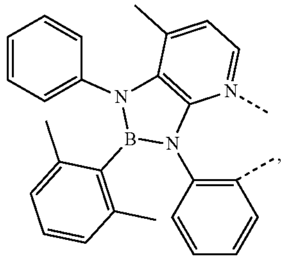
$L_{B514}$
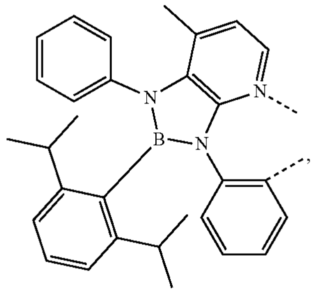
$L_{B515}$ -continued
$L_{B516}$
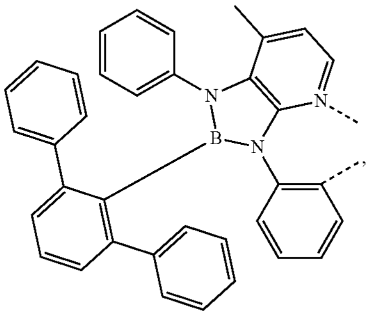
$L_{B517}$
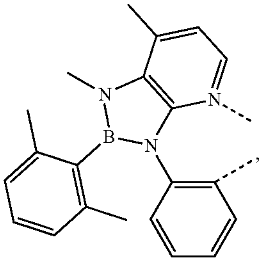
$L_{B518}$
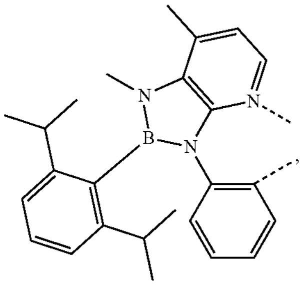
$L_{B519}$
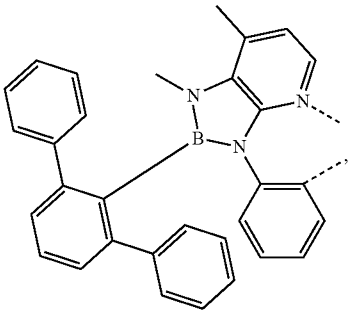
$L_{B520}$
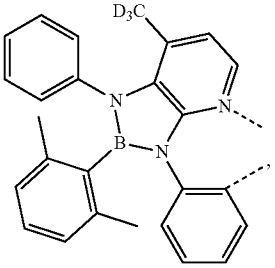
-continued
$L_{B521}$
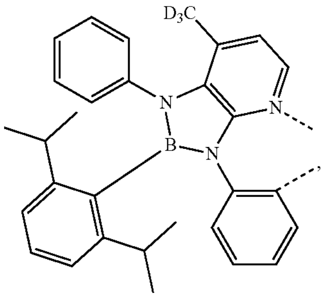
$L_{B522}$
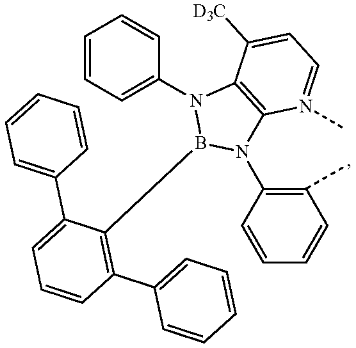
$L_{B523}$
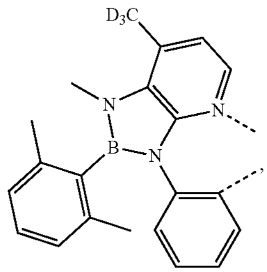
$L_{B524}$
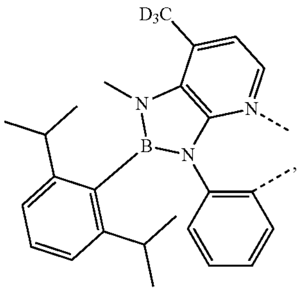
$L_{B525}$
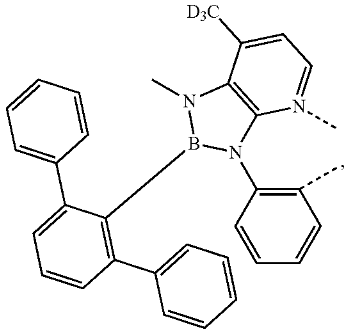

-continued
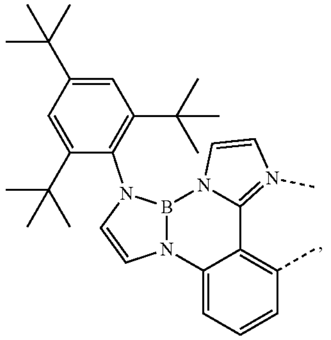
$L_{B526}$
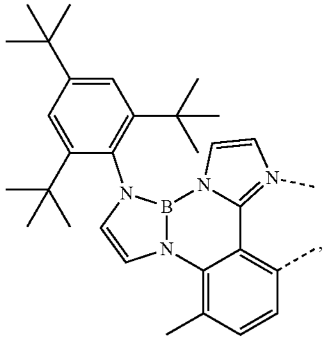
$L_{B527}$
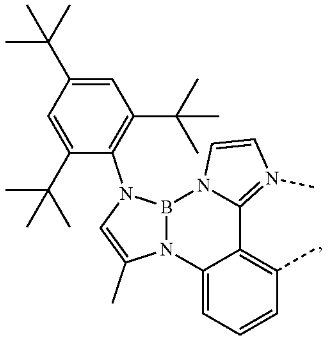
$L_{B528}$
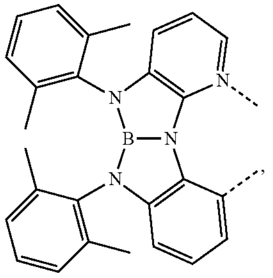
$L_{B529}$
-continued
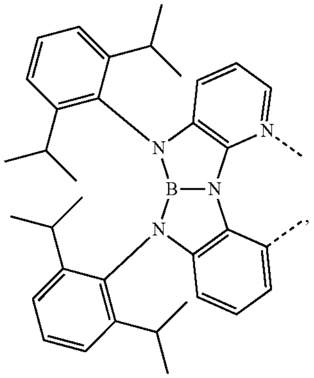
$L_{B530}$
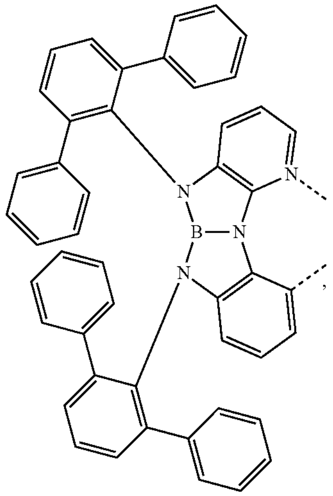
$L_{B531}$
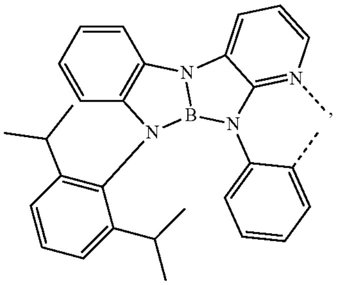
$L_{B532}$
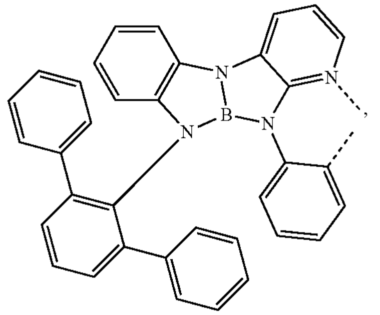
$L_{B533}$ -continued
$L_{B534}$
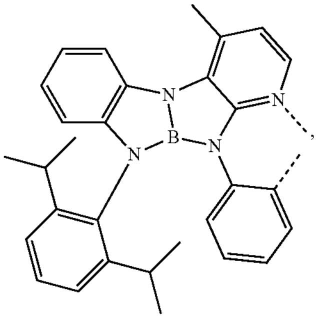
$L_{B535}$
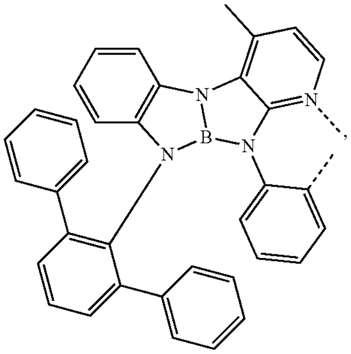
$L_{B536}$
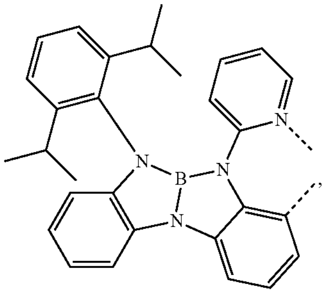
$L_{B537}$
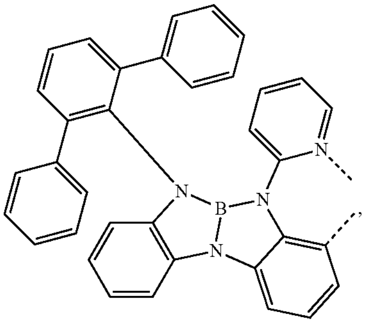
$L_{B538}$
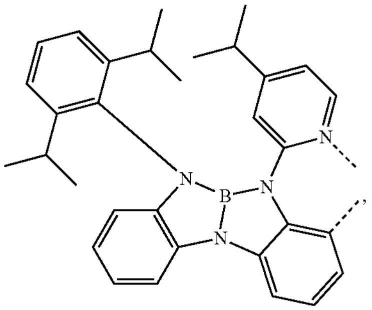
-continued
$L_{B539}$
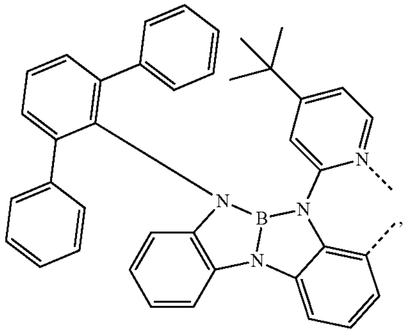
$L_{B540}$
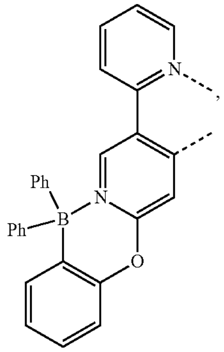
$L_{B541}$
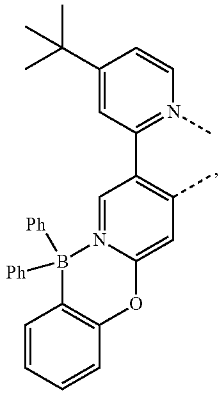
$L_{B542}$
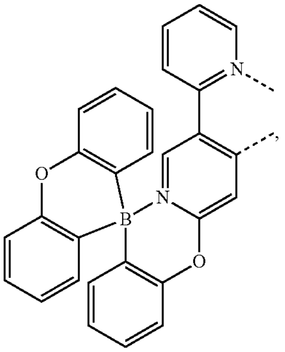

-continued
$L_{B543}$
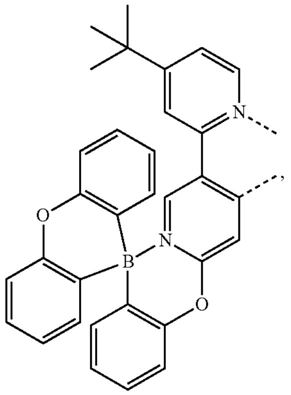
$L_{B544}$
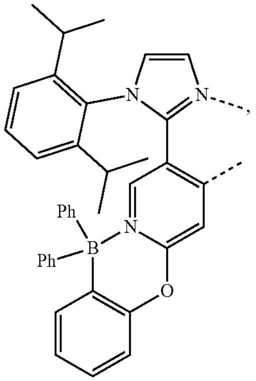
$L_{B545}$
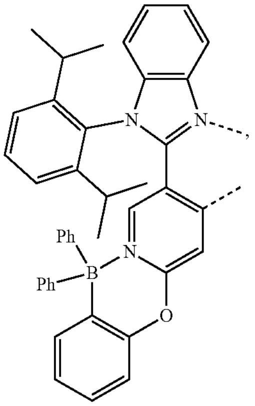
$L_{B546}$
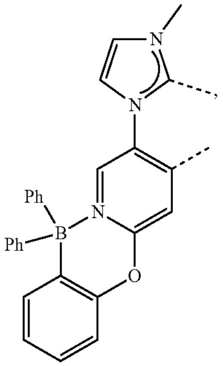
-continued
$L_{B547}$
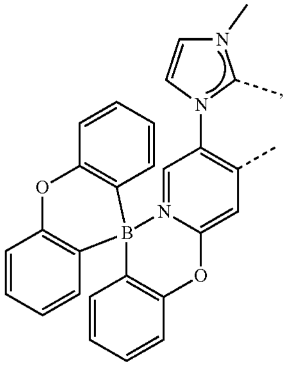
$L_{B548}$
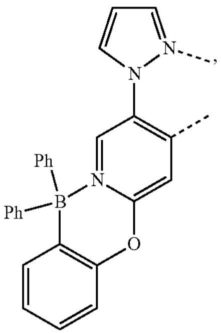
$L_{B549}$
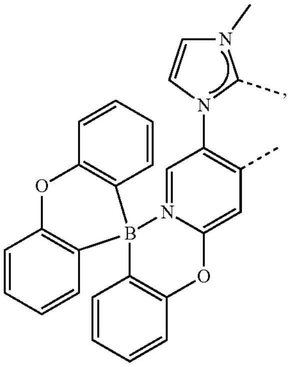
$L_{B550}$
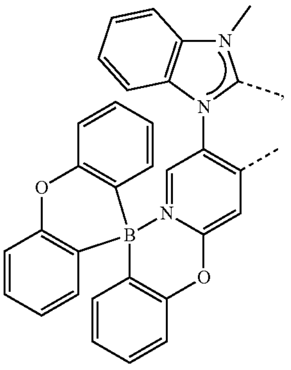

-continued
$L_{B551}$
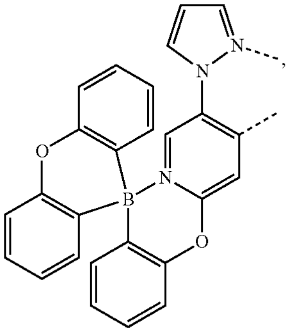
$L_{B552}$
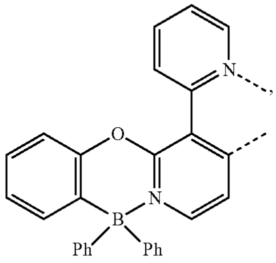
$L_{B553}$
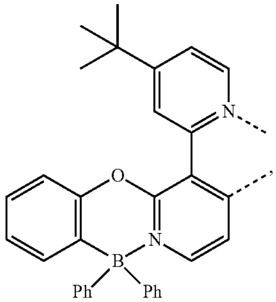
$L_{B554}$
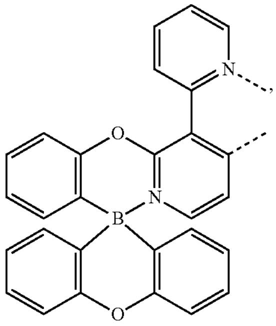
$L_{B555}$
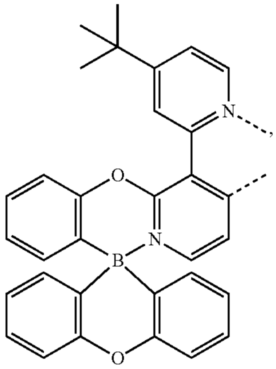
-continued
$L_{B556}$
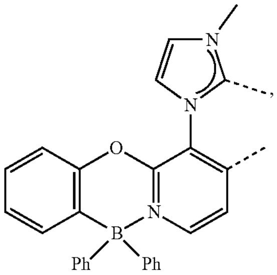
$L_{B557}$
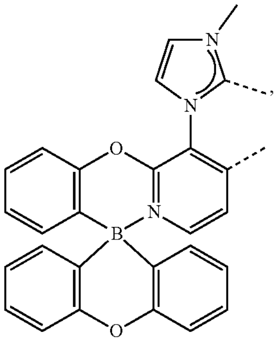
$L_{B558}$
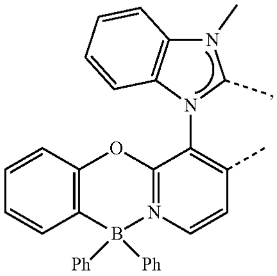
$L_{B559}$
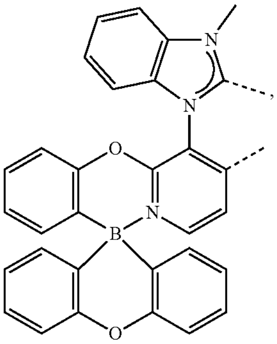
$L_{B560}$
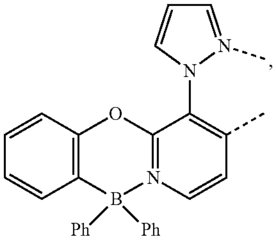
and -continued $L_{B561}$

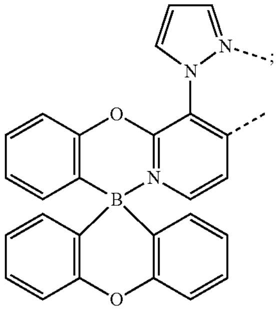

wherein each $L_{Cj-I}$ has a structure based on formula

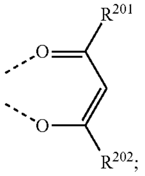

and each $L_{Cj-II}$ has a structure based on formula

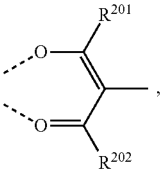

wherein for each $L_{Cj}$ in $L_{Cj-I}$ and $L_{Cj-II}$, $R^{201}$ and $R^{202}$ are each independently defined in the following table:

| $L_{Cj}$ | $R^{201}$ | $R^{202}$ |
|---|---|---|
| $L_{C1}$ | $R^{D1}$ | $R^{D1}$ |
| $L_{C2}$ | $R^{D2}$ | $R^{D2}$ |
| $L_{C3}$ | $R^{D3}$ | $R^{D3}$ |
| $L_{C4}$ | $R^{D4}$ | $R^{D4}$ |
| $L_{C5}$ | $R^{D5}$ | $R^{D5}$ |
| $L_{C6}$ | $R^{D6}$ | $R^{D6}$ |
| $L_{C7}$ | $R^{D7}$ | $R^{D7}$ |
| $L_{C8}$ | $R^{D8}$ | $R^{D8}$ |
| $L_{C9}$ | $R^{D9}$ | $R^{D9}$ |
| $L_{C10}$ | $R^{D10}$ | $R^{D10}$ |
| $L_{C11}$ | $R^{D11}$ | $R^{D11}$ |
| $L_{C12}$ | $R^{D12}$ | $R^{D12}$ |
| $L_{C13}$ | $R^{D13}$ | $R^{D13}$ |
| $L_{C14}$ | $R^{D14}$ | $R^{D14}$ |
| $L_{C15}$ | $R^{D15}$ | $R^{D15}$ |
| $L_{C16}$ | $R^{D16}$ | $R^{D16}$ |
| $L_{C17}$ | $R^{D17}$ | $R^{D17}$ |
| $L_{C18}$ | $R^{D18}$ | $R^{D18}$ |
| $L_{C19}$ | $R^{D19}$ | $R^{D19}$ |
| $L_{C20}$ | $R^{D20}$ | $R^{D20}$ |
| $L_{C21}$ | $R^{D21}$ | $R^{D21}$ |
| $L_{C22}$ | $R^{D22}$ | $R^{D22}$ |
| $L_{C23}$ | $R^{D23}$ | $R^{D23}$ |
| $L_{C24}$ | $R^{D24}$ | $R^{D24}$ |
| $L_{C25}$ | $R^{D25}$ | $R^{D25}$ |
| $L_{C26}$ | $R^{D26}$ | $R^{D26}$ |
| $L_{C27}$ | $R^{D27}$ | $R^{D27}$ |
| $L_{C28}$ | $R^{D28}$ | $R^{D28}$ |
| $L_{C29}$ | $R^{D29}$ | $R^{D29}$ |
| $L_{C30}$ | $R^{D30}$ | $R^{D30}$ |
| $L_{C31}$ | $R^{D31}$ | $R^{D31}$ |
| $L_{C32}$ | $R^{D32}$ | $R^{D32}$ |
| $L_{C33}$ | $R^{D33}$ | $R^{D33}$ |
| $L_{C34}$ | $R^{D34}$ | $R^{D34}$ |
| $L_{C35}$ | $R^{D35}$ | $R^{D35}$ |
| $L_{C36}$ | $R^{D36}$ | $R^{D36}$ |
| $L_{C37}$ | $R^{D37}$ | $R^{D37}$ |
| $L_{C38}$ | $R^{D38}$ | $R^{D38}$ |
| $L_{C39}$ | $R^{D39}$ | $R^{D39}$ |
| $L_{C40}$ | $R^{D40}$ | $R^{D40}$ |
| $L_{C41}$ | $R^{D41}$ | $R^{D41}$ |
| $L_{C42}$ | $R^{D42}$ | $R^{D42}$ |
| $L_{C43}$ | $R^{D43}$ | $R^{D43}$ |
| $L_{C44}$ | $R^{D44}$ | $R^{D44}$ |
| $L_{C45}$ | $R^{D45}$ | $R^{D45}$ |
| $L_{C46}$ | $R^{D46}$ | $R^{D46}$ |
| $L_{C47}$ | $R^{D47}$ | $R^{D47}$ |
| $L_{C48}$ | $R^{D48}$ | $R^{D48}$ |
| $L_{C49}$ | $R^{D49}$ | $R^{D49}$ |
| $L_{C50}$ | $R^{D50}$ | $R^{D50}$ |
| $L_{C51}$ | $R^{D51}$ | $R^{D51}$ |
| $L_{C52}$ | $R^{D52}$ | $R^{D52}$ |
| $L_{C53}$ | $R^{D53}$ | $R^{D53}$ |
| $L_{C54}$ | $R^{D54}$ | $R^{D54}$ |
| $L_{C55}$ | $R^{D55}$ | $R^{D55}$ |
| $L_{C56}$ | $R^{D56}$ | $R^{D56}$ |
| $L_{C57}$ | $R^{D57}$ | $R^{D57}$ |
| $L_{C58}$ | $R^{D58}$ | $R^{D58}$ |
| $L_{C59}$ | $R^{D59}$ | $R^{D59}$ |
| $L_{C60}$ | $R^{D60}$ | $R^{D60}$ |
| $L_{C61}$ | $R^{D61}$ | $R^{D61}$ |
| $L_{C62}$ | $R^{D62}$ | $R^{D62}$ |
| $L_{C63}$ | $R^{D63}$ | $R^{D63}$ |
| $L_{C64}$ | $R^{D64}$ | $R^{D64}$ |
| $L_{C65}$ | $R^{D65}$ | $R^{D65}$ |
| $L_{C66}$ | $R^{D66}$ | $R^{D66}$ |
| $L_{C67}$ | $R^{D67}$ | $R^{D67}$ |
| $L_{C68}$ | $R^{D68}$ | $R^{D68}$ |
| $L_{C69}$ | $R^{D69}$ | $R^{D69}$ |
| $L_{C70}$ | $R^{D70}$ | $R^{D70}$ |
| $L_{C71}$ | $R^{D71}$ | $R^{D71}$ |
| $L_{C72}$ | $R^{D72}$ | $R^{D72}$ |
| $L_{C73}$ | $R^{D73}$ | $R^{D73}$ |
| $L_{C74}$ | $R^{D74}$ | $R^{D74}$ |
| $L_{C75}$ | $R^{D75}$ | $R^{D75}$ |
| $L_{C76}$ | $R^{D76}$ | $R^{D76}$ |
| $L_{C77}$ | $R^{D77}$ | $R^{D77}$ |
| $L_{C78}$ | $R^{D78}$ | $R^{D78}$ |
| $L_{C79}$ | $R^{D79}$ | $R^{D79}$ |
| $L_{C80}$ | $R^{D80}$ | $R^{D80}$ |
| $L_{C81}$ | $R^{D81}$ | $R^{D81}$ |
| $L_{C82}$ | $R^{D82}$ | $R^{D82}$ |
| $L_{C83}$ | $R^{D83}$ | $R^{D83}$ |
| $L_{C84}$ | $R^{D84}$ | $R^{D84}$ |
| $L_{C85}$ | $R^{D85}$ | $R^{D85}$ |
| $L_{C86}$ | $R^{D86}$ | $R^{D86}$ |
| $L_{C87}$ | $R^{D87}$ | $R^{D87}$ |
| $L_{C88}$ | $R^{D88}$ | $R^{D88}$ |
| $L_{C89}$ | $R^{D89}$ | $R^{D89}$ |
| $L_{C90}$ | $R^{D90}$ | $R^{D90}$ |
| $L_{C91}$ | $R^{D91}$ | $R^{D91}$ |
| $L_{C92}$ | $R^{D92}$ | $R^{D92}$ |
| $L_{C93}$ | $R^{D93}$ | $R^{D93}$ |
| $L_{C94}$ | $R^{D94}$ | $R^{D94}$ |
| $L_{C95}$ | $R^{D95}$ | $R^{D95}$ |
| $L_{C96}$ | $R^{D96}$ | $R^{D96}$ |
| $L_{C97}$ | $R^{D97}$ | $R^{D97}$ |
| $L_{C98}$ | $R^{D98}$ | $R^{D98}$ |
| $L_{C99}$ | $R^{D99}$ | $R^{D99}$ |
| $L_{C100}$ | $R^{D100}$ | $R^{D100}$ |
| $L_{C101}$ | $R^{D101}$ | $R^{D101}$ |
| $L_{C102}$ | $R^{D102}$ | $R^{D102}$ |
| $L_{C103}$ | $R^{D103}$ | $R^{D103}$ |
| $L_{C104}$ | $R^{D104}$ | $R^{D104}$ |
| $L_{C105}$ | $R^{D105}$ | $R^{D105}$ |

-continued

| $L_{Cj}$ | $R^{201}$ | $R^{202}$ |
|---|---|---|
| $L_{C106}$ | $R^{D106}$ | $R^{D106}$ |
| $L_{C107}$ | $R^{D107}$ | $R^{D107}$ |
| $L_{C108}$ | $R^{D108}$ | $R^{D108}$ |
| $L_{C109}$ | $R^{D109}$ | $R^{D109}$ |
| $L_{C110}$ | $R^{D110}$ | $R^{D110}$ |
| $L_{C111}$ | $R^{D111}$ | $R^{D111}$ |
| $L_{C112}$ | $R^{D112}$ | $R^{D112}$ |
| $L_{C113}$ | $R^{D113}$ | $R^{D113}$ |
| $L_{C114}$ | $R^{D114}$ | $R^{D114}$ |
| $L_{C115}$ | $R^{D115}$ | $R^{D115}$ |
| $L_{C116}$ | $R^{D116}$ | $R^{D116}$ |
| $L_{C117}$ | $R^{D117}$ | $R^{D117}$ |
| $L_{C118}$ | $R^{D118}$ | $R^{D118}$ |
| $L_{C119}$ | $R^{D119}$ | $R^{D119}$ |
| $L_{C120}$ | $R^{D120}$ | $R^{D120}$ |
| $L_{C121}$ | $R^{D121}$ | $R^{D121}$ |
| $L_{C122}$ | $R^{D122}$ | $R^{D122}$ |
| $L_{C123}$ | $R^{D123}$ | $R^{D123}$ |
| $L_{C124}$ | $R^{D124}$ | $R^{D124}$ |
| $L_{C125}$ | $R^{D125}$ | $R^{D125}$ |
| $L_{C126}$ | $R^{D126}$ | $R^{D126}$ |
| $L_{C127}$ | $R^{D127}$ | $R^{D127}$ |
| $L_{C128}$ | $R^{D128}$ | $R^{D128}$ |
| $L_{C129}$ | $R^{D129}$ | $R^{D129}$ |
| $L_{C130}$ | $R^{D130}$ | $R^{D130}$ |
| $L_{C131}$ | $R^{D131}$ | $R^{D131}$ |
| $L_{C132}$ | $R^{D132}$ | $R^{D132}$ |
| $L_{C133}$ | $R^{D133}$ | $R^{D133}$ |
| $L_{C134}$ | $R^{D134}$ | $R^{D134}$ |
| $L_{C135}$ | $R^{D135}$ | $R^{D135}$ |
| $L_{C136}$ | $R^{D136}$ | $R^{D136}$ |
| $L_{C137}$ | $R^{D137}$ | $R^{D137}$ |
| $L_{C138}$ | $R^{D138}$ | $R^{D138}$ |
| $L_{C139}$ | $R^{D139}$ | $R^{D139}$ |
| $L_{C140}$ | $R^{D140}$ | $R^{D140}$ |
| $L_{C141}$ | $R^{D141}$ | $R^{D141}$ |
| $L_{C142}$ | $R^{D142}$ | $R^{D142}$ |
| $L_{C143}$ | $R^{D143}$ | $R^{D143}$ |
| $L_{C144}$ | $R^{D144}$ | $R^{D144}$ |
| $L_{C145}$ | $R^{D145}$ | $R^{D145}$ |
| $L_{C146}$ | $R^{D146}$ | $R^{D146}$ |
| $L_{C147}$ | $R^{D147}$ | $R^{D147}$ |
| $L_{C148}$ | $R^{D148}$ | $R^{D148}$ |
| $L_{C149}$ | $R^{D149}$ | $R^{D149}$ |
| $L_{C150}$ | $R^{D150}$ | $R^{D150}$ |
| $L_{C151}$ | $R^{D151}$ | $R^{D151}$ |
| $L_{C152}$ | $R^{D152}$ | $R^{D152}$ |
| $L_{C153}$ | $R^{D153}$ | $R^{D153}$ |
| $L_{C154}$ | $R^{D154}$ | $R^{D154}$ |
| $L_{C155}$ | $R^{D155}$ | $R^{D155}$ |
| $L_{C156}$ | $R^{D156}$ | $R^{D156}$ |
| $L_{C157}$ | $R^{D157}$ | $R^{D157}$ |
| $L_{C158}$ | $R^{D158}$ | $R^{D158}$ |
| $L_{C159}$ | $R^{D159}$ | $R^{D159}$ |
| $L_{C160}$ | $R^{D160}$ | $R^{D160}$ |
| $L_{C161}$ | $R^{D161}$ | $R^{D161}$ |
| $L_{C162}$ | $R^{D162}$ | $R^{D162}$ |
| $L_{C163}$ | $R^{D163}$ | $R^{D163}$ |
| $L_{C164}$ | $R^{D164}$ | $R^{D164}$ |
| $L_{C165}$ | $R^{D165}$ | $R^{D165}$ |
| $L_{C166}$ | $R^{D166}$ | $R^{D166}$ |
| $L_{C167}$ | $R^{D167}$ | $R^{D167}$ |
| $L_{C168}$ | $R^{D168}$ | $R^{D168}$ |
| $L_{C169}$ | $R^{D169}$ | $R^{D169}$ |
| $L_{C170}$ | $R^{D170}$ | $R^{D170}$ |
| $L_{C171}$ | $R^{D171}$ | $R^{D171}$ |
| $L_{C172}$ | $R^{D172}$ | $R^{D172}$ |
| $L_{C173}$ | $R^{D173}$ | $R^{D173}$ |
| $L_{C174}$ | $R^{D174}$ | $R^{D174}$ |
| $L_{C175}$ | $R^{D175}$ | $R^{D175}$ |
| $L_{C176}$ | $R^{D176}$ | $R^{D176}$ |
| $L_{C177}$ | $R^{D177}$ | $R^{D177}$ |
| $L_{C178}$ | $R^{D178}$ | $R^{D178}$ |
| $L_{C179}$ | $R^{D179}$ | $R^{D179}$ |
| $L_{C180}$ | $R^{D180}$ | $R^{D180}$ |
| $L_{C181}$ | $R^{D181}$ | $R^{D181}$ |
| $L_{C182}$ | $R^{D182}$ | $R^{D182}$ |

-continued

| $L_{Cj}$ | $R^{201}$ | $R^{202}$ |
|---|---|---|
| $L_{C183}$ | $R^{D183}$ | $R^{D183}$ |
| $L_{C184}$ | $R^{D184}$ | $R^{D184}$ |
| $L_{C185}$ | $R^{D185}$ | $R^{D185}$ |
| $L_{C186}$ | $R^{D186}$ | $R^{D186}$ |
| $L_{C187}$ | $R^{D187}$ | $R^{D187}$ |
| $L_{C188}$ | $R^{D188}$ | $R^{D188}$ |
| $L_{C189}$ | $R^{D189}$ | $R^{D189}$ |
| $L_{C190}$ | $R^{D190}$ | $R^{D190}$ |
| $L_{C191}$ | $R^{D191}$ | $R^{D191}$ |
| $L_{C192}$ | $R^{D192}$ | $R^{D192}$ |
| $L_{C193}$ | $R^{D1}$ | $R^{D3}$ |
| $L_{C194}$ | $R^{D1}$ | $R^{D4}$ |
| $L_{C195}$ | $R^{D1}$ | $R^{D5}$ |
| $L_{C196}$ | $R^{D1}$ | $R^{D9}$ |
| $L_{C197}$ | $R^{D1}$ | $R^{D10}$ |
| $L_{C198}$ | $R^{D1}$ | $R^{D17}$ |
| $L_{C199}$ | $R^{D1}$ | $R^{D18}$ |
| $L_{C200}$ | $R^{D1}$ | $R^{D20}$ |
| $L_{C201}$ | $R^{D1}$ | $R^{D22}$ |
| $L_{C202}$ | $R^{D1}$ | $R^{D37}$ |
| $L_{C203}$ | $R^{D1}$ | $R^{D40}$ |
| $L_{C204}$ | $R^{D1}$ | $R^{D41}$ |
| $L_{C205}$ | $R^{D1}$ | $R^{D42}$ |
| $L_{C206}$ | $R^{D1}$ | $R^{D43}$ |
| $L_{C207}$ | $R^{D1}$ | $R^{D48}$ |
| $L_{C208}$ | $R^{D1}$ | $R^{D49}$ |
| $L_{C209}$ | $R^{D1}$ | $R^{D50}$ |
| $L_{C210}$ | $R^{D1}$ | $R^{D54}$ |
| $L_{C211}$ | $R^{D1}$ | $R^{D55}$ |
| $L_{C212}$ | $R^{D1}$ | $R^{D58}$ |
| $L_{C213}$ | $R^{D1}$ | $R^{D59}$ |
| $L_{C214}$ | $R^{D1}$ | $R^{D78}$ |
| $L_{C215}$ | $R^{D1}$ | $R^{D79}$ |
| $L_{C216}$ | $R^{D1}$ | $R^{D81}$ |
| $L_{C217}$ | $R^{D1}$ | $R^{D87}$ |
| $L_{C218}$ | $R^{D1}$ | $R^{D88}$ |
| $L_{C219}$ | $R^{D1}$ | $R^{D89}$ |
| $L_{C220}$ | $R^{D1}$ | $R^{D93}$ |
| $L_{C221}$ | $R^{D1}$ | $R^{D116}$ |
| $L_{C222}$ | $R^{D1}$ | $R^{D117}$ |
| $L_{C223}$ | $R^{D1}$ | $R^{D118}$ |
| $L_{C224}$ | $R^{D1}$ | $R^{D119}$ |
| $L_{C225}$ | $R^{D1}$ | $R^{D120}$ |
| $L_{C226}$ | $R^{D1}$ | $R^{D133}$ |
| $L_{C227}$ | $R^{D1}$ | $R^{D134}$ |
| $L_{C228}$ | $R^{D1}$ | $R^{D135}$ |
| $L_{C229}$ | $R^{D1}$ | $R^{D136}$ |
| $L_{C230}$ | $R^{D1}$ | $R^{D143}$ |
| $L_{C231}$ | $R^{D1}$ | $R^{D144}$ |
| $L_{C232}$ | $R^{D1}$ | $R^{D145}$ |
| $L_{C233}$ | $R^{D1}$ | $R^{D146}$ |
| $L_{C234}$ | $R^{D1}$ | $R^{D147}$ |
| $L_{C235}$ | $R^{D1}$ | $R^{D149}$ |
| $L_{C236}$ | $R^{D1}$ | $R^{D151}$ |
| $L_{C237}$ | $R^{D1}$ | $R^{D154}$ |
| $L_{C238}$ | $R^{D1}$ | $R^{D155}$ |
| $L_{C239}$ | $R^{D1}$ | $R^{D161}$ |
| $L_{C240}$ | $R^{D1}$ | $R^{D175}$ |
| $L_{C241}$ | $R^{D4}$ | $R^{D3}$ |
| $L_{C242}$ | $R^{D4}$ | $R^{D5}$ |
| $L_{C243}$ | $R^{D4}$ | $R^{D9}$ |
| $L_{C244}$ | $R^{D4}$ | $R^{D10}$ |
| $L_{C245}$ | $R^{D4}$ | $R^{D17}$ |
| $L_{C246}$ | $R^{D4}$ | $R^{D18}$ |
| $L_{C247}$ | $R^{D4}$ | $R^{D20}$ |
| $L_{C248}$ | $R^{D4}$ | $R^{D22}$ |
| $L_{C249}$ | $R^{D4}$ | $R^{D37}$ |
| $L_{C250}$ | $R^{D4}$ | $R^{D40}$ |
| $L_{C251}$ | $R^{D4}$ | $R^{D41}$ |
| $L_{C252}$ | $R^{D4}$ | $R^{D42}$ |
| $L_{C253}$ | $R^{D4}$ | $R^{D43}$ |
| $L_{C254}$ | $R^{D4}$ | $R^{D48}$ |
| $L_{C255}$ | $R^{D4}$ | $R^{D49}$ |
| $L_{C256}$ | $R^{D4}$ | $R^{D50}$ |
| $L_{C257}$ | $R^{D4}$ | $R^{D54}$ |
| $L_{C258}$ | $R^{D4}$ | $R^{D55}$ |
| $L_{C259}$ | $R^{D4}$ | $R^{D58}$ |

-continued

| $L_{Cj}$ | $R^{201}$ | $R^{202}$ |
|---|---|---|
| $L_{C260}$ | $R^{D4}$ | $R^{D59}$ |
| $L_{C261}$ | $R^{D4}$ | $R^{D78}$ |
| $L_{C262}$ | $R^{D4}$ | $R^{D79}$ |
| $L_{C263}$ | $R^{D4}$ | $R^{D81}$ |
| $L_{C264}$ | $R^{D4}$ | $R^{D87}$ |
| $L_{C265}$ | $R^{D4}$ | $R^{D88}$ |
| $L_{C266}$ | $R^{D4}$ | $R^{D89}$ |
| $L_{C267}$ | $R^{D4}$ | $R^{D93}$ |
| $L_{C268}$ | $R^{D4}$ | $R^{D116}$ |
| $L_{C269}$ | $R^{D4}$ | $R^{D117}$ |
| $L_{C270}$ | $R^{D4}$ | $R^{D118}$ |
| $L_{C271}$ | $R^{D4}$ | $R^{D119}$ |
| $L_{C272}$ | $R^{D4}$ | $R^{D120}$ |
| $L_{C273}$ | $R^{D4}$ | $R^{D133}$ |
| $L_{C274}$ | $R^{D4}$ | $R^{D134}$ |
| $L_{C275}$ | $R^{D4}$ | $R^{D135}$ |
| $L_{C276}$ | $R^{D4}$ | $R^{D136}$ |
| $L_{C277}$ | $R^{D4}$ | $R^{D143}$ |
| $L_{C278}$ | $R^{D4}$ | $R^{D144}$ |
| $L_{C279}$ | $R^{D4}$ | $R^{D145}$ |
| $L_{C280}$ | $R^{D4}$ | $R^{D146}$ |
| $L_{C281}$ | $R^{D4}$ | $R^{D147}$ |
| $L_{C282}$ | $R^{D4}$ | $R^{D149}$ |
| $L_{C283}$ | $R^{D4}$ | $R^{D151}$ |
| $L_{C284}$ | $R^{D4}$ | $R^{D154}$ |
| $L_{C285}$ | $R^{D4}$ | $R^{D155}$ |
| $L_{C286}$ | $R^{D4}$ | $R^{D161}$ |
| $L_{C287}$ | $R^{D4}$ | $R^{D175}$ |
| $L_{C288}$ | $R^{D9}$ | $R^{D3}$ |
| $L_{C289}$ | $R^{D9}$ | $R^{D5}$ |
| $L_{C290}$ | $R^{D9}$ | $R^{D10}$ |
| $L_{C291}$ | $R^{D9}$ | $R^{D17}$ |
| $L_{C292}$ | $R^{D9}$ | $R^{D18}$ |
| $L_{C293}$ | $R^{D9}$ | $R^{D20}$ |
| $L_{C294}$ | $R^{D9}$ | $R^{D22}$ |
| $L_{C295}$ | $R^{D9}$ | $R^{D37}$ |
| $L_{C296}$ | $R^{D9}$ | $R^{D40}$ |
| $L_{C297}$ | $R^{D9}$ | $R^{D41}$ |
| $L_{C298}$ | $R^{D9}$ | $R^{D42}$ |
| $L_{C299}$ | $R^{D9}$ | $R^{D43}$ |
| $L_{C300}$ | $R^{D9}$ | $R^{D48}$ |
| $L_{C301}$ | $R^{D9}$ | $R^{D49}$ |
| $L_{C302}$ | $R^{D9}$ | $R^{D50}$ |
| $L_{C303}$ | $R^{D9}$ | $R^{D54}$ |
| $L_{C304}$ | $R^{D9}$ | $R^{D55}$ |
| $L_{C305}$ | $R^{D9}$ | $R^{D58}$ |
| $L_{C306}$ | $R^{D9}$ | $R^{D59}$ |
| $L_{C307}$ | $R^{D9}$ | $R^{D78}$ |
| $L_{C308}$ | $R^{D9}$ | $R^{D79}$ |
| $L_{C309}$ | $R^{D9}$ | $R^{D81}$ |
| $L_{C310}$ | $R^{D9}$ | $R^{D87}$ |
| $L_{C311}$ | $R^{D9}$ | $R^{D88}$ |
| $L_{C312}$ | $R^{D9}$ | $R^{D89}$ |
| $L_{C313}$ | $R^{D9}$ | $R^{D93}$ |
| $L_{C314}$ | $R^{D9}$ | $R^{D116}$ |
| $L_{C315}$ | $R^{D9}$ | $R^{D117}$ |
| $L_{C316}$ | $R^{D9}$ | $R^{D118}$ |
| $L_{C317}$ | $R^{D9}$ | $R^{D119}$ |
| $L_{C318}$ | $R^{D9}$ | $R^{D120}$ |
| $L_{C319}$ | $R^{D9}$ | $R^{D133}$ |
| $L_{C320}$ | $R^{D9}$ | $R^{D134}$ |
| $L_{C321}$ | $R^{D9}$ | $R^{D135}$ |
| $L_{C322}$ | $R^{D9}$ | $R^{D136}$ |
| $L_{C323}$ | $R^{D9}$ | $R^{D143}$ |
| $L_{C324}$ | $R^{D9}$ | $R^{D144}$ |
| $L_{C325}$ | $R^{D9}$ | $R^{D145}$ |
| $L_{C326}$ | $R^{D9}$ | $R^{D146}$ |
| $L_{C327}$ | $R^{D9}$ | $R^{D147}$ |
| $L_{C328}$ | $R^{D9}$ | $R^{D149}$ |
| $L_{C329}$ | $R^{D9}$ | $R^{D151}$ |
| $L_{C330}$ | $R^{D9}$ | $R^{D154}$ |
| $L_{C331}$ | $R^{D9}$ | $R^{D155}$ |
| $L_{C332}$ | $R^{D9}$ | $R^{D161}$ |
| $L_{C333}$ | $R^{D9}$ | $R^{D175}$ |
| $L_{C334}$ | $R^{D10}$ | $R^{D3}$ |
| $L_{C335}$ | $R^{D10}$ | $R^{D5}$ |
| $L_{C336}$ | $R^{D10}$ | $R^{D17}$ |

-continued

| $L_{Cj}$ | $R^{201}$ | $R^{202}$ |
|---|---|---|
| $L_{C337}$ | $R^{D10}$ | $R^{D18}$ |
| $L_{C338}$ | $R^{D10}$ | $R^{D20}$ |
| $L_{C339}$ | $R^{D10}$ | $R^{D22}$ |
| $L_{C340}$ | $R^{D10}$ | $R^{D37}$ |
| $L_{C341}$ | $R^{D10}$ | $R^{D40}$ |
| $L_{C342}$ | $R^{D10}$ | $R^{D41}$ |
| $L_{C343}$ | $R^{D10}$ | $R^{D42}$ |
| $L_{C344}$ | $R^{D10}$ | $R^{D43}$ |
| $L_{C345}$ | $R^{D10}$ | $R^{D48}$ |
| $L_{C346}$ | $R^{D10}$ | $R^{D49}$ |
| $L_{C347}$ | $R^{D10}$ | $R^{D50}$ |
| $L_{C348}$ | $R^{D10}$ | $R^{D54}$ |
| $L_{C349}$ | $R^{D10}$ | $R^{D55}$ |
| $L_{C350}$ | $R^{D10}$ | $R^{D58}$ |
| $L_{C351}$ | $R^{D10}$ | $R^{D59}$ |
| $L_{C352}$ | $R^{D10}$ | $R^{D78}$ |
| $L_{C353}$ | $R^{D10}$ | $R^{D79}$ |
| $L_{C354}$ | $R^{D10}$ | $R^{D81}$ |
| $L_{C355}$ | $R^{D10}$ | $R^{D87}$ |
| $L_{C356}$ | $R^{D10}$ | $R^{D88}$ |
| $L_{C357}$ | $R^{D10}$ | $R^{D89}$ |
| $L_{C358}$ | $R^{D10}$ | $R^{D93}$ |
| $L_{C359}$ | $R^{D10}$ | $R^{D116}$ |
| $L_{C360}$ | $R^{D10}$ | $R^{D117}$ |
| $L_{C361}$ | $R^{D10}$ | $R^{D118}$ |
| $L_{C362}$ | $R^{D10}$ | $R^{D119}$ |
| $L_{C363}$ | $R^{D10}$ | $R^{D120}$ |
| $L_{C364}$ | $R^{D10}$ | $R^{D133}$ |
| $L_{C365}$ | $R^{D10}$ | $R^{D134}$ |
| $L_{C366}$ | $R^{D10}$ | $R^{D135}$ |
| $L_{C367}$ | $R^{D10}$ | $R^{D136}$ |
| $L_{C368}$ | $R^{D10}$ | $R^{D143}$ |
| $L_{C369}$ | $R^{D10}$ | $R^{D144}$ |
| $L_{C370}$ | $R^{D10}$ | $R^{D145}$ |
| $L_{C371}$ | $R^{D10}$ | $R^{D146}$ |
| $L_{C372}$ | $R^{D10}$ | $R^{D147}$ |
| $L_{C373}$ | $R^{D10}$ | $R^{D149}$ |
| $L_{C374}$ | $R^{D10}$ | $R^{D151}$ |
| $L_{C375}$ | $R^{D10}$ | $R^{D154}$ |
| $L_{C376}$ | $R^{D10}$ | $R^{D155}$ |
| $L_{C377}$ | $R^{D10}$ | $R^{D161}$ |
| $L_{C378}$ | $R^{D10}$ | $R^{D175}$ |
| $L_{C379}$ | $R^{D17}$ | $R^{D3}$ |
| $L_{C380}$ | $R^{D17}$ | $R^{D5}$ |
| $L_{C381}$ | $R^{D17}$ | $R^{D18}$ |
| $L_{C382}$ | $R^{D17}$ | $R^{D20}$ |
| $L_{C383}$ | $R^{D17}$ | $R^{D22}$ |
| $L_{C384}$ | $R^{D17}$ | $R^{D37}$ |
| $L_{C385}$ | $R^{D17}$ | $R^{D40}$ |
| $L_{C386}$ | $R^{D17}$ | $R^{D41}$ |
| $L_{C387}$ | $R^{D17}$ | $R^{D42}$ |
| $L_{C388}$ | $R^{D17}$ | $R^{D43}$ |
| $L_{C389}$ | $R^{D17}$ | $R^{D48}$ |
| $L_{C390}$ | $R^{D17}$ | $R^{D49}$ |
| $L_{C391}$ | $R^{D17}$ | $R^{D50}$ |
| $L_{C392}$ | $R^{D17}$ | $R^{D54}$ |
| $L_{C393}$ | $R^{D17}$ | $R^{D55}$ |
| $L_{C394}$ | $R^{D17}$ | $R^{D58}$ |
| $L_{C395}$ | $R^{D17}$ | $R^{D59}$ |
| $L_{C396}$ | $R^{D17}$ | $R^{D78}$ |
| $L_{C397}$ | $R^{D17}$ | $R^{D79}$ |
| $L_{C398}$ | $R^{D17}$ | $R^{D81}$ |
| $L_{C399}$ | $R^{D17}$ | $R^{D87}$ |
| $L_{C400}$ | $R^{D17}$ | $R^{D88}$ |
| $L_{C401}$ | $R^{D17}$ | $R^{D89}$ |
| $L_{C402}$ | $R^{D17}$ | $R^{D93}$ |
| $L_{C403}$ | $R^{D17}$ | $R^{D116}$ |
| $L_{C404}$ | $R^{D17}$ | $R^{D117}$ |
| $L_{C405}$ | $R^{D17}$ | $R^{D118}$ |
| $L_{C406}$ | $R^{D17}$ | $R^{D119}$ |
| $L_{C407}$ | $R^{D17}$ | $R^{D120}$ |
| $L_{C408}$ | $R^{D17}$ | $R^{D133}$ |
| $L_{C409}$ | $R^{D17}$ | $R^{D134}$ |
| $L_{C410}$ | $R^{D17}$ | $R^{D135}$ |
| $L_{C411}$ | $R^{D17}$ | $R^{D136}$ |
| $L_{C412}$ | $R^{D17}$ | $R^{D143}$ |
| $L_{C413}$ | $R^{D17}$ | $R^{D144}$ |

-continued

| $L_{Cj}$ | $R^{201}$ | $R^{202}$ |
|---|---|---|
| $L_{C414}$ | $R^{D17}$ | $R^{D145}$ |
| $L_{C415}$ | $R^{D17}$ | $R^{D146}$ |
| $L_{C416}$ | $R^{D17}$ | $R^{D147}$ |
| $L_{C417}$ | $R^{D17}$ | $R^{D149}$ |
| $L_{C418}$ | $R^{D17}$ | $R^{D151}$ |
| $L_{C419}$ | $R^{D17}$ | $R^{D154}$ |
| $L_{C420}$ | $R^{D17}$ | $R^{D155}$ |
| $L_{C421}$ | $R^{D17}$ | $R^{D161}$ |
| $L_{C422}$ | $R^{D17}$ | $R^{D175}$ |
| $L_{C423}$ | $R^{D50}$ | $R^{D3}$ |
| $L_{C424}$ | $R^{D50}$ | $R^{D5}$ |
| $L_{C425}$ | $R^{D50}$ | $R^{D18}$ |
| $L_{C426}$ | $R^{D50}$ | $R^{D20}$ |
| $L_{C427}$ | $R^{D50}$ | $R^{D22}$ |
| $L_{C428}$ | $R^{D50}$ | $R^{D37}$ |
| $L_{C429}$ | $R^{D50}$ | $R^{D40}$ |
| $L_{C430}$ | $R^{D50}$ | $R^{D41}$ |
| $L_{C431}$ | $R^{D50}$ | $R^{D42}$ |
| $L_{C432}$ | $R^{D50}$ | $R^{D43}$ |
| $L_{C433}$ | $R^{D50}$ | $R^{D48}$ |
| $L_{C434}$ | $R^{D50}$ | $R^{D49}$ |
| $L_{C435}$ | $R^{D50}$ | $R^{D54}$ |
| $L_{C436}$ | $R^{D50}$ | $R^{D55}$ |
| $L_{C437}$ | $R^{D50}$ | $R^{D58}$ |
| $L_{C438}$ | $R^{D50}$ | $R^{D59}$ |
| $L_{C439}$ | $R^{D50}$ | $R^{D78}$ |
| $L_{C440}$ | $R^{D50}$ | $R^{D79}$ |
| $L_{C441}$ | $R^{D50}$ | $R^{D81}$ |
| $L_{C442}$ | $R^{D50}$ | $R^{D87}$ |
| $L_{C443}$ | $R^{D50}$ | $R^{D88}$ |
| $L_{C444}$ | $R^{D50}$ | $R^{D89}$ |
| $L_{C445}$ | $R^{D50}$ | $R^{D93}$ |
| $L_{C446}$ | $R^{D50}$ | $R^{D116}$ |
| $L_{C447}$ | $R^{D50}$ | $R^{D117}$ |
| $L_{C448}$ | $R^{D50}$ | $R^{D118}$ |
| $L_{C449}$ | $R^{D50}$ | $R^{D119}$ |
| $L_{C450}$ | $R^{D50}$ | $R^{D120}$ |
| $L_{C451}$ | $R^{D50}$ | $R^{D133}$ |
| $L_{C452}$ | $R^{D50}$ | $R^{D134}$ |
| $L_{C453}$ | $R^{D50}$ | $R^{D135}$ |
| $L_{C454}$ | $R^{D50}$ | $R^{D136}$ |
| $L_{C455}$ | $R^{D50}$ | $R^{D143}$ |
| $L_{C456}$ | $R^{D50}$ | $R^{D144}$ |
| $L_{C457}$ | $R^{D50}$ | $R^{D145}$ |
| $L_{C458}$ | $R^{D50}$ | $R^{D146}$ |
| $L_{C459}$ | $R^{D50}$ | $R^{D147}$ |
| $L_{C460}$ | $R^{D50}$ | $R^{D149}$ |
| $L_{C461}$ | $R^{D50}$ | $R^{D151}$ |
| $L_{C462}$ | $R^{D50}$ | $R^{D154}$ |
| $L_{C463}$ | $R^{D50}$ | $R^{D155}$ |
| $L_{C464}$ | $R^{D50}$ | $R^{D161}$ |
| $L_{C465}$ | $R^{D50}$ | $R^{D175}$ |
| $L_{C466}$ | $R^{D55}$ | $R^{D3}$ |
| $L_{C467}$ | $R^{D55}$ | $R^{D5}$ |
| $L_{C468}$ | $R^{D55}$ | $R^{D18}$ |
| $L_{C469}$ | $R^{D55}$ | $R^{D20}$ |
| $L_{C470}$ | $R^{D55}$ | $R^{D22}$ |
| $L_{C471}$ | $R^{D55}$ | $R^{D37}$ |
| $L_{C472}$ | $R^{D55}$ | $R^{D40}$ |
| $L_{C473}$ | $R^{D55}$ | $R^{D41}$ |
| $L_{C474}$ | $R^{D55}$ | $R^{D42}$ |
| $L_{C475}$ | $R^{D55}$ | $R^{D43}$ |
| $L_{C476}$ | $R^{D55}$ | $R^{D48}$ |
| $L_{C477}$ | $R^{D55}$ | $R^{D49}$ |
| $L_{C478}$ | $R^{D55}$ | $R^{D54}$ |
| $L_{C479}$ | $R^{D55}$ | $R^{D58}$ |
| $L_{C480}$ | $R^{D55}$ | $R^{D59}$ |
| $L_{C481}$ | $R^{D55}$ | $R^{D78}$ |
| $L_{C482}$ | $R^{D55}$ | $R^{D79}$ |
| $L_{C483}$ | $R^{D55}$ | $R^{D81}$ |
| $L_{C484}$ | $R^{D55}$ | $R^{D87}$ |
| $L_{C485}$ | $R^{D55}$ | $R^{D88}$ |
| $L_{C486}$ | $R^{D55}$ | $R^{D89}$ |
| $L_{C487}$ | $R^{D55}$ | $R^{D93}$ |
| $L_{C488}$ | $R^{D55}$ | $R^{D116}$ |
| $L_{C489}$ | $R^{D55}$ | $R^{D117}$ |
| $L_{C490}$ | $R^{D55}$ | $R^{D118}$ |

-continued

| $L_{Cj}$ | $R^{201}$ | $R^{202}$ |
|---|---|---|
| $L_{C491}$ | $R^{D55}$ | $R^{D119}$ |
| $L_{C492}$ | $R^{D55}$ | $R^{D120}$ |
| $L_{C493}$ | $R^{D55}$ | $R^{D133}$ |
| $L_{C494}$ | $R^{D55}$ | $R^{D134}$ |
| $L_{C495}$ | $R^{D55}$ | $R^{D135}$ |
| $L_{C496}$ | $R^{D55}$ | $R^{D136}$ |
| $L_{C497}$ | $R^{D55}$ | $R^{D143}$ |
| $L_{C498}$ | $R^{D55}$ | $R^{D144}$ |
| $L_{C499}$ | $R^{D55}$ | $R^{D145}$ |
| $L_{C500}$ | $R^{D55}$ | $R^{D146}$ |
| $L_{C501}$ | $R^{D55}$ | $R^{D147}$ |
| $L_{C502}$ | $R^{D55}$ | $R^{D149}$ |
| $L_{C503}$ | $R^{D55}$ | $R^{D151}$ |
| $L_{C504}$ | $R^{D55}$ | $R^{D154}$ |
| $L_{C505}$ | $R^{D55}$ | $R^{D155}$ |
| $L_{C506}$ | $R^{D55}$ | $R^{D161}$ |
| $L_{C507}$ | $R^{D55}$ | $R^{D175}$ |
| $L_{C508}$ | $R^{D116}$ | $R^{D3}$ |
| $L_{C509}$ | $R^{D116}$ | $R^{D5}$ |
| $L_{C510}$ | $R^{D116}$ | $R^{D17}$ |
| $L_{C511}$ | $R^{D116}$ | $R^{D18}$ |
| $L_{C512}$ | $R^{D116}$ | $R^{D20}$ |
| $L_{C513}$ | $R^{D116}$ | $R^{D22}$ |
| $L_{C514}$ | $R^{D116}$ | $R^{D37}$ |
| $L_{C515}$ | $R^{D116}$ | $R^{D40}$ |
| $L_{C516}$ | $R^{D116}$ | $R^{D41}$ |
| $L_{C517}$ | $R^{D116}$ | $R^{D42}$ |
| $L_{C518}$ | $R^{D116}$ | $R^{D43}$ |
| $L_{C519}$ | $R^{D116}$ | $R^{D48}$ |
| $L_{C520}$ | $R^{D116}$ | $R^{D49}$ |
| $L_{C521}$ | $R^{D116}$ | $R^{D54}$ |
| $L_{C522}$ | $R^{D116}$ | $R^{D58}$ |
| $L_{C523}$ | $R^{D116}$ | $R^{D59}$ |
| $L_{C524}$ | $R^{D116}$ | $R^{D78}$ |
| $L_{C525}$ | $R^{D116}$ | $R^{D79}$ |
| $L_{C526}$ | $R^{D116}$ | $R^{D81}$ |
| $L_{C527}$ | $R^{D116}$ | $R^{D87}$ |
| $L_{C528}$ | $R^{D116}$ | $R^{D88}$ |
| $L_{C529}$ | $R^{D116}$ | $R^{D89}$ |
| $L_{C530}$ | $R^{D116}$ | $R^{D93}$ |
| $L_{C531}$ | $R^{D116}$ | $R^{D117}$ |
| $L_{C532}$ | $R^{D116}$ | $R^{D118}$ |
| $L_{C533}$ | $R^{D116}$ | $R^{D119}$ |
| $L_{C534}$ | $R^{D116}$ | $R^{D120}$ |
| $L_{C535}$ | $R^{D116}$ | $R^{D133}$ |
| $L_{C536}$ | $R^{D116}$ | $R^{D134}$ |
| $L_{C537}$ | $R^{D116}$ | $R^{D135}$ |
| $L_{C538}$ | $R^{D116}$ | $R^{D136}$ |
| $L_{C539}$ | $R^{D116}$ | $R^{D143}$ |
| $L_{C540}$ | $R^{D116}$ | $R^{D144}$ |
| $L_{C541}$ | $R^{D116}$ | $R^{D145}$ |
| $L_{C542}$ | $R^{D116}$ | $R^{D146}$ |
| $L_{C543}$ | $R^{D116}$ | $R^{D147}$ |
| $L_{C544}$ | $R^{D116}$ | $R^{D149}$ |
| $L_{C545}$ | $R^{D116}$ | $R^{D151}$ |
| $L_{C546}$ | $R^{D116}$ | $R^{D154}$ |
| $L_{C547}$ | $R^{D116}$ | $R^{D155}$ |
| $L_{C548}$ | $R^{D116}$ | $R^{D161}$ |
| $L_{C549}$ | $R^{D116}$ | $R^{D175}$ |
| $L_{C550}$ | $R^{D143}$ | $R^{D3}$ |
| $L_{C551}$ | $R^{D143}$ | $R^{D5}$ |
| $L_{C552}$ | $R^{D143}$ | $R^{D17}$ |
| $L_{C553}$ | $R^{D143}$ | $R^{D18}$ |
| $L_{C554}$ | $R^{D143}$ | $R^{D20}$ |
| $L_{C555}$ | $R^{D143}$ | $R^{D22}$ |
| $L_{C556}$ | $R^{D143}$ | $R^{D37}$ |
| $L_{C557}$ | $R^{D143}$ | $R^{D40}$ |
| $L_{C558}$ | $R^{D143}$ | $R^{D41}$ |
| $L_{C559}$ | $R^{D143}$ | $R^{D42}$ |
| $L_{C560}$ | $R^{D143}$ | $R^{D43}$ |
| $L_{C561}$ | $R^{D143}$ | $R^{D48}$ |
| $L_{C562}$ | $R^{D143}$ | $R^{D49}$ |
| $L_{C563}$ | $R^{D143}$ | $R^{D54}$ |
| $L_{C564}$ | $R^{D143}$ | $R^{D58}$ |
| $L_{C565}$ | $R^{D143}$ | $R^{D59}$ |
| $L_{C566}$ | $R^{D143}$ | $R^{D78}$ |
| $L_{C567}$ | $R^{D143}$ | $R^{D79}$ |

-continued

| $L_{Cj}$ | $R^{201}$ | $R^{202}$ |
|---|---|---|
| $L_{C568}$ | $R^{D143}$ | $R^{D81}$ |
| $L_{C569}$ | $R^{D143}$ | $R^{D87}$ |
| $L_{C570}$ | $R^{D143}$ | $R^{D88}$ |
| $L_{C571}$ | $R^{D143}$ | $R^{D89}$ |
| $L_{C572}$ | $R^{D143}$ | $R^{D93}$ |
| $L_{C573}$ | $R^{D143}$ | $R^{D116}$ |
| $L_{C574}$ | $R^{D143}$ | $R^{D117}$ |
| $L_{C575}$ | $R^{D143}$ | $R^{D118}$ |
| $L_{C576}$ | $R^{D143}$ | $R^{D119}$ |
| $L_{C577}$ | $R^{D143}$ | $R^{D120}$ |
| $L_{C578}$ | $R^{D143}$ | $R^{D133}$ |
| $L_{C579}$ | $R^{D143}$ | $R^{D134}$ |
| $L_{C580}$ | $R^{D143}$ | $R^{D135}$ |
| $L_{C581}$ | $R^{D143}$ | $R^{D136}$ |
| $L_{C582}$ | $R^{D143}$ | $R^{D144}$ |
| $L_{C583}$ | $R^{D143}$ | $R^{D145}$ |
| $L_{C584}$ | $R^{D143}$ | $R^{D146}$ |
| $L_{C585}$ | $R^{D143}$ | $R^{D147}$ |
| $L_{C586}$ | $R^{D143}$ | $R^{D149}$ |
| $L_{C587}$ | $R^{D143}$ | $R^{D151}$ |
| $L_{C588}$ | $R^{D143}$ | $R^{D154}$ |
| $L_{C589}$ | $R^{D143}$ | $R^{D155}$ |
| $L_{C590}$ | $R^{D143}$ | $R^{D161}$ |
| $L_{C591}$ | $R^{D143}$ | $R^{D175}$ |
| $L_{C592}$ | $R^{D144}$ | $R^{D3}$ |
| $L_{C593}$ | $R^{D144}$ | $R^{D5}$ |
| $L_{C594}$ | $R^{D144}$ | $R^{D17}$ |
| $L_{C595}$ | $R^{D144}$ | $R^{D18}$ |
| $L_{C596}$ | $R^{D144}$ | $R^{D20}$ |
| $L_{C597}$ | $R^{D144}$ | $R^{D22}$ |
| $L_{C598}$ | $R^{D144}$ | $R^{D37}$ |
| $L_{C599}$ | $R^{D144}$ | $R^{D40}$ |
| $L_{C600}$ | $R^{D144}$ | $R^{D41}$ |
| $L_{C601}$ | $R^{D144}$ | $R^{D42}$ |
| $L_{C602}$ | $R^{D144}$ | $R^{D43}$ |
| $L_{C603}$ | $R^{D144}$ | $R^{D48}$ |
| $L_{C604}$ | $R^{D144}$ | $R^{D49}$ |
| $L_{C605}$ | $R^{D144}$ | $R^{D54}$ |
| $L_{C606}$ | $R^{D144}$ | $R^{D58}$ |
| $L_{C607}$ | $R^{D144}$ | $R^{D59}$ |
| $L_{C608}$ | $R^{D144}$ | $R^{D78}$ |
| $L_{C609}$ | $R^{D144}$ | $R^{D79}$ |
| $L_{C610}$ | $R^{D144}$ | $R^{D81}$ |
| $L_{C611}$ | $R^{D144}$ | $R^{D87}$ |
| $L_{C612}$ | $R^{D144}$ | $R^{D88}$ |
| $L_{C613}$ | $R^{D144}$ | $R^{D89}$ |
| $L_{C614}$ | $R^{D144}$ | $R^{D93}$ |
| $L_{C615}$ | $R^{D144}$ | $R^{D116}$ |
| $L_{C616}$ | $R^{D144}$ | $R^{D117}$ |
| $L_{C617}$ | $R^{D144}$ | $R^{D118}$ |
| $L_{C618}$ | $R^{D144}$ | $R^{D119}$ |
| $L_{C619}$ | $R^{D144}$ | $R^{D120}$ |
| $L_{C620}$ | $R^{D144}$ | $R^{D133}$ |
| $L_{C621}$ | $R^{D144}$ | $R^{D134}$ |
| $L_{C622}$ | $R^{D144}$ | $R^{D135}$ |
| $L_{C623}$ | $R^{D144}$ | $R^{D136}$ |
| $L_{C624}$ | $R^{D144}$ | $R^{D145}$ |
| $L_{C625}$ | $R^{D144}$ | $R^{D146}$ |
| $L_{C626}$ | $R^{D144}$ | $R^{D147}$ |
| $L_{C627}$ | $R^{D144}$ | $R^{D149}$ |
| $L_{C628}$ | $R^{D144}$ | $R^{D151}$ |
| $L_{C629}$ | $R^{D144}$ | $R^{D154}$ |
| $L_{C630}$ | $R^{D144}$ | $R^{D155}$ |
| $L_{C631}$ | $R^{D144}$ | $R^{D161}$ |
| $L_{C632}$ | $R^{D144}$ | $R^{D175}$ |
| $L_{C633}$ | $R^{D145}$ | $R^{D3}$ |
| $L_{C634}$ | $R^{D145}$ | $R^{D5}$ |
| $L_{C635}$ | $R^{D145}$ | $R^{D17}$ |
| $L_{C636}$ | $R^{D145}$ | $R^{D18}$ |
| $L_{C637}$ | $R^{D145}$ | $R^{D20}$ |
| $L_{C638}$ | $R^{D145}$ | $R^{D22}$ |
| $L_{C639}$ | $R^{D145}$ | $R^{D37}$ |
| $L_{C640}$ | $R^{D145}$ | $R^{D40}$ |
| $L_{C641}$ | $R^{D145}$ | $R^{D41}$ |
| $L_{C642}$ | $R^{D145}$ | $R^{D42}$ |
| $L_{C643}$ | $R^{D145}$ | $R^{D43}$ |
| $L_{C644}$ | $R^{D145}$ | $R^{D48}$ |

-continued

| $L_{Cj}$ | $R^{201}$ | $R^{202}$ |
|---|---|---|
| $L_{C645}$ | $R^{D145}$ | $R^{D49}$ |
| $L_{C646}$ | $R^{D145}$ | $R^{D54}$ |
| $L_{C647}$ | $R^{D145}$ | $R^{D58}$ |
| $L_{C648}$ | $R^{D145}$ | $R^{D59}$ |
| $L_{C649}$ | $R^{D145}$ | $R^{D78}$ |
| $L_{C650}$ | $R^{D145}$ | $R^{D79}$ |
| $L_{C651}$ | $R^{D145}$ | $R^{D81}$ |
| $L_{C652}$ | $R^{D145}$ | $R^{D87}$ |
| $L_{C653}$ | $R^{D145}$ | $R^{D88}$ |
| $L_{C654}$ | $R^{D145}$ | $R^{D89}$ |
| $L_{C655}$ | $R^{D145}$ | $R^{D93}$ |
| $L_{C656}$ | $R^{D145}$ | $R^{D116}$ |
| $L_{C657}$ | $R^{D145}$ | $R^{D117}$ |
| $L_{C658}$ | $R^{D145}$ | $R^{D118}$ |
| $L_{C659}$ | $R^{D145}$ | $R^{D119}$ |
| $L_{C660}$ | $R^{D145}$ | $R^{D120}$ |
| $L_{C661}$ | $R^{D145}$ | $R^{D133}$ |
| $L_{C662}$ | $R^{D145}$ | $R^{D134}$ |
| $L_{C663}$ | $R^{D145}$ | $R^{D135}$ |
| $L_{C664}$ | $R^{D145}$ | $R^{D136}$ |
| $L_{C665}$ | $R^{D145}$ | $R^{D146}$ |
| $L_{C666}$ | $R^{D145}$ | $R^{D147}$ |
| $L_{C667}$ | $R^{D145}$ | $R^{D149}$ |
| $L_{C668}$ | $R^{D145}$ | $R^{D151}$ |
| $L_{C669}$ | $R^{D145}$ | $R^{D154}$ |
| $L_{C670}$ | $R^{D145}$ | $R^{D155}$ |
| $L_{C671}$ | $R^{D145}$ | $R^{D161}$ |
| $L_{C672}$ | $R^{D145}$ | $R^{D175}$ |
| $L_{C673}$ | $R^{D146}$ | $R^{D3}$ |
| $L_{C674}$ | $R^{D146}$ | $R^{D5}$ |
| $L_{C675}$ | $R^{D146}$ | $R^{D17}$ |
| $L_{C676}$ | $R^{D146}$ | $R^{D18}$ |
| $L_{C677}$ | $R^{D146}$ | $R^{D20}$ |
| $L_{C678}$ | $R^{D146}$ | $R^{D22}$ |
| $L_{C679}$ | $R^{D146}$ | $R^{D37}$ |
| $L_{C680}$ | $R^{D146}$ | $R^{D40}$ |
| $L_{C681}$ | $R^{D146}$ | $R^{D41}$ |
| $L_{C682}$ | $R^{D146}$ | $R^{D42}$ |
| $L_{C683}$ | $R^{D146}$ | $R^{D43}$ |
| $L_{C684}$ | $R^{D146}$ | $R^{D48}$ |
| $L_{C685}$ | $R^{D146}$ | $R^{D49}$ |
| $L_{C686}$ | $R^{D146}$ | $R^{D54}$ |
| $L_{C687}$ | $R^{D146}$ | $R^{D58}$ |
| $L_{C688}$ | $R^{D146}$ | $R^{D59}$ |
| $L_{C689}$ | $R^{D146}$ | $R^{D78}$ |
| $L_{C690}$ | $R^{D146}$ | $R^{D79}$ |
| $L_{C691}$ | $R^{D146}$ | $R^{D81}$ |
| $L_{C692}$ | $R^{D146}$ | $R^{D87}$ |
| $L_{C693}$ | $R^{D146}$ | $R^{D88}$ |
| $L_{C694}$ | $R^{D146}$ | $R^{D89}$ |
| $L_{C695}$ | $R^{D146}$ | $R^{D93}$ |
| $L_{C696}$ | $R^{D146}$ | $R^{D117}$ |
| $L_{C697}$ | $R^{D146}$ | $R^{D118}$ |
| $L_{C698}$ | $R^{D146}$ | $R^{D119}$ |
| $L_{C699}$ | $R^{D146}$ | $R^{D120}$ |
| $L_{C700}$ | $R^{D146}$ | $R^{D133}$ |
| $L_{C701}$ | $R^{D146}$ | $R^{D134}$ |
| $L_{C702}$ | $R^{D146}$ | $R^{D135}$ |
| $L_{C703}$ | $R^{D146}$ | $R^{D136}$ |
| $L_{C704}$ | $R^{D146}$ | $R^{D146}$ |
| $L_{C705}$ | $R^{D146}$ | $R^{D147}$ |
| $L_{C706}$ | $R^{D146}$ | $R^{D149}$ |
| $L_{C707}$ | $R^{D146}$ | $R^{D151}$ |
| $L_{C708}$ | $R^{D146}$ | $R^{D154}$ |
| $L_{C709}$ | $R^{D146}$ | $R^{D155}$ |
| $L_{C710}$ | $R^{D146}$ | $R^{D161}$ |
| $L_{C711}$ | $R^{D146}$ | $R^{D175}$ |
| $L_{C712}$ | $R^{D133}$ | $R^{D3}$ |
| $L_{C713}$ | $R^{D133}$ | $R^{D5}$ |
| $L_{C714}$ | $R^{D133}$ | $R^{D3}$ |
| $L_{C715}$ | $R^{D133}$ | $R^{D18}$ |
| $L_{C716}$ | $R^{D133}$ | $R^{D20}$ |
| $L_{C717}$ | $R^{D133}$ | $R^{D22}$ |
| $L_{C718}$ | $R^{D133}$ | $R^{D37}$ |
| $L_{C719}$ | $R^{D133}$ | $R^{D40}$ |
| $L_{C720}$ | $R^{D133}$ | $R^{D41}$ |
| $L_{C721}$ | $R^{D133}$ | $R^{D42}$ |

-continued

| $L_{Cj}$ | $R^{201}$ | $R^{202}$ |
|---|---|---|
| $L_{C722}$ | $R^{D133}$ | $R^{D43}$ |
| $L_{C723}$ | $R^{D133}$ | $R^{D48}$ |
| $L_{C724}$ | $R^{D133}$ | $R^{D49}$ |
| $L_{C725}$ | $R^{D133}$ | $R^{D54}$ |
| $L_{C726}$ | $R^{D133}$ | $R^{D58}$ |
| $L_{C727}$ | $R^{D133}$ | $R^{D59}$ |
| $L_{C728}$ | $R^{D133}$ | $R^{D78}$ |
| $L_{C729}$ | $R^{D133}$ | $R^{D79}$ |
| $L_{C730}$ | $R^{D133}$ | $R^{D81}$ |
| $L_{C731}$ | $R^{D133}$ | $R^{D87}$ |
| $L_{C732}$ | $R^{D133}$ | $R^{D88}$ |
| $L_{C733}$ | $R^{D133}$ | $R^{D89}$ |
| $L_{C734}$ | $R^{D133}$ | $R^{D93}$ |
| $L_{C735}$ | $R^{D133}$ | $R^{D117}$ |
| $L_{C736}$ | $R^{D133}$ | $R^{D118}$ |
| $L_{C737}$ | $R^{D133}$ | $R^{D119}$ |
| $L_{C738}$ | $R^{D133}$ | $R^{D120}$ |
| $L_{C739}$ | $R^{D133}$ | $R^{D133}$ |
| $L_{C740}$ | $R^{D133}$ | $R^{D134}$ |
| $L_{C741}$ | $R^{D133}$ | $R^{D135}$ |
| $L_{C742}$ | $R^{D133}$ | $R^{D136}$ |
| $L_{C743}$ | $R^{D133}$ | $R^{D146}$ |
| $L_{C744}$ | $R^{D133}$ | $R^{D147}$ |
| $L_{C745}$ | $R^{D133}$ | $R^{D149}$ |
| $L_{C746}$ | $R^{D133}$ | $R^{D151}$ |
| $L_{C747}$ | $R^{D133}$ | $R^{D154}$ |
| $L_{C748}$ | $R^{D133}$ | $R^{D155}$ |
| $L_{C749}$ | $R^{D133}$ | $R^{D161}$ |
| $L_{C750}$ | $R^{D133}$ | $R^{D175}$ |
| $L_{C751}$ | $R^{D175}$ | $R^{D3}$ |
| $L_{C752}$ | $R^{D175}$ | $R^{D5}$ |
| $L_{C753}$ | $R^{D175}$ | $R^{D18}$ |
| $L_{C754}$ | $R^{D175}$ | $R^{D20}$ |
| $L_{C755}$ | $R^{D175}$ | $R^{D22}$ |
| $L_{C756}$ | $R^{D175}$ | $R^{D37}$ |
| $L_{C757}$ | $R^{D175}$ | $R^{D40}$ |
| $L_{C758}$ | $R^{D175}$ | $R^{D41}$ |
| $L_{C759}$ | $R^{D175}$ | $R^{D42}$ |
| $L_{C760}$ | $R^{D175}$ | $R^{D43}$ |
| $L_{C761}$ | $R^{D175}$ | $R^{D48}$ |
| $L_{C762}$ | $R^{D175}$ | $R^{D49}$ |
| $L_{C763}$ | $R^{D175}$ | $R^{D54}$ |
| $L_{C764}$ | $R^{D175}$ | $R^{D58}$ |
| $L_{C765}$ | $R^{D175}$ | $R^{D59}$ |
| $L_{C766}$ | $R^{D175}$ | $R^{D78}$ |
| $L_{C767}$ | $R^{D175}$ | $R^{D79}$ |
| $L_{C768}$ | $R^{D175}$ | $R^{D81}$ |
| $L_{C769}$ | $R^{D193}$ | $R^{D193}$ |
| $L_{C770}$ | $R^{D194}$ | $R^{D194}$ |
| $L_{C771}$ | $R^{D195}$ | $R^{D195}$ |
| $L_{C772}$ | $R^{D196}$ | $R^{D196}$ |
| $L_{C773}$ | $R^{D197}$ | $R^{D197}$ |
| $L_{C774}$ | $R^{D198}$ | $R^{D198}$ |
| $L_{C775}$ | $R^{D199}$ | $R^{D199}$ |
| $L_{C776}$ | $R^{D200}$ | $R^{D200}$ |
| $L_{C777}$ | $R^{D201}$ | $R^{D201}$ |
| $L_{C778}$ | $R^{D202}$ | $R^{D202}$ |
| $L_{C779}$ | $R^{D203}$ | $R^{D203}$ |
| $L_{C780}$ | $R^{D204}$ | $R^{D204}$ |
| $L_{C781}$ | $R^{D205}$ | $R^{D205}$ |
| $L_{C782}$ | $R^{D206}$ | $R^{D206}$ |
| $L_{C783}$ | $R^{D207}$ | $R^{D207}$ |
| $L_{C784}$ | $R^{D208}$ | $R^{D208}$ |
| $L_{C785}$ | $R^{D209}$ | $R^{D209}$ |
| $L_{C786}$ | $R^{D210}$ | $R^{D210}$ |
| $L_{C787}$ | $R^{D211}$ | $R^{D211}$ |
| $L_{C788}$ | $R^{D212}$ | $R^{D212}$ |
| $L_{C789}$ | $R^{D213}$ | $R^{D213}$ |
| $L_{C790}$ | $R^{D214}$ | $R^{D214}$ |
| $L_{C791}$ | $R^{D215}$ | $R^{D215}$ |
| $L_{C792}$ | $R^{D216}$ | $R^{D216}$ |
| $L_{C793}$ | $R^{D217}$ | $R^{D217}$ |
| $L_{C794}$ | $R^{D218}$ | $R^{D218}$ |
| $L_{C795}$ | $R^{D219}$ | $R^{D219}$ |
| $L_{C796}$ | $R^{D220}$ | $R^{D220}$ |
| $L_{C797}$ | $R^{D221}$ | $R^{D221}$ |
| $L_{C798}$ | $R^{D222}$ | $R^{D222}$ |

-continued

| $L_{Cj}$ | $R^{201}$ | $R^{202}$ |
|---|---|---|
| $L_{C799}$ | $R^{D223}$ | $R^{D223}$ |
| $L_{C800}$ | $R^{D224}$ | $R^{D224}$ |
| $L_{C801}$ | $R^{D225}$ | $R^{D225}$ |
| $L_{C802}$ | $R^{D226}$ | $R^{D226}$ |
| $L_{C803}$ | $R^{D227}$ | $R^{D227}$ |
| $L_{C804}$ | $R^{D228}$ | $R^{D228}$ |
| $L_{C805}$ | $R^{D229}$ | $R^{D229}$ |
| $L_{C806}$ | $R^{D230}$ | $R^{D230}$ |
| $L_{C807}$ | $R^{D231}$ | $R^{D231}$ |
| $L_{C808}$ | $R^{D232}$ | $R^{D232}$ |
| $L_{C809}$ | $R^{D233}$ | $R^{D233}$ |
| $L_{C810}$ | $R^{D234}$ | $R^{D234}$ |
| $L_{C811}$ | $R^{D235}$ | $R^{D235}$ |
| $L_{C812}$ | $R^{D236}$ | $R^{D236}$ |
| $L_{C813}$ | $R^{D237}$ | $R^{D237}$ |
| $L_{C814}$ | $R^{D238}$ | $R^{D238}$ |
| $L_{C815}$ | $R^{D239}$ | $R^{D239}$ |
| $L_{C816}$ | $R^{D240}$ | $R^{D240}$ |
| $L_{C817}$ | $R^{D241}$ | $R^{D241}$ |
| $L_{C818}$ | $R^{D242}$ | $R^{D242}$ |
| $L_{C819}$ | $R^{D243}$ | $R^{D243}$ |
| $L_{C820}$ | $R^{D244}$ | $R^{D244}$ |
| $L_{C821}$ | $R^{D245}$ | $R^{D245}$ |
| $L_{C822}$ | $R^{D246}$ | $R^{D246}$ |
| $L_{C823}$ | $R^{D17}$ | $R^{D193}$ |
| $L_{C824}$ | $R^{D17}$ | $R^{D194}$ |
| $L_{C825}$ | $R^{D17}$ | $R^{D195}$ |
| $L_{C826}$ | $R^{D17}$ | $R^{D196}$ |
| $L_{C827}$ | $R^{D17}$ | $R^{D197}$ |
| $L_{C828}$ | $R^{D17}$ | $R^{D198}$ |
| $L_{C829}$ | $R^{D17}$ | $R^{D199}$ |
| $L_{C830}$ | $R^{D17}$ | $R^{D200}$ |
| $L_{C831}$ | $R^{D17}$ | $R^{D201}$ |
| $L_{C832}$ | $R^{D17}$ | $R^{D202}$ |
| $L_{C833}$ | $R^{D17}$ | $R^{D203}$ |
| $L_{C834}$ | $R^{D17}$ | $R^{D204}$ |
| $L_{C835}$ | $R^{D17}$ | $R^{D205}$ |
| $L_{C836}$ | $R^{D17}$ | $R^{D206}$ |
| $L_{C837}$ | $R^{D17}$ | $R^{D207}$ |
| $L_{C838}$ | $R^{D17}$ | $R^{D208}$ |
| $L_{C839}$ | $R^{D17}$ | $R^{D209}$ |
| $L_{C840}$ | $R^{D17}$ | $R^{D210}$ |
| $L_{C841}$ | $R^{D17}$ | $R^{D211}$ |
| $L_{C842}$ | $R^{D17}$ | $R^{D212}$ |
| $L_{C843}$ | $R^{D17}$ | $R^{D213}$ |
| $L_{C844}$ | $R^{D17}$ | $R^{D214}$ |
| $L_{C845}$ | $R^{D17}$ | $R^{D215}$ |
| $L_{C846}$ | $R^{D17}$ | $R^{D216}$ |
| $L_{C847}$ | $R^{D17}$ | $R^{D217}$ |
| $L_{C848}$ | $R^{D17}$ | $R^{D218}$ |
| $L_{C849}$ | $R^{D17}$ | $R^{D219}$ |
| $L_{C850}$ | $R^{D17}$ | $R^{D220}$ |
| $L_{C851}$ | $R^{D17}$ | $R^{D221}$ |
| $L_{C852}$ | $R^{D17}$ | $R^{D222}$ |
| $L_{C853}$ | $R^{D17}$ | $R^{D223}$ |
| $L_{C854}$ | $R^{D17}$ | $R^{D224}$ |
| $L_{C855}$ | $R^{D17}$ | $R^{D225}$ |
| $L_{C856}$ | $R^{D17}$ | $R^{D226}$ |
| $L_{C857}$ | $R^{D17}$ | $R^{D227}$ |
| $L_{C858}$ | $R^{D17}$ | $R^{D228}$ |
| $L_{C859}$ | $R^{D17}$ | $R^{D229}$ |
| $L_{C860}$ | $R^{D17}$ | $R^{D230}$ |
| $L_{C861}$ | $R^{D17}$ | $R^{D231}$ |
| $L_{C862}$ | $R^{D17}$ | $R^{D232}$ |
| $L_{C863}$ | $R^{D17}$ | $R^{D233}$ |
| $L_{C864}$ | $R^{D17}$ | $R^{D234}$ |
| $L_{C865}$ | $R^{D17}$ | $R^{D235}$ |
| $L_{C866}$ | $R^{D17}$ | $R^{D236}$ |
| $L_{C867}$ | $R^{D17}$ | $R^{D237}$ |
| $L_{C868}$ | $R^{D17}$ | $R^{D238}$ |
| $L_{C869}$ | $R^{D17}$ | $R^{D239}$ |
| $L_{C870}$ | $R^{D17}$ | $R^{D240}$ |
| $L_{C871}$ | $R^{D17}$ | $R^{D241}$ |
| $L_{C872}$ | $R^{D17}$ | $R^{D242}$ |
| $L_{C873}$ | $R^{D17}$ | $R^{D243}$ |
| $L_{C874}$ | $R^{D17}$ | $R^{D244}$ |
| $L_{C875}$ | $R^{D17}$ | $R^{D245}$ |

-continued

| $L_{Cj}$ | $R^{201}$ | $R^{202}$ |
|---|---|---|
| $L_{C876}$ | $R^{D17}$ | $R^{D246}$ |
| $L_{C877}$ | $R^{D17}$ | $R^{D193}$ |
| $L_{C878}$ | $R^{D1}$ | $R^{D194}$ |
| $L_{C879}$ | $R^{D1}$ | $R^{D195}$ |
| $L_{C880}$ | $R^{D1}$ | $R^{D196}$ |
| $L_{C881}$ | $R^{D1}$ | $R^{D197}$ |
| $L_{C882}$ | $R^{D1}$ | $R^{D198}$ |
| $L_{C883}$ | $R^{D1}$ | $R^{D199}$ |
| $L_{C884}$ | $R^{D1}$ | $R^{D200}$ |
| $L_{C885}$ | $R^{D1}$ | $R^{D201}$ |
| $L_{C886}$ | $R^{D1}$ | $R^{D202}$ |
| $L_{C887}$ | $R^{D1}$ | $R^{D203}$ |
| $L_{C888}$ | $R^{D1}$ | $R^{D204}$ |
| $L_{C889}$ | $R^{D1}$ | $R^{D205}$ |
| $L_{C890}$ | $R^{D1}$ | $R^{D206}$ |
| $L_{C891}$ | $R^{D1}$ | $R^{D207}$ |
| $L_{C892}$ | $R^{D1}$ | $R^{D208}$ |
| $L_{C893}$ | $R^{D1}$ | $R^{D209}$ |
| $L_{C894}$ | $R^{D1}$ | $R^{D210}$ |
| $L_{C895}$ | $R^{D1}$ | $R^{D211}$ |
| $L_{C896}$ | $R^{D1}$ | $R^{D212}$ |
| $L_{C897}$ | $R^{D1}$ | $R^{D213}$ |
| $L_{C898}$ | $R^{D1}$ | $R^{D214}$ |
| $L_{C899}$ | $R^{D1}$ | $R^{D215}$ |
| $L_{C900}$ | $R^{D1}$ | $R^{D216}$ |
| $L_{C901}$ | $R^{D1}$ | $R^{D217}$ |
| $L_{C902}$ | $R^{D1}$ | $R^{D218}$ |
| $L_{C903}$ | $R^{D1}$ | $R^{D219}$ |
| $L_{C904}$ | $R^{D1}$ | $R^{D220}$ |
| $L_{C905}$ | $R^{D1}$ | $R^{D221}$ |
| $L_{C906}$ | $R^{D1}$ | $R^{D222}$ |
| $L_{C907}$ | $R^{D1}$ | $R^{D223}$ |
| $L_{C908}$ | $R^{D1}$ | $R^{D224}$ |
| $L_{C909}$ | $R^{D1}$ | $R^{D225}$ |
| $L_{C910}$ | $R^{D1}$ | $R^{D226}$ |
| $L_{C911}$ | $R^{D1}$ | $R^{D227}$ |
| $L_{C912}$ | $R^{D1}$ | $R^{D228}$ |
| $L_{C913}$ | $R^{D1}$ | $R^{D229}$ |
| $L_{C914}$ | $R^{D1}$ | $R^{D230}$ |
| $L_{C915}$ | $R^{D1}$ | $R^{D231}$ |
| $L_{C916}$ | $R^{D1}$ | $R^{D232}$ |
| $L_{C917}$ | $R^{D1}$ | $R^{D233}$ |
| $L_{C918}$ | $R^{D1}$ | $R^{D234}$ |
| $L_{C919}$ | $R^{D1}$ | $R^{D235}$ |
| $L_{C920}$ | $R^{D1}$ | $R^{D236}$ |
| $L_{C921}$ | $R^{D1}$ | $R^{D237}$ |
| $L_{C922}$ | $R^{D1}$ | $R^{D238}$ |
| $L_{C923}$ | $R^{D1}$ | $R^{D239}$ |
| $L_{C924}$ | $R^{D1}$ | $R^{D240}$ |
| $L_{C925}$ | $R^{D1}$ | $R^{D241}$ |
| $L_{C926}$ | $R^{D1}$ | $R^{D242}$ |
| $L_{C927}$ | $R^{D1}$ | $R^{D243}$ |
| $L_{C928}$ | $R^{D1}$ | $R^{D244}$ |
| $L_{C929}$ | $R^{D1}$ | $R^{D245}$ |
| $L_{C930}$ | $R^{D1}$ | $R^{D246}$ |
| $L_{C931}$ | $R^{D50}$ | $R^{D193}$ |
| $L_{C932}$ | $R^{D50}$ | $R^{D194}$ |
| $L_{C933}$ | $R^{D50}$ | $R^{D195}$ |
| $L_{C934}$ | $R^{D50}$ | $R^{D196}$ |
| $L_{C935}$ | $R^{D50}$ | $R^{D197}$ |
| $L_{C936}$ | $R^{D50}$ | $R^{D198}$ |
| $L_{C937}$ | $R^{D50}$ | $R^{D199}$ |
| $L_{C938}$ | $R^{D50}$ | $R^{D200}$ |
| $L_{C939}$ | $R^{D50}$ | $R^{D201}$ |
| $L_{C940}$ | $R^{D50}$ | $R^{D202}$ |
| $L_{C941}$ | $R^{D50}$ | $R^{D203}$ |
| $L_{C942}$ | $R^{D50}$ | $R^{D204}$ |
| $L_{C943}$ | $R^{D50}$ | $R^{D205}$ |
| $L_{C944}$ | $R^{D50}$ | $R^{D206}$ |
| $L_{C945}$ | $R^{D50}$ | $R^{D207}$ |
| $L_{C946}$ | $R^{D50}$ | $R^{D208}$ |
| $L_{C947}$ | $R^{D50}$ | $R^{D209}$ |
| $L_{C948}$ | $R^{D50}$ | $R^{D210}$ |
| $L_{C949}$ | $R^{D50}$ | $R^{D211}$ |
| $L_{C950}$ | $R^{D50}$ | $R^{D212}$ |
| $L_{C951}$ | $R^{D50}$ | $R^{D213}$ |
| $L_{C952}$ | $R^{D50}$ | $R^{D214}$ |

-continued

| $L_{Cj}$ | $R^{201}$ | $R^{202}$ |
|---|---|---|
| $L_{C953}$ | $R^{D50}$ | $R^{D215}$ |
| $L_{C954}$ | $R^{D50}$ | $R^{D216}$ |
| $L_{C955}$ | $R^{D50}$ | $R^{D217}$ |
| $L_{C956}$ | $R^{D50}$ | $R^{D218}$ |
| $L_{C957}$ | $R^{D50}$ | $R^{D219}$ |
| $L_{C958}$ | $R^{D50}$ | $R^{D220}$ |
| $L_{C959}$ | $R^{D50}$ | $R^{D221}$ |
| $L_{C960}$ | $R^{D50}$ | $R^{D222}$ |
| $L_{C961}$ | $R^{D50}$ | $R^{D223}$ |
| $L_{C962}$ | $R^{D50}$ | $R^{D224}$ |
| $L_{C963}$ | $R^{D50}$ | $R^{D225}$ |
| $L_{C964}$ | $R^{D50}$ | $R^{D226}$ |
| $L_{C965}$ | $R^{D50}$ | $R^{D227}$ |
| $L_{C966}$ | $R^{D50}$ | $R^{D228}$ |
| $L_{C967}$ | $R^{D50}$ | $R^{D229}$ |
| $L_{C968}$ | $R^{D50}$ | $R^{D230}$ |
| $L_{C969}$ | $R^{D50}$ | $R^{D231}$ |
| $L_{C970}$ | $R^{D50}$ | $R^{D232}$ |
| $L_{C971}$ | $R^{D50}$ | $R^{D233}$ |
| $L_{C972}$ | $R^{D50}$ | $R^{D234}$ |
| $L_{C973}$ | $R^{D50}$ | $R^{D235}$ |
| $L_{C974}$ | $R^{D50}$ | $R^{D236}$ |
| $L_{C975}$ | $R^{D50}$ | $R^{D237}$ |
| $L_{C976}$ | $R^{D50}$ | $R^{D238}$ |
| $L_{C977}$ | $R^{D50}$ | $R^{D239}$ |
| $L_{C978}$ | $R^{D50}$ | $R^{D240}$ |
| $L_{C979}$ | $R^{D50}$ | $R^{D241}$ |
| $L_{C980}$ | $R^{D50}$ | $R^{D242}$ |
| $L_{C981}$ | $R^{D50}$ | $R^{D243}$ |
| $L_{C982}$ | $R^{D50}$ | $R^{D244}$ |
| $L_{C983}$ | $R^{D50}$ | $R^{D245}$ |
| $L_{C984}$ | $R^{D50}$ | $R^{D246}$ |
| $L_{C985}$ | $R^{D143}$ | $R^{D193}$ |
| $L_{C986}$ | $R^{D4}$ | $R^{D194}$ |
| $L_{C987}$ | $R^{D4}$ | $R^{D195}$ |
| $L_{C988}$ | $R^{D4}$ | $R^{D196}$ |
| $L_{C989}$ | $R^{D4}$ | $R^{D197}$ |
| $L_{C990}$ | $R^{D4}$ | $R^{D198}$ |
| $L_{C991}$ | $R^{D4}$ | $R^{D199}$ |
| $L_{C992}$ | $R^{D4}$ | $R^{D200}$ |
| $L_{C993}$ | $R^{D4}$ | $R^{D201}$ |
| $L_{C994}$ | $R^{D4}$ | $R^{D202}$ |
| $L_{C995}$ | $R^{D4}$ | $R^{D203}$ |
| $L_{C996}$ | $R^{D4}$ | $R^{D204}$ |
| $L_{C997}$ | $R^{D4}$ | $R^{D205}$ |
| $L_{C998}$ | $R^{D4}$ | $R^{D206}$ |
| $L_{C999}$ | $R^{D4}$ | $R^{D207}$ |
| $L_{C1000}$ | $R^{D4}$ | $R^{D208}$ |
| $L_{C1001}$ | $R^{D4}$ | $R^{D209}$ |
| $L_{C1002}$ | $R^{D4}$ | $R^{D210}$ |
| $L_{C1003}$ | $R^{D4}$ | $R^{D211}$ |
| $L_{C1004}$ | $R^{D4}$ | $R^{D212}$ |
| $L_{C1005}$ | $R^{D4}$ | $R^{D213}$ |
| $L_{C1006}$ | $R^{D4}$ | $R^{D214}$ |
| $L_{C1007}$ | $R^{D4}$ | $R^{D215}$ |
| $L_{C1008}$ | $R^{D4}$ | $R^{D216}$ |
| $L_{C1009}$ | $R^{D4}$ | $R^{D217}$ |
| $L_{C1010}$ | $R^{D4}$ | $R^{D218}$ |
| $L_{C1011}$ | $R^{D4}$ | $R^{D219}$ |
| $L_{C1012}$ | $R^{D4}$ | $R^{D220}$ |
| $L_{C1013}$ | $R^{D4}$ | $R^{D221}$ |
| $L_{C1014}$ | $R^{D4}$ | $R^{D222}$ |
| $L_{C1015}$ | $R^{D4}$ | $R^{D223}$ |
| $L_{C1016}$ | $R^{D4}$ | $R^{D224}$ |
| $L_{C1017}$ | $R^{D4}$ | $R^{D225}$ |
| $L_{C1018}$ | $R^{D4}$ | $R^{D226}$ |
| $L_{C1019}$ | $R^{D4}$ | $R^{D227}$ |
| $L_{C1020}$ | $R^{D4}$ | $R^{D228}$ |
| $L_{C1021}$ | $R^{D4}$ | $R^{D229}$ |
| $L_{C1022}$ | $R^{D4}$ | $R^{D230}$ |
| $L_{C1023}$ | $R^{D4}$ | $R^{D231}$ |
| $L_{C1024}$ | $R^{D4}$ | $R^{D232}$ |
| $L_{C1025}$ | $R^{D4}$ | $R^{D233}$ |
| $L_{C1026}$ | $R^{D4}$ | $R^{D234}$ |
| $L_{C1027}$ | $R^{D4}$ | $R^{D235}$ |
| $L_{C1028}$ | $R^{D4}$ | $R^{D236}$ |
| $L_{C1029}$ | $R^{D4}$ | $R^{D237}$ |

-continued

| $L_{Cj}$ | $R^{201}$ | $R^{202}$ |
|---|---|---|
| $L_{C1030}$ | $R^{D4}$ | $R^{D238}$ |
| $L_{C1031}$ | $R^{D4}$ | $R^{D239}$ |
| $L_{C1032}$ | $R^{D4}$ | $R^{D240}$ |
| $L_{C1033}$ | $R^{D4}$ | $R^{D241}$ |
| $L_{C1034}$ | $R^{D4}$ | $R^{D242}$ |
| $L_{C1035}$ | $R^{D4}$ | $R^{D243}$ |
| $L_{C1036}$ | $R^{D4}$ | $R^{D244}$ |
| $L_{C1037}$ | $R^{D4}$ | $R^{D245}$ |
| $L_{C1038}$ | $R^{D4}$ | $R^{D246}$ |
| $L_{C1039}$ | $R^{D145}$ | $R^{D193}$ |
| $L_{C1040}$ | $R^{D145}$ | $R^{D194}$ |
| $L_{C1041}$ | $R^{D145}$ | $R^{D195}$ |
| $L_{C1042}$ | $R^{D145}$ | $R^{D196}$ |
| $L_{C1043}$ | $R^{D145}$ | $R^{D197}$ |
| $L_{C1044}$ | $R^{D145}$ | $R^{D198}$ |
| $L_{C1045}$ | $R^{D145}$ | $R^{D199}$ |
| $L_{C1046}$ | $R^{D145}$ | $R^{D200}$ |
| $L_{C1047}$ | $R^{D145}$ | $R^{D201}$ |
| $L_{C1048}$ | $R^{D145}$ | $R^{D202}$ |
| $L_{C1049}$ | $R^{D145}$ | $R^{D203}$ |
| $L_{C1050}$ | $R^{D145}$ | $R^{D204}$ |
| $L_{C1051}$ | $R^{D145}$ | $R^{D205}$ |
| $L_{C1052}$ | $R^{D145}$ | $R^{D206}$ |
| $L_{C1053}$ | $R^{D145}$ | $R^{D207}$ |
| $L_{C1054}$ | $R^{D145}$ | $R^{D208}$ |
| $L_{C1055}$ | $R^{D145}$ | $R^{D209}$ |
| $L_{C1056}$ | $R^{D145}$ | $R^{D210}$ |
| $L_{C1057}$ | $R^{D145}$ | $R^{D211}$ |
| $L_{C1058}$ | $R^{D145}$ | $R^{D212}$ |
| $L_{C1059}$ | $R^{D145}$ | $R^{D213}$ |
| $L_{C1060}$ | $R^{D145}$ | $R^{D214}$ |
| $L_{C1061}$ | $R^{D145}$ | $R^{D215}$ |
| $L_{C1062}$ | $R^{D145}$ | $R^{D216}$ |
| $L_{C1063}$ | $R^{D145}$ | $R^{D217}$ |
| $L_{C1064}$ | $R^{D145}$ | $R^{D218}$ |
| $L_{C1065}$ | $R^{D145}$ | $R^{D219}$ |
| $L_{C1066}$ | $R^{D145}$ | $R^{D220}$ |
| $L_{C1067}$ | $R^{D145}$ | $R^{D221}$ |
| $L_{C1068}$ | $R^{D145}$ | $R^{D222}$ |
| $L_{C1069}$ | $R^{D145}$ | $R^{D223}$ |
| $L_{C1070}$ | $R^{D145}$ | $R^{D224}$ |
| $L_{C1071}$ | $R^{D145}$ | $R^{D225}$ |
| $L_{C1072}$ | $R^{D145}$ | $R^{D226}$ |
| $L_{C1073}$ | $R^{D145}$ | $R^{D227}$ |
| $L_{C1074}$ | $R^{D145}$ | $R^{D228}$ |
| $L_{C1075}$ | $R^{D145}$ | $R^{D229}$ |
| $L_{C1076}$ | $R^{D145}$ | $R^{D230}$ |
| $L_{C1077}$ | $R^{D145}$ | $R^{D231}$ |
| $L_{C1078}$ | $R^{D145}$ | $R^{D232}$ |
| $L_{C1079}$ | $R^{D145}$ | $R^{D233}$ |
| $L_{C1080}$ | $R^{D145}$ | $R^{D234}$ |
| $L_{C1081}$ | $R^{D145}$ | $R^{D235}$ |
| $L_{C1082}$ | $R^{D145}$ | $R^{D236}$ |
| $L_{C1083}$ | $R^{D145}$ | $R^{D237}$ |
| $L_{C1084}$ | $R^{D145}$ | $R^{D238}$ |
| $L_{C1085}$ | $R^{D145}$ | $R^{D239}$ |
| $L_{C1086}$ | $R^{D145}$ | $R^{D240}$ |
| $L_{C1087}$ | $R^{D145}$ | $R^{D241}$ |
| $L_{C1088}$ | $R^{D145}$ | $R^{D242}$ |
| $L_{C1089}$ | $R^{D145}$ | $R^{D243}$ |
| $L_{C1090}$ | $R^{D145}$ | $R^{D244}$ |
| $L_{C1091}$ | $R^{D145}$ | $R^{D245}$ |
| $L_{C1092}$ | $R^{D145}$ | $R^{D246}$ |
| $L_{C1093}$ | $R^{D9}$ | $R^{D193}$ |
| $L_{C1094}$ | $R^{D9}$ | $R^{D194}$ |
| $L_{C1095}$ | $R^{D9}$ | $R^{D195}$ |
| $L_{C1096}$ | $R^{D9}$ | $R^{D196}$ |
| $L_{C1097}$ | $R^{D9}$ | $R^{D197}$ |
| $L_{C1098}$ | $R^{D9}$ | $R^{D198}$ |
| $L_{C1099}$ | $R^{D9}$ | $R^{D199}$ |
| $L_{C1100}$ | $R^{D9}$ | $R^{D200}$ |
| $L_{C1101}$ | $R^{D9}$ | $R^{D201}$ |
| $L_{C1102}$ | $R^{D9}$ | $R^{D202}$ |
| $L_{C1103}$ | $R^{D9}$ | $R^{D203}$ |
| $L_{C1104}$ | $R^{D9}$ | $R^{D204}$ |
| $L_{C1105}$ | $R^{D9}$ | $R^{D205}$ |
| $L_{C1106}$ | $R^{D9}$ | $R^{D206}$ |

-continued

| $L_{Cj}$ | $R^{201}$ | $R^{202}$ |
|---|---|---|
| $L_{C1107}$ | $R^{D9}$ | $R^{D207}$ |
| $L_{C1108}$ | $R^{D9}$ | $R^{D208}$ |
| $L_{C1109}$ | $R^{D9}$ | $R^{D209}$ |
| $L_{C1110}$ | $R^{D9}$ | $R^{D210}$ |
| $L_{C1111}$ | $R^{D9}$ | $R^{D211}$ |
| $L_{C1112}$ | $R^{D9}$ | $R^{D212}$ |
| $L_{C1113}$ | $R^{D9}$ | $R^{D213}$ |
| $L_{C1114}$ | $R^{D9}$ | $R^{D214}$ |
| $L_{C1115}$ | $R^{D9}$ | $R^{D215}$ |
| $L_{C1116}$ | $R^{D9}$ | $R^{D216}$ |
| $L_{C1117}$ | $R^{D9}$ | $R^{D217}$ |
| $L_{C1118}$ | $R^{D9}$ | $R^{D218}$ |
| $L_{C1119}$ | $R^{D9}$ | $R^{D219}$ |
| $L_{C1120}$ | $R^{D9}$ | $R^{D220}$ |
| $L_{C1121}$ | $R^{D9}$ | $R^{D221}$ |
| $L_{C1122}$ | $R^{D9}$ | $R^{D222}$ |
| $L_{C1123}$ | $R^{D9}$ | $R^{D223}$ |
| $L_{C1124}$ | $R^{D9}$ | $R^{D224}$ |
| $L_{C1125}$ | $R^{D9}$ | $R^{D225}$ |
| $L_{C1126}$ | $R^{D9}$ | $R^{D226}$ |
| $L_{C1127}$ | $R^{D9}$ | $R^{D227}$ |
| $L_{C1128}$ | $R^{D9}$ | $R^{D228}$ |
| $L_{C1129}$ | $R^{D9}$ | $R^{D229}$ |
| $L_{C1130}$ | $R^{D9}$ | $R^{D230}$ |
| $L_{C1131}$ | $R^{D9}$ | $R^{D231}$ |
| $L_{C1132}$ | $R^{D9}$ | $R^{D232}$ |
| $L_{C1133}$ | $R^{D9}$ | $R^{D233}$ |
| $L_{C1134}$ | $R^{D9}$ | $R^{D234}$ |
| $L_{C1135}$ | $R^{D9}$ | $R^{D235}$ |
| $L_{C1136}$ | $R^{D9}$ | $R^{D236}$ |
| $L_{C1137}$ | $R^{D9}$ | $R^{D237}$ |
| $L_{C1138}$ | $R^{D9}$ | $R^{D238}$ |
| $L_{C1139}$ | $R^{D9}$ | $R^{D239}$ |
| $L_{C1140}$ | $R^{D9}$ | $R^{D240}$ |
| $L_{C1141}$ | $R^{D9}$ | $R^{D241}$ |
| $L_{C1142}$ | $R^{D9}$ | $R^{D242}$ |
| $L_{C1143}$ | $R^{D9}$ | $R^{D243}$ |
| $L_{C1144}$ | $R^{D9}$ | $R^{D244}$ |
| $L_{C1145}$ | $R^{D9}$ | $R^{D245}$ |
| $L_{C1146}$ | $R^{D9}$ | $R^{D246}$ |
| $L_{C1147}$ | $R^{D168}$ | $R^{D193}$ |
| $L_{C1148}$ | $R^{D168}$ | $R^{D194}$ |
| $L_{C1149}$ | $R^{D168}$ | $R^{D195}$ |
| $L_{C1150}$ | $R^{D168}$ | $R^{D196}$ |
| $L_{C1151}$ | $R^{D168}$ | $R^{D197}$ |
| $L_{C1152}$ | $R^{D168}$ | $R^{D198}$ |
| $L_{C1153}$ | $R^{D168}$ | $R^{D199}$ |
| $L_{C1154}$ | $R^{D168}$ | $R^{D200}$ |
| $L_{C1155}$ | $R^{D168}$ | $R^{D201}$ |
| $L_{C1156}$ | $R^{D168}$ | $R^{D202}$ |
| $L_{C1157}$ | $R^{D168}$ | $R^{D203}$ |
| $L_{C1158}$ | $R^{D168}$ | $R^{D204}$ |
| $L_{C1159}$ | $R^{D168}$ | $R^{D205}$ |
| $L_{C1160}$ | $R^{D168}$ | $R^{D206}$ |
| $L_{C1161}$ | $R^{D168}$ | $R^{D207}$ |
| $L_{C1162}$ | $R^{D168}$ | $R^{D208}$ |
| $L_{C1163}$ | $R^{D168}$ | $R^{D209}$ |
| $L_{C1164}$ | $R^{D168}$ | $R^{D210}$ |
| $L_{C1165}$ | $R^{D168}$ | $R^{D211}$ |
| $L_{C1166}$ | $R^{D168}$ | $R^{D212}$ |
| $L_{C1167}$ | $R^{D168}$ | $R^{D213}$ |
| $L_{C1168}$ | $R^{D168}$ | $R^{D214}$ |
| $L_{C1169}$ | $R^{D168}$ | $R^{D215}$ |
| $L_{C1170}$ | $R^{D168}$ | $R^{D216}$ |
| $L_{C1171}$ | $R^{D168}$ | $R^{D217}$ |
| $L_{C1172}$ | $R^{D168}$ | $R^{D218}$ |
| $L_{C1173}$ | $R^{D168}$ | $R^{D219}$ |
| $L_{C1174}$ | $R^{D168}$ | $R^{D220}$ |
| $L_{C1175}$ | $R^{D168}$ | $R^{D221}$ |
| $L_{C1176}$ | $R^{D168}$ | $R^{D222}$ |
| $L_{C1177}$ | $R^{D168}$ | $R^{D223}$ |
| $L_{C1178}$ | $R^{D168}$ | $R^{D224}$ |
| $L_{C1179}$ | $R^{D168}$ | $R^{D225}$ |
| $L_{C1180}$ | $R^{D168}$ | $R^{D226}$ |
| $L_{C1181}$ | $R^{D168}$ | $R^{D227}$ |
| $L_{C1182}$ | $R^{D168}$ | $R^{D228}$ |
| $L_{C1183}$ | $R^{D168}$ | $R^{D229}$ |

| $L_{Cj}$ | $R^{201}$ | $R^{202}$ |
|---|---|---|
| $L_{C1184}$ | $R^{D168}$ | $R^{D230}$ |
| $L_{C1185}$ | $R^{D168}$ | $R^{D231}$ |
| $L_{C1186}$ | $R^{D168}$ | $R^{D232}$ |
| $L_{C1187}$ | $R^{D168}$ | $R^{D233}$ |
| $L_{C1188}$ | $R^{D168}$ | $R^{D234}$ |
| $L_{C1189}$ | $R^{D168}$ | $R^{D235}$ |
| $L_{C1190}$ | $R^{D168}$ | $R^{D236}$ |
| $L_{C1191}$ | $R^{D168}$ | $R^{D237}$ |
| $L_{C1192}$ | $R^{D168}$ | $R^{D238}$ |
| $L_{C1193}$ | $R^{D168}$ | $R^{D239}$ |
| $L_{C1194}$ | $R^{D168}$ | $R^{D240}$ |
| $L_{C1195}$ | $R^{D168}$ | $R^{D241}$ |
| $L_{C1196}$ | $R^{D168}$ | $R^{D242}$ |
| $L_{C1197}$ | $R^{D168}$ | $R^{D243}$ |
| $L_{C1198}$ | $R^{D168}$ | $R^{D244}$ |
| $L_{C1199}$ | $R^{D168}$ | $R^{D245}$ |
| $L_{C1200}$ | $R^{D168}$ | $R^{D246}$ |
| $L_{C1201}$ | $R^{D10}$ | $R^{D193}$ |
| $L_{C1202}$ | $R^{D10}$ | $R^{D194}$ |
| $L_{C1203}$ | $R^{D10}$ | $R^{D195}$ |
| $L_{C1204}$ | $R^{D10}$ | $R^{D196}$ |
| $L_{C1205}$ | $R^{D10}$ | $R^{D197}$ |
| $L_{C1206}$ | $R^{D10}$ | $R^{D198}$ |
| $L_{C1207}$ | $R^{D10}$ | $R^{D199}$ |
| $L_{C1208}$ | $R^{D10}$ | $R^{D200}$ |
| $L_{C1209}$ | $R^{D10}$ | $R^{D201}$ |
| $L_{C1210}$ | $R^{D10}$ | $R^{D202}$ |
| $L_{C1211}$ | $R^{D10}$ | $R^{D203}$ |
| $L_{C1212}$ | $R^{D10}$ | $R^{D204}$ |
| $L_{C1213}$ | $R^{D10}$ | $R^{D205}$ |
| $L_{C1214}$ | $R^{D10}$ | $R^{D206}$ |
| $L_{C1215}$ | $R^{D10}$ | $R^{D207}$ |
| $L_{C1216}$ | $R^{D10}$ | $R^{D208}$ |
| $L_{C1217}$ | $R^{D10}$ | $R^{D209}$ |
| $L_{C1218}$ | $R^{D10}$ | $R^{D210}$ |
| $L_{C1219}$ | $R^{D10}$ | $R^{D211}$ |
| $L_{C1220}$ | $R^{D10}$ | $R^{D212}$ |
| $L_{C1221}$ | $R^{D10}$ | $R^{D213}$ |
| $L_{C1222}$ | $R^{D10}$ | $R^{D214}$ |
| $L_{C1223}$ | $R^{D10}$ | $R^{D215}$ |
| $L_{C1224}$ | $R^{D10}$ | $R^{D216}$ |
| $L_{C1225}$ | $R^{D10}$ | $R^{D217}$ |
| $L_{C1226}$ | $R^{D10}$ | $R^{D218}$ |
| $L_{C1227}$ | $R^{D10}$ | $R^{D219}$ |
| $L_{C1228}$ | $R^{D10}$ | $R^{D220}$ |
| $L_{C1229}$ | $R^{D10}$ | $R^{D221}$ |
| $L_{C1230}$ | $R^{D10}$ | $R^{D222}$ |
| $L_{C1231}$ | $R^{D10}$ | $R^{D223}$ |
| $L_{C1232}$ | $R^{D10}$ | $R^{D224}$ |
| $L_{C1233}$ | $R^{D10}$ | $R^{D225}$ |
| $L_{C1234}$ | $R^{D10}$ | $R^{D226}$ |
| $L_{C1235}$ | $R^{D10}$ | $R^{D227}$ |
| $L_{C1236}$ | $R^{D10}$ | $R^{D228}$ |
| $L_{C1237}$ | $R^{D10}$ | $R^{D229}$ |
| $L_{C1238}$ | $R^{D10}$ | $R^{D230}$ |
| $L_{C1239}$ | $R^{D10}$ | $R^{D231}$ |
| $L_{C1240}$ | $R^{D10}$ | $R^{D232}$ |
| $L_{C1241}$ | $R^{D10}$ | $R^{D233}$ |
| $L_{C1242}$ | $R^{D10}$ | $R^{D234}$ |
| $L_{C1243}$ | $R^{D10}$ | $R^{D235}$ |
| $L_{C1244}$ | $R^{D10}$ | $R^{D236}$ |
| $L_{C1245}$ | $R^{D10}$ | $R^{D237}$ |
| $L_{C1246}$ | $R^{D10}$ | $R^{D238}$ |
| $L_{C1247}$ | $R^{D10}$ | $R^{D239}$ |
| $L_{C1248}$ | $R^{D10}$ | $R^{D240}$ |
| $L_{C1249}$ | $R^{D10}$ | $R^{D241}$ |
| $L_{C1250}$ | $R^{D10}$ | $R^{D242}$ |
| $L_{C1251}$ | $R^{D10}$ | $R^{D243}$ |
| $L_{C1252}$ | $R^{D10}$ | $R^{D244}$ |
| $L_{C1253}$ | $R^{D10}$ | $R^{D245}$ |
| $L_{C1254}$ | $R^{D10}$ | $R^{D246}$ |
| $L_{C1255}$ | $R^{D55}$ | $R^{D193}$ |
| $L_{C1256}$ | $R^{D55}$ | $R^{D194}$ |
| $L_{C1257}$ | $R^{D55}$ | $R^{D195}$ |
| $L_{C1258}$ | $R^{D55}$ | $R^{D196}$ |
| $L_{C1259}$ | $R^{D55}$ | $R^{D197}$ |
| $L_{C1260}$ | $R^{D55}$ | $R^{D198}$ |

| $L_{Cj}$ | $R^{201}$ | $R^{202}$ |
|---|---|---|
| $L_{C1261}$ | $R^{D55}$ | $R^{D199}$ |
| $L_{C1262}$ | $R^{D55}$ | $R^{D200}$ |
| $L_{C1263}$ | $R^{D55}$ | $R^{D201}$ |
| $L_{C1264}$ | $R^{D55}$ | $R^{D202}$ |
| $L_{C1265}$ | $R^{D55}$ | $R^{D203}$ |
| $L_{C1266}$ | $R^{D55}$ | $R^{D204}$ |
| $L_{C1267}$ | $R^{D55}$ | $R^{D205}$ |
| $L_{C1268}$ | $R^{D55}$ | $R^{D206}$ |
| $L_{C1269}$ | $R^{D55}$ | $R^{D207}$ |
| $L_{C1270}$ | $R^{D55}$ | $R^{D208}$ |
| $L_{C1271}$ | $R^{D55}$ | $R^{D209}$ |
| $L_{C1272}$ | $R^{D55}$ | $R^{D210}$ |
| $L_{C1273}$ | $R^{D55}$ | $R^{D211}$ |
| $L_{C1274}$ | $R^{D55}$ | $R^{D212}$ |
| $L_{C1275}$ | $R^{D55}$ | $R^{D213}$ |
| $L_{C1276}$ | $R^{D55}$ | $R^{D214}$ |
| $L_{C1277}$ | $R^{D55}$ | $R^{D215}$ |
| $L_{C1278}$ | $R^{D55}$ | $R^{D216}$ |
| $L_{C1279}$ | $R^{D55}$ | $R^{D217}$ |
| $L_{C1280}$ | $R^{D55}$ | $R^{D218}$ |
| $L_{C1281}$ | $R^{D55}$ | $R^{D219}$ |
| $L_{C1282}$ | $R^{D55}$ | $R^{D220}$ |
| $L_{C1283}$ | $R^{D55}$ | $R^{D221}$ |
| $L_{C1284}$ | $R^{D55}$ | $R^{D222}$ |
| $L_{C1285}$ | $R^{D55}$ | $R^{D223}$ |
| $L_{C1286}$ | $R^{D55}$ | $R^{D224}$ |
| $L_{C1287}$ | $R^{D55}$ | $R^{D225}$ |
| $L_{C1288}$ | $R^{D55}$ | $R^{D226}$ |
| $L_{C1289}$ | $R^{D55}$ | $R^{D227}$ |
| $L_{C1290}$ | $R^{D55}$ | $R^{D228}$ |
| $L_{C1291}$ | $R^{D55}$ | $R^{D229}$ |
| $L_{C1292}$ | $R^{D55}$ | $R^{D230}$ |
| $L_{C1293}$ | $R^{D55}$ | $R^{D231}$ |
| $L_{C1294}$ | $R^{D55}$ | $R^{D232}$ |
| $L_{C1295}$ | $R^{D55}$ | $R^{D233}$ |
| $L_{C1296}$ | $R^{D55}$ | $R^{D234}$ |
| $L_{C1297}$ | $R^{D55}$ | $R^{D235}$ |
| $L_{C1298}$ | $R^{D55}$ | $R^{D236}$ |
| $L_{C1299}$ | $R^{D55}$ | $R^{D237}$ |
| $L_{C1300}$ | $R^{D55}$ | $R^{D238}$ |
| $L_{C1301}$ | $R^{D55}$ | $R^{D239}$ |
| $L_{C1302}$ | $R^{D55}$ | $R^{D240}$ |
| $L_{C1303}$ | $R^{D55}$ | $R^{D241}$ |
| $L_{C1304}$ | $R^{D55}$ | $R^{D242}$ |
| $L_{C1305}$ | $R^{D55}$ | $R^{D243}$ |
| $L_{C1306}$ | $R^{D55}$ | $R^{D244}$ |
| $L_{C1307}$ | $R^{D55}$ | $R^{D245}$ |
| $L_{C1308}$ | $R^{D55}$ | $R^{D246}$ |
| $L_{C1309}$ | $R^{D37}$ | $R^{D193}$ |
| $L_{C1310}$ | $R^{D37}$ | $R^{D194}$ |
| $L_{C1311}$ | $R^{D37}$ | $R^{D195}$ |
| $L_{C1312}$ | $R^{D37}$ | $R^{D196}$ |
| $L_{C1313}$ | $R^{D37}$ | $R^{D197}$ |
| $L_{C1314}$ | $R^{D37}$ | $R^{D198}$ |
| $L_{C1315}$ | $R^{D37}$ | $R^{D199}$ |
| $L_{C1316}$ | $R^{D37}$ | $R^{D200}$ |
| $L_{C1317}$ | $R^{D37}$ | $R^{D201}$ |
| $L_{C1318}$ | $R^{D37}$ | $R^{D202}$ |
| $L_{C1319}$ | $R^{D37}$ | $R^{D203}$ |
| $L_{C1320}$ | $R^{D37}$ | $R^{D204}$ |
| $L_{C1321}$ | $R^{D37}$ | $R^{D205}$ |
| $L_{C1322}$ | $R^{D37}$ | $R^{D206}$ |
| $L_{C1323}$ | $R^{D37}$ | $R^{D207}$ |
| $L_{C1324}$ | $R^{D37}$ | $R^{D208}$ |
| $L_{C1325}$ | $R^{D37}$ | $R^{D209}$ |
| $L_{C1326}$ | $R^{D37}$ | $R^{D210}$ |
| $L_{C1327}$ | $R^{D37}$ | $R^{D211}$ |
| $L_{C1328}$ | $R^{D37}$ | $R^{D212}$ |
| $L_{C1329}$ | $R^{D37}$ | $R^{D213}$ |
| $L_{C1330}$ | $R^{D37}$ | $R^{D214}$ |
| $L_{C1331}$ | $R^{D37}$ | $R^{D215}$ |
| $L_{C1332}$ | $R^{D37}$ | $R^{D216}$ |
| $L_{C1333}$ | $R^{D37}$ | $R^{D217}$ |
| $L_{C1334}$ | $R^{D37}$ | $R^{D218}$ |
| $L_{C1335}$ | $R^{D37}$ | $R^{D219}$ |
| $L_{C1336}$ | $R^{D37}$ | $R^{D220}$ |
| $L_{C1337}$ | $R^{D37}$ | $R^{D221}$ |

-continued

| $L_{Cj}$ | $R^{201}$ | $R^{202}$ |
|---|---|---|
| $L_{C1338}$ | $R^{D37}$ | $R^{D222}$ |
| $L_{C1339}$ | $R^{D37}$ | $R^{D223}$ |
| $L_{C1340}$ | $R^{D37}$ | $R^{D224}$ |
| $L_{C1341}$ | $R^{D37}$ | $R^{D225}$ |
| $L_{C1342}$ | $R^{D37}$ | $R^{D226}$ |
| $L_{C1343}$ | $R^{D37}$ | $R^{D227}$ |
| $L_{C1344}$ | $R^{D37}$ | $R^{D228}$ |
| $L_{C1345}$ | $R^{D37}$ | $R^{D229}$ |
| $L_{C1346}$ | $R^{D37}$ | $R^{D230}$ |
| $L_{C1347}$ | $R^{D37}$ | $R^{D231}$ |
| $L_{C1348}$ | $R^{D37}$ | $R^{D232}$ |
| $L_{C1349}$ | $R^{D37}$ | $R^{D233}$ |
| $L_{C1350}$ | $R^{D37}$ | $R^{D234}$ |
| $L_{C1351}$ | $R^{D37}$ | $R^{D235}$ |
| $L_{C1352}$ | $R^{D37}$ | $R^{D236}$ |
| $L_{C1353}$ | $R^{D37}$ | $R^{D237}$ |
| $L_{C1354}$ | $R^{D37}$ | $R^{D238}$ |
| $L_{C1355}$ | $R^{D37}$ | $R^{D239}$ |
| $L_{C1356}$ | $R^{D37}$ | $R^{D240}$ |
| $L_{C1357}$ | $R^{D37}$ | $R^{D241}$ |
| $L_{C1358}$ | $R^{D37}$ | $R^{D242}$ |
| $L_{C1359}$ | $R^{D37}$ | $R^{D243}$ |
| $L_{C1360}$ | $R^{D37}$ | $R^{D244}$ |
| $L_{C1361}$ | $R^{D37}$ | $R^{D245}$ |
| $L_{C1362}$ | $R^{D37}$ | $R^{D246}$ |
| $L_{C1363}$ | $R^{D143}$ | $R^{D193}$ |
| $L_{C1364}$ | $R^{D143}$ | $R^{D194}$ |
| $L_{C1365}$ | $R^{D143}$ | $R^{D195}$ |
| $L_{C1366}$ | $R^{D143}$ | $R^{D196}$ |
| $L_{C1367}$ | $R^{D143}$ | $R^{D197}$ |
| $L_{C1368}$ | $R^{D143}$ | $R^{D198}$ |
| $L_{C1369}$ | $R^{D143}$ | $R^{D199}$ |
| $L_{C1370}$ | $R^{D143}$ | $R^{D200}$ |
| $L_{C1371}$ | $R^{D143}$ | $R^{D201}$ |
| $L_{C1372}$ | $R^{D143}$ | $R^{D202}$ |
| $L_{C1373}$ | $R^{D143}$ | $R^{D203}$ |
| $L_{C1374}$ | $R^{D143}$ | $R^{D204}$ |
| $L_{C1375}$ | $R^{D143}$ | $R^{D205}$ |
| $L_{C1376}$ | $R^{D143}$ | $R^{D206}$ |
| $L_{C1377}$ | $R^{D143}$ | $R^{D207}$ |
| $L_{C1378}$ | $R^{D143}$ | $R^{D208}$ |
| $L_{C1379}$ | $R^{D143}$ | $R^{D209}$ |
| $L_{C1380}$ | $R^{D143}$ | $R^{D210}$ |
| $L_{C1381}$ | $R^{D143}$ | $R^{D211}$ |
| $L_{C1382}$ | $R^{D143}$ | $R^{D212}$ |
| $L_{C1383}$ | $R^{D143}$ | $R^{D213}$ |
| $L_{C1384}$ | $R^{D143}$ | $R^{D214}$ |
| $L_{C1385}$ | $R^{D143}$ | $R^{D215}$ |
| $L_{C1386}$ | $R^{D143}$ | $R^{D216}$ |
| $L_{C1387}$ | $R^{D143}$ | $R^{D217}$ |
| $L_{C1388}$ | $R^{D143}$ | $R^{D218}$ |
| $L_{C1389}$ | $R^{D143}$ | $R^{D219}$ |
| $L_{C1390}$ | $R^{D143}$ | $R^{D220}$ |
| $L_{C1391}$ | $R^{D143}$ | $R^{D221}$ |
| $L_{C1392}$ | $R^{D143}$ | $R^{D222}$ |
| $L_{C1393}$ | $R^{D143}$ | $R^{D223}$ |
| $L_{C1394}$ | $R^{D143}$ | $R^{D224}$ |
| $L_{C1395}$ | $R^{D143}$ | $R^{D225}$ |
| $L_{C1396}$ | $R^{D143}$ | $R^{D226}$ |
| $L_{C1397}$ | $R^{D143}$ | $R^{D227}$ |
| $L_{C1398}$ | $R^{D143}$ | $R^{D228}$ |
| $L_{C1399}$ | $R^{D143}$ | $R^{D229}$ |
| $L_{C1400}$ | $R^{D143}$ | $R^{D230}$ |
| $L_{C1401}$ | $R^{D143}$ | $R^{D231}$ |
| $L_{C1402}$ | $R^{D143}$ | $R^{D232}$ |
| $L_{C1403}$ | $R^{D143}$ | $R^{D233}$ |
| $L_{C1404}$ | $R^{D143}$ | $R^{D234}$ |
| $L_{C1405}$ | $R^{D143}$ | $R^{D235}$ |
| $L_{C1406}$ | $R^{D143}$ | $R^{D236}$ |
| $L_{C1407}$ | $R^{D143}$ | $R^{D237}$ |
| $L_{C1408}$ | $R^{D143}$ | $R^{D238}$ |
| $L_{C1409}$ | $R^{D143}$ | $R^{D239}$ |
| $L_{C1410}$ | $R^{D143}$ | $R^{D240}$ |
| $L_{C1411}$ | $R^{D143}$ | $R^{D241}$ |
| $L_{C1412}$ | $R^{D143}$ | $R^{D242}$ |
| $L_{C1413}$ | $R^{D143}$ | $R^{D243}$ |
| $L_{C1414}$ | $R^{D143}$ | $R^{D244}$ |

-continued

| $L_{Cj}$ | $R^{201}$ | $R^{202}$ |
|---|---|---|
| $L_{C1415}$ | $R^{D143}$ | $R^{D245}$ |
| $L_{C1416}$ | $R^{D143}$ | $R^{D246}$ |

wherein $R^{D1}$ to $R^{D246}$ have the following structures as defined as follows:

$R^{D1}$

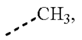

$R^{D2}$

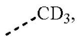

$R^{D3}$

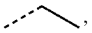

$R^{D4}$

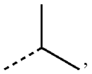

$R^{D5}$

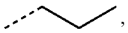

$R^{D6}$

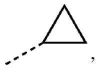

$R^{D7}$

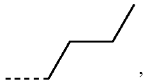

$R^{D8}$

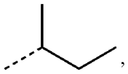

$R^{D9}$

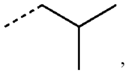

$R^{D10}$

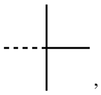

$R^{D11}$

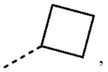

$R^{D12}$

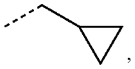

$R^{D13}$

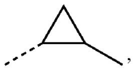

$R^{D14}$

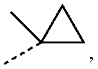

$R^{D15}$

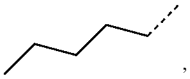

$R^{D16}$

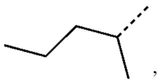

-continued
$R^{D17}$
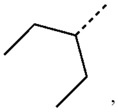
,
$R^{D18}$
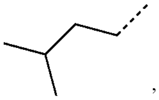
,
$R^{D19}$
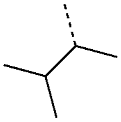
,
$R^{D20}$
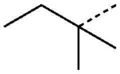
,
$R^{D21}$
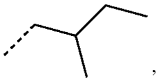
,
$R^{D22}$
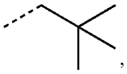
,
$R^{D23}$
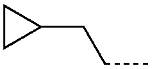
,
$R^{D24}$
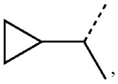
,
$R^{D25}$
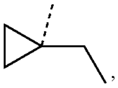
,
$R^{D26}$
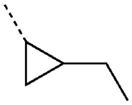
,
$R^{D27}$
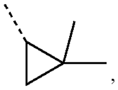
,
$R^{D28}$
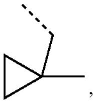
,
$R^{D29}$
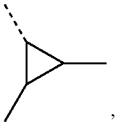
,
$R^{D30}$
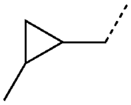
,
-continued
$R^{D31}$
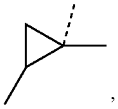
,
$R^{D32}$
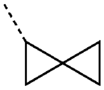
,
$R^{D33}$
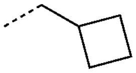
,
$R^{D34}$
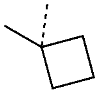
,
$R^{D35}$
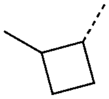
,
$R^{D36}$
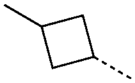
,
$R^{D37}$
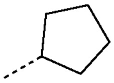
,
$R^{D38}$
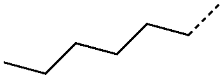
,
$R^{D39}$
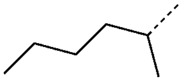
,
$R^{D40}$
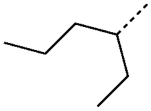
,
$R^{D41}$
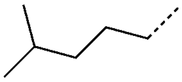
,
$R^{D42}$
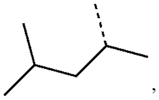
,
$R^{D43}$
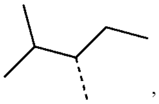
,
$R^{D44}$
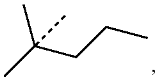
, -continued
$R^{D45}$
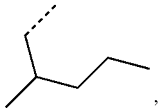,
$R^{D46}$
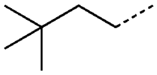,
$R^{D47}$
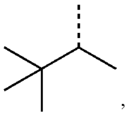,
$R^{D48}$
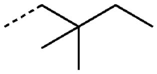,
$R^{D49}$
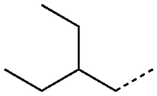,
$R^{D50}$
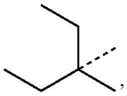,
$R^{D51}$
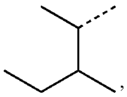,
$R^{D52}$
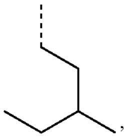,
$R^{D53}$
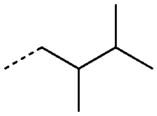,
$R^{D54}$
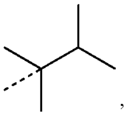,
$R^{D55}$
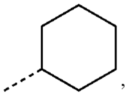,
$R^{D56}$
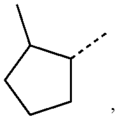,
$R^{D57}$
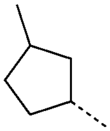,
-continued
$R^{D58}$
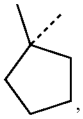,
$R^{D59}$
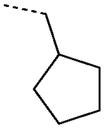,
$R^{D60}$
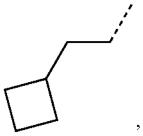,
$R^{D61}$
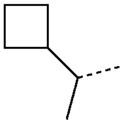,
$R^{D62}$
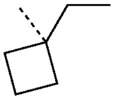,
$R^{D63}$
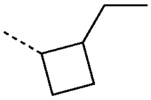,
$R^{D64}$
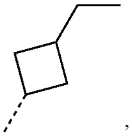,
$R^{D65}$
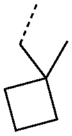,
$R^{D66}$
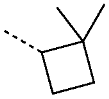,
$R^{D67}$
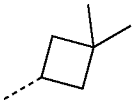,
$R^{D68}$
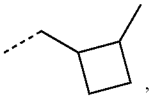,
$R^{D69}$
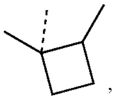, -continued
$R^{D70}$
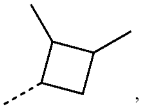,
$R^{D71}$
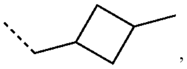,
$R^{D72}$
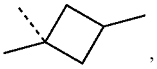,
$R^{D73}$
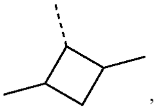,
$R^{D74}$
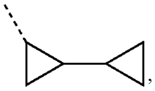,
$R^{D75}$
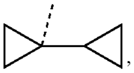,
$R^{D76}$
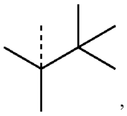,
$R^{D77}$
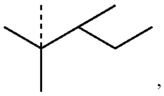,
$R^{D78}$
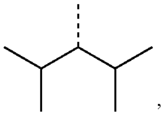,
$R^{D79}$
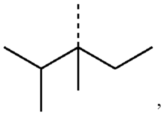,
$R^{D80}$
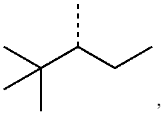,
$R^{D81}$
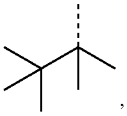,
$R^{D82}$
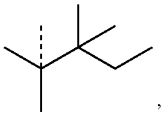,
-continued
$R^{D83}$
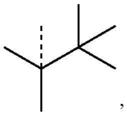,
$R^{D84}$
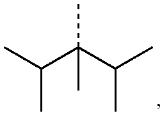,
$R^{D85}$
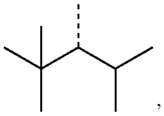,
$R^{D86}$
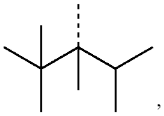,
$R^{D87}$
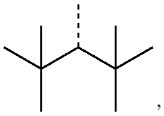,
$R^{D88}$
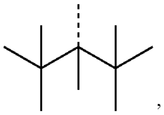,
$R^{D89}$
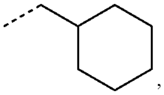,
$R^{D90}$
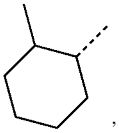,
$R^{D91}$
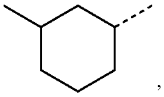,
$R^{D92}$
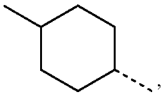,
$R^{D93}$
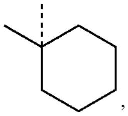,
$R^{D94}$
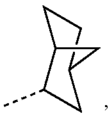, -continued
$R^{D95}$
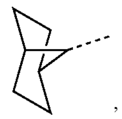
,
$R^{D96}$
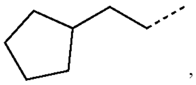
,
$R^{D97}$
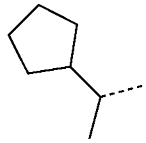
,
$R^{D98}$
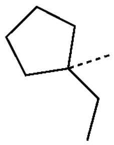
,
$R^{D99}$
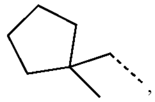
,
$R^{D100}$
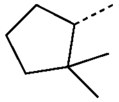
,
$R^{D101}$
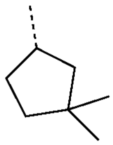
,
$R^{D102}$
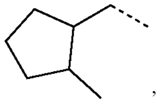
,
$R^{D103}$
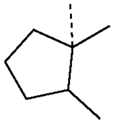
,
$R^{D104}$
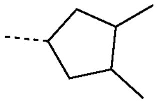
,
$R^{D105}$
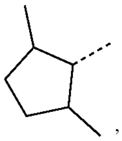
,
-continued
$R^{D106}$
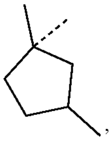
,
$R^{D107}$
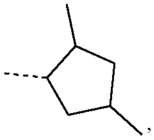
,
$R^{D108}$
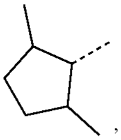
,
$R^{D109}$
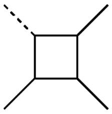
,
$R^{D110}$
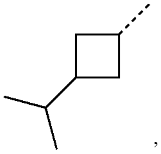
,
$R^{D111}$
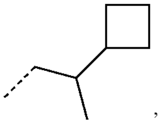
,
$R^{D112}$
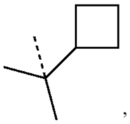
,
$R^{D113}$
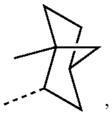
,
$R^{D114}$
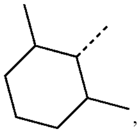
,
$R^{D115}$
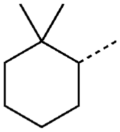
,
$R^{D116}$
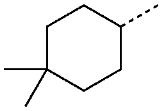
, -continued
$R^{D117}$
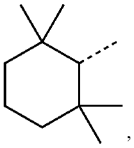
,
$R^{D118}$
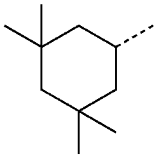
,
$R^{D119}$
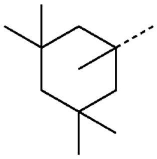
,
$R^{D120}$
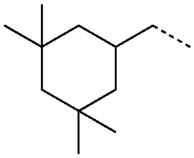
,
$R^{D121}$
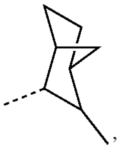
,
$R^{D122}$
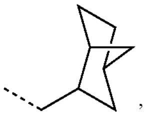
,
$R^{D123}$
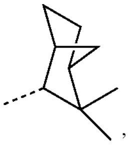
,
$R^{D124}$
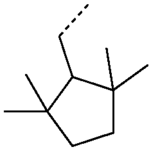
,
$R^{D125}$
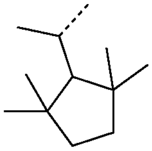
,
-continued
$R^{D126}$
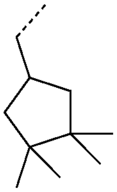
,
$R^{D127}$
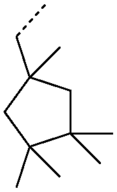
,
$R^{D128}$
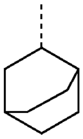
,
$R^{D129}$
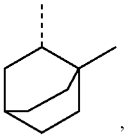
,
$R^{D130}$
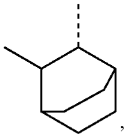
,
$R^{D131}$
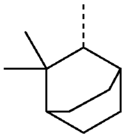
,
$R^{D132}$
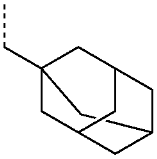
,
$R^{D133}$
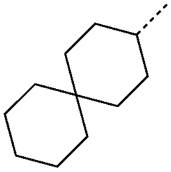
,
$R^{D134}$
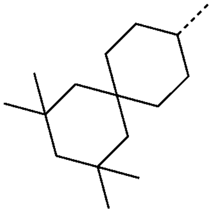
, -continued
$R^{D135}$
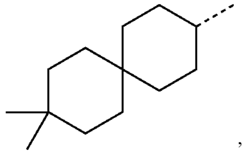
,
$R^{D136}$
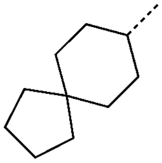
,
$R^{D137}$
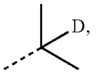
$R^{D138}$
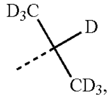
$R^{D139}$
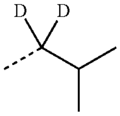
,
$R^{D140}$
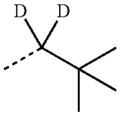
,
$R^{D141}$
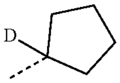
,
$R^{D142}$
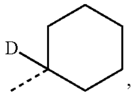
,
$R^{D143}$
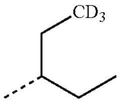
,
$R^{D144}$
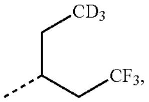
$R^{D145}$
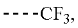
$R^{D146}$
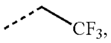
$R^{D147}$
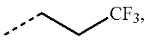
$R^{D148}$
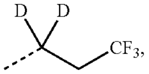
-continued
$R^{D149}$
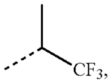
$R^{D150}$
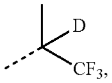
$R^{D151}$
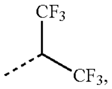
$R^{D152}$
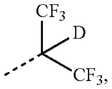
$R^{D153}$
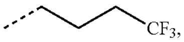
$R^{D154}$
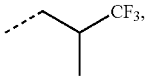
$R^{D155}$
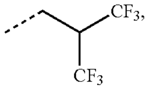
$R^{D156}$
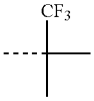
$R^{D157}$
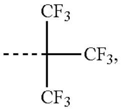
$R^{D158}$
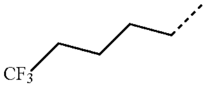
,
$R^{D159}$
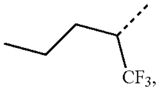
$R^{D160}$
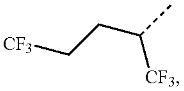
$R^{D161}$
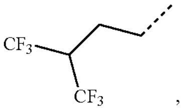
,
$R^{D162}$
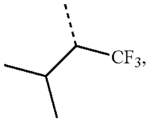
$R^{D163}$
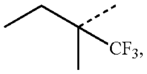

-continued
$R^{D164}$
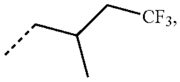
$R^{D165}$
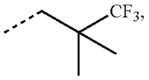
$R^{D166}$
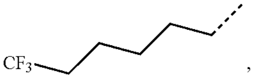
$R^{D167}$
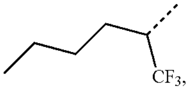
$R^{D168}$
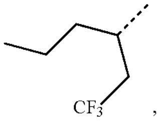
$R^{D169}$
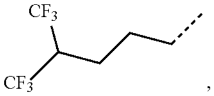
$R^{D170}$
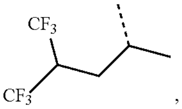
$R^{D171}$
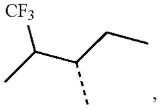
$R^{D172}$
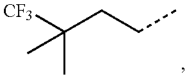
$R^{D173}$
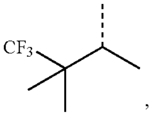
$R^{D174}$
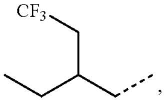
$R^{D175}$
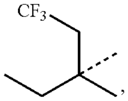
$R^{D176}$
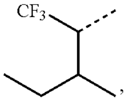
-continued
$R^{D177}$
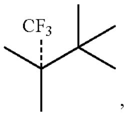
$R^{D178}$
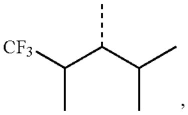
$R^{D179}$
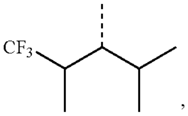
$R^{D180}$
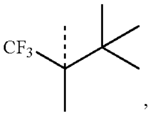
$R^{D181}$
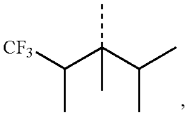
$R^{D182}$
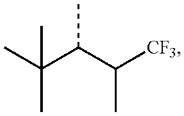
$R^{D183}$
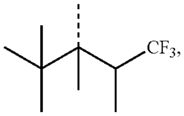
$R^{D184}$
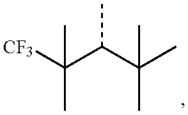
$R^{D185}$
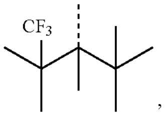
$R^{D186}$
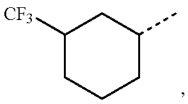
$R^{D187}$
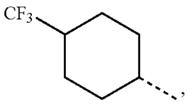
$R^{D188}$
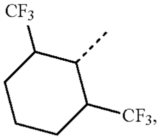

-continued
$R^{D189}$
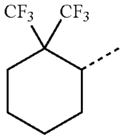
,
$R^{D190}$
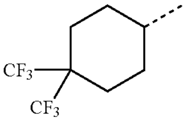
,
$R^{D191}$
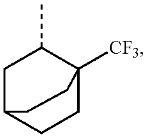
$R^{D192}$
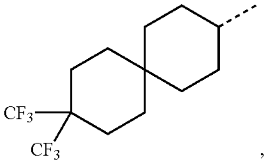
,
$R^{D193}$
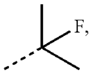
$R^{D194}$
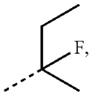
$R^{D195}$
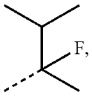
$R^{D196}$
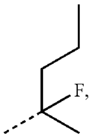
$R^{D197}$
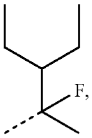
$R^{D198}$
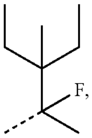
$R^{D199}$
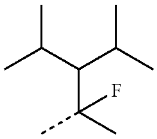
,
-continued
$R^{D200}$
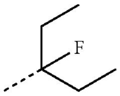
,
$R^{D201}$
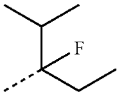
,
$R^{D202}$
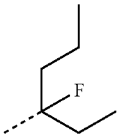
,
$R^{D203}$
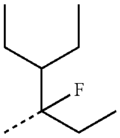
,
$R^{D204}$
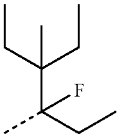
,
$R^{D205}$
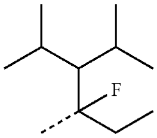
,
$R^{D206}$
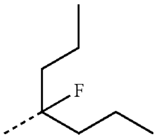
,
$R^{D207}$
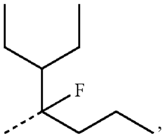
,
$R^{D208}$
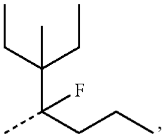
,
$R^{D209}$
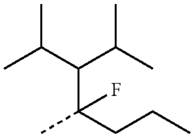
,
$R^{D210}$
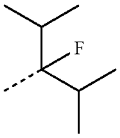
, -continued
$R^{D211}$
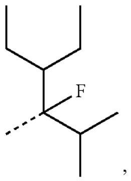
$R^{D212}$
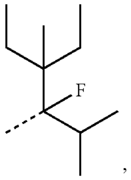
$R^{D213}$
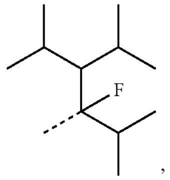
$R^{D214}$
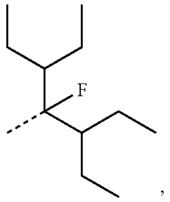
$R^{D215}$
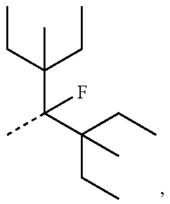
$R^{D216}$
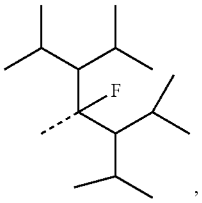
$R^{D217}$
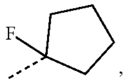
$R^{D218}$
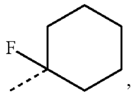
$R^{D219}$
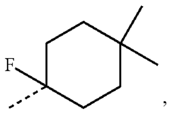
-continued
$R^{D220}$
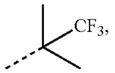
$R^{D221}$
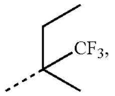
$R^{D222}$
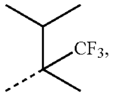
$R^{D223}$
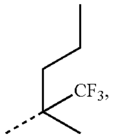
$R^{D224}$
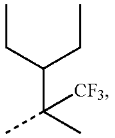
$R^{D225}$
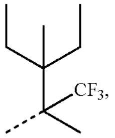
$R^{D226}$
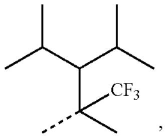
$R^{D227}$
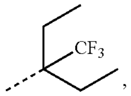
$R^{D228}$
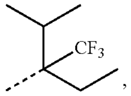
$R^{D229}$
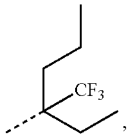
$R^{D230}$
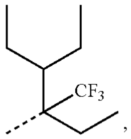
$R^{D231}$
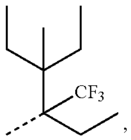

-continued $R^{D232}$

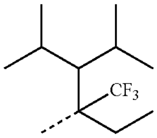, $R^{D233}$

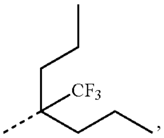, $R^{D234}$

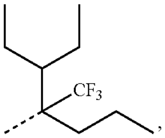, $R^{D235}$

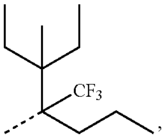, $R^{D236}$

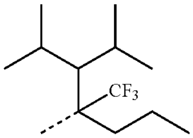, $R^{D237}$

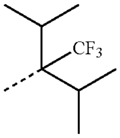, $R^{D238}$

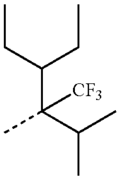, $R^{D239}$

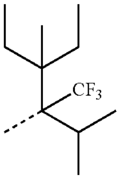, $R^{D240}$

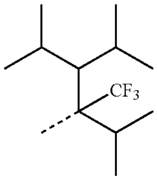,

-continued $R^{D241}$

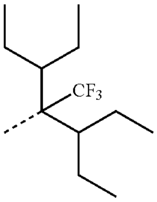, $R^{D242}$

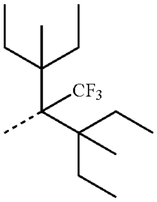, $R^{D243}$

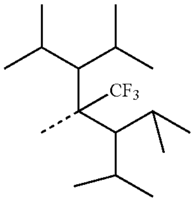, $R^{D244}$

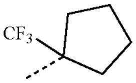, $R^{D245}$

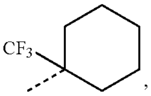, and $R^{D246}$

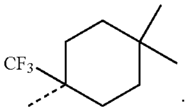.

In further embodiments, the compound is selected from the group consisting of only those compounds whose $L_{Bk}$ corresponds to one of the following: $L_{B1}$, $L_{B2}$, $L_{B18}$, $L_{B28}$, $L_{B38}$, $L_{B108}$, $L_{B118}$, $L_{B122}$, $L_{B124}$, $L_{B126}$, $L_{B128}$, $L_{B130}$, $L_{B132}$, $L_{B134}$, $L_{B136}$, $L_{B138}$, $L_{B140}$, $L_{B142}$, $L_{B144}$, $L_{B156}$, $L_{B158}$, $L_{B160}$, $L_{B162}$, $L_{B164}$, $L_{B168}$, $L_{B172}$, $L_{B175}$, $L_{B204}$, $L_{B206}$, $L_{B214}$, $L_{B216}$, $L_{B218}$, $L_{B220}$, $L_{B222}$, $L_{B231}$, $L_{B233}$, $L_{B235}$, $L_{B237}$, $L_{B240}$, $L_{B242}$, $L_{B244}$, $L_{B246}$, $L_{B248}$, $L_{B250}$, $L_{B252}$, $L_{B254}$, $L_{B256}$, $L_{B258}$, $L_{B260}$, $L_{B262}$ and $L_{B264}$, $L_{B265}$, $L_{B266}$, $L_{B267}$, $L_{B268}$, $L_{B269}$, and $L_{B270}$.

In further embodiments, the compound is selected from the group consisting of only those compounds whose $L_{Bk}$ corresponds to one of the following: $L_{B1}$, $L_{B2}$, $L_{B18}$, $L_{B28}$, $L_{B38}$, $L_{B108}$, $L_{B118}$, $L_{B122}$, $L_{B126}$, $L_{B128}$, $L_{B132}$, $L_{B136}$, $L_{B138}$, $L_{B142}$, $L_{B156}$, $L_{B162}$, $L_{B204}$, $L_{B206}$, $L_{B214}$, $L_{B216}$, $L_{B218}$, $L_{B220}$, $L_{B231}$, $L_{B233}$, $L_{B237}$, $L_{B264}$, $L_{B265}$, $L_{B266}$, $L_{B267}$, $L_{B268}$, $L_{B269}$, and $L_{B270}$.

In further embodiments, the compound is selected from the group consisting of only those compounds having $L_{Cj-I}$ or $L_{Cj-II}$ ligand whose corresponding $R^{201}$ and $R^{202}$ are defined to be one of the following structures: $R^{D1}$, $R^{D3}$, $R^{D4}$, $R^{D5}$, $R^{D9}$, $R^{D10}$, $R^{D17}$, $R^{D18}$, $R^{D20}$, $R^{D22}$, $R^{D37}$, $R^{D40}$, $R^{D41}$, $R^{D42}$, $R^{D43}$, $R^{D48}$, $R^{D49}$, $R^{D50}$, $R^{D54}$, $R^{D5}$, $R^{D58}$, $R^{D59}$, $R^{D78}$, $R^{D79}$, $R^{D81}$, $R^{D87}$, $R^{D88}$, $R^{D89}$, $R^{D93}$, $R^{D116}$, $R^{D117}$, $R^{D118}$, $R^{D119}$, $R^{D120}$, $R^{D133}$, $R^{D134}$, $R^{D135}$, $R^{D136}$, $R^{D143}$, $R^{D144}$, $R^{D145}$, $R^{D146}$, $R^{D147}$, $R^{D149}$, $R^{D151}$, $R^{D154}$, $R^{D115}$, $R^{D161}$, $R^{D175}$, $R^{D190}$, $R^{D193}$, $R^{D200}$, $R^{D201}$, $R^{D206}$, $R^{D210}$, $R^{D214}$, $R^{D21}$, $R^{D216}$, $R^{D218}$, $R^{D219}$, $R^{D220}$, $R^{D227}$, $R^{D237}$, $R^{D241}$, $R^{D242}$, $R^{D245}$, and $R^{D246}$.

In further embodiments, the compound is selected from the group consisting of only those compounds having $L_{Cj-I}$ or $L_{Cj-II}$ ligand whose corresponding $R^{201}$ and $R^{202}$ are defined to be one of selected from the following structures $R^{D1}$, $R^{D3}$, $R^{D4}$, $R^{D5}$, $R^{D9}$, $R^{D10}$, $R^{D17}$, $R^{D22}$, $R^{D43}$, $R^{D50}$, $R^{D78}$, $R^{D116}$, $R^{D118}$, $R^{D133}$, $R^{D134}$, $R^{D135}$, $R^{D136}$, $R^{D143}$, $R^{D144}$, $R^{D145}$, $R^{D146}$, $R^{D149}$, $R^{D151}$, $R^{D154}$, $R^{D155}$, $R^{D190}$, $R^{D193}$, $R^{D200}$, $R^{D201}$, $R^{D206}$, $R^{D210}$, $R^{D214}$, $R^{D215}$, $R^{D216}$, $R^{D218}$, $R^{D219}$, $R^{D220}$, $R^{D227}$, $R^{D237}$, $R^{D241}$, $R^{D242}$, $R^{D245}$, and $R^{D246}$.

In further embodiments, the compound is selected from the group consisting of only those compounds having one of the following structures for the $L_{Cj-I}$ ligand as defined as follows:

$L_{C1-I}$

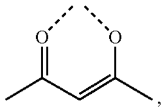

$L_{C4-I}$

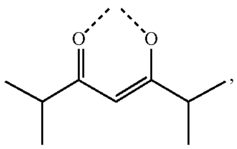

$L_{C9-I}$

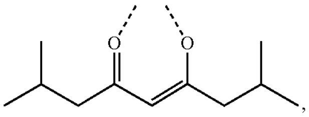

$L_{C10-I}$

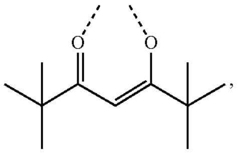

$L_{C17-I}$

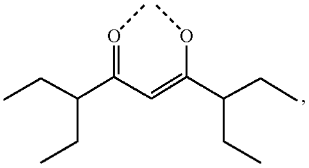

$L_{C55-I}$

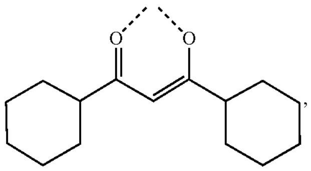

$L_{C116-I}$

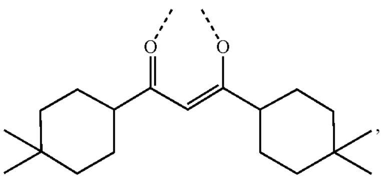

-continued $L_{C50-I}$

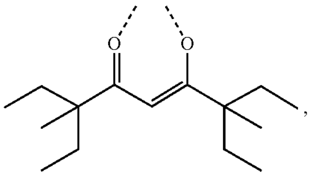

$L_{C190-I}$

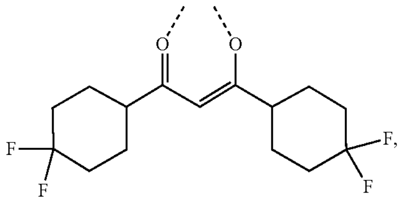

$L_{C144-I}$

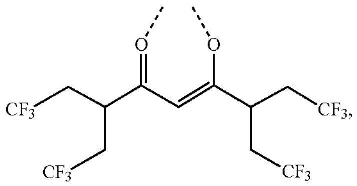

$L_{C145-I}$

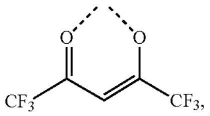

$L_{C143-I}$

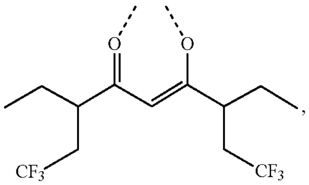

$L_{C232-I}$

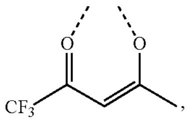

$L_{C279-I}$

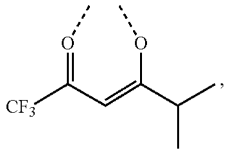

$L_{C325-I}$

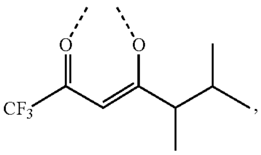

$L_{C414-I}$

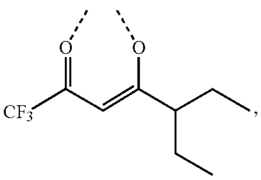

-continued
$L_{C457\text{-}I}$
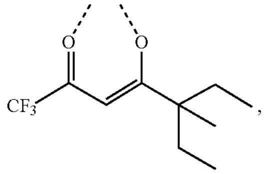
,
$L_{C230\text{-}I}$
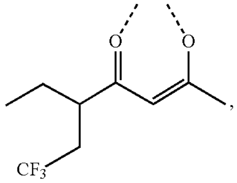
,
$L_{C277\text{-}I}$
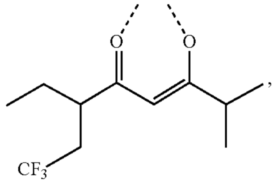
,
$L_{C412\text{-}I}$
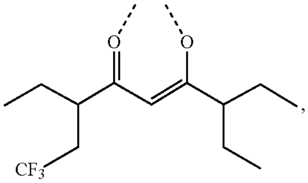
,
$L_{C231\text{-}I}$
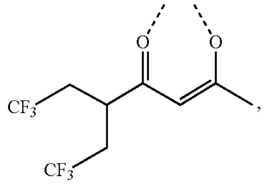
,
$L_{C278\text{-}I}$
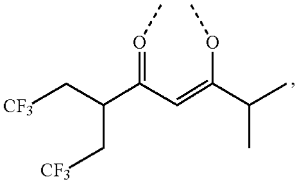
,
$L_{C413\text{-}I}$
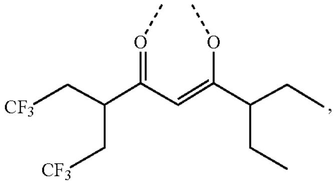
,
$L_{C985\text{-}I}$
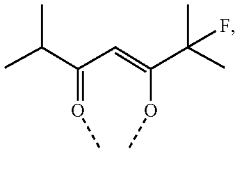
,
-continued
$L_{C1093\text{-}I}$
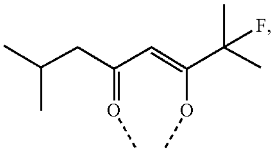
,
$L_{C823\text{-}I}$
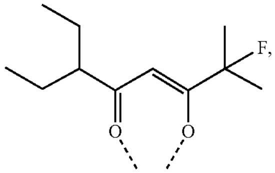
,
$L_{C1039\text{-}I}$
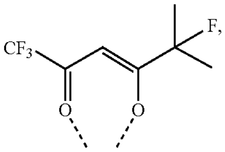
,
$L_{C1147\text{-}I}$
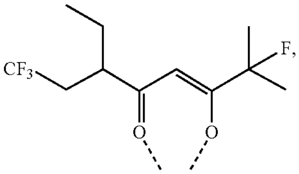
,
$L_{C1012\text{-}I}$
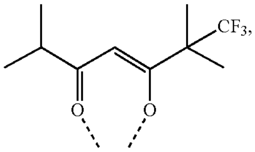
,
$L_{C1120\text{-}I}$
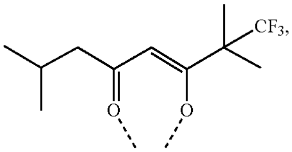
,
$L_{C850\text{-}I}$
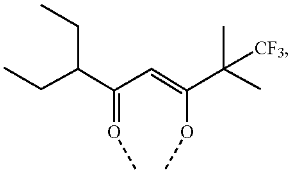
,
$L_{C1066\text{-}I}$
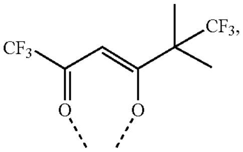
,
$L_{C1174\text{-}I}$
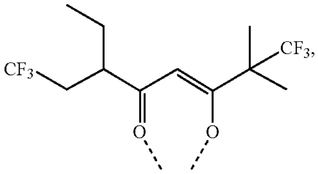
, -continued
$L_{C769\text{-}I}$
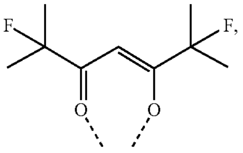
$L_{C1201\text{-}I}$
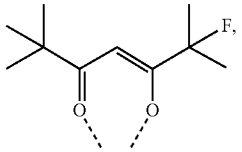
$L_{C796\text{-}I}$
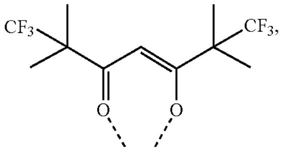
$L_{C1228\text{-}I}$
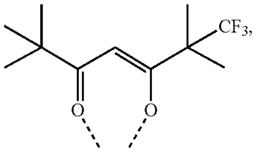
$L_{C803\text{-}I}$
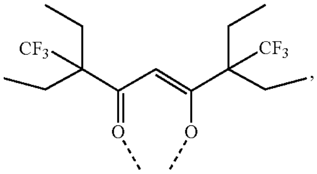
and
$L_{C776\text{-}I}$
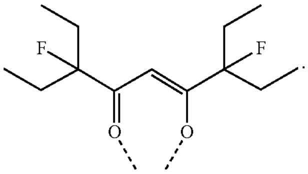
In further embodiments, the compound is selected from the group consisting of structures as defined as follows:
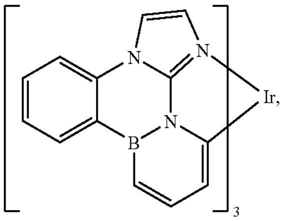
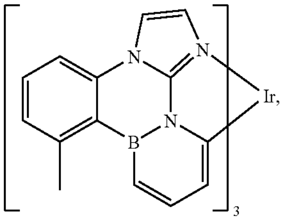
-continued
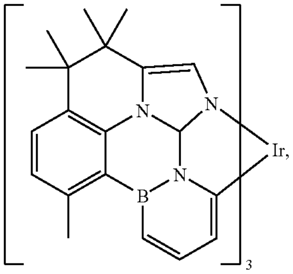
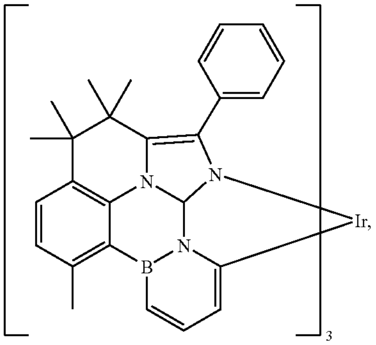
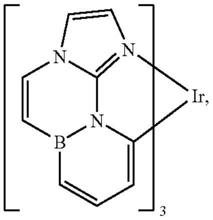
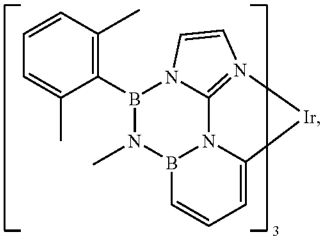
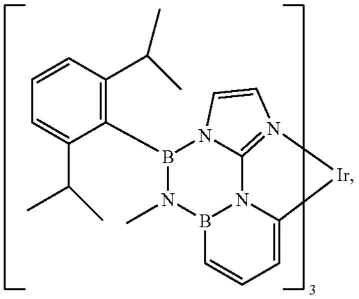
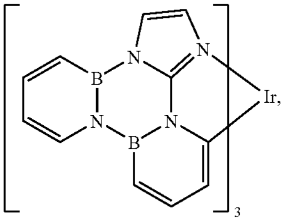
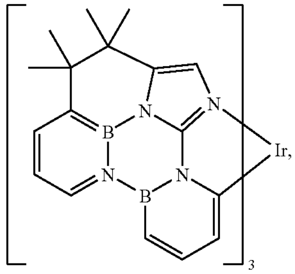

-continued
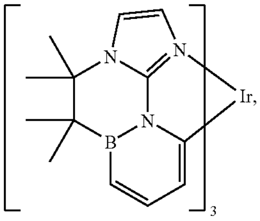
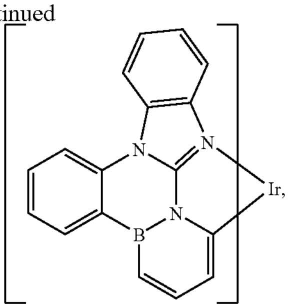
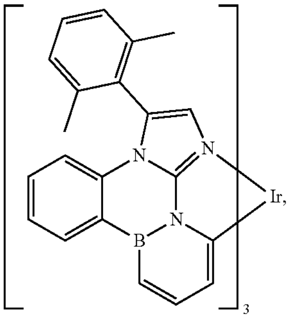
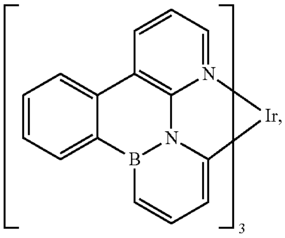
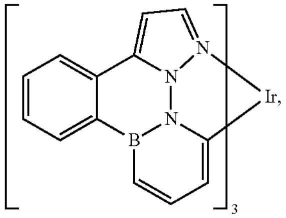
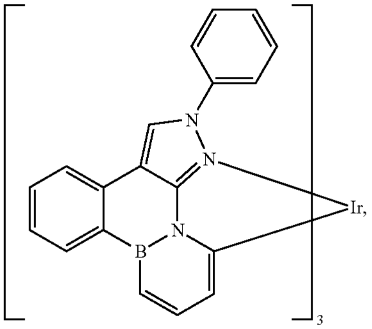
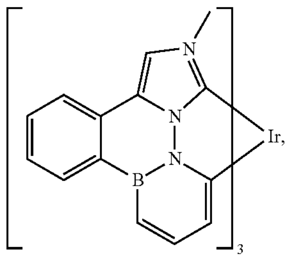
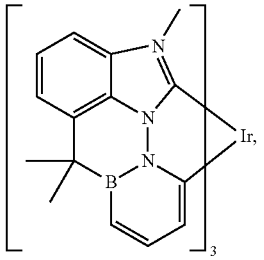
-continued
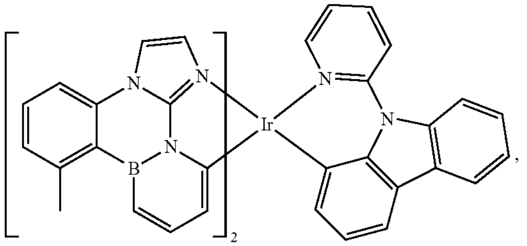
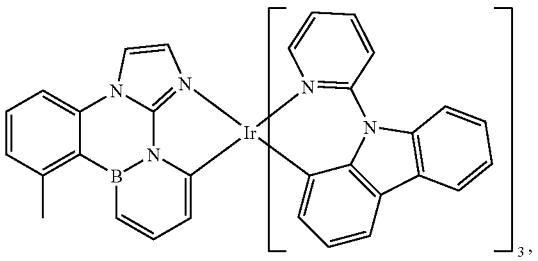
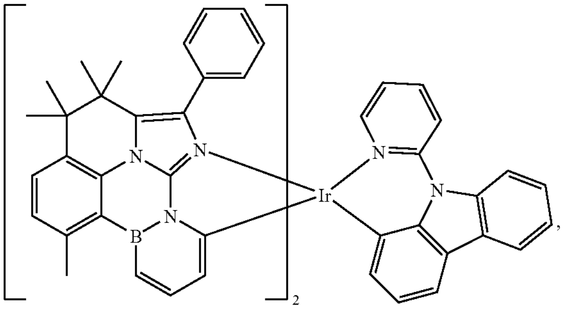
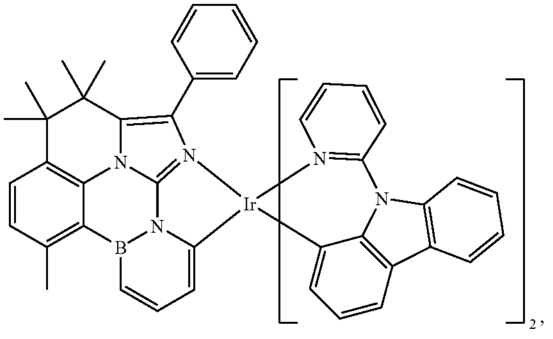
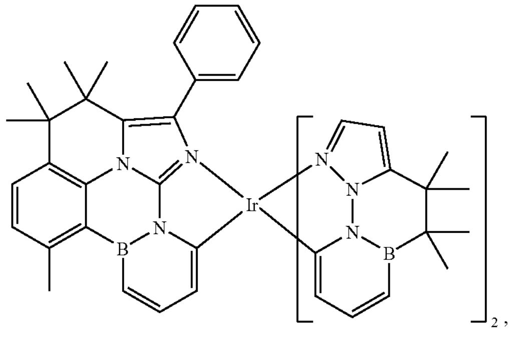

-continued

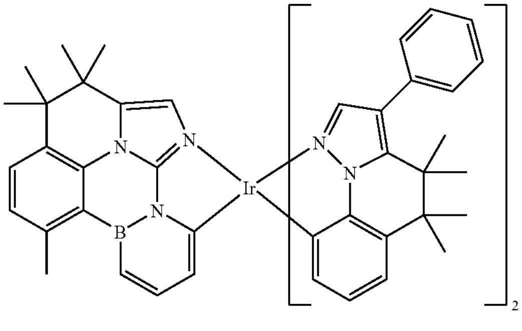

,

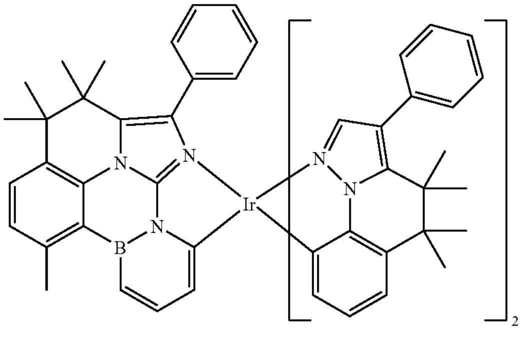

,

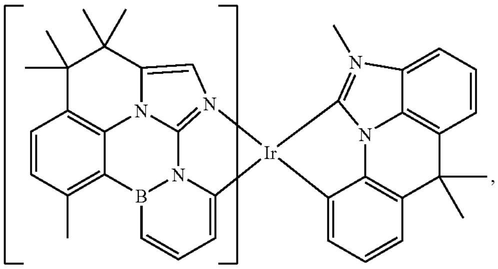

,

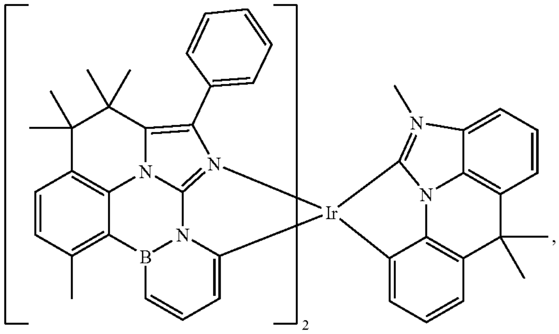

,

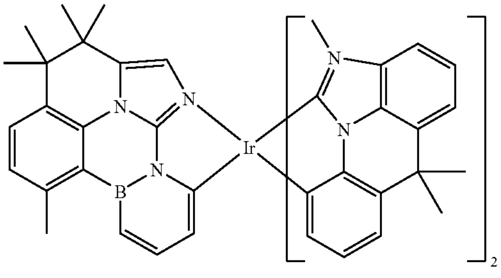

, and

-continued

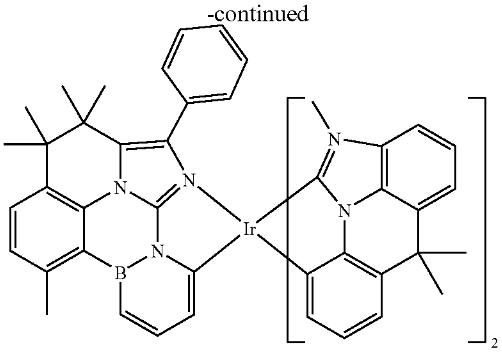

.

In further embodiments, the compound has the Formula II:

Formula II

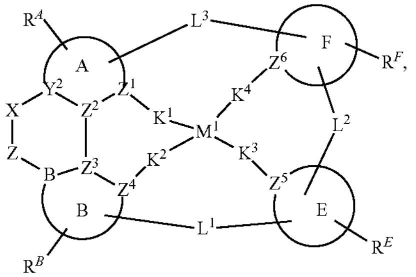

wherein:

$M^1$ is Pd or Pt;

moieties E and F are each independently monocyclic or polycyclic ring structure comprising 5-membered and/or 6-membered carbocyclic or heterocyclic rings;

$Z^3$ and $Z^4$ are each independently C or N;

$K^3$ and $K^4$ are each independently selected from the group consisting of a direct bond, O, and S, wherein at least two of them are direct bonds;

$L^1$, $L^2$, and $L^3$ are each independently selected from the group consisting of a single bond, absent a bond, O, S, CRR', SiRR', BR, and NR, wherein at least one of $L^1$ and $L^2$ is present;

$R^E$ and $R^F$ each independently represent zero, mono, or up to a maximum allowed number of substitutions to its associated ring;

each of R, R', $R^E$, and $R^F$ is independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof;

two adjacent $R^A$, $R^B$, $R^C$, $R^E$, and $R^F$ can be joined or fused together to form a ring where chemically feasible; and $K^1$, $K^2$, $Z^1$, $Z^2$, $Y^1$, $Y^2$, X, Z, $R^A$, $R^B$, ring A, and ring B are all defined the same as above.

In further embodiments, ring E and ring F are both 6-membered aromatic rings.

In further embodiments, ring F is a 5-membered or 6-membered heteroaromatic ring.

In further embodiments, $L^1$ is O or CR'R".

In further embodiments, $Z^4$ is N and $Z^3$ is C.

In further embodiments, $Z^4$ is C and $Z^3$ is N.

In further embodiments, $L^2$ is a direct bond.

In further embodiments, $L^2$ is NR'.

In further embodiments, $K^1$, $K^2$, $K^3$, and $K^4$ are all direct bonds.

In further embodiments, one of $K^1$, $K^2$, $K^3$, and $K^4$ is O.

In further embodiments, the compound is selected from the group consisting of compounds having the formula of $Pt(L_{A'})(Ly)$:

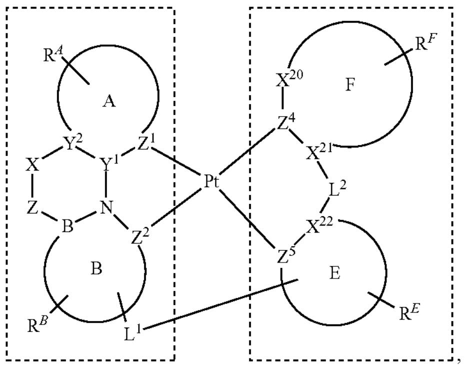

($L_{A'}$) ($L_y$)

wherein $L_{A'}$ selected from the group consisting of the structures shown below:

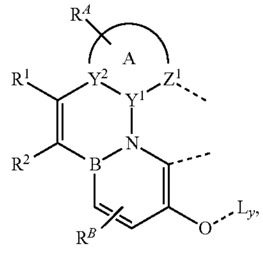

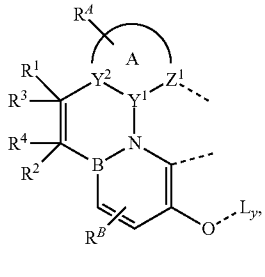

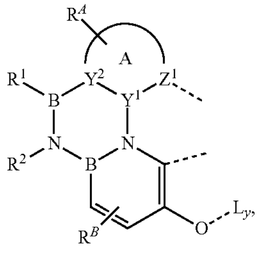

and

-continued

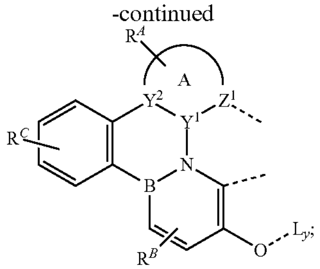

wherein ring

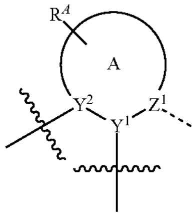

is selected from the list consisting of:

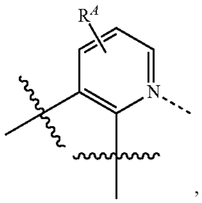

,

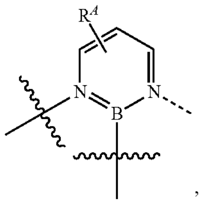

,

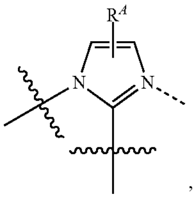

,

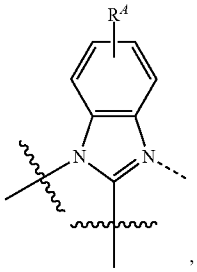

,

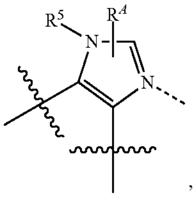

,

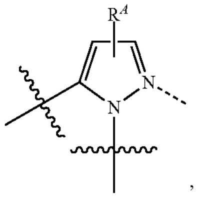

,

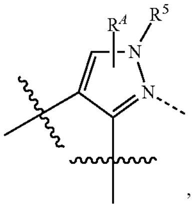

, and

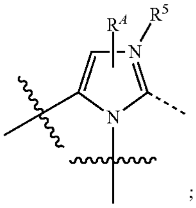

;

wherein $Z^1$ is C or N; $R^A$ and $R^B$ each independently represent zero, mono, or up to the maximum allowed number of substitutions to its associated ring; each of $R^1$, $R^2$, $R^3$, $R^4$, and $R^5$ is independently a hydrogen or a substituent selected from the group consisting of the general substituents defined herein; $Y^1$ and $Y^2$ are each independently C, N, or B; $X^1$ and $X^2$ are each independently C or Si; and $Q^1$ and $Q^2$ are each independently O, S, NR, CR, or BR;
wherein $L_y$ is selected from the group consisting of the structures defined below:
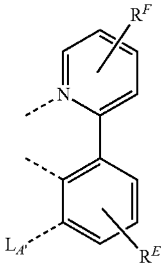
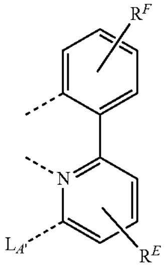
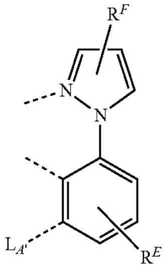
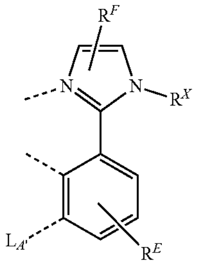
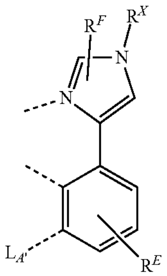
-continued
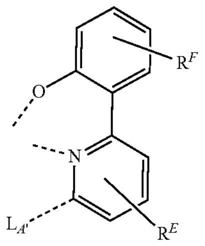
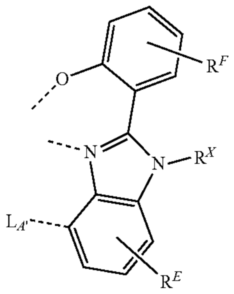
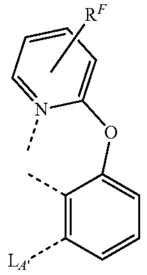
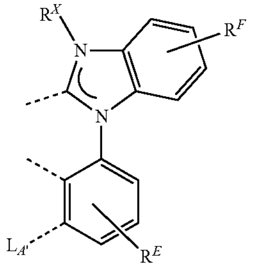
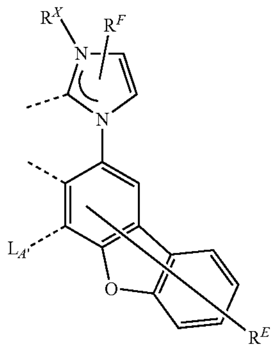

-continued
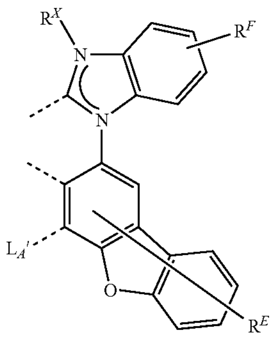
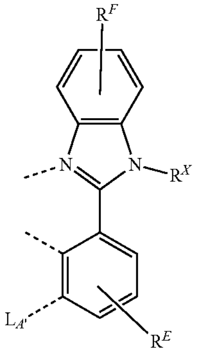
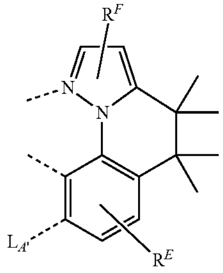
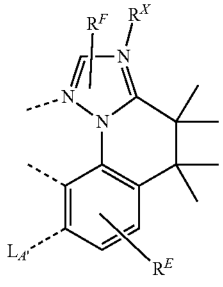
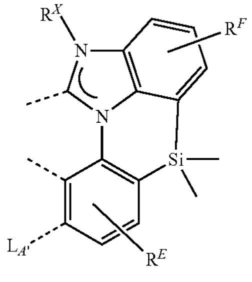
-continued
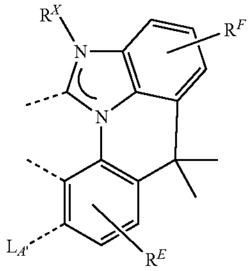
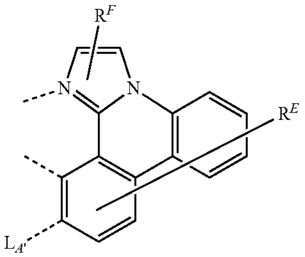
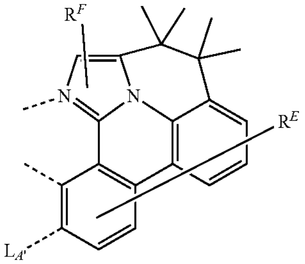
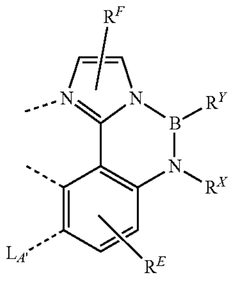
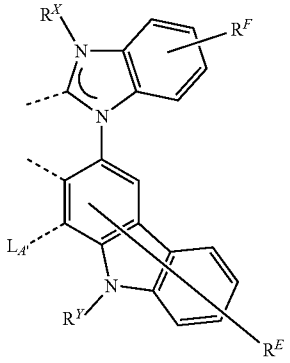

-continued
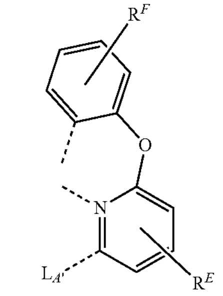
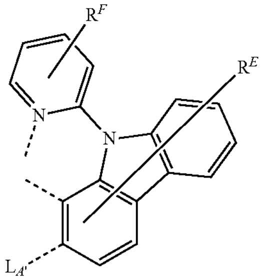
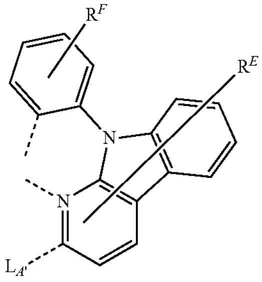
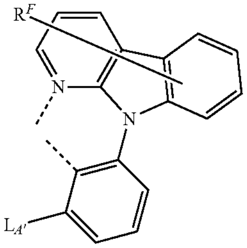
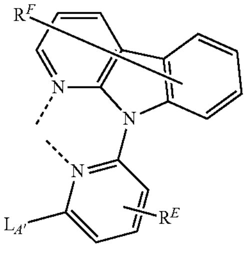
-continued
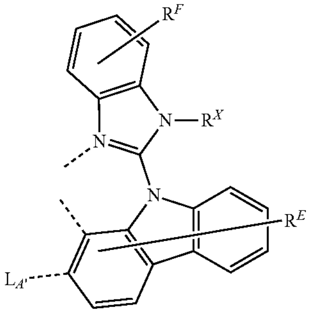
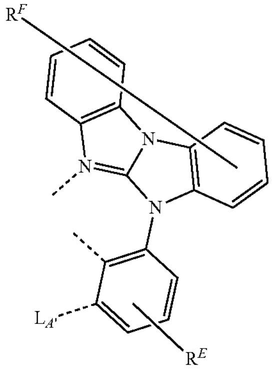
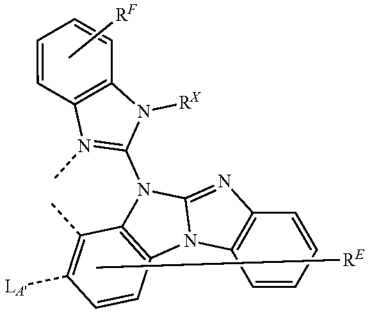
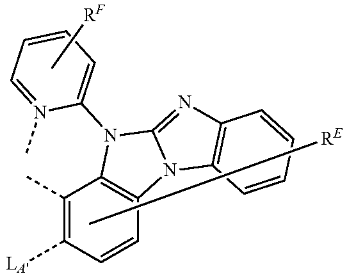
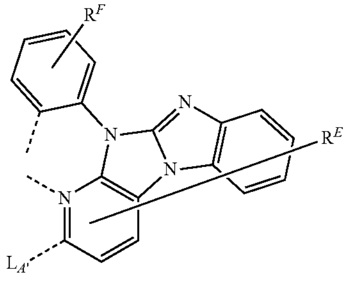

-continued
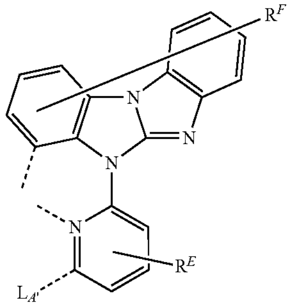
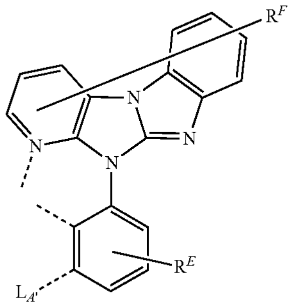
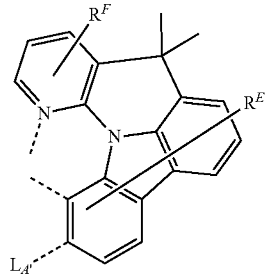
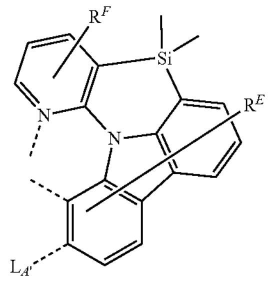
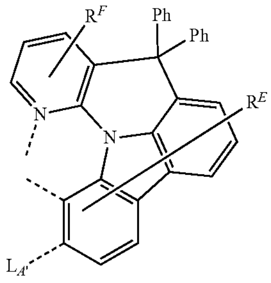
-continued
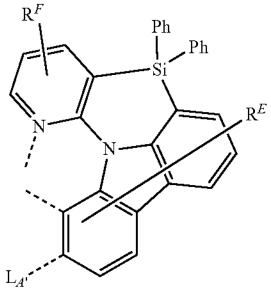
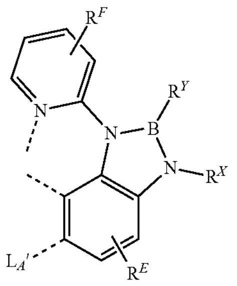
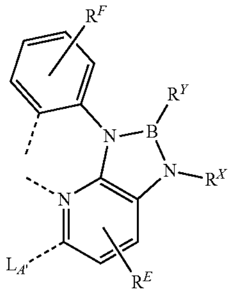
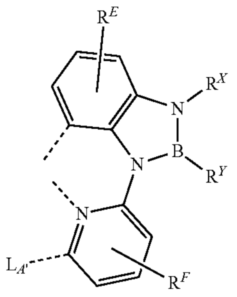
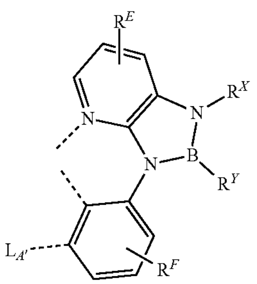

-continued
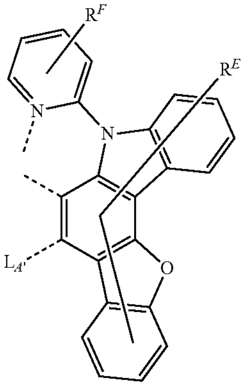
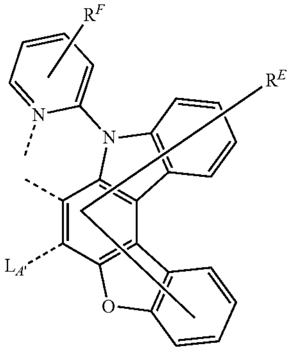
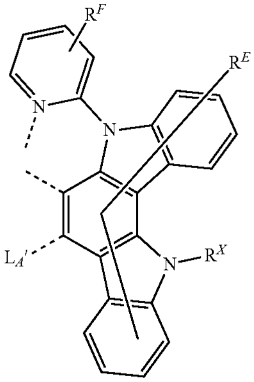
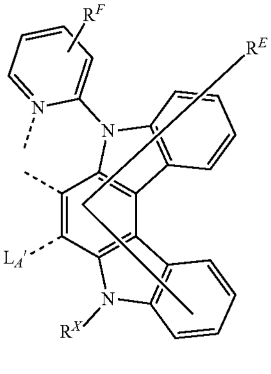
-continued
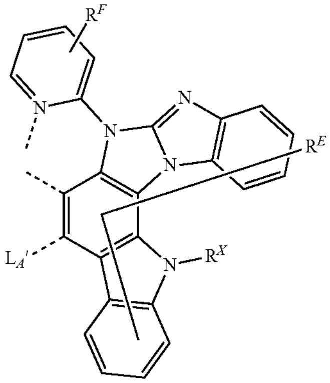
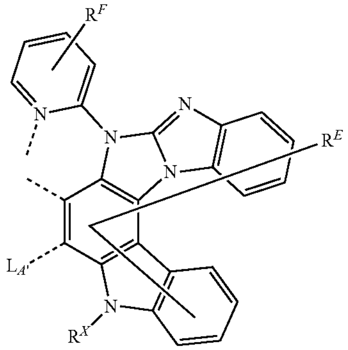
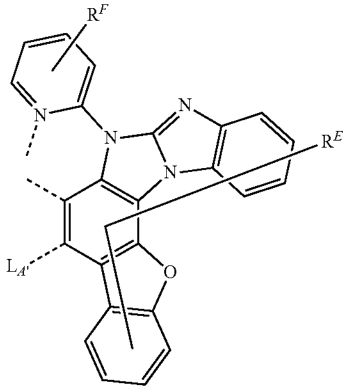
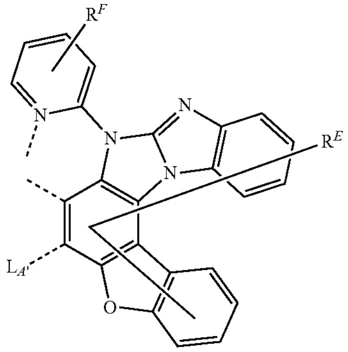
wherein $R^E$ and $R^F$ are each independently each independently represent mono, up to a maximum allowed substitutions, or no substitutions;
wherein each $R^E$, $R^F$, $R^X$, and $R^Y$ is independently selected from the list consisting of the following structures

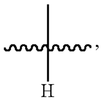, 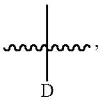, 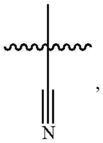, Me, iPr, tBu, $CD_3$,
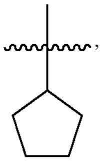, 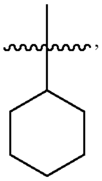, 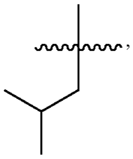, 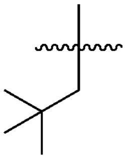,
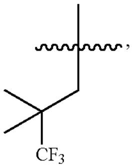, 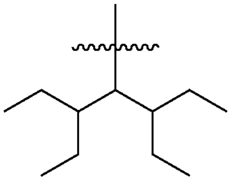, 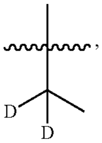,
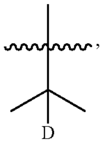, 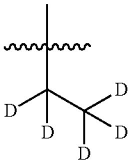, 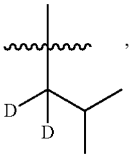, 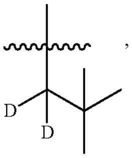,
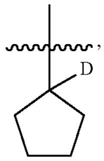, 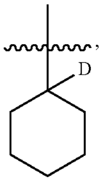, 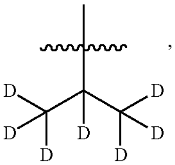, 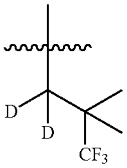,
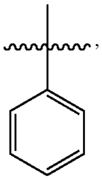, 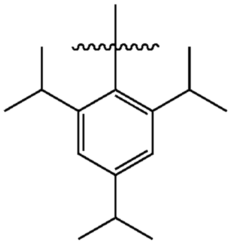,
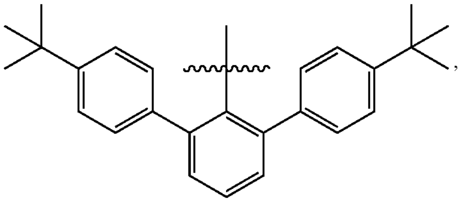,
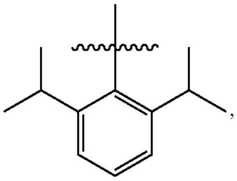, 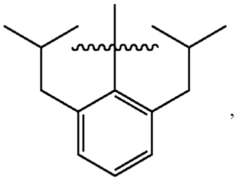,
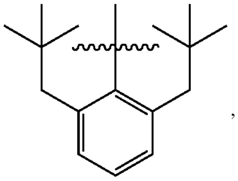, 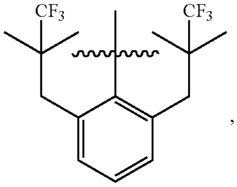,
-continued
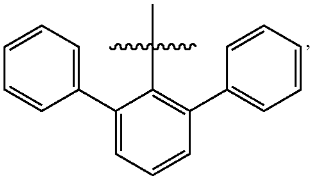,
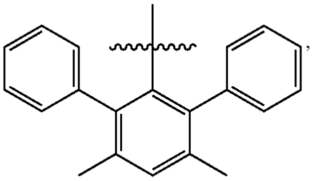,
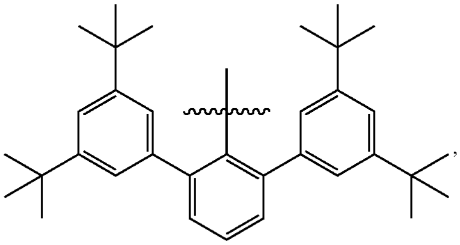,
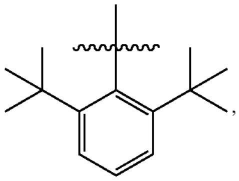, 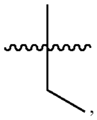,
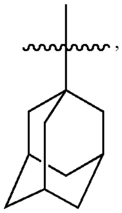, 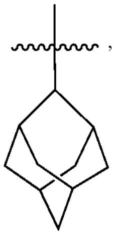, 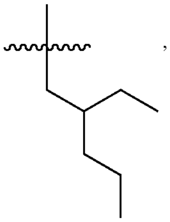, 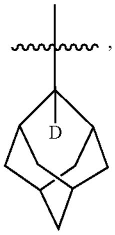,
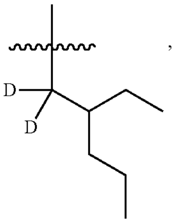, 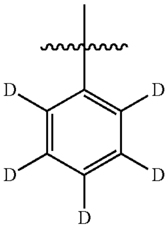,
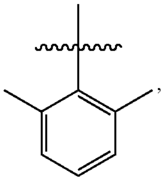, 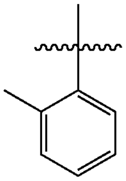, 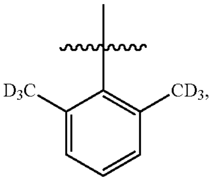
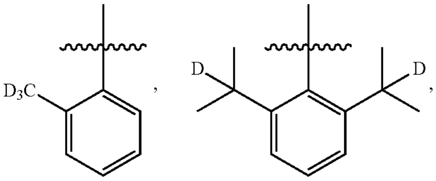, -continued
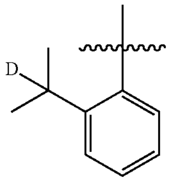,
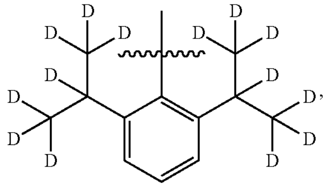,
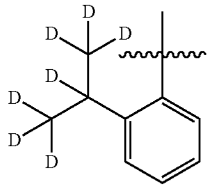,
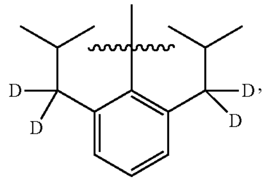,
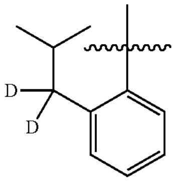,
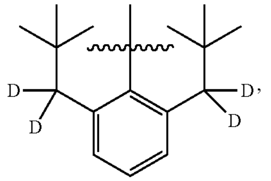,
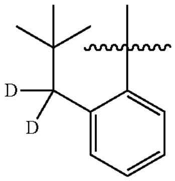,
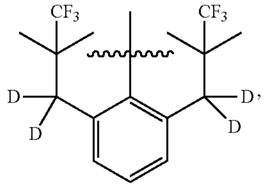,
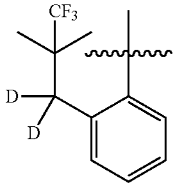,
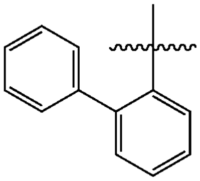,
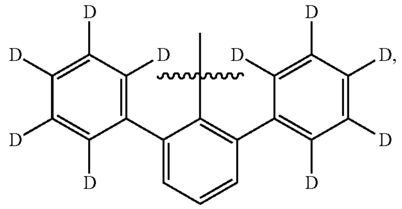
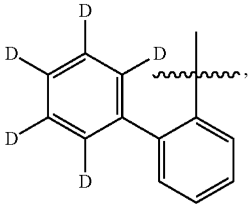,
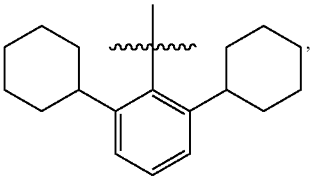,
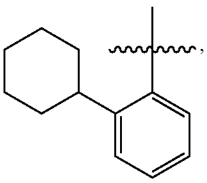,
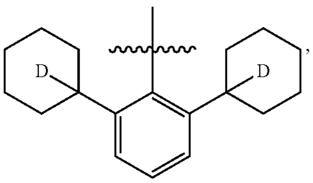,
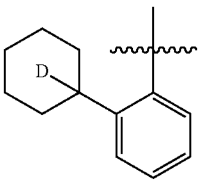,
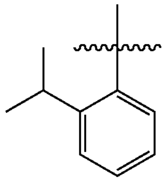,
-continued
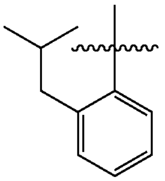,
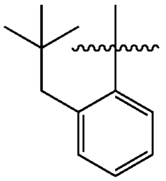,
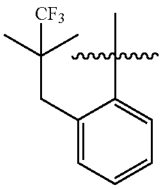,
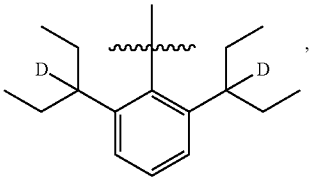,
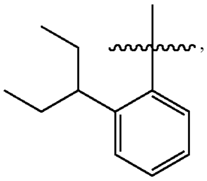,
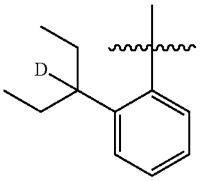,
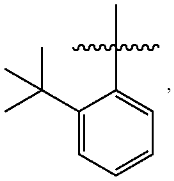,
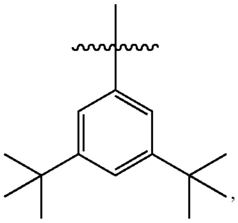,
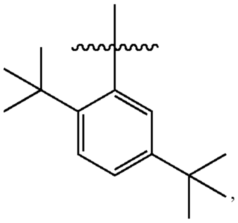,
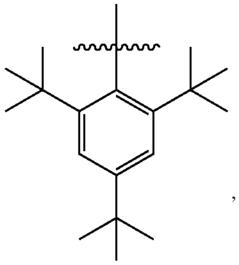,
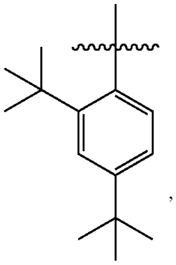,
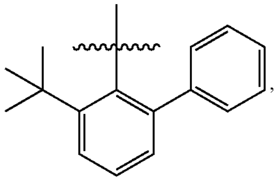,
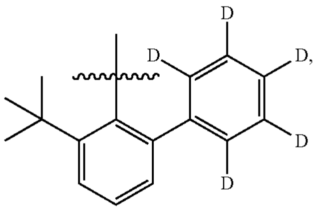
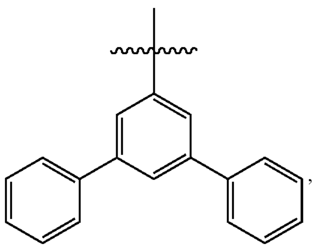, -continued
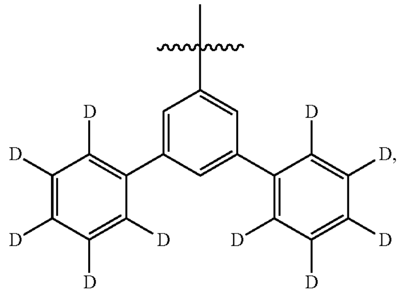
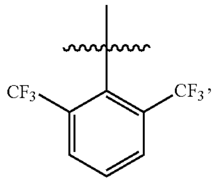,
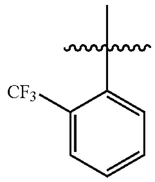,
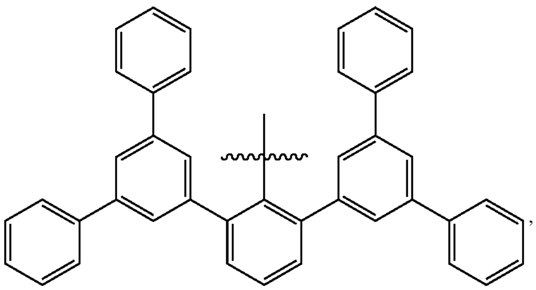,
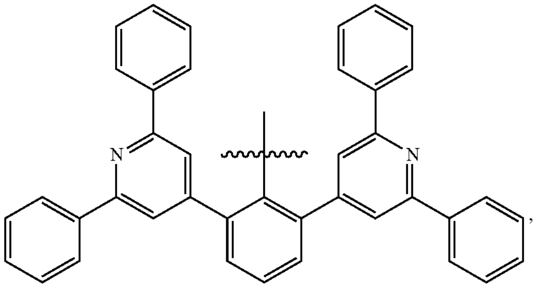,
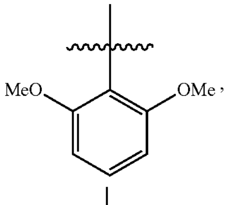,
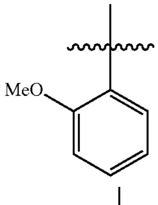,
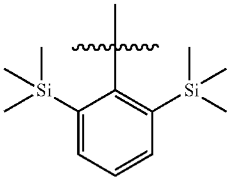,
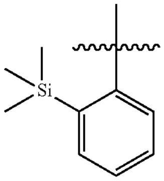,
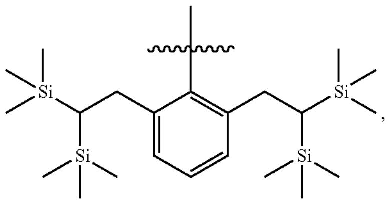,
-continued
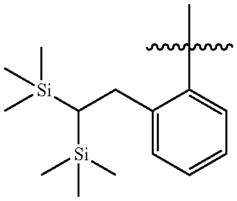,
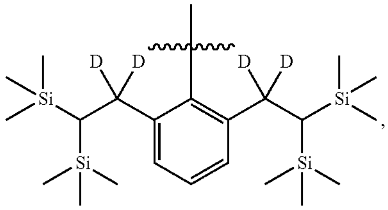,
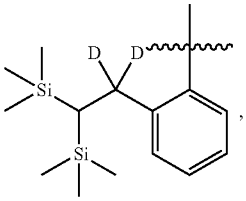,
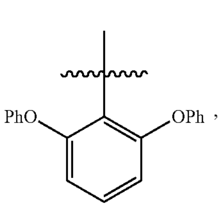,
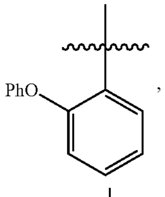,
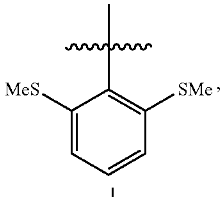,
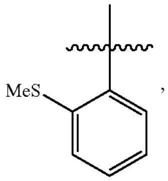,
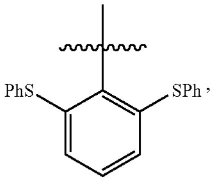,
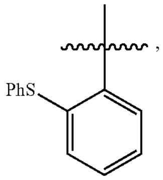,
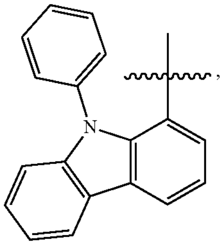,
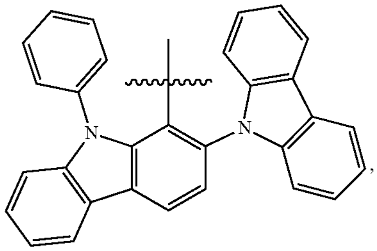,
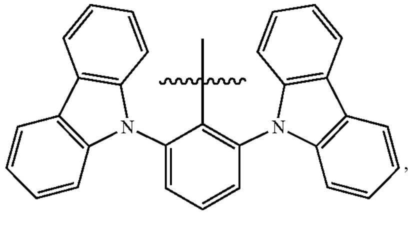, -continued
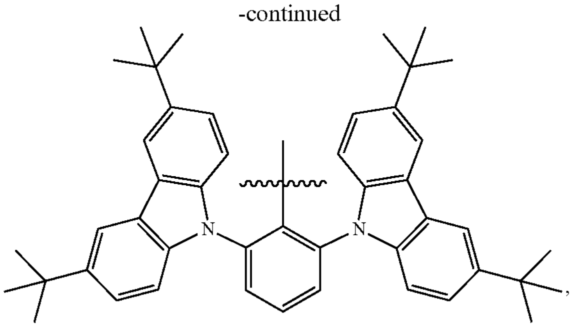
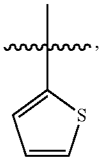
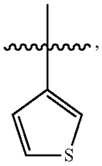
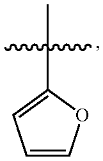
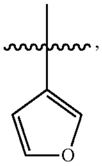
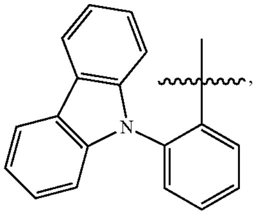
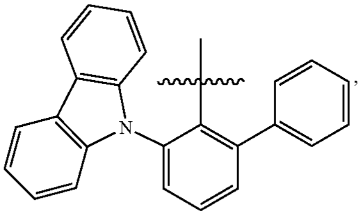
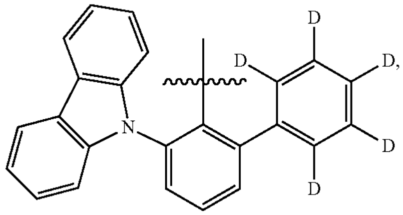
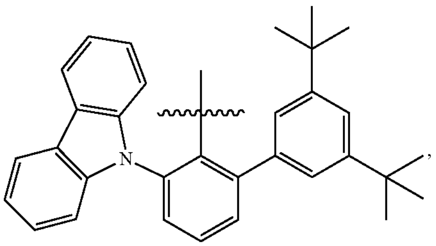
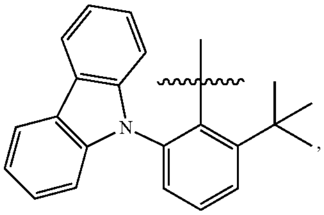
-continued
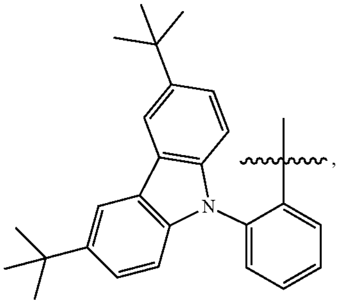
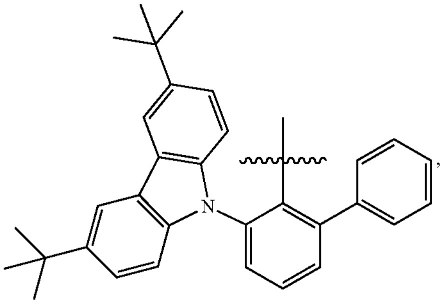
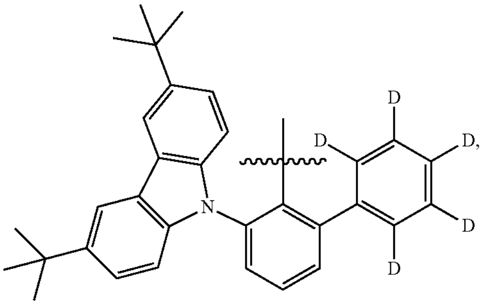
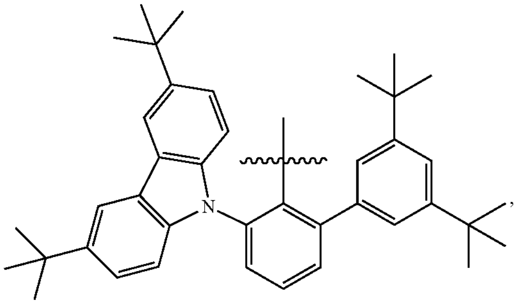
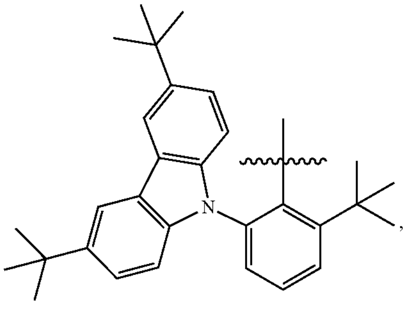

-continued
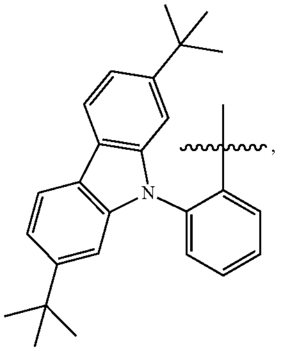
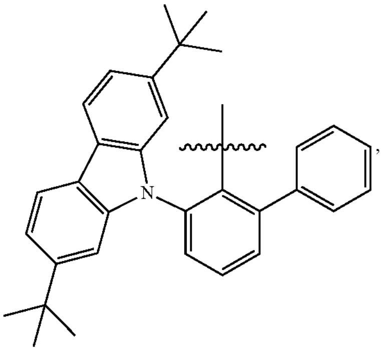
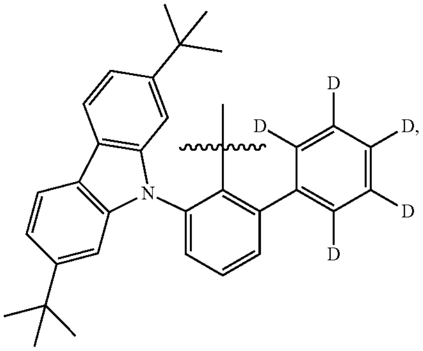
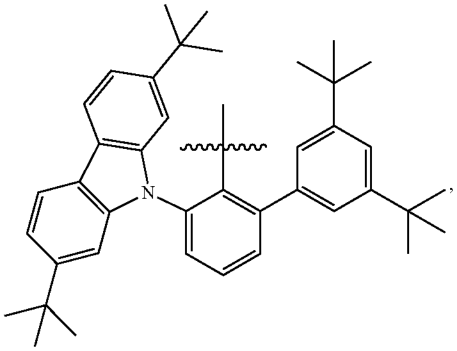
-continued
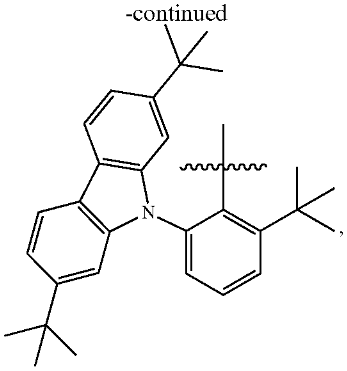
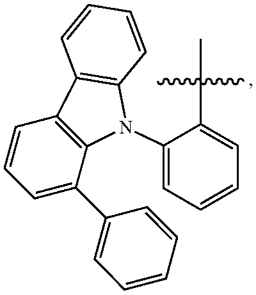
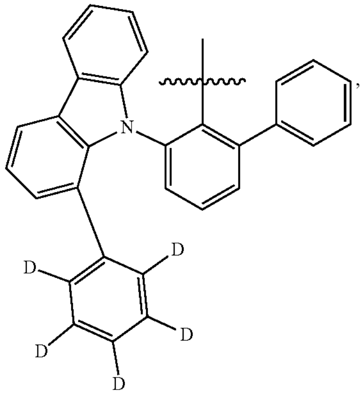
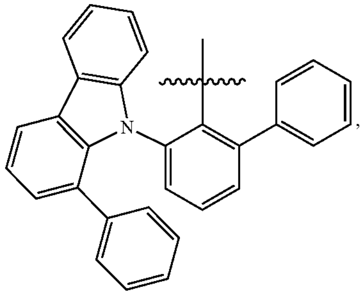
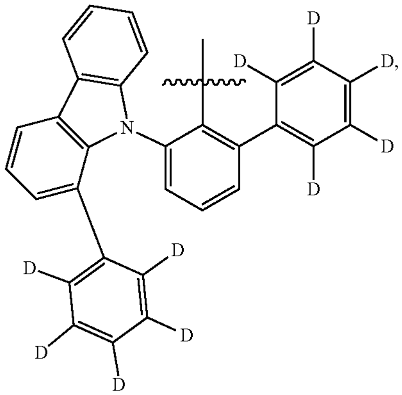

-continued
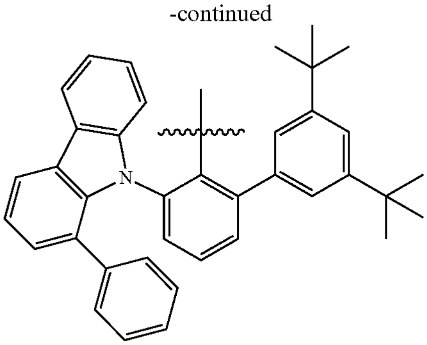
,
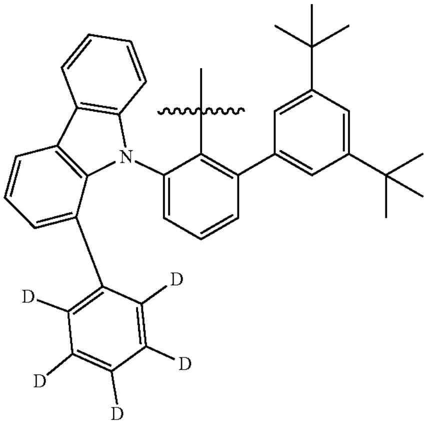
,
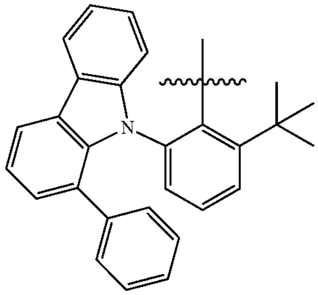
,
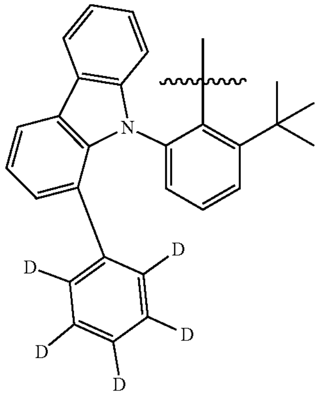
,
-continued
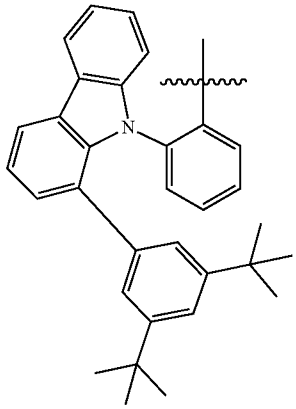
,
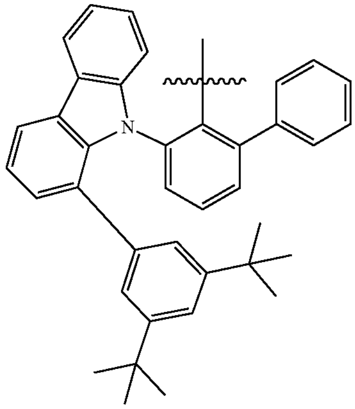
,
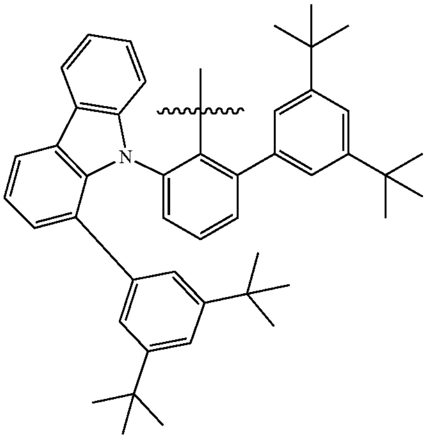
,
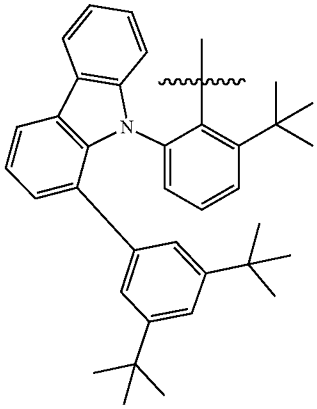
, -continued
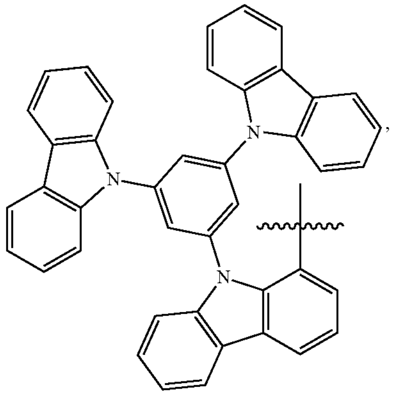
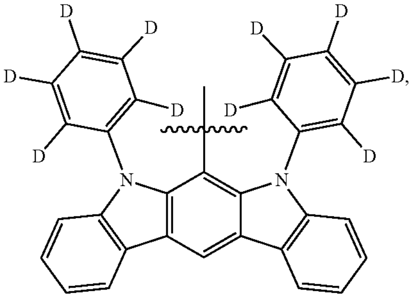
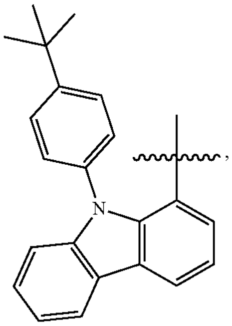
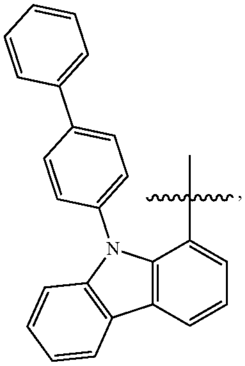
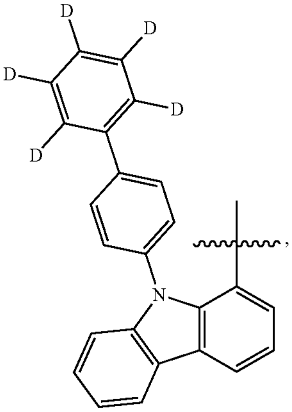
-continued
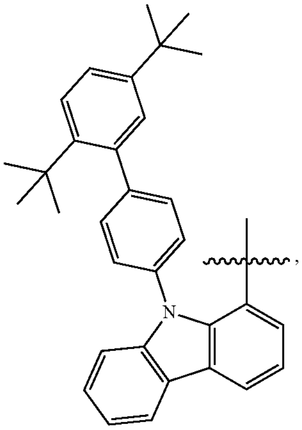
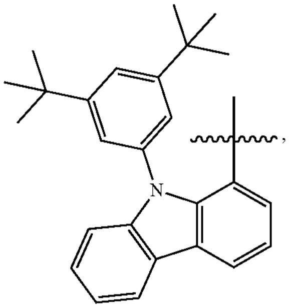
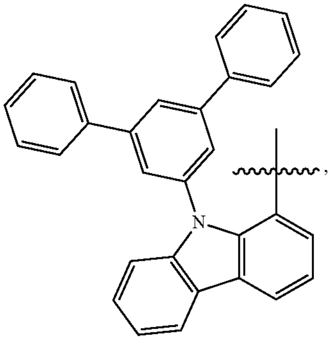
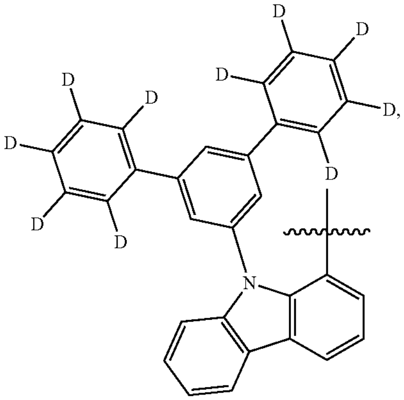

-continued
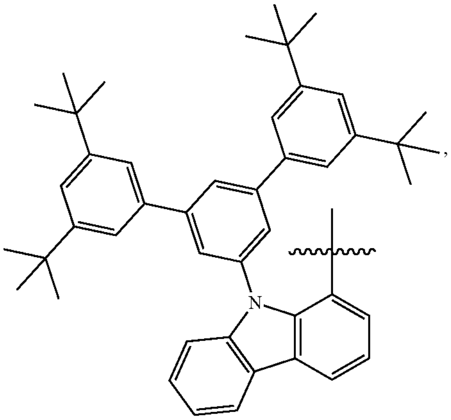
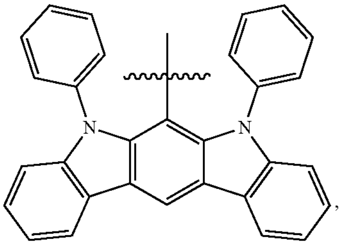
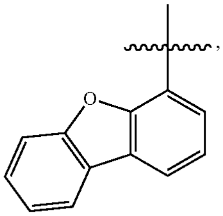
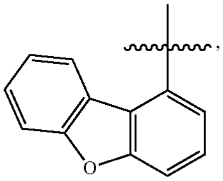
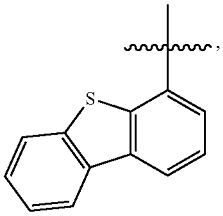
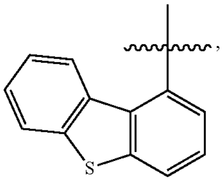
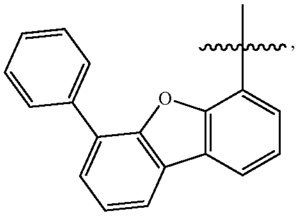
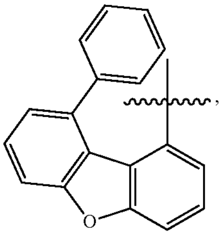
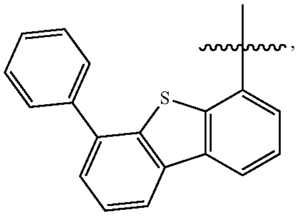
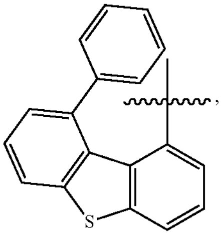
-continued
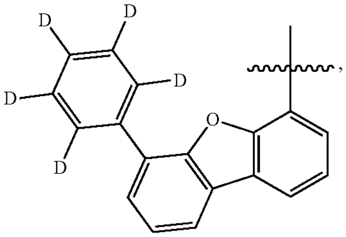
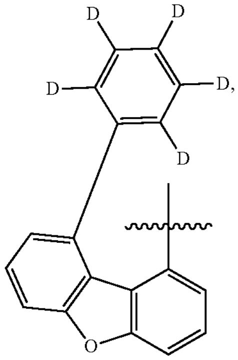
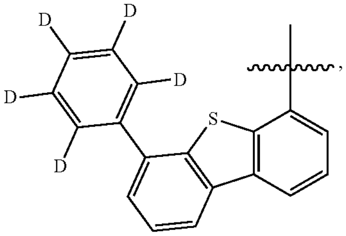
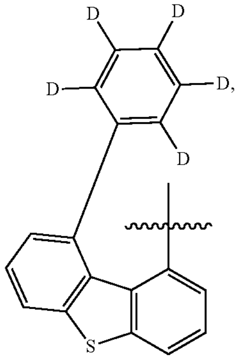
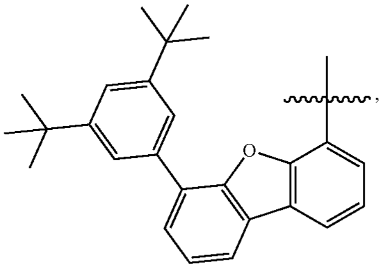

-continued
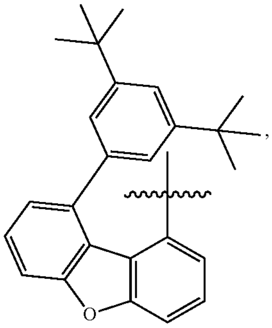,
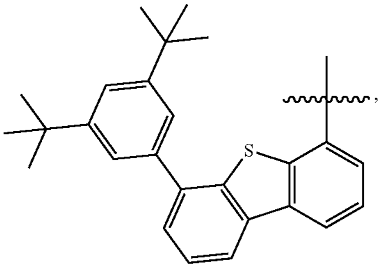,
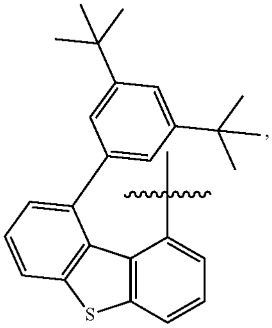,
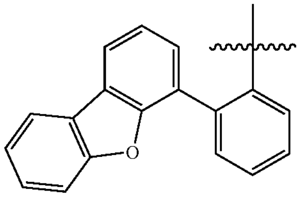, 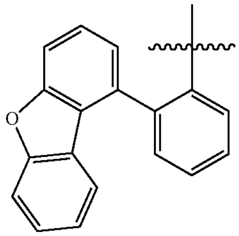,
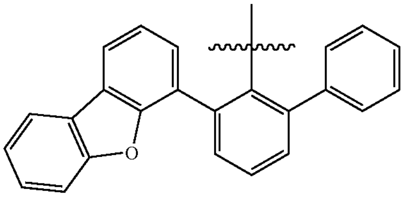,
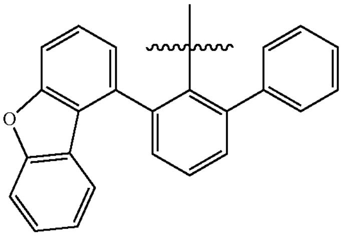,
-continued
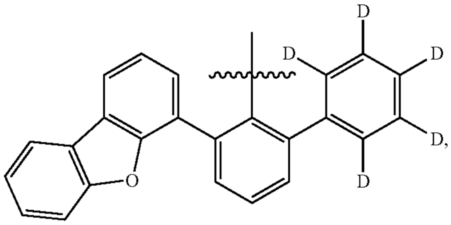,
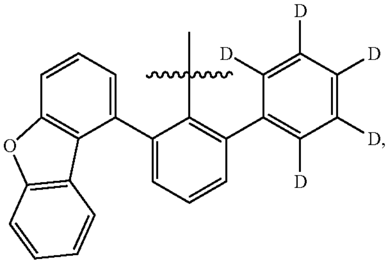,
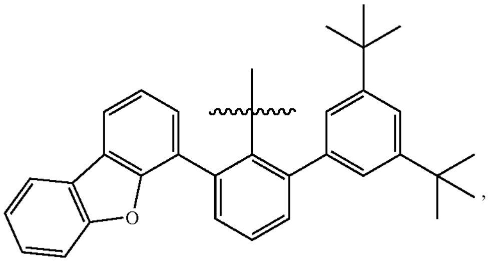,
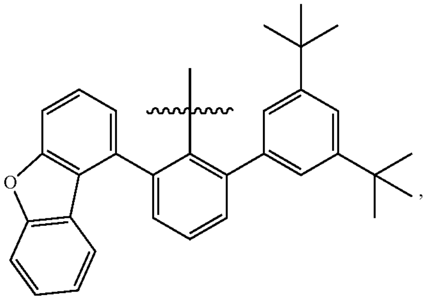,
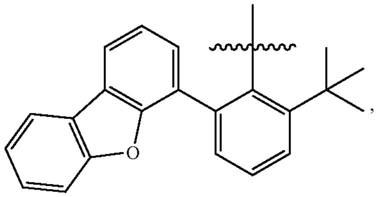,
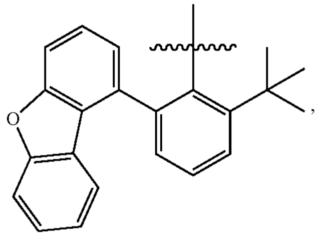,
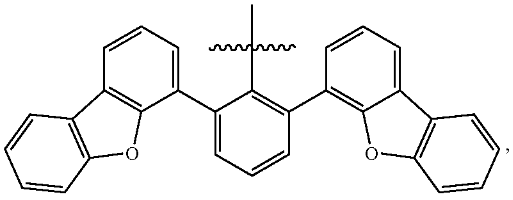, -continued
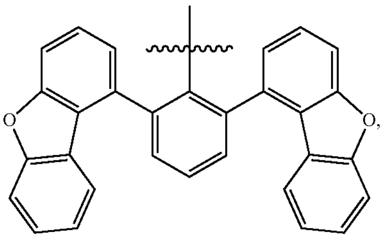
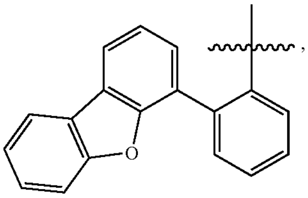,
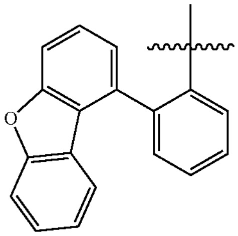,
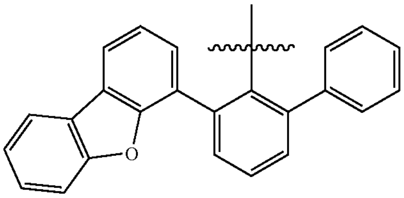,
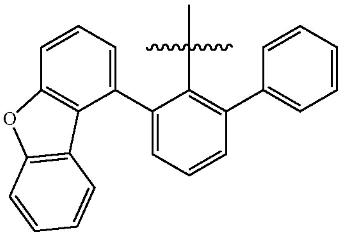,
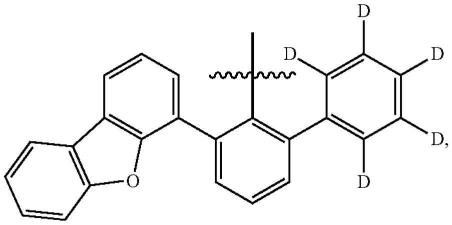
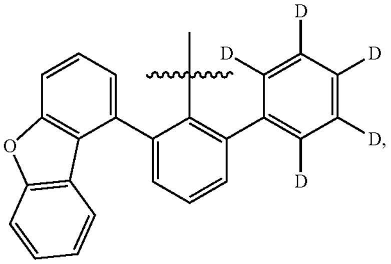
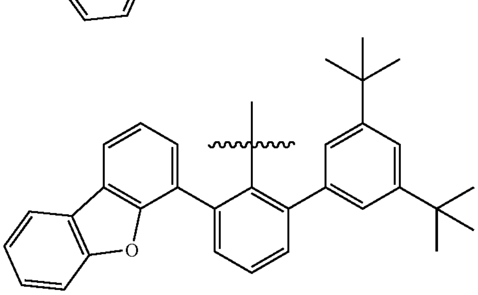,
-continued
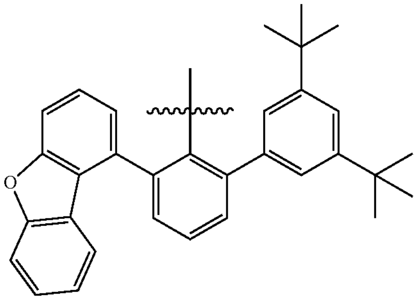,
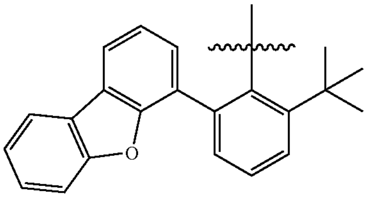,
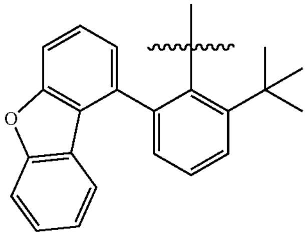,
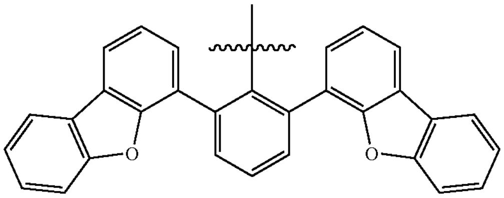,
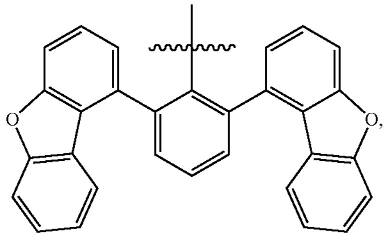
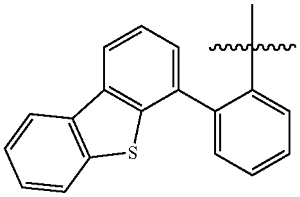,
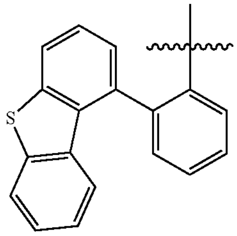,
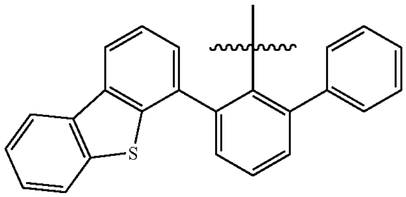, -continued
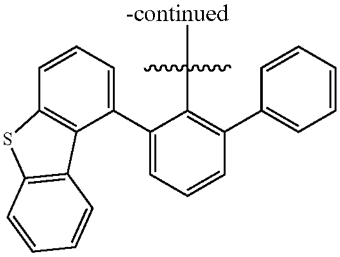
,
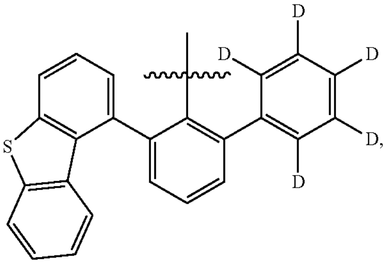
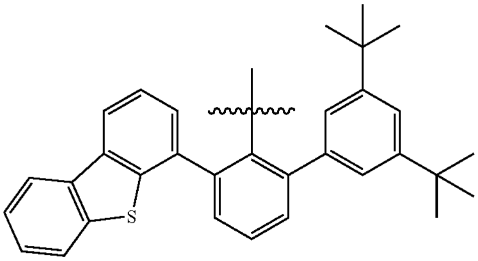
,
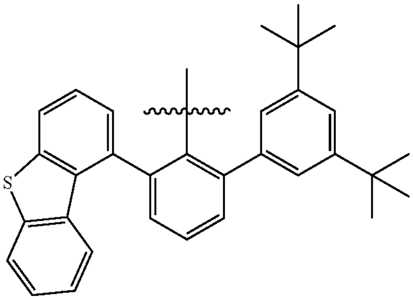
,
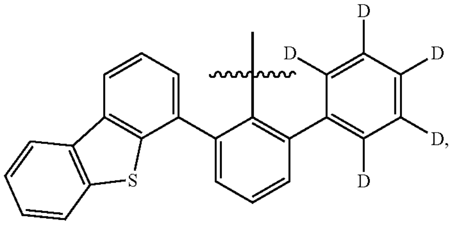
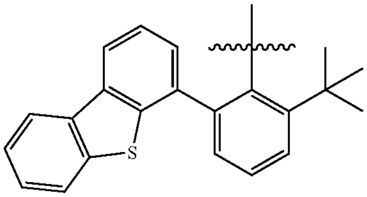
,
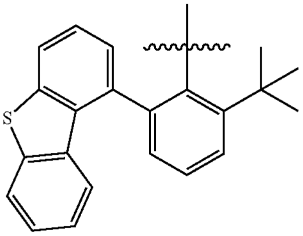
,
-continued
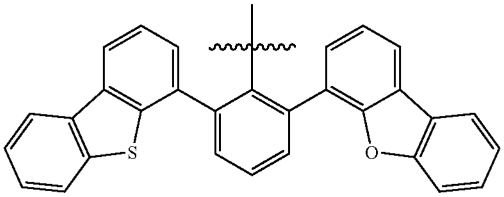
,
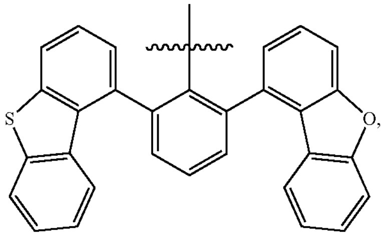
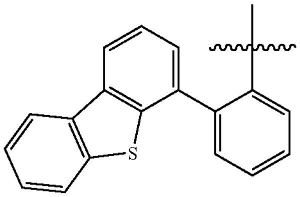
,
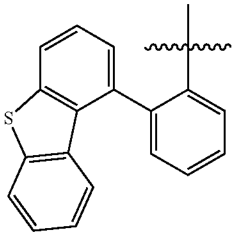
,
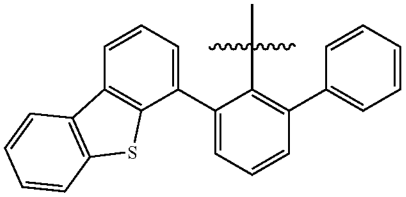
,
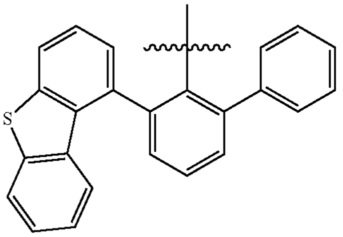
,
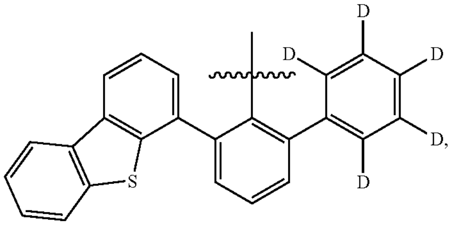
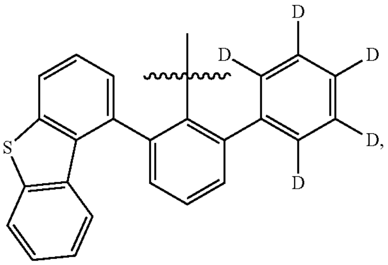

-continued
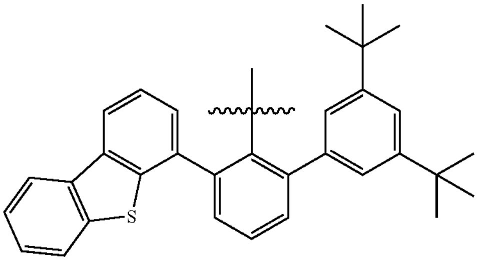
,
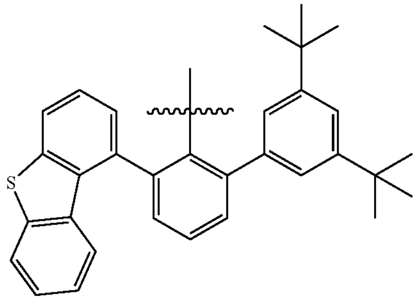
,
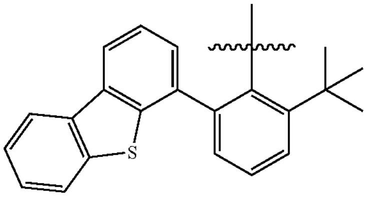
,
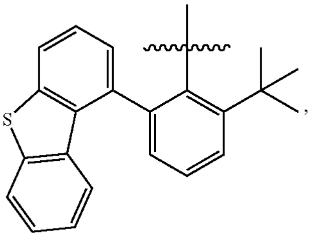
,
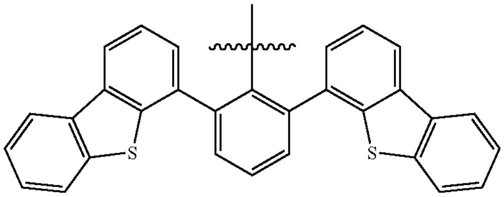
,
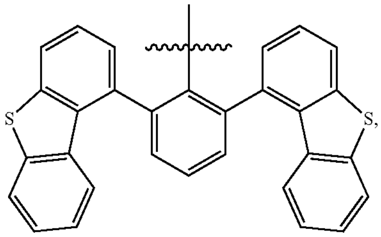
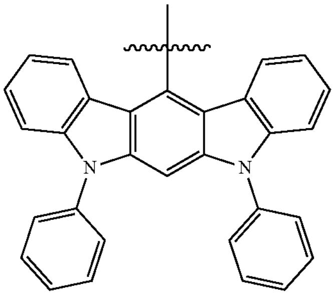
,
-continued
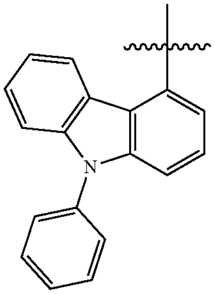
,
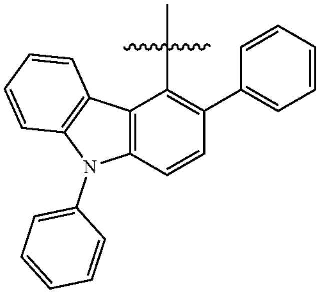
,
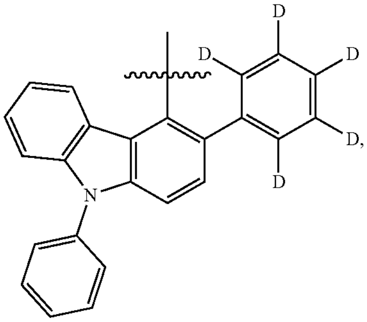
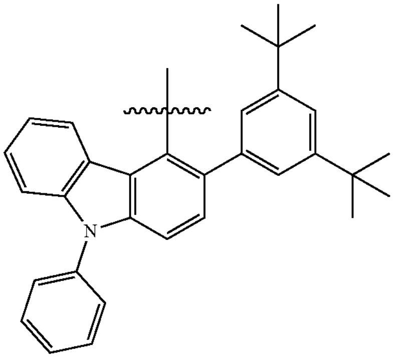
,
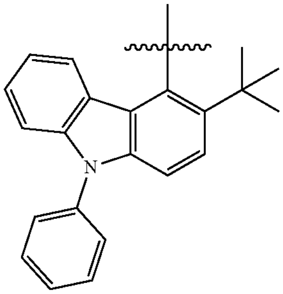
,
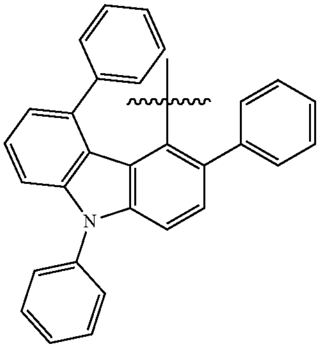
, -continued
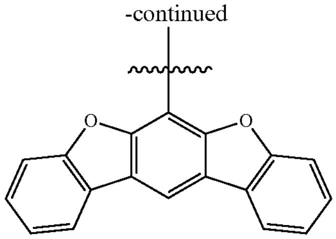
,
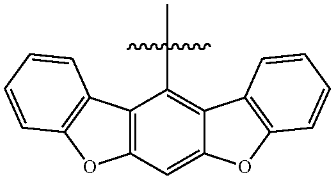
,
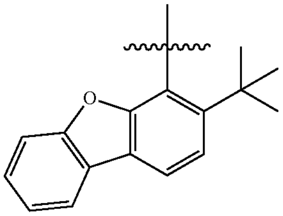
,
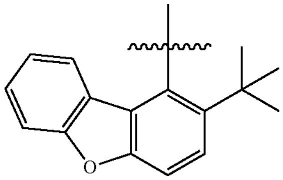
,
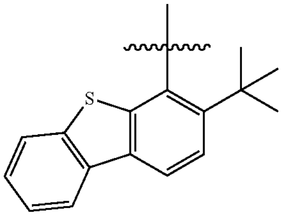
,
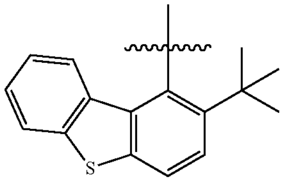
,
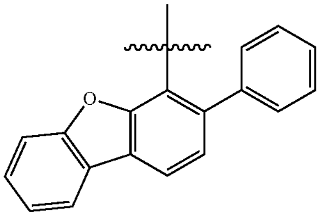
,
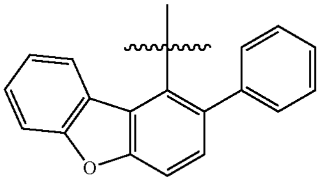
,
-continued
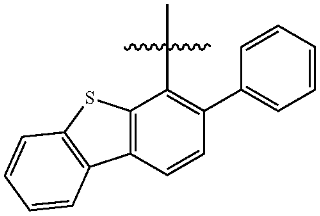
,
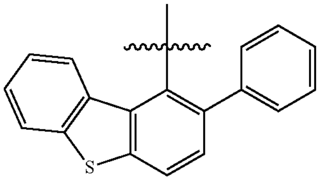
,
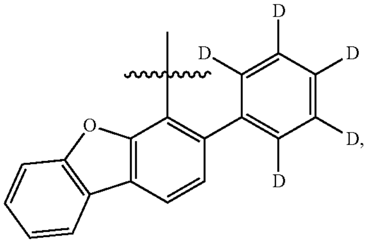
,
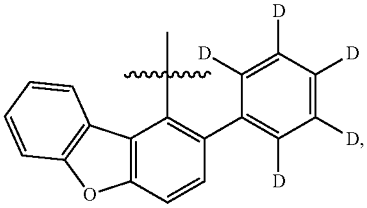
,
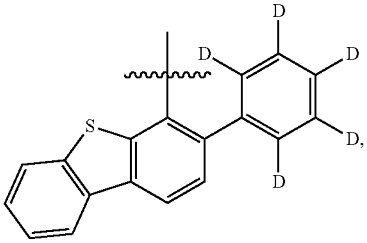
,
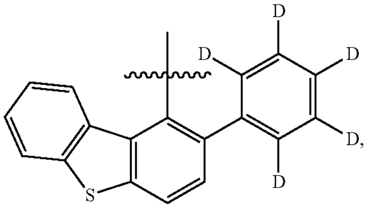
,
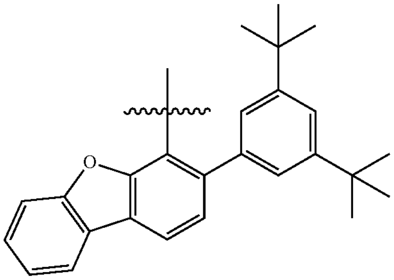
, -continued
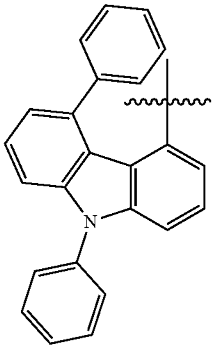
,
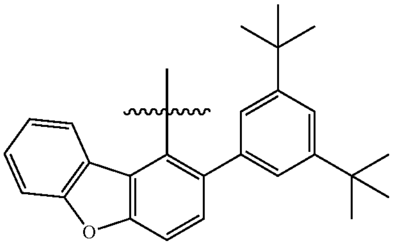
,
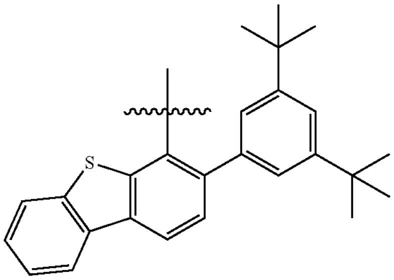
,
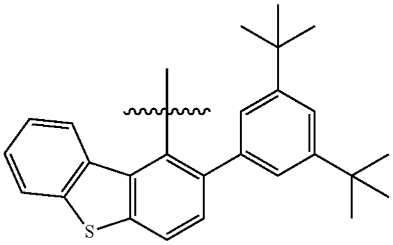
,
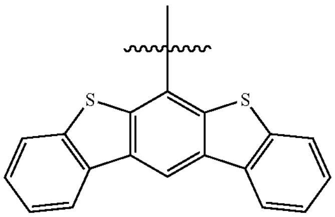
,
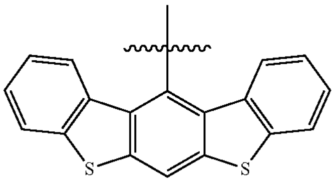
,
-continued
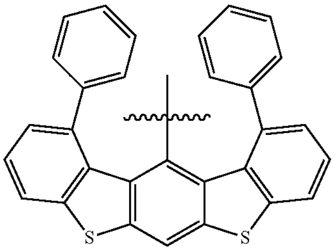
,
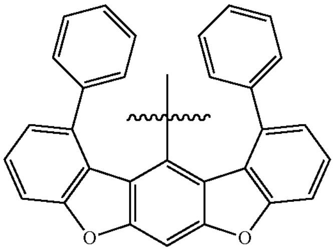
,
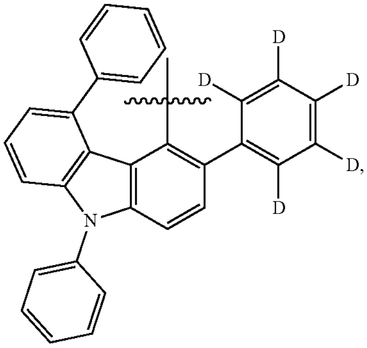
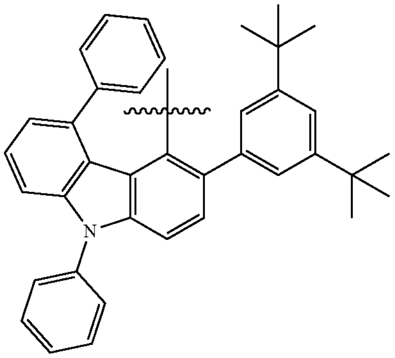
,
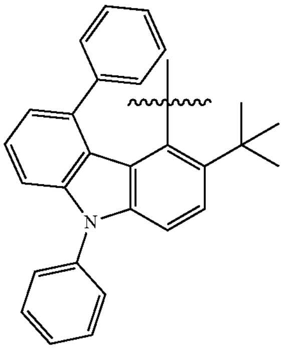
, -continued
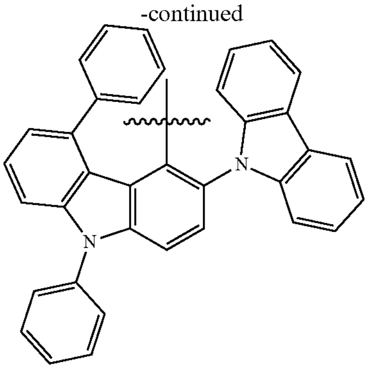
,
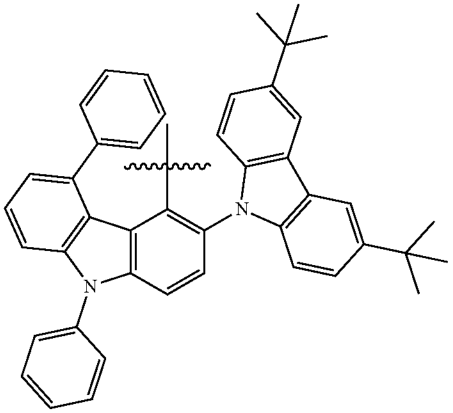
,
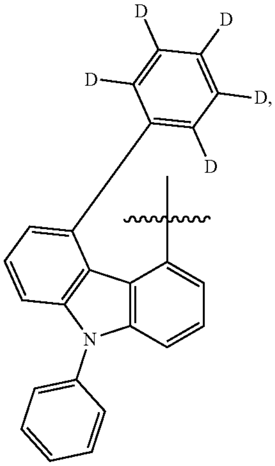
,
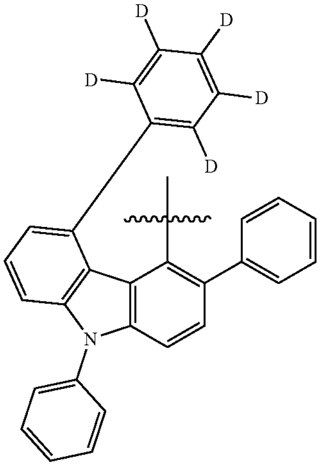
,
-continued
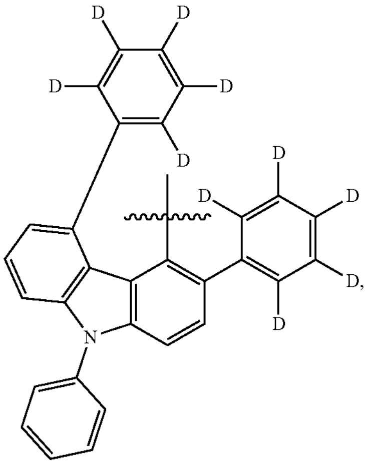
,
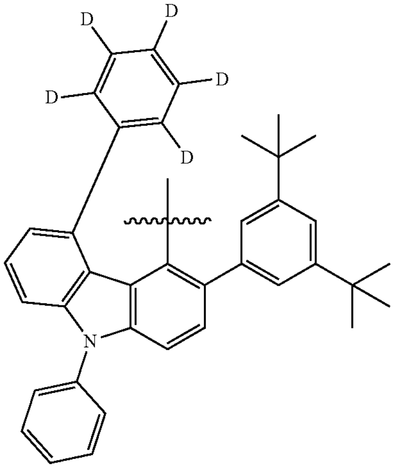
,
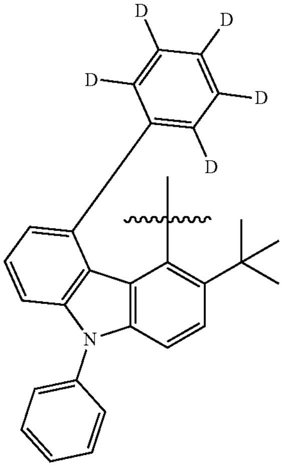
, -continued
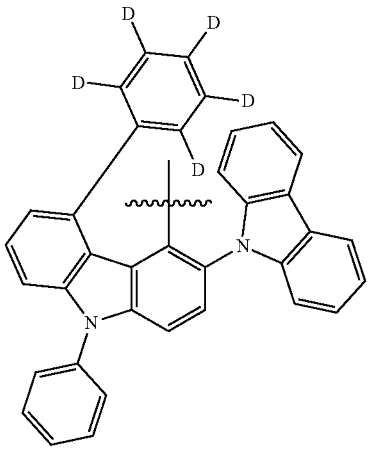
,
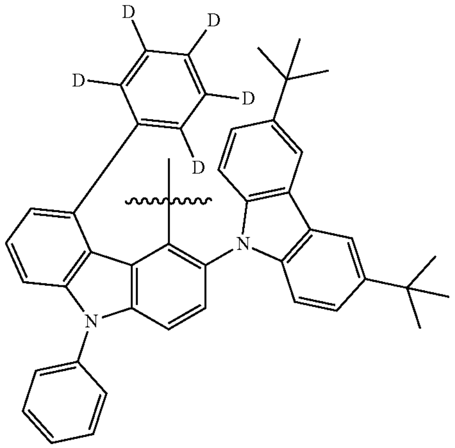
,
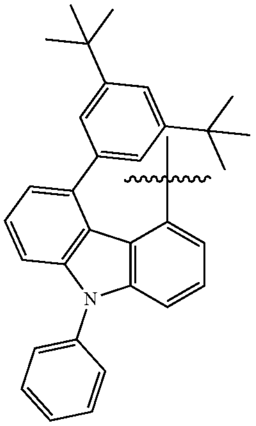
,
-continued
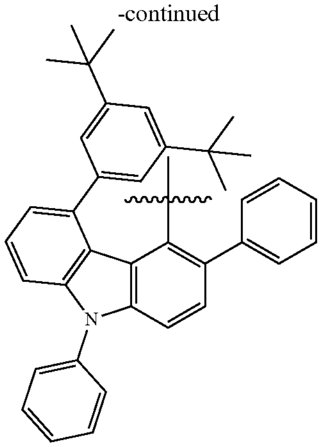
,
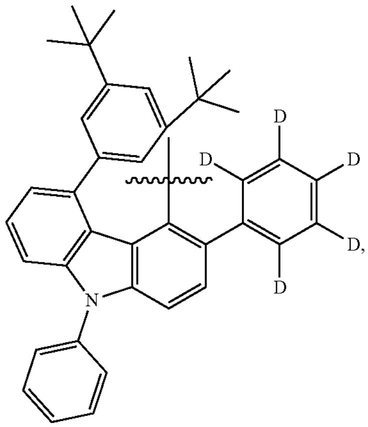
,
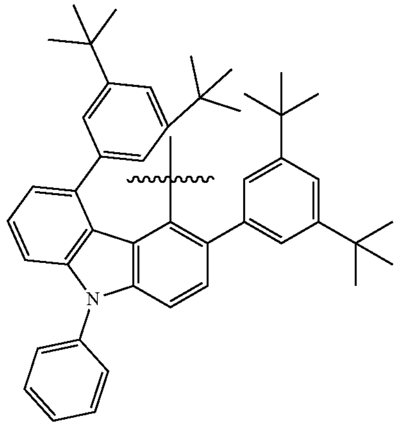
,
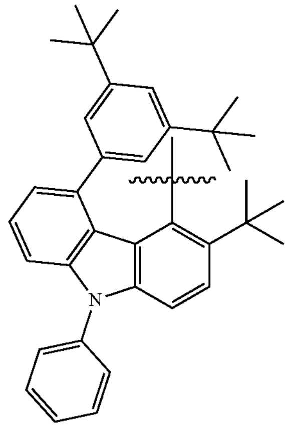
,

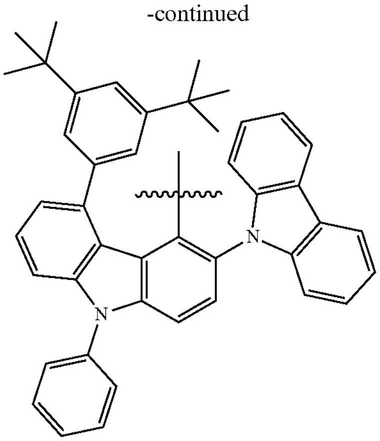
,
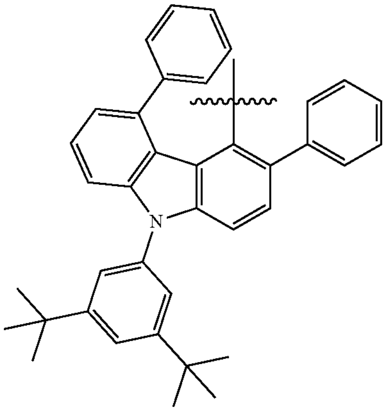
,
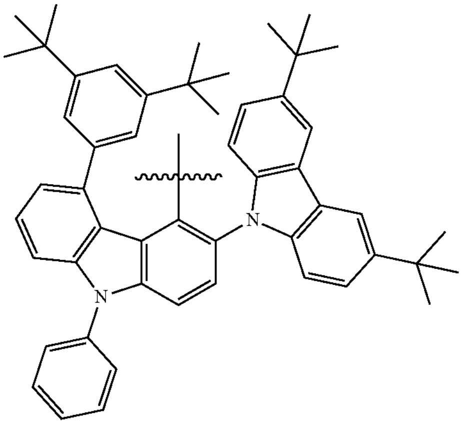
,
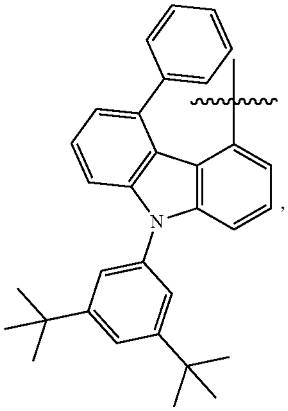
,
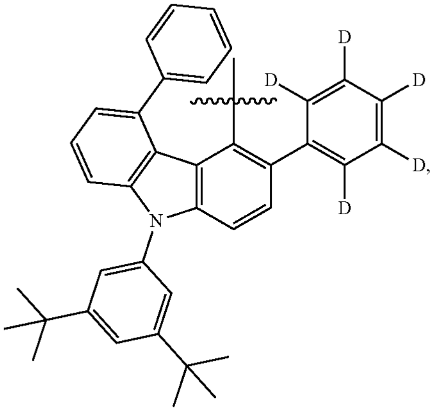
,
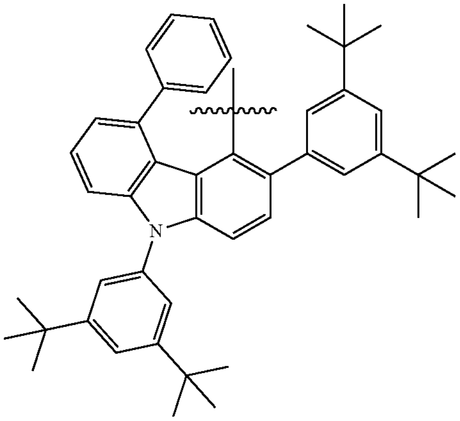
,
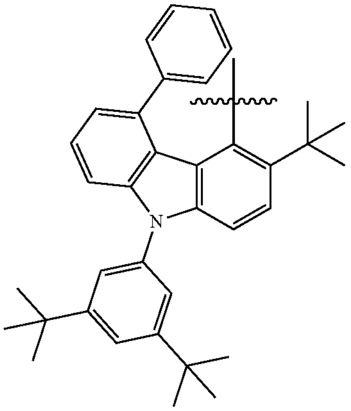
,
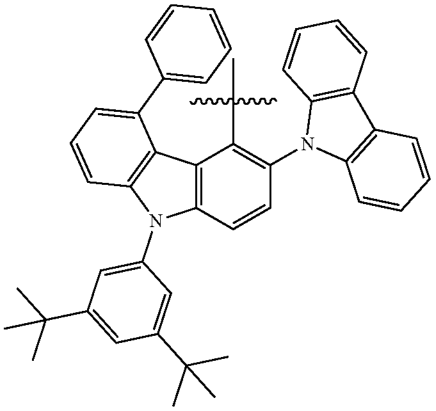
, -continued
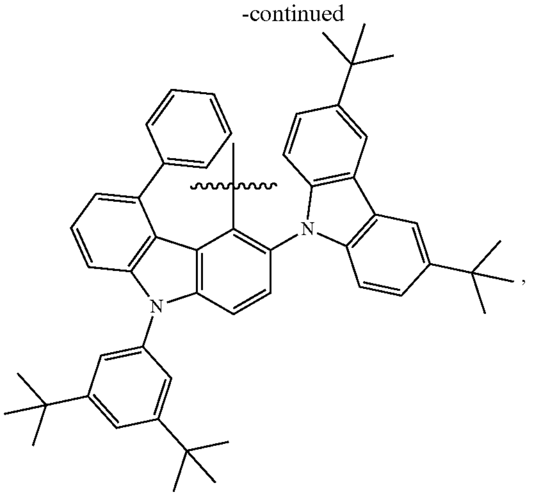
,
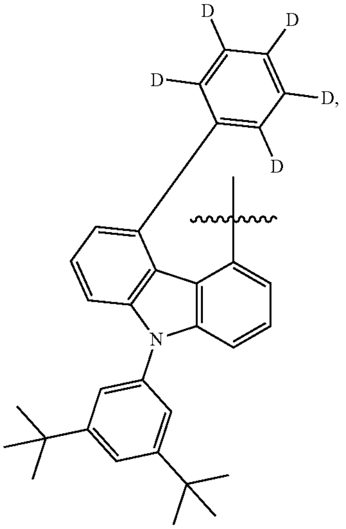
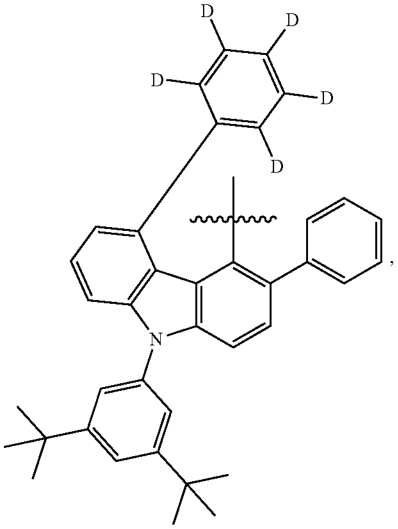
-continued
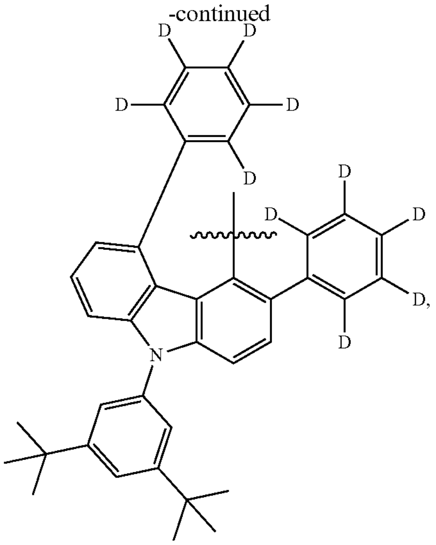
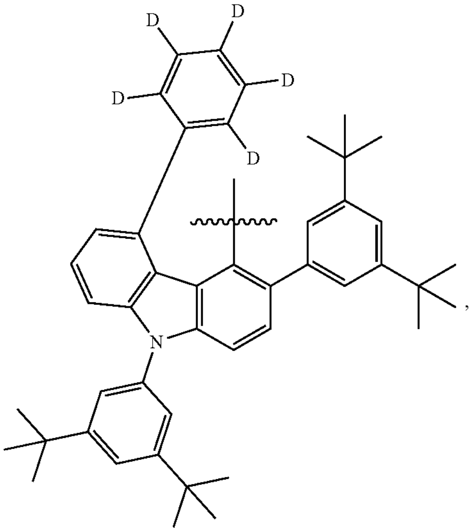
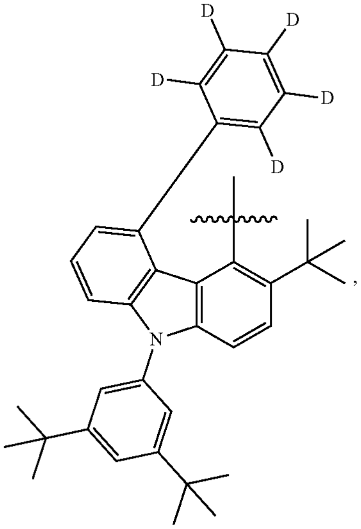

-continued
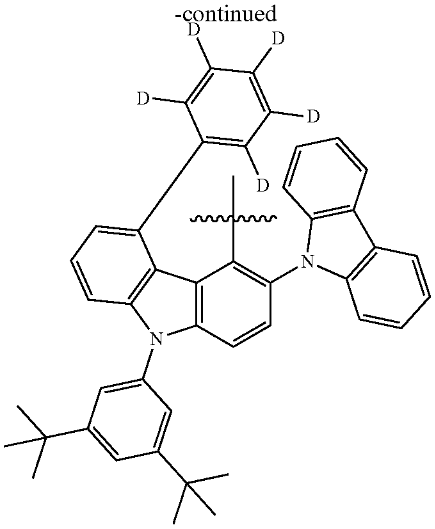
,
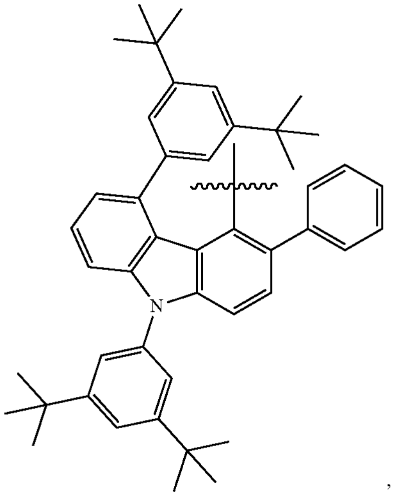
,
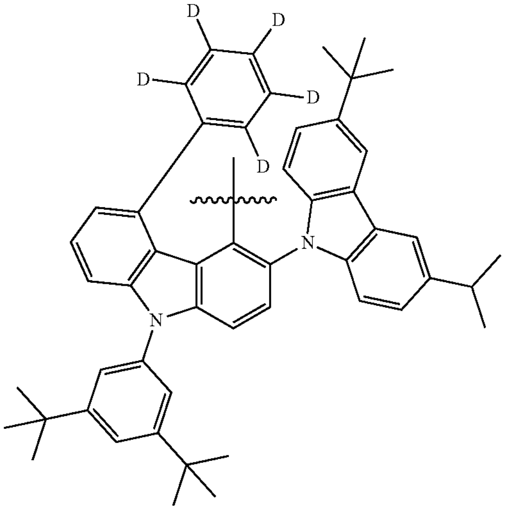
,
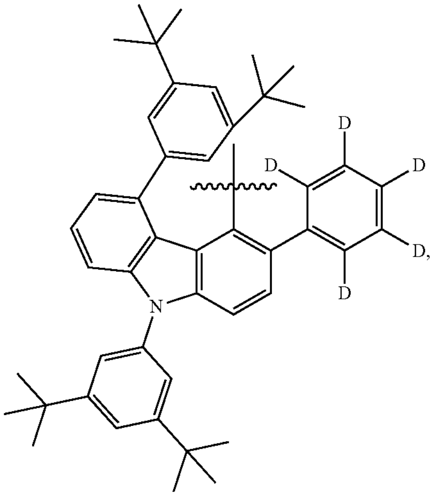
,
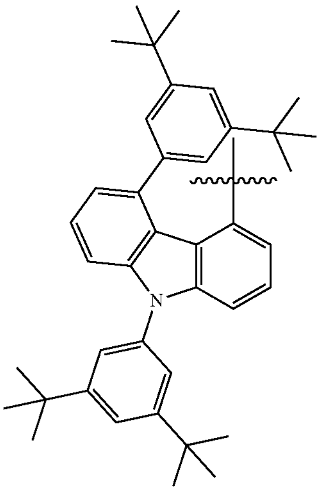
,
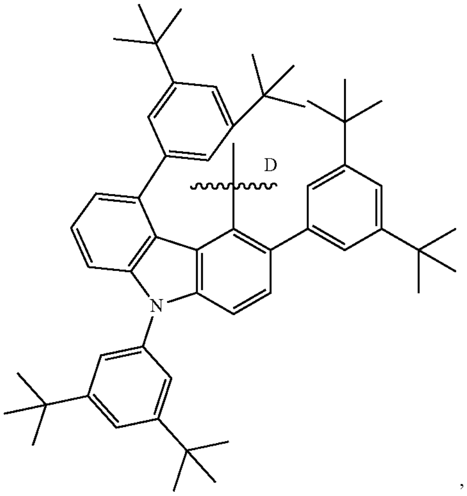
, -continued
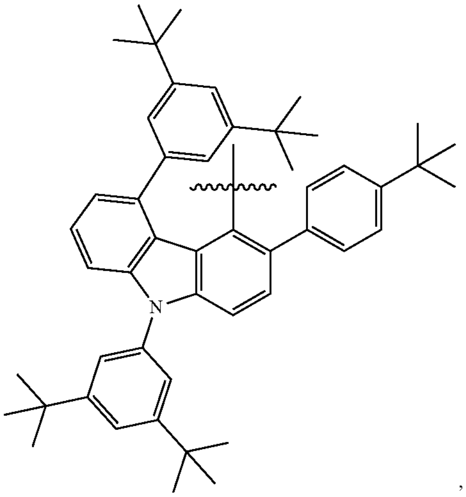
,
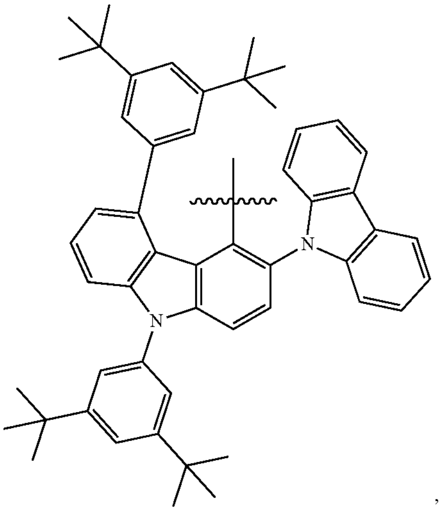
,
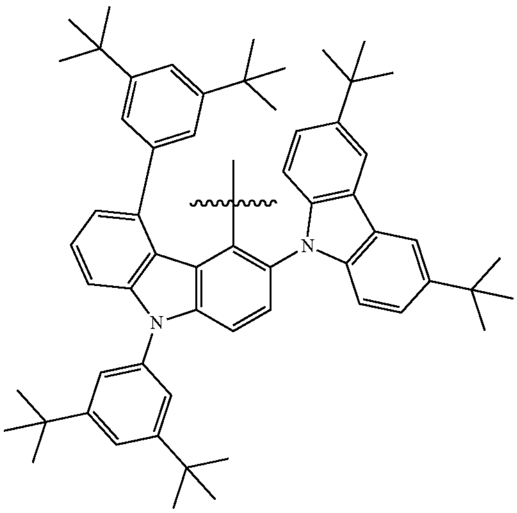
,
-continued
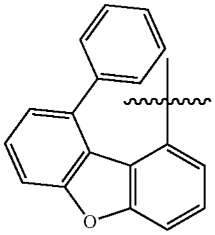
,
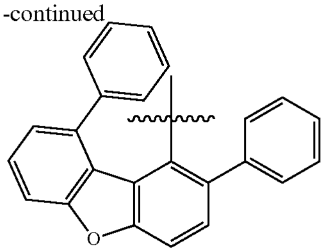
,
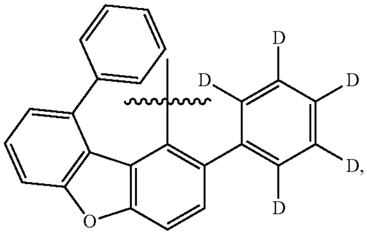
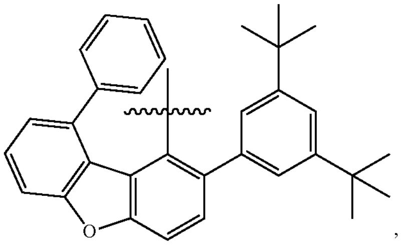
,
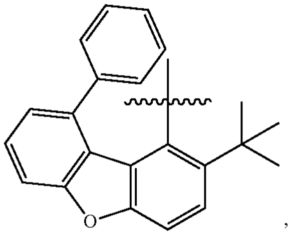
,
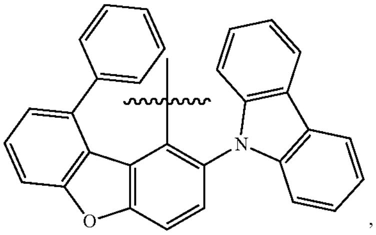
,
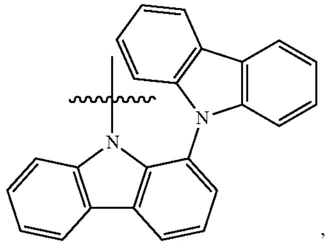
,
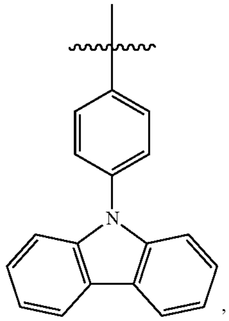
, -continued
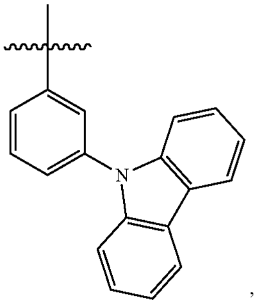
,
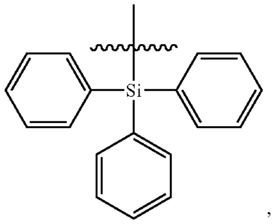
,
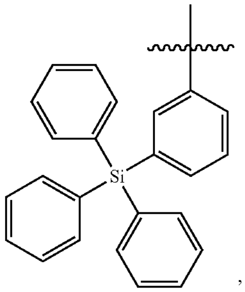
,
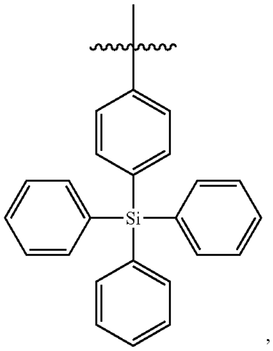
,
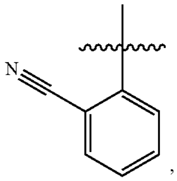
,
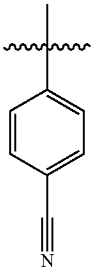
,
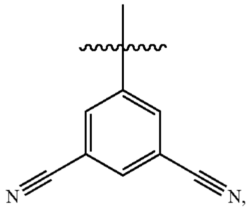
,
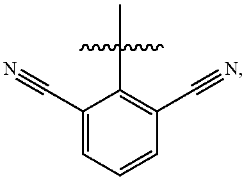
,
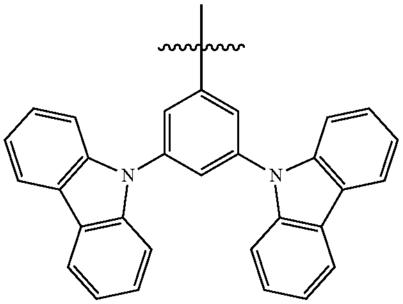
,
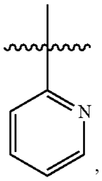
,
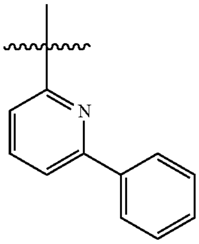
,
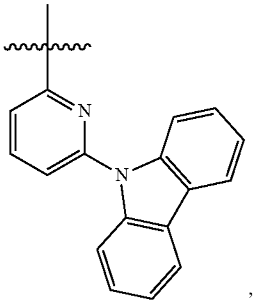
,
-continued
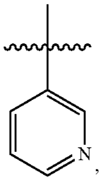
,
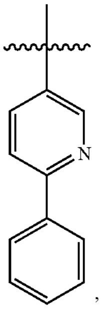
,
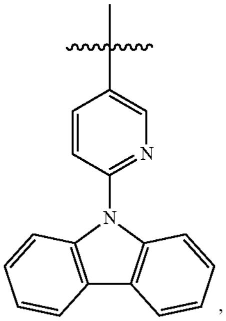
,
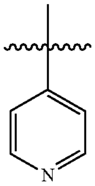
,
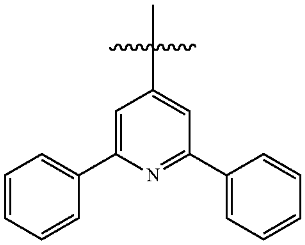
,
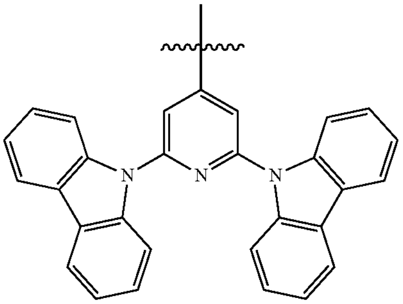
,
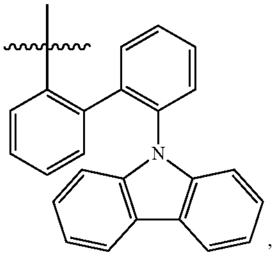
,
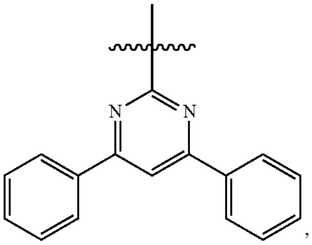
,
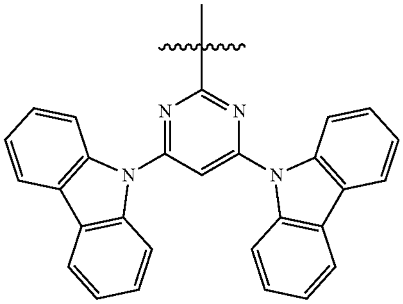
,
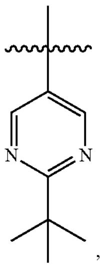
, -continued
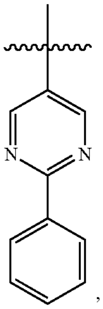,
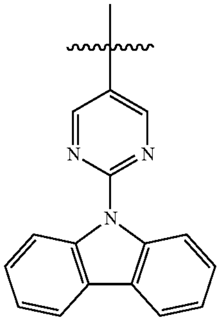,
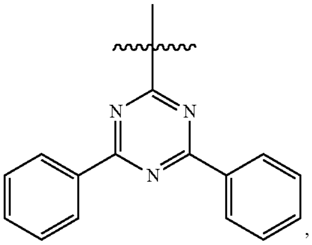,
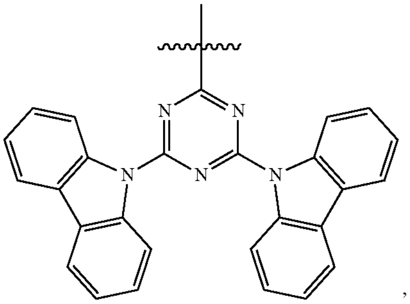,
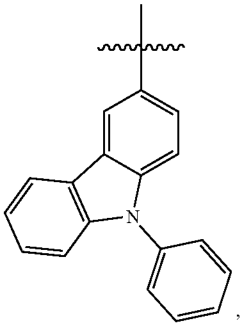,
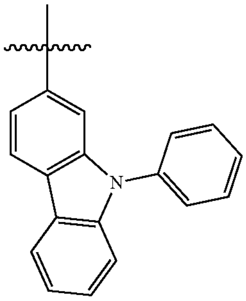,
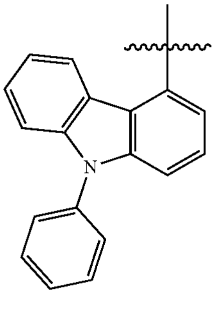,
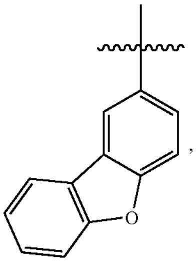,
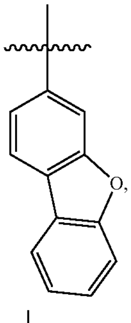,
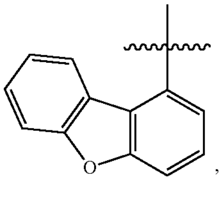,
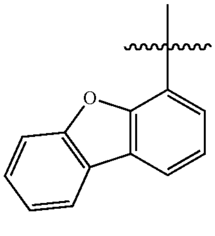,
-continued
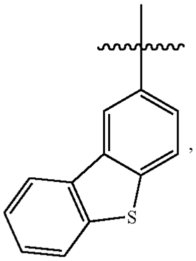,
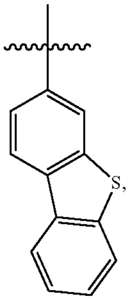,
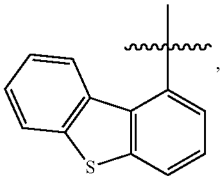,
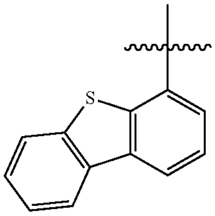,
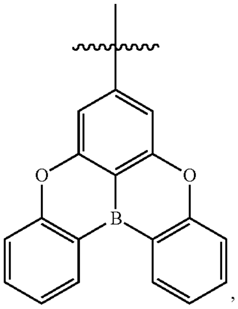,
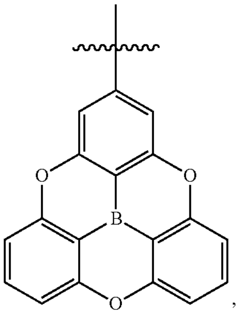,
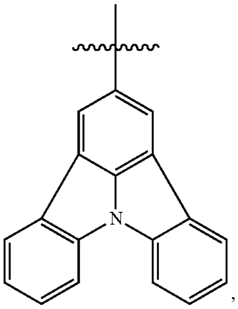,
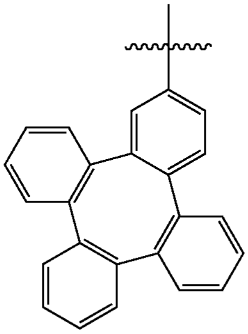,
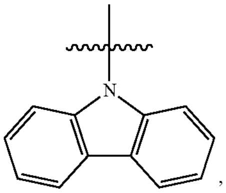,
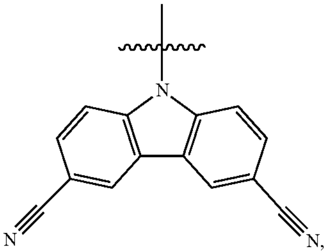, -continued

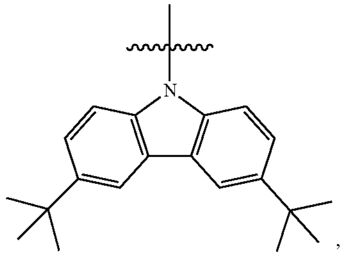

,

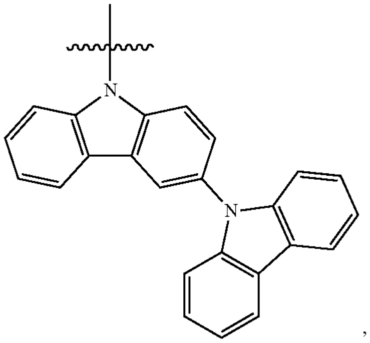

,

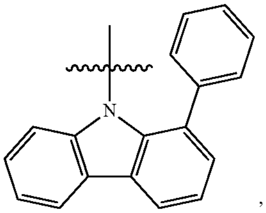

, and

-continued

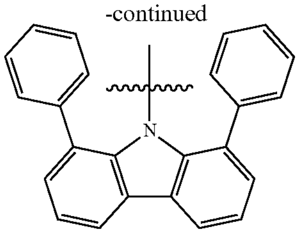

.

In further embodiments, the compound is selected from the group consisting of the compounds having the formula of Pt($L_{A'}$)(Ly):

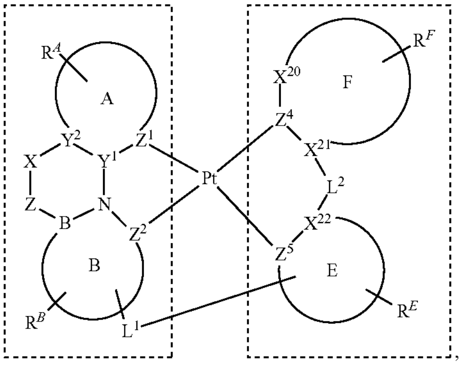

, ($L_{A'}$) ($L_y$)

wherein $L_{A'}$ is selected from the group consisting of the structures shown in the following table:

| $L_A$' | Structure of $L_A$' | $L_A$' | Structure of $L_A$' |
|---|---|---|---|
| For $L_{A'}$1-(Rl)(Rm)(Rn), $L_{A'}$1-(R1)(R1)(R1) to $L_{A'}$1-(R70)(R70)(R70) have the structure, | 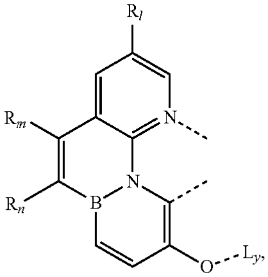 | For $L_{A'}$21-(Rl)(Rm)(Rn)(Ro), $L_{A'}$21-(R1)(R1)(R1)(R1) to $L_{A'}$21-(R70)(R70)(R70)(R70) have the structure, | 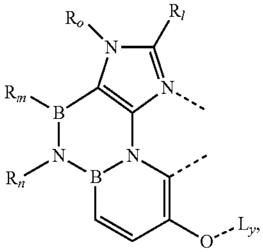 |
| For $L_{A'}$2-(Rl)(Rm)(Rn), $L_{A'}$2-(R1)(R1)(R1) to $L_{A'}$2-(R70)(R70)(R70) have the structure, | 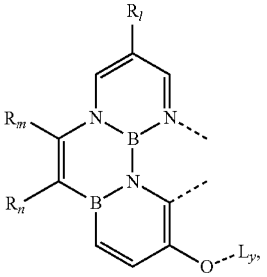 | For $L_{A'}$22-(Rl)(Rm)(Rn), $L_{A'}$22-(R1)(R1)(R1) to $L_{A'}$22-(R70)(R70)(R70) have the structure, | 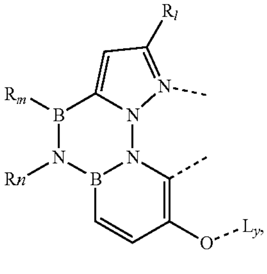 |

-continued

| $L_{A'}$ | Structure of $L_{A'}$ | $L_{A'}$ | Structure of $L_{A'}$ |
|---|---|---|---|
| For $L_{A}$3-(Rl)(Rm)(Rn), $L_{A'}$3-(R1)(R1)(R1) to $L_{A'}$3-(R70)(R70)(R70) have the structure, | 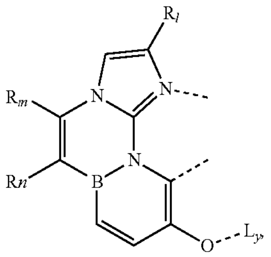 | For $L_{A'}$23-(Rl)(Rm)(Rn), $L_{A'}$23-(R1)(R1)(R1) to $L_{A'}$23-(R70)(R70)(R70) have the structure, | 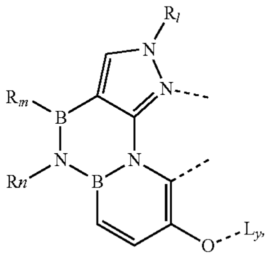 |
| For $L_{A}$4-(Rm)(Rn), $L_{A'}$4-(R1)(R1) to $L_{A'}$4-(R70)(R70) have the structure, | 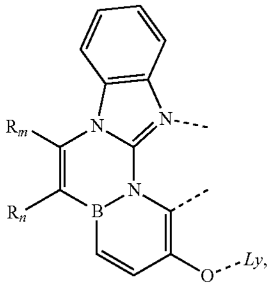 | For $L_{A'}$24-(Rl)(Rm)(Rn), $L_{A'}$24-(R1)(R1)(R1) to $L_{A'}$24-(R70)(R70)(R70) have the structure, | 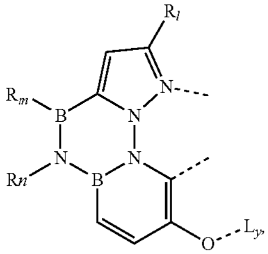 |
| For $L_{A'}$5-(Rl)(Rm)(Rn)(Ro), $L_{A'}$5-(R1)(R1)(R1)(R1) to $L_{A'}$5-(R70)(R70)(R70)(R70) have the structure, | 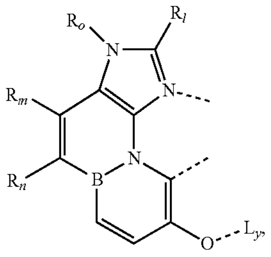 | For $L_{A'}$25-(Rl)(Rm)(Rn), $L_{A'}$25-(R1)(Rl)(R1) to $L_{A'}$25-(R70)(R70)(R70) have the structure, | 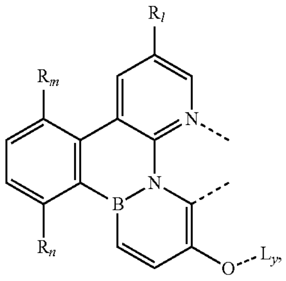 |
| For $L_A$'6-(Rl)(Rm)(Rn), $L_{A'}$6-(R1)(R1)(R1) to $L_{A'}$6-(R70)(R70)(R70) have the structure, | 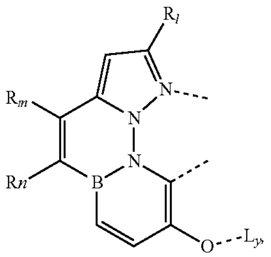 | For $L_{A'}$26-(Rl)(Rm)(Rn), $L_{A'}$26-(R1)(R1)(R1) to $L_{A'}$26-(R70)(R70)(R70) have the structure, | 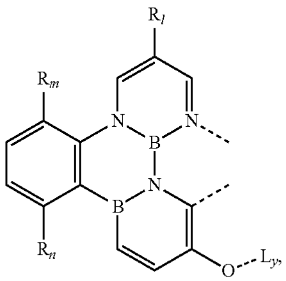 |
| For $L_{A}$7-(Rl)(Rm)(Rn), $L_{A'}$7-(R1)(R1)(R1) to $L_{A'}$7-(R70)(R70)(R70) have the structure, | 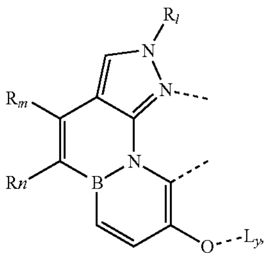 | For $L_{A'}$27-(Rl)(Rm)(Rn)(Ro), $L_{A'}$27-(R1)(R1)(R1)(R1) to $L_{A'}$27-(R70)(R70)(R70)(R70) have the structure, | 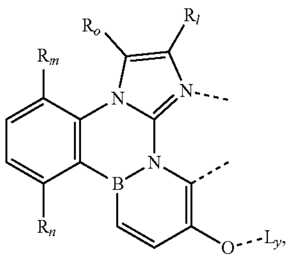 |

-continued

| $L_{A'}$ | Structure of $L_{A'}$ | $L_{A'}$ | Structure of $L_{A'}$ |
|---|---|---|---|
| For $L_{A'}$8-(Rl)(Rm)(Rn), $L_{A'}$8-(R1)(R1)(R1) to $L_{A'}$8-(R70)(R70)(R70) have the structure, | 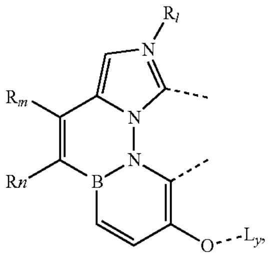 | For $L_{A'}$28-(Rl)(Rm), $L_{A'}$28-(R1)(R1) to $L_{A'}$28-(R70)(R70) have the structure, | 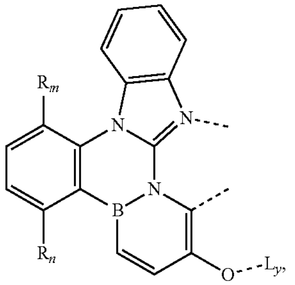 |
| For $L_{A'}$9-(Rl)(Lz), $L_{A'}$9-(R1)(L1) to $L_{A'}$9-(R70)(L5) have the structure, | 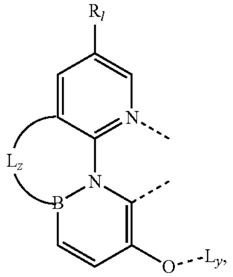 | For $L_{A'}$29-(Rl)(Rm)(Rn)(Ro), $L_{A'}$29-(R1)(R1)(R1)(R1) to $L_{A'}$29-(R70)(R70)(R70)(R70) have the structure, | 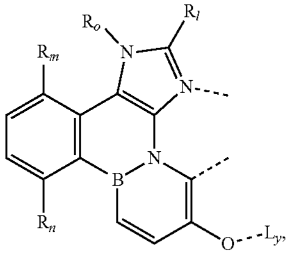 |
| For $L_{A'}$10-(Rl)(Lz), $L_{A'}$10-(R1)(L1) to $L_{A'}$10-(R70)(L5) have the structure, | 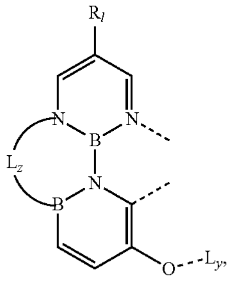 | For $L_{A'}$30-(Rl)(Rm)(Rn), $L_{A'}$30-(R1)(R1)(R1) to $L_{A'}$30-(R70)(R70)(R70) have the structure, | 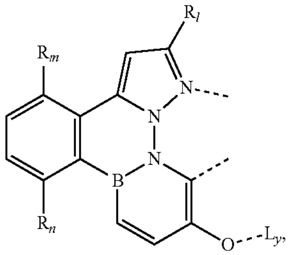 |
| For $L_{A'}$11-(Rl)(Lz), $L_{A'}$ 11-(R1)(LI) to $L_{A'}$11-(R70)(L5) have the structure, | 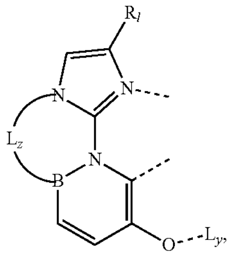 | For $L_{A'}$31-(Rl)(Rm)(Rn), $L_{A'}$31-(R1)(R1)(R1) to $L_{A'}$31-(R70)(R70)(R70) have the structure, | 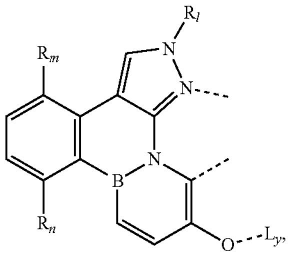 |
| For $L_{A'}$12-(Lz), $L_{A'}$12-(L1) to $L_{A'}$12-(L5) have the structure, | 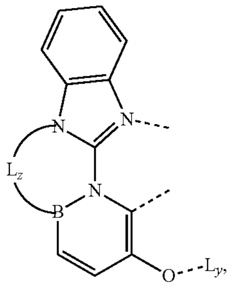 | For $L_{A'}$32-(Rl)(Rm)(Rn), $L_{A'}$32-(R1)(R1)(R1) to $L_{A'}$32-(R70)(R70)(R70) have the structure, | 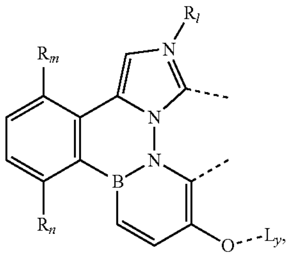 |

-continued

| $L_A$' | Structure of $L_A$' | $L_A$' | Structure of $L_A$' |
|---|---|---|---|
| For $L_A$' 13-(Rl)(Ro)(Lz), $L_A$'13-(R1)(Rl)(L1) to $L_A$'13-(R70)(R70)(L5) have the structure, | 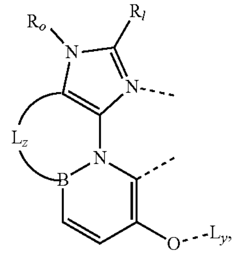 | For $L_A$'33-(Rl)(Rm)(Rn), $L_A$'33-(R1)(R1)(R1) to $L_A$'33-(R70)(R70)(R70) have the structure, | 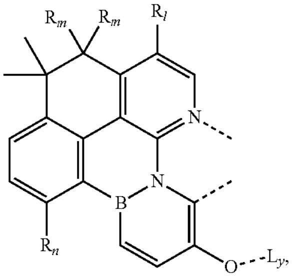 |
| For $L_A$'14-(Rl)(Lz), $L_A$'14-(R1)(L1) to $L_A$'14-(R70)(L5) have the structure, | 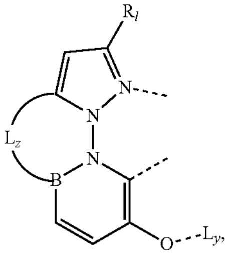 | For $L_A$'34-(Rl)(Rm)(Rn), $L_A$'34-(R1)(R1)(R1) to $L_A$'34-(R70)(R70)(R70) have the structure, | 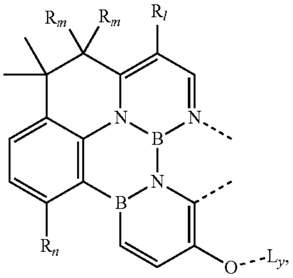 |
| For $L_A$'15-(Rl)(Lz), $L_A$'15-(R1)(LI) to $L_A$'15-(R70)(L5) have the structure, | 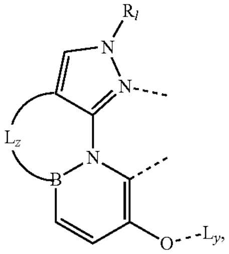 | For $L_A$'35-(Rl)(Rm)(Rn), $L_A$'35-(R1)(R1)(R1) to $L_A$'35-(R70)(R70)(R70) have the structure, | 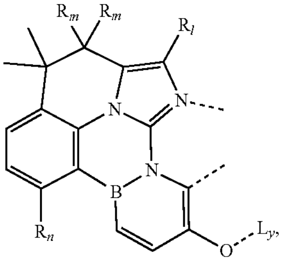 |
| For $L_A$'16-(Rl)(Lz), $L_A$'16-(R1)(L1) to $L_A$'16-(R70)(L5) have the structure, | 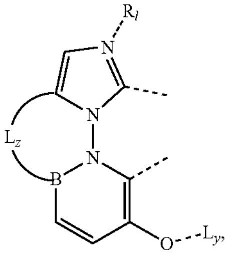 | For $L_A$'36-(Rl)(Rm)(Rn), $L_A$'36-(R1)(R1)(R1) to $L_A$'36-(R70)(R70)(R70) have the structure, | 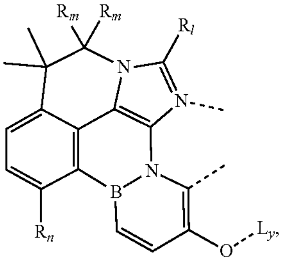 |
| For $L_A$'17-(Rl)(Rm)(Rn), $L_A$'17-(R1)(R1)(R1) to $L_A$'17-(R70)(R70)(R70) have the structure, | 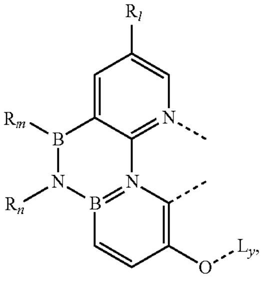 | For $L_A$'37-(Rl)(Rm)(Rn), $L_A$'37-(R1)(R1)(R1) to $L_A$'37-(R70)(R70)(R70) have the structure, | 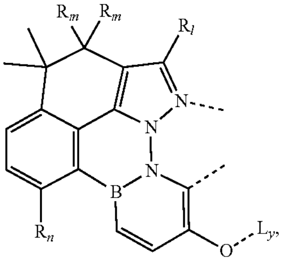 |

-continued

| $L_{A}$' | Structure of $L_{A}$' | $L_{A}$' | Structure of $L_{A}$' |
|---|---|---|---|
| For $L_{A}$'18-(Rl)(Rm)(Rn), $L_{A}$'18-(R1)(R1)(R1) to $L_{A}$'18-(R70)(R70)(R70) have the structure, | 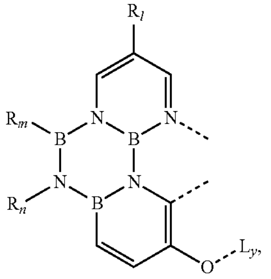 | For $L_{A}$'38-(Rl)(Rm)(Rn), $L_{A}$'38-(R1)(R1)(R1) to $L_{A}$'38-(R70)(R70)(R70) have the structure, | 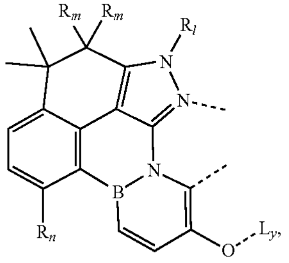 |
| For $L_{A}$'19-(Rl)(Rm)(Rn), $L_{A}$'19-(R1)(R1)(R1) to $L_{A}$'19-(R70)(R70)(R70) have the structure, | 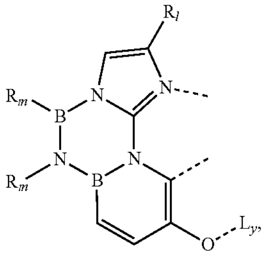 | For $L_{A}$'39-(Rl)(Rm)(Rn), $L_{A}$'39-(R1)(R1)(R1) to $L_{A}$'30-(R70)(R70)(R70) have the structure, | 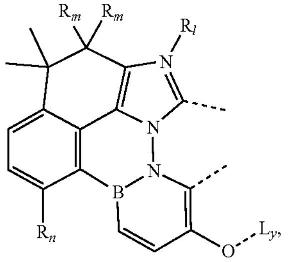 |
| For $L_{A}$'20-(Rm)(Rn), $L_{A}$'20-(R1)(R1) to $L_{A}$'20-(R70)(R70) have the structure, | 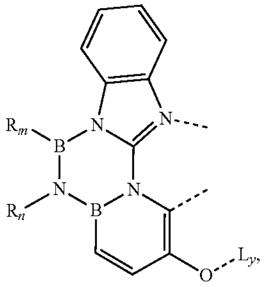 | | |

wherein $L_1$ through $L_5$ have the following structures:

L1

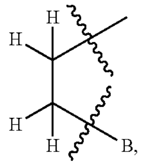

L2

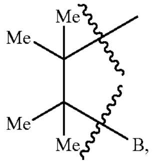

L3

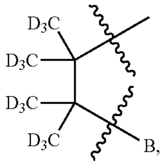

-continued

L4

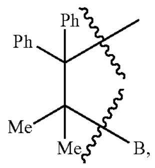

and

L5

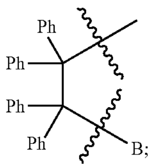

wherein $L_y$ is selected from the group consisting of the structures shown below in the following table:

| $L_y$ | Structure of $L_y$ | $L_y$ | Structure of $L_y$ |
|---|---|---|---|
| $L_y$1-(Ro)(Rp)(Rq), wherein $L_y$1-(R1)(R1)(R1) to $L_y$1-(R70)(R70)(R70) have the structure | 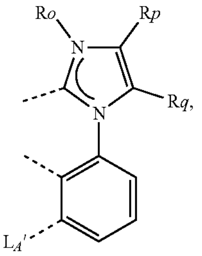 | $L_y$18-(Ro)(Rp)(Rq), wherein $L_y$18-(R1)(R1)(R1) to $L_y$18-(R70)(R70)(R70) have the structure | 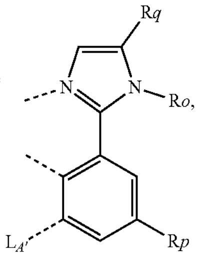 |
| $L_y$2-(Ro)(Rp)(Rq), wherein $L_y$2-(R1)(R1)(R1) to $L_y$2-(R70)(R70)(R70) have the structure | 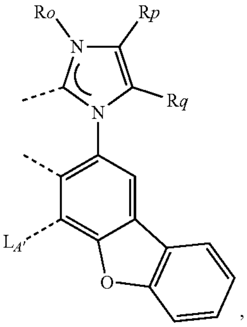 , | $L_y$19-(Ro)(Rp)(Rq), wherein $L_y$19-(R1)(R1)(R1) to $L_y$19-(R70)(R70)(R70) have the structure | 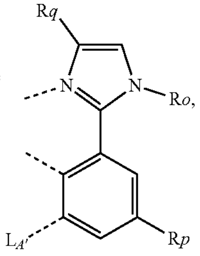 |
| $L_y$3-(Ro)(Rp)(Rq), wherein $L_y$3-(R1)(R1)(R1) to $L_y$3-(R70)(R70)(R70) have the structure | 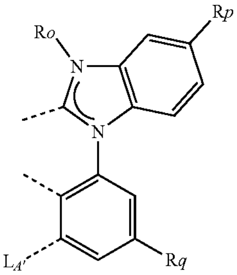 , | $L_y$20-(Ro)(Rp)(Rq), wherein $L_y$20-(R1)(R1)(R1) to $L_y$20-(R70)(R70)(R70) have the structure | 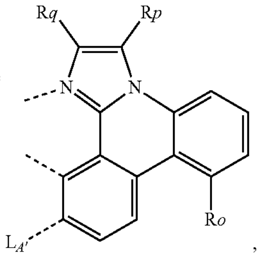 , |
| $L_y$4-(o)(p)(q), wherein $L_y$4-(1)(1)(1) to $L_y$4-(70)(70)(70) have the structure | 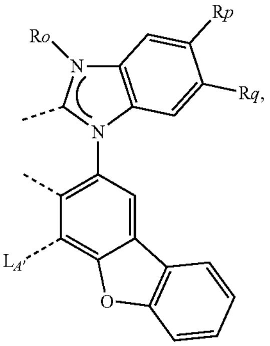 | $L_y$21-(Ro)(Rp)(Rq), wherein $L_y$21-(R1)(R1)(R1) to $L_y$21-(R70)(R70)(R70) have the structure | 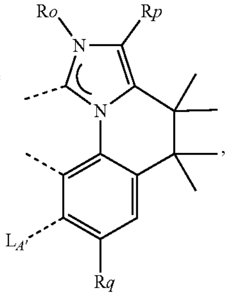 |
| $L_y$5-(Ro)(Rp)(Rq), wherein $L_y$5-(R1)(R1)(R1) to $L_y$5-(R70)(R70)(R70) have the structure | 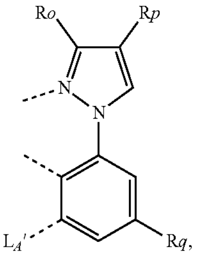 | $L_y$22-(Ro)(Rp)(Rq), wherein $L_y$22-(R1)(R1)(R1) to $L_y$22-(R70)(R70)(R70) have the structure | 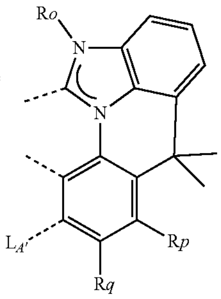 |

-continued

| $L_y$ | Structure of $L_y$ | $L_y$ | Structure of $L_y$ |
|---|---|---|---|
| $L_y$6-(Ro)(Rp)(Rq), wherein $L_y$6-(R1)(R1)(R1) to $L_y$6-(R70)(R70)(R70) have the structure | 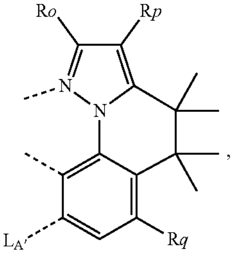 | $L_y$23-(Ro)(Rp)(Rq), wherein $L_y$23-(R1)(R1)(R1) to $L_y$23-(R70)(R70)(R70) have the structure | 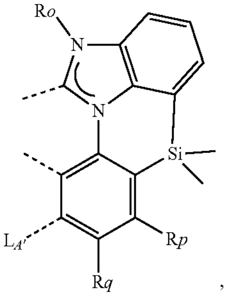 |
| $L_y$7-(Ro)(Rp)(Rq), wherein $L_y$7-(R1)(R1)(R1) to $L_y$7-(R70)(R70)(R70) have the structure | 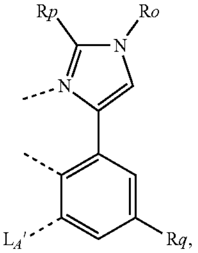 | $L_y$24-(Ro)(Rp)(Rq), wherein $L_y$24-(R1)(R1)(R1) to $L_y$24-(R70)(R70)(R70) have the structure | 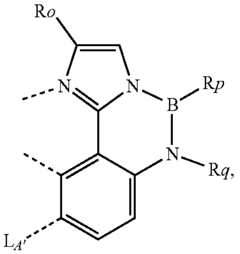 |
| $L_y$8-(Ro)(Rp)(Rq), wherein $L_y$8-(R1)(R1)(R1) to $L_y$8-(R70)(R70)(R70) have the structure | 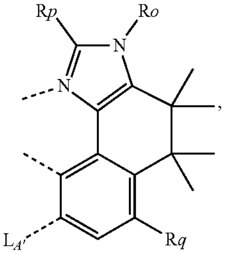 | $L_y$25-(Ro)(Rp)(Rq), wherein $L_y$25-(R1)(R1)(R1) to $L_y$25-(R70)(R70)(R70) have the structure | 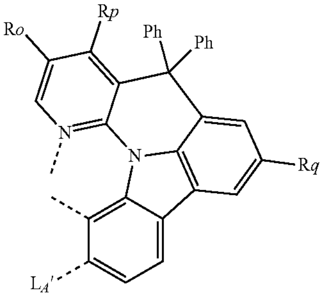 |
| $L_y$9-(Ro)(Rp)(Rq), wherein $L_y$9-(R1)(R1)(R1) to $L_y$9-(R70)(R70)(R70) have the structure | 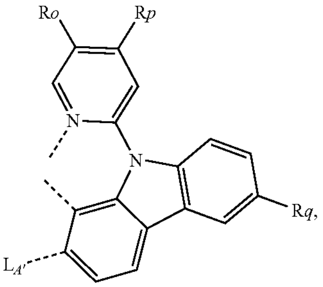 | $L_y$26-(Ro)(Rp)(Rq), wherein $L_y$26-(R1)(R1)(R1) to $L_y$26-(R70)(R70)(R70) have the structure | 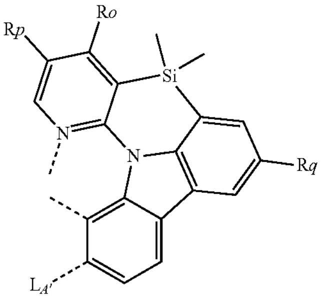 |
| $L_y$10-(Ro)(Rp)(Rq), wherein $L_y$10-(R1)(R1)(R1) to $L_y$10-(R70)(R70)(R70) have the structure | 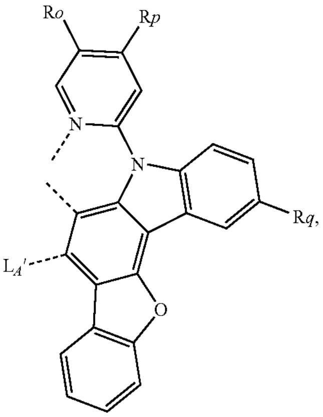 | $L_y$27-(Ro)(Rp)(Rq), wherein $L_y$27-(R1)(R1)(R1) to $L_y$27-(R70)(R70)(R70) have the structure | 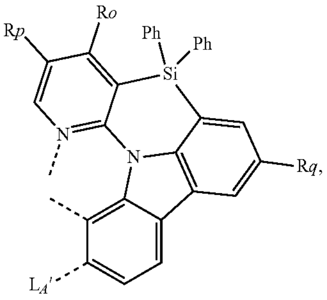 |

-continued

| $L_y$ | Structure of $L_y$ | $L_y$ | Structure of $L_y$ |
|---|---|---|---|
| $L_y$11-(Ro)(Rp)(Rq), wherein $L_y$11-(R1)(R1)(R1) to $L_y$11-(R70)(R70)(R70) have the structure | 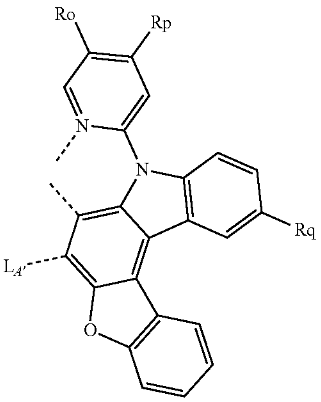 | $L_y$28-(Ro)(Rp)(Rq), wherein $L_y$28-(R1)(R1)(R1) to $L_y$28-(R70)(R70)(R70) have the structure | 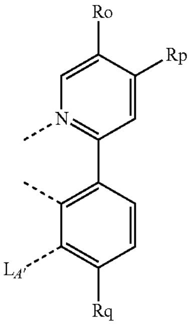 |
| $L_y$12-(Ro)(Rp)(Rq), wherein $L_y$12-(R1)(R1)(R1) to $L_y$12-(R70)(R70)(R70) have the structure | 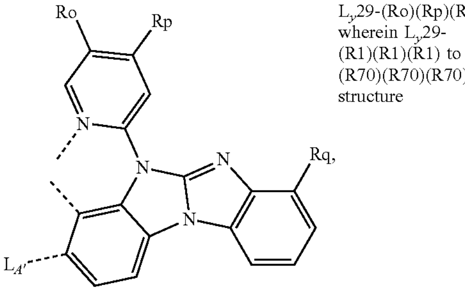 | $L_y$29-(Ro)(Rp)(Rq), wherein $L_y$29-(R1)(R1)(R1) to $L_y$29-(R70)(R70)(R70) have the structure | 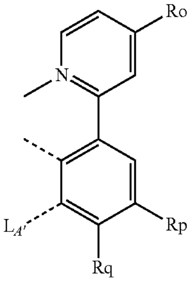 |
| $L_y$13-(Ro)(Rp)(Rq), wherein $L_y$13-(R1)( R1)(R1) to $L_y$13-(R70)(R70)( R70) have the structure | 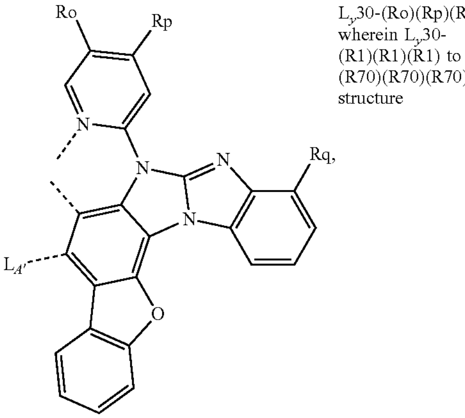 | $L_y$30-(Ro)(Rp)(Rq), wherein $L_y$30-(R1)(R1)(R1) to $L_y$30-(R70)(R70)(R70) have the structure | 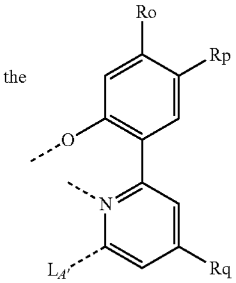 |
| $L_y$14-(Ro)(Rp)(Rq), wherein $L_y$14-(R1)(R1)(R1) to $L_y$14-(R70)(R70)(R70) have the structure | 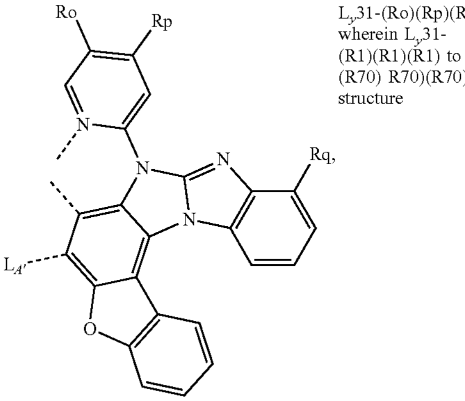 | $L_y$31-(Ro)(Rp)(Rq), wherein $L_y$31-(R1)(R1)(R1) to $L_y$31-(R70) R70)(R70) have the structure | 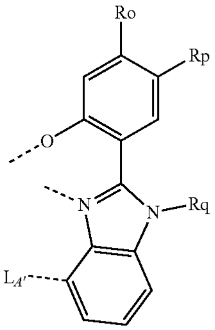 |

-continued

| $L_y$ | Structure of $L_y$ | $L_y$ | Structure of $L_y$ |
|---|---|---|---|
| $L_y$15-(Ro)(Rp)(Rq), wherein $L_y$15-(R1)(R1)(R1) to $L_y$15-(R70)(R70)(R70) have the structure | 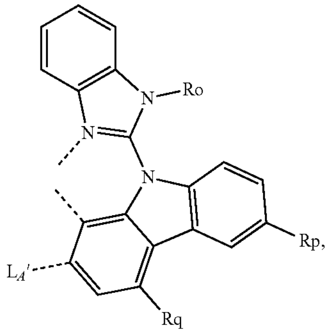 | $L_y$32-(Ro)(Rp)(Rq), wherein $L_y$32-(R1)(R1)(R1) to $L_y$32-(R70)(R70)(R70) have the structure | 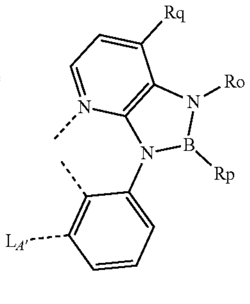 |
| $L_y$16-(Ro)(Rp)(Rq), wherein $L_y$16-(R1)(R1)(R1) to $L_y$16-(R70)(R70)(R70) have the structure | 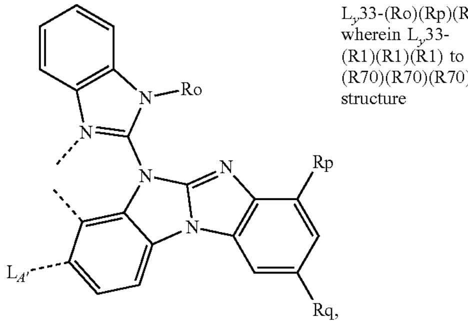 | $L_y$33-(Ro)(Rp)(Rq), wherein $L_y$33-(R1)(R1)(R1) to $L_y$33-(R70)(R70)(R70) have the structure | 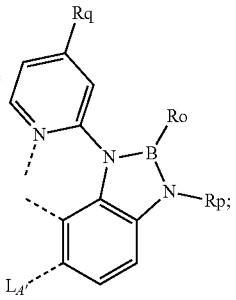 |
| $L_y$17-(Ro)(Rp)(Rq), wherein $L_y$17-(R1)(R1)(R1) to $L_y$17-(R70)(R70)(R70) have the structure | 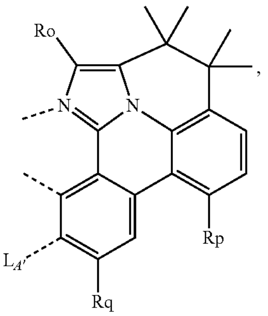 | | |

wherein R1 to R70 have the structures as defined as follows:

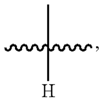 R1

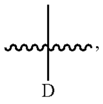 R2

Me, R3 iPr, R4 tBu, R5

$CD_3$, R6

-continued

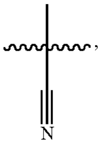 R7

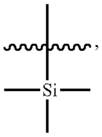 R8

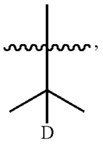 R9

-continued
R10
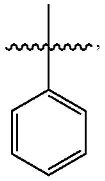
R11
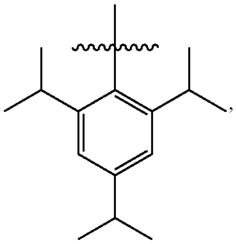
R12
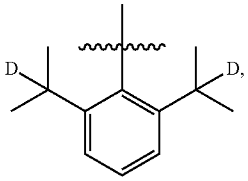
R13
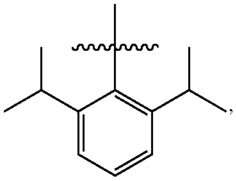
R14
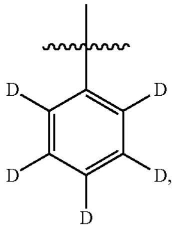
R15
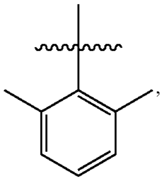
R16
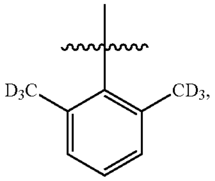
R17
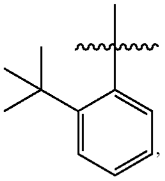
-continued
R18
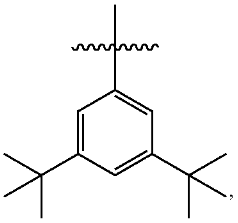
R19
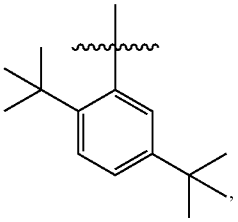
R20
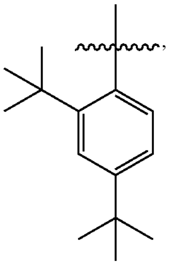
R21
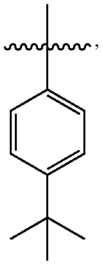
R22
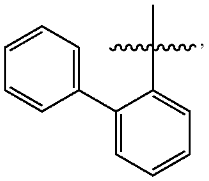
R23
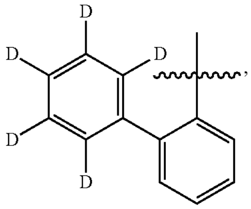

-continued
R24
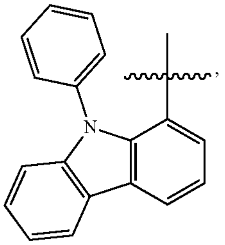
R25
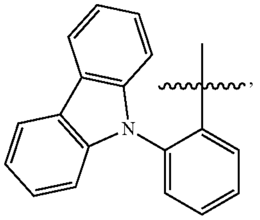
R26
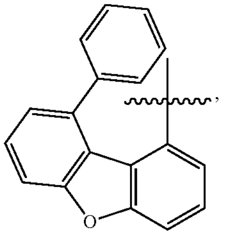
R27
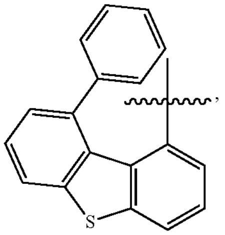
R28
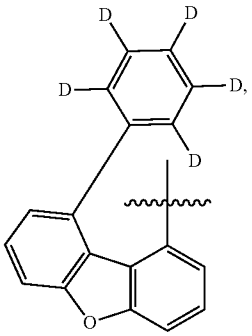
R29
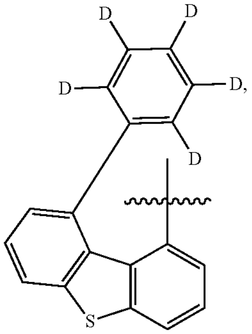
R30
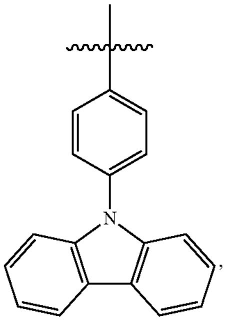
R31
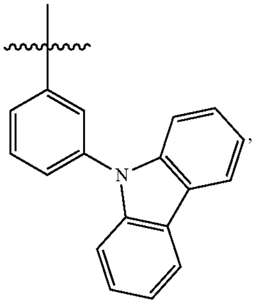
R32
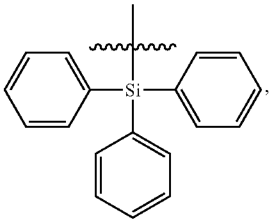
R33
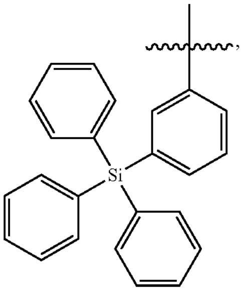
R34
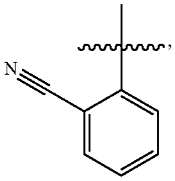
R35
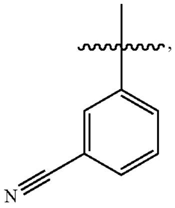

-continued
R36
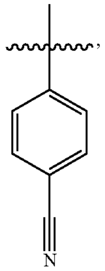
R37
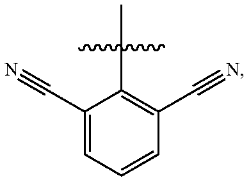
R38
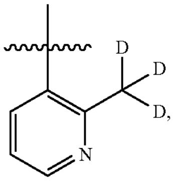
R39
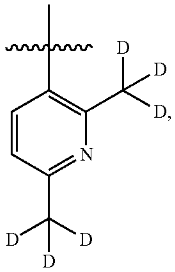
R40
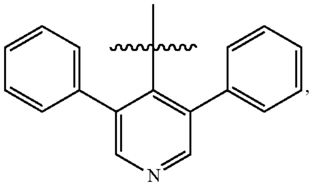
R41
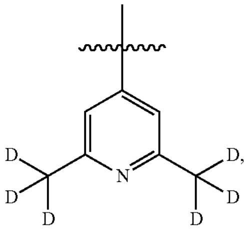
R42
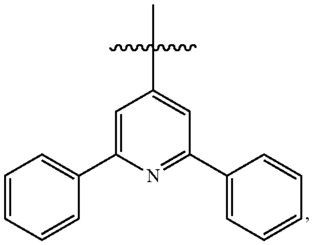
-continued
R43
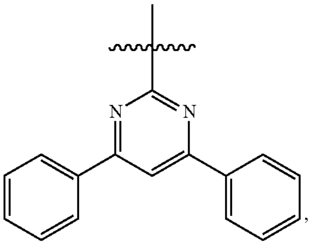
R44
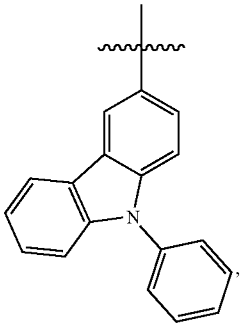
R45
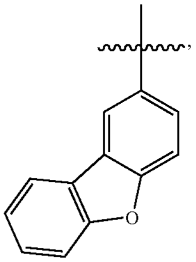
R46
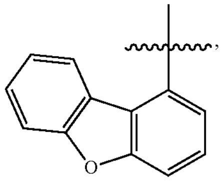
R47
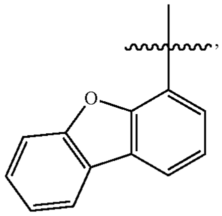
R48
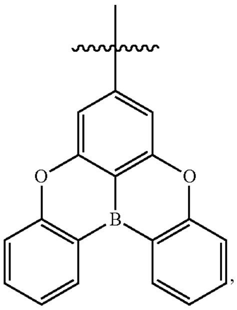

-continued
R49
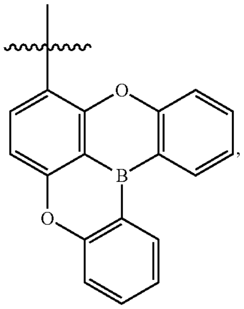
R50
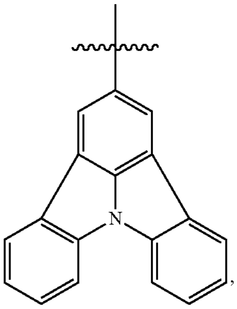
R51
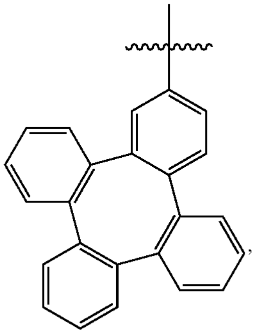
R52
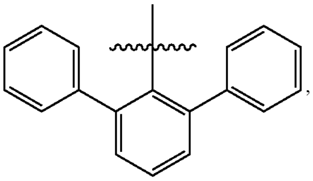
R53
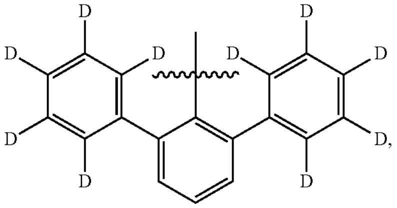
R54
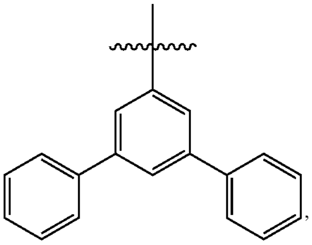
-continued
R55
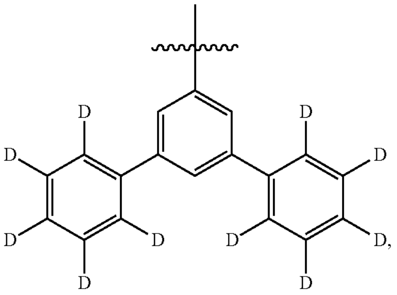
R56
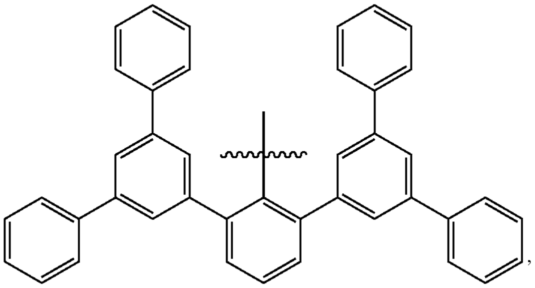
R57
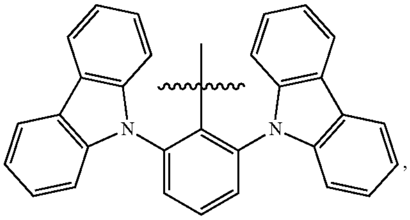
R58
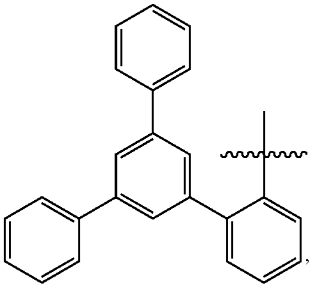
R59
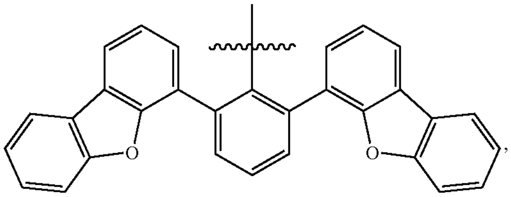
R60
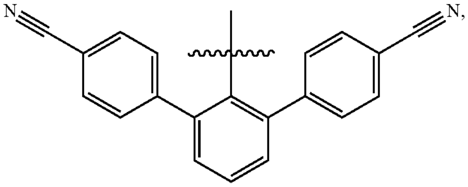

-continued
R61
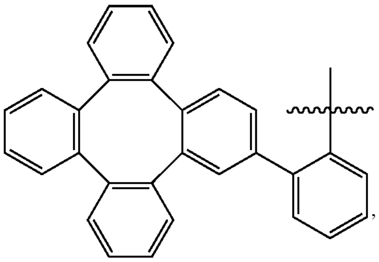
R62
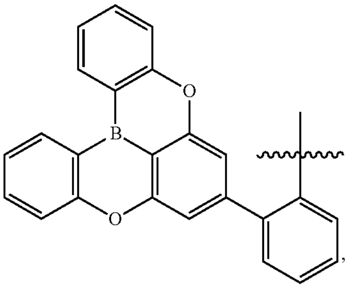
R63
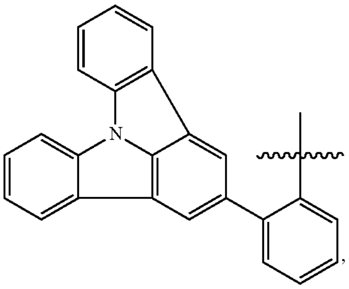
R64
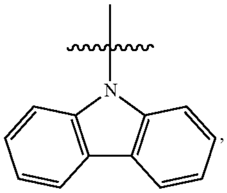
R65
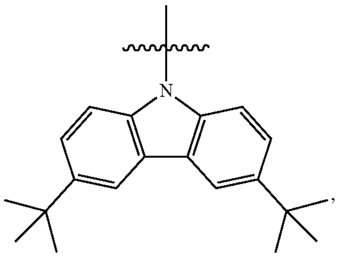
-continued
R66
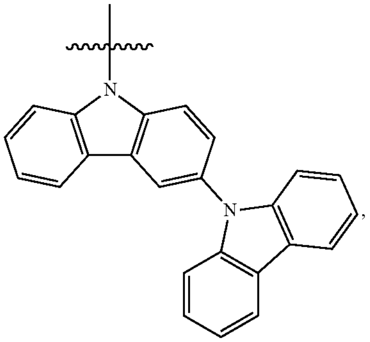
R67
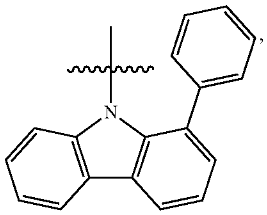
R68
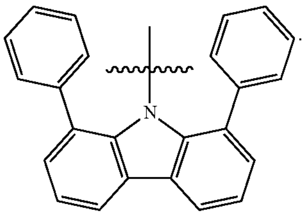
R69
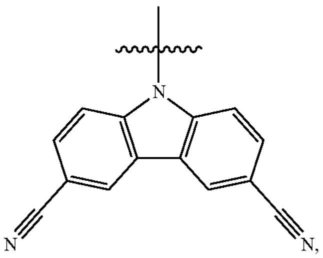
and
R70
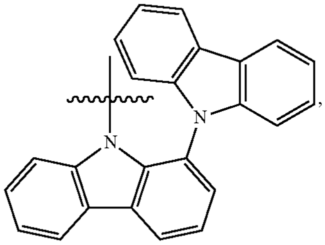
In further embodiments, the compound is selected from the group consisting of the structures as defined as follows:

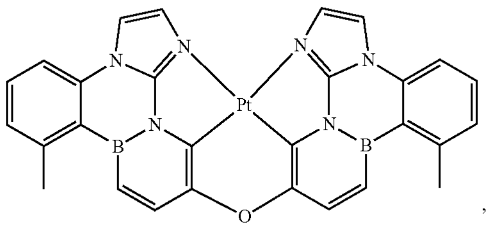

,

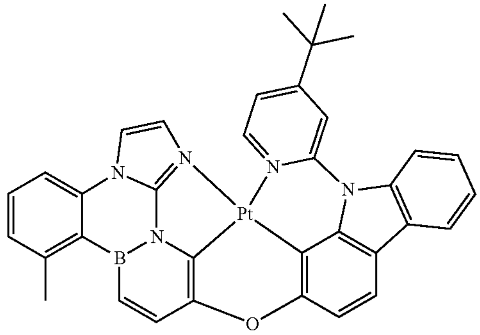

,

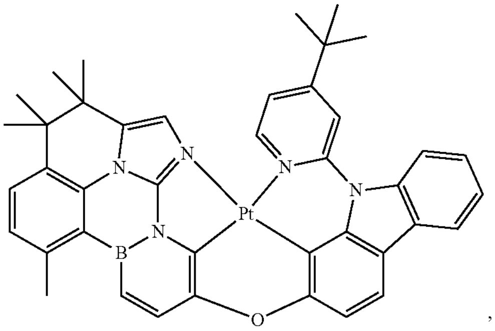

,

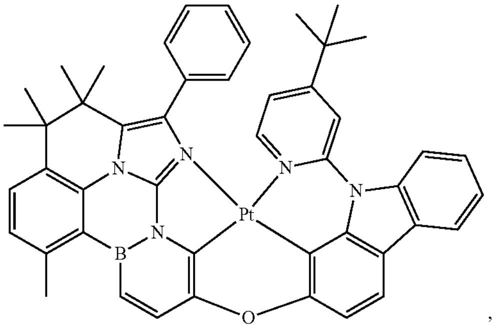

,

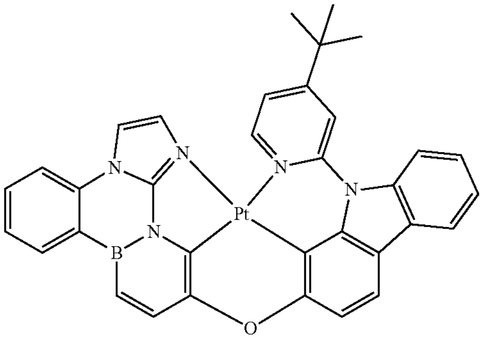

,

-continued

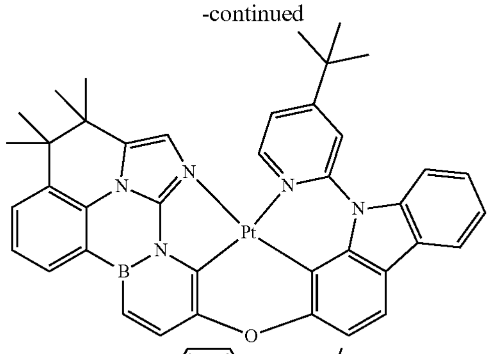

,

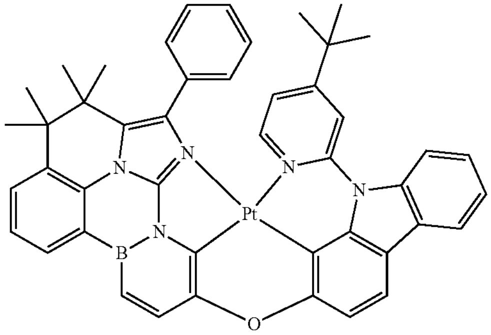

,

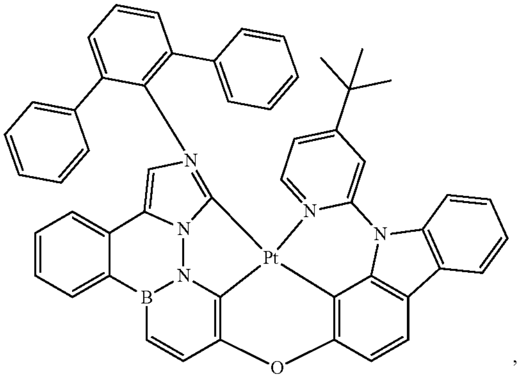

, and

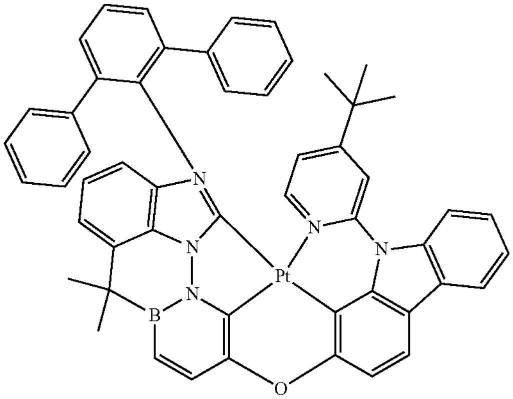

.

In some embodiments, the compound having a first ligand $L_A$ of Formula I described herein can be at least 30% deuterated, at least 40% deuterated, at least 50% deuterated, at least 60% deuterated, at least 70% deuterated, at least 80% deuterated, at least 90% deuterated, at least 95% deuterated, at least 99% deuterated, or 100% deuterated. As used herein, percent deuteration has its ordinary meaning and includes the percent of possible hydrogen atoms (e.g., positions that are hydrogen, deuterium, or halogen) that are replaced by deuterium atoms.

C. The OLEDs and the Devices of the Present Disclosure

In another aspect, the present disclosure also provides an OLED device comprising a first organic layer that contains a compound as disclosed in the above compounds section of the present disclosure.

In some embodiments, the first organic layer may comprise a compound as described herein.

In some embodiments, the organic layer may be an emissive layer and the compound as described herein may be an emissive dopant or a non-emissive dopant.

In some embodiments, the organic layer may further comprise a host, wherein the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH{=}CH{-}C_nH_{2n+1}$, $C{\equiv}CC_nH_{2n+1}$, $Ar_1$, $Ar_1$-$Ar_2$, $C_nH_{2n}{-}Ar_1$, or no substitution, wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In some embodiments, the organic layer may further comprise a host, wherein host comprises at least one chemical group selected from the group consisting of triphenylene, carbazole, indolocarbazole, dibenzothiphene, dibenzofuran, dibenzoselenophene, 5λ2-benzo[d]benzo[4,5]imidazo[3,2-a]imidazole, 5,9-dioxa-13b-boranaphtho[3,2,1-de]anthracene, triazine, aza-triphenylene, aza-carbazole, aza-indolocarbazole, aza-dibenzothiophene, aza-dibenzofuran, aza-dibenzoselenophene, aza-5λ2-benzo[d]benzo[4,5]imidazo[3,2-a]imidazole, and aza-(5,9-dioxa-13b-boranaphtho[3,2,1-de]anthracene).

In some embodiments, the host may be selected from the HOST Group consisting of the structures as defined as follows:

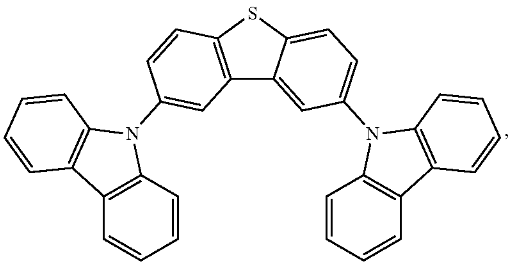
,

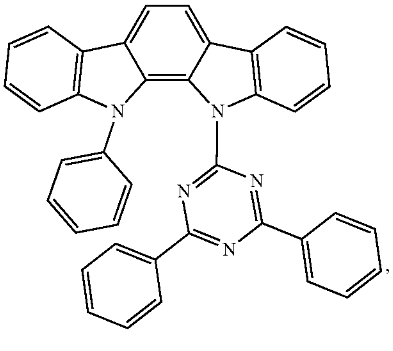
,

-continued

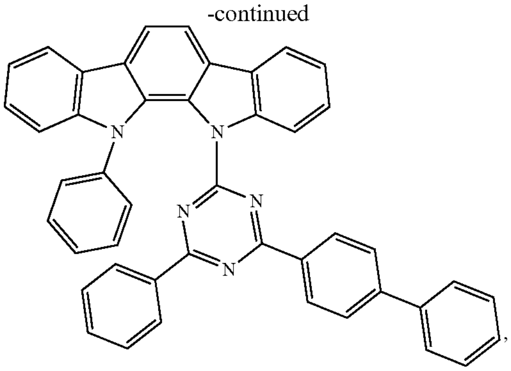
,

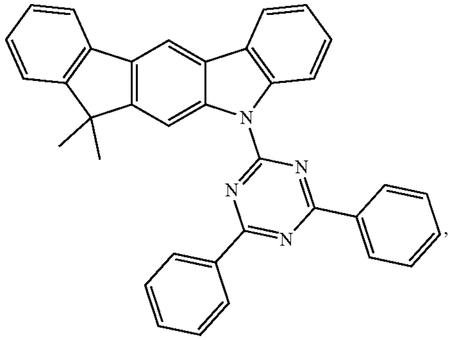
,

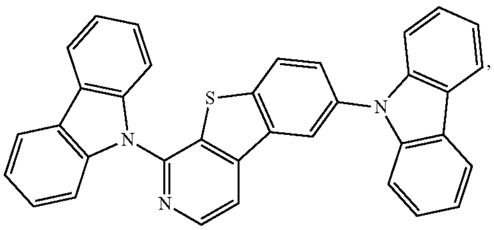
,

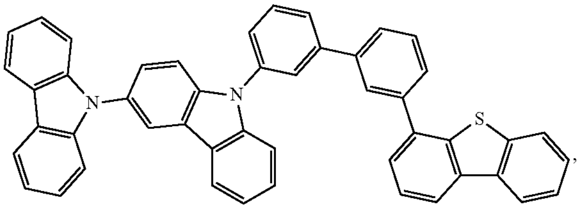
,

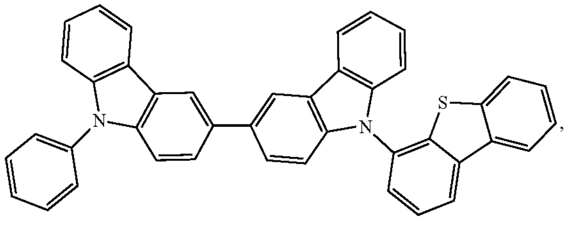
,

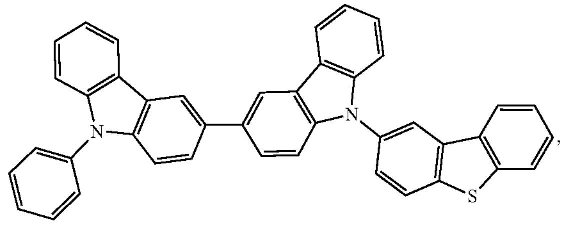
,

-continued
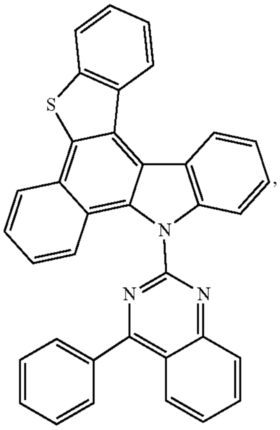
,
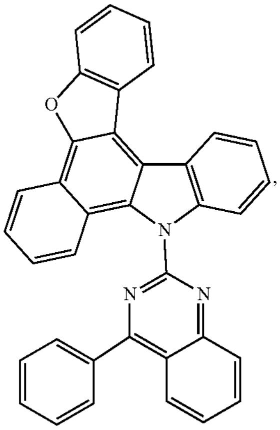
,
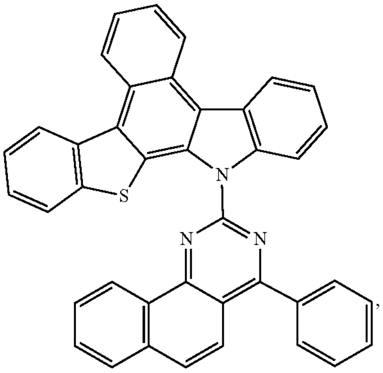
,
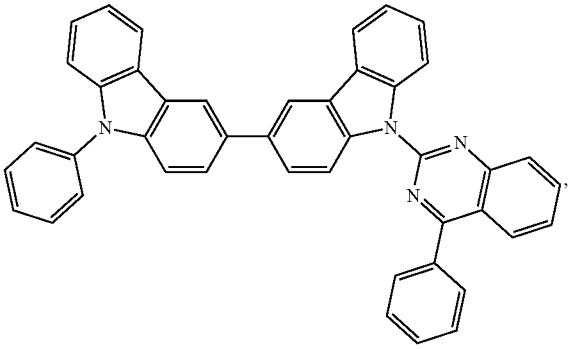
,
-continued
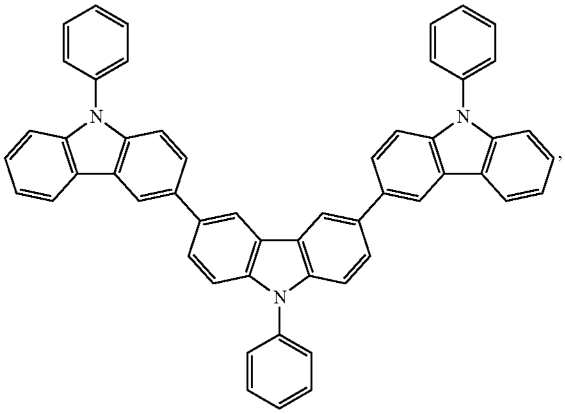
,
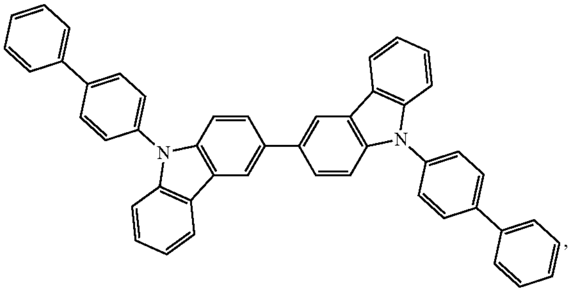
,
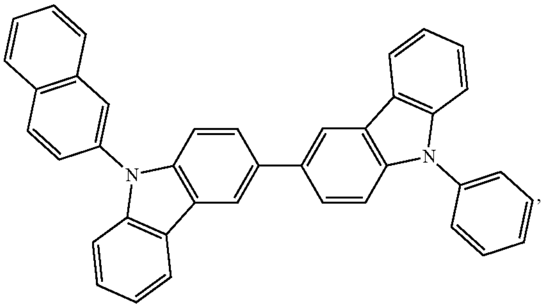
,
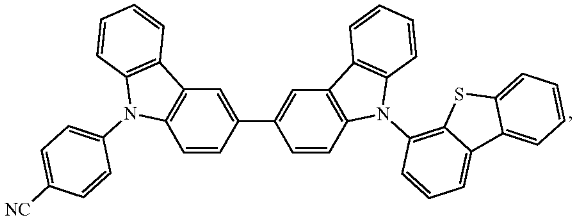
,
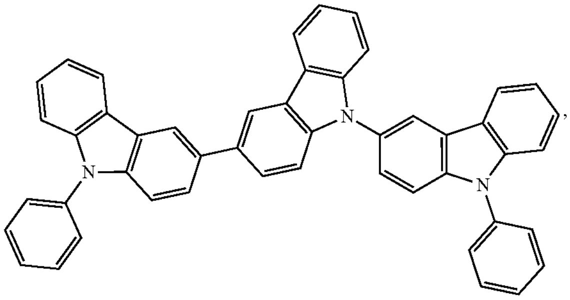
, -continued
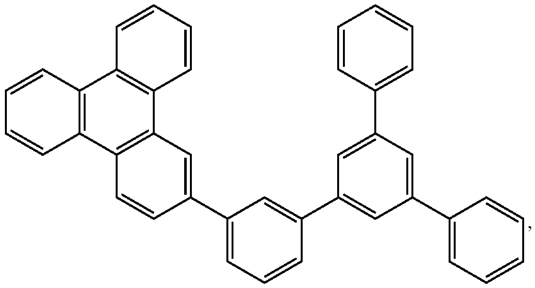
,
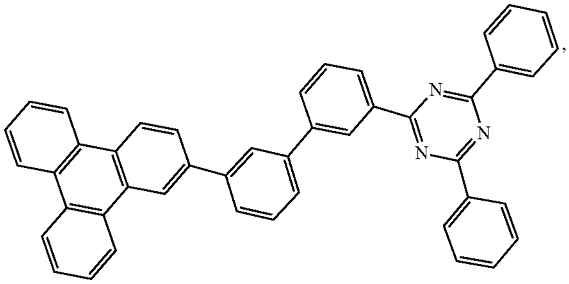
,
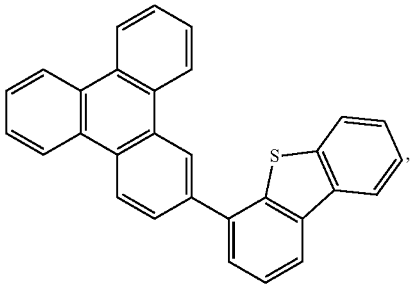
,
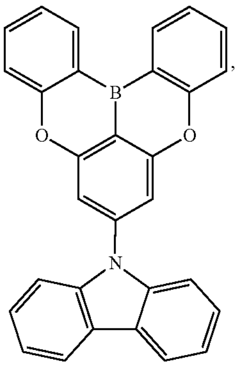
,
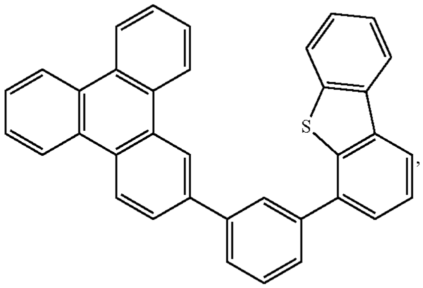
,
-continued
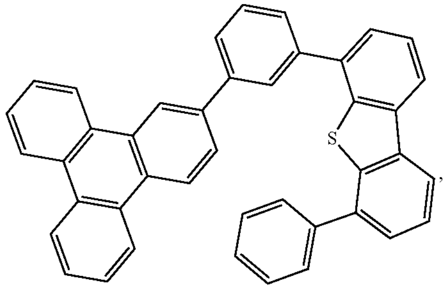
,
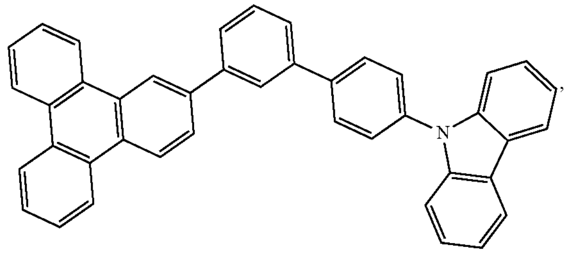
,
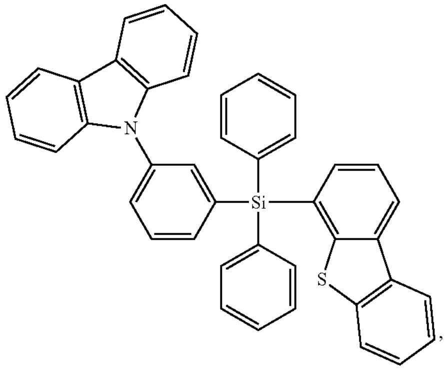
,
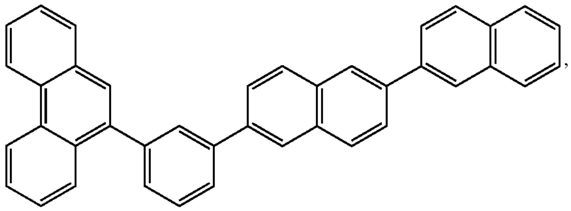
,
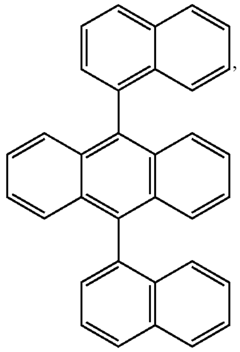
, -continued

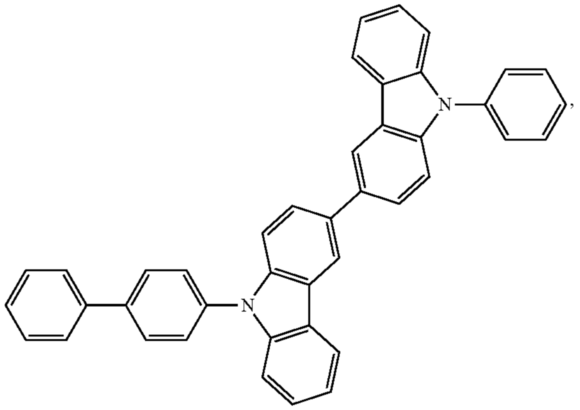

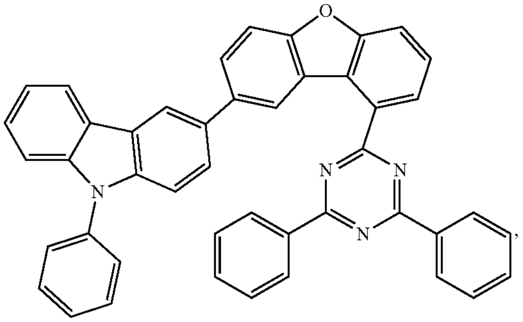

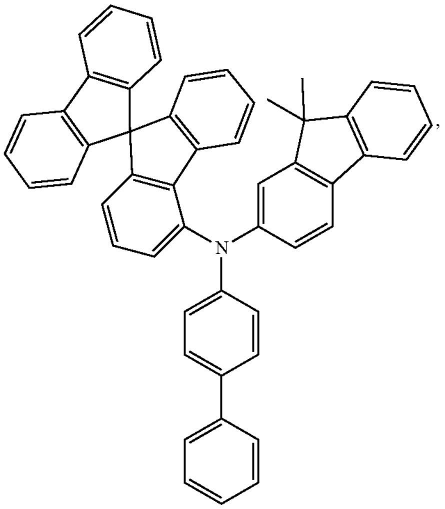

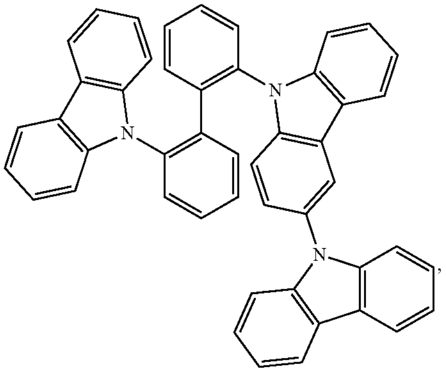

-continued

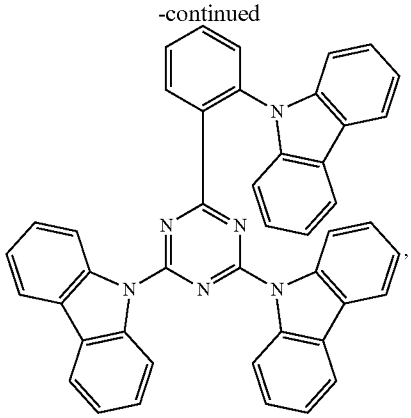

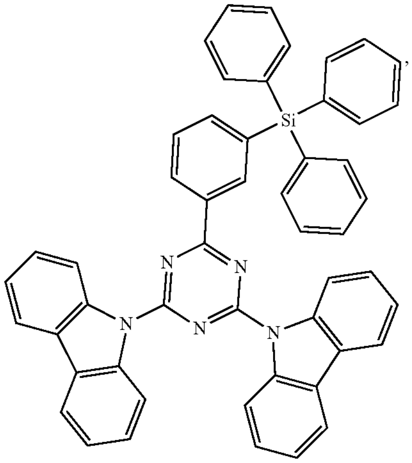 [SMILES: c1ccc([Si](c2ccccc2)(c2ccccc2)c2cccc(-c3nc(-n4c5ccccc5c5ccccc54)nc(-n4c5ccccc5c5ccccc54)n3)c2)cc1]

and combinations thereof.

In some embodiments, the organic layer may further comprise a host, wherein the host comprises a metal complex.

In some embodiments, the compound as described herein may be a sensitizer; wherein the device may further comprise an acceptor; and wherein the acceptor may be selected from the group consisting of fluorescent emitter, delayed fluorescence emitter, and combination thereof.

In yet another aspect, the OLED of the present disclosure may also comprise an emissive region containing a compound as disclosed in the above compounds section of the present disclosure.

In some embodiments, the emissive region may comprise the compound as described herein.

In some embodiments, at least one of the anode, the cathode, or a new layer disposed over the organic emissive layer functions as an enhancement layer. The enhancement layer comprises a plasmonic material exhibiting surface plasmon resonance that non-radiatively couples to the emitter material and transfers excited state energy from the emitter material to non-radiative mode of surface plasmon polariton. The enhancement layer is provided no more than a threshold distance away from the organic emissive layer, wherein the emitter material has a total non-radiative decay rate constant and a total radiative decay rate constant due to the presence of the enhancement layer and the threshold distance is where the total non-radiative decay rate constant is equal to the total radiative decay rate constant. In some embodiments, the OLED further comprises an outcoupling layer. In some embodiments, the outcoupling layer is disposed over the enhancement layer on the opposite side of the organic emissive layer. In some embodiments, the outcoupling layer is disposed on opposite side of the emissive layer from the enhancement layer but still outcouples energy from the surface plasmon mode of the enhancement layer. The outcoupling layer scatters the energy from the surface plasmon polaritons. In some embodiments this energy is scattered as photons to free space. In other embodiments, the energy is scattered from the surface plasmon mode into other modes of the device such as but not limited to the organic waveguide mode, the substrate mode, or another waveguiding mode. If energy is scattered to the non-free space mode of the OLED other outcoupling schemes could be incorporated to extract that energy to free space.

In some embodiments, one or more intervening layer can be disposed between the enhancement layer and the outcoupling layer. The examples for interventing layer(s) can be dielectric materials, including organic, inorganic, perovskites, oxides, and may include stacks and/or mixtures of these materials.

The enhancement layer modifies the effective properties of the medium in which the emitter material resides resulting in any or all of the following: a decreased rate of emission, a modification of emission line-shape, a change in emission intensity with angle, a change in the stability of the emitter material, a change in the efficiency of the OLED, and reduced efficiency roll-off of the OLED device. Placement of the enhancement layer on the cathode side, anode side, or on both sides results in OLED devices which take advantage of any of the above-mentioned effects. In addition to the specific functional layers mentioned herein and illustrated in the various OLED examples shown in the figures, the OLEDs according to the present disclosure may include any of the other functional layers often found in OLEDs.

The enhancement layer can be comprised of plasmonic materials, optically active metamaterials, or hyperbolic metamaterials. As used herein, a plasmonic material is a material in which the real part of the dielectric constant crosses zero in the visible or ultraviolet region of the electromagnetic spectrum. In some embodiments, the plasmonic material includes at least one metal. In such embodiments the metal may include at least one of Ag, Al, Au, Ir, Pt, Ni, Cu, W, Ta, Fe, Cr, Mg, Ga, Rh, Ti, Ru, Pd, In, Bi, Ca alloys or mixtures of these materials, and stacks of these materials. In general, a metamaterial is a medium composed of different materials where the medium as a whole acts differently than the sum of its material parts. In particular, we define optically active metamaterials as materials which have both negative permittivity and negative permeability. Hyperbolic metamaterials, on the other hand, are anisotropic media in which the permittivity or permeability are of different sign for different spatial directions. Optically active metamaterials and hyperbolic metamaterials are strictly distinguished from many other photonic structures such as Distributed Bragg Reflectors ("DBRs") in that the medium should appear uniform in the direction of propagation on the length scale of the wavelength of light. Using terminology that one skilled in the art can understand: the dielectric constant of the metamaterials in the direction of propagation can be described with the effective medium approximation. Plasmonic materials and metamaterials provide methods for controlling the propagation of light that can enhance OLED performance in a number of ways.

In some embodiments, the enhancement layer is provided as a planar layer. In other embodiments, the enhancement layer has wavelength-sized features that are arranged periodically, quasi-periodically, or randomly, or sub-wavelength-sized features that are arranged periodically, quasi-periodically, or randomly. In some embodiments, the wavelength-sized features and the sub-wavelength-sized features have sharp edges.

In some embodiments, the outcoupling layer has wavelength-sized features that are arranged periodically, quasi-periodically, or randomly, or sub-wavelength-sized features that are arranged periodically, quasi-periodically, or randomly. In some embodiments, the outcoupling layer may be composed of a plurality of nanoparticles and in other embodiments the outcoupling layer is composed of a plurality of nanoparticles disposed over a material. In these embodiments the outcoupling may be tunable by at least one of varying a size of the plurality of nanoparticles, varying a shape of the plurality of nanoparticles, changing a material of the plurality of nanoparticles, adjusting a thickness of the material, changing the refractive index of the material or an additional layer disposed on the plurality of nanoparticles, varying a thickness of the enhancement layer, and/or varying the material of the enhancement layer. The plurality of nanoparticles of the device may be formed from at least one of metal, dielectric material, semiconductor materials, an alloy of metal, a mixture of dielectric materials, a stack or layering of one or more materials, and/or a core of one type of material and that is coated with a shell of a different type of material. In some embodiments, the outcoupling layer is composed of at least metal nanoparticles wherein the metal is selected from the group consisting of Ag, Al, Au, Ir, Pt, Ni, Cu, W, Ta, Fe, Cr, Mg, Ga, Rh, Ti, Ru, Pd, In, Bi, Ca, alloys or mixtures of these materials, and stacks of these materials. The plurality of nanoparticles may have additional layer disposed over them. In some embodiments, the polarization of the emission can be tuned using the outcoupling layer. Varying the dimensionality and periodicity of the outcoupling layer can select a type of polarization that is preferentially outcoupled to air. In some embodiments the outcoupling layer also acts as an electrode of the device.

In yet another aspect, the present disclosure also provides a consumer product comprising an organic light-emitting device (OLED) having an anode; a cathode; and an organic layer disposed between the anode and the cathode, wherein the organic layer may comprise a compound as disclosed in the above compounds section of the present disclosure.

In some embodiments, the consumer product comprises an organic light-emitting device (OLED) having an anode; a cathode; and an organic layer disposed between the anode and the cathode, wherein the organic layer may comprise the compound as described herein.

In some embodiments, the consumer product can be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
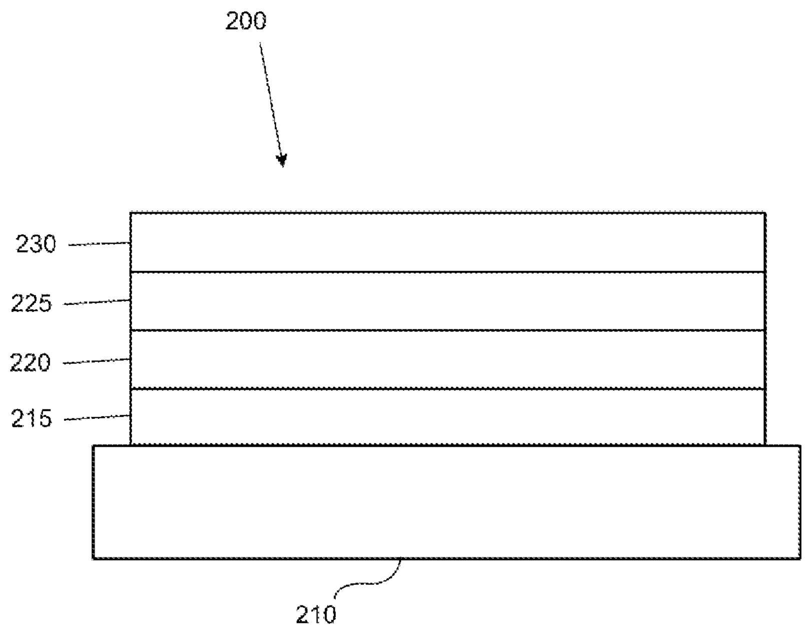
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18 degrees C. to 30 degrees C., and more preferably at room temperature (20-25° C.), but could be used outside this temperature range, for example, from −40 degree C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiments, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer.

As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers. In some embodiments, the acceptor is a TADF emitter. In some embodiments, the acceptor is a fluorescent emitter. In some embodiments, the emission can arise from any or all of the sensitizer, acceptor, and final emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

D. Combination of the Compounds of the Present Disclosure with Other Materials The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

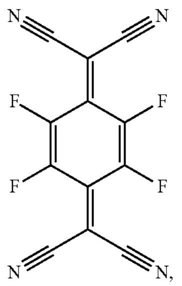

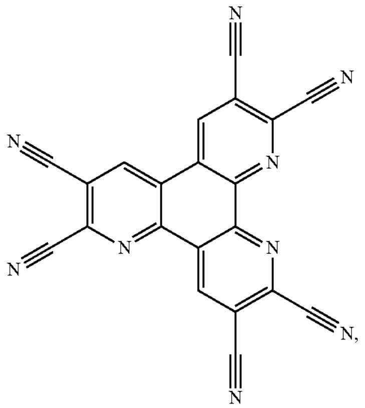

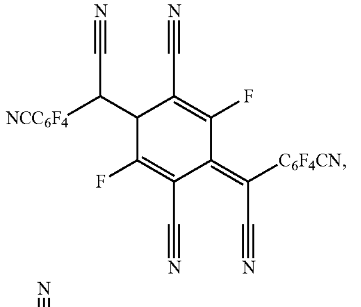

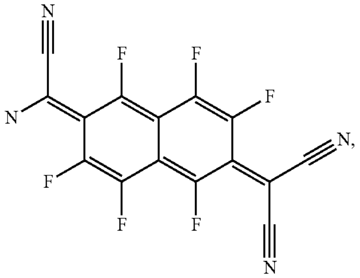

-continued

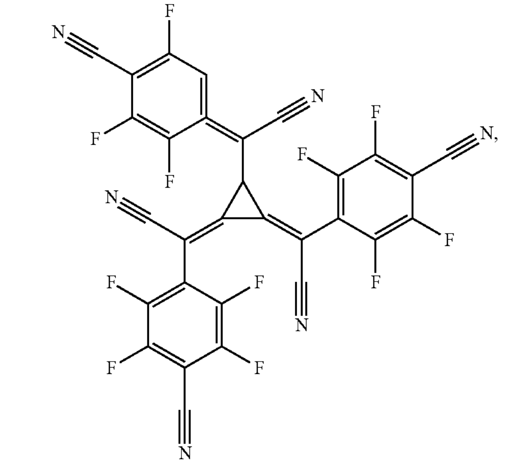

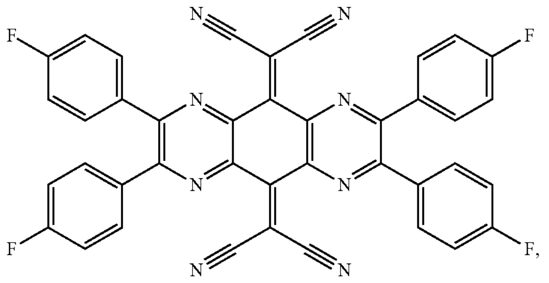

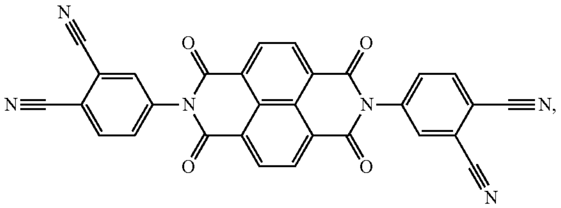

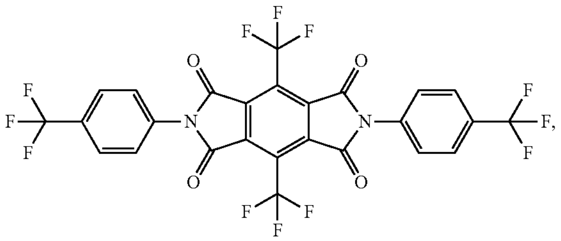

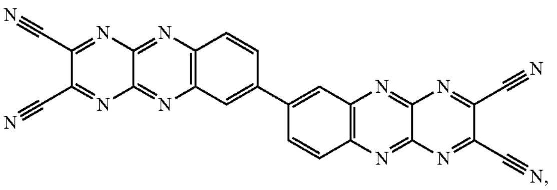

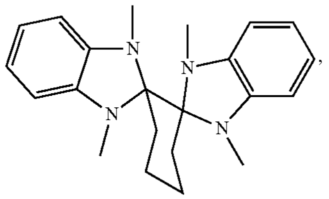

-continued

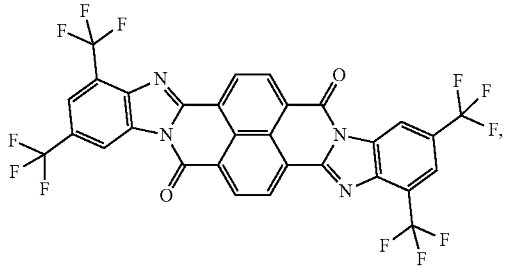

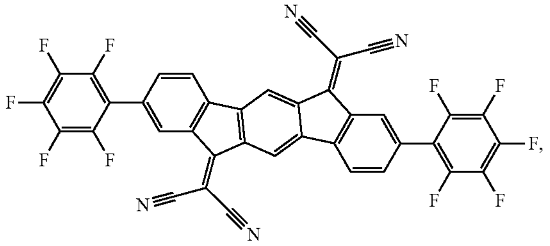

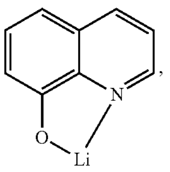

and

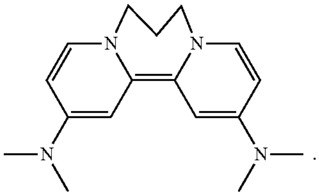

b) HIL/HTL:

A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

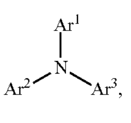

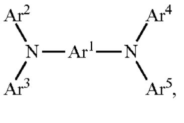

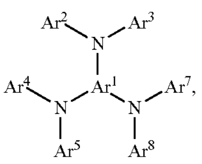

-continued

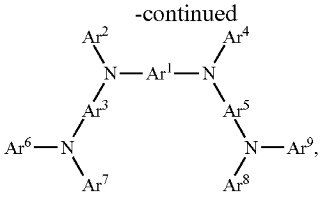

, and

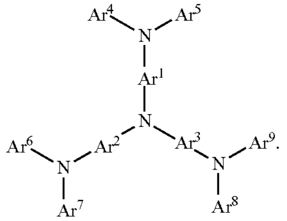

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

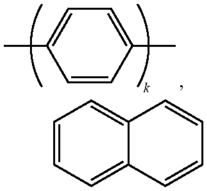

,

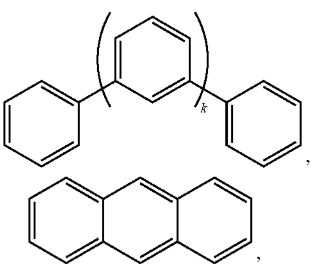

,

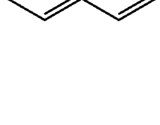

,

,

-continued

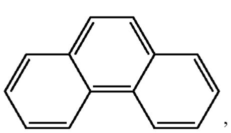

,

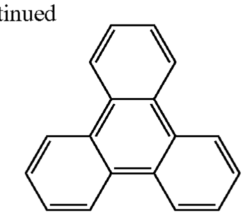

,

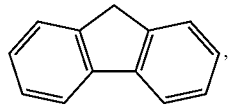

, and

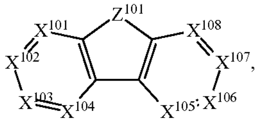

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

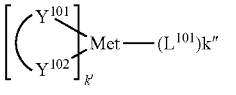

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

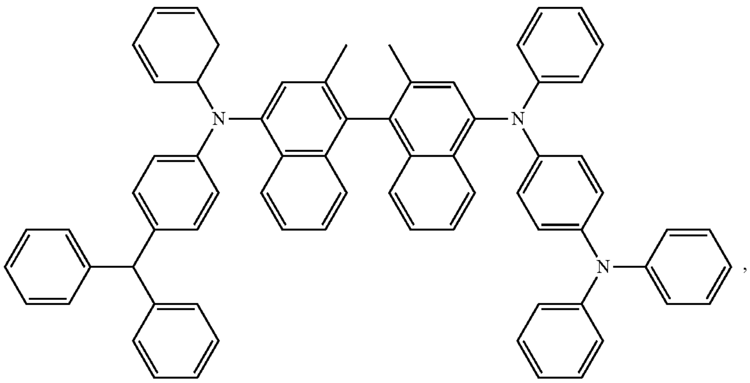
,
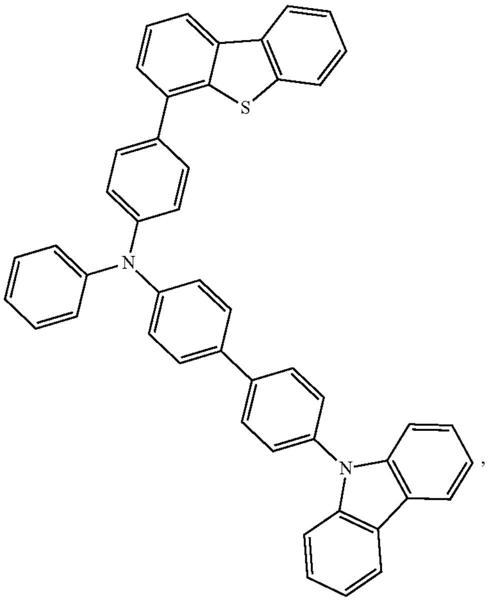
,
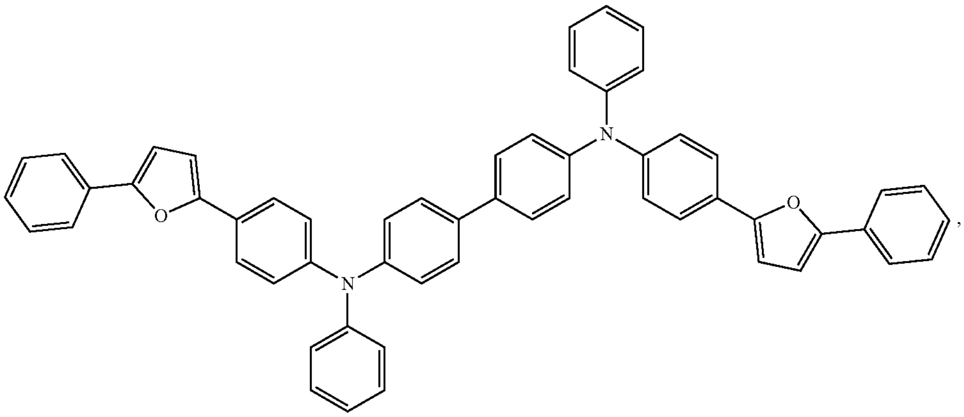
,

-continued
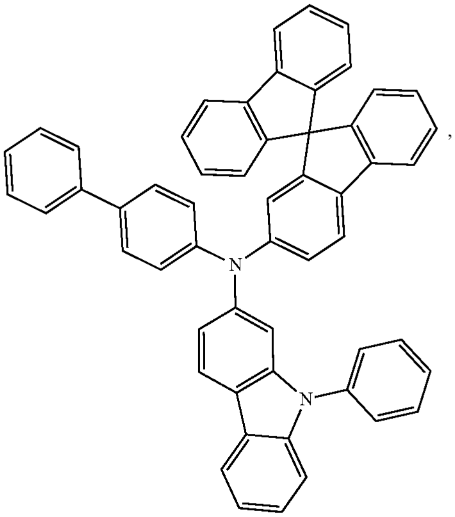
,
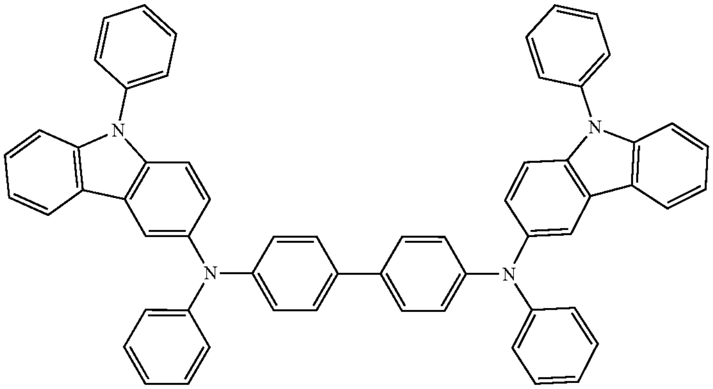
,
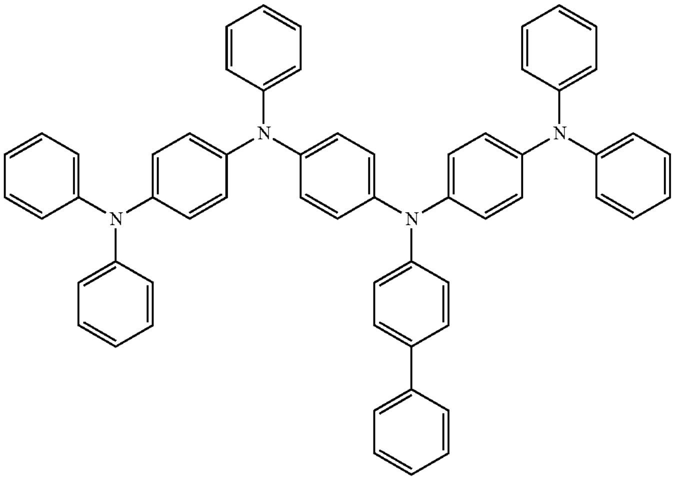
,

-continued
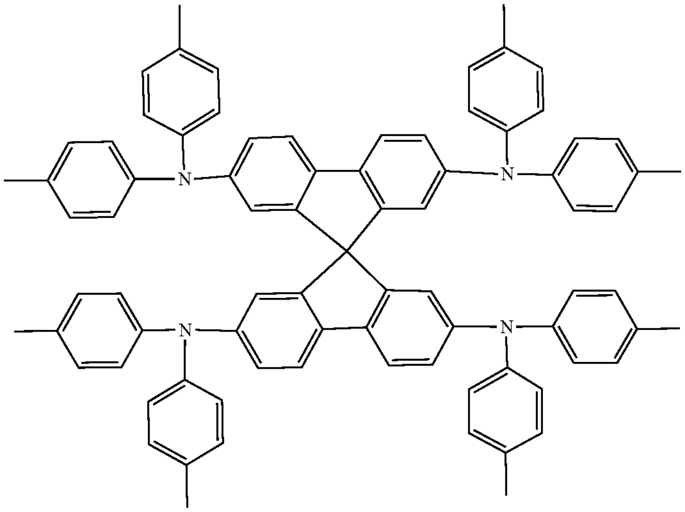
,
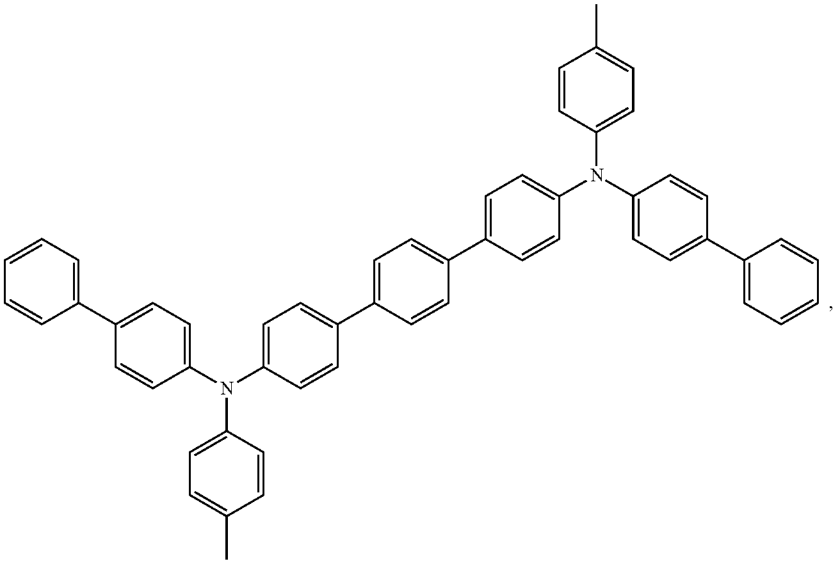
,

-continued
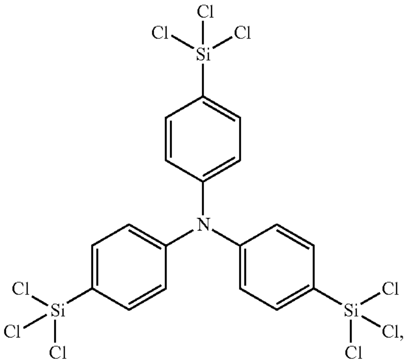
,
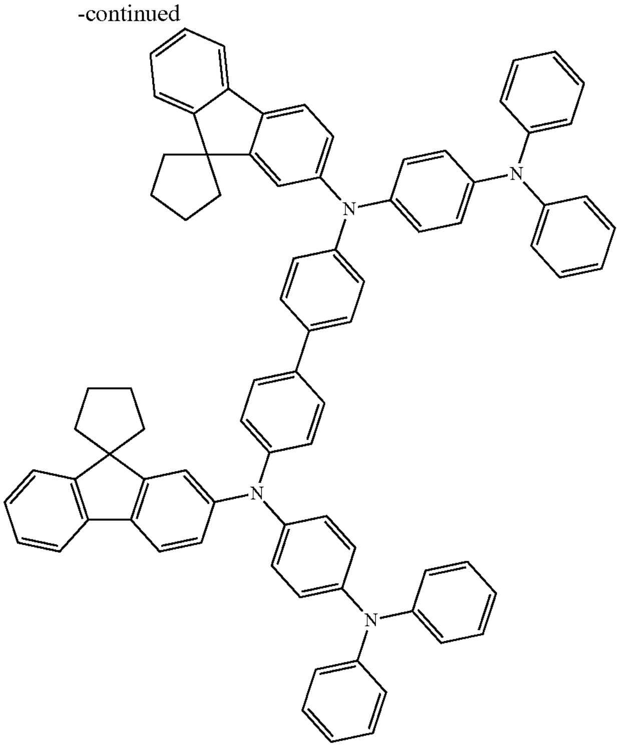
,
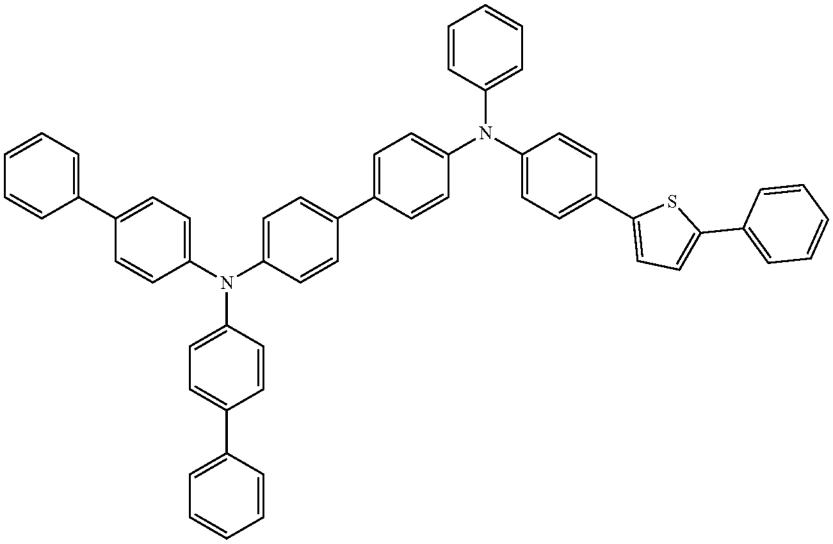
,
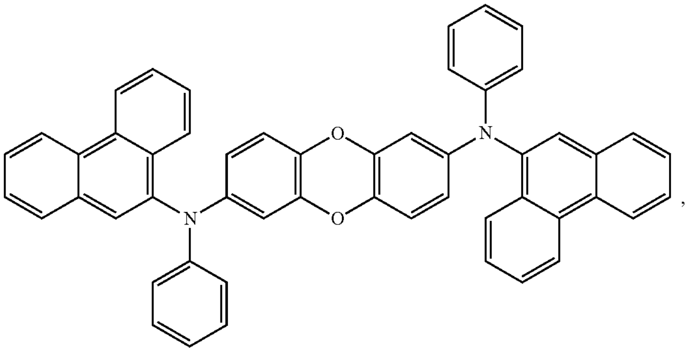
,

-continued
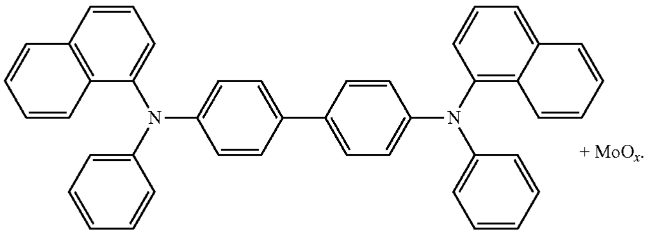
+ $MoO_x$.
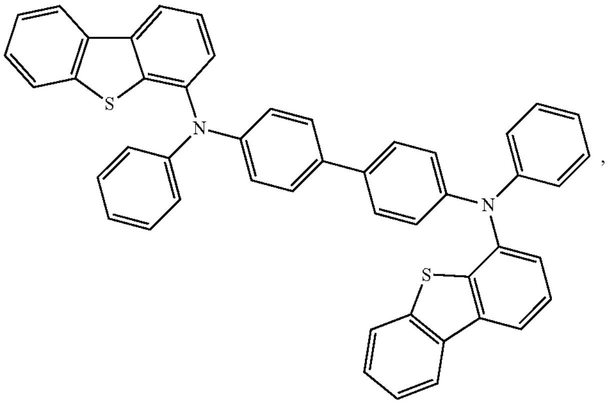
,
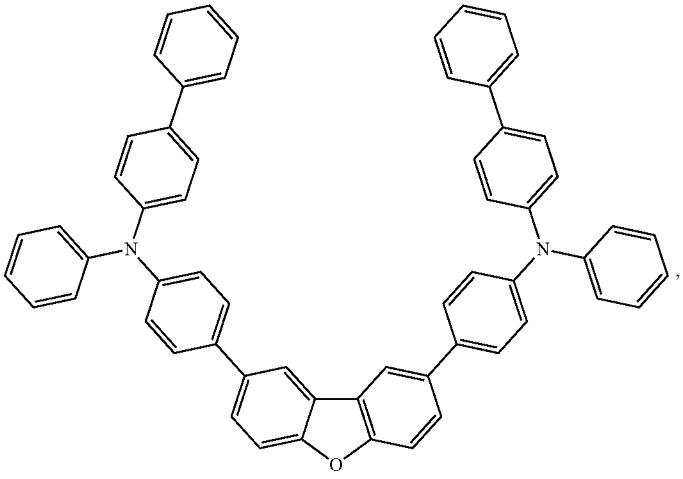
,
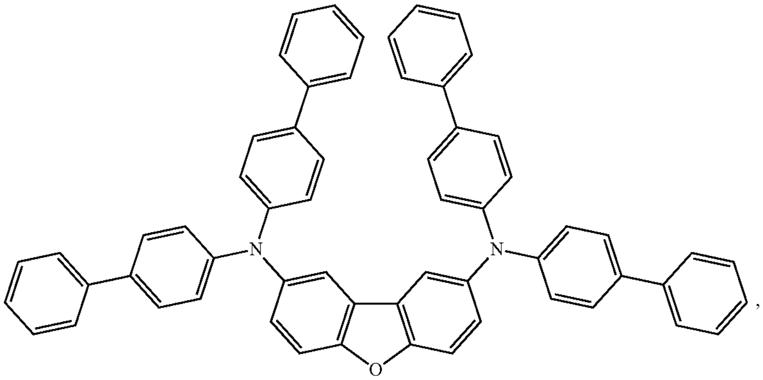
,

-continued
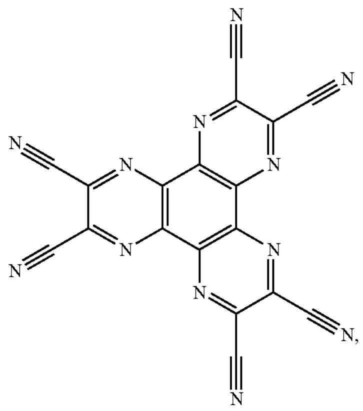
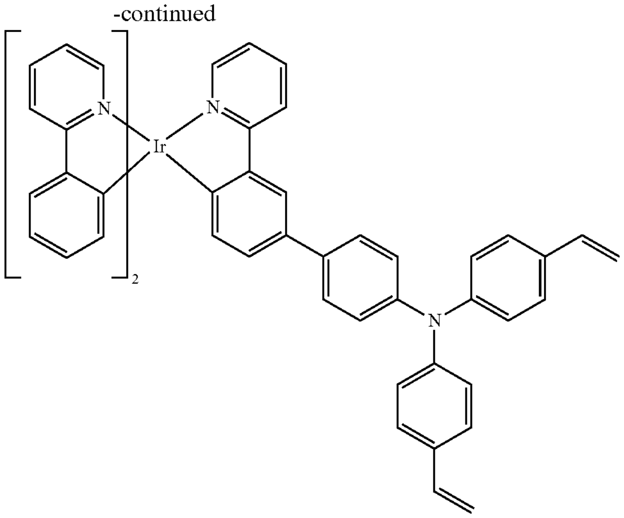
,
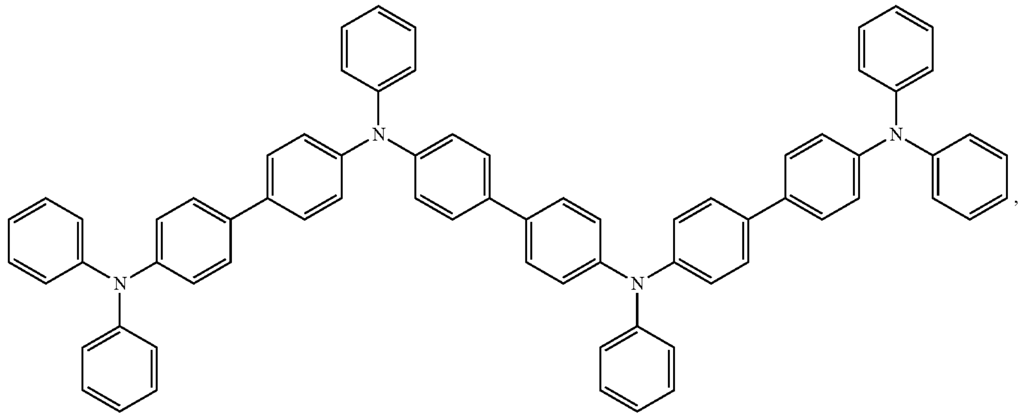
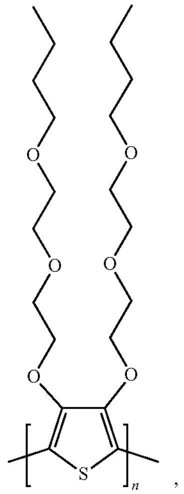
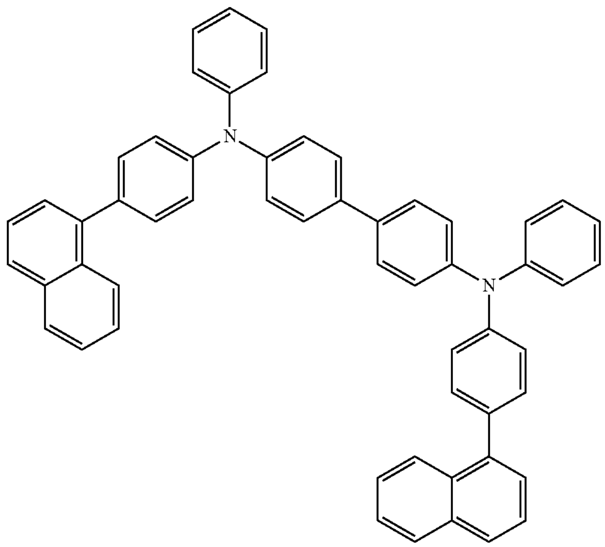
,

-continued
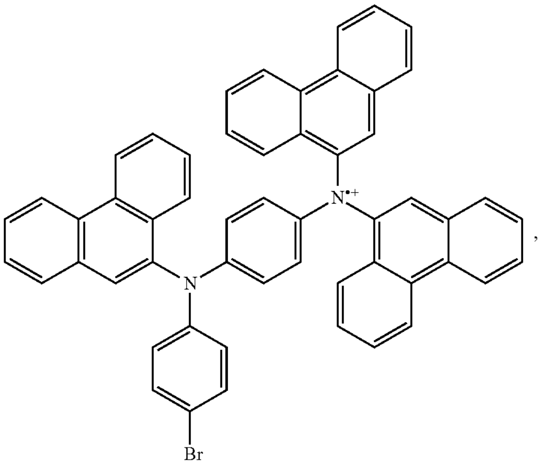
,
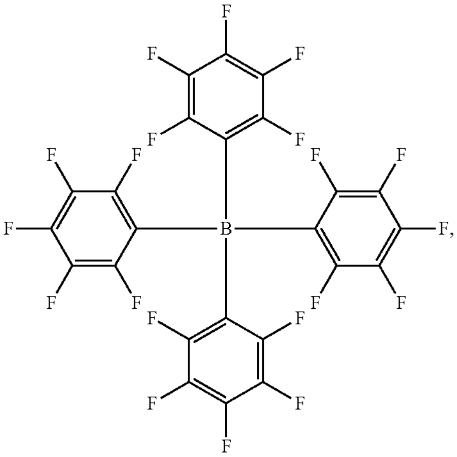
,
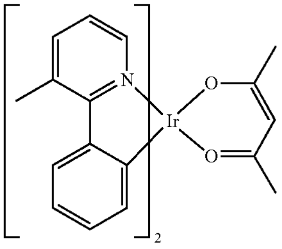
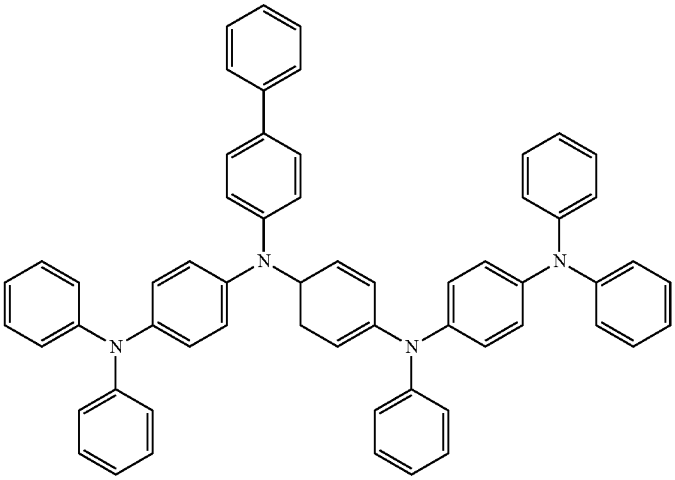
,
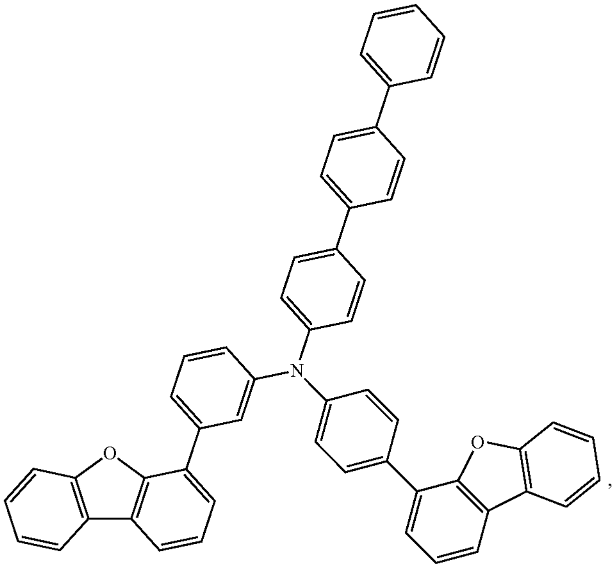
, -continued
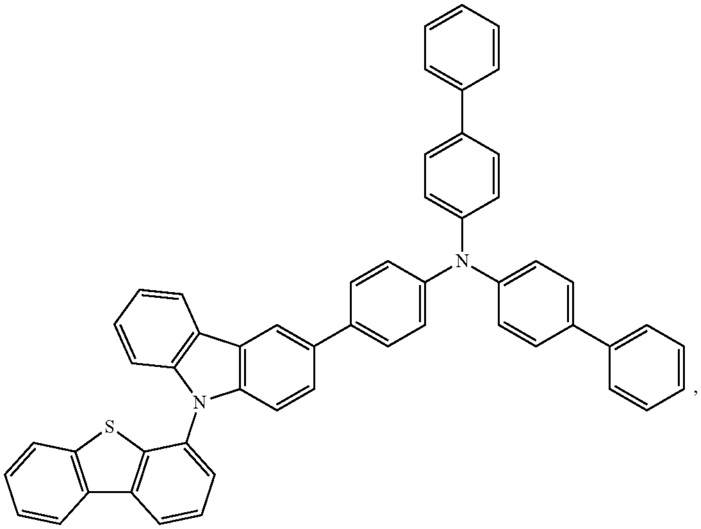
,
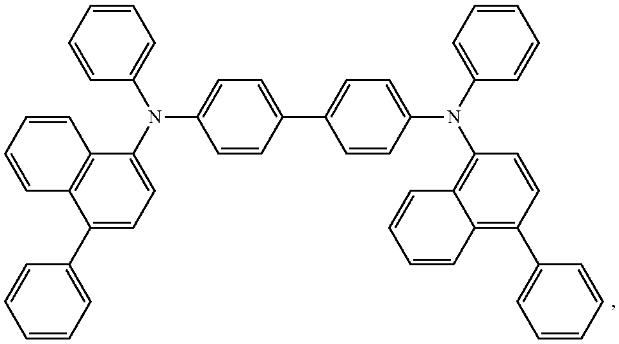
,
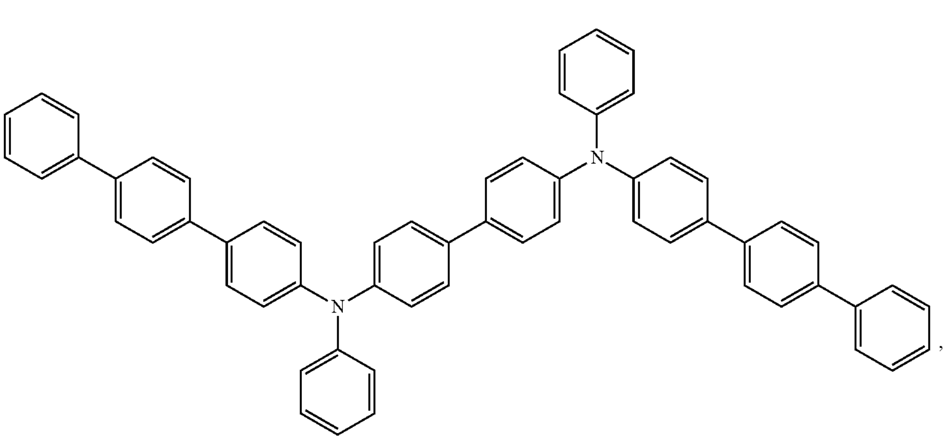
, -continued
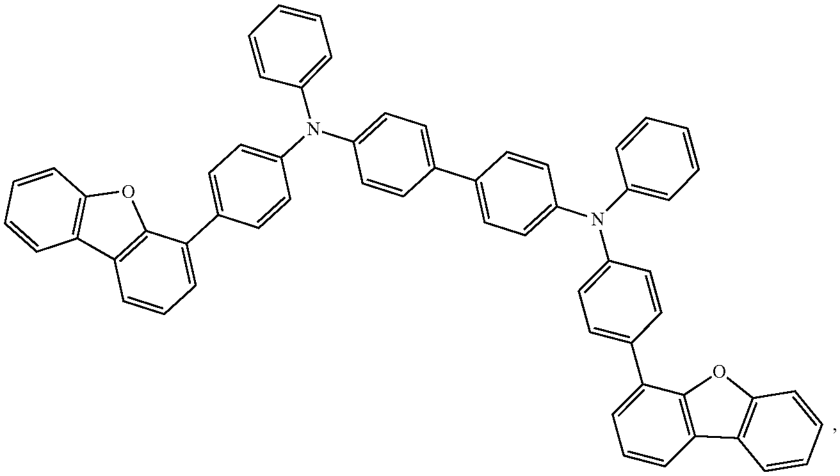
,
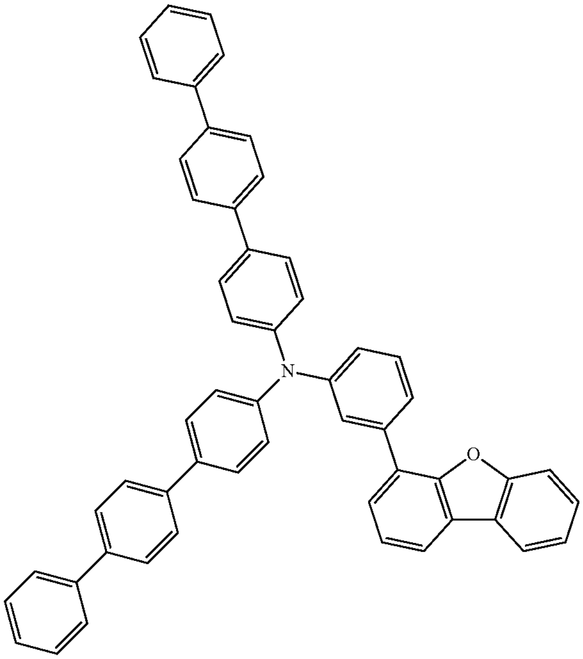
,
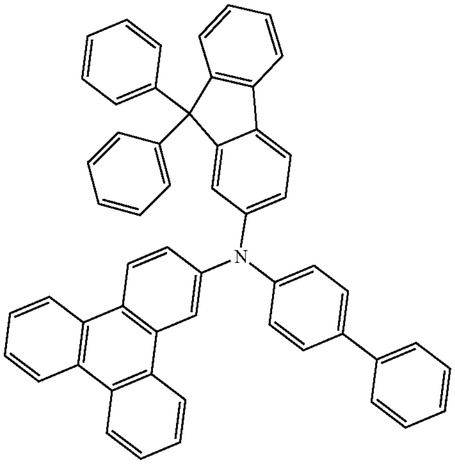
,
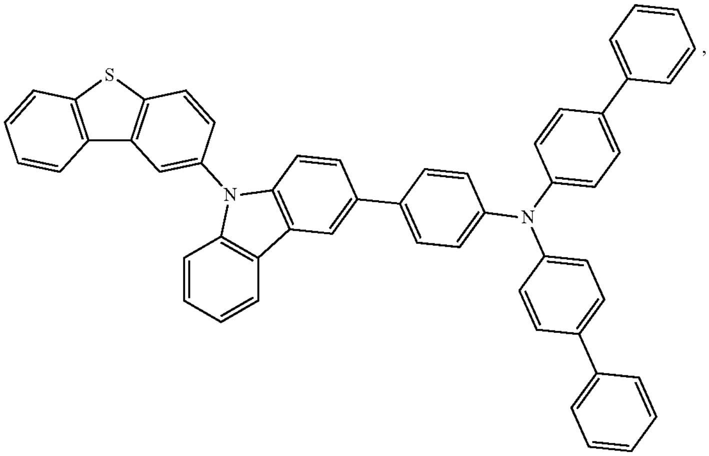
, -continued
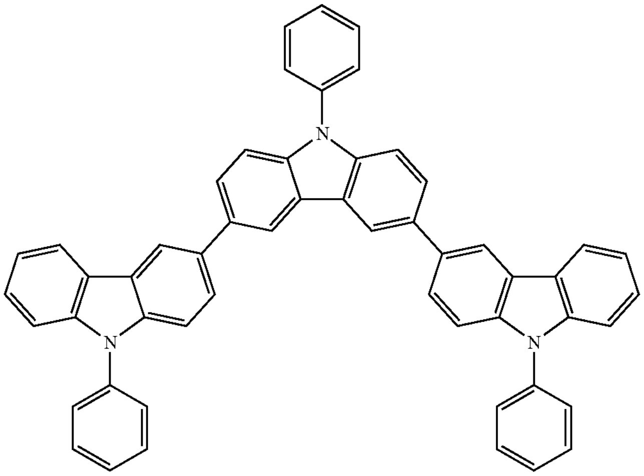
,
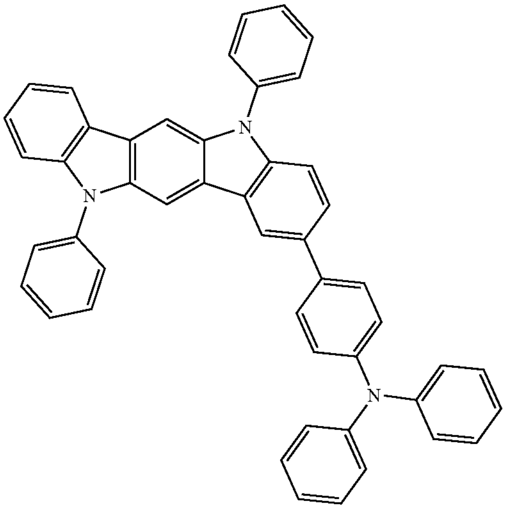
,
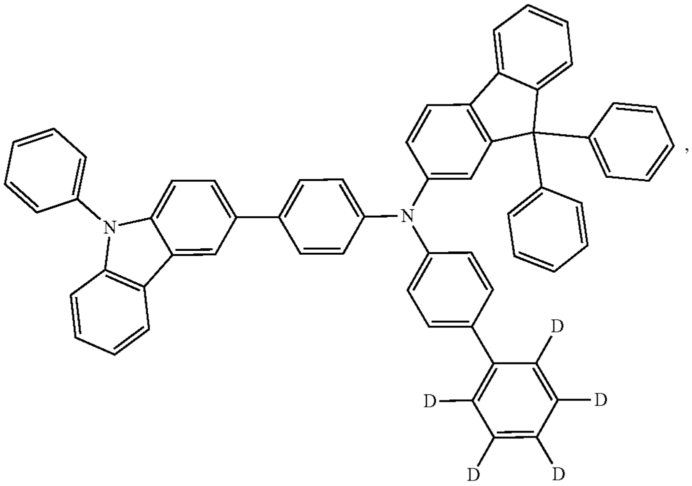
,
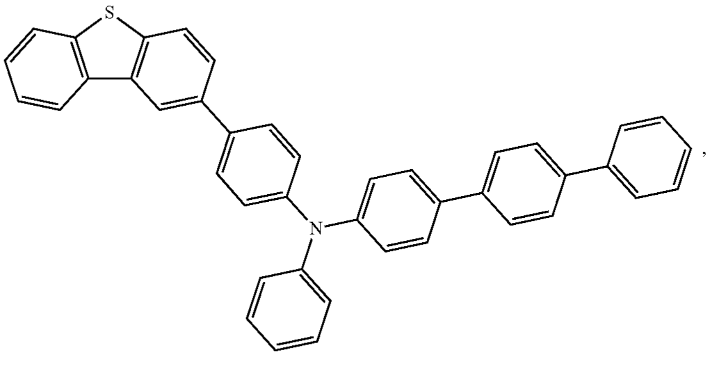
, -continued
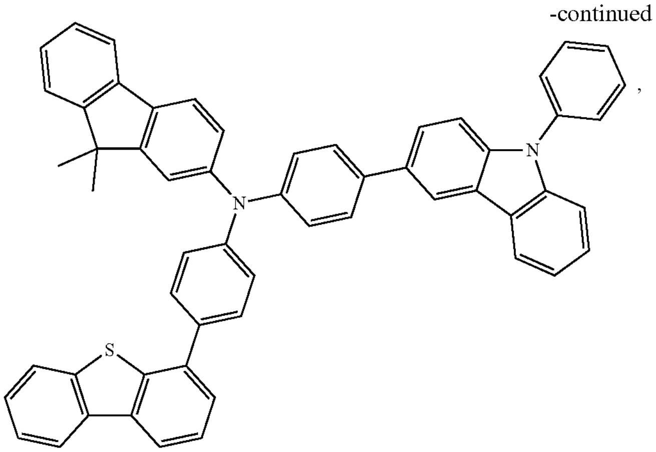
,
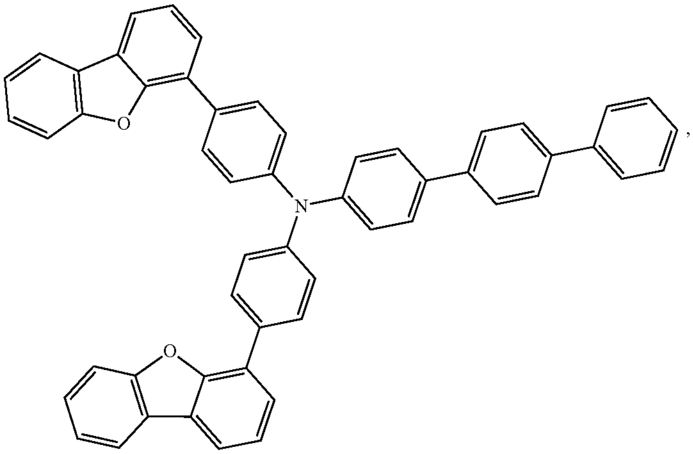
,
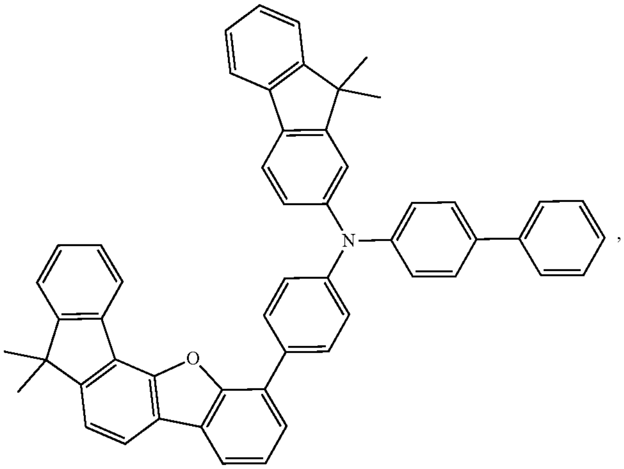
, -continued
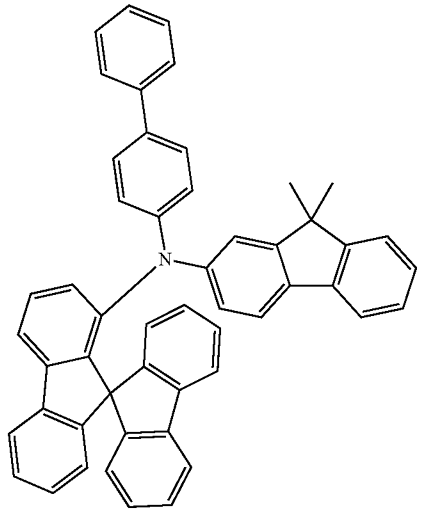
,
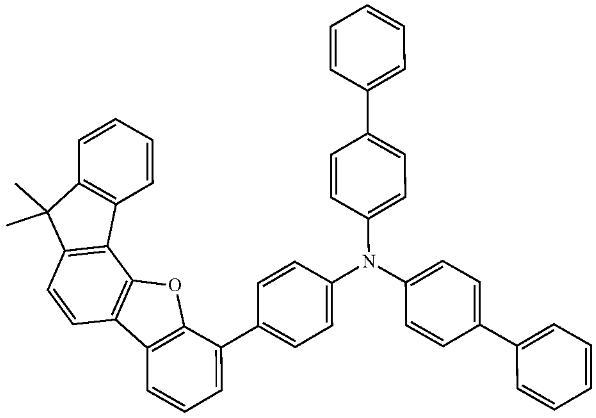
,
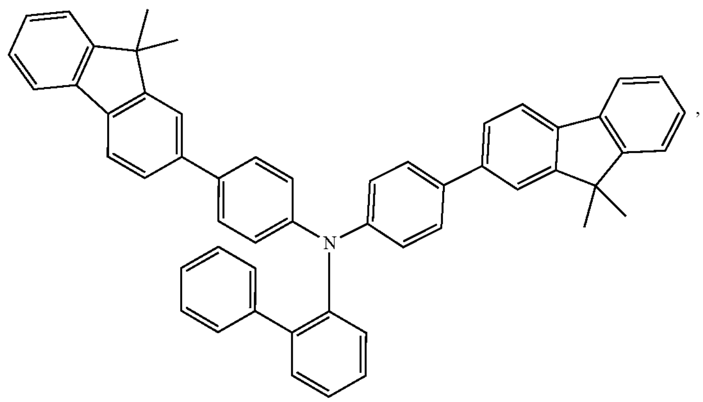
,
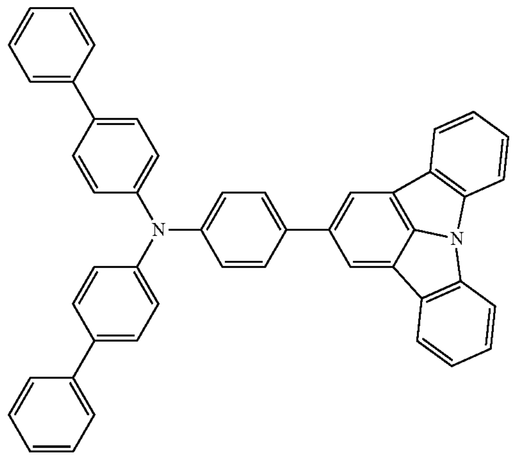
,
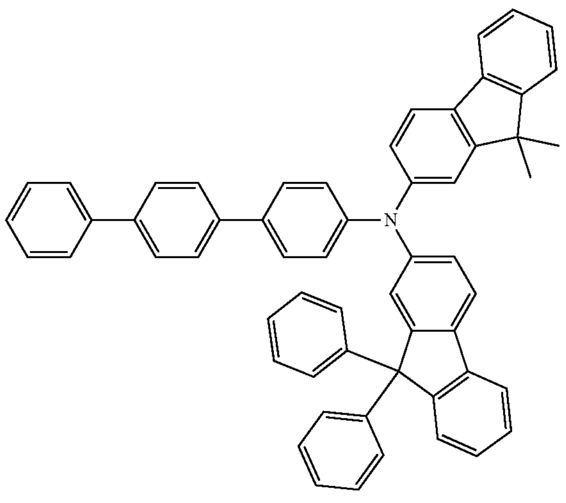
, -continued
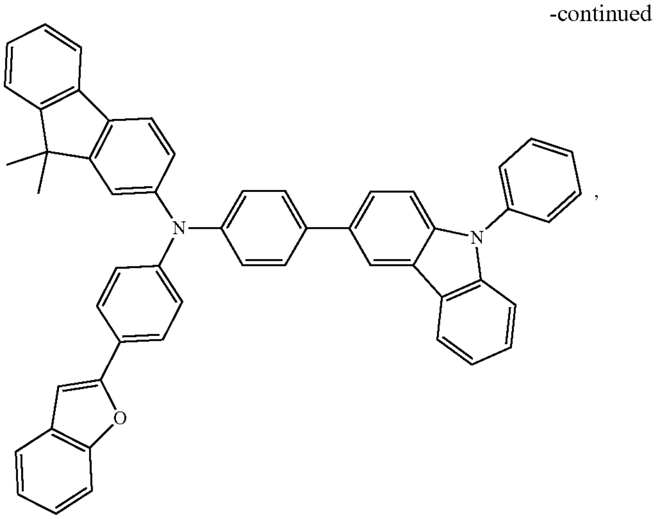
,
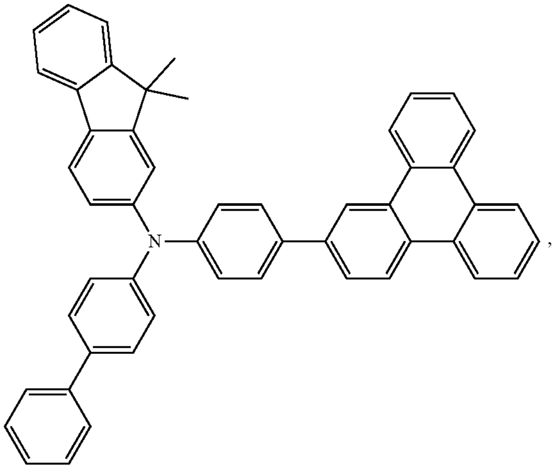
,
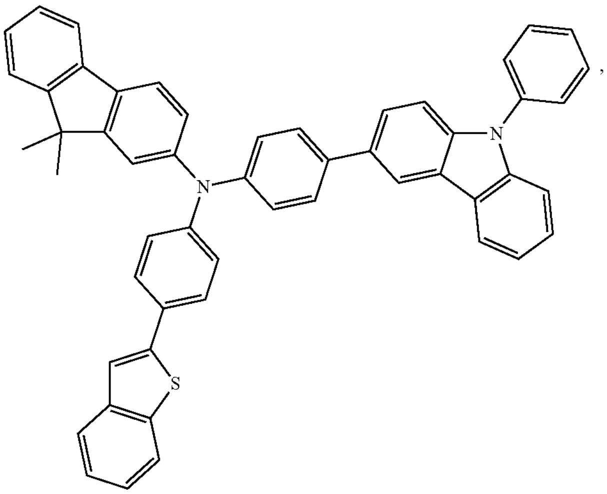
, -continued
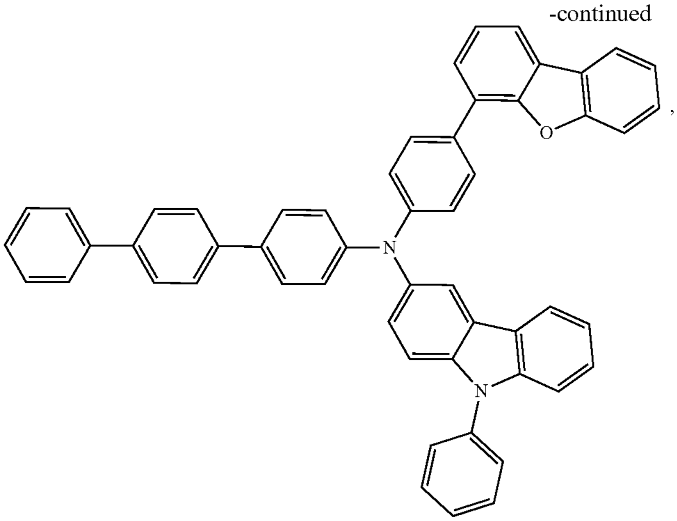
,
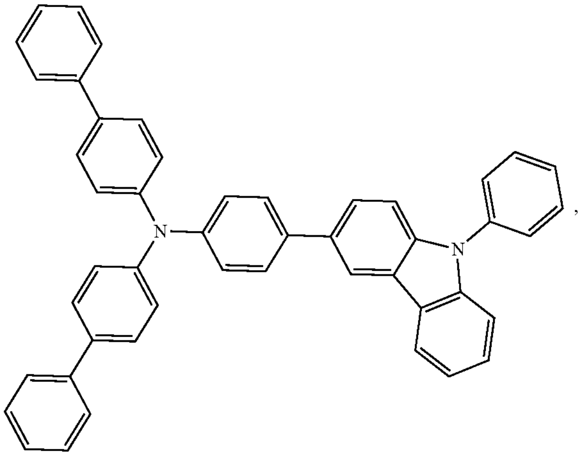
,
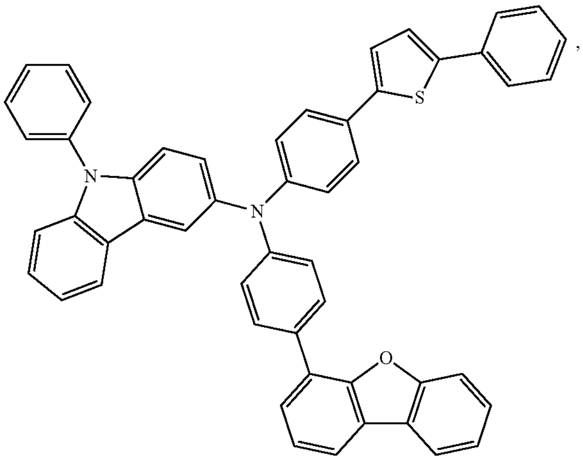
, -continued
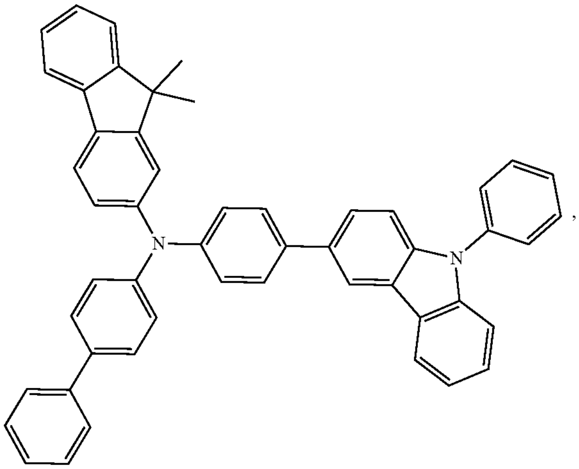
,
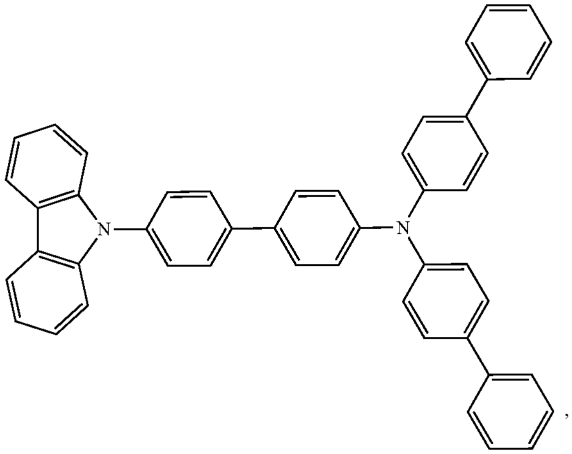
,
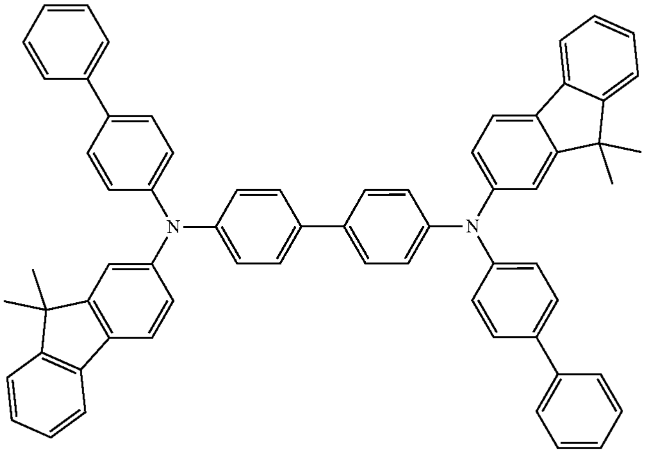
, -continued
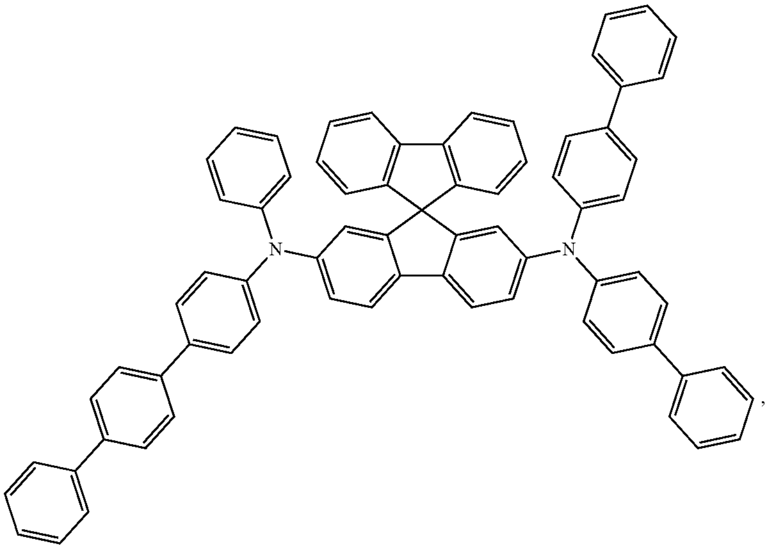
,
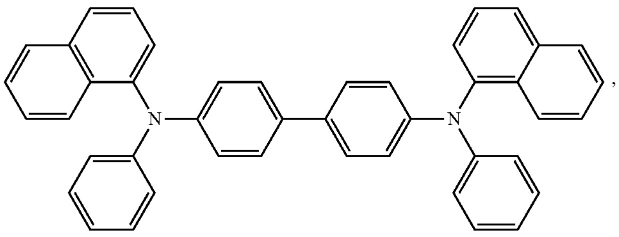
,
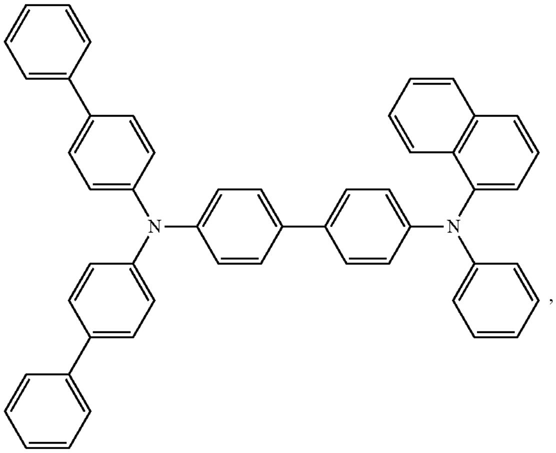
,

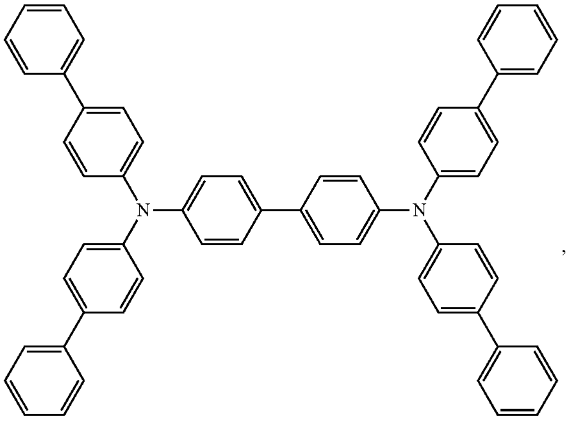
,
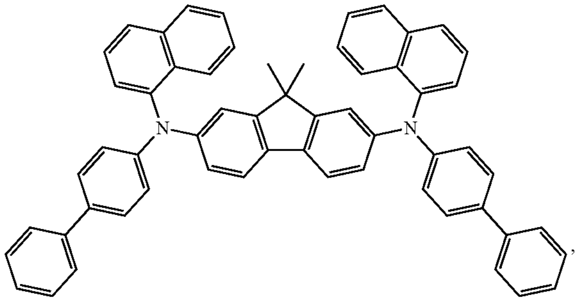
,
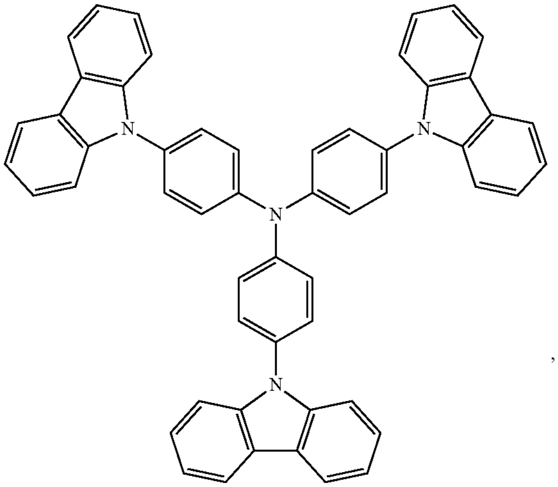
,
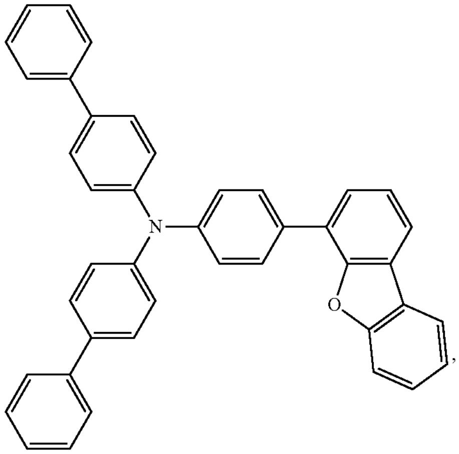
,
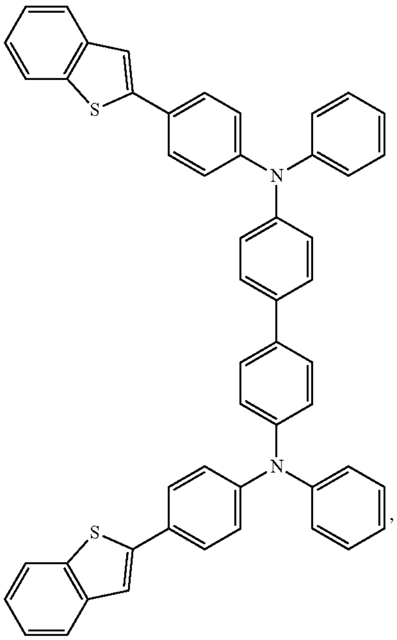
, and

-continued

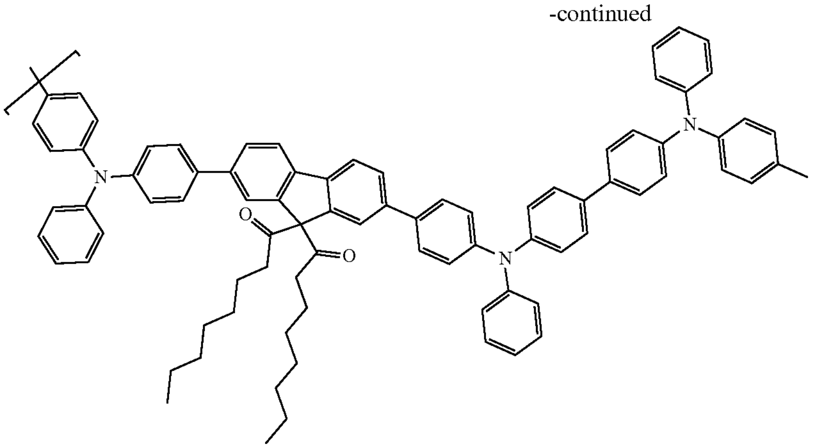

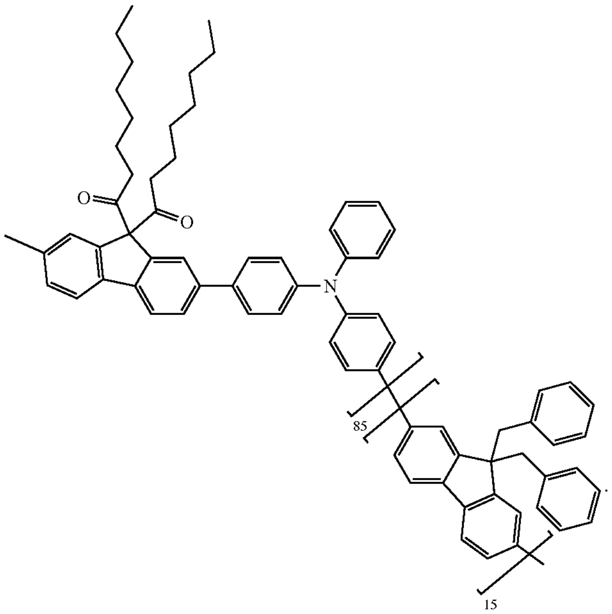

c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Hosts:

The light emitting layer of the organic EL device of the present disclosure preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

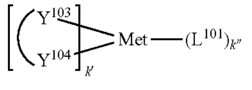

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

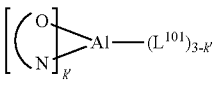 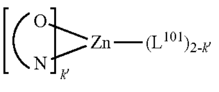

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

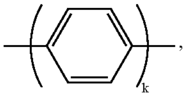
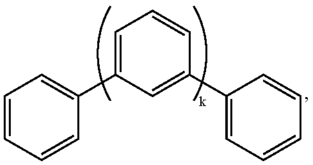
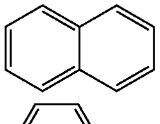
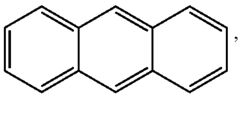
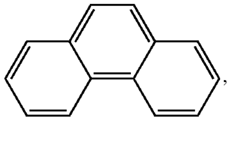
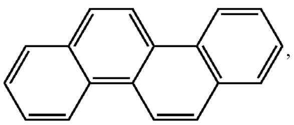
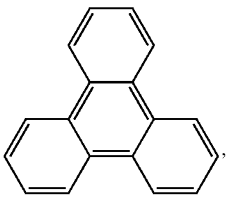
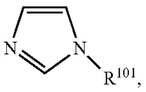
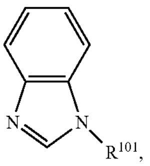

-continued

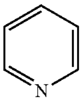
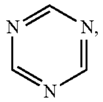
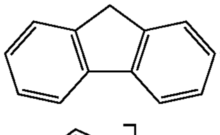
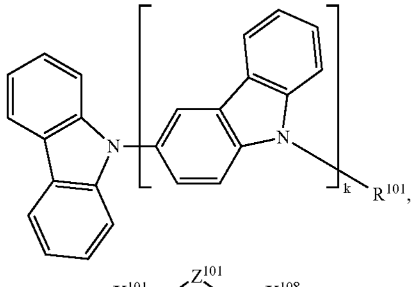
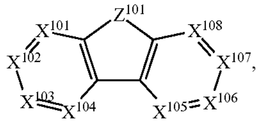
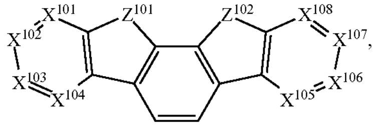
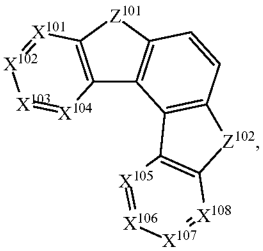
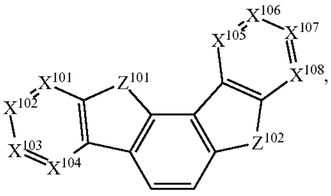
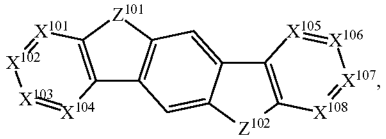 and
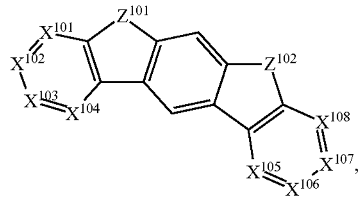

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or a N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,
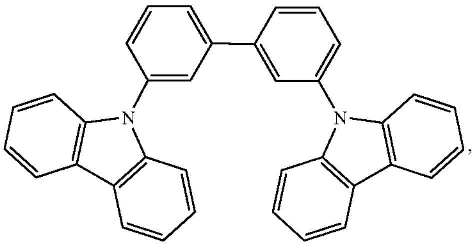
,
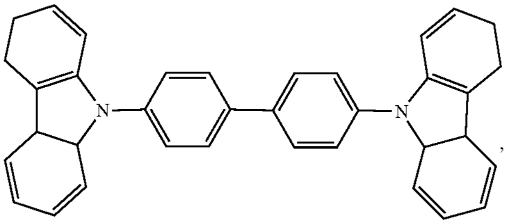
,
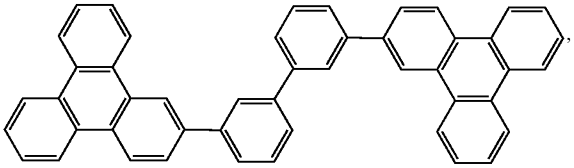
,
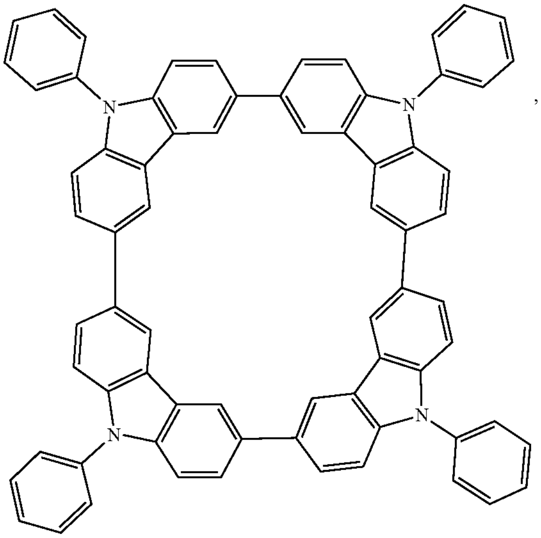
,
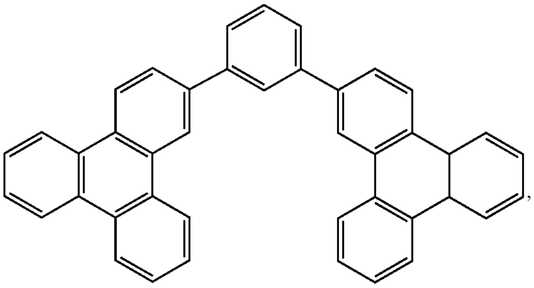
,
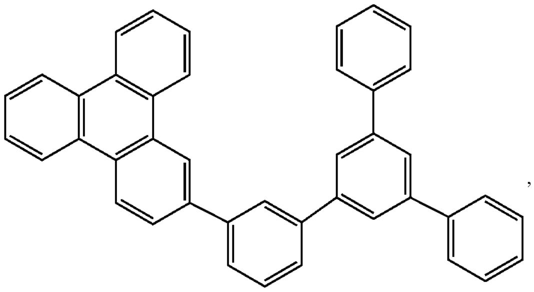
, -continued
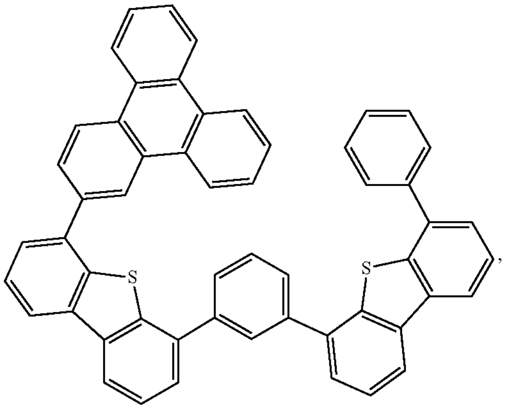
,
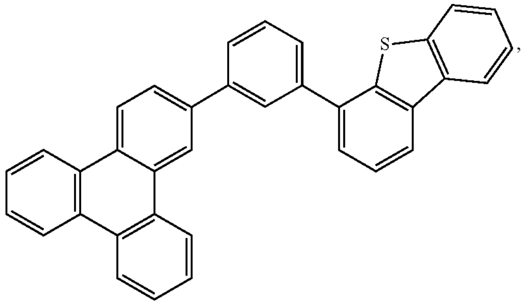
,
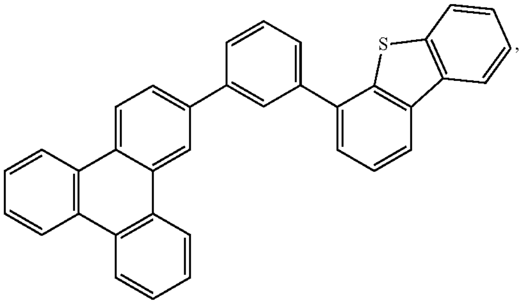
,
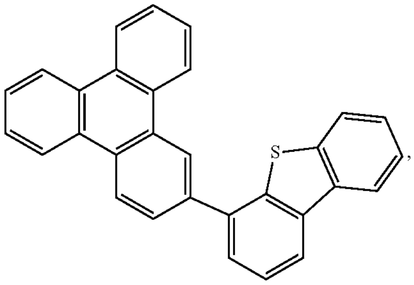
,
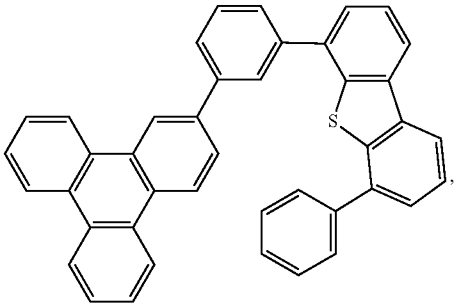
,
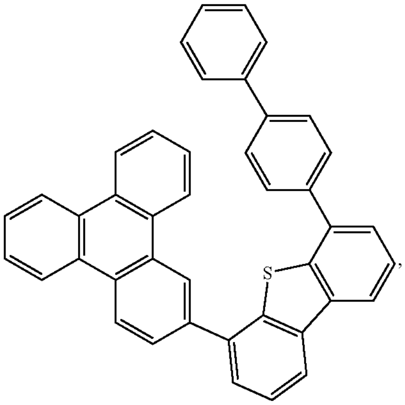
,
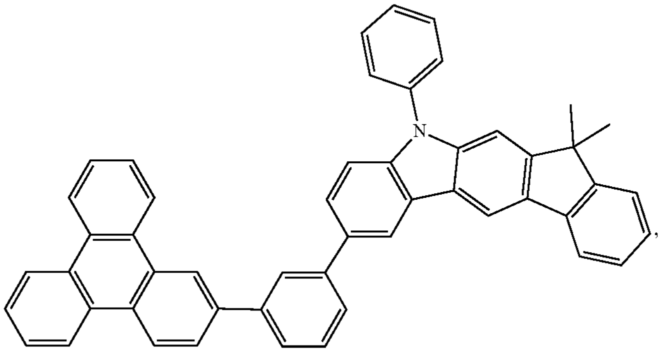
, -continued
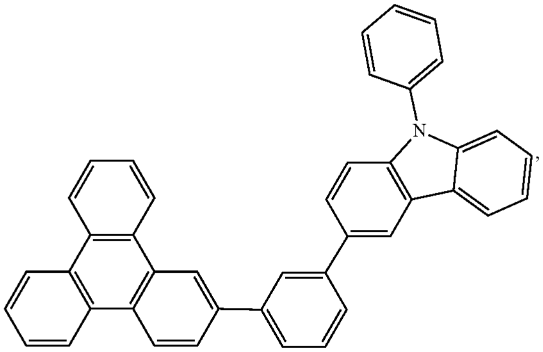,
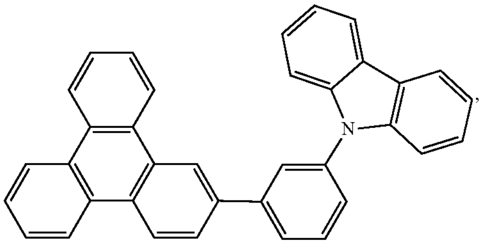,
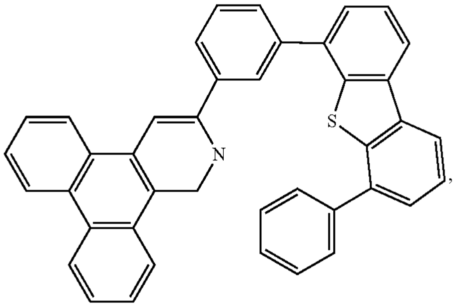,
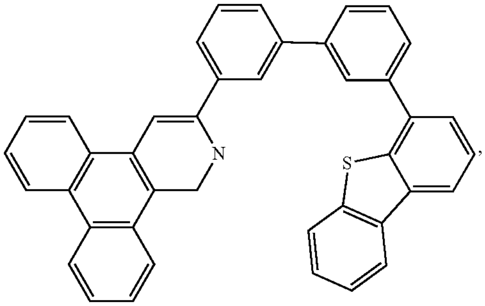,
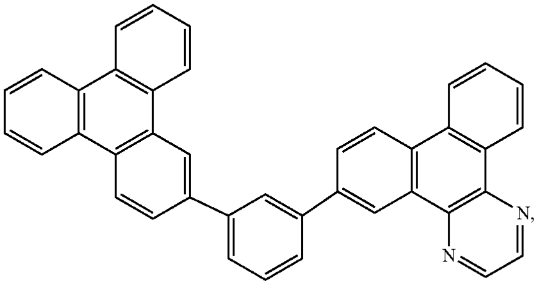,
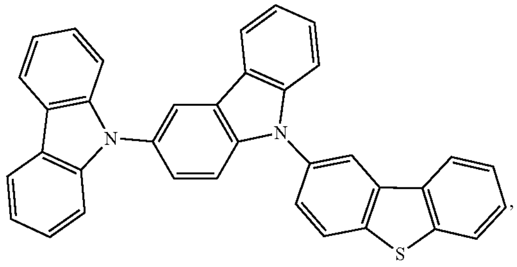,
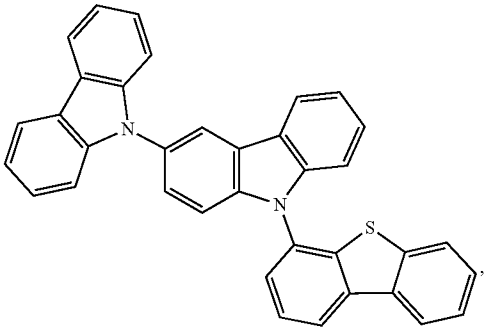,
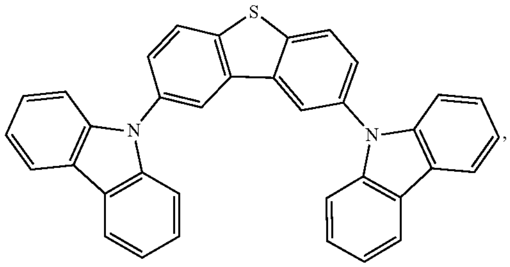,
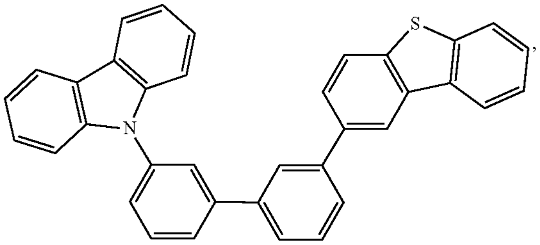,
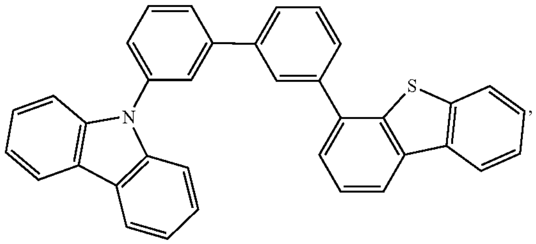, -continued
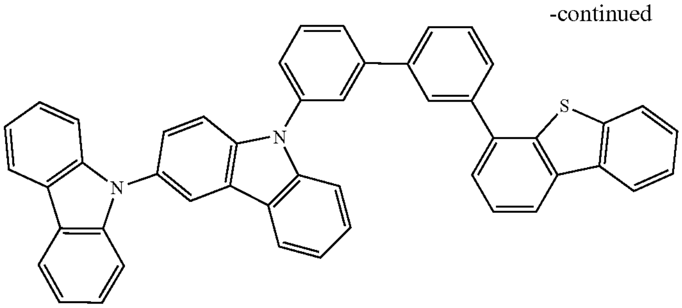
,
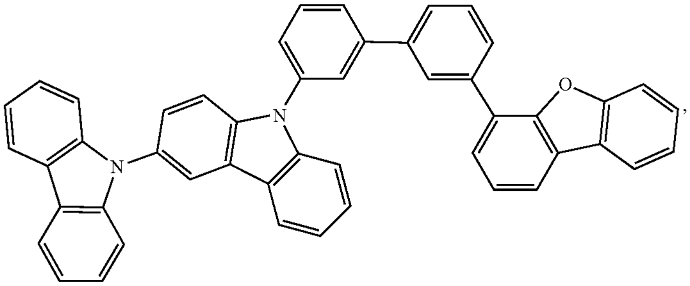
,
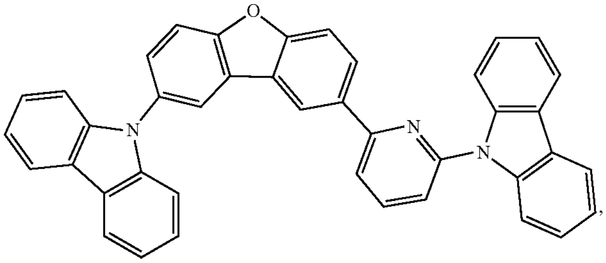
,
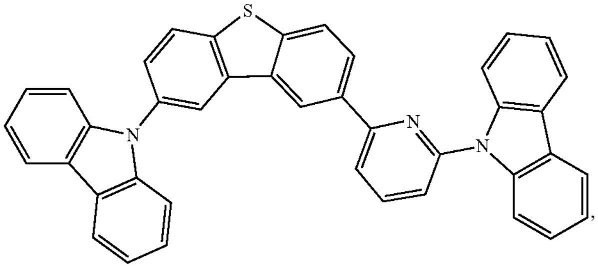
,
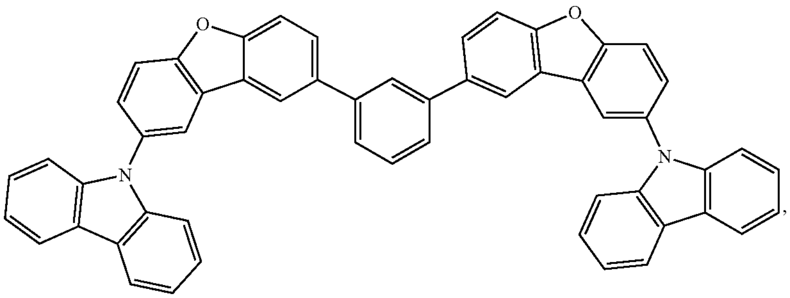
,
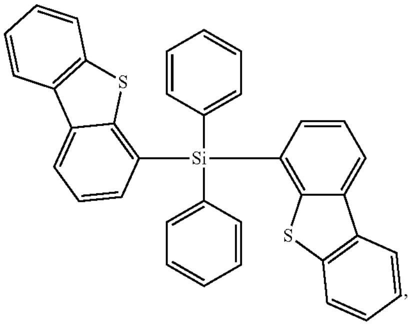
,
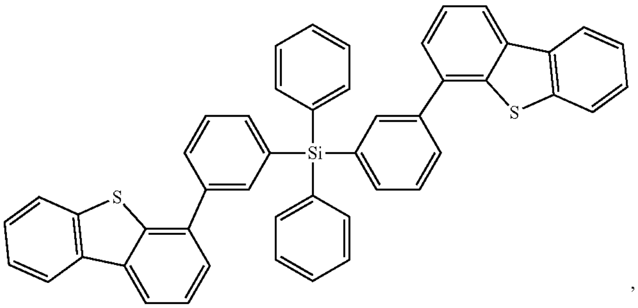
, -continued
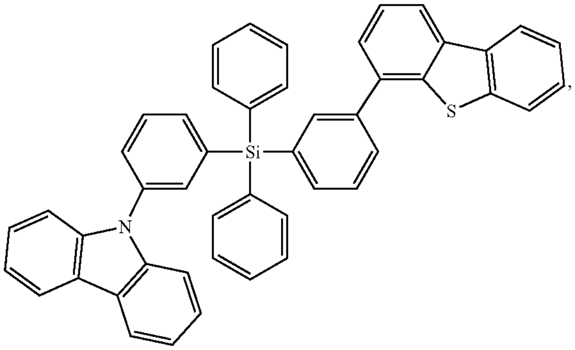
,
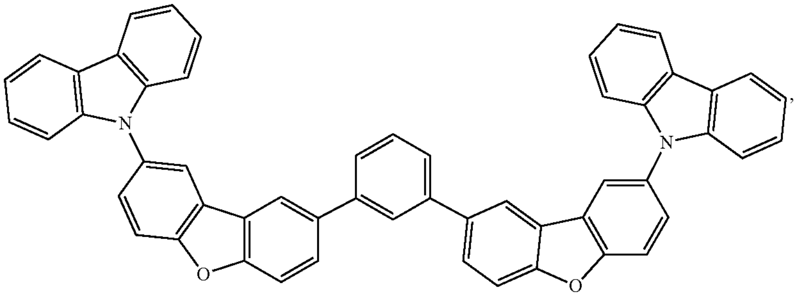
,
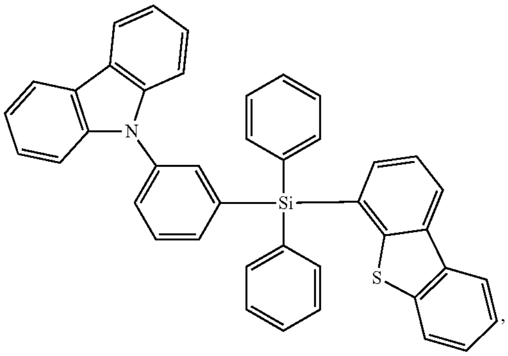
,
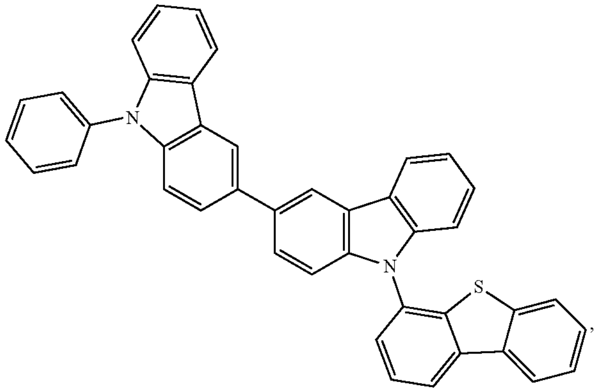
,
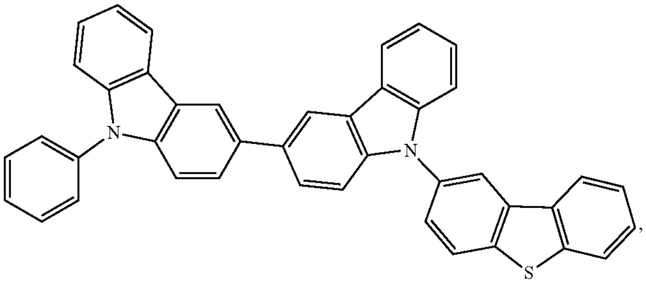
,
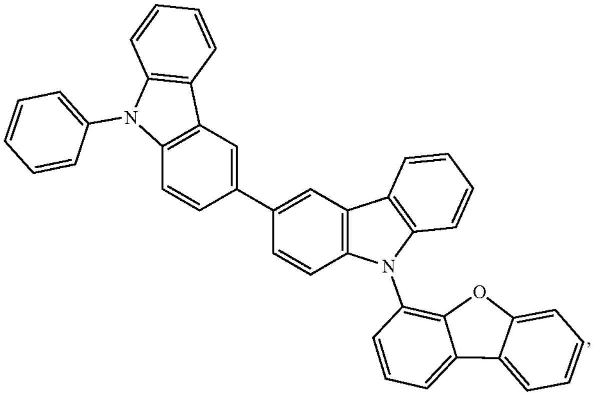
, -continued
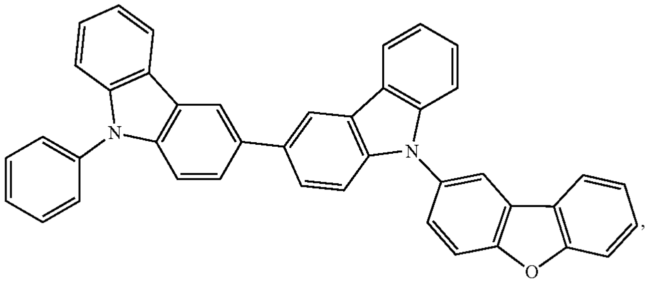,
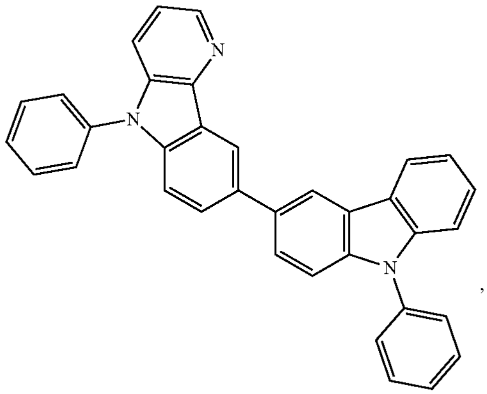,
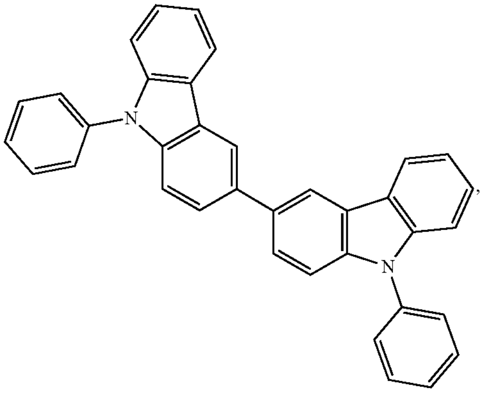,
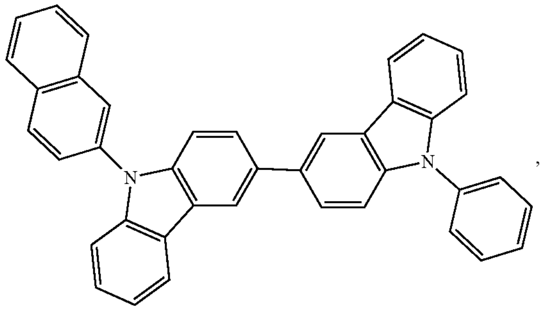,
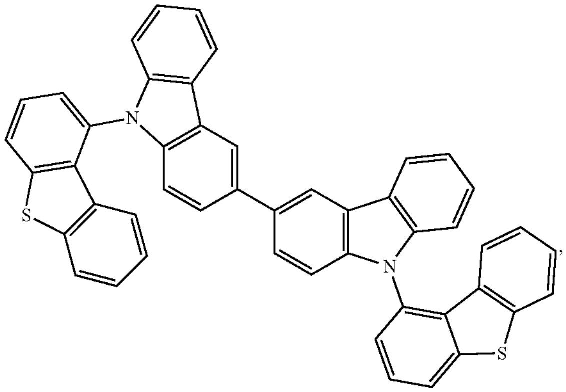,
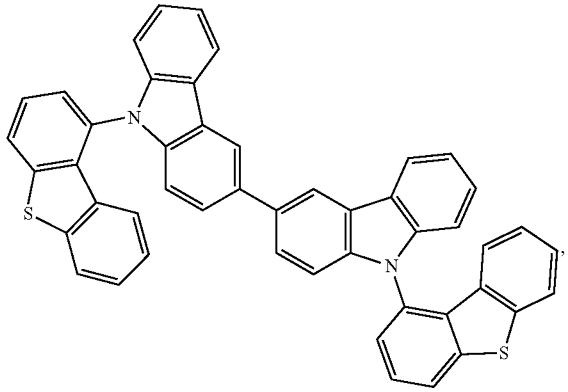,
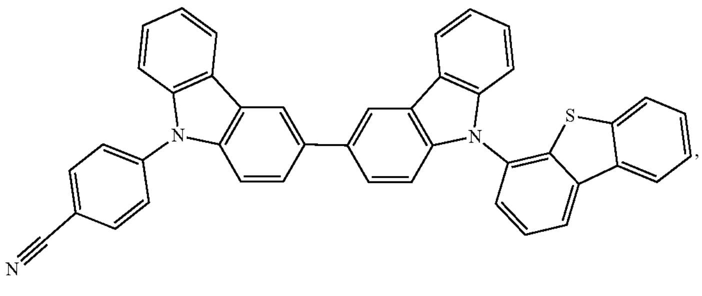, -continued
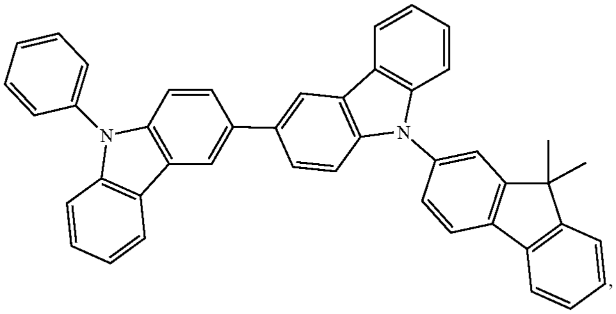
,
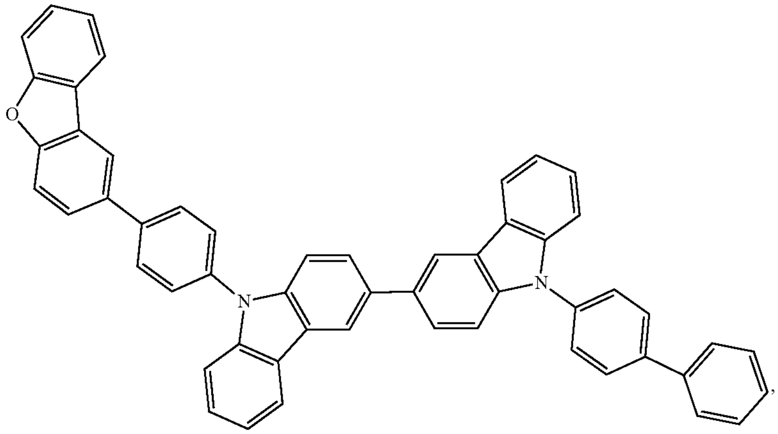
,
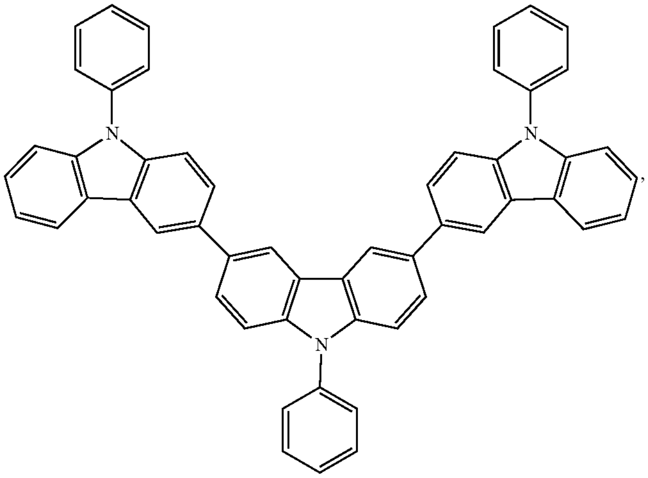
,
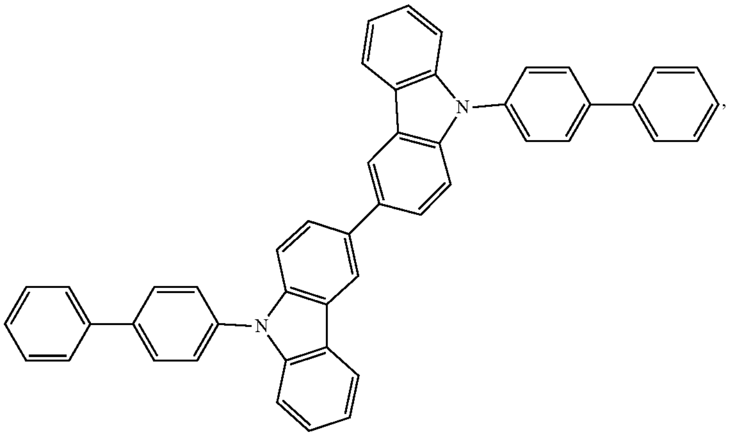
, -continued
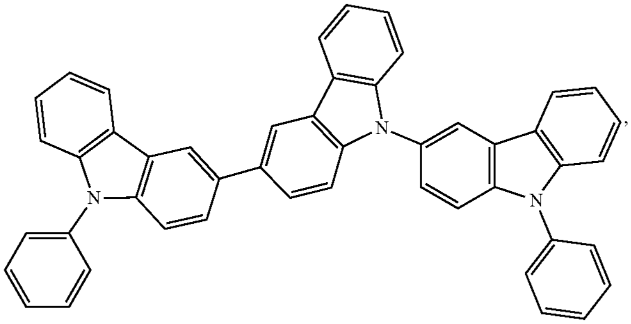
,
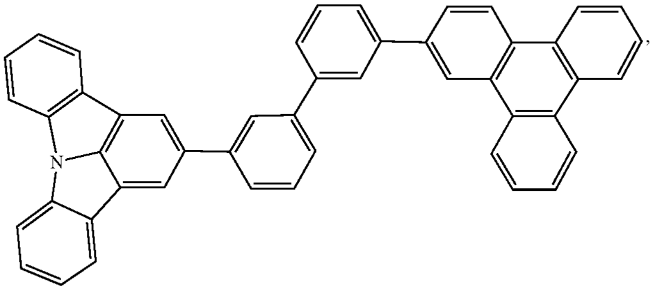
,
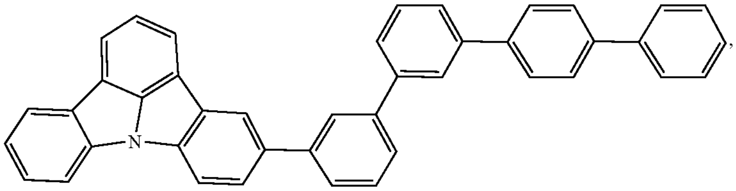
,
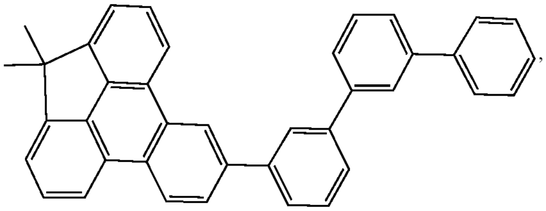
,
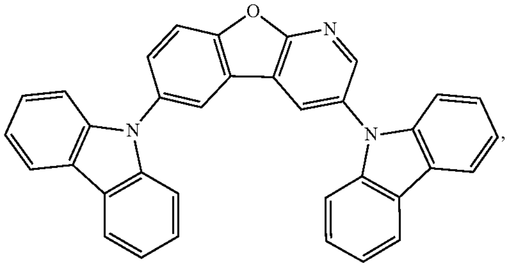
,
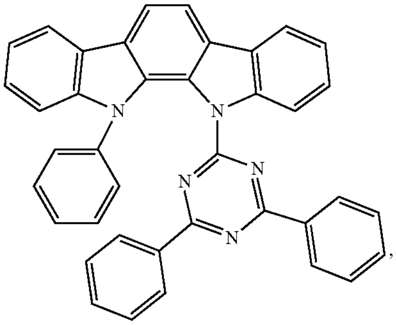
,
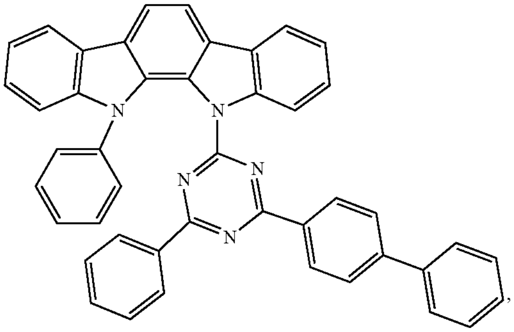
, -continued
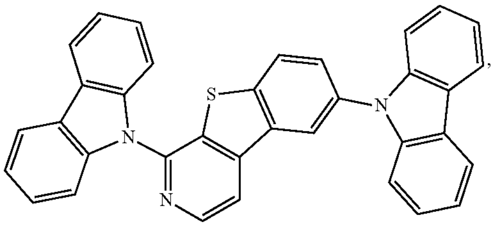,
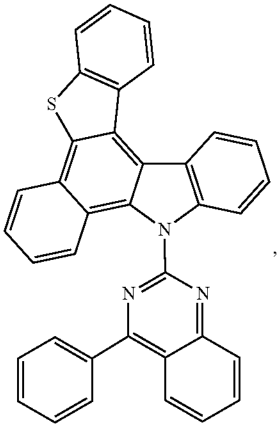,
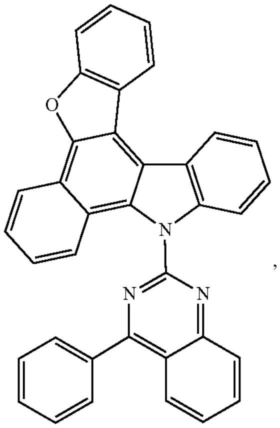,
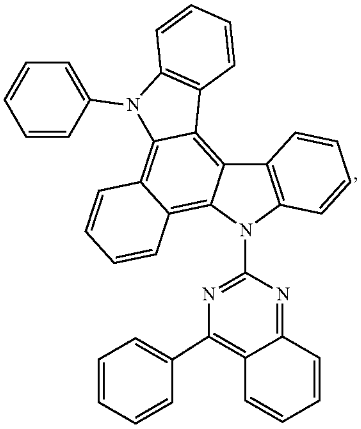,
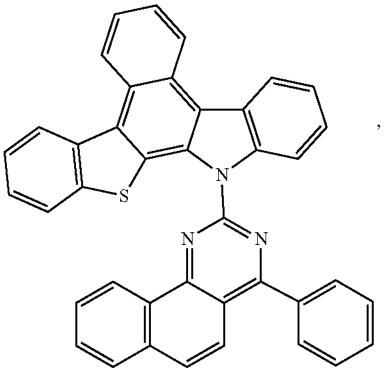,
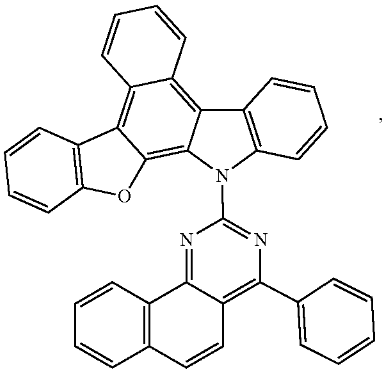,
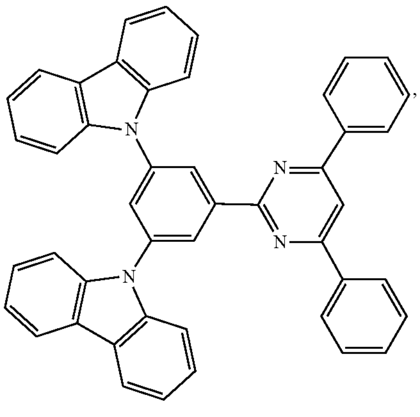,
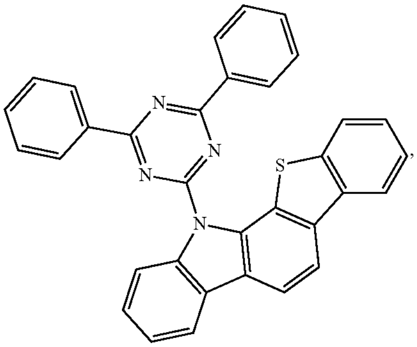, -continued
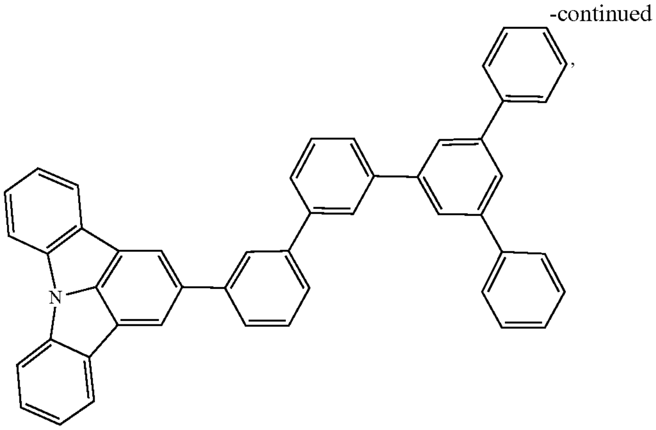
,
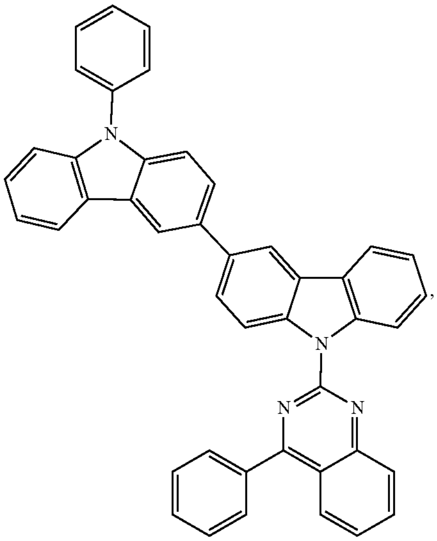
,
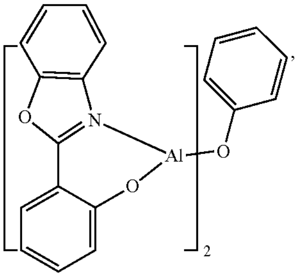
,
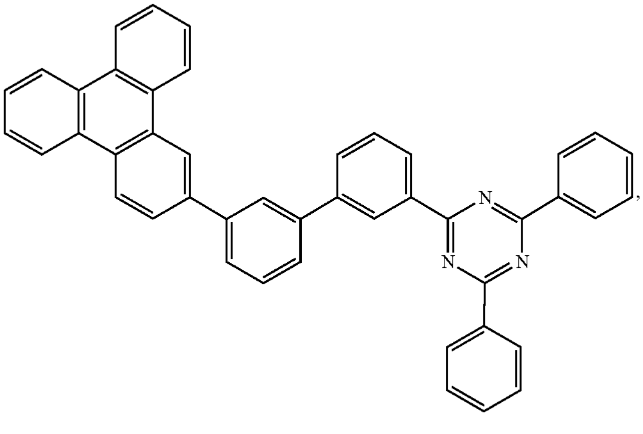
,
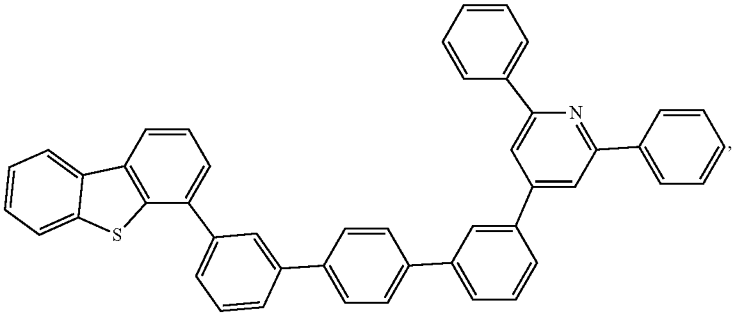
, -continued
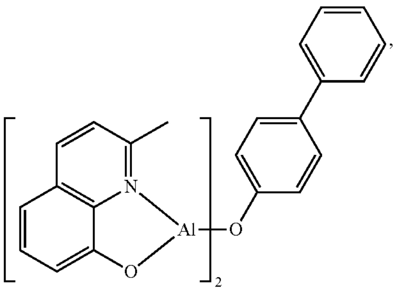
,
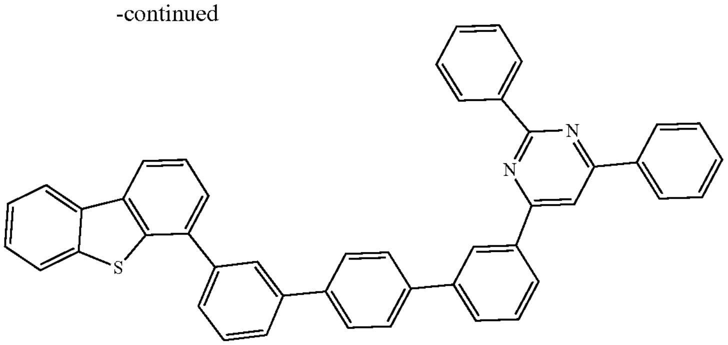
,
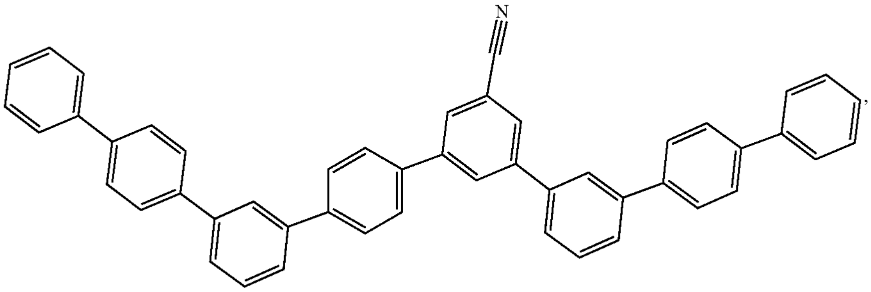
,
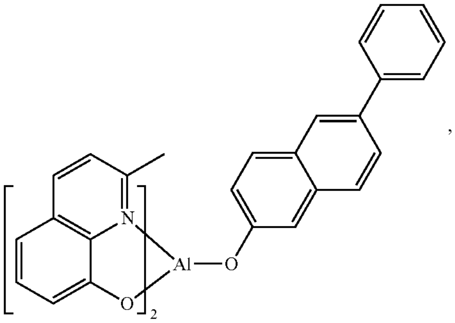
,
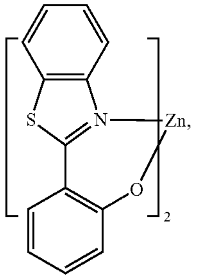
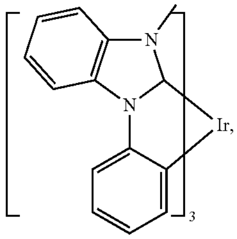
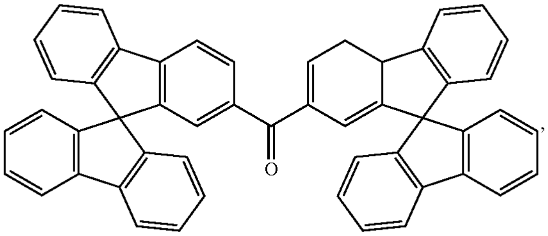
,
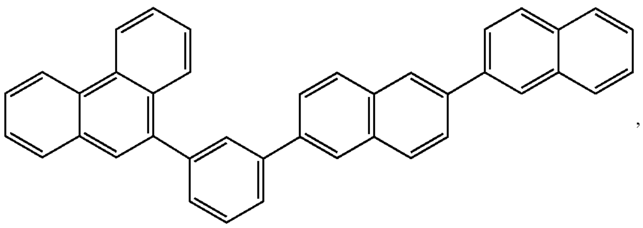
,
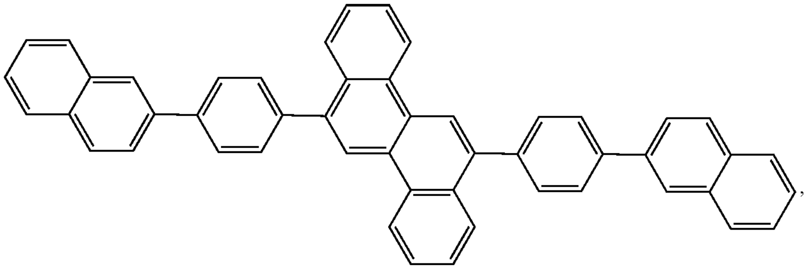
, -continued

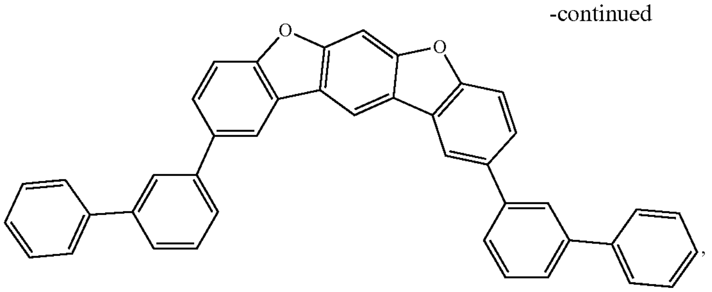, e) Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

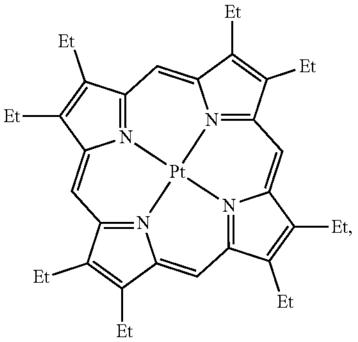,

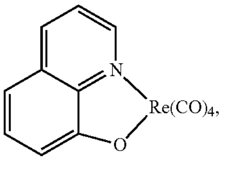,

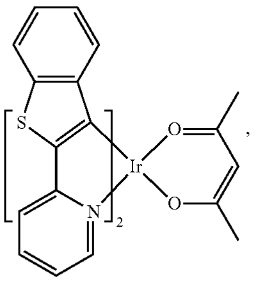,

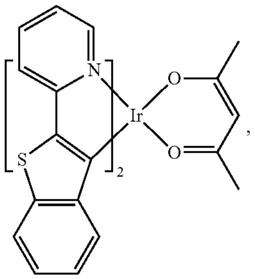,

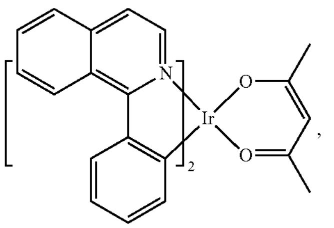,

-continued
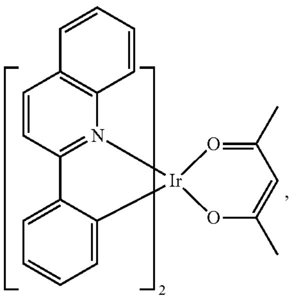
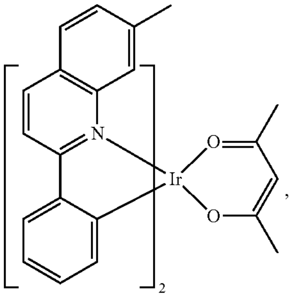
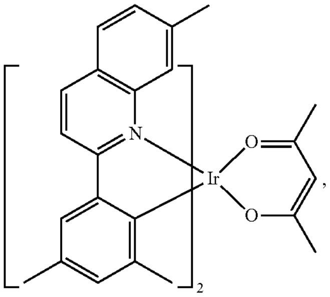
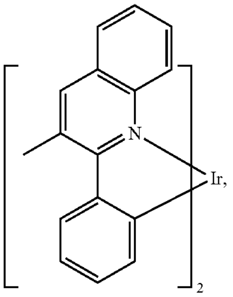
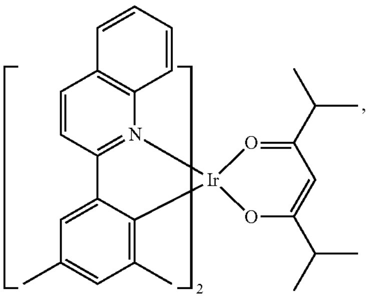
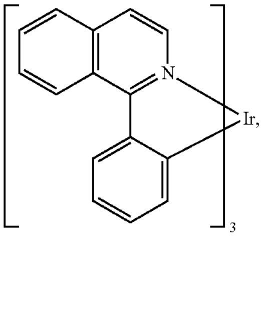
-continued
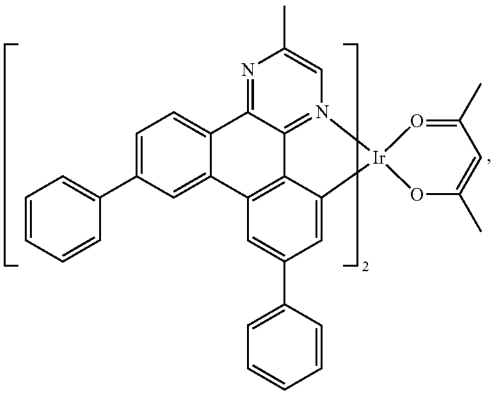
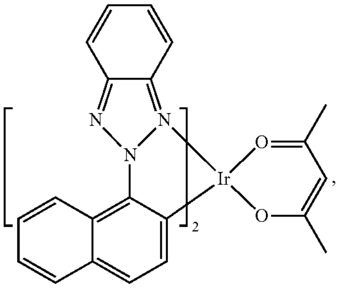
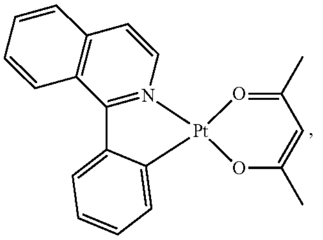
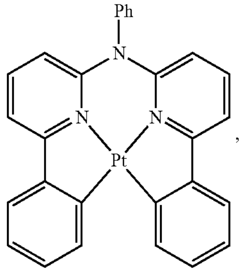
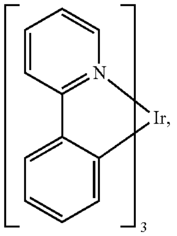
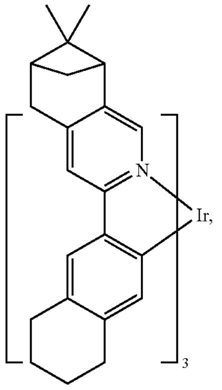
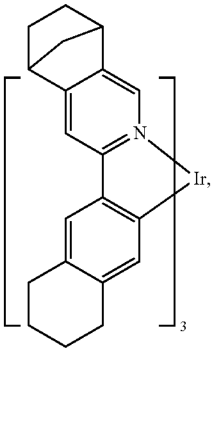

-continued
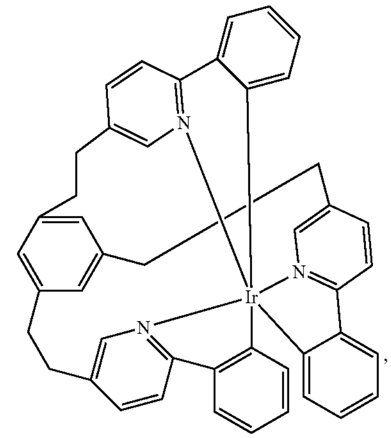,
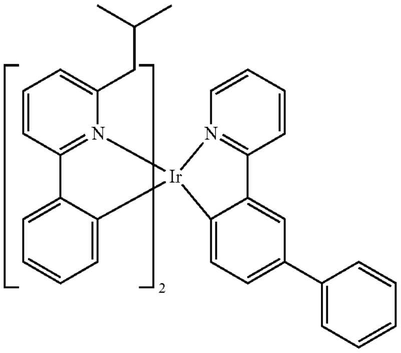,
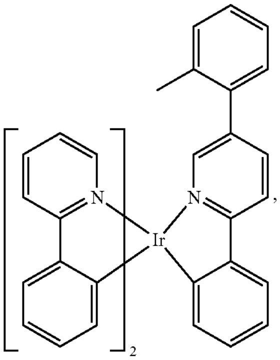,
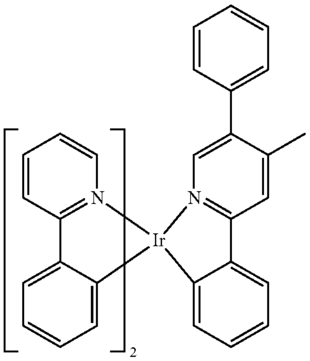,
-continued
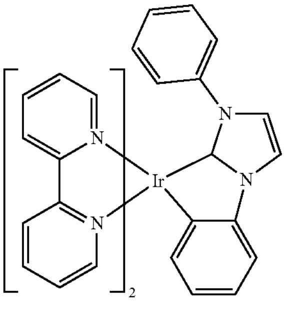,
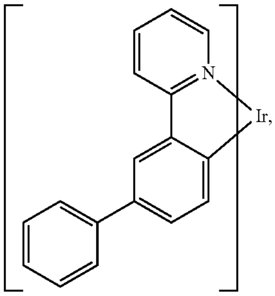
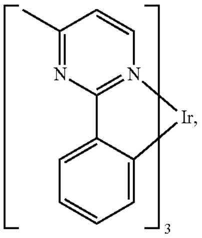
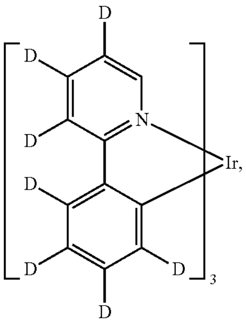
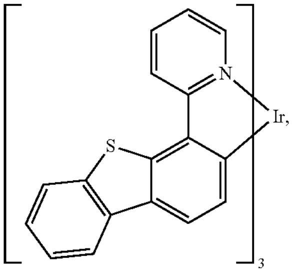
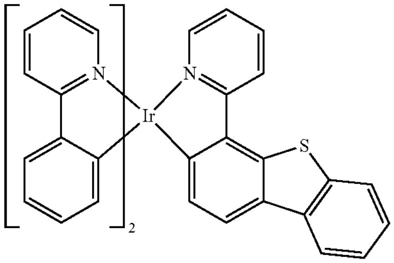,
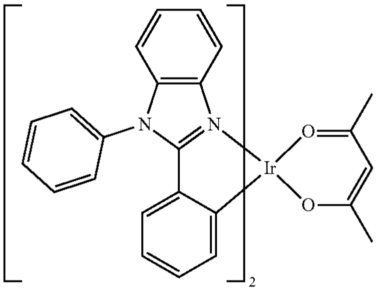, -continued
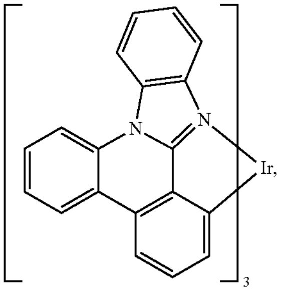
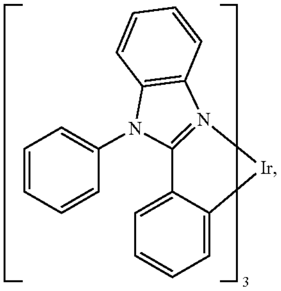
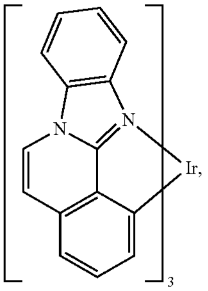
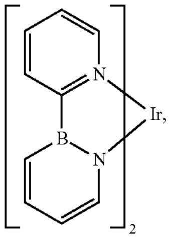
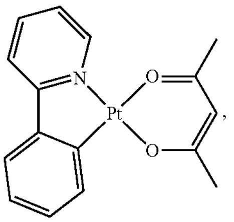
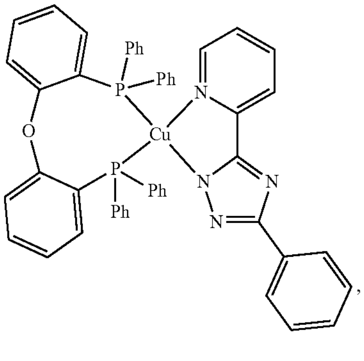
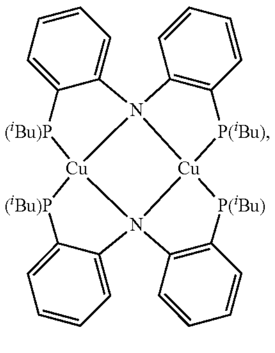
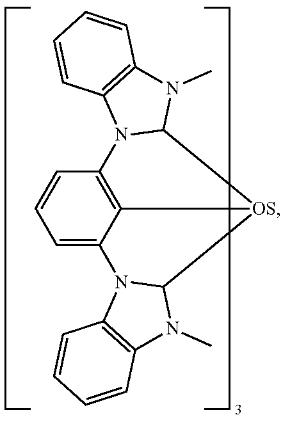
-continued
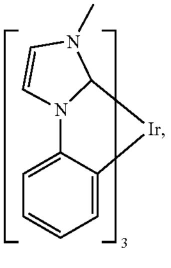
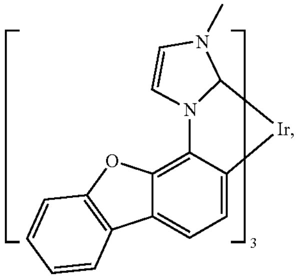
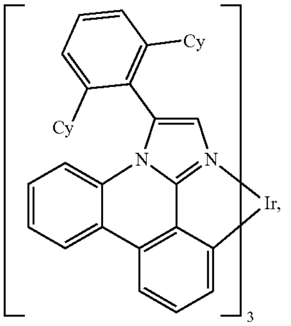
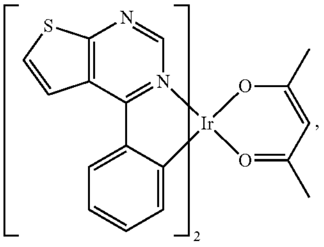
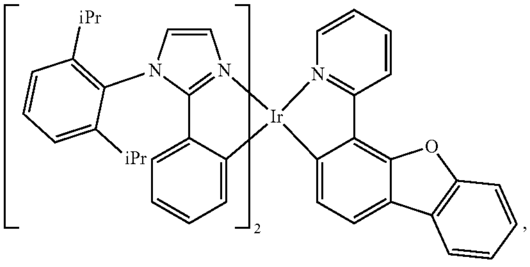
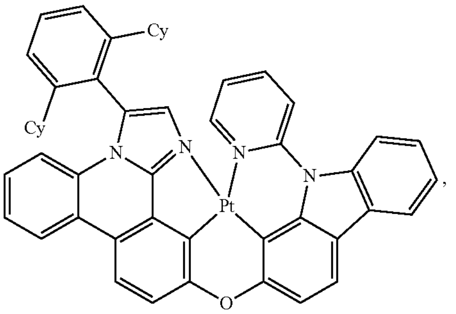

-continued
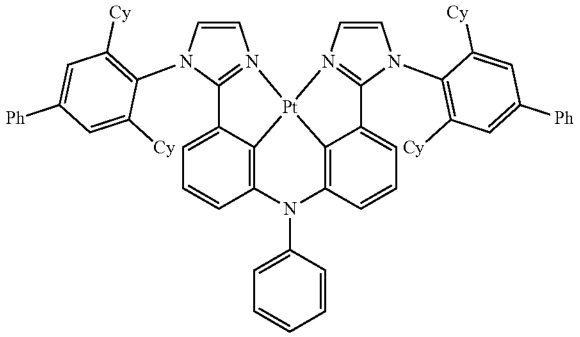
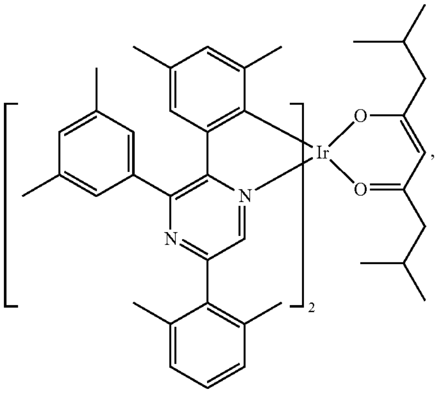
,
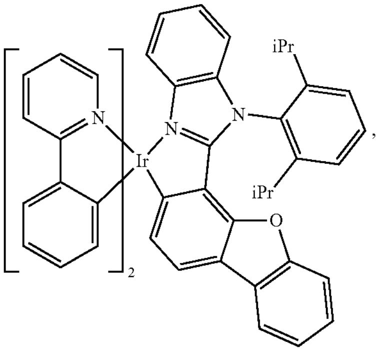
,
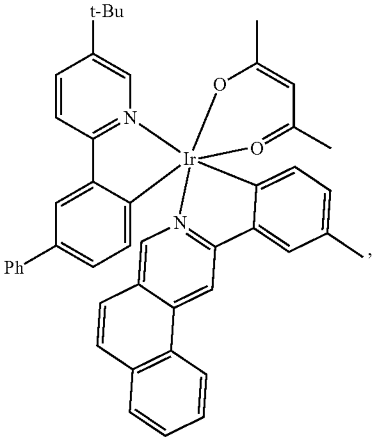
,
-continued
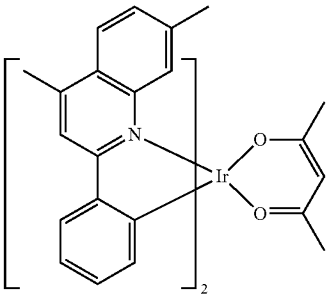
,
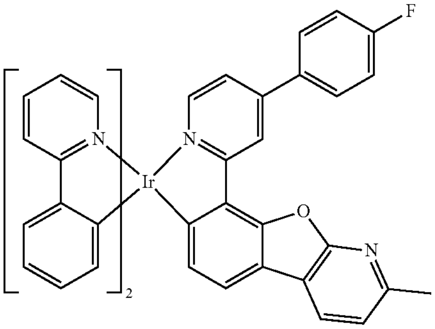
,
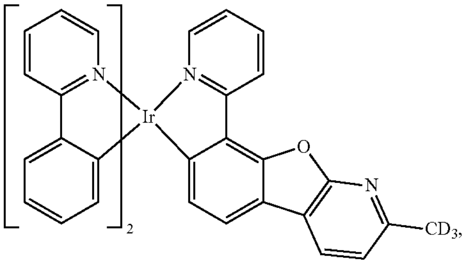
,
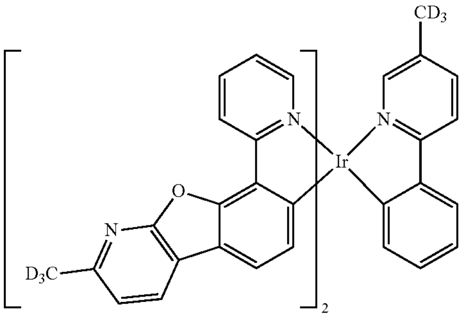
,
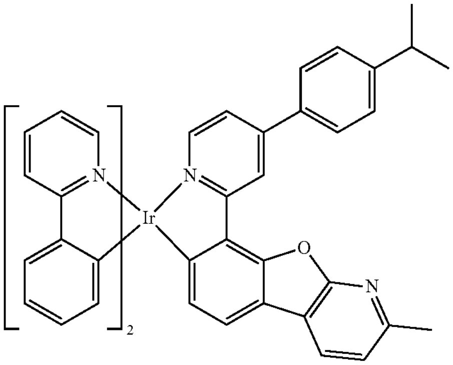
, -continued
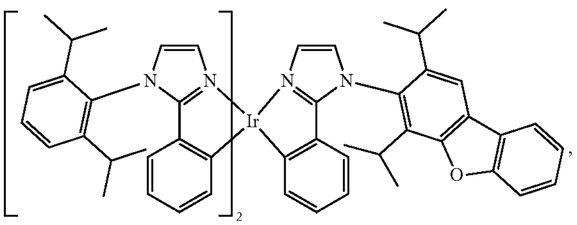
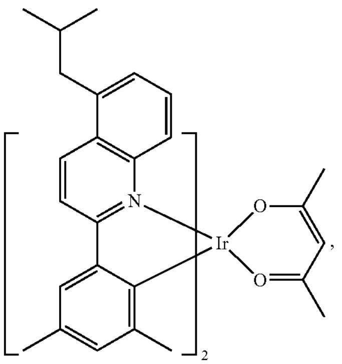
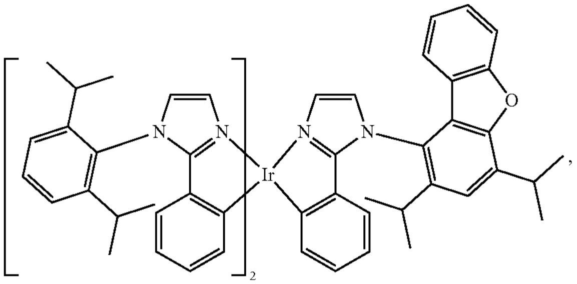
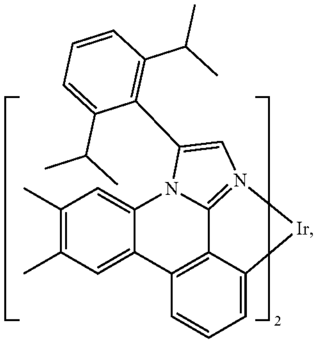
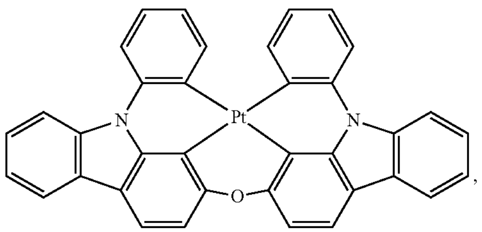
-continued
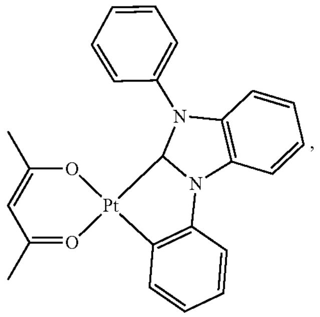
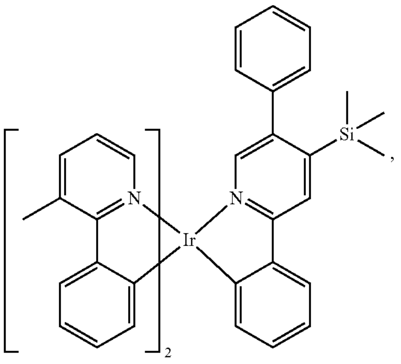
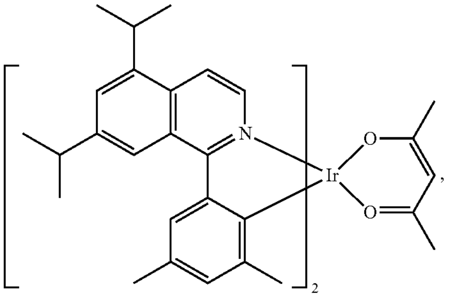
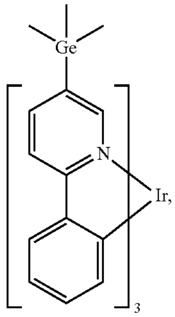
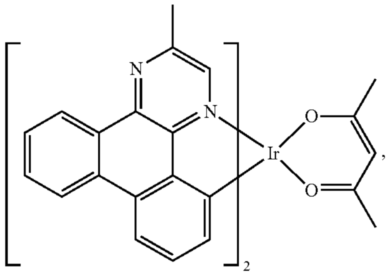
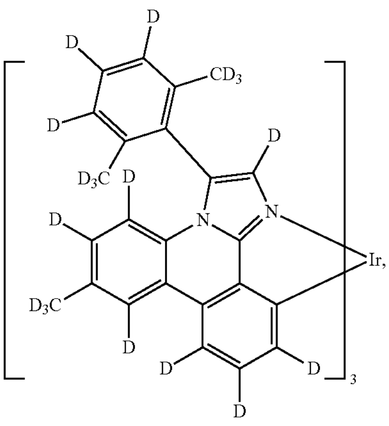

-continued
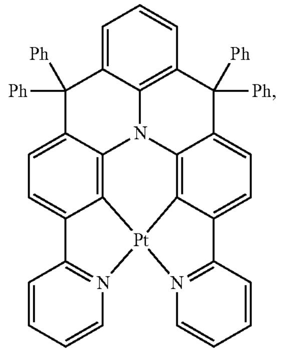
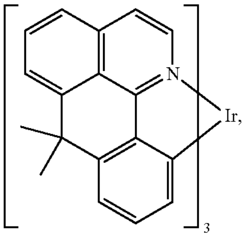
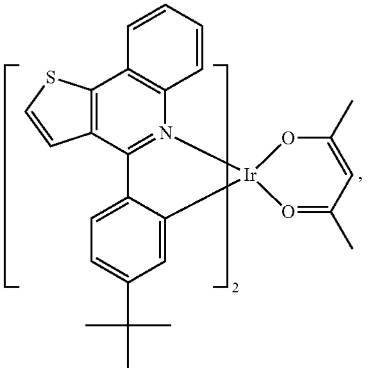
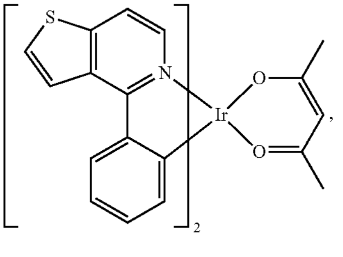
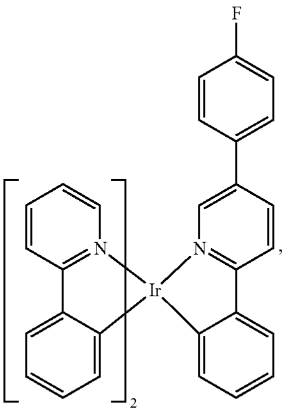
-continued
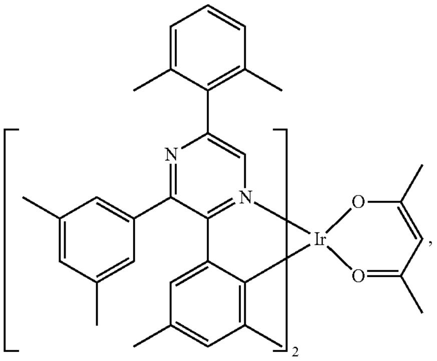
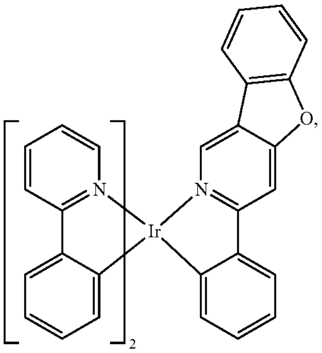
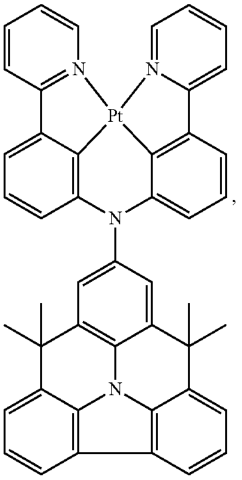
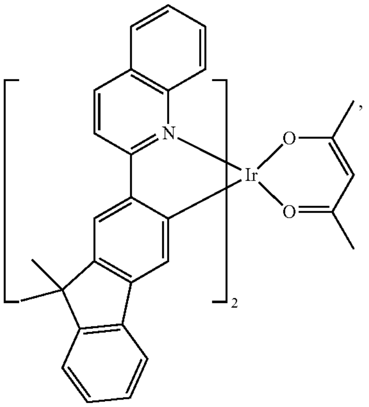

-continued
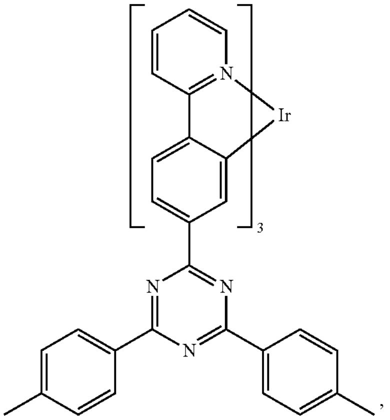
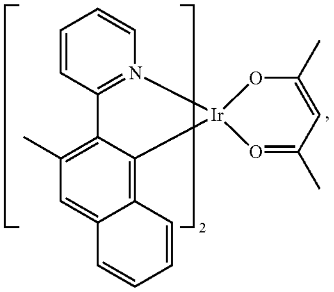
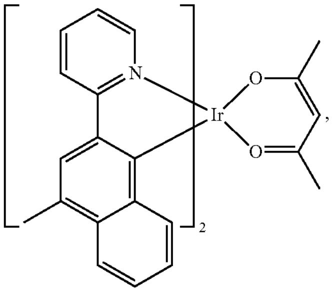
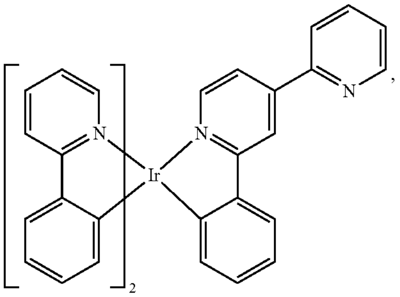
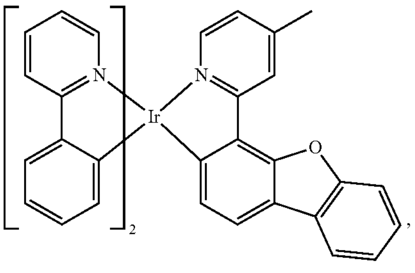
-continued
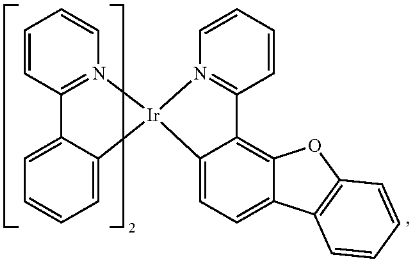
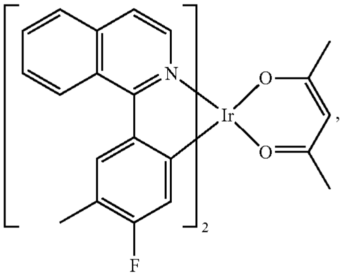
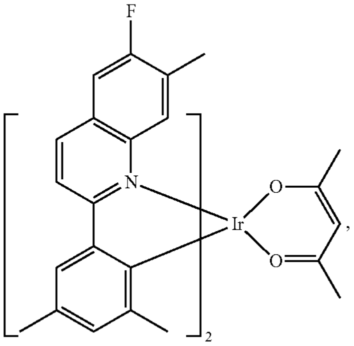
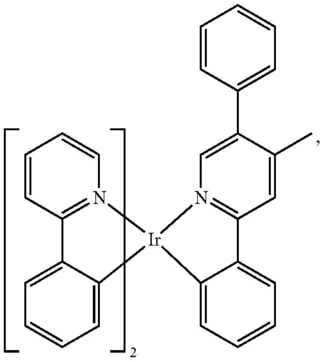
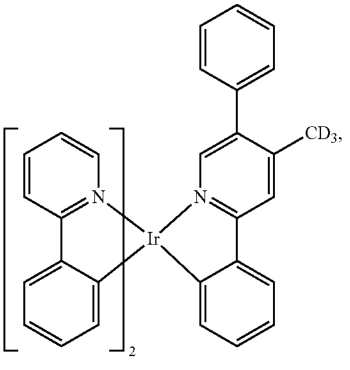

-continued
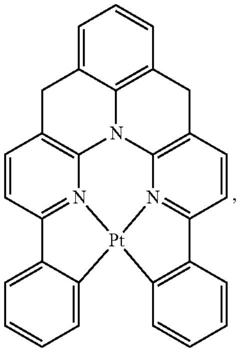
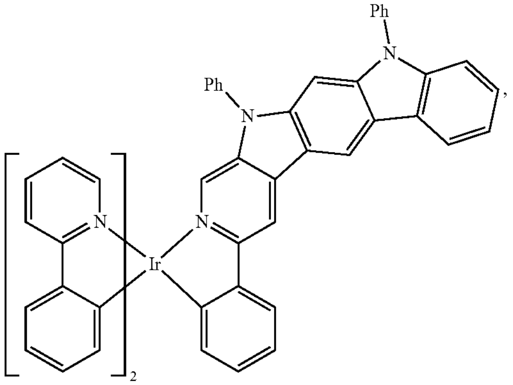
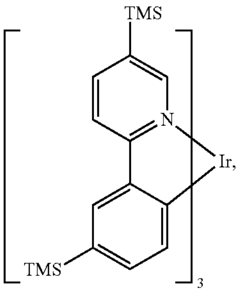
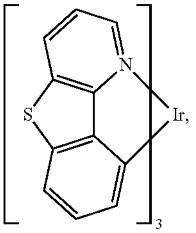
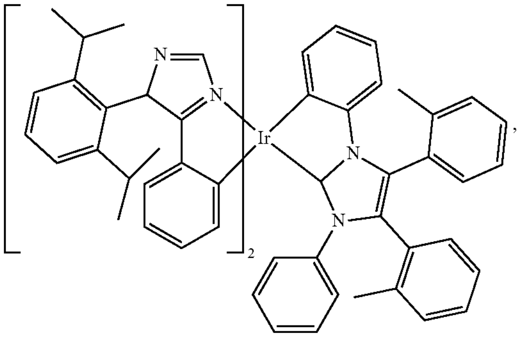
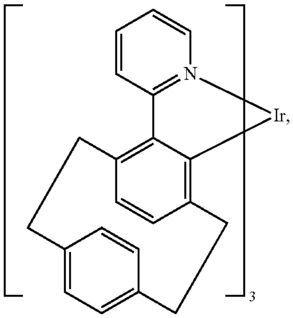
-continued
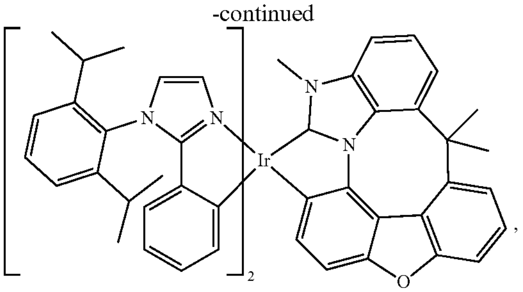
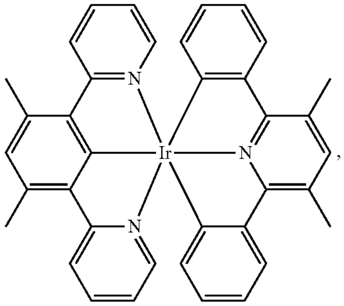
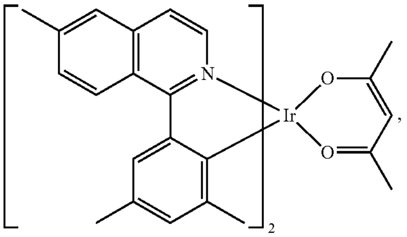
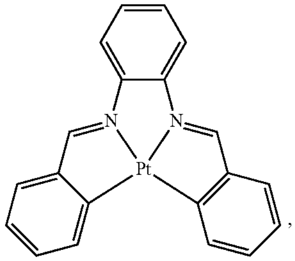
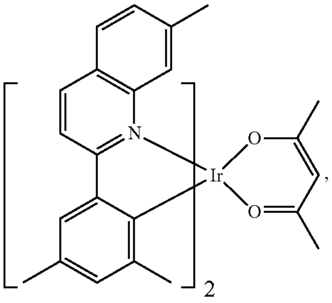
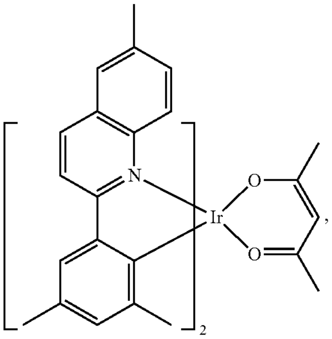

-continued
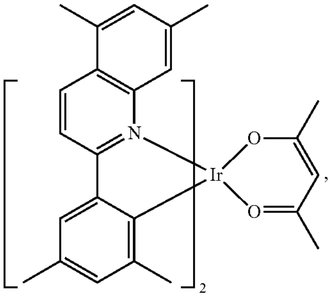
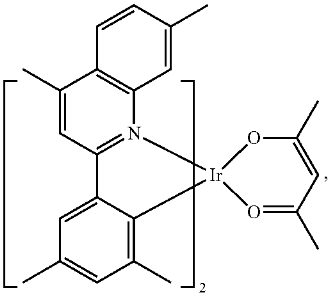
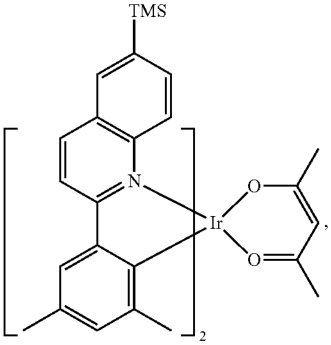
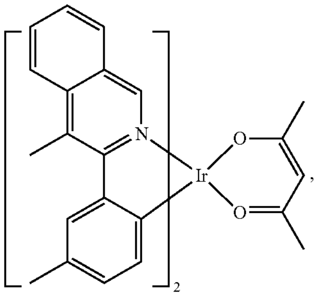
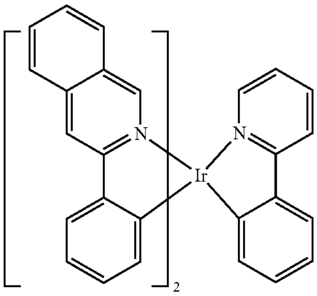
-continued
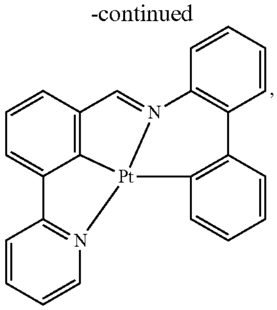
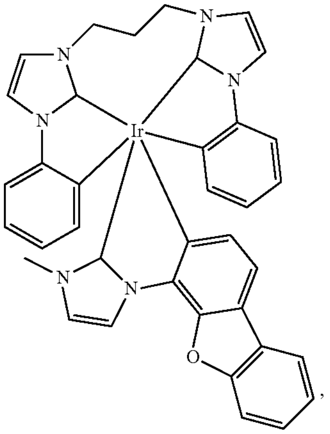
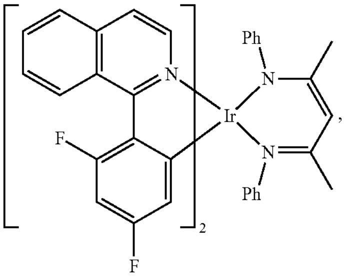
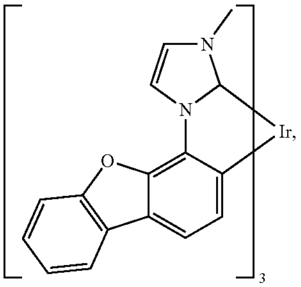
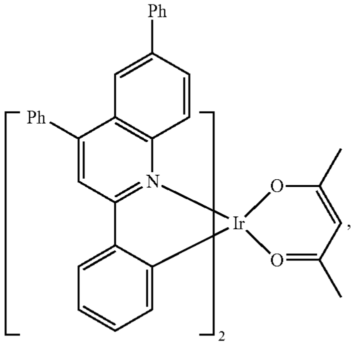

-continued
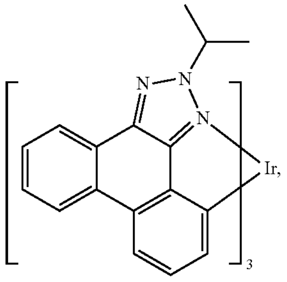
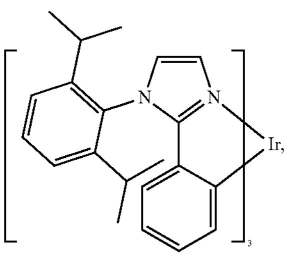
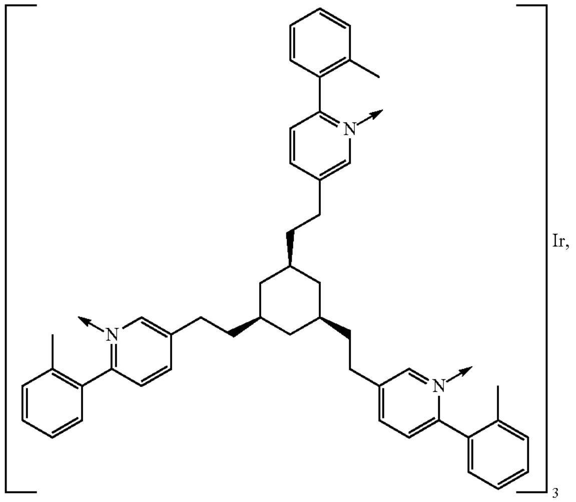
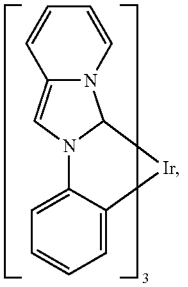
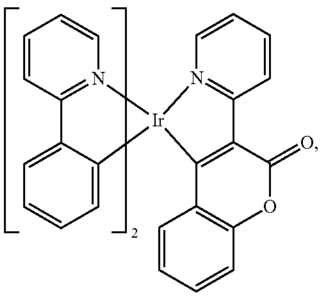
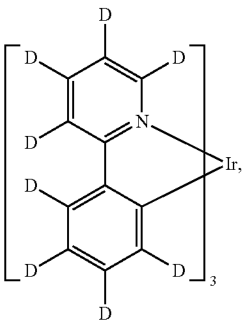
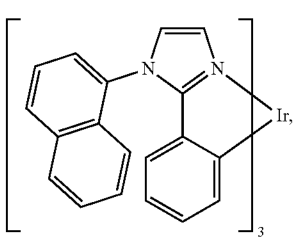
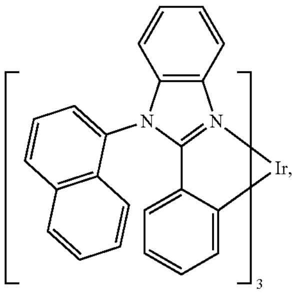
-continued
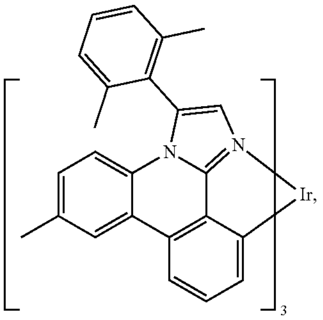
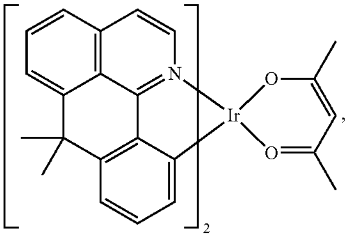
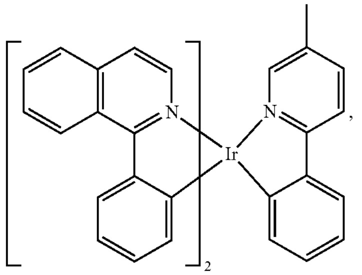
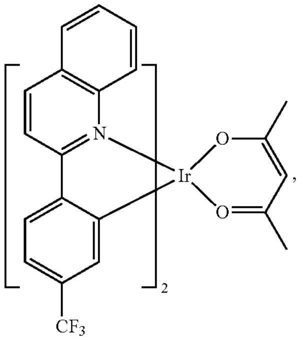
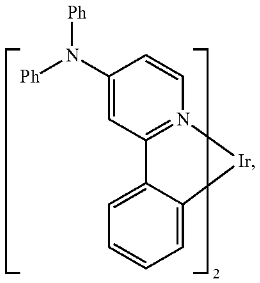
and -continued

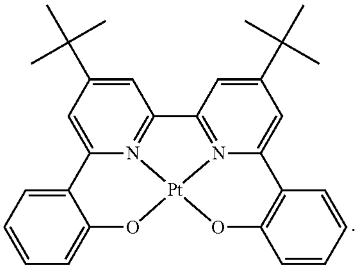

f) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

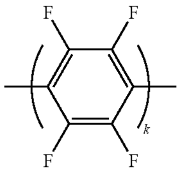
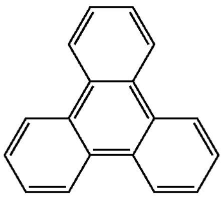
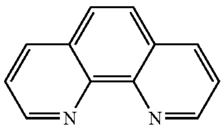
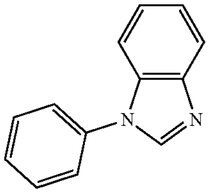
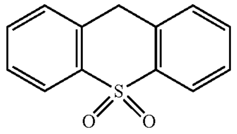
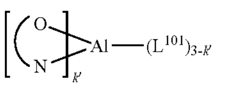

wherein k is an integer from 1 to 20; $L^{101}$ is another ligand, k' is an integer from 1 to 3.

g) ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

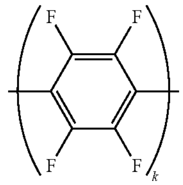
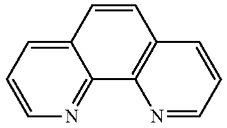
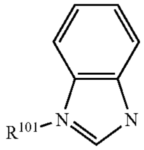
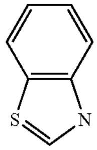
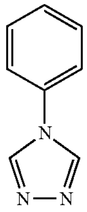
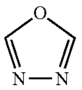
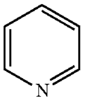
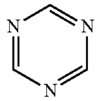
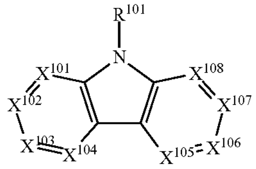
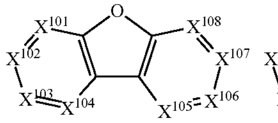
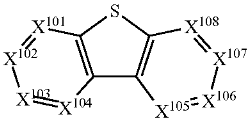
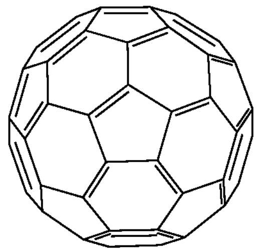
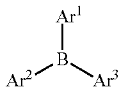

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

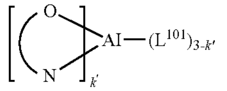
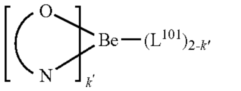
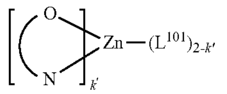
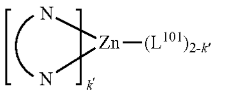

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,
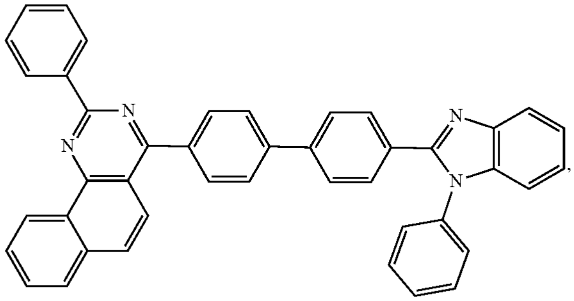
,
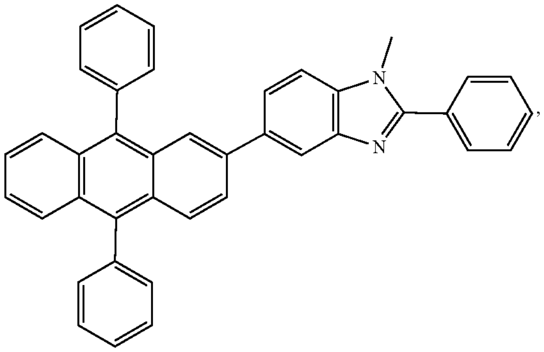
,
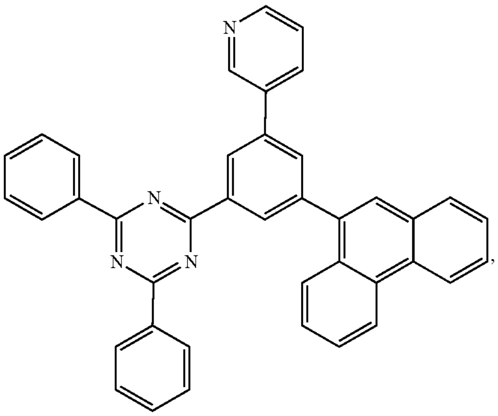
,
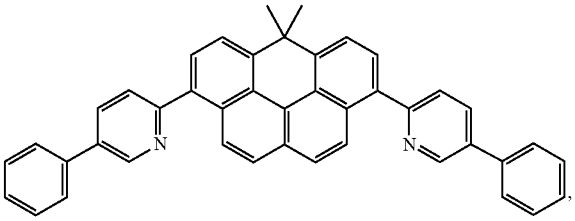
,
-continued
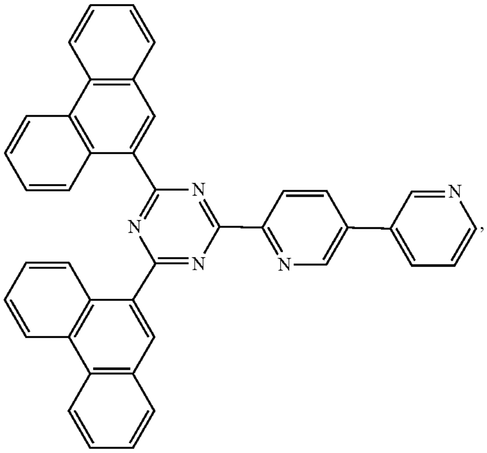
,
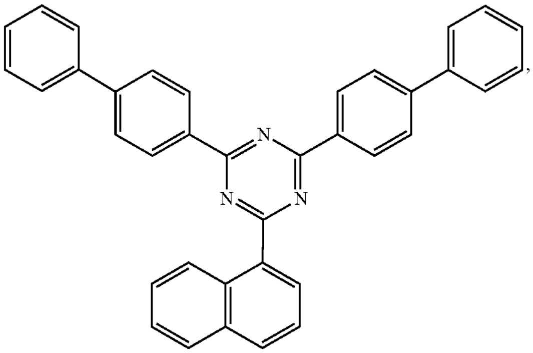
,
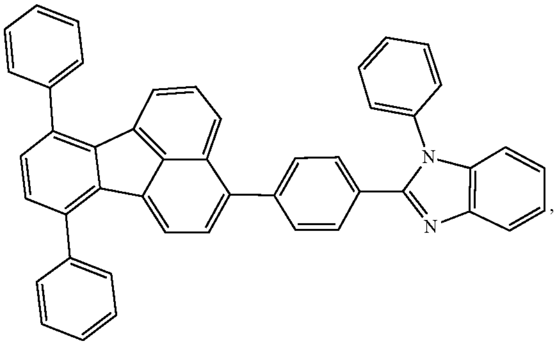
,
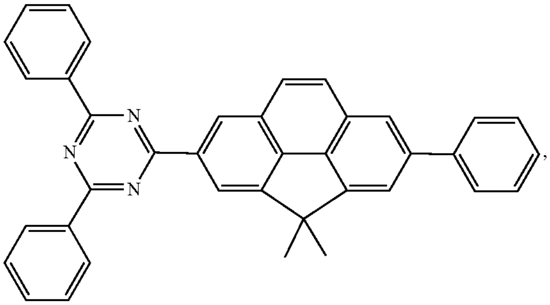
, -continued
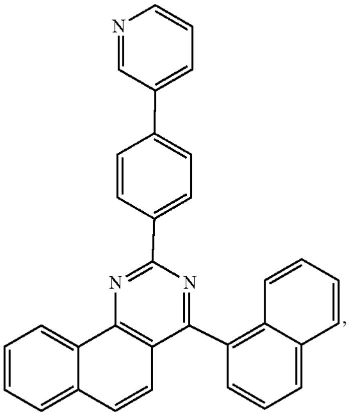
,
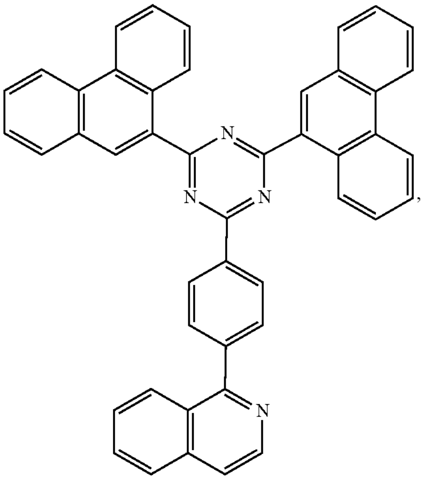
,
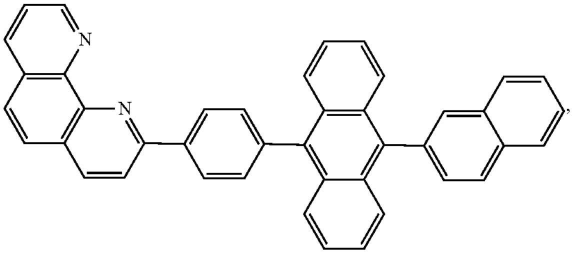
,
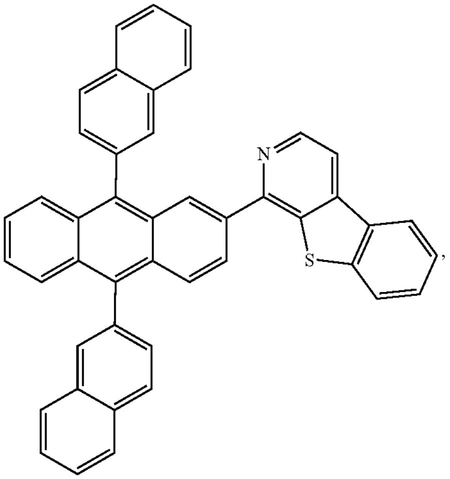
,
-continued
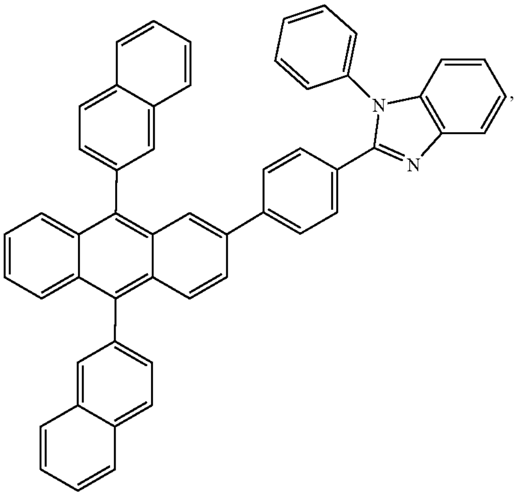
,
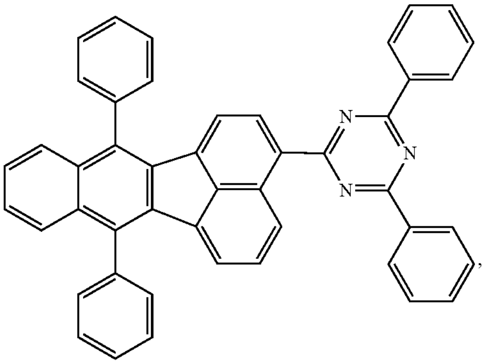
,
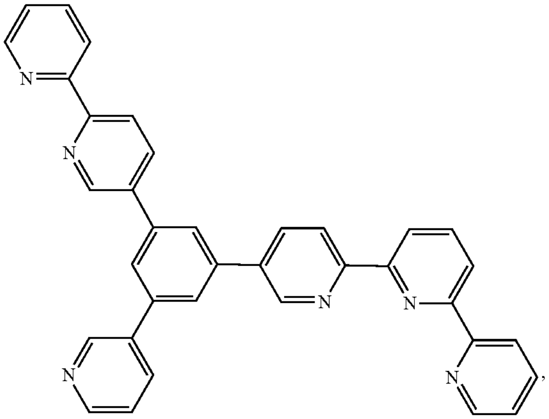
, -continued
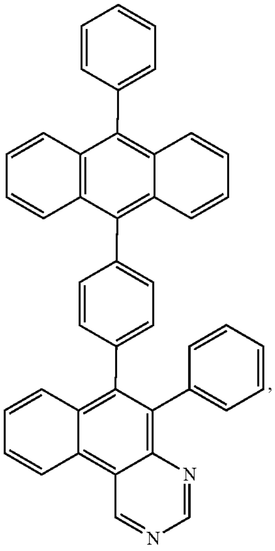
,
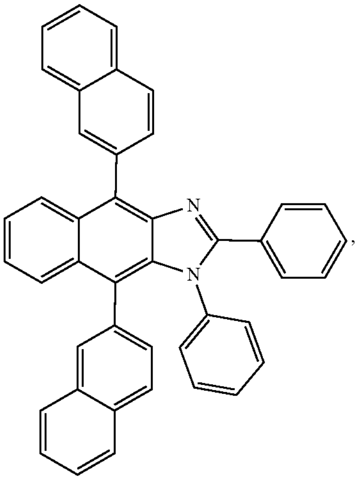
,
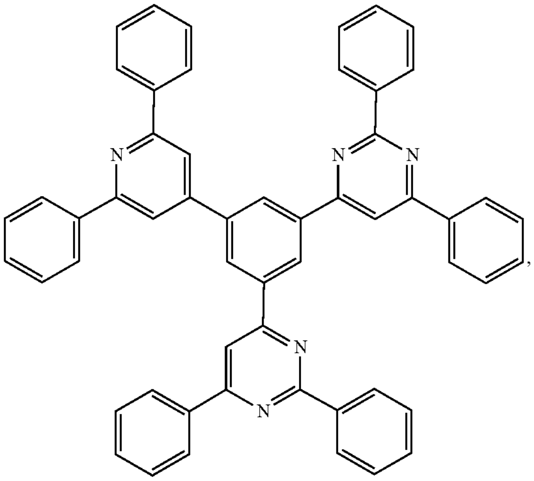
,
-continued
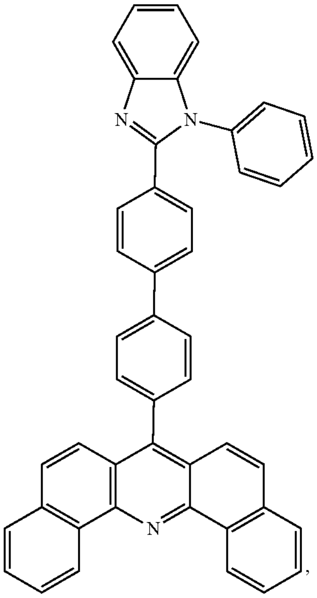
,
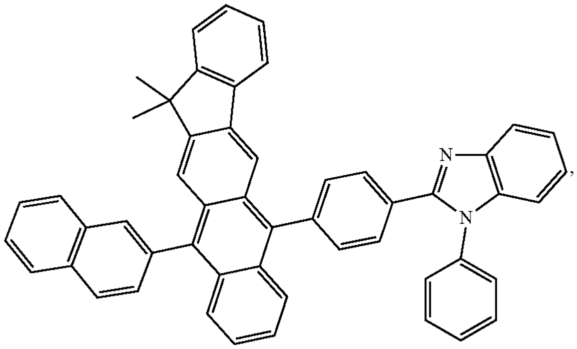
,
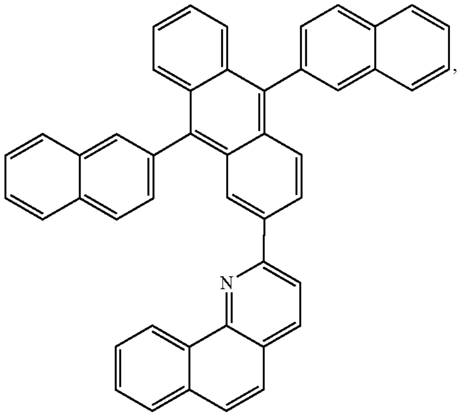
,
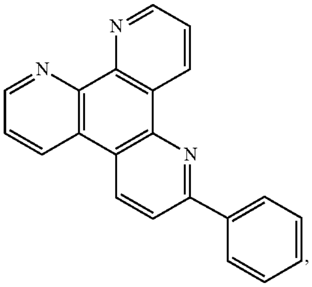
, -continued
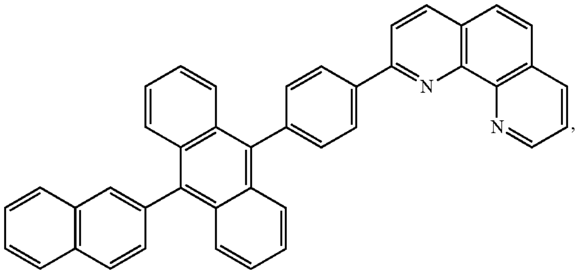,
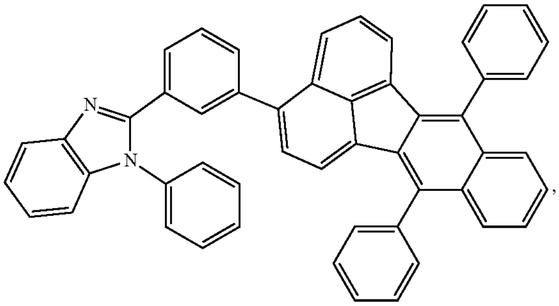,
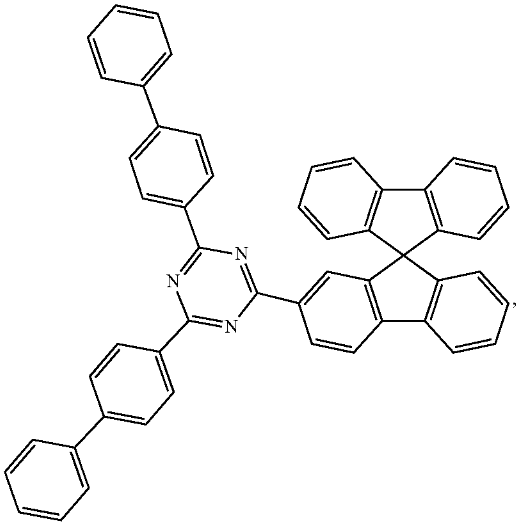,
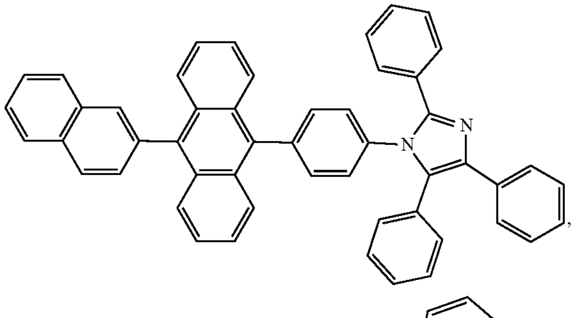,
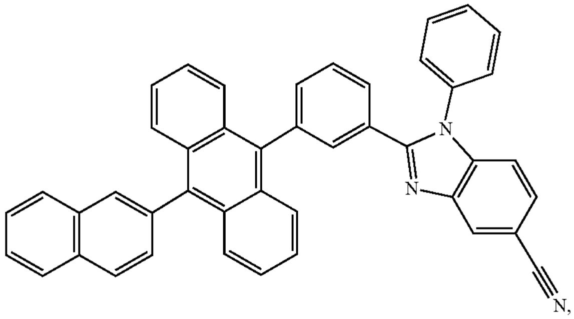,
-continued
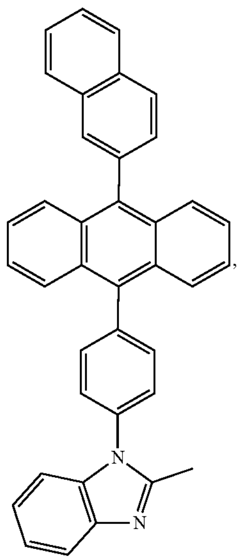,
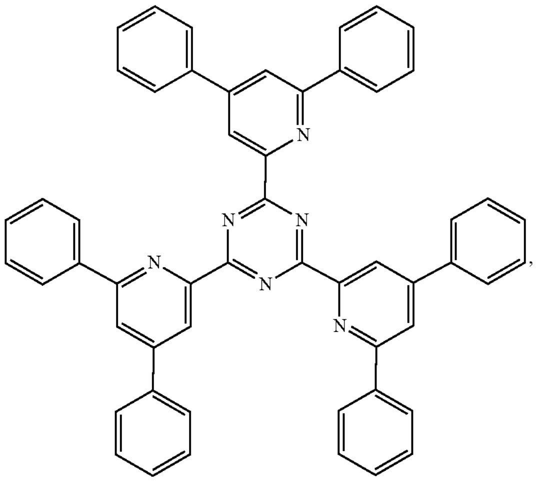,
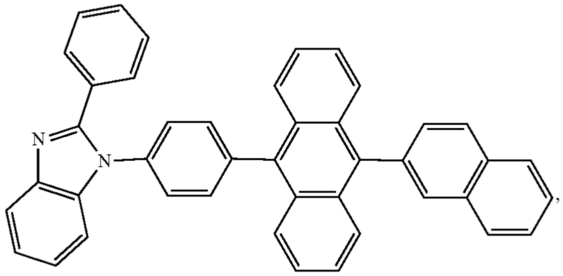,
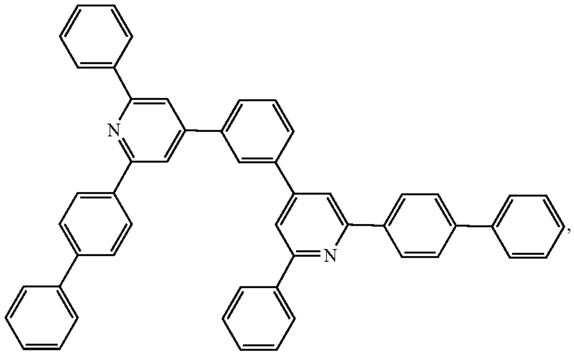, -continued

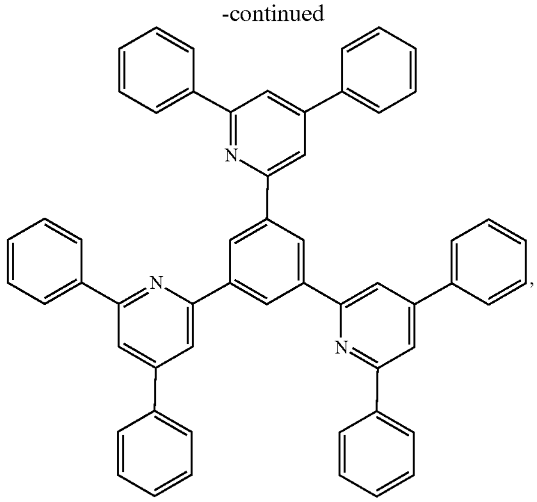

,

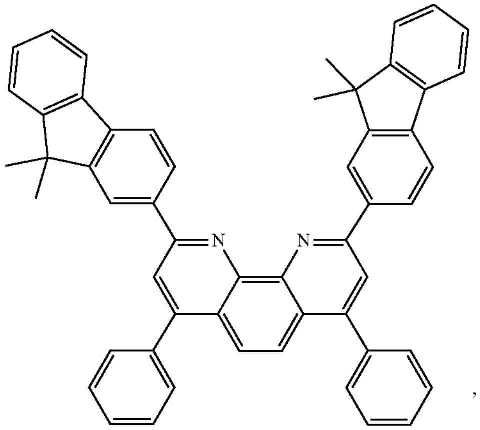

, and

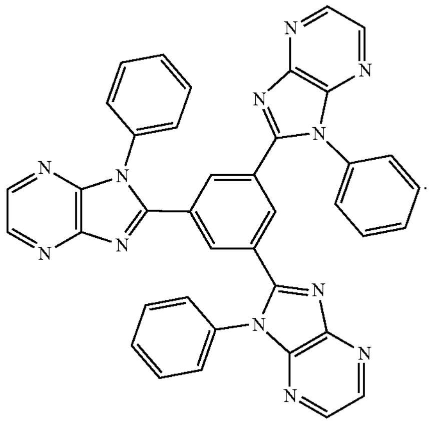

.

h) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. The minimum amount of hydrogen of the compound being deuterated is selected from the group consisting of 30%, 40%, 50%, 60%, 70%, 80%, 90%, 95%, 99%, and 100%. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

Experimental Data

Calculation of Bond Dissociation Energies:

Density functional theory (DFT) was used to calculate the HOMO, LUMO, singlet (Si) energy, and triplet (T1) energy of the compounds. Calculations were performed using the B3LYP functional with a CEP-31G basis set. Geometry optimizations were performed in vacuum. Excitation energies were obtained at these optimized geometries using time-dependent density functional theory (TDDFT). A continuum solvent model was applied in the TDDFT calculation to simulate tetrahydrofuran solvent. All calculations were caried out using the program Gaussian.

TABLE 1

| Compound | $T_1$(calc.) (nm) |
|---|---|
| 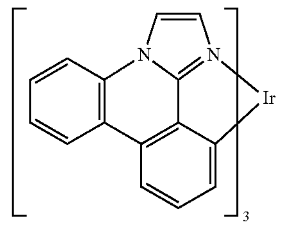 Reference Compound 1 | 468 |
| 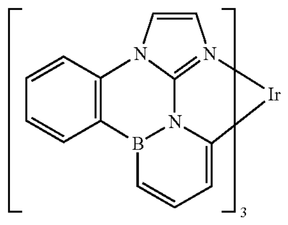 Ir[$L_A$27-(R1)(R1)(R1)(R1)]$_3$ | 459 |
| 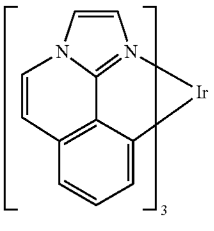 Reference Compound 2 | 472 |

TABLE 1-continued

| Compound | $T_1$(calc.) (nm) |
|---|---|
| 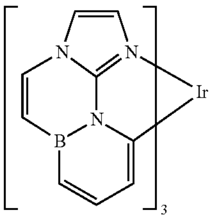 Ir[$L_A$3-(R1)(R1)(R1)]$_3$ | 456 |
| 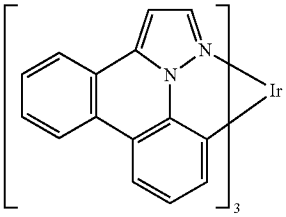 Reference Compound 3 | 471 |
| 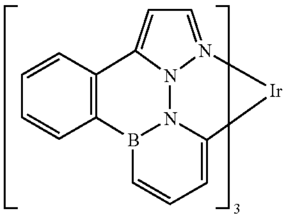 Ir[$L_A$30-(R1)(R1)(R1)]$_3$ | 454 |
| 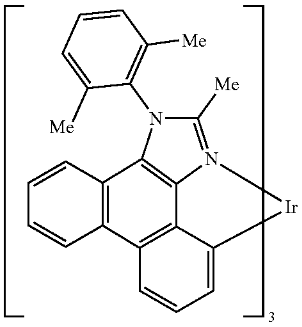 Reference Compound 4 | 485 |
| 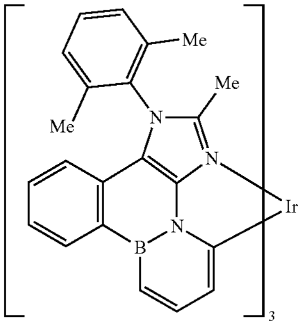 Ir[$L_A$29-(R3)(R1)(R2)(R43)]$_3$ | 455 |

The current invention describes a method to blue shift the emission wavelength of phosphorescent cyclometallated compounds while maintaining other desirable properties such as electroluminescent device stability and efficiency. As an isostere of a C═C bond, we envisioned that judicious incorporation of a B—N linkage into the aromatic ligand scaffold could afford a way to tune the electronic properties of a phosphorescent organometallic complex while simultaneously causing little change to the steric environment and overall molecular geometry. As the table above shows, by replacing analogous C═C linkages in Reference Compounds 1-5, calculated emission is blue shifted by up to 30 nm for the corresponding B—N isosteres. The resulting hypsochromic shift can be attributed to a successful perturbation of the fontier molecular orbitals by lowering the HOMO and/or raising the LUMO energies.

Synthesis of 2-chloro-1-vinyl-1H-imidazole

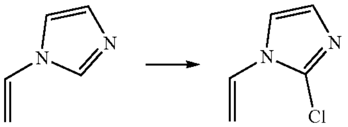

1-vinyl-1H-imidazole (4.40 g, 46.8 mmol) was dissolved in 40 mL THF and cooled to −78° C. n-butyllithium (20.00 ml, 2.5M in hexane, 50.0 mmol) was then added dropwise and the yellow solution and stirred −78° C. for 1 h followed by the dropwise addition (dropping funnel) of a 40 mL THF soln of perchloroethane (13.28 g, 56.1 mmol). After addition was complete (over ~20 min), the cooling bath was removed and the dark red solution was warmed to room temperature followed by quenching with sat. aq. $NH_4Cl$. The mixture was extracted 3× with DCM and the organics were combined, dried over $Na_2SO_4$, and concentrated in vacuo. Purification by column chromatography afforded the desired chloroimidazole as a pale yellow liquid (4.61 g, 77%).

Synthesis of N-(but-3-en-1-yl)-1-vinyl-1H-imidazol-2-amine

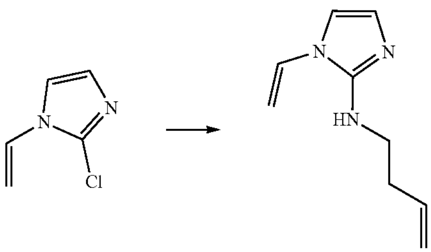

2-chloro-1-vinyl-1H-imidazole (1.0 eq.), $Pd_2(dba)_3$ (2.5 mol %), rac-BINAP (7.5 mol %), but-3-en-1-ammonium chloride, and NaOtBu (2.6 eq.) are dissolved in toluene and sparged with $N_2$ for 30 min followed by heating to 85° C. for 16 h. The reaction mixture is then cooled to room temperature, quenched with water, and extracted with DCM three times. Organics are combined, dried over $Na_2SO_4$ and coated onto Celite. Purification by column chromatography affords the desired diene.

Synthesis of 1-(but-3-en-1-yl)-2-vinyl-1,2-dihydroimidazo[1,2-e][1,5,2]diazaborinine

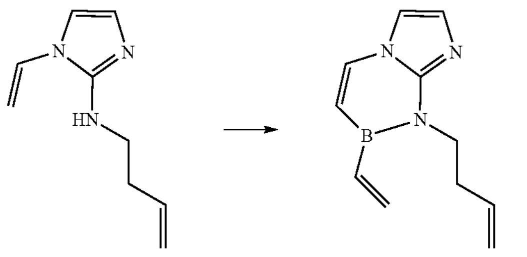

An oven-dried Schlenk flask is charged with potassium vinyltrifluoroborate (1.0 eq.) and cycled vacuum/$N_2$ three times followed by addition of a 1:1 mixture of CPME/toluene. A toluene solution of N-(but-3-en-1-yl)-1-vinyl-1H-imidazol-2-amine (1.2 eq.) is then added followed by $SiCl_4$ (1.0 eq.) and $Et_3N$ (1.5 eq.), and the mixture is heated to 80° C. for 3 d. After cooling to room temperature, the mixture is diluted with DCM and passed through a plug of silica, flushing with DCM. Purification by column chromatography affords the desired azaborinine.

Synthesis of 10,11-dihydro-[1,2]azaborinino[1,2-a]imidazo[1,2-e][1,5,2]diazaborinine

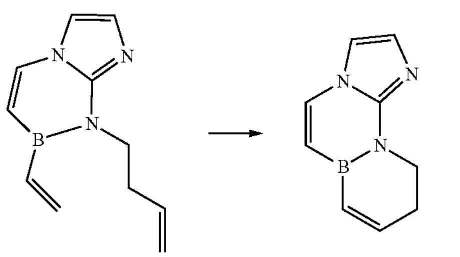

Grubbs Second Generation Catalyst (10 mol %) is dissolved in dry DCM and added to a DCM solution of 1-(but-3-en-1-yl)-2-vinyl-1,2-dihydroimidazo[1,2-e][1,5,2]diazaborinine under $N_2$ followed by heating to 40° C. for 24 h. The reaction mixture is then cooled to room temperature followed by coating onto Celite. Purification by column chromatography affords the desired tricyclic compound.

Synthesis of $L_A$3-(R1)(R1)(R1)

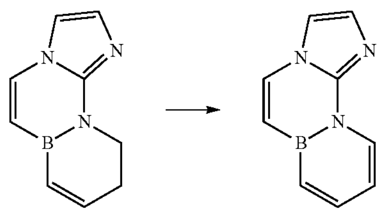 [SMILES: C1=CB2C=Cn3ccnc3N2CC1 ; C1=CB2C=Cn3ccnc3N2C=C1]

An oven-dried round bottom flask is charged with 10,11-dihydro-[1,2]azaborinino[1,2-a]imidazo[1,2-e][1,5,2]diazaborinine and dissolved in n-decane followed by the addition of 30% Pd/C. The mixture is then heated under $N_2$ for 24 h. The reaction mixture is cooled to room temperature, diluted with DCM, and filtered through celite. Upon removal of solvent, the crude residue is purified by column chromatography to afford the desired ligand.

Synthesis of Ir[$L_A$3-(R1)(R1)(R1)]$_3$

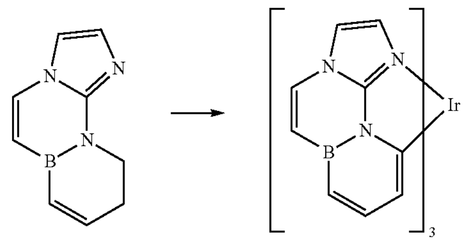

$L_A$3-(R1)(R1)(R1) is metalated to make Ir[$L_A$3-(R1)(R1)(R1)]$_3$ following the methodology described in Macor et al., US20200354390 A1 2020-11-12 and purified by column chromatography.

What is claimed is:

1. A compound comprising a first ligand $L_A$ of Formula I:

Formula I

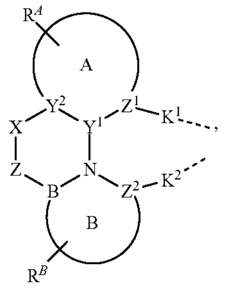

wherein ring A is a 5-membered or 6-membered carbocyclic or heterocyclic ring;

wherein ring B is a 5-membered or 6-membered heterocyclic ring;

wherein at least one of ring A and ring B is a 6-membered ring, wherein $K^1$ and $K^2$ are each independently selected from the group consisting of a direct bond, O, and S;

wherein at least one of $K^1$ and $K^2$ is a direct bond;

wherein $Z^1$ and $Z^2$ are each independently C or N;

wherein $Z^1$ is C if $K^1$ is O or S;

wherein $Z^2$ is C if $K^2$ is O or S;

wherein $Y^1$ and $Y^2$ are each independently selected from the group consisting of C, N, and B;

wherein X and Z are each independently selected from the group consisting of CR, CRR', SiRR', GeRR', BR, BRR', N, NR, O, and S;

wherein $R^A$ and $R^B$ each independently represent mono to the maximum allowable substitution, or no substitution;

wherein each R, R', $R^A$ and $R^B$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, germyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof;

wherein $L_A$ is coordinated to a metal M through the indicated dashed lines;

wherein M may be coordinated to other ligands;

wherein $L_A$ may be joined with other ligands to comprise a tridentate, tetradentate, pentadentate, or hexadentate ligand; and wherein any two R, R', $R^A$ and $R^B$ may be joined or fused to form a ring.

2. The compound of claim 1, wherein each R, R', $R^A$ and $R^B$ is independently a hydrogen or a substituent selected from the group consisting of deuterium, fluorine, alkyl, cycloalkyl, heteroalkyl, alkoxy, aryloxy, amino, silyl, boryl, germyl, alkenyl, cycloalkenyl, heteroalkenyl, aryl, heteroaryl, nitrile, isonitrile, sulfanyl, boryl, and combinations thereof.

3. The compound of claim 1, wherein ring A is a five-membered heterocyclic ring.

4. The compound of claim 1, wherein ring B is an aromatic six-membered ring.

5. The compound of claim 1, wherein $K^1$ and $K^2$ are both direct bonds.

6. The compound of claim 1, wherein X is C, or wherein X is B.

7. The compound of claim 1, wherein exactly one of X, Z, $Y^1$, and $Y^2$ is N.

8. The compound of claim 1, wherein a further ring is fused to X and Z.

9. The compound of claim 1, wherein the ligand $L_A$ is selected from the group consisting of:

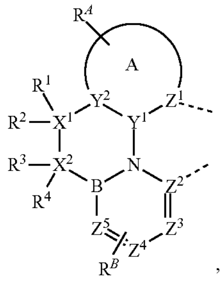
,
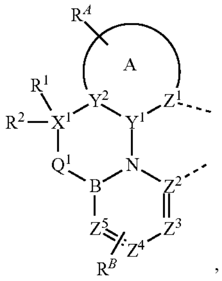
, and
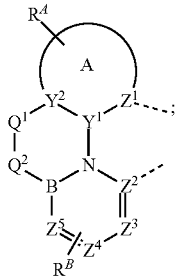

wherein ring

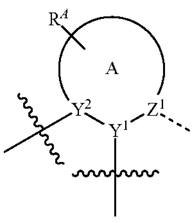

is selected from the list consisting of:

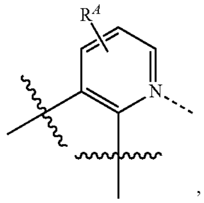
,
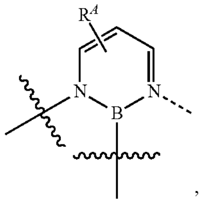
,
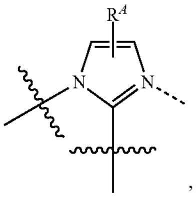
,
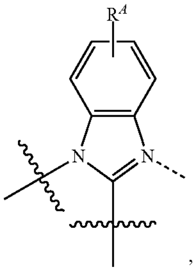
,
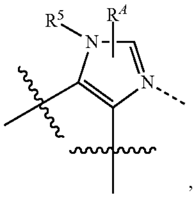
,
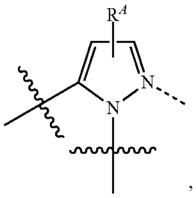
,
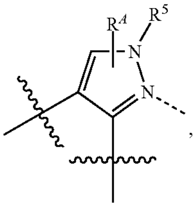
and
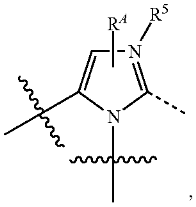
, wherein $Z^1$ through Z are each independently C or N; $R^A$ and $R^B$ each independently represent zero, mono, or up to the maximum allowed number of substitutions to its associated ring; each of $R^1$, $R^2$, $R^3$, $R^4$, and $R^5$ is independently a hydrogen or a substituent selected from the group consisting of the general substituents defined herein; $Y^1$ and $Y^2$ are each independently C, N, or B; $X^1$ and $X^2$ are each independently C or Si; and $Q^1$ and $Q^2$ are each independently O, S, NR, CR, or BR; wherein any two adjacent substituents may be joined or fused to form a ring.

10. The compound of claim 1, wherein the ligand $L_A$ is selected from the group consisting of:

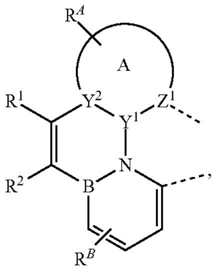
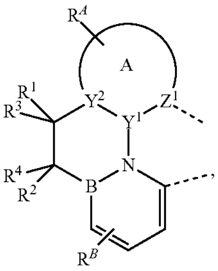

-continued

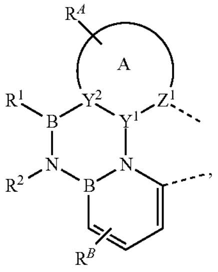

, and

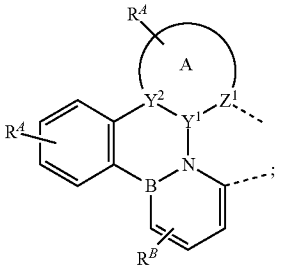

;

wherein ring

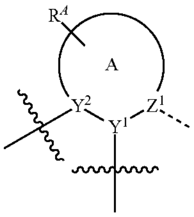

is selected from the list consisting of:

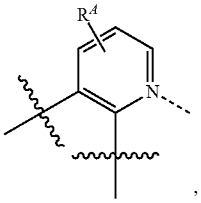

,

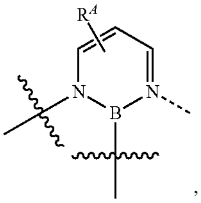

,

-continued

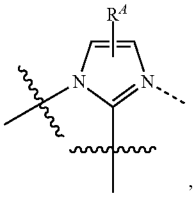

,

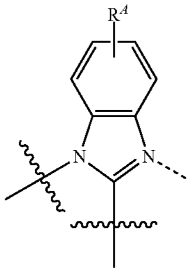

,

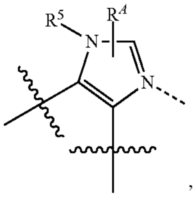

,

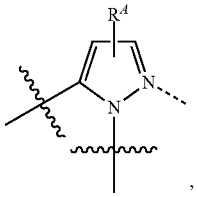

,

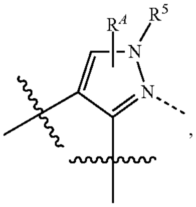

, and

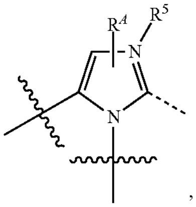

, wherein $Z^1$ is C or N; $R^A$ and $R^B$ each independently represent zero, mono, or up to the maximum allowed number of substitutions to its associated ring; each of $R^1$, $R^2$, $R^3$, $R^4$ and $R^5$ is independently a hydrogen or a substituent selected from the group consisting of the general substituents defined herein; $Y^1$ and $Y^2$ are each independently C, N, or B; $X^1$ and $X^2$ are each independently C or Si; and $Q^1$ and $Q^2$ are each independently O, S, NR, CR, or BR.

11. The compound of claim 1, wherein the ligand $L_A$ is selected from the group consisting of the structures as defined in the following table;

| $L_A$ | Structure of $L_A$ | $L_A$ | Structure of $L_A$ |
|---|---|---|---|
| For $L_A$1-(Rl)(Rm)(Rn), $L_A$1-(R1)(R1)(R1) to $L_A$1-(R134)(R134)(R134) have the structure, | 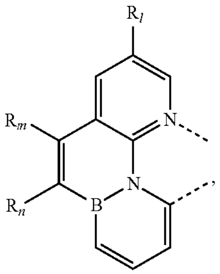 , | For $L_A$21-(Rl)(Rm)(Rn)(Ro), $L_A$21-(R1)(R1)(R1)(R1) to $L_A$21-(R134)(R134)(R134)(R134) have the structure, | 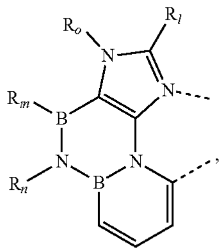 , |
| For $L_A$2-(Rl)(Rm)(Rn), $L_A$2-(R1)(R1)(R1) to $L_A$2-(R134)(R134)(R134) have the structure, | 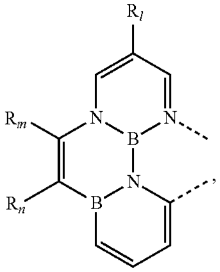 , | For $L_A$22-(Rl)(Rm)(Rn), $L_A$22-(R1)(R1)(R1) to $L_A$22-(R134)(R134)(R134) have the structure, | 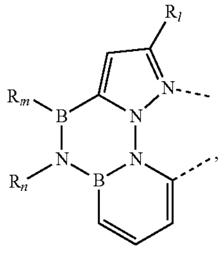 , |

-continued

| $L_A$ | Structure of $L_A$ | $L_A$ | Structure of $L_A$ |
|---|---|---|---|
| For $L_A$3-(Rl)(Rm)(Rn), $L_A$3-(R1)(R1)(R1) to $L_A$3-(R134)(R134)(R134) have the structure, | 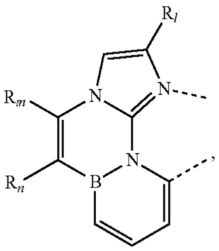 | For $L_A$23-(Rl)(Rm)(Rn), $L_A$23-(R1)(R1)(R1) to $L_A$23-(R134)(R134)(R134) have the structure, | 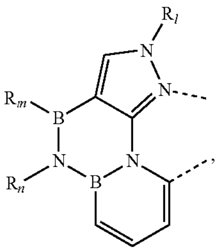 |
| For $L_A$4-(Rm)(Rn), $L_A$4-(R1)(R1) to $L_A$4-(R134)(R134) have the structure, | 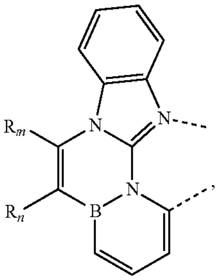 | For $L_A$24-(Rl)(Rm)(Rn), $L_A$24-(R1)(R1)(R1) to $L_A$24-(R134)(R134)(R134) have the structure, | 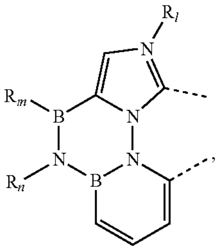 |
| For $L_A$5-(Rl)(Rm)(Rn)(Ro), $L_A$5-(R1)(R1)(R1)(R1) to $L_A$5-(R134)(R134)(R134)(R134) have the structure, | 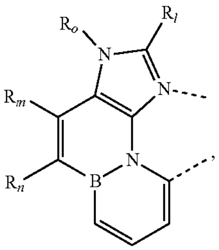 | For $L_A$25-(Rl)(Rm)(Rn), $L_A$25-(R1)(R1)(R1) to $L_A$25-(R134)(R134)(R134) have the structure, | 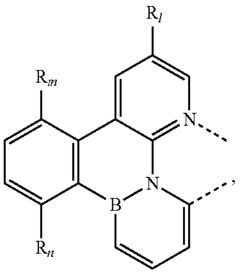 |
| For $L_A$6-(Rl)(Rm)(Rn), $L_A$6-(R1)(R1)(R1) to $L_A$6-(R134)(R134)(R134) have the structure, | 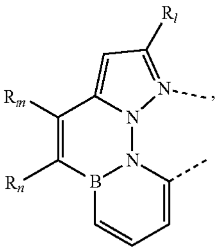 | For $L_A$26-(Rl)(Rm)(Rn), $L_A$26-(R1)(R1)(R1) to $L_A$26-(R134)(R134)(R134) have the structure, | 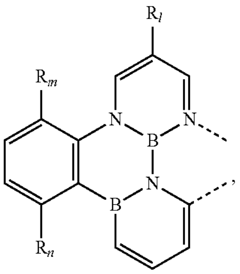 |
| For $L_A$7-(Rl)(Rm)(Rn), $L_A$7-(R1)(R1)(R1) to $L_A$7-(R134)(R134)(R134) have the structure, | 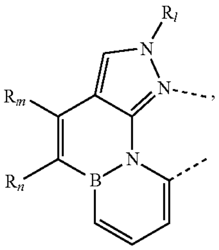 | For $L_A$27-(Rl)(Rm)(Rn)(Ro), $L_A$27-(R1)(R1)(R1)(R1) to $L_A$27-(R134)(R134)(R134)(R134) have the structure, | 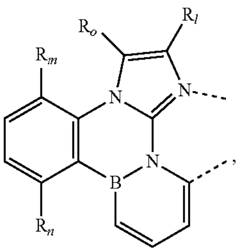 |

-continued

| $L_A$ | Structure of $L_A$ | $L_A$ | Structure of $L_A$ |
|---|---|---|---|
| For $L_A$8-(Rl)(Rm)(Rn), $L_A$8-(R1)(R1)(R1) to $L_A$8-(R134)(R134)(R134) have the structure, | 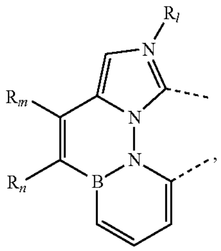 | For $L_A$28-(Rl)(Rm), $L_A$28-(R1)(R1) to $L_A$28-(R134)(R134) have the structure, | 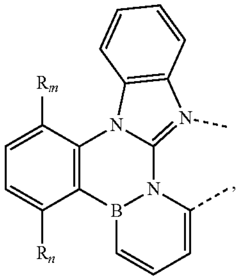 |
| For $L_A$9-(Rl)(Lz), $L_A$9-(R1)(L1) to $L_A$9-(R134)(L5) have the structure, | 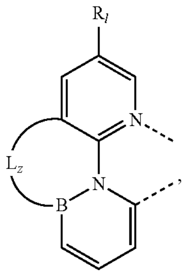 | For $L_A$29-(Rl)(Rm)(Rn)(Ro), $L_A$29-(R1)(R1)(R1)(R1) to $L_A$29-(R134)(R134)(R134)(R134) have the structure, | 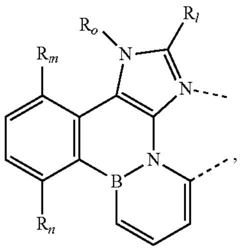 |
| For $L_A$10-(Rl)(Lz), $L_A$10-(R1)(L1) to $L_A$10-(R134)(L5) have the structure, | 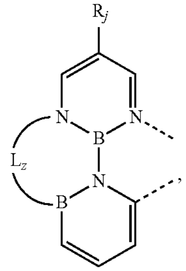 | For $L_A$30-(Rl)(Rm)(Rn), $L_A$30-(R1)(R1)(R1) to $L_A$30-(R134)(R134)(R134) have the structure, | 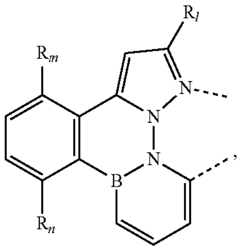 |
| For $L_A$11-(Rl)(Lz), $L_A$11-(R1)(L1) to $L_A$11-(R134)(L5) have the structure, | 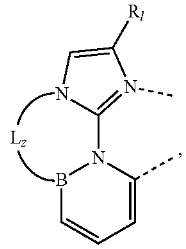 | For $L_A$31-(Rl)(Rm)(Rn), $L_A$31-(R1)(R1)(R1) to $L_A$31-(R134)(R134)(R134) have the structure, | 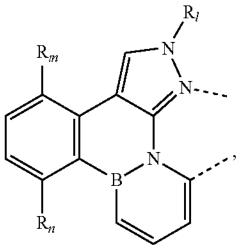 |
| For $L_A$12-(Lz), $L_A$12-(L1) to $L_A$12-(L5) have the structure, | 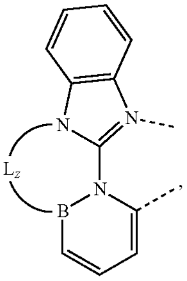 | For $L_A$32-(Rl)(Rm)(Rn), $L_A$32-(R1)(R1)(R1) to $L_A$32-(R134)(R134)(R134) have the structure, | 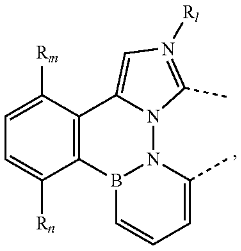 |

-continued

| $L_A$ | Structure of $L_A$ | $L_A$ | Structure of $L_A$ |
|---|---|---|---|
| For $L_A$13-(Rl)(Ro)(Lz), $L_A$13-(R1)(R1)(L1) to $L_A$13-(R134)(R134)(L5) have the structure, | 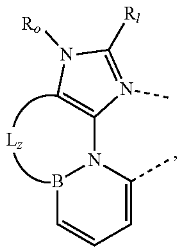 | For $L_A$33-(Rl)(Rm)(Rn), $L_A$33-(R1)(R1)(R1) to $L_A$33-(R134)(R134)(R134) have the structure, | 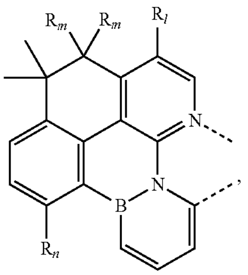 |
| For $L_A$14-(Rl)(Lz), $L_A$14-(R1)(L1) to $L_A$14-(R134)(L5) have the structure, | 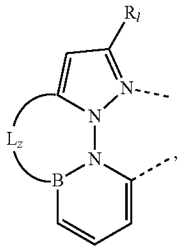 | For $L_A$34-(Rl)(Rm)(Rn), $L_A$34-(R1)(R1)(R1) to $L_A$34-(R134)(R134)(R134) have the structure, | 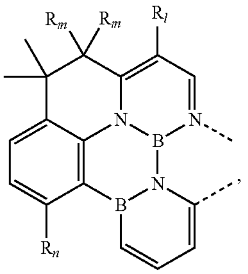 |
| For $L_A$15-(Rl)(Lz), $L_A$15-(R1)(L1) to $L_A$15-(R134)(L5) have the structure, | 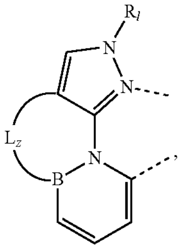 | For $L_A$35-(Rl)(Rm)(Rn), $L_A$35-(R1)(R1)(R1) to $L_A$35-(R134)(R134)(R134) have the structure, | 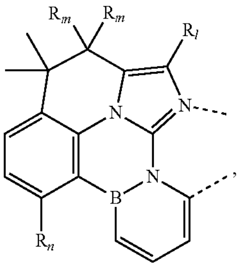 |
| For $L_A$16-(Rl)(Lz), $L_A$16-(R1)(L1) to $L_A$16-(R134)(L5) have the structure, | 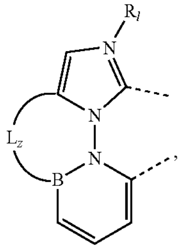 | For $L_A$36-(Rl)(Rm)(Rn), $L_A$36-(R1)(R1)(R1) to $L_A$36-(R134)(R134)(R134) have the structure, | 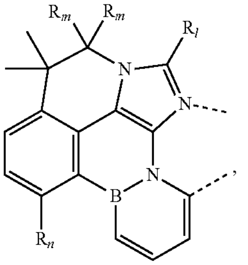 |
| For $L_A$17-(Rl)(Rm)(Rn), $L_A$17-(R1)(R1)(R1) to $L_A$17-(R134)(R134)(R134) have the structure, | 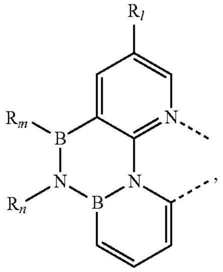 | For $L_A$37-(Rl)(Rm)(Rn), $L_A$37-(R1)(R1)(R1) to $L_A$37-(R134)(R134)(R134) have the structure, | 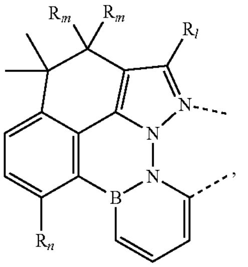 |

-continued

| $L_A$ | Structure of $L_A$ | $L_A$ | Structure of $L_A$ |
|---|---|---|---|
| For $L_A$18-(Rl)(Rm)(Rn), $L_A$18-(R1)(R1)(R1) to $L_A$18-(R134)(R134)(R134) have the structure, | 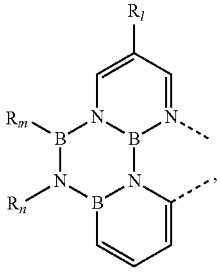 | For $L_A$38-(Rl)(Rm)(Rn), $L_A$38-(R1)(R1)(R1) to $L_A$38-(R134)(R134)(R134) have the structure, | 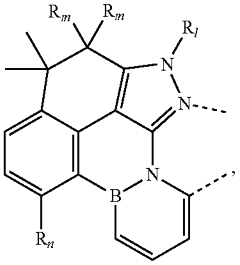 |
| For $L_A$19-(Rl)(Rm)(Rn), $L_A$19-(R1)(R1)(R1) to $L_A$19-(R134)(R134)(R134) have the structure, | 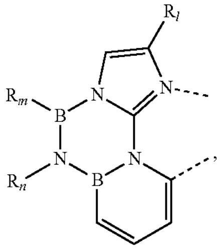 | For $L_A$39-(Rl)(Rm)(Rn), $L_A$39-(R1)(R1)(R1) to $L_A$30-(R134)(R134)(R134) have the structure, | 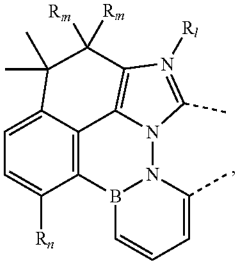 |
| For $L_A$20-(Rm)(Rn), $L_A$20-(R1)(R1) to $L_A$20-(R134)(R134) have the structure, | 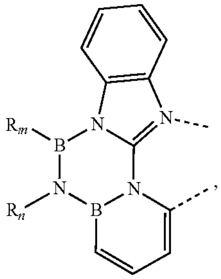 | | |

wherein R1 to R134 have the structures as defined as follows:

R1

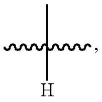

R2

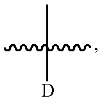

R3

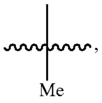

R4

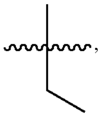

-continued

R5

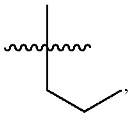

R6

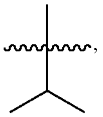

R7

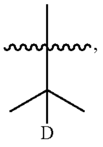

R8

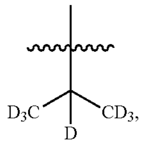

-continued
R9
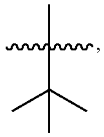
R10
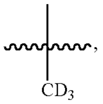
R11
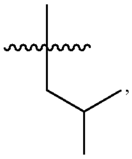
R12
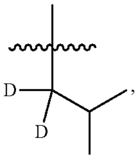
R13
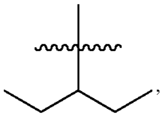
R14
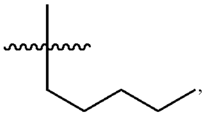
R15
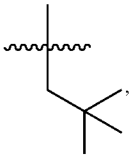
R16
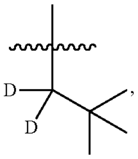
R17
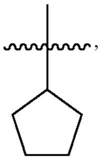
R18
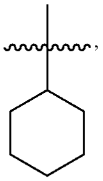
-continued
R19
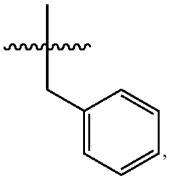
R20
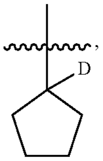
R21
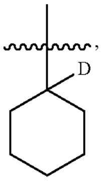
R22
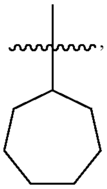
R23
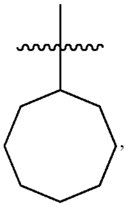
R24
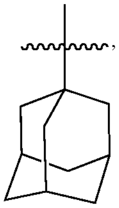
R25
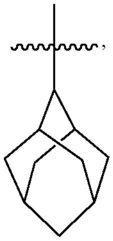
R26
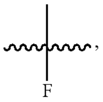

-continued
R27
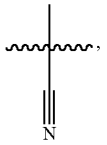
R28
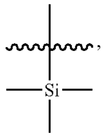
R29
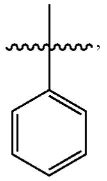
R30
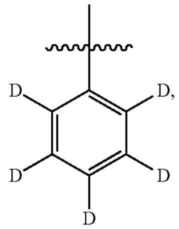
R31
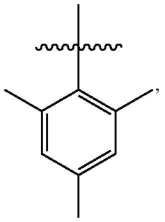
R32
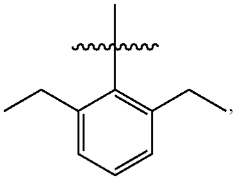
R33
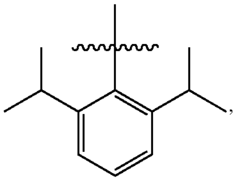
R34
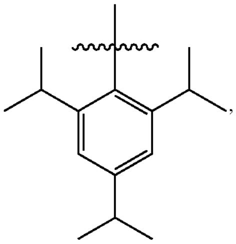
-continued
R35
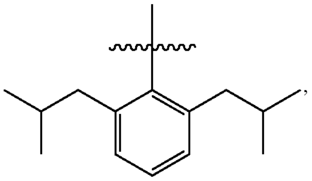
R36
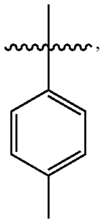
R37
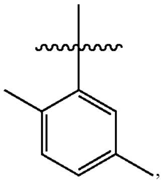
R38
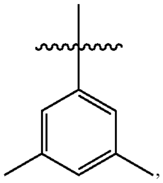
R39
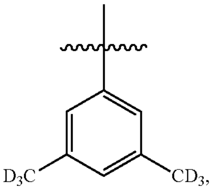
R40
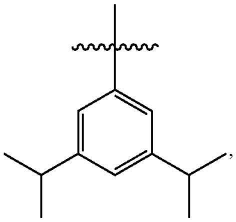
R41
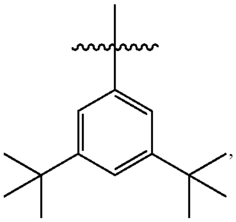

-continued
R42
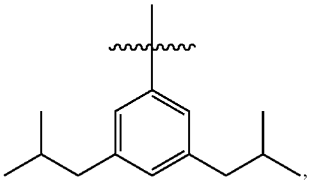
R43
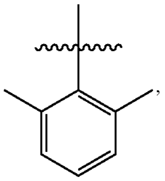
R44
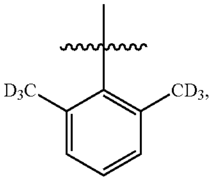
R45
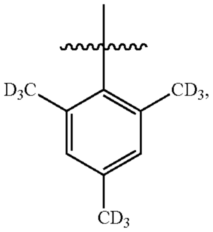
R46
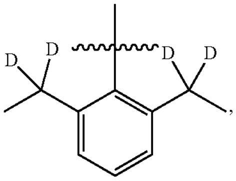
R47
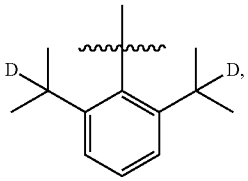
R48
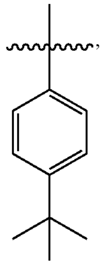
-continued
R49
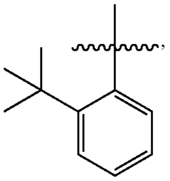
R50
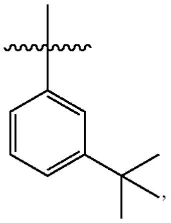
R51
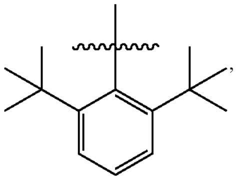
R52
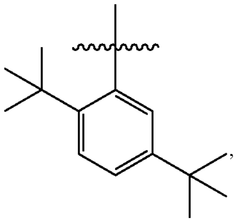
R53
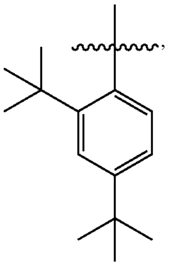
R54
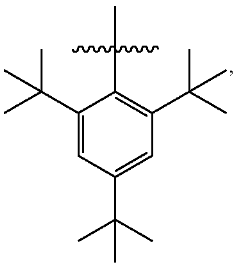
R55
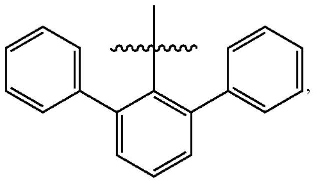

-continued
R56
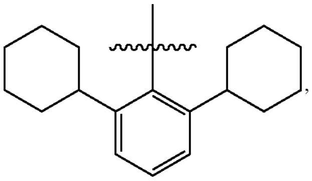
R57
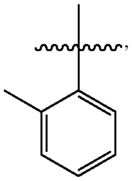
R58
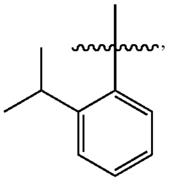
R59
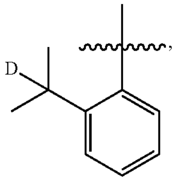
R60
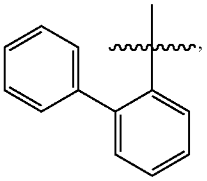
R61
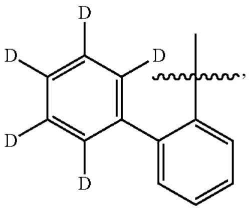
R62
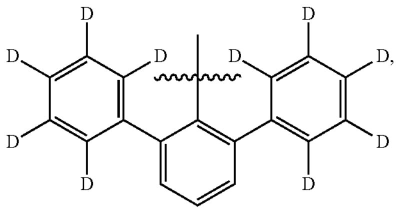
R63
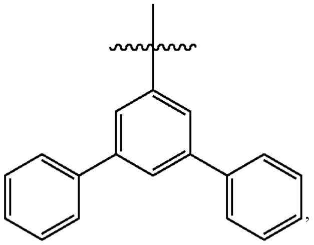
-continued
R64
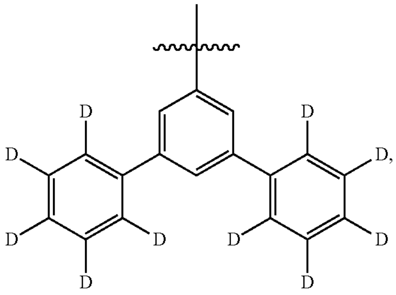
R65
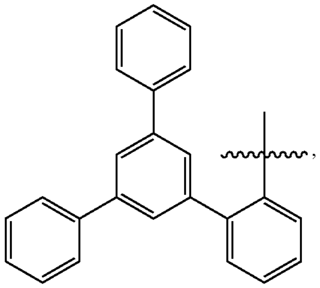
R66
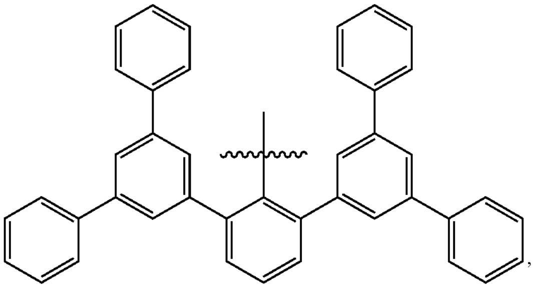
R67
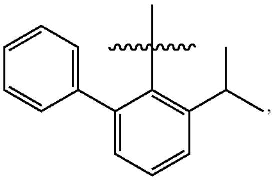
R68
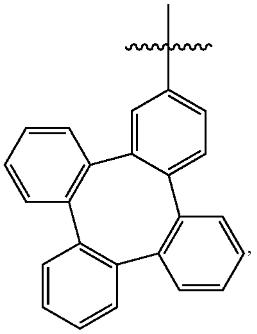

-continued
R69
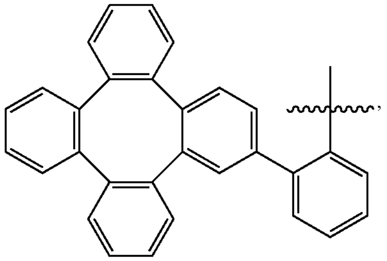
R70
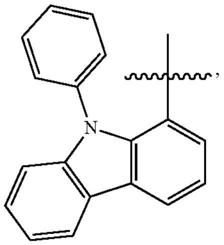
R71
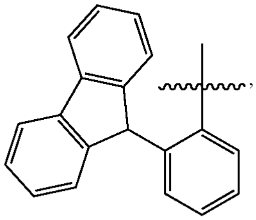
R72
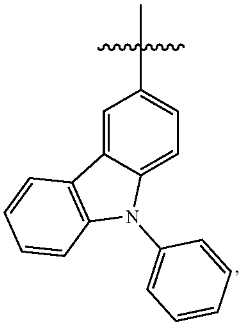
R73
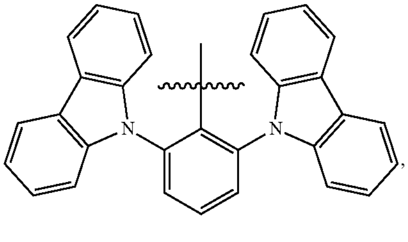
R74
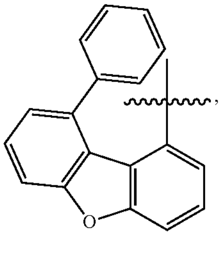
-continued
R75
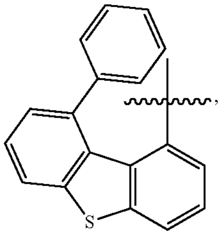
R76
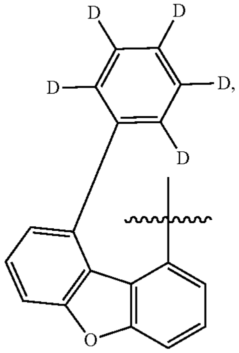
R77
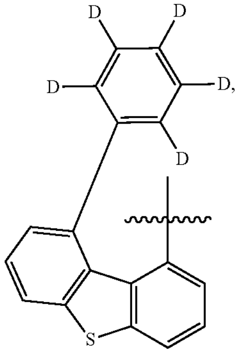
R78
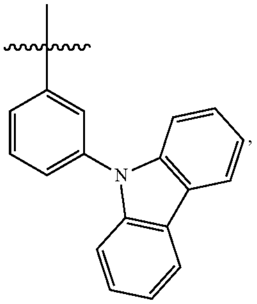
R79
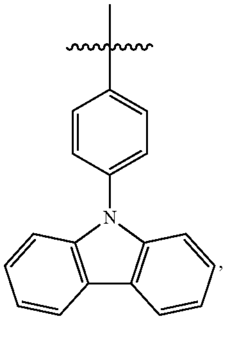

-continued
R80
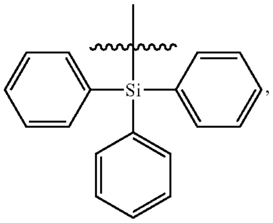
R81
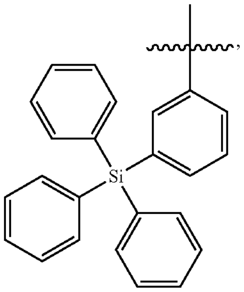
R82
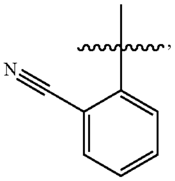
R83
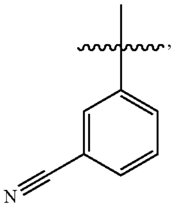
R84
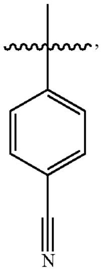
R85
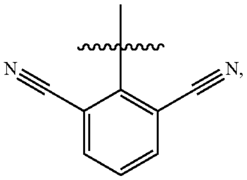
R86
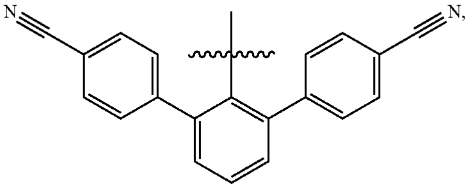
-continued
R87
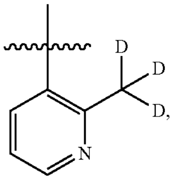
R88
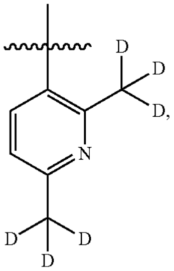
R89
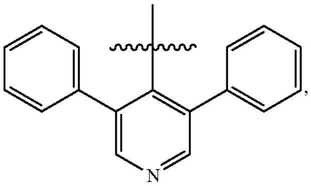
R90
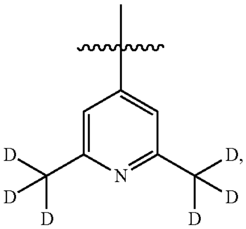
R91
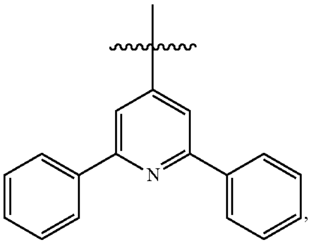
R92
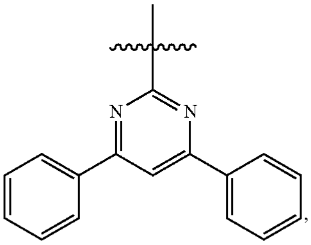

-continued
R93
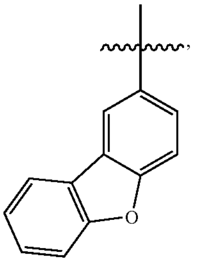
R94
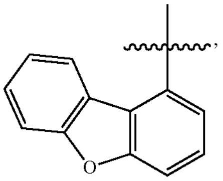
R95
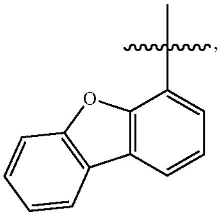
R96
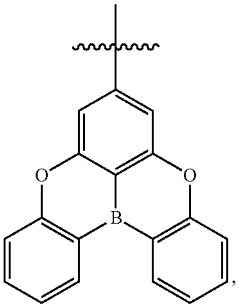
R97
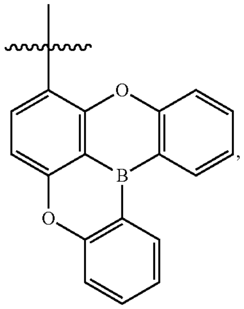
R98
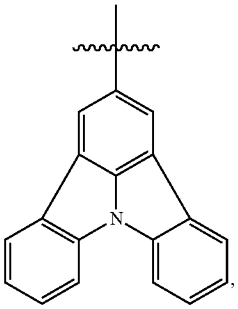
-continued
R99
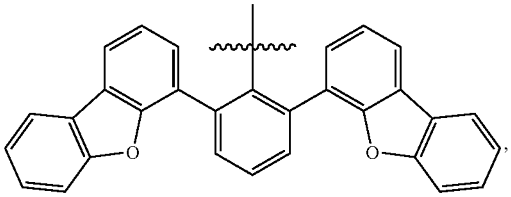
R100
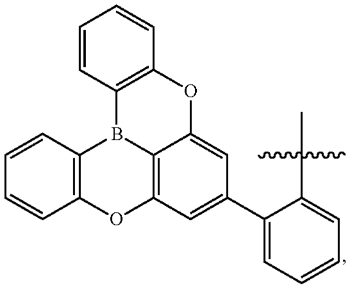
R101
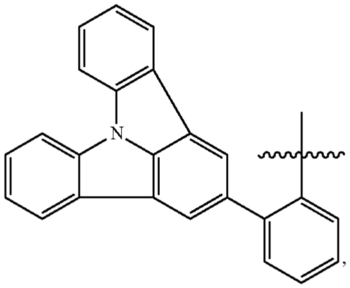
R102
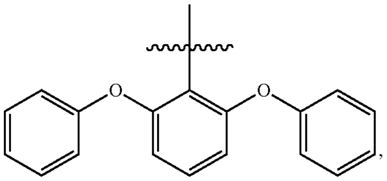
R103
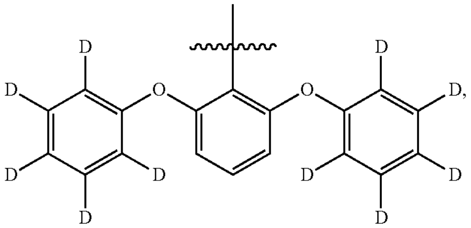
R104
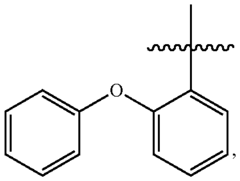

R105
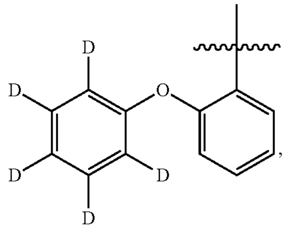
R106
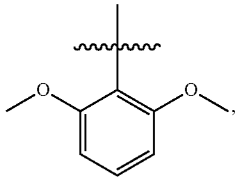
R107
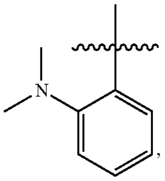
R108
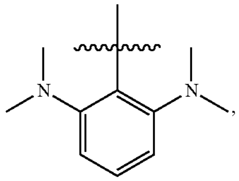
R109
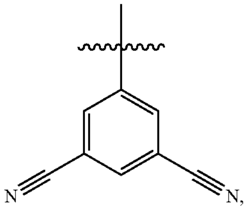
R110
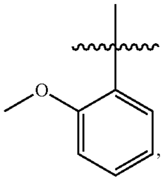
R111
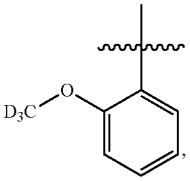
R112
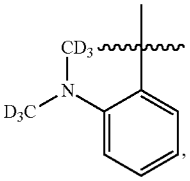
R113
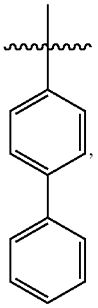
R114
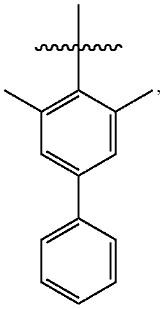
R115
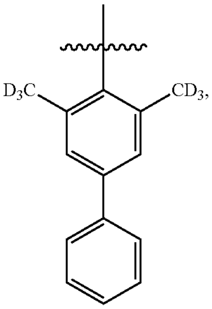
R116
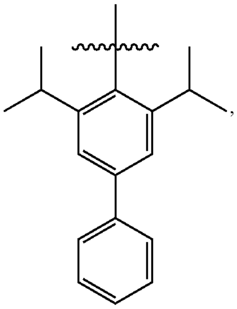
R117
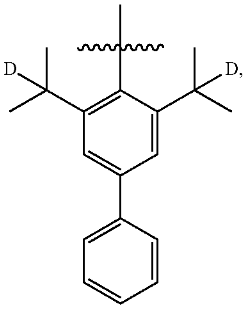

-continued
R118
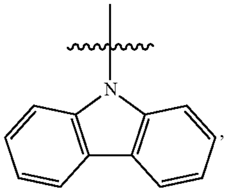
R119
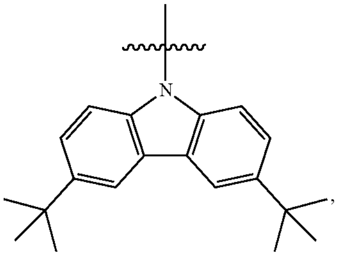
R120
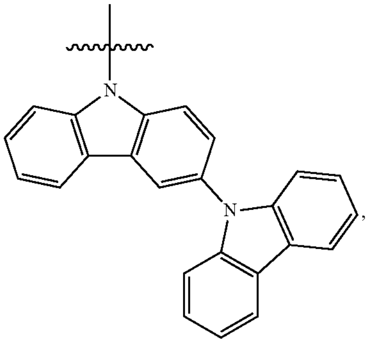
R121
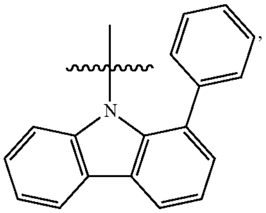
R122
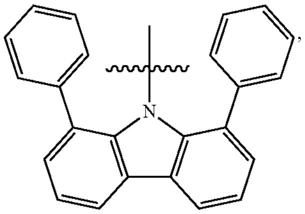
R123
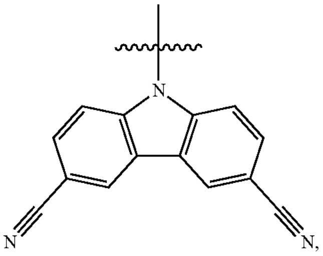
-continued
R124
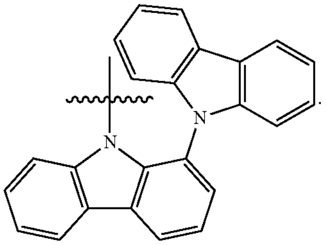
R125
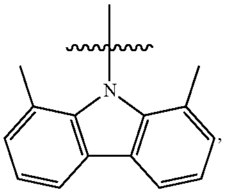
R126
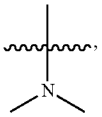
R127
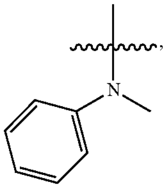
R128
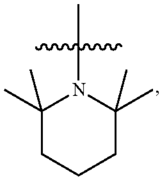
R129
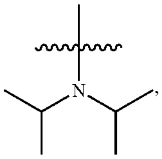
R130
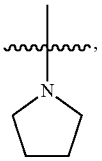
R131
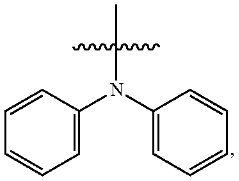

-continued

R132

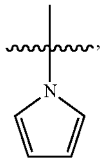

R133

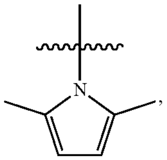

and

R134

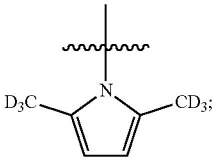

wherein $L_1$ through $L_5$ have the following structures:

L1

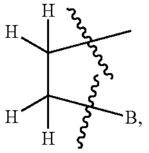

L2

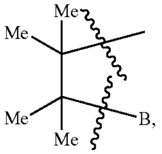

L3

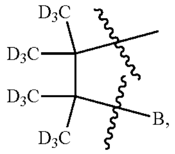

L4

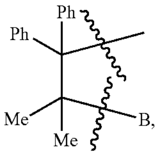

and

L5

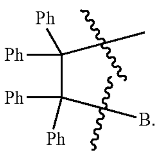

12. The compound of claim 1, wherein the compound has a formula of $M(L_A)_p(L_B)_q(L_C)_r$ wherein $L_B$ and $L_C$ are each a bidentate ligand; and wherein p is 1, 2, or 3; q is 0, 1, or 2; r is 0, 1, or 2; and p+q+r is the oxidation state of the metal M.

13. The compound of claim 12, wherein $L_B$ and $L_C$ are each independently selected from the group consisting of the structures as defined as follows:

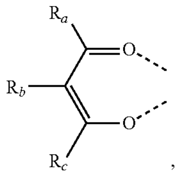

,

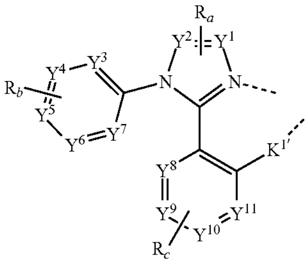

,

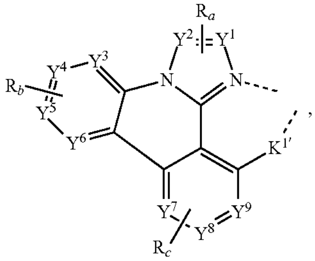

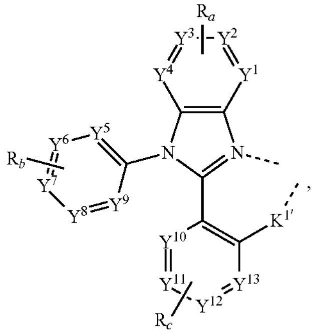

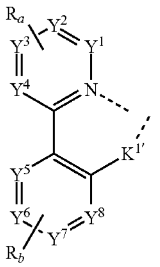

,

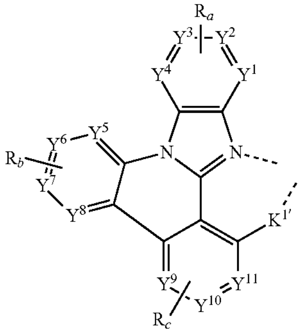

,

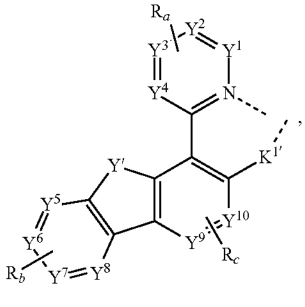

-continued
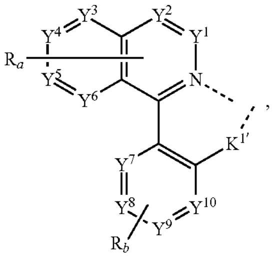
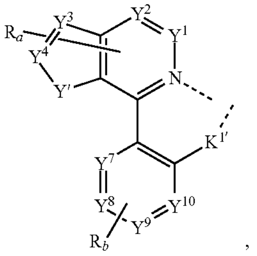
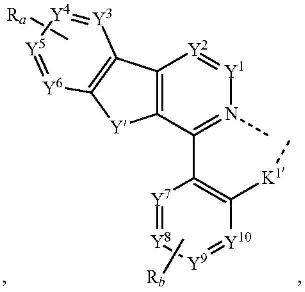
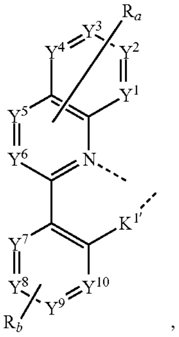
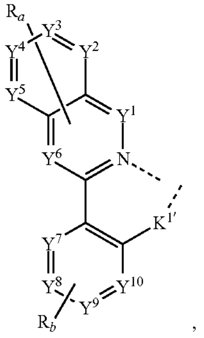
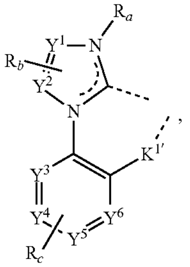
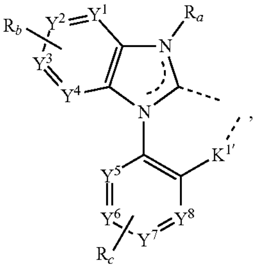
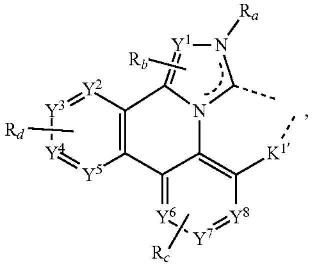
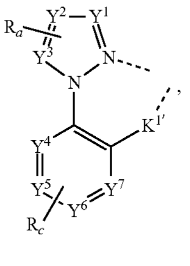
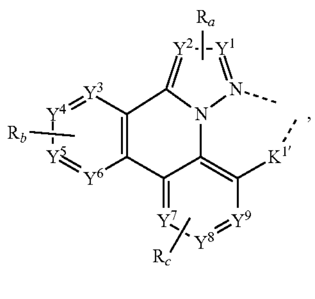
-continued
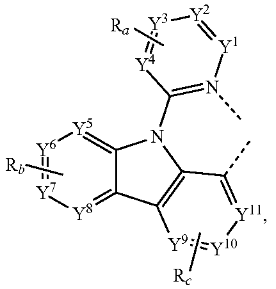
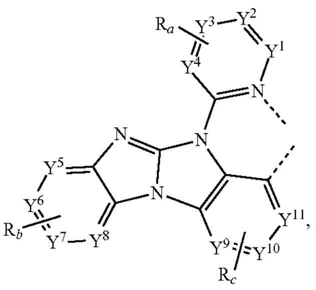
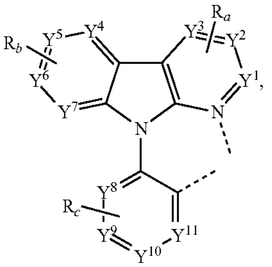
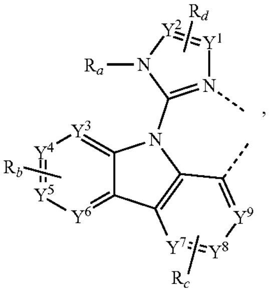
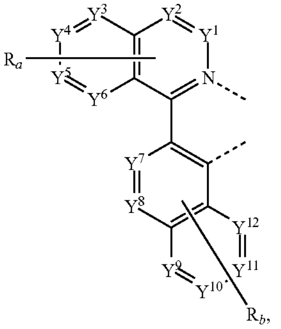
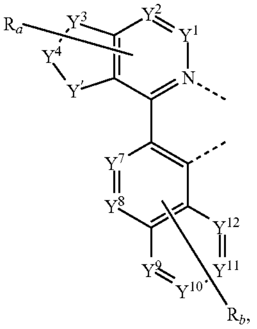
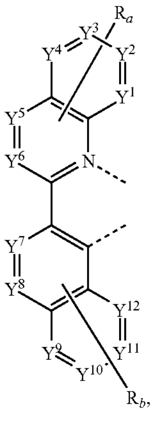
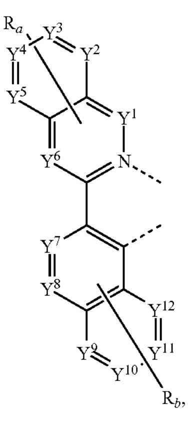

-continued

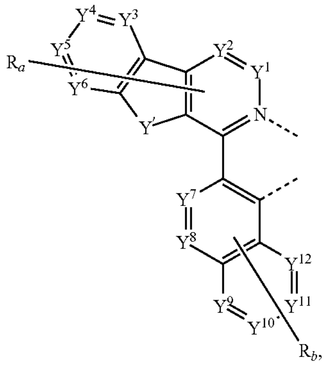

,

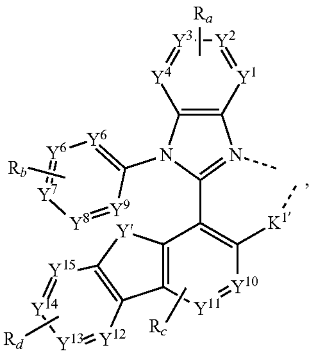

,

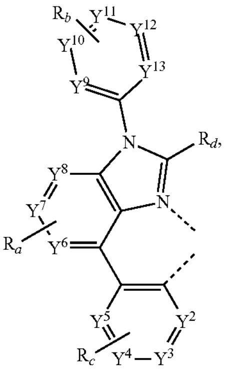

,

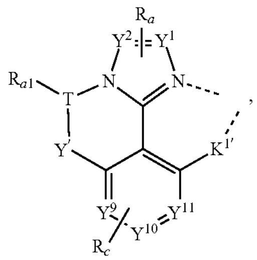

,

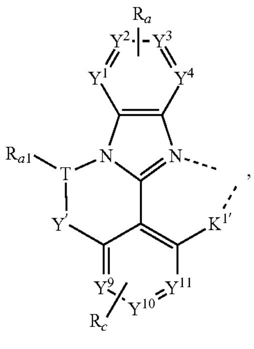

,

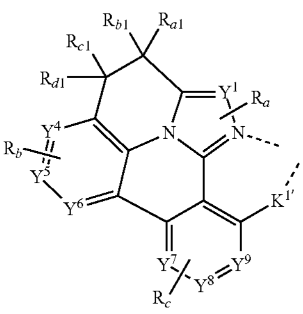

,

-continued

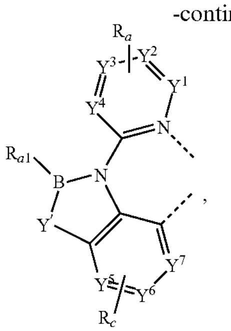

,

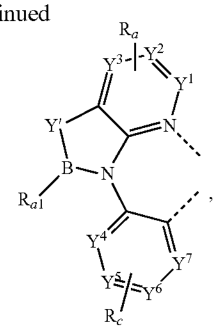

,

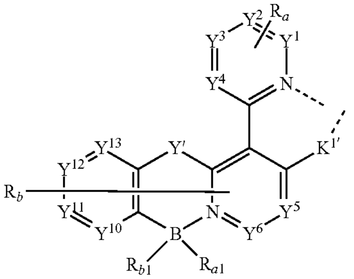

, and

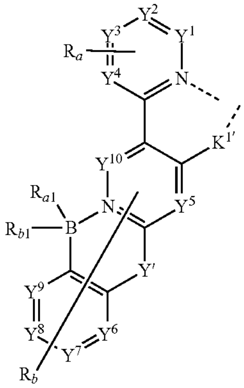

;

wherein:

T is selected from the group consisting of B, Al, Ga, and In;

wherein $K^{1'}$ is a direct bond or is selected from the group consisting of $NR_e$, $PR_e$, O, S, and Se;

each of $Y^1$ to $Y^{13}$ is independently selected from the group consisting of carbon and nitrogen;

Y' is selected from the group consisting of $BR_e$, $NR_e$, $PR_e$, O, S, Se, C═O, C═S, C═Se, C═$NR_e$, C═$CR_eR_f$, S═O, $SO_2$, $P(O)R_e$, $CR_eR_f$, $SiR_eR_f$, and $GeR_eR_f$;

$R_e$ and $R_f$ can be fused or joined to form a ring;

each $R_a$, $R_b$, $R_c$, and $R_d$ independently represent zero, mono, or up to a maximum allowed number of substitutions to its associated ring;

each of $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of deuterium, halide, alkyl, cycloalkyl, heteroalkyl, arylalkyl, alkoxy, aryloxy, amino, silyl, germyl, boryl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, selenyl, and combinations thereof; the general substituents defined herein; and any two adjacent $R_a$, $R_b$, $R_c$, $R_d$, $R_e$ and $R_f$ can be fused or joined to form a ring or form a multidentate ligand.

14. The compound of claim 12, wherein $L_A$ Can be selected from $L_{Ai}$, wherein i is an integer from 1 to 39; and $L_B$ can be selected from $L_{Bk}$, wherein k is an integer from 1 to 561, wherein:

when the compound has formula $Ir(L_{Ai})_3$, the compound is selected from the group consisting of $Ir(L_{A1})_3$ to $Ir(L_{A39})_3$;

when the compound has formula $Ir(L_{Ai})(L_{Bk})_2$, the compound is selected from the group consisting of $Ir(L_{A1})(L_{B1})_2$ to $Ir(L_{A39})(L_{B561})_2$;

when the compound has formula $Ir(L_{Ai})_2(L_{Bk})$, the compound is selected from the group consisting of $Ir(L_{A1})_2(L_{B1})$ to $Ir(L_{A39})_2(L_{B561})$;

when the compound has formula $Ir(L_{Ai})_2(L_{Cj-I})$, the compound is selected from the group consisting of $Ir(L_{A1})_2(L_{C1-I})$ to $Ir(L_{A39})_2(L_{C1416-I})$; and when the compound has formula $Ir(L_{Ai})_2(L_{Cj-II})$, the compound is selected from the group consisting of $Ir(L_{A1})_2(L_{C1-II})$ to $Ir(L_{A39})_2$ $(L_{C1416-II})$;

wherein the structures of each $L_{Ai}$ is defined in claim 11;

wherein each $L_{Bk}$ has the structure as defined as follows;

$L_{B1}$

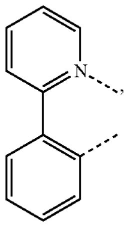

$L_{B2}$

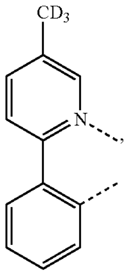

$L_{B3}$

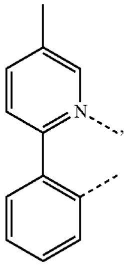

$L_{B4}$

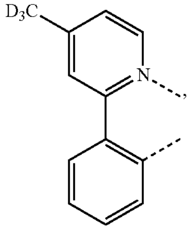

-continued $L_{B5}$

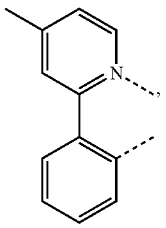

$L_{B6}$

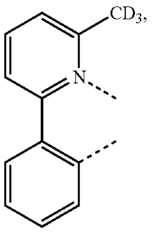

$L_{B7}$

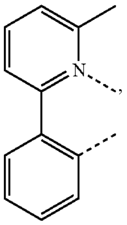

$L_{B8}$

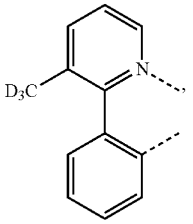

$L_{B9}$

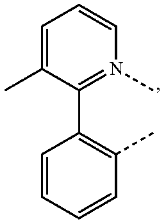

$L_{B10}$

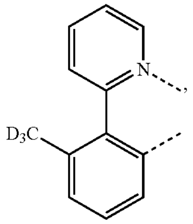

-continued
$L_{B11}$
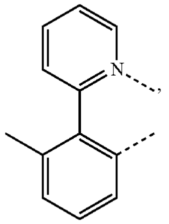
$L_{B12}$
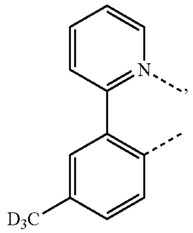
$L_{B13}$
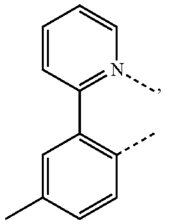
$L_{B14}$
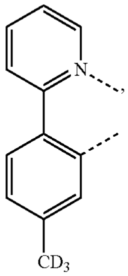
$L_{B15}$
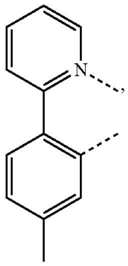
$L_{B16}$
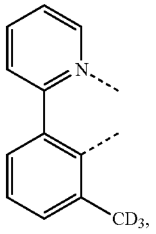
-continued
$L_{B17}$
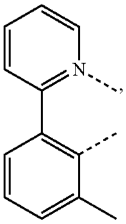
$L_{B18}$
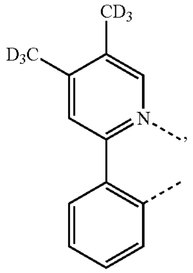
$L_{B19}$
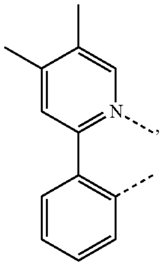
$L_{B20}$
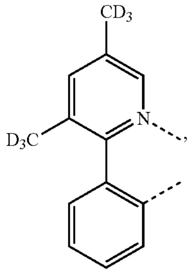
$L_{B21}$
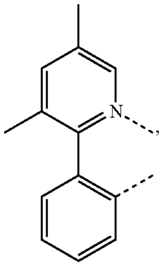
$L_{B22}$
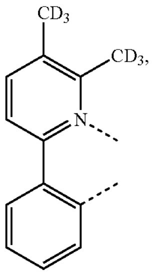

-continued
$L_{B23}$
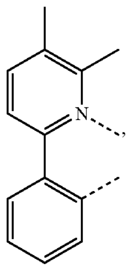
$L_{B24}$
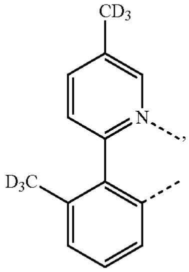
$L_{B25}$
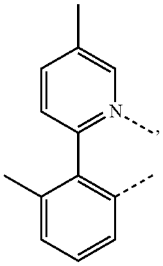
$L_{B26}$
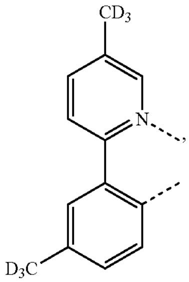
$L_{B27}$
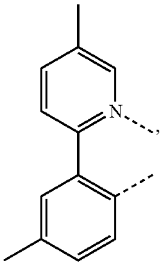
-continued
$L_{B28}$
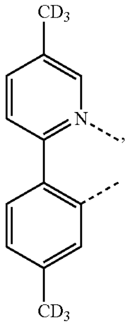
$L_{B29}$
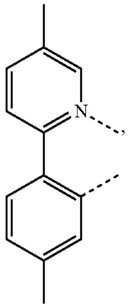
$L_{B30}$
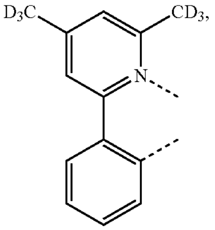
$L_{B31}$
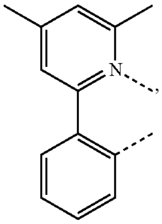
$L_{B32}$
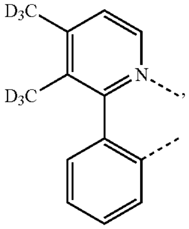
$L_{B33}$
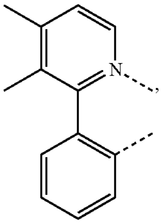

-continued
$L_{B34}$
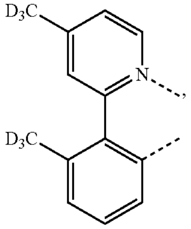
$L_{B35}$
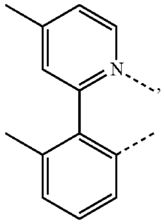
$L_{B36}$
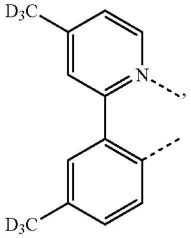
$L_{B37}$
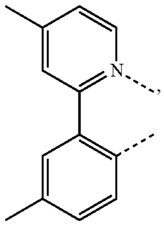
$L_{B38}$
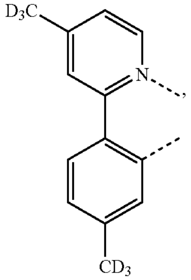
$L_{B39}$
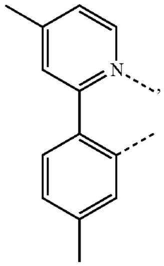
-continued
$L_{B40}$
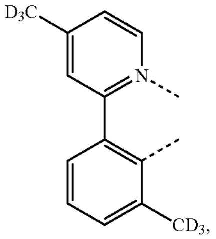
$L_{B41}$
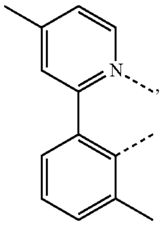
$L_{B42}$
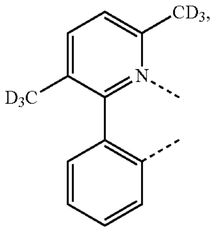
$L_{B43}$
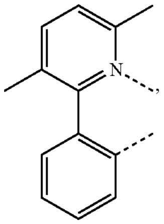
$L_{B44}$
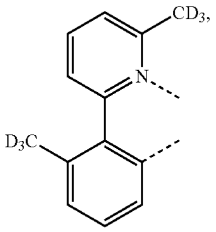
$L_{B45}$
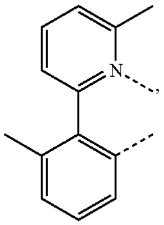

-continued
$L_{B46}$
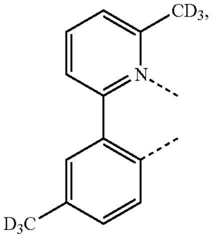
$L_{B47}$
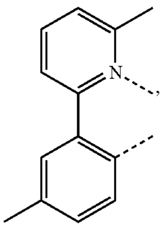
$L_{B48}$
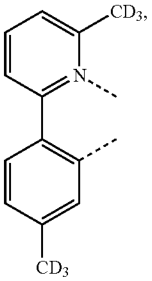
$L_{B49}$
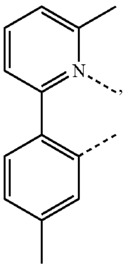
$L_{B50}$
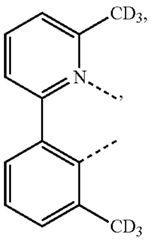
$L_{B51}$
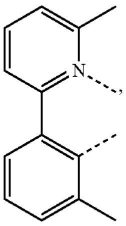
-continued
$L_{B52}$
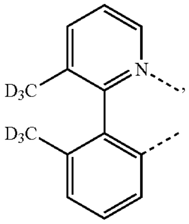
$L_{B53}$
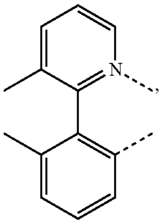
$L_{B54}$
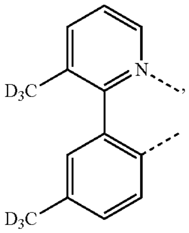
$L_{B55}$
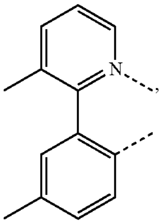
$L_{B56}$
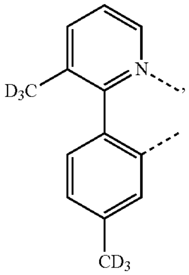
$L_{B57}$
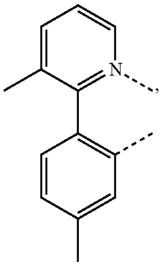

-continued
$L_{B58}$
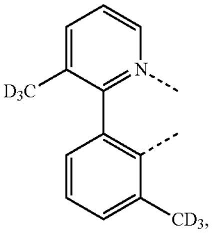
$L_{B59}$
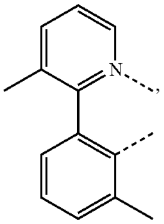
$L_{B60}$
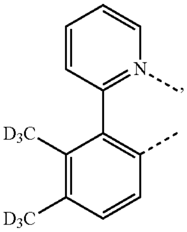
$L_{B61}$
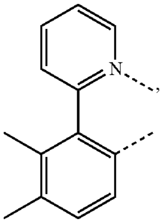
$L_{B62}$
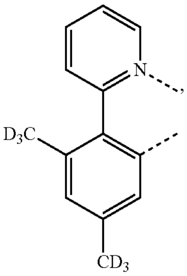
$L_{B63}$
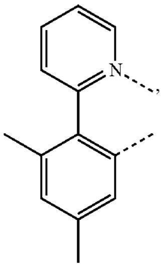
-continued
$L_{B64}$
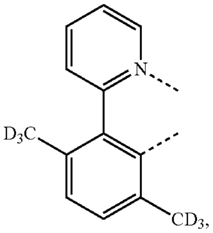
$L_{B65}$
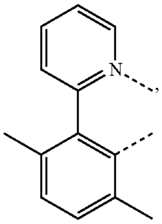
$L_{B66}$
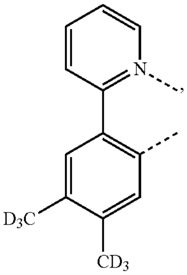
$L_{B67}$
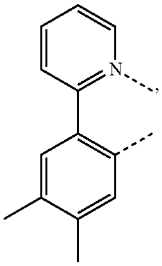
$L_{B68}$
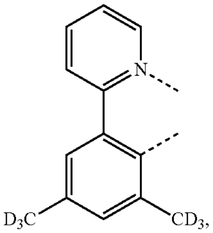
$L_{B69}$
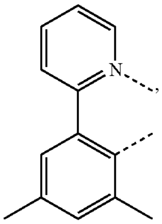

-continued
$L_{B70}$
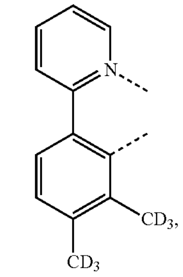
$L_{B71}$
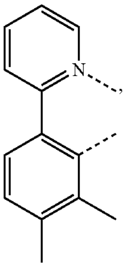
$L_{B72}$
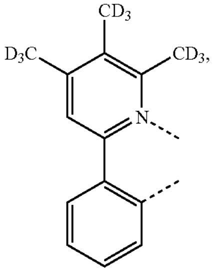
$L_{B73}$
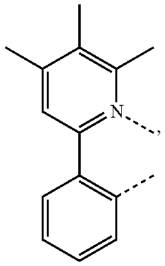
$L_{B74}$
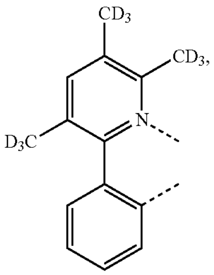
-continued
$L_{B75}$
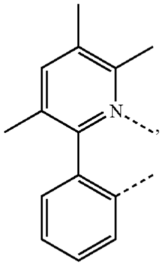
$L_{B76}$
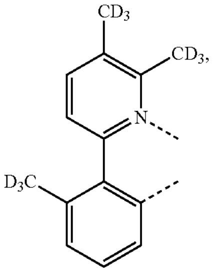
$L_{B77}$
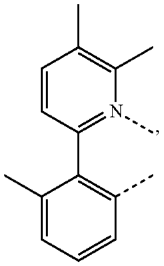
$L_{B78}$
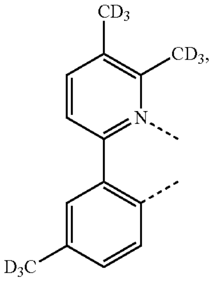
$L_{B79}$
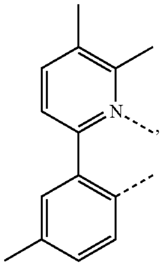

-continued
$L_{B80}$
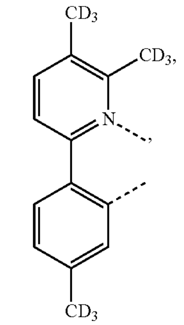
$L_{B81}$
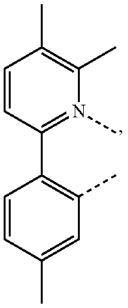
$L_{B82}$
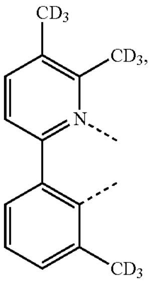
$L_{B83}$
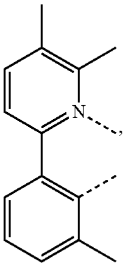
$L_{B84}$
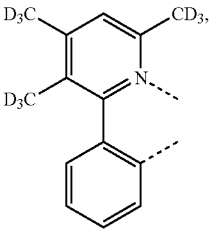
-continued
$L_{B85}$
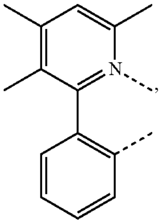
$L_{B86}$
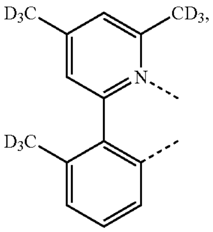
$L_{B87}$
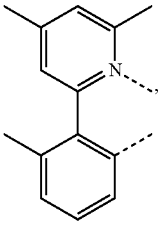
$L_{B88}$
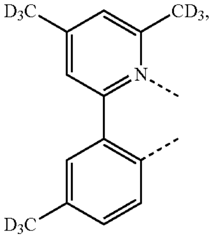
$L_{B89}$
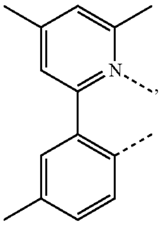
$L_{B90}$
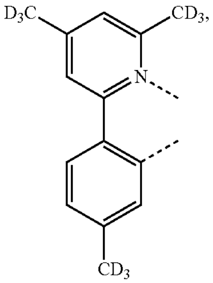

-continued
$L_{B91}$
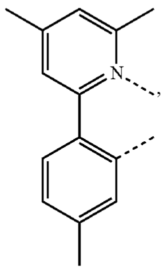
$L_{B92}$
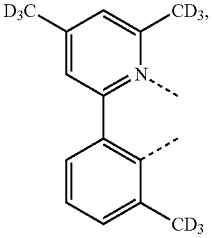
$L_{B93}$
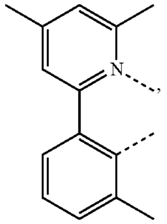
$L_{B94}$
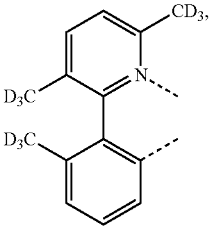
$L_{B95}$
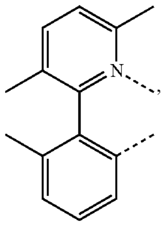
$L_{B96}$
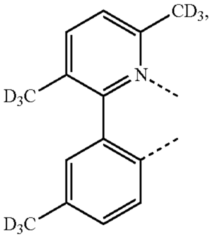
-continued
$L_{B97}$
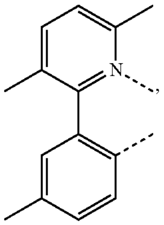
$L_{B98}$
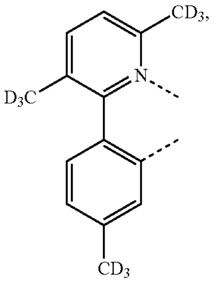
$L_{B99}$
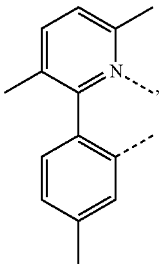
$L_{B100}$
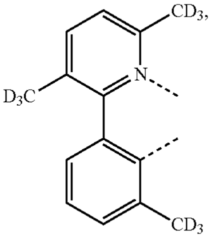
$L_{B101}$
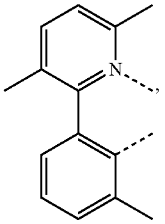
$L_{B102}$
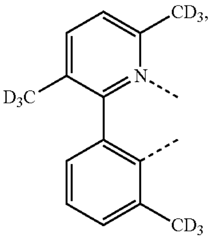

-continued
$L_{B103}$
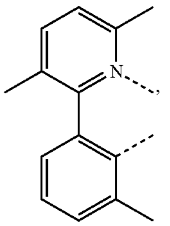
$L_{B104}$
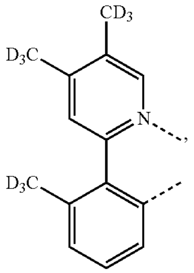
$L_{B105}$
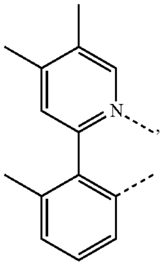
$L_{B106}$
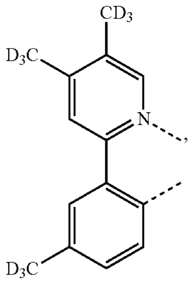
$L_{B107}$
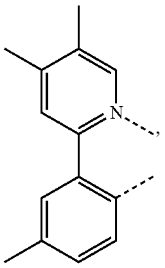
-continued
$L_{B108}$
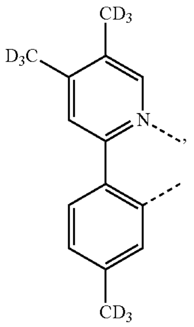
$L_{B109}$
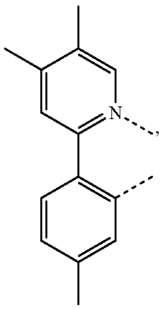
$L_{B110}$
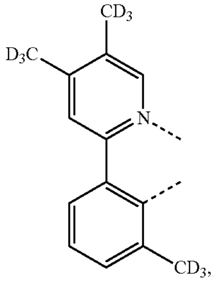
$L_{B111}$
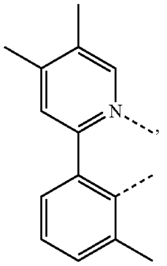
$L_{B112}$
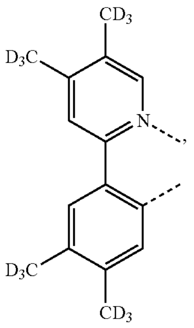

-continued
$L_{B113}$
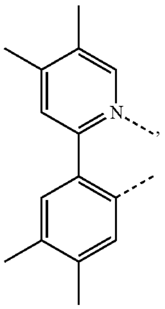
$L_{B114}$
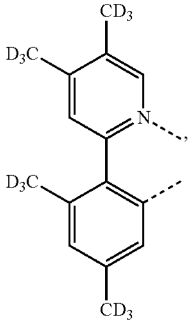
$L_{B115}$
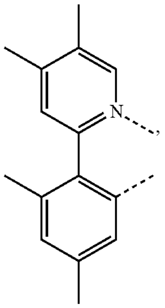
$L_{B116}$
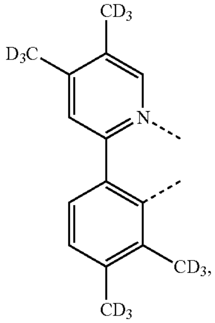
$L_{B117}$
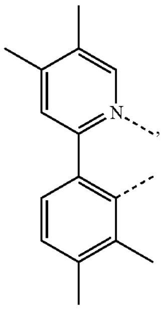
-continued
$L_{B118}$
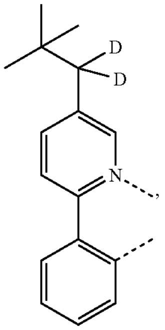
$L_{B119}$
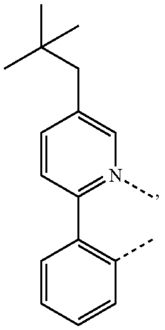
$L_{B120}$
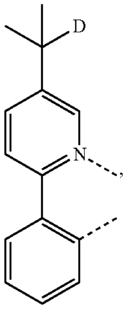
$L_{B121}$
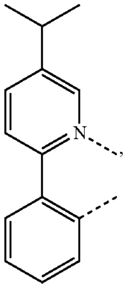
$L_{B122}$
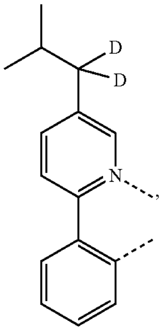

-continued
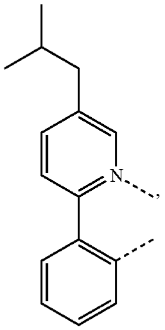
$L_{B123}$
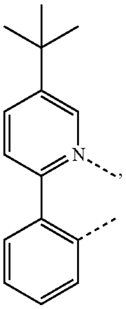
$L_{B124}$
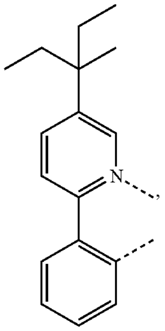
$L_{B125}$
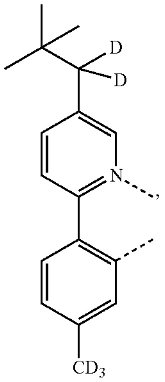
$L_{B126}$
-continued
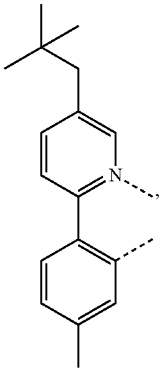
$L_{B127}$
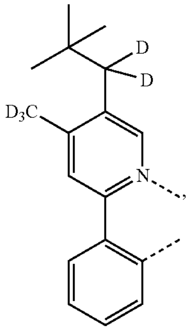
$L_{B128}$
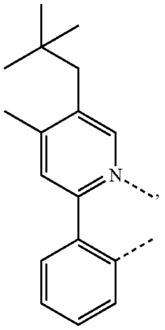
$L_{B129}$
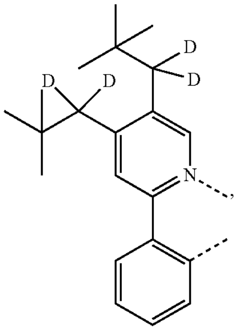
$L_{B130}$ -continued
$L_{B131}$
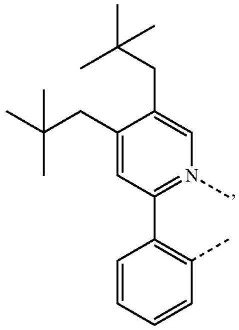
$L_{B132}$
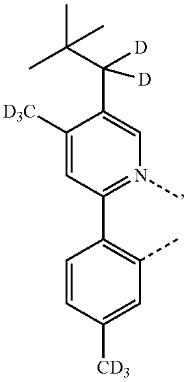
$L_{B133}$
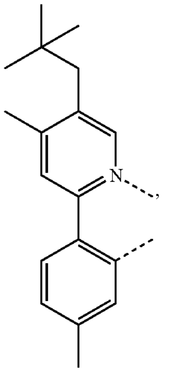
$L_{B134}$
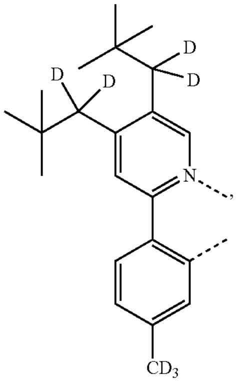
-continued
$L_{B135}$
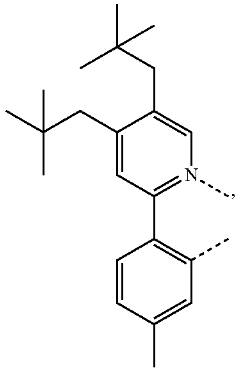
$L_{B136}$
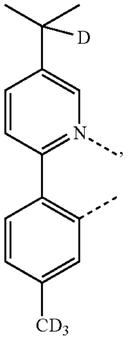
$L_{B137}$
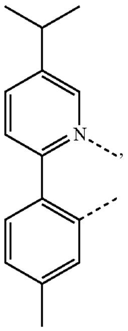
$L_{B138}$
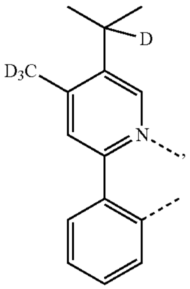

-continued
$L_{B139}$
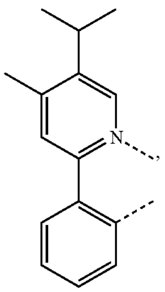
$L_{B140}$
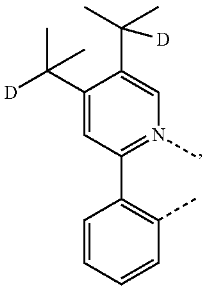
$L_{B141}$
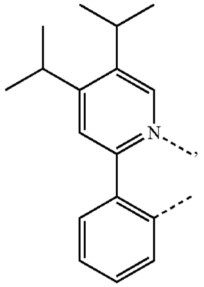
$L_{B142}$
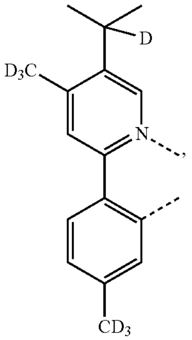
$L_{B143}$
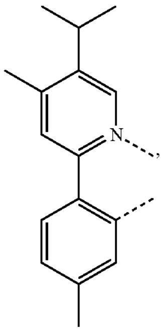
-continued
$L_{B144}$
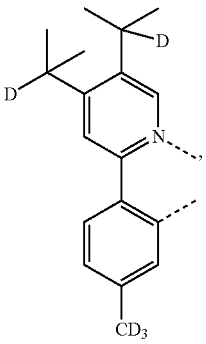
$L_{B145}$
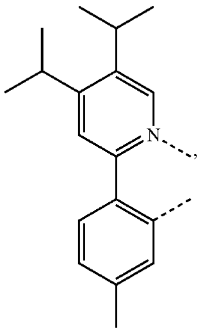
$L_{B146}$
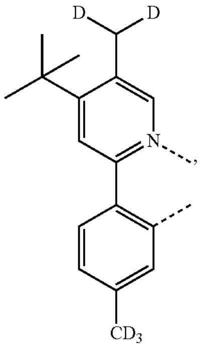
$L_{B147}$
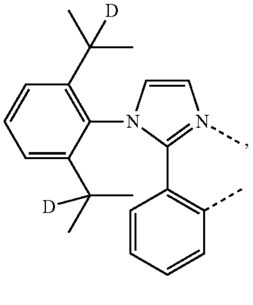
$L_{B148}$
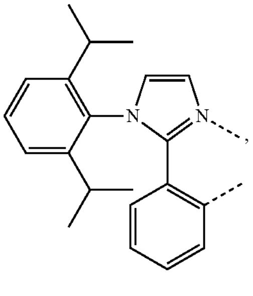

-continued
$L_{B149}$
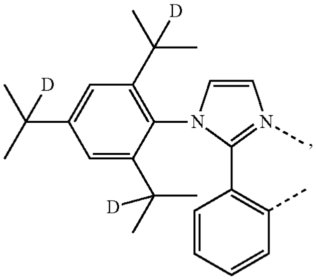
$L_{B150}$
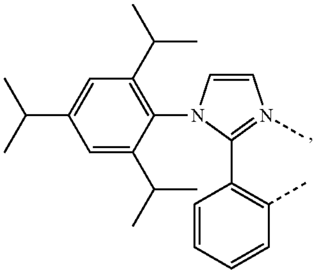
$L_{B151}$
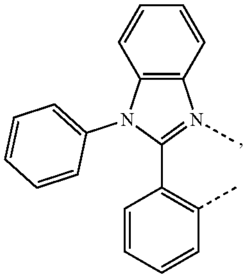
$L_{B152}$
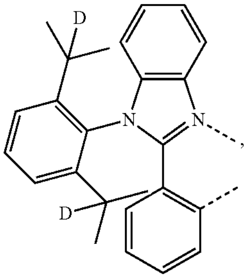
$L_{B153}$
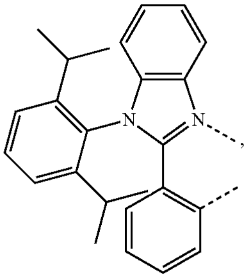
-continued
$L_{B154}$
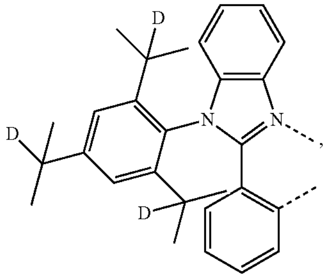
$L_{B155}$
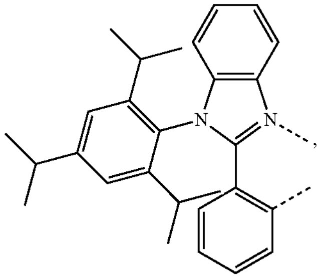
$L_{B156}$
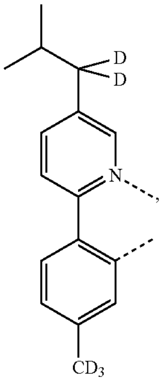
$L_{B157}$
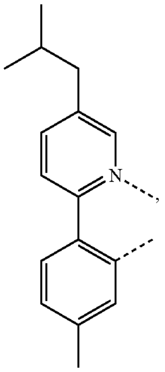

-continued
$L_{B158}$
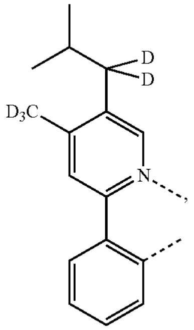
$L_{B159}$
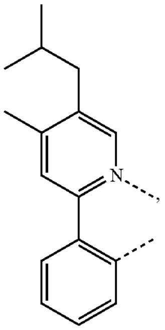
$L_{B160}$
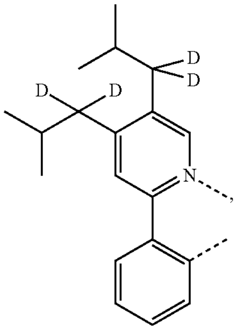
$L_{B161}$
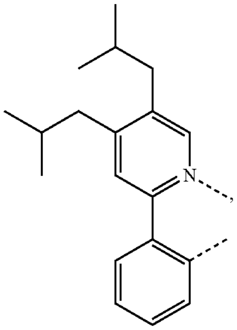
-continued
$L_{B162}$
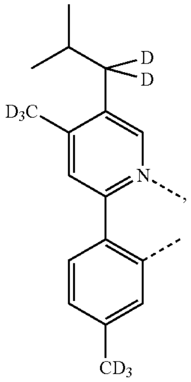
$L_{B163}$
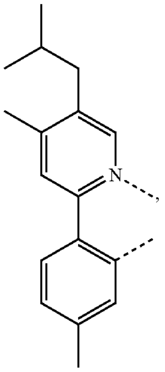
$L_{B164}$
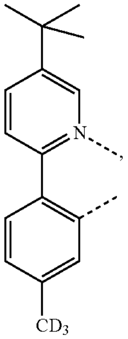
$L_{B165}$
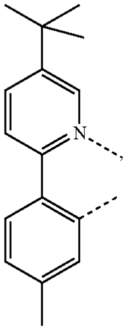

-continued
$L_{B166}$
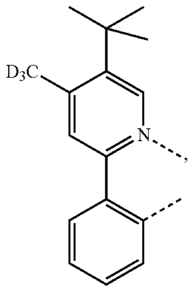
$L_{B167}$
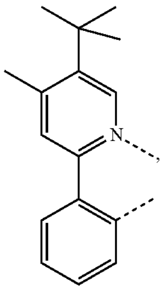
$L_{B168}$
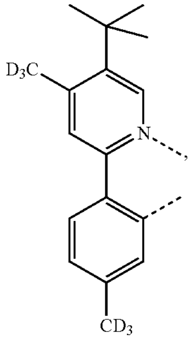
$L_{B169}$
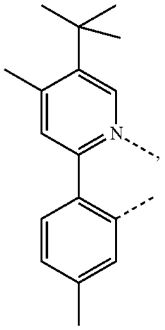
-continued
$L_{B170}$
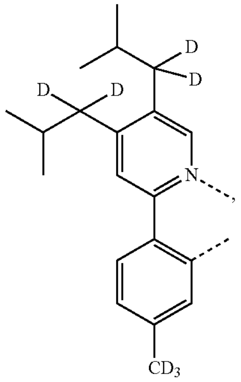
$L_{B171}$
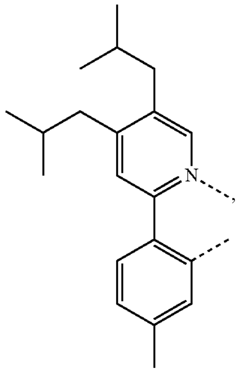
$L_{B172}$
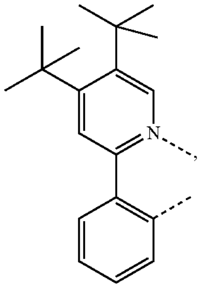
$L_{B173}$
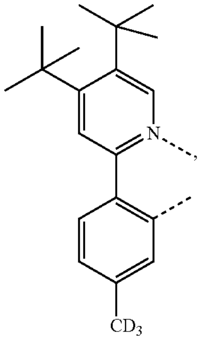

-continued
$L_{B174}$
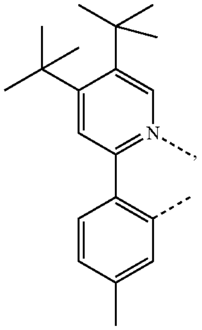
$L_{B175}$
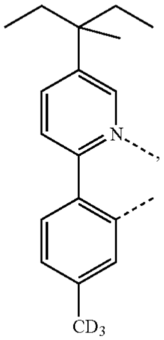
$L_{B176}$
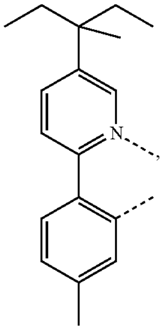
$L_{B177}$
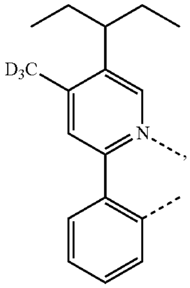
$L_{B178}$
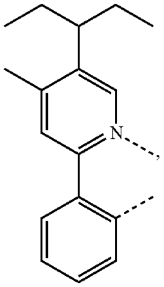
-continued
$L_{B179}$
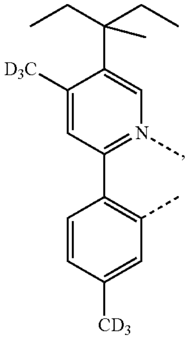
$L_{B180}$
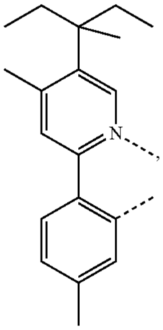
$L_{B181}$
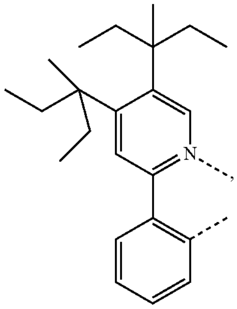
$L_{B182}$
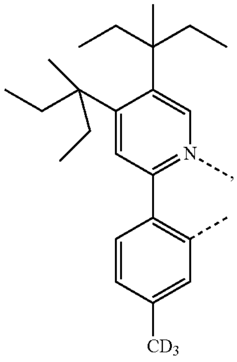

-continued
$L_{B183}$
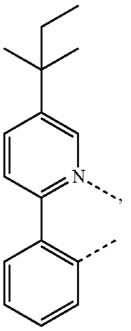
$L_{B184}$
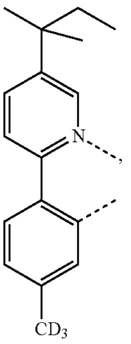
$L_{B185}$
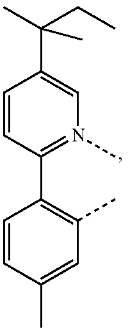
$L_{B186}$
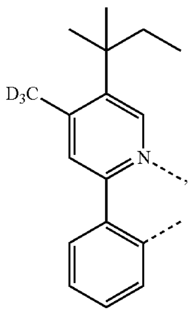
-continued
$L_{B187}$
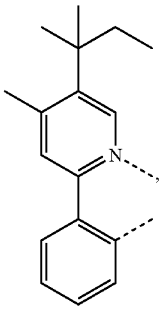
$L_{B188}$
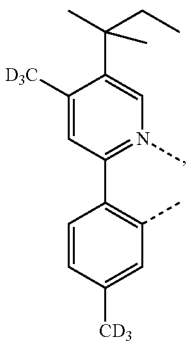
$L_{B189}$
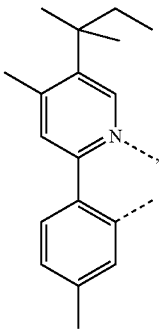
$L_{B190}$
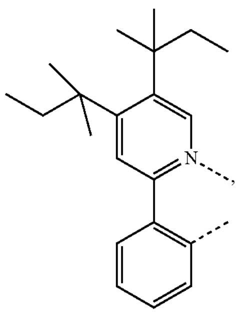

-continued
$L_{B191}$
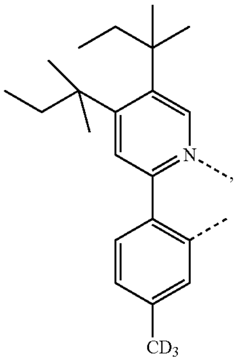
$L_{B192}$
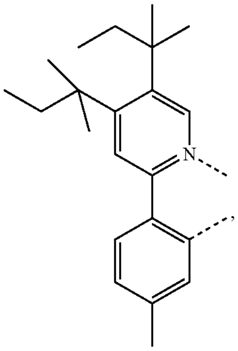
$L_{B193}$
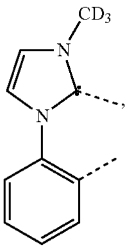
$L_{B194}$
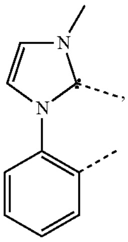
$L_{B195}$
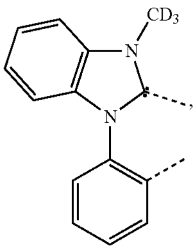
-continued
$L_{B196}$
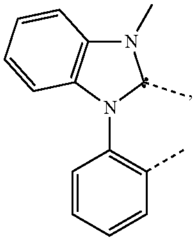
$L_{B197}$
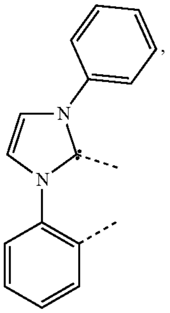
$L_{B198}$
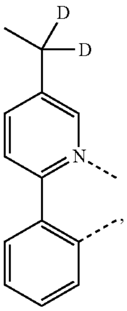
$L_{B199}$
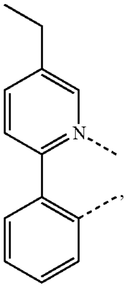
$L_{B200}$
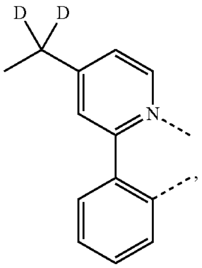

-continued
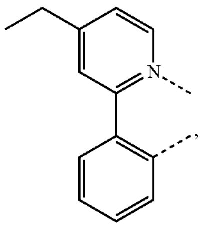
$L_{B201}$
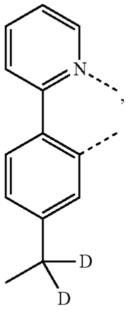
$L_{B202}$
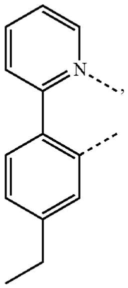
$L_{B203}$
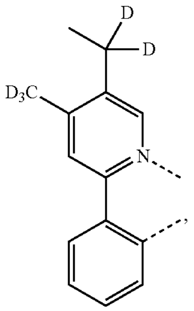
$L_{B204}$
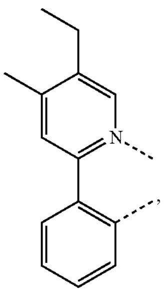
$L_{B205}$
-continued
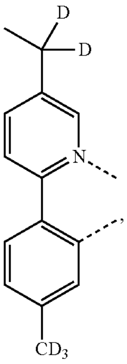
$L_{B206}$
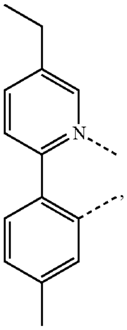
$L_{B207}$
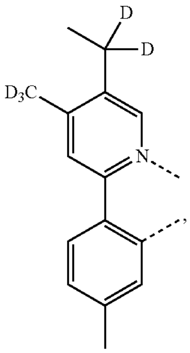
$L_{B208}$
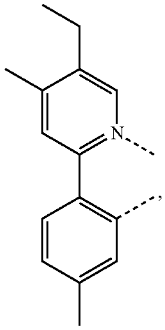
$L_{B209}$ -continued
$L_{B210}$
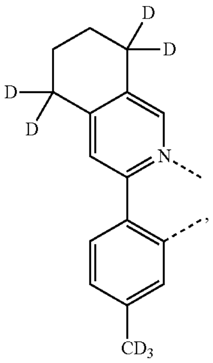
$L_{B211}$
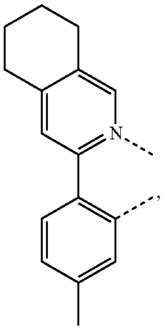
$L_{B212}$
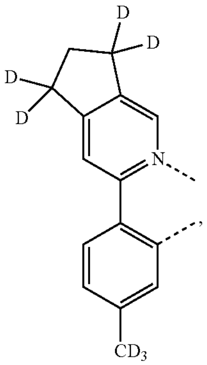
$L_{B213}$
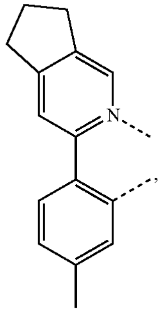
-continued
$L_{B214}$
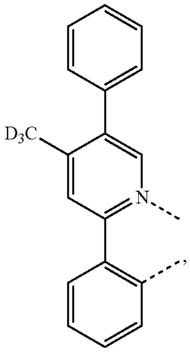
$L_{B215}$
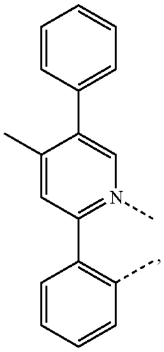
$L_{B216}$
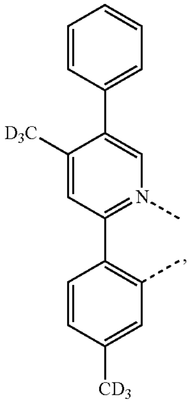
$L_{B217}$
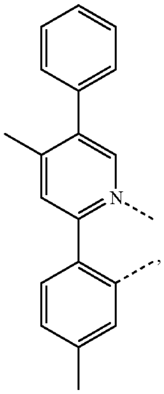

-continued
$L_{B218}$
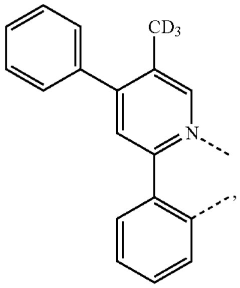
$L_{B219}$
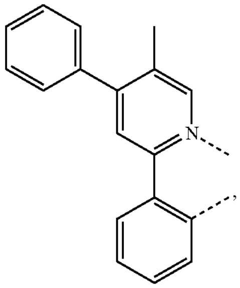
$L_{B220}$
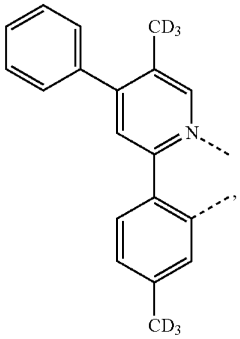
$L_{B221}$
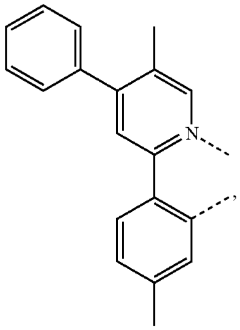
-continued
$L_{B222}$
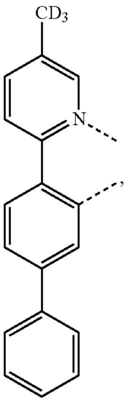
$L_{B223}$
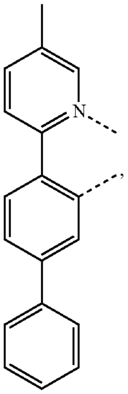
$L_{B224}$
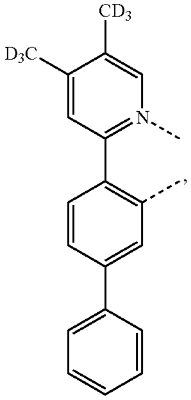
$L_{B225}$
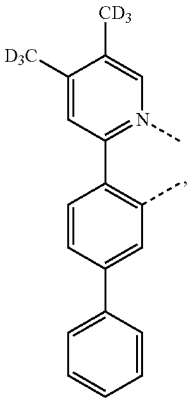

-continued
$L_{B226}$
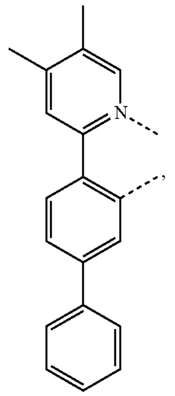
$L_{B227}$
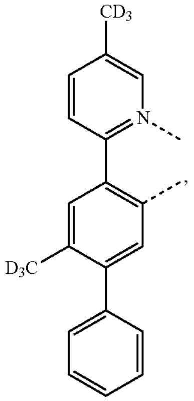
$L_{B228}$
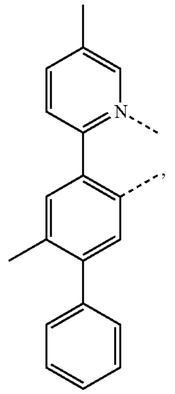
$L_{B229}$
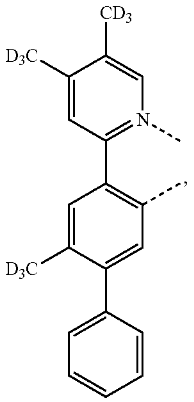
-continued
$L_{B230}$
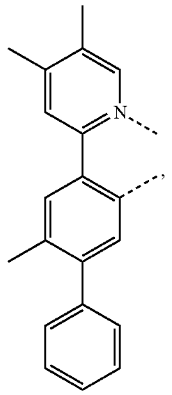
$L_{B231}$
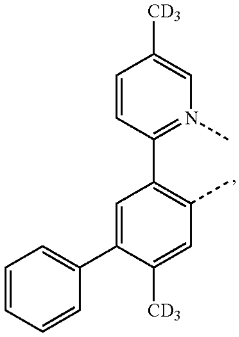
$L_{B232}$
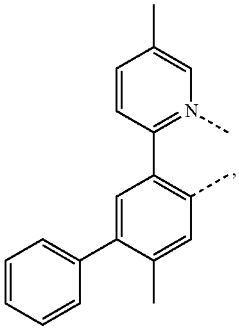
$L_{B233}$
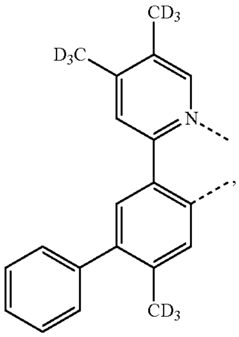

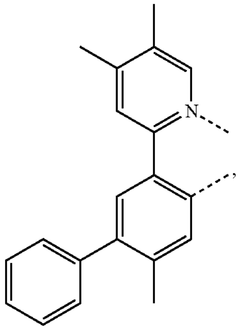
$L_{B234}$
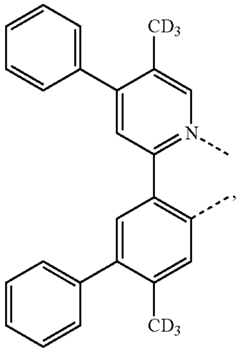
$L_{B235}$
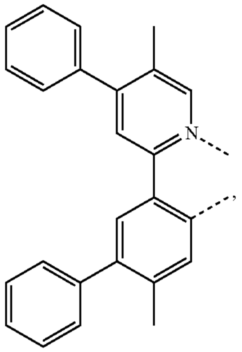
$L_{B236}$
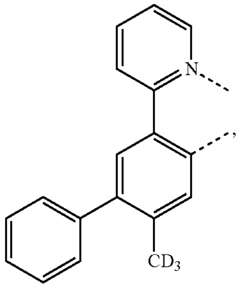
$L_{B237}$
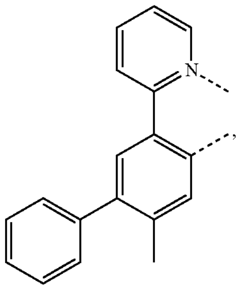
$L_{B238}$
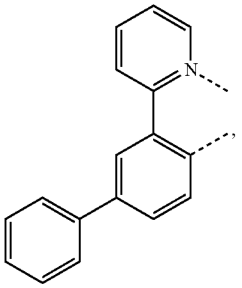
$L_{B239}$
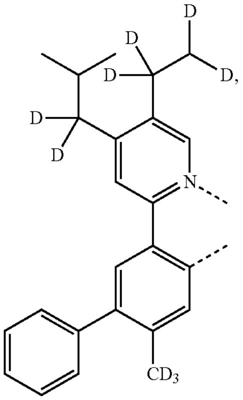
$L_{B240}$
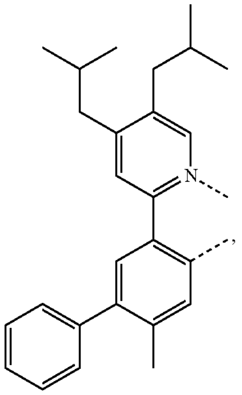
$L_{B241}$
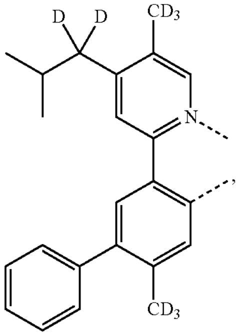
$L_{B242}$ -continued
$L_{B243}$
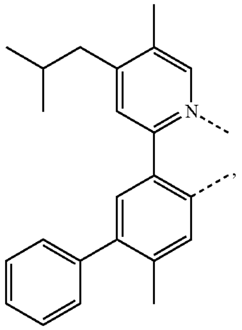
$L_{B244}$
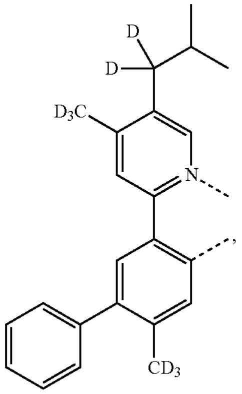
$L_{B245}$
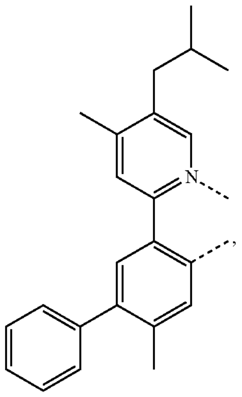
$L_{B246}$
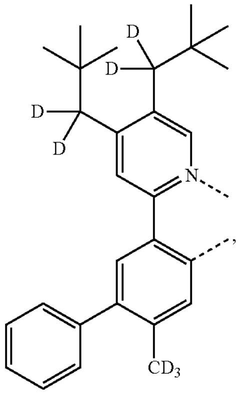
-continued
$L_{B247}$
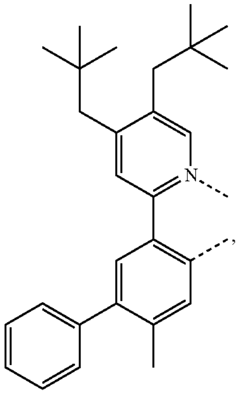
$L_{B248}$
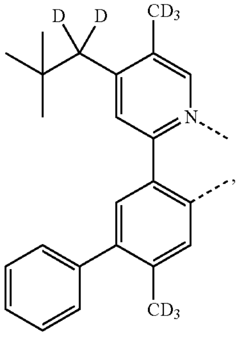
$L_{B249}$
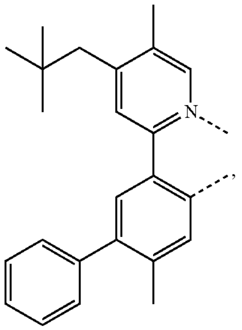
$L_{B250}$
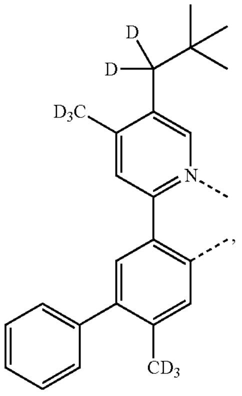

-continued
$L_{B251}$
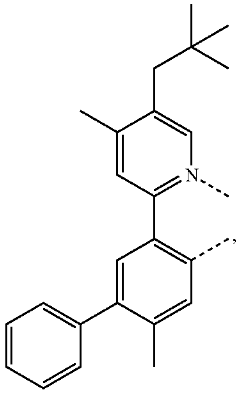
$L_{B252}$
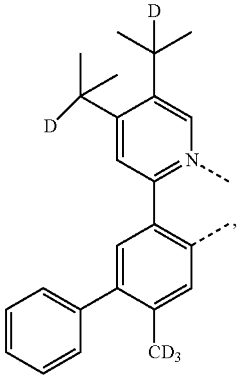
$L_{B253}$
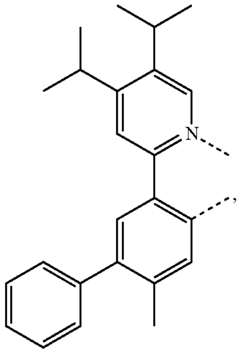
$L_{B254}$
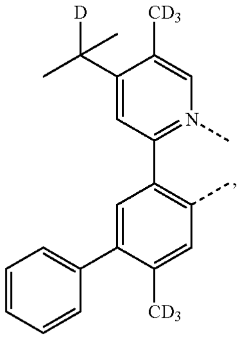
-continued
$L_{B255}$
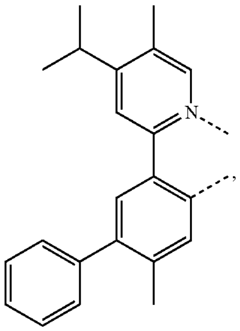
$L_{B256}$
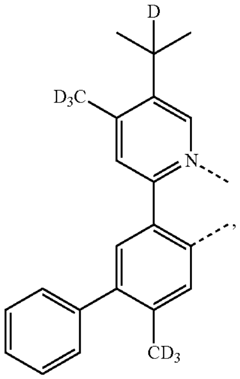
$L_{B257}$
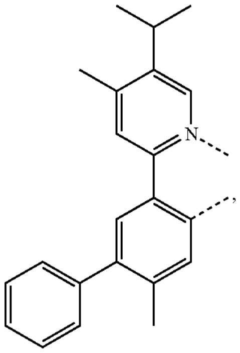
$L_{B258}$
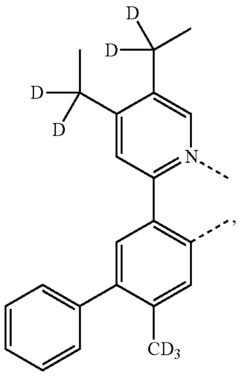

-continued
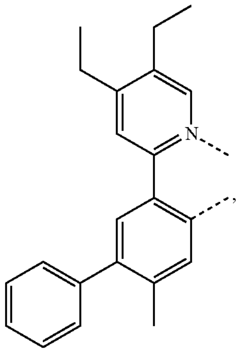
$L_{B259}$
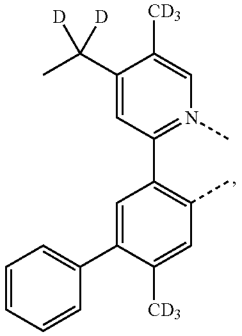
$L_{B260}$
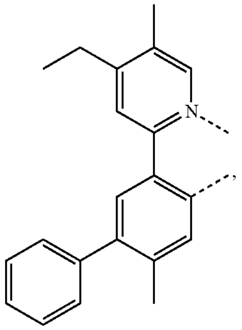
$L_{B261}$
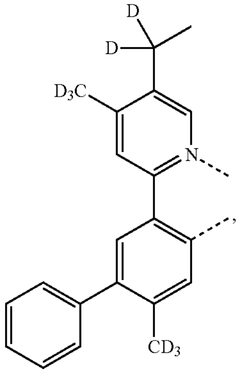
$L_{B262}$
-continued
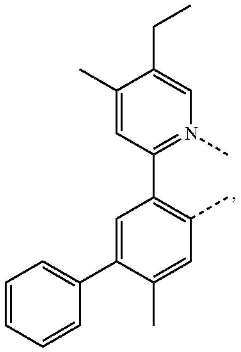
$L_{B263}$
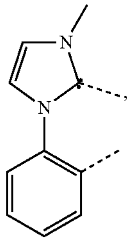
$L_{B264}$
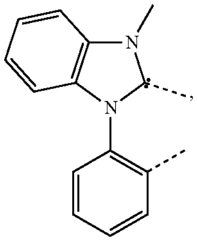
$L_{B265}$
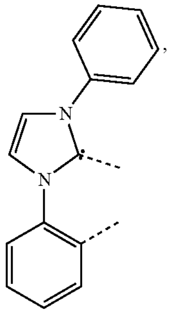
$L_{B266}$
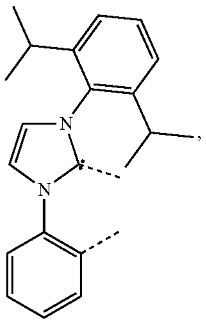
$L_{B267}$ -continued
$L_{B268}$
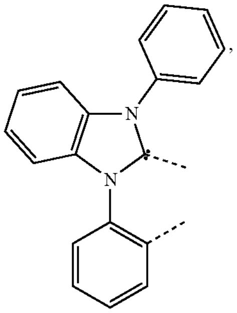
$L_{B269}$
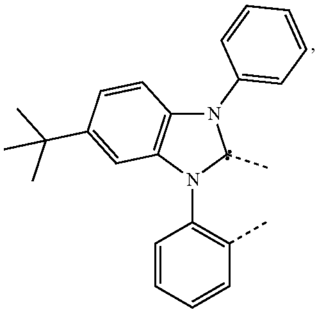
$L_{B270}$
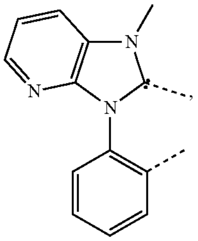
$L_{B271}$
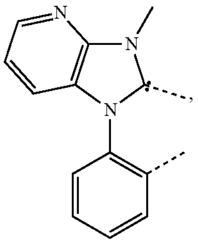
$L_{B272}$
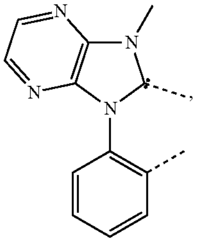
-continued
$L_{B273}$
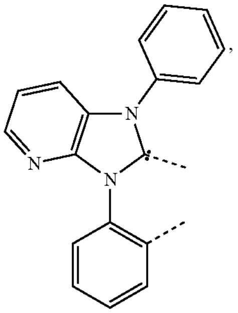
$L_{B274}$
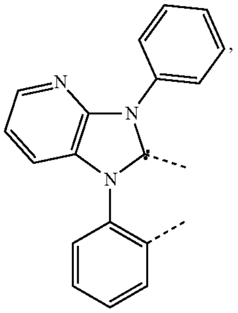
$L_{B275}$
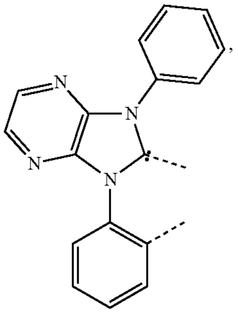
$L_{B276}$
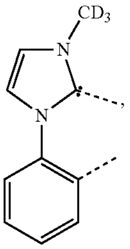
$L_{B277}$
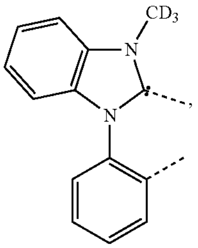

-continued
$L_{B278}$
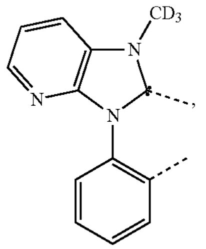
$L_{B279}$
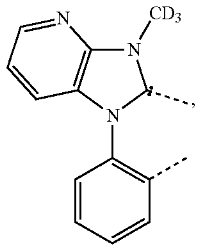
$L_{B280}$
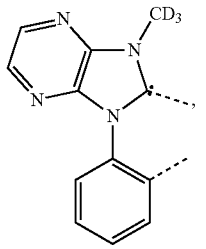
$L_{B281}$
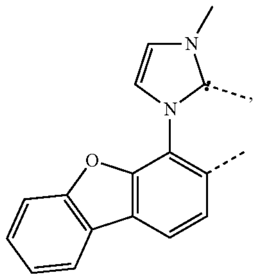
$L_{B282}$
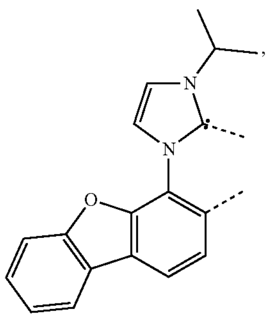
-continued
$L_{B283}$
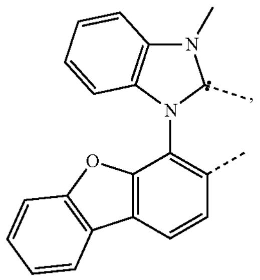
$L_{B284}$
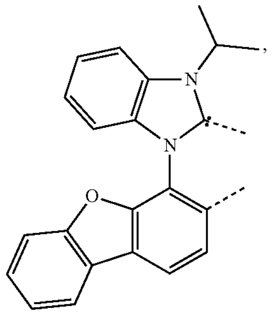
$L_{B285}$
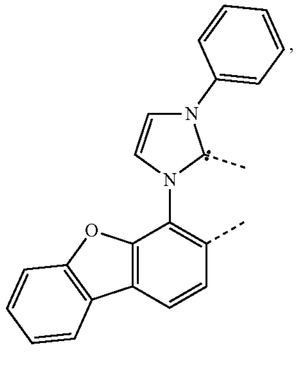
$L_{B286}$
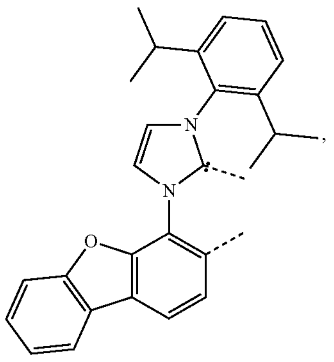

-continued
$L_{B287}$
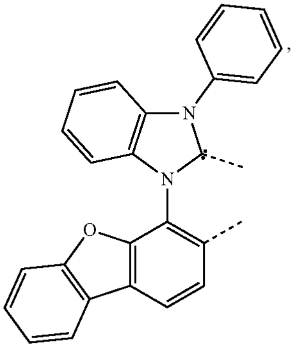
$L_{B288}$
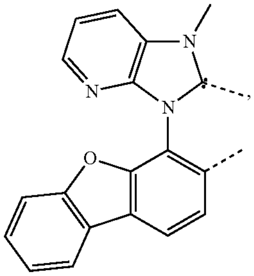
$L_{B289}$
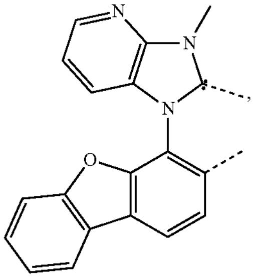
$L_{B290}$
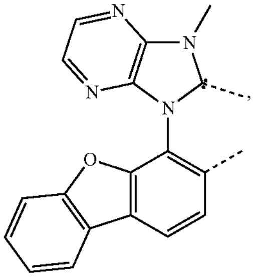
$L_{B291}$
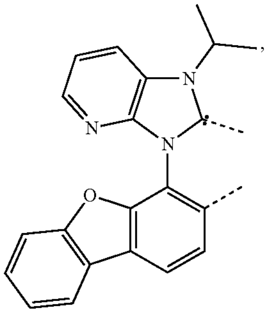
-continued
$L_{B292}$
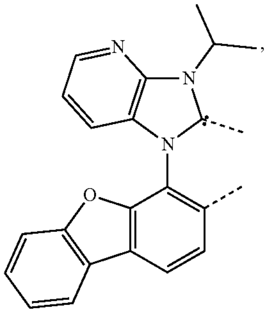
$L_{B293}$
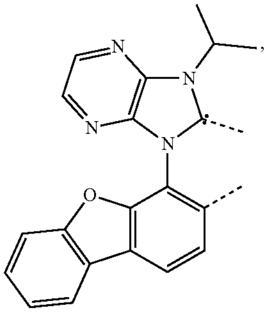
$L_{B294}$
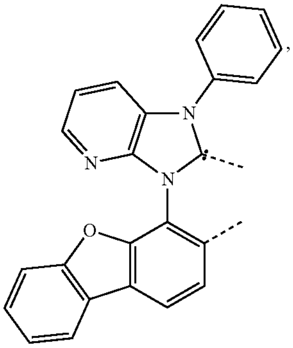
$L_{B295}$
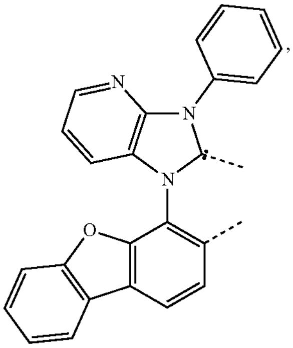

-continued
$L_{B296}$
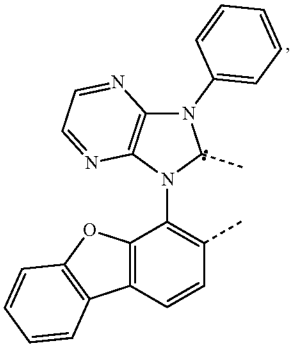
$L_{B297}$
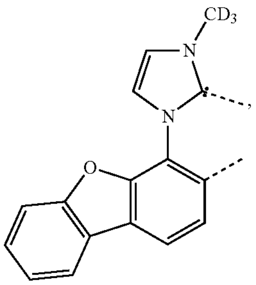
$L_{B298}$
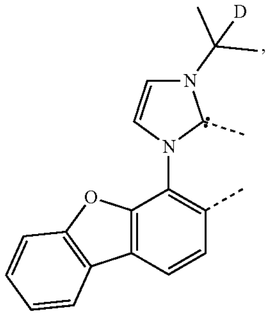
$L_{B299}$
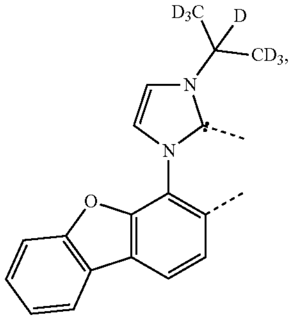
$L_{B300}$
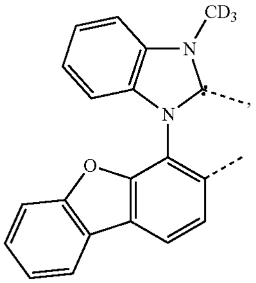
-continued
$L_{B301}$
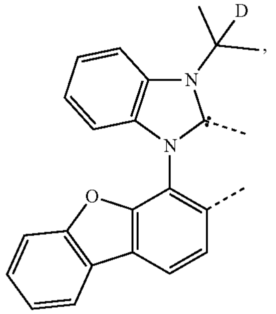
$L_{B302}$
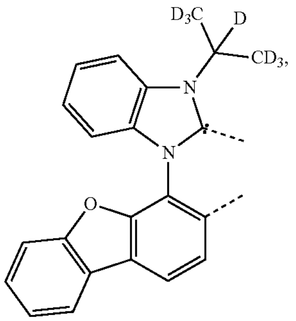
$L_{B303}$
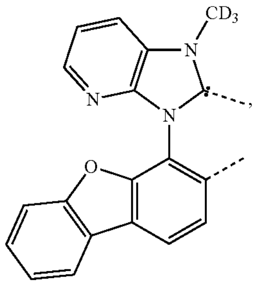
$L_{B304}$
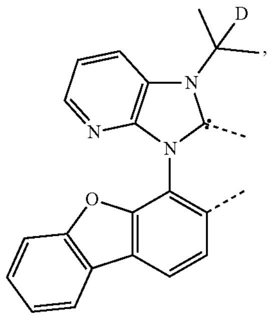
$L_{B305}$
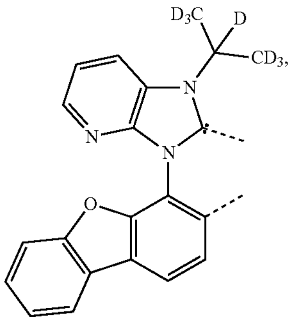

-continued
L$_{B306}$
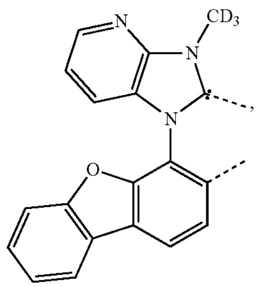
L$_{B307}$
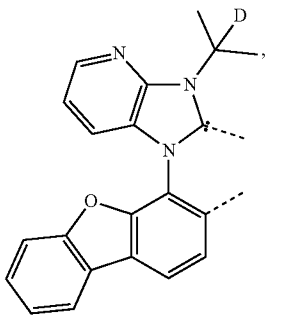
L$_{B308}$
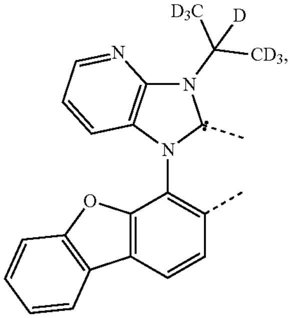
L$_{B309}$
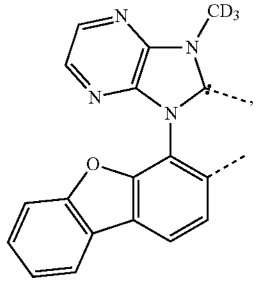
L$_{B310}$
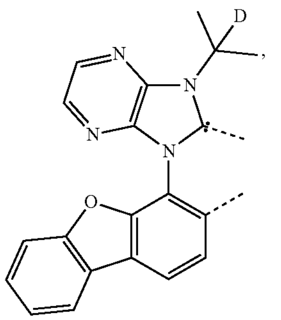
-continued
L$_{B311}$
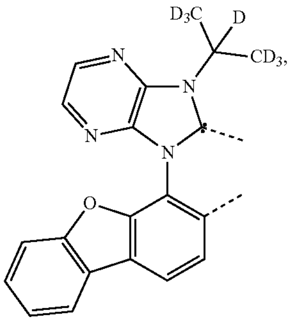
L$_{B312}$
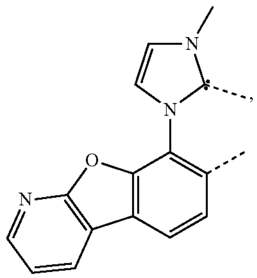
L$_{B313}$
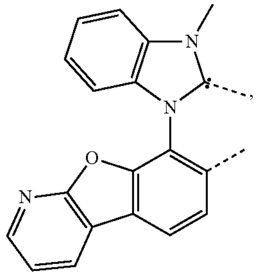
L$_{B314}$
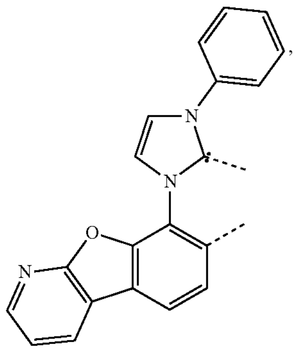
L$_{B315}$
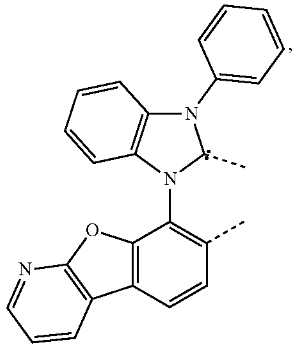

-continued
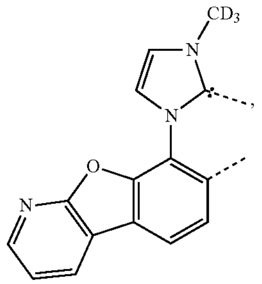
$L_{B316}$
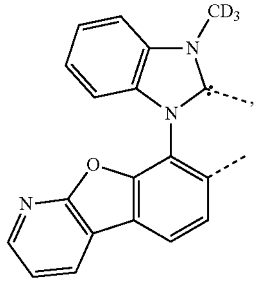
$L_{B317}$
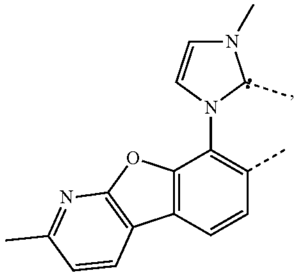
$L_{B318}$
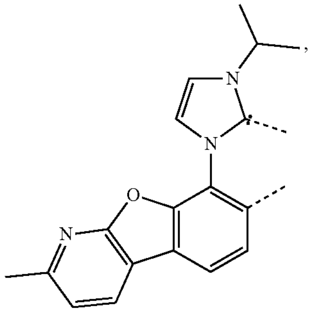
$L_{B319}$
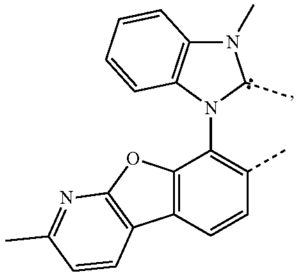
$L_{B320}$
-continued
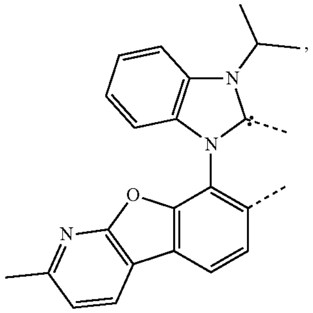
$L_{B321}$
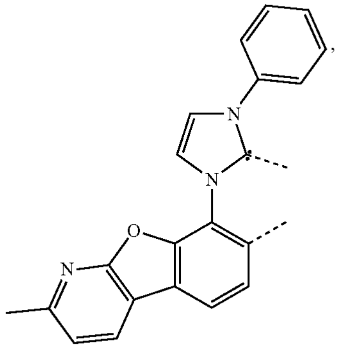
$L_{B323}$
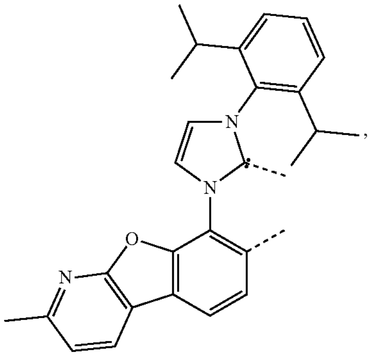
$L_{B324}$
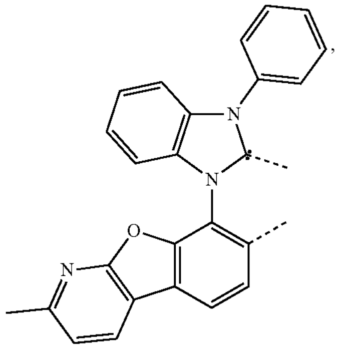
$L_{B325}$

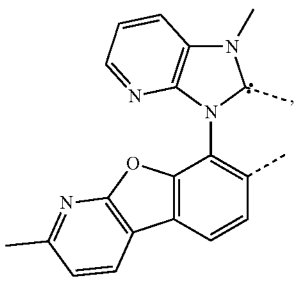
$L_{B326}$
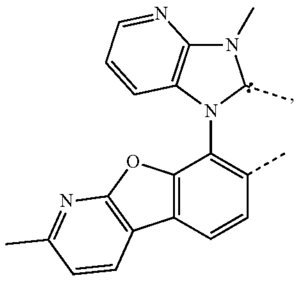
$L_{B327}$
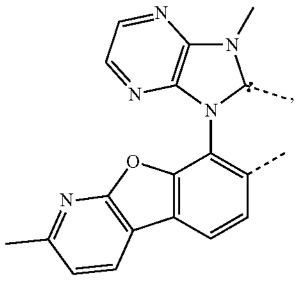
$L_{B328}$
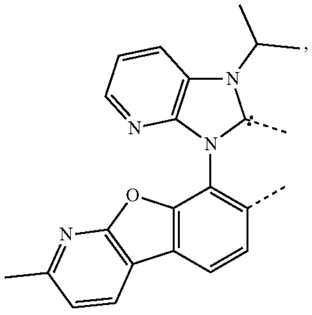
$L_{B329}$
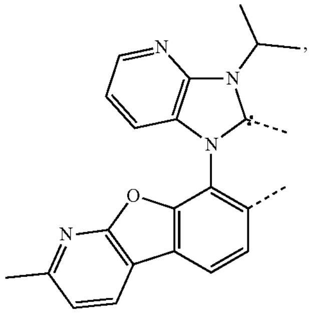
$L_{B330}$
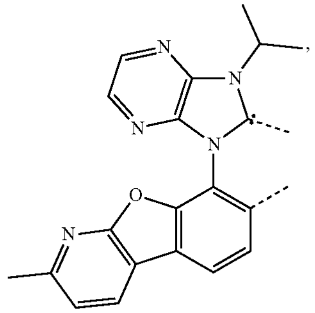
$L_{B331}$
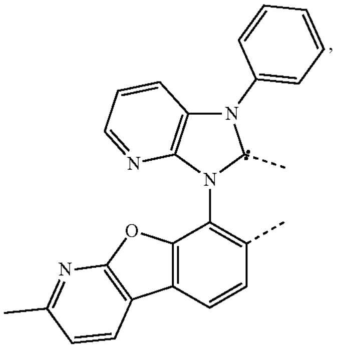
$L_{B332}$
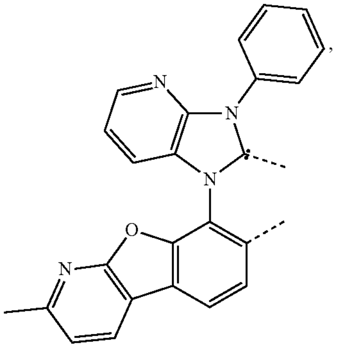
$L_{B333}$
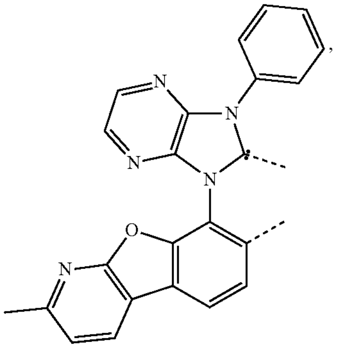
$L_{B334}$ -continued
$L_{B335}$
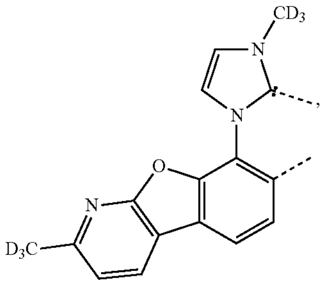
$L_{B336}$
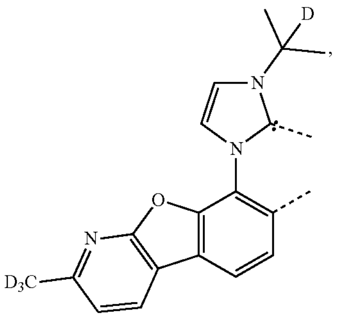
$L_{B337}$
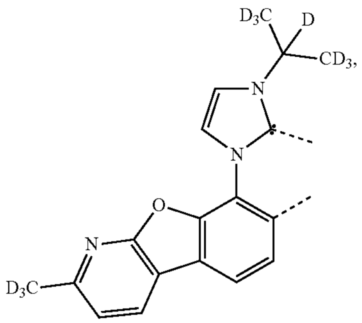
$L_{B338}$
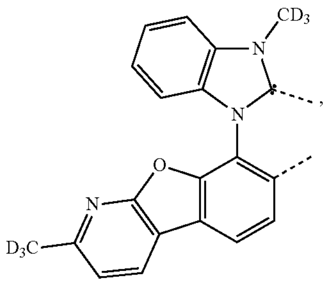
$L_{B339}$
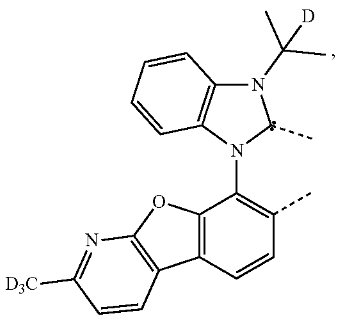
-continued
$L_{B340}$
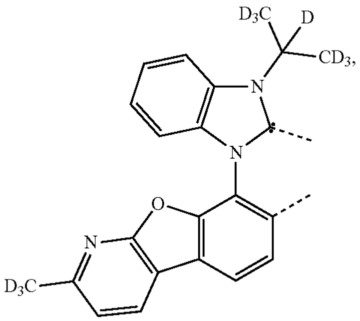
$L_{B341}$
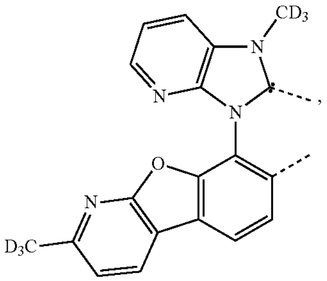
$L_{B342}$
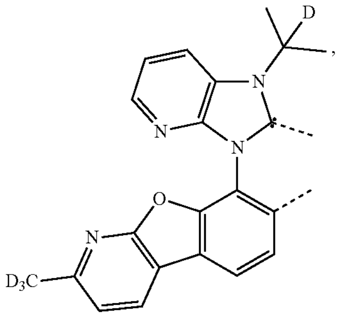
$L_{B343}$
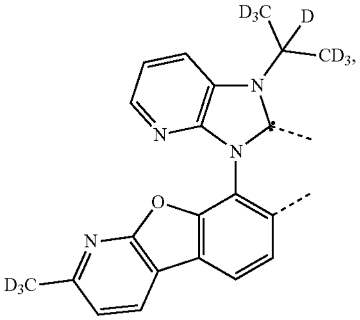
$L_{B344}$
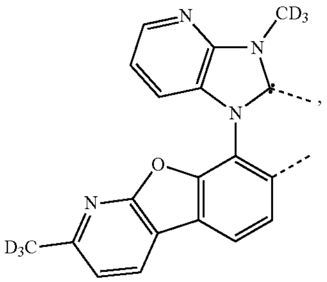

-continued
$L_{B345}$
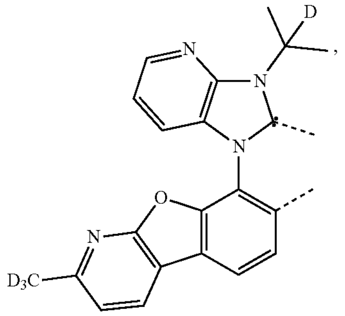
$L_{B346}$
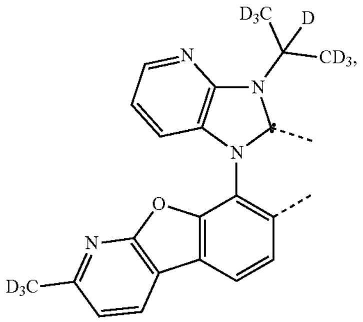
$L_{B347}$
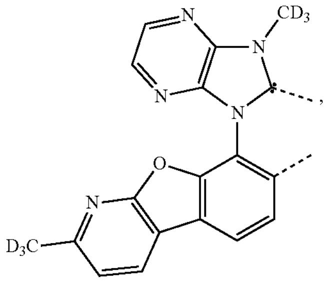
$L_{B348}$
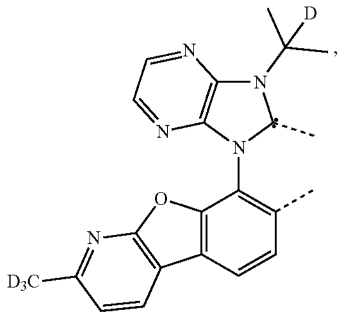
$L_{B349}$
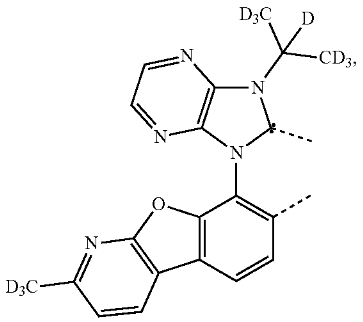
-continued
$L_{B350}$
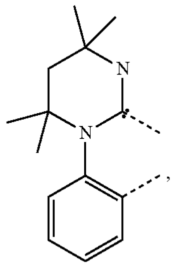
$L_{B351}$
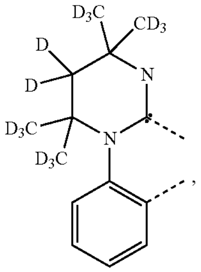
$L_{B352}$
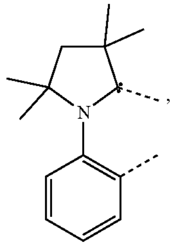
$L_{B353}$
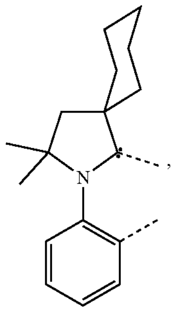
$L_{B354}$
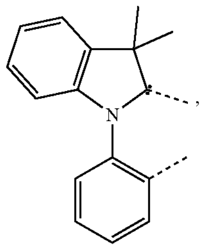

-continued
$L_{B355}$
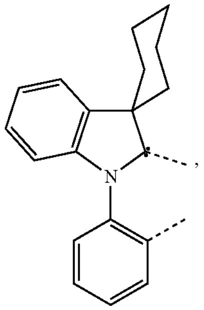
$L_{B356}$
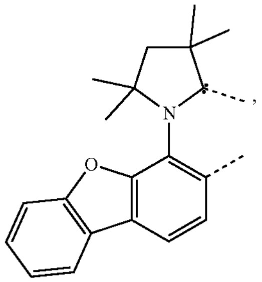
$L_{B357}$
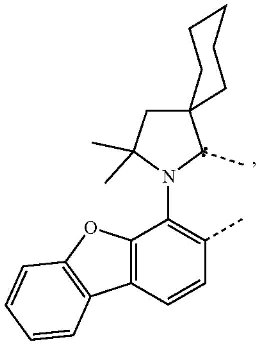
$L_{B358}$
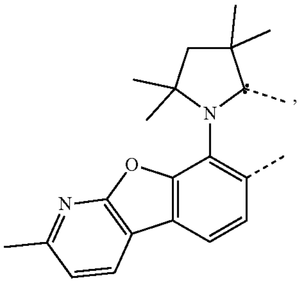
$L_{B359}$
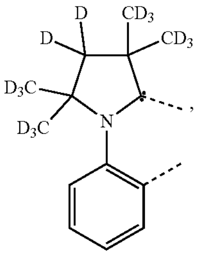
-continued
$L_{B360}$
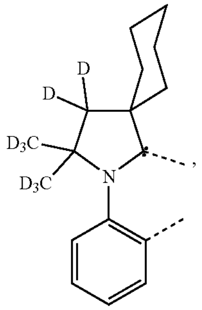
$L_{B361}$
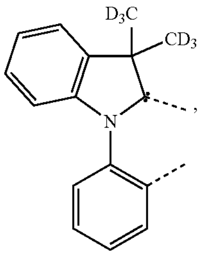
$L_{B362}$
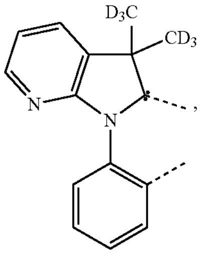
$L_{B363}$
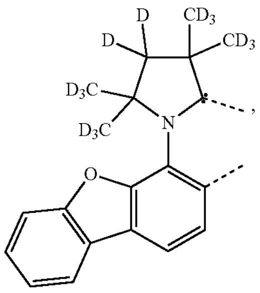
$L_{B364}$
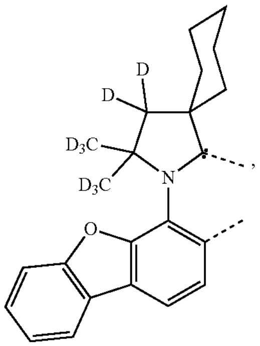

-continued
$L_{B365}$
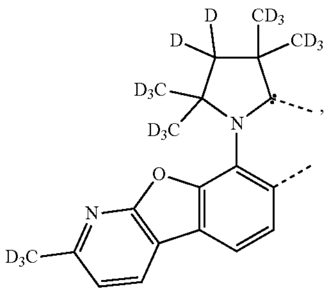
$L_{B366}$
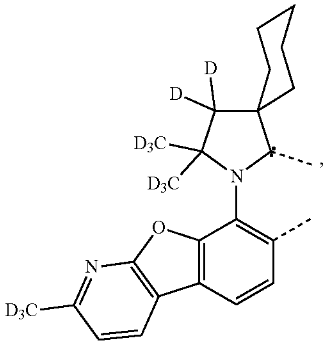
$L_{B367}$
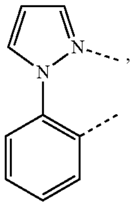
$L_{B368}$
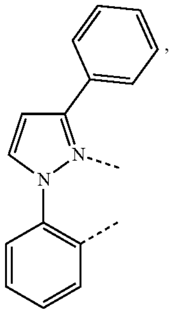
$L_{B369}$
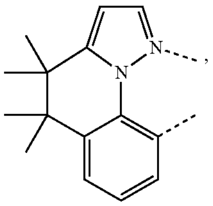
-continued
$L_{B370}$
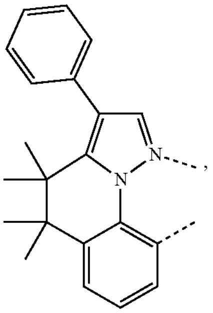
$L_{B371}$
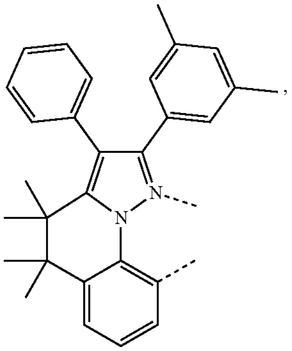
$L_{B372}$
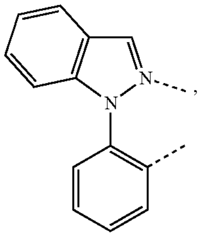
$L_{B373}$
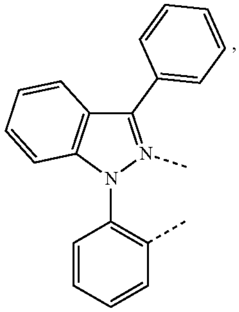
$L_{B374}$
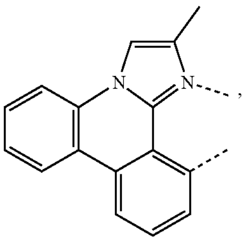

-continued
L$_{B375}$
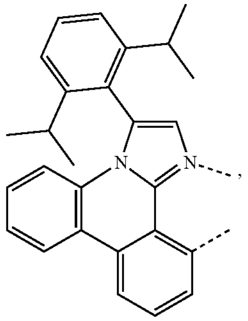
L$_{B376}$
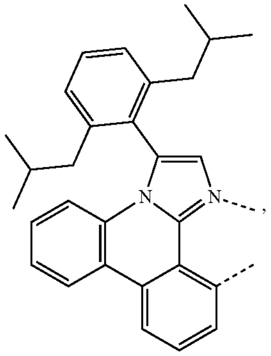
L$_{B377}$
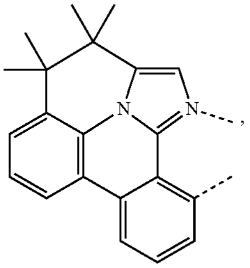
L$_{B378}$
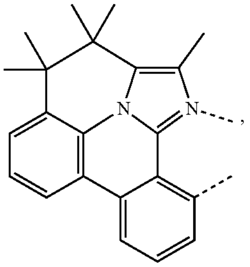
L$_{B379}$
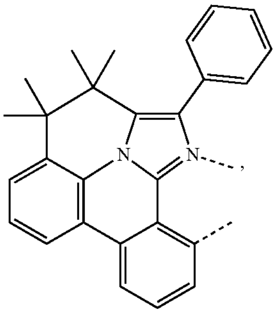
-continued
L$_{B380}$
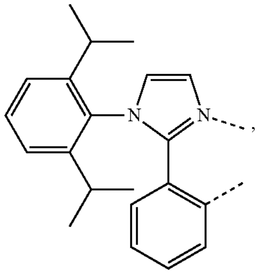
L$_{B381}$
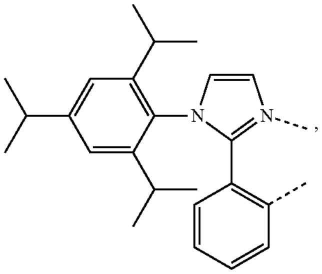
L$_{B382}$
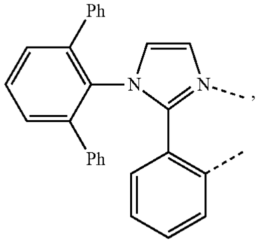
L$_{B383}$
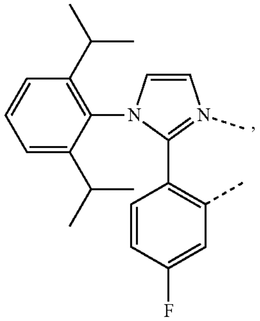
L$_{B384}$
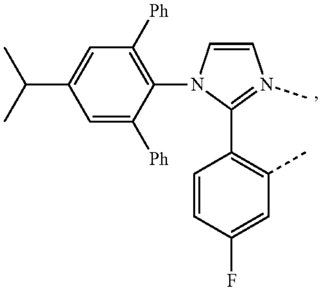

-continued
$L_{B385}$
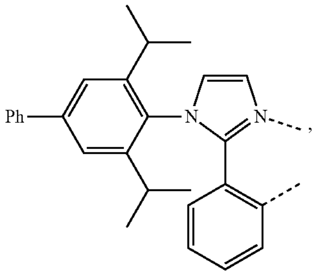
$L_{B386}$
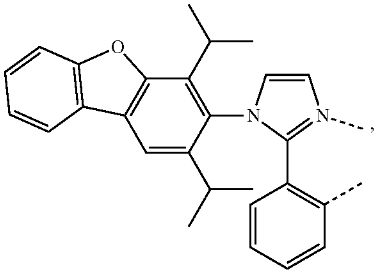
$L_{B387}$
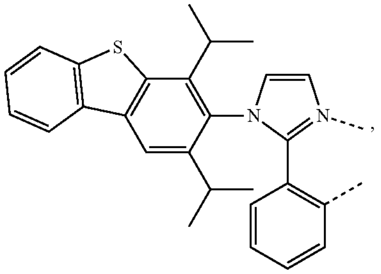
$L_{B388}$
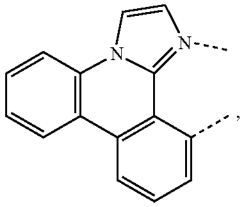
$L_{B389}$
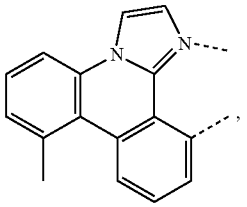
$L_{B390}$
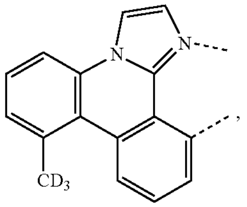
-continued
$L_{B391}$
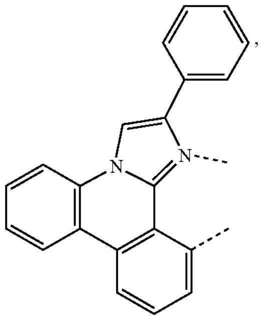
$L_{B392}$
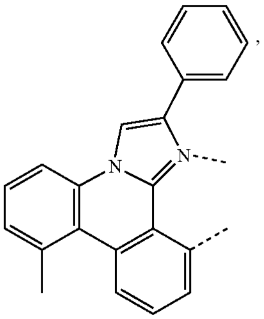
$L_{B393}$
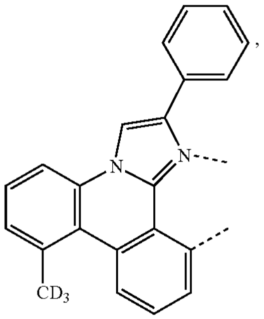
$L_{B394}$
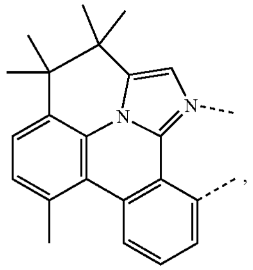
$L_{B395}$
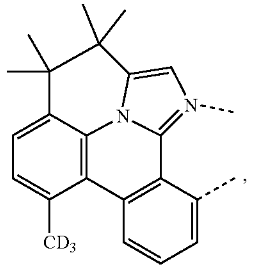

-continued
$L_{B396}$
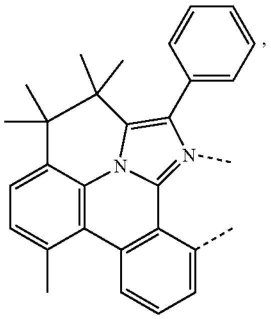
$L_{B397}$
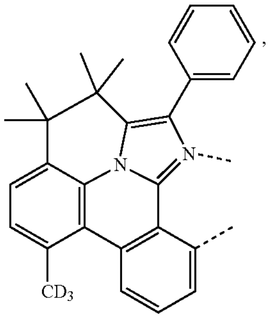
$L_{B398}$
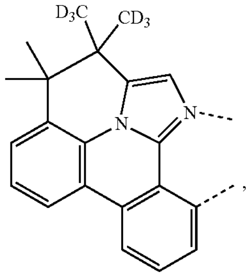
$L_{B399}$
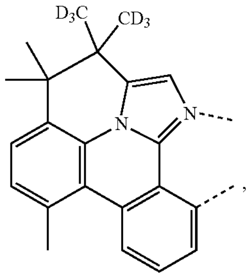
$L_{B400}$
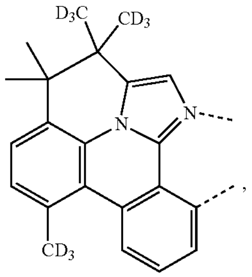
-continued
$L_{B401}$
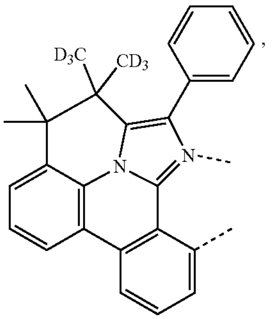
$L_{B402}$
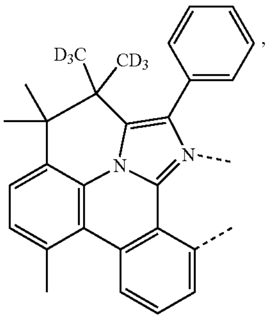
$L_{B403}$
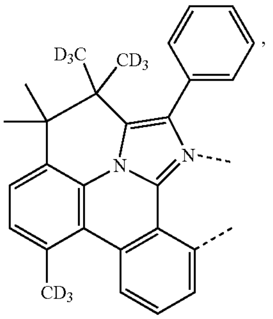
$L_{B404}$
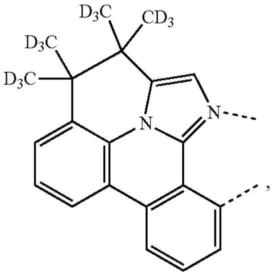
$L_{B405}$
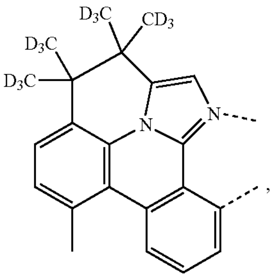

-continued
$L_{B406}$
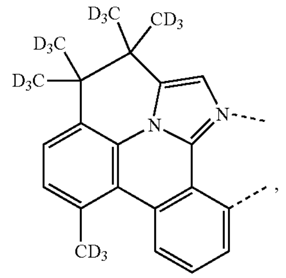
$L_{B407}$
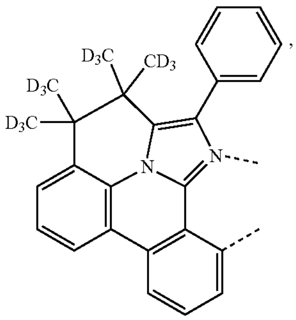
$L_{B408}$
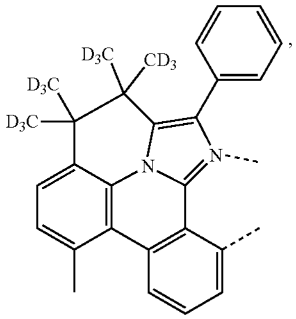
$L_{B409}$
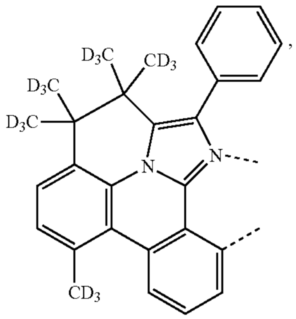
$L_{B410}$
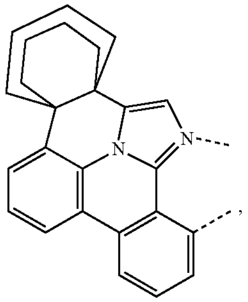
-continued
$L_{B411}$
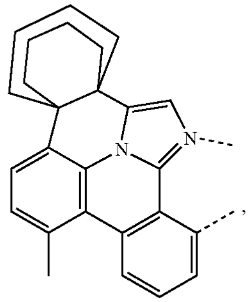
$L_{B412}$
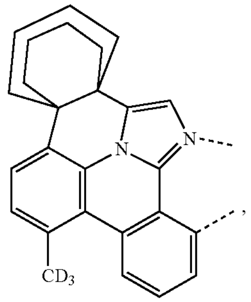
$L_{B413}$
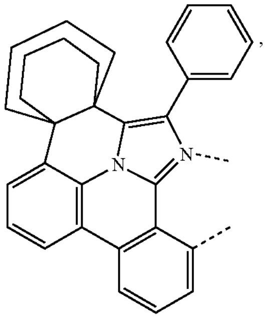
$L_{B414}$
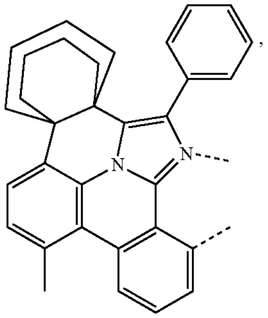
$L_{B415}$
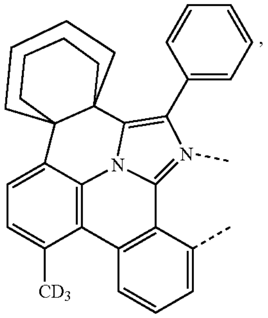

-continued
$L_{B416}$
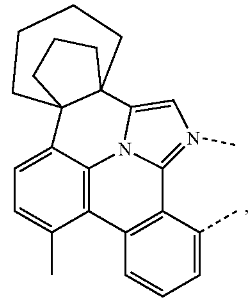
$L_{B417}$
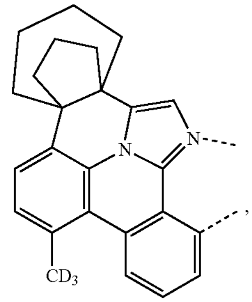
$L_{B418}$
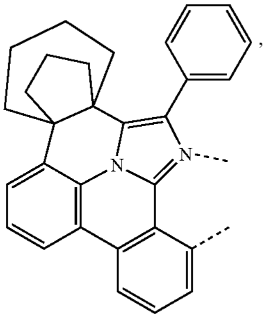
$L_{B419}$
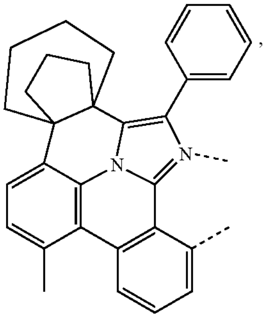
$L_{B420}$
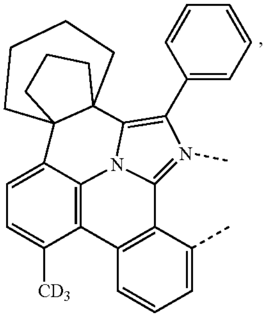
-continued
$L_{B421}$
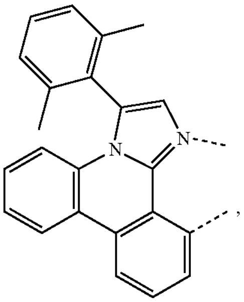
$L_{B422}$
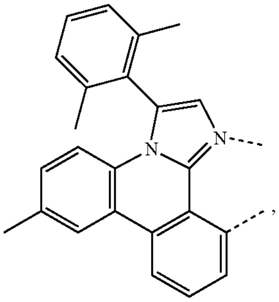
$L_{B435}$
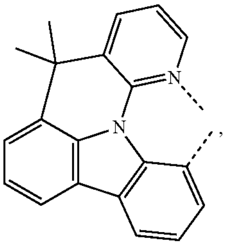
$L_{B443}$
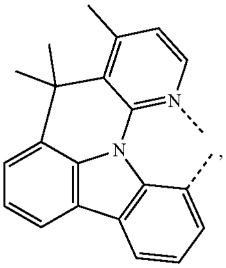
$L_{B425}$
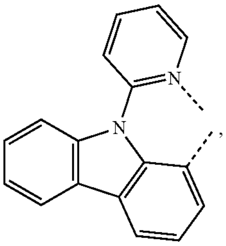

-continued
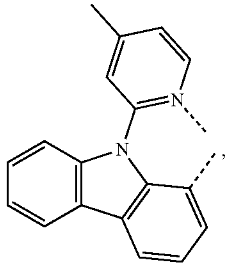
$L_{B426}$
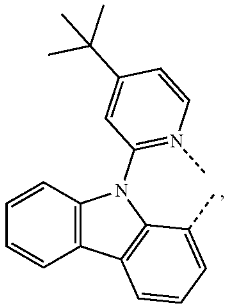
$L_{B427}$
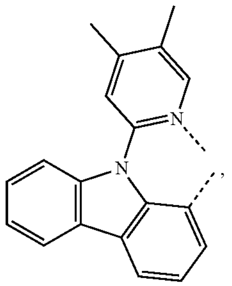
$L_{B428}$
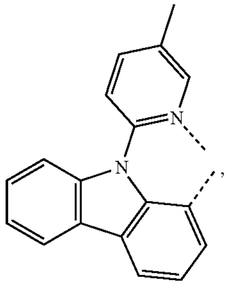
$L_{B429}$
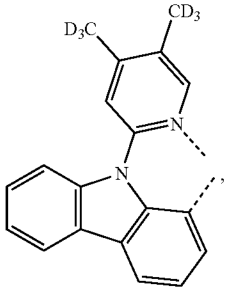
$L_{B430}$
-continued
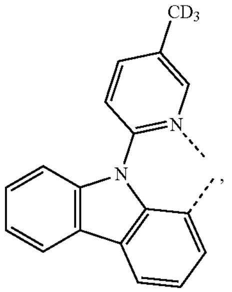
$L_{B431}$
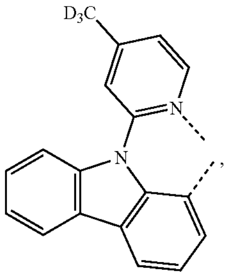
$L_{B432}$
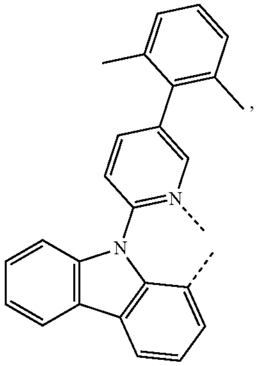
$L_{B433}$
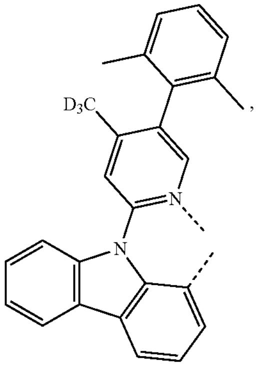
$L_{B434}$ -continued
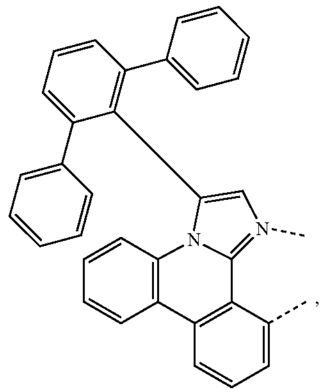
$L_{B423}$
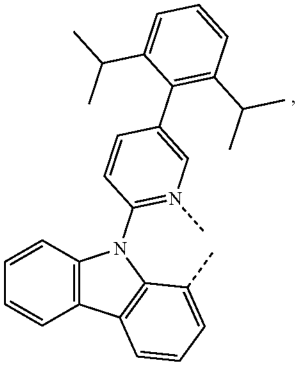
$L_{B436}$
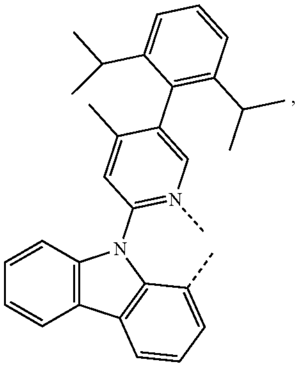
$L_{B437}$
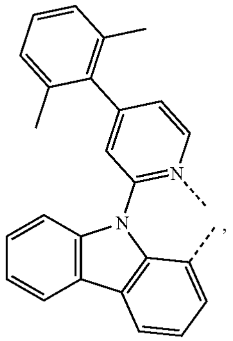
$L_{B438}$
-continued
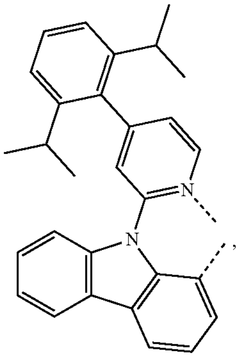
$L_{B439}$
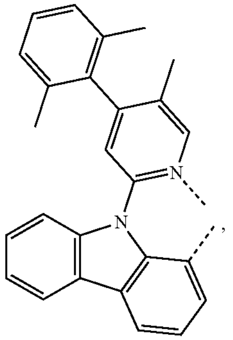
$L_{B440}$
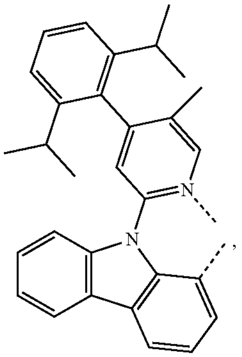
$L_{B441}$
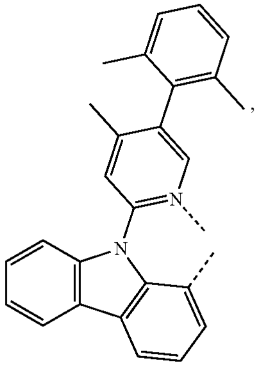
$L_{B442}$ -continued
$L_{B424}$
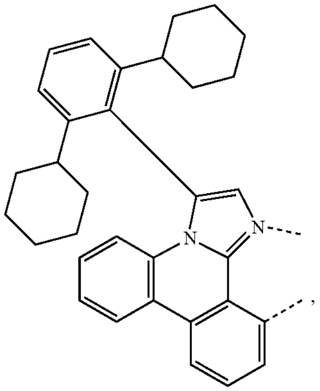
$L_{B444}$
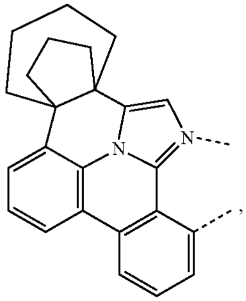
$L_{B445}$
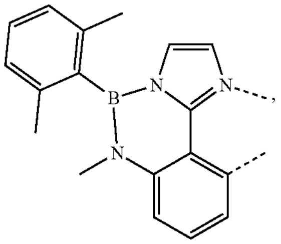
$L_{B446}$
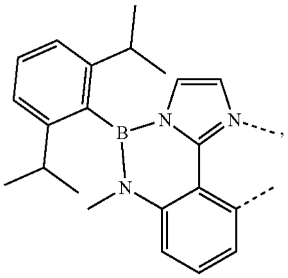
$L_{B447}$
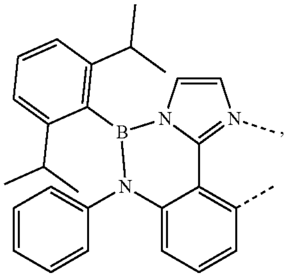
-continued
$L_{B448}$
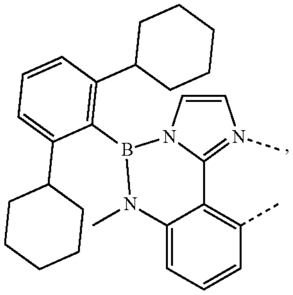
$L_{B449}$
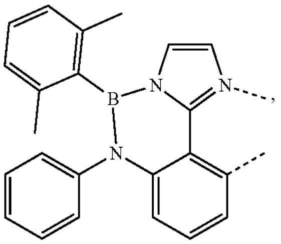
$L_{B450}$
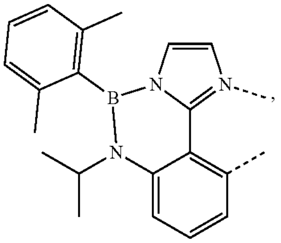
$L_{B452}$
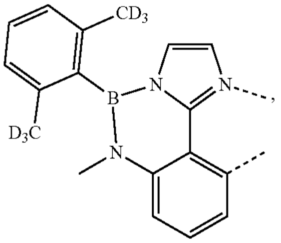
$L_{B454}$
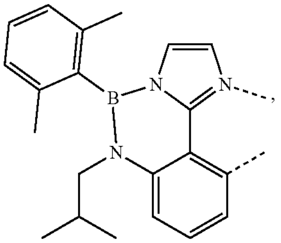
$L_{B456}$
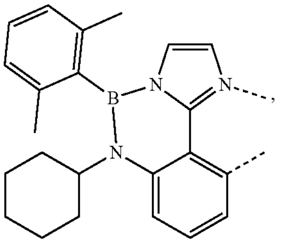

-continued
$L_{B453}$
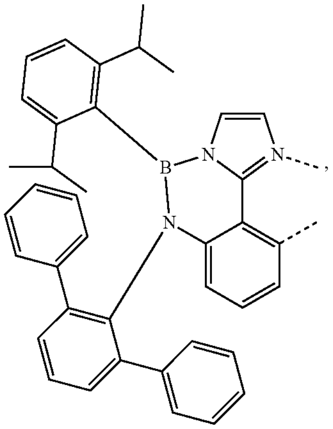
$L_{B455}$
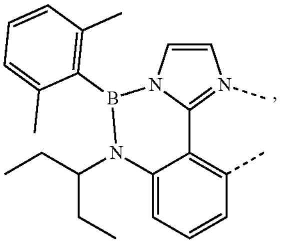
$L_{B451}$
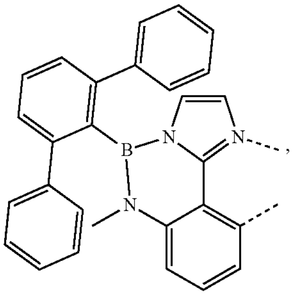
$L_{B457}$
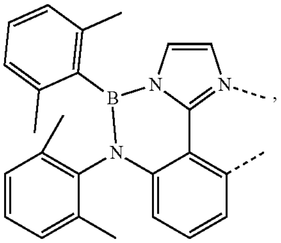
$L_{B458}$
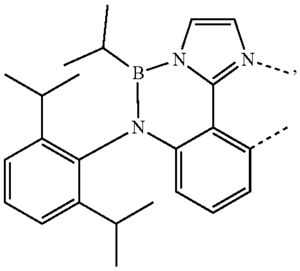
-continued
$L_{B459}$
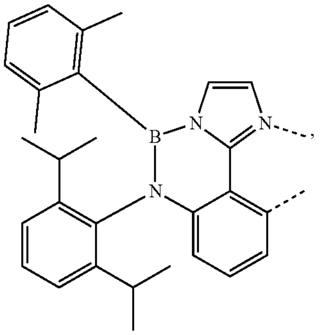
$L_{B460}$
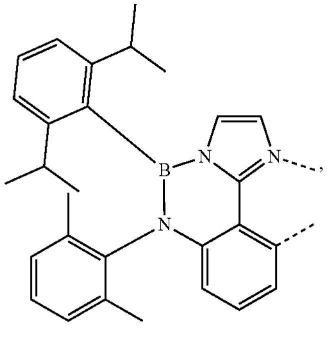
$L_{B461}$
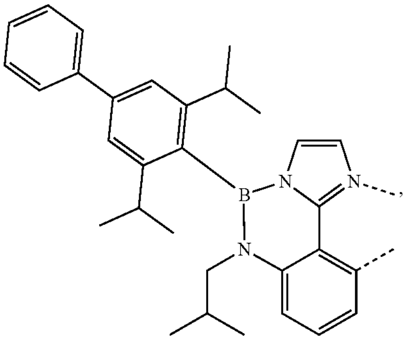
$L_{B462}$
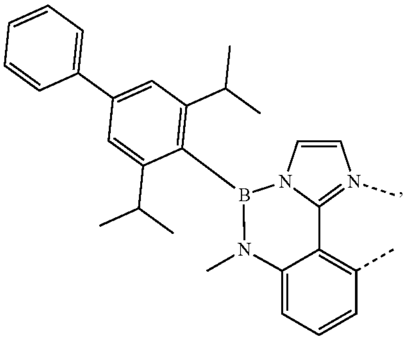

$L_{B463}$
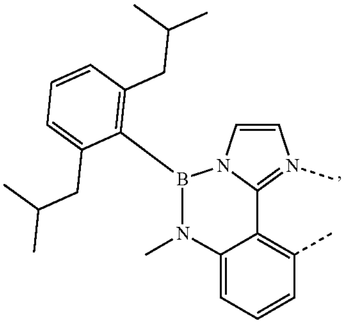
$L_{B464}$
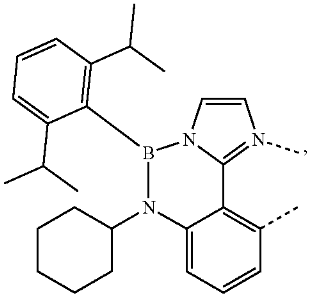
$L_{B465}$
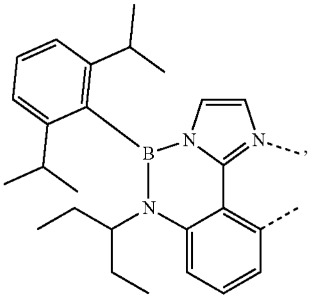
$L_{B466}$
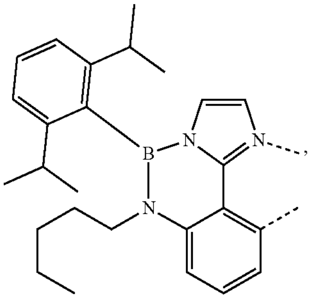
$L_{B467}$
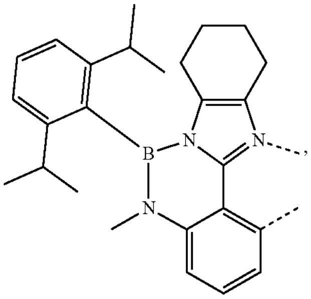
$L_{B468}$
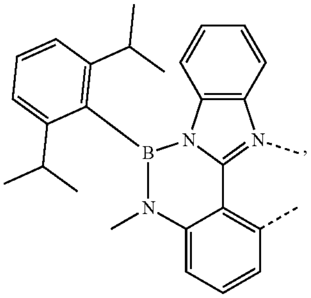
$L_{B469}$
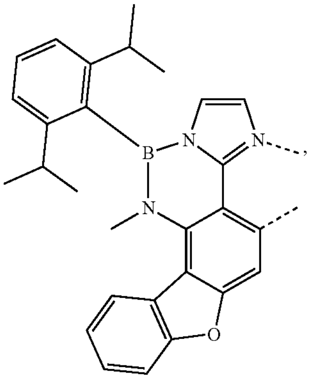
$L_{B470}$
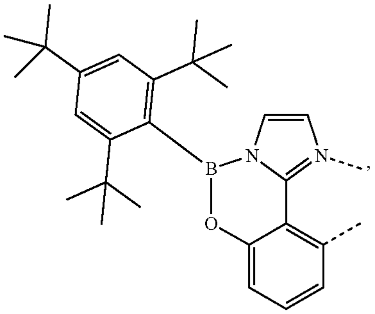
$L_{B471}$
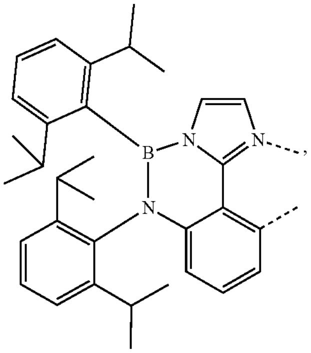

-continued
$L_{B472}$
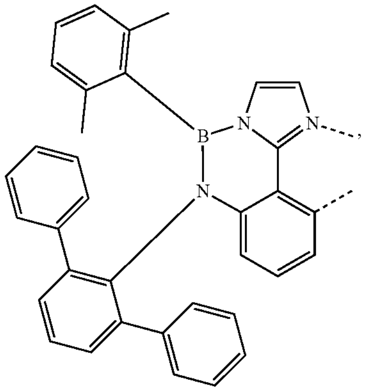
$L_{B473}$
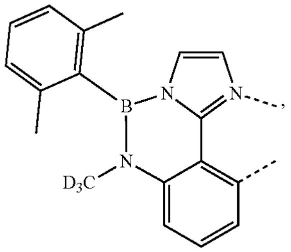
$L_{B474}$
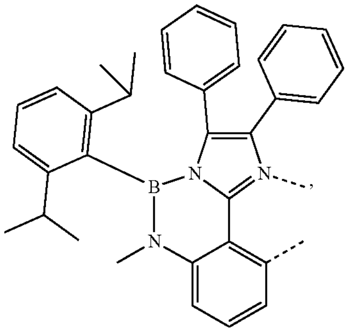
$L_{B475}$
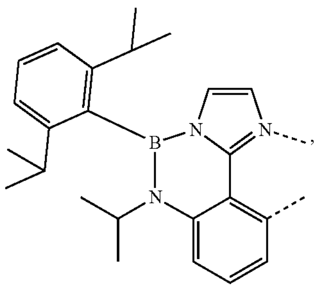
-continued
$L_{B476}$
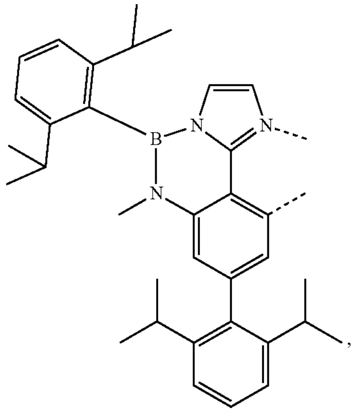
$L_{B477}$
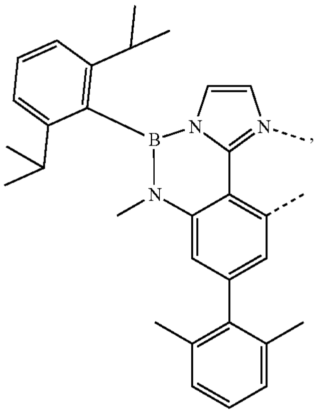
$L_{B478}$
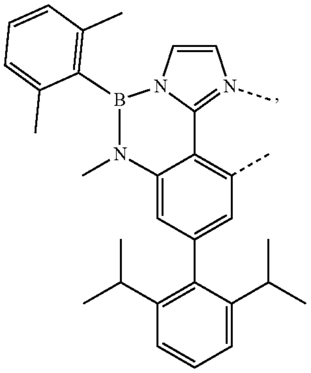
$L_{B479}$
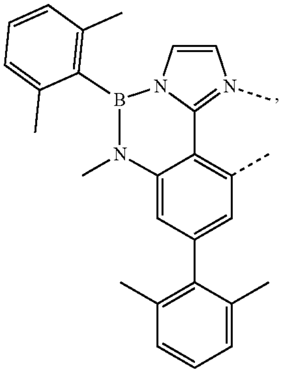

-continued
L_B480
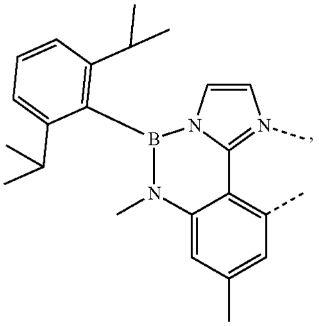
L_B481
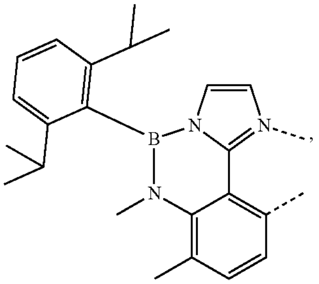
L_B482
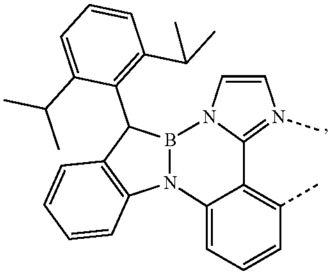
and
L_B483
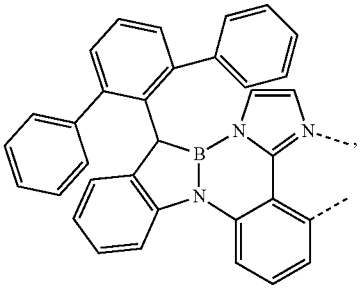
L_B484
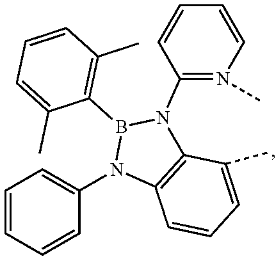
-continued
L_B485
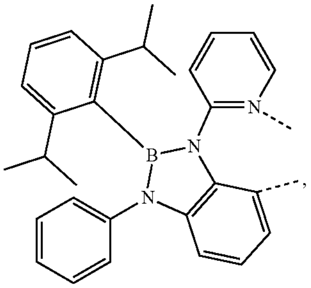
L_B486
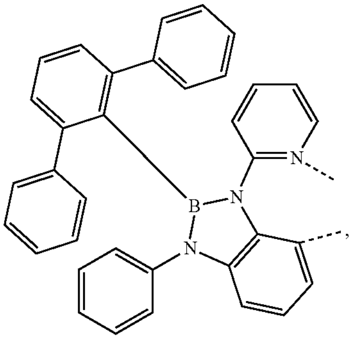
L_B487
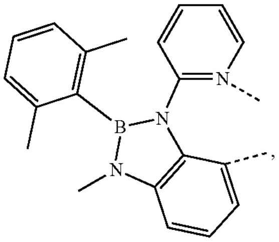
L_B488
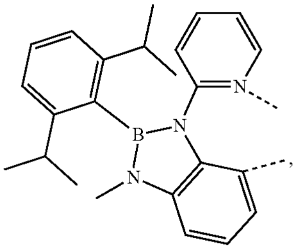
L_B489
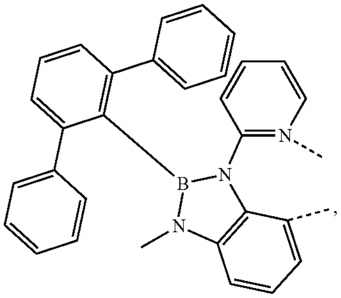

-continued
$L_{B490}$
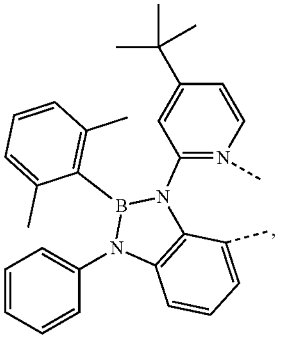
$L_{B491}$
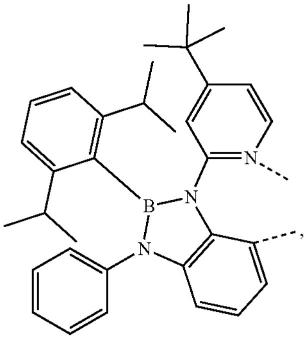
$L_{B492}$
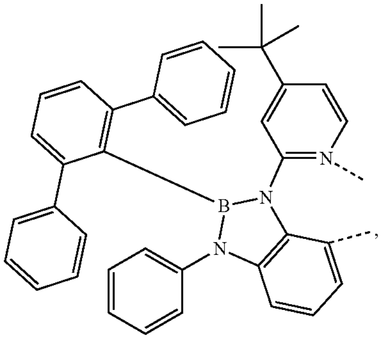
$L_{B493}$
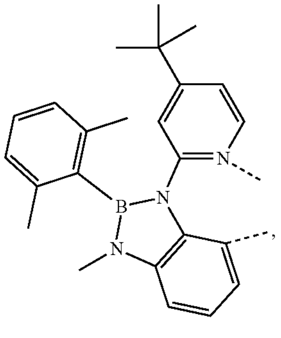
-continued
$L_{B494}$
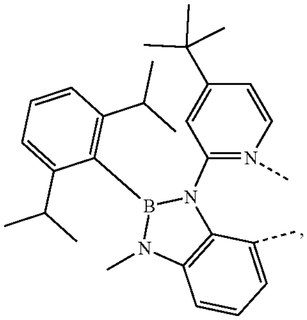
$L_{B495}$
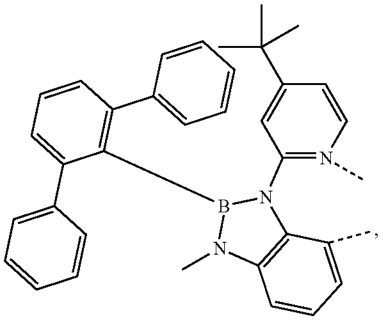
$L_{B496}$
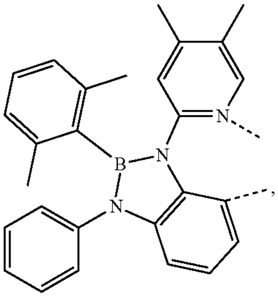
$L_{B497}$
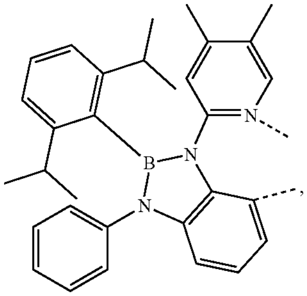
$L_{B498}$
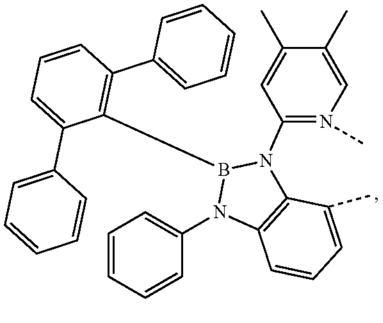

-continued
$L_{B499}$
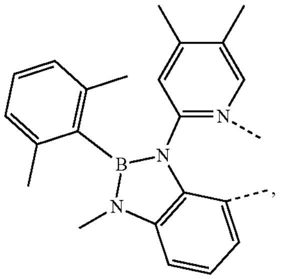
$L_{B500}$
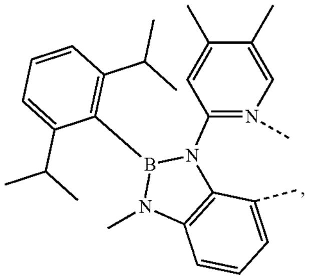
$L_{B501}$
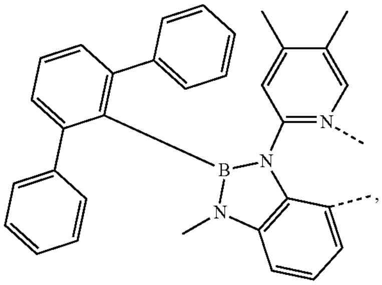
$L_{B502}$
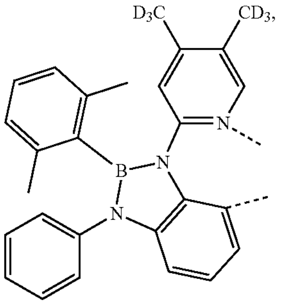
$L_{B503}$
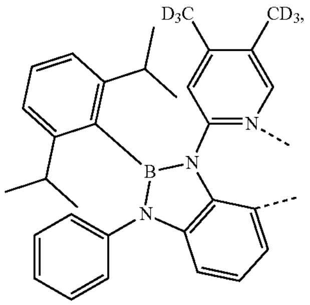
-continued
$L_{B504}$
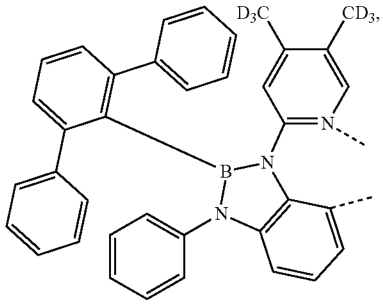
$L_{B505}$
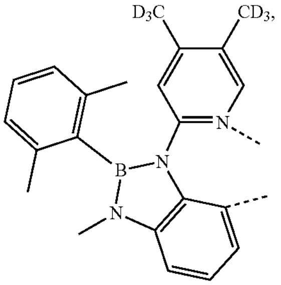
$L_{B506}$
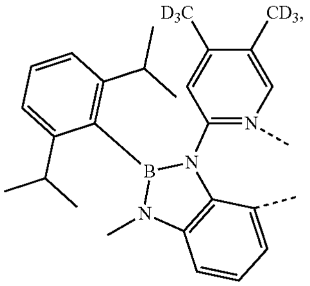
$L_{B507}$
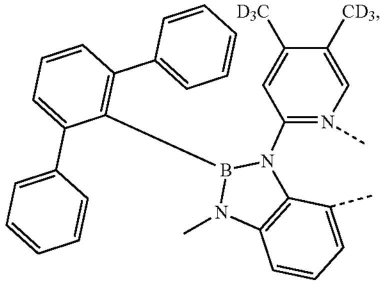
$L_{B508}$
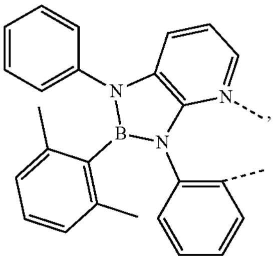

-continued
L$_{B509}$
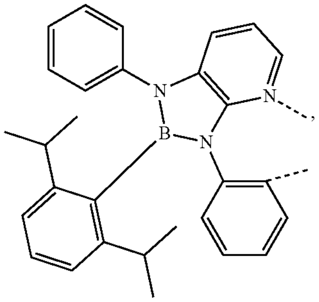
L$_{B510}$
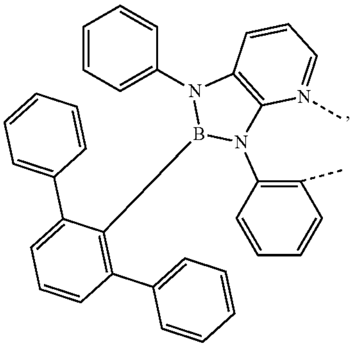
L$_{B511}$
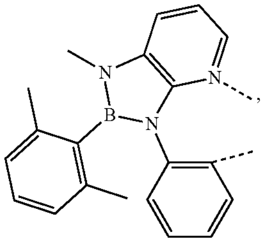
L$_{B512}$
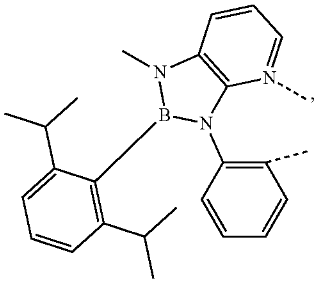
L$_{B513}$
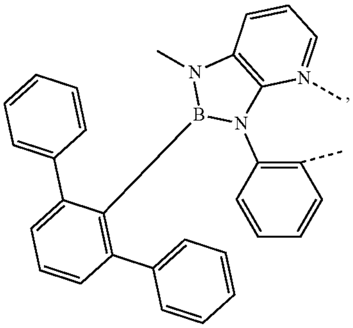
-continued
L$_{B514}$
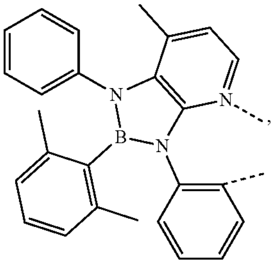
L$_{B515}$
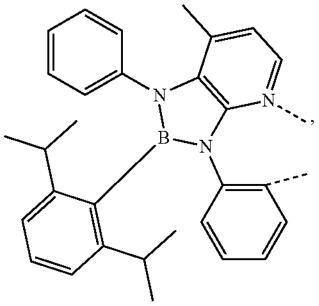
L$_{B516}$
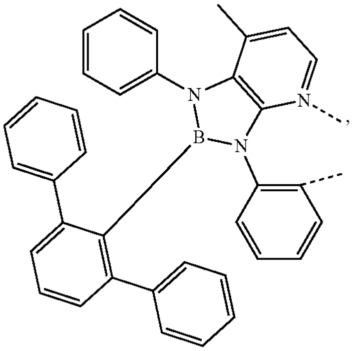
L$_{B517}$
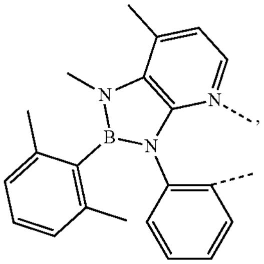
L$_{B518}$
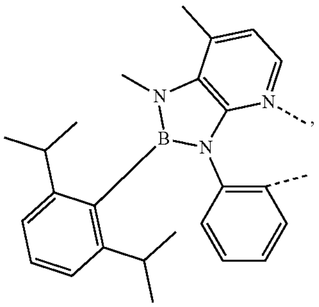

-continued
$L_{B519}$
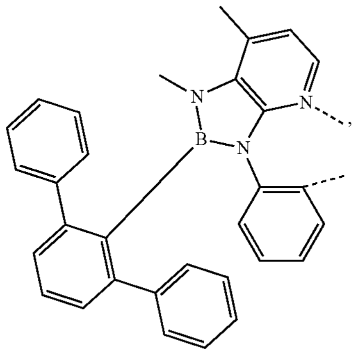
$L_{B520}$
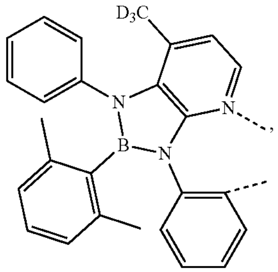
$L_{B521}$
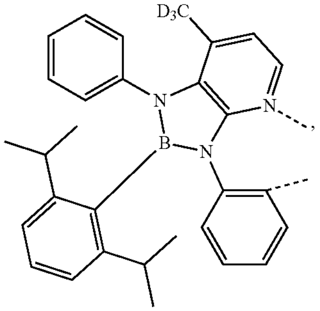
$L_{B522}$
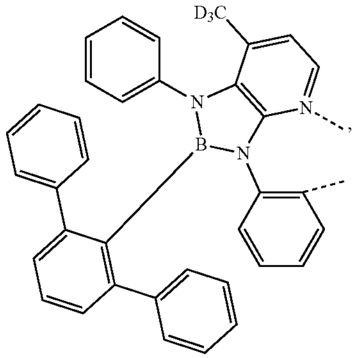
$L_{B523}$
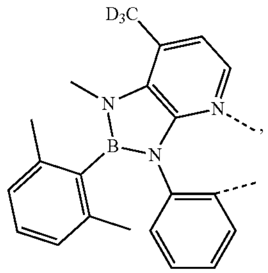
-continued
$L_{B524}$
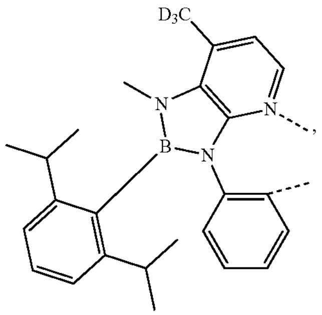
$L_{B525}$
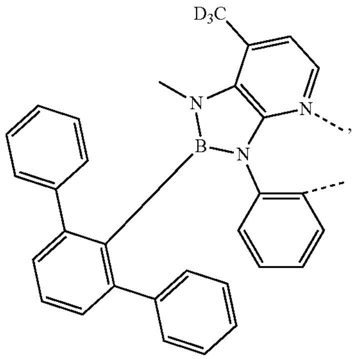
$L_{B526}$
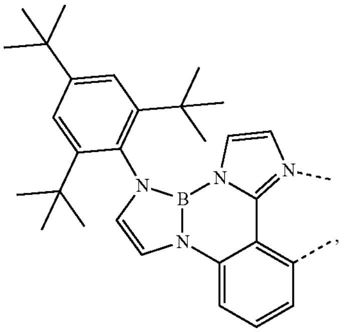
$L_{B527}$
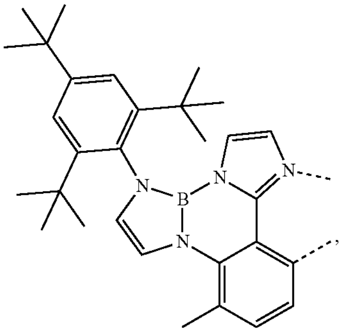

-continued
L$_{B528}$
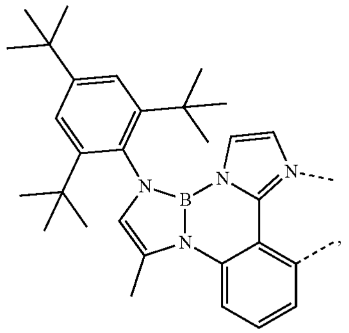
L$_{B529}$
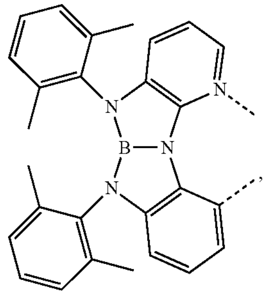
L$_{B530}$
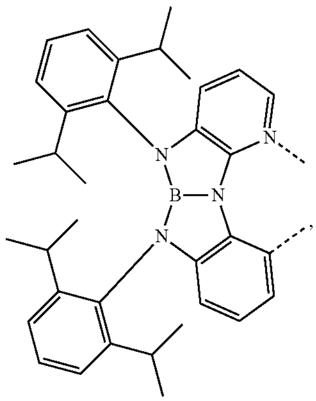
L$_{B531}$
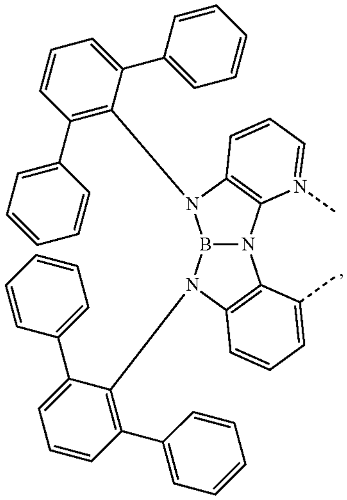
-continued
L$_{B532}$
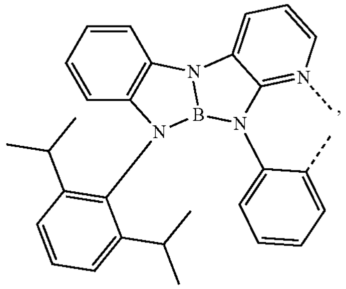
L$_{B533}$
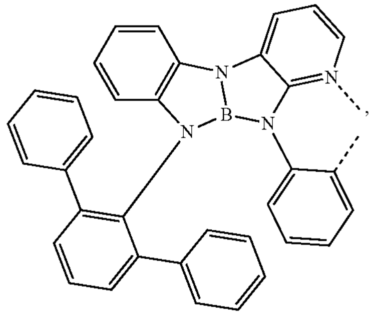
L$_{B534}$
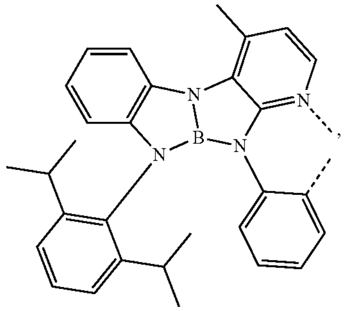
L$_{B535}$
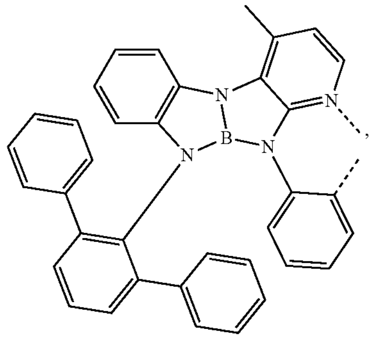
L$_{B536}$
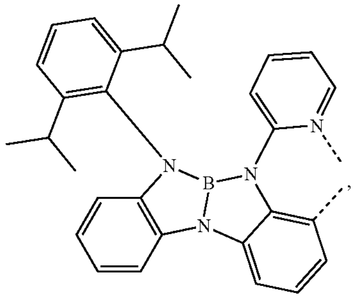

-continued
$L_{B537}$
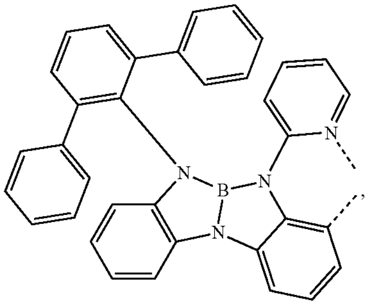
$L_{B538}$
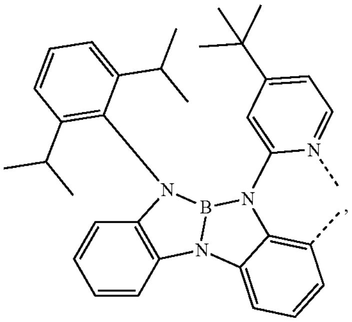
$L_{B539}$
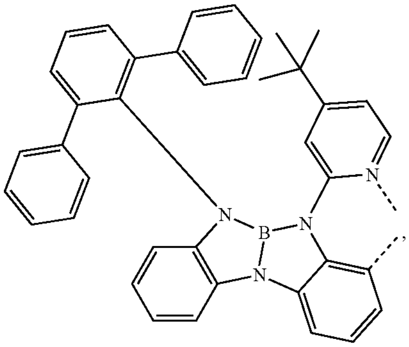
$L_{B540}$
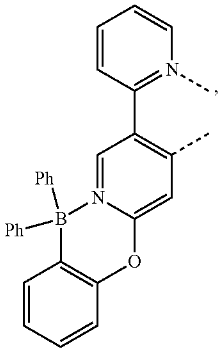
-continued
$L_{B541}$
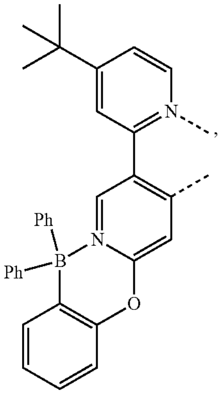
$L_{B542}$
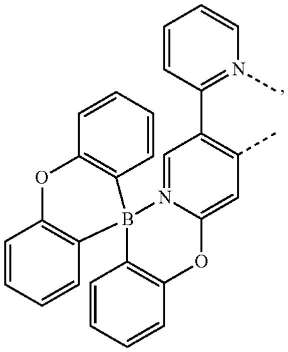
$L_{B543}$
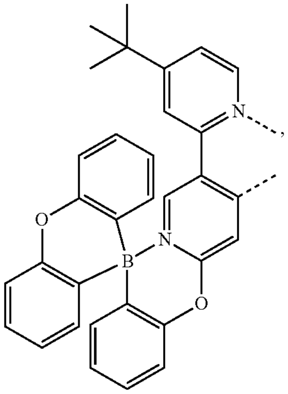
$L_{B544}$
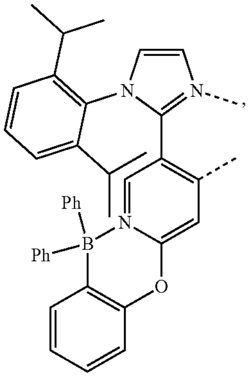

-continued
$L_{B545}$
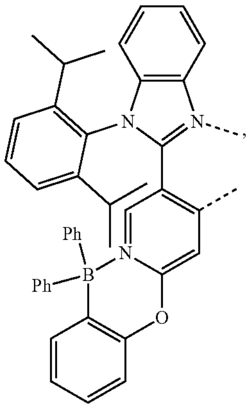
$L_{B546}$
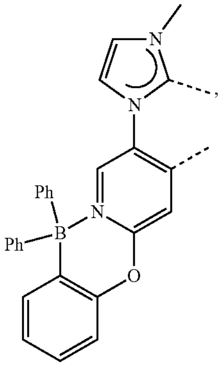
$L_{B547}$
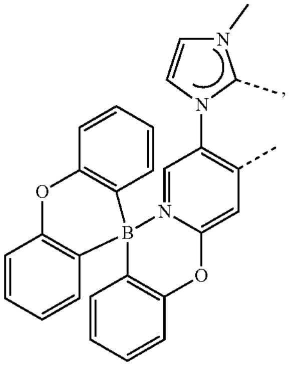
$L_{B548}$
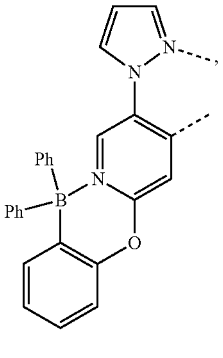
$L_{B549}$
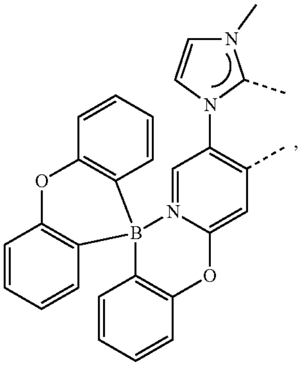
$L_{B550}$
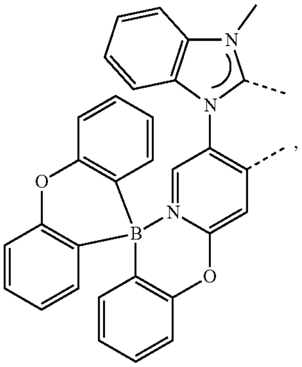
$L_{B551}$
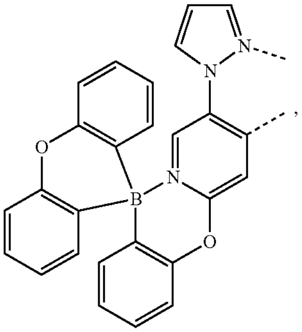
$L_{B552}$
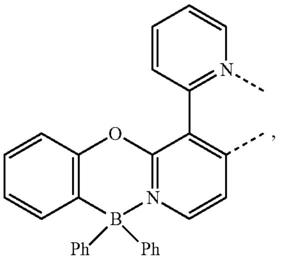

-continued
$L_{B553}$
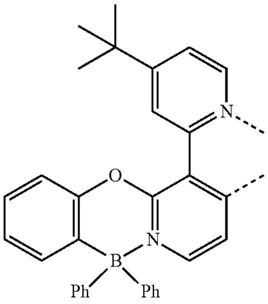
,
$L_{B554}$
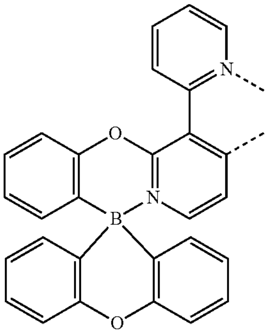
,
$L_{B555}$
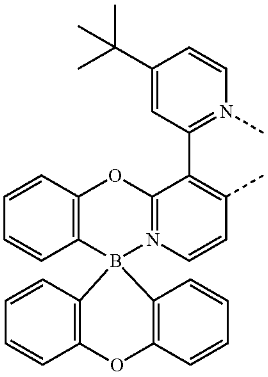
,
$L_{B556}$
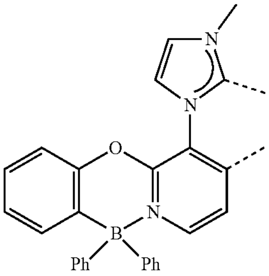
,
-continued
$L_{B557}$
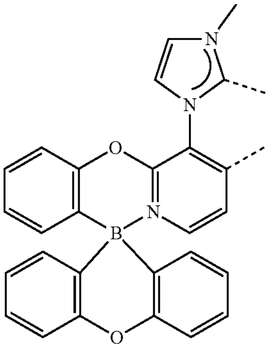
,
$L_{B558}$
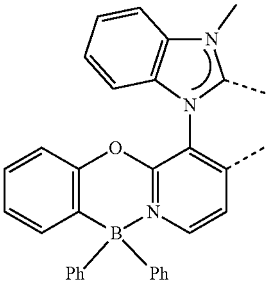
,
$L_{B559}$
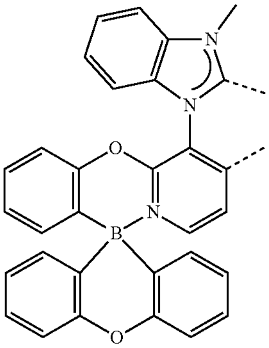
,
$L_{B560}$
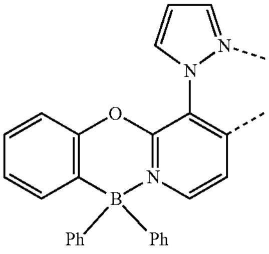
, and
$L_{B561}$
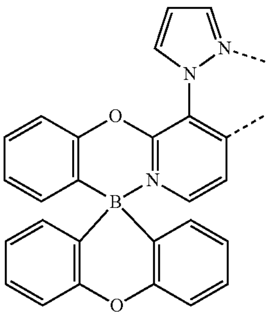
;

wherein each $L_{Cj-I}$ has a structure based on formula

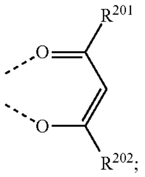

and each $L_{Cj-II}$ has a structure based on formula

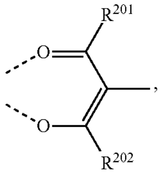

wherein for each $L_{Cj}$ in $L_{Cj-I}$ and $L_{Cj-II}$, $R^{201}$ and $R^{202}$ are each independently as defined in the following table:

| $L_{Cj}$ | $R^{201}$ | $R^{202}$ |
|---|---|---|
| $L_{C1}$ | $R^{D1}$ | $R^{D1}$ |
| $L_{C2}$ | $R^{D2}$ | $R^{D2}$ |
| $L_{C3}$ | $R^{D3}$ | $R^{D3}$ |
| $L_{C4}$ | $R^{D4}$ | $R^{D4}$ |
| $L_{C5}$ | $R^{D5}$ | $R^{D5}$ |
| $L_{C6}$ | $R^{D6}$ | $R^{D6}$ |
| $L_{C7}$ | $R^{D7}$ | $R^{D7}$ |
| $L_{C8}$ | $R^{D8}$ | $R^{D8}$ |
| $L_{C9}$ | $R^{D9}$ | $R^{D9}$ |
| $L_{C10}$ | $R^{D10}$ | $R^{D10}$ |
| $L_{C11}$ | $R^{D11}$ | $R^{D11}$ |
| $L_{C12}$ | $R^{D12}$ | $R^{D12}$ |
| $L_{C13}$ | $R^{D13}$ | $R^{D13}$ |
| $L_{C14}$ | $R^{D14}$ | $R^{D14}$ |
| $L_{C15}$ | $R^{D15}$ | $R^{D15}$ |
| $L_{C16}$ | $R^{D16}$ | $R^{D16}$ |
| $L_{C17}$ | $R^{D17}$ | $R^{D17}$ |
| $L_{C18}$ | $R^{D18}$ | $R^{D18}$ |
| $L_{C19}$ | $R^{D19}$ | $R^{D19}$ |
| $L_{C20}$ | $R^{D20}$ | $R^{D20}$ |
| $L_{C21}$ | $R^{D21}$ | $R^{D21}$ |
| $L_{C22}$ | $R^{D22}$ | $R^{D22}$ |
| $L_{C23}$ | $R^{D23}$ | $R^{D23}$ |
| $L_{C24}$ | $R^{D24}$ | $R^{D24}$ |
| $L_{C25}$ | $R^{D25}$ | $R^{D25}$ |
| $L_{C26}$ | $R^{D26}$ | $R^{D26}$ |
| $L_{C27}$ | $R^{D27}$ | $R^{D27}$ |
| $L_{C28}$ | $R^{D28}$ | $R^{D28}$ |
| $L_{C29}$ | $R^{D29}$ | $R^{D29}$ |
| $L_{C30}$ | $R^{D30}$ | $R^{D30}$ |
| $L_{C31}$ | $R^{D31}$ | $R^{D31}$ |
| $L_{C32}$ | $R^{D32}$ | $R^{D32}$ |
| $L_{C33}$ | $R^{D33}$ | $R^{D33}$ |
| $L_{C34}$ | $R^{D34}$ | $R^{D34}$ |
| $L_{C35}$ | $R^{D35}$ | $R^{D35}$ |
| $L_{C36}$ | $R^{D36}$ | $R^{D36}$ |
| $L_{C37}$ | $R^{D37}$ | $R^{D37}$ |
| $L_{C38}$ | $R^{D38}$ | $R^{D38}$ |
| $L_{C39}$ | $R^{D39}$ | $R^{D39}$ |
| $L_{C40}$ | $R^{D40}$ | $R^{D40}$ |
| $L_{C41}$ | $R^{D41}$ | $R^{D41}$ |
| $L_{C42}$ | $R^{D42}$ | $R^{D42}$ |
| $L_{C43}$ | $R^{D43}$ | $R^{D43}$ |
| $L_{C44}$ | $R^{D44}$ | $R^{D44}$ |
| $L_{C45}$ | $R^{D45}$ | $R^{D45}$ |
| $L_{C46}$ | $R^{D46}$ | $R^{D46}$ |
| $L_{C47}$ | $R^{D47}$ | $R^{D47}$ |

-continued

| $L_{Cj}$ | $R^{201}$ | $R^{202}$ |
|---|---|---|
| $L_{C48}$ | $R^{D48}$ | $R^{D48}$ |
| $L_{C49}$ | $R^{D49}$ | $R^{D49}$ |
| $L_{C50}$ | $R^{D50}$ | $R^{D50}$ |
| $L_{C51}$ | $R^{D51}$ | $R^{D51}$ |
| $L_{C52}$ | $R^{D52}$ | $R^{D52}$ |
| $L_{C53}$ | $R^{D53}$ | $R^{D53}$ |
| $L_{C54}$ | $R^{D54}$ | $R^{D54}$ |
| $L_{C55}$ | $R^{D55}$ | $R^{D55}$ |
| $L_{C56}$ | $R^{D56}$ | $R^{D56}$ |
| $L_{C57}$ | $R^{D57}$ | $R^{D57}$ |
| $L_{C58}$ | $R^{D58}$ | $R^{D58}$ |
| $L_{C59}$ | $R^{D59}$ | $R^{D59}$ |
| $L_{C60}$ | $R^{D60}$ | $R^{D60}$ |
| $L_{C61}$ | $R^{D61}$ | $R^{D61}$ |
| $L_{C62}$ | $R^{D62}$ | $R^{D62}$ |
| $L_{C63}$ | $R^{D63}$ | $R^{D63}$ |
| $L_{C64}$ | $R^{D64}$ | $R^{D64}$ |
| $L_{C65}$ | $R^{D65}$ | $R^{D65}$ |
| $L_{C66}$ | $R^{D66}$ | $R^{D66}$ |
| $L_{C67}$ | $R^{D67}$ | $R^{D67}$ |
| $L_{C68}$ | $R^{D68}$ | $R^{D68}$ |
| $L_{C69}$ | $R^{D69}$ | $R^{D69}$ |
| $L_{C70}$ | $R^{D70}$ | $R^{D70}$ |
| $L_{C71}$ | $R^{D71}$ | $R^{D71}$ |
| $L_{C72}$ | $R^{D72}$ | $R^{D72}$ |
| $L_{C73}$ | $R^{D73}$ | $R^{D73}$ |
| $L_{C74}$ | $R^{D74}$ | $R^{D74}$ |
| $L_{C75}$ | $R^{D75}$ | $R^{D75}$ |
| $L_{C76}$ | $R^{D76}$ | $R^{D76}$ |
| $L_{C77}$ | $R^{D77}$ | $R^{D77}$ |
| $L_{C78}$ | $R^{D78}$ | $R^{D78}$ |
| $L_{C79}$ | $R^{D79}$ | $R^{D79}$ |
| $L_{C80}$ | $R^{D80}$ | $R^{D80}$ |
| $L_{C81}$ | $R^{D81}$ | $R^{D81}$ |
| $L_{C82}$ | $R^{D82}$ | $R^{D82}$ |
| $L_{C83}$ | $R^{D83}$ | $R^{D83}$ |
| $L_{C84}$ | $R^{D84}$ | $R^{D84}$ |
| $L_{C85}$ | $R^{D85}$ | $R^{D85}$ |
| $L_{C86}$ | $R^{D86}$ | $R^{D86}$ |
| $L_{C87}$ | $R^{D87}$ | $R^{D87}$ |
| $L_{C88}$ | $R^{D88}$ | $R^{D88}$ |
| $L_{C89}$ | $R^{D89}$ | $R^{D89}$ |
| $L_{C90}$ | $R^{D90}$ | $R^{D90}$ |
| $L_{C91}$ | $R^{D91}$ | $R^{D91}$ |
| $L_{C92}$ | $R^{D92}$ | $R^{D92}$ |
| $L_{C93}$ | $R^{D93}$ | $R^{D93}$ |
| $L_{C94}$ | $R^{D94}$ | $R^{D94}$ |
| $L_{C95}$ | $R^{D95}$ | $R^{D95}$ |
| $L_{C96}$ | $R^{D96}$ | $R^{D96}$ |
| $L_{C97}$ | $R^{D97}$ | $R^{D97}$ |
| $L_{C98}$ | $R^{D98}$ | $R^{D98}$ |
| $L_{C99}$ | $R^{D99}$ | $R^{D99}$ |
| $L_{C100}$ | $R^{D100}$ | $R^{D100}$ |
| $L_{C101}$ | $R^{D101}$ | $R^{D101}$ |
| $L_{C102}$ | $R^{D102}$ | $R^{D102}$ |
| $L_{C103}$ | $R^{D103}$ | $R^{D103}$ |
| $L_{C104}$ | $R^{D104}$ | $R^{D104}$ |
| $L_{C105}$ | $R^{D105}$ | $R^{D105}$ |
| $L_{C106}$ | $R^{D106}$ | $R^{D106}$ |
| $L_{C107}$ | $R^{D107}$ | $R^{D107}$ |
| $L_{C108}$ | $R^{D108}$ | $R^{D108}$ |
| $L_{C109}$ | $R^{D109}$ | $R^{D109}$ |
| $L_{C110}$ | $R^{D110}$ | $R^{D110}$ |
| $L_{C111}$ | $R^{D111}$ | $R^{D111}$ |
| $L_{C112}$ | $R^{D112}$ | $R^{D112}$ |
| $L_{C113}$ | $R^{D113}$ | $R^{D113}$ |
| $L_{C114}$ | $R^{D114}$ | $R^{D114}$ |
| $L_{C115}$ | $R^{D115}$ | $R^{D115}$ |
| $L_{C116}$ | $R^{D116}$ | $R^{D116}$ |
| $L_{C117}$ | $R^{D117}$ | $R^{D117}$ |
| $L_{C118}$ | $R^{D118}$ | $R^{D118}$ |
| $L_{C119}$ | $R^{D119}$ | $R^{D119}$ |
| $L_{C120}$ | $R^{D120}$ | $R^{D120}$ |
| $L_{C121}$ | $R^{D121}$ | $R^{D121}$ |
| $L_{C122}$ | $R^{D122}$ | $R^{D122}$ |
| $L_{C123}$ | $R^{D123}$ | $R^{D123}$ |
| $L_{C124}$ | $R^{D124}$ | $R^{D124}$ |

-continued

| $L_{Cj}$ | $R^{201}$ | $R^{202}$ |
|---|---|---|
| $L_{C125}$ | $R^{D125}$ | $R^{D125}$ |
| $L_{C126}$ | $R^{D126}$ | $R^{D126}$ |
| $L_{C127}$ | $R^{D127}$ | $R^{D127}$ |
| $L_{C128}$ | $R^{D128}$ | $R^{D128}$ |
| $L_{C129}$ | $R^{D129}$ | $R^{D129}$ |
| $L_{C130}$ | $R^{D130}$ | $R^{D130}$ |
| $L_{C131}$ | $R^{D131}$ | $R^{D131}$ |
| $L_{C132}$ | $R^{D132}$ | $R^{D132}$ |
| $L_{C133}$ | $R^{D133}$ | $R^{D133}$ |
| $L_{C134}$ | $R^{D134}$ | $R^{D134}$ |
| $L_{C135}$ | $R^{D135}$ | $R^{D135}$ |
| $L_{C136}$ | $R^{D136}$ | $R^{D136}$ |
| $L_{C137}$ | $R^{D137}$ | $R^{D137}$ |
| $L_{C138}$ | $R^{D138}$ | $R^{D138}$ |
| $L_{C139}$ | $R^{D139}$ | $R^{D139}$ |
| $L_{C140}$ | $R^{D140}$ | $R^{D140}$ |
| $L_{C141}$ | $R^{D141}$ | $R^{D141}$ |
| $L_{C142}$ | $R^{D142}$ | $R^{D142}$ |
| $L_{C143}$ | $R^{D143}$ | $R^{D143}$ |
| $L_{C144}$ | $R^{D144}$ | $R^{D144}$ |
| $L_{C145}$ | $R^{D145}$ | $R^{D145}$ |
| $L_{C146}$ | $R^{D146}$ | $R^{D146}$ |
| $L_{C147}$ | $R^{D147}$ | $R^{D147}$ |
| $L_{C148}$ | $R^{D148}$ | $R^{D148}$ |
| $L_{C149}$ | $R^{D149}$ | $R^{D149}$ |
| $L_{C150}$ | $R^{D150}$ | $R^{D150}$ |
| $L_{C151}$ | $R^{D151}$ | $R^{D151}$ |
| $L_{C152}$ | $R^{D152}$ | $R^{D152}$ |
| $L_{C153}$ | $R^{D153}$ | $R^{D153}$ |
| $L_{C154}$ | $R^{D154}$ | $R^{D154}$ |
| $L_{C155}$ | $R^{D155}$ | $R^{D155}$ |
| $L_{C156}$ | $R^{D156}$ | $R^{D156}$ |
| $L_{C157}$ | $R^{D157}$ | $R^{D157}$ |
| $L_{C158}$ | $R^{D158}$ | $R^{D158}$ |
| $L_{C159}$ | $R^{D159}$ | $R^{D159}$ |
| $L_{C160}$ | $R^{D160}$ | $R^{D160}$ |
| $L_{C161}$ | $R^{D161}$ | $R^{D161}$ |
| $L_{C162}$ | $R^{D162}$ | $R^{D162}$ |
| $L_{C163}$ | $R^{D163}$ | $R^{D163}$ |
| $L_{C164}$ | $R^{D164}$ | $R^{D164}$ |
| $L_{C165}$ | $R^{D165}$ | $R^{D165}$ |
| $L_{C166}$ | $R^{D166}$ | $R^{D166}$ |
| $L_{C167}$ | $R^{D167}$ | $R^{D167}$ |
| $L_{C168}$ | $R^{D168}$ | $R^{D168}$ |
| $L_{C169}$ | $R^{D169}$ | $R^{D169}$ |
| $L_{C170}$ | $R^{D170}$ | $R^{D170}$ |
| $L_{C171}$ | $R^{D171}$ | $R^{D171}$ |
| $L_{C172}$ | $R^{D172}$ | $R^{D172}$ |
| $L_{C173}$ | $R^{D173}$ | $R^{D173}$ |
| $L_{C174}$ | $R^{D174}$ | $R^{D174}$ |
| $L_{C175}$ | $R^{D175}$ | $R^{D175}$ |
| $L_{C176}$ | $R^{D176}$ | $R^{D176}$ |
| $L_{C177}$ | $R^{D177}$ | $R^{D177}$ |
| $L_{C178}$ | $R^{D178}$ | $R^{D178}$ |
| $L_{C179}$ | $R^{D179}$ | $R^{D179}$ |
| $L_{C180}$ | $R^{D180}$ | $R^{D180}$ |
| $L_{C181}$ | $R^{D181}$ | $R^{D181}$ |
| $L_{C182}$ | $R^{D182}$ | $R^{D182}$ |
| $L_{C183}$ | $R^{D183}$ | $R^{D183}$ |
| $L_{C184}$ | $R^{D184}$ | $R^{D184}$ |
| $L_{C185}$ | $R^{D185}$ | $R^{D185}$ |
| $L_{C186}$ | $R^{D186}$ | $R^{D186}$ |
| $L_{C187}$ | $R^{D187}$ | $R^{D187}$ |
| $L_{C188}$ | $R^{D188}$ | $R^{D188}$ |
| $L_{C189}$ | $R^{D189}$ | $R^{D189}$ |
| $L_{C190}$ | $R^{D190}$ | $R^{D190}$ |
| $L_{C191}$ | $R^{D191}$ | $R^{D191}$ |
| $L_{C192}$ | $R^{D192}$ | $R^{D192}$ |
| $L_{C193}$ | $R^{D1}$ | $R^{D3}$ |
| $L_{C194}$ | $R^{D1}$ | $R^{D4}$ |
| $L_{C195}$ | $R^{D1}$ | $R^{D5}$ |
| $L_{C196}$ | $R^{D1}$ | $R^{D9}$ |
| $L_{C197}$ | $R^{D1}$ | $R^{D10}$ |
| $L_{C198}$ | $R^{D1}$ | $R^{D17}$ |
| $L_{C199}$ | $R^{D1}$ | $R^{D18}$ |
| $L_{C200}$ | $R^{D1}$ | $R^{D20}$ |
| $L_{C201}$ | $R^{D1}$ | $R^{D22}$ |

-continued

| $L_{Cj}$ | $R^{201}$ | $R^{202}$ |
|---|---|---|
| $L_{C202}$ | $R^{D1}$ | $R^{D37}$ |
| $L_{C203}$ | $R^{D1}$ | $R^{D40}$ |
| $L_{C204}$ | $R^{D1}$ | $R^{D41}$ |
| $L_{C205}$ | $R^{D1}$ | $R^{D42}$ |
| $L_{C206}$ | $R^{D1}$ | $R^{D43}$ |
| $L_{C207}$ | $R^{D1}$ | $R^{D48}$ |
| $L_{C208}$ | $R^{D1}$ | $R^{D49}$ |
| $L_{C209}$ | $R^{D1}$ | $R^{D50}$ |
| $L_{C210}$ | $R^{D1}$ | $R^{D54}$ |
| $L_{C211}$ | $R^{D1}$ | $R^{D55}$ |
| $L_{C212}$ | $R^{D1}$ | $R^{D58}$ |
| $L_{C213}$ | $R^{D1}$ | $R^{D59}$ |
| $L_{C214}$ | $R^{D1}$ | $R^{D78}$ |
| $L_{C215}$ | $R^{D1}$ | $R^{D79}$ |
| $L_{C216}$ | $R^{D1}$ | $R^{D81}$ |
| $L_{C217}$ | $R^{D1}$ | $R^{D87}$ |
| $L_{C218}$ | $R^{D1}$ | $R^{D88}$ |
| $L_{C219}$ | $R^{D1}$ | $R^{D89}$ |
| $L_{C220}$ | $R^{D1}$ | $R^{D93}$ |
| $L_{C221}$ | $R^{D1}$ | $R^{D116}$ |
| $L_{C222}$ | $R^{D1}$ | $R^{D117}$ |
| $L_{C223}$ | $R^{D1}$ | $R^{D118}$ |
| $L_{C224}$ | $R^{D1}$ | $R^{D119}$ |
| $L_{C225}$ | $R^{D1}$ | $R^{D120}$ |
| $L_{C226}$ | $R^{D1}$ | $R^{D133}$ |
| $L_{C227}$ | $R^{D1}$ | $R^{D134}$ |
| $L_{C228}$ | $R^{D1}$ | $R^{D135}$ |
| $L_{C229}$ | $R^{D1}$ | $R^{D136}$ |
| $L_{C230}$ | $R^{D1}$ | $R^{D143}$ |
| $L_{C231}$ | $R^{D1}$ | $R^{D144}$ |
| $L_{C232}$ | $R^{D1}$ | $R^{D145}$ |
| $L_{C233}$ | $R^{D1}$ | $R^{D146}$ |
| $L_{C234}$ | $R^{D1}$ | $R^{D147}$ |
| $L_{C235}$ | $R^{D1}$ | $R^{D149}$ |
| $L_{C236}$ | $R^{D1}$ | $R^{D151}$ |
| $L_{C237}$ | $R^{D1}$ | $R^{D154}$ |
| $L_{C238}$ | $R^{D1}$ | $R^{D155}$ |
| $L_{C239}$ | $R^{D1}$ | $R^{D161}$ |
| $L_{C240}$ | $R^{D1}$ | $R^{D175}$ |
| $L_{C241}$ | $R^{D4}$ | $R^{D3}$ |
| $L_{C242}$ | $R^{D4}$ | $R^{D5}$ |
| $L_{C243}$ | $R^{D4}$ | $R^{D9}$ |
| $L_{C244}$ | $R^{D4}$ | $R^{D10}$ |
| $L_{C245}$ | $R^{D4}$ | $R^{D17}$ |
| $L_{C246}$ | $R^{D4}$ | $R^{D18}$ |
| $L_{C247}$ | $R^{D4}$ | $R^{D20}$ |
| $L_{C248}$ | $R^{D4}$ | $R^{D22}$ |
| $L_{C249}$ | $R^{D4}$ | $R^{D37}$ |
| $L_{C250}$ | $R^{D4}$ | $R^{D40}$ |
| $L_{C251}$ | $R^{D4}$ | $R^{D41}$ |
| $L_{C252}$ | $R^{D4}$ | $R^{D42}$ |
| $L_{C253}$ | $R^{D4}$ | $R^{D43}$ |
| $L_{C254}$ | $R^{D4}$ | $R^{D48}$ |
| $L_{C255}$ | $R^{D4}$ | $R^{D49}$ |
| $L_{C256}$ | $R^{D4}$ | $R^{D50}$ |
| $L_{C257}$ | $R^{D4}$ | $R^{D54}$ |
| $L_{C258}$ | $R^{D4}$ | $R^{D55}$ |
| $L_{C259}$ | $R^{D4}$ | $R^{D58}$ |
| $L_{C260}$ | $R^{D4}$ | $R^{D59}$ |
| $L_{C261}$ | $R^{D4}$ | $R^{D78}$ |
| $L_{C262}$ | $R^{D4}$ | $R^{D79}$ |
| $L_{C263}$ | $R^{D4}$ | $R^{D81}$ |
| $L_{C264}$ | $R^{D4}$ | $R^{D87}$ |
| $L_{C265}$ | $R^{D4}$ | $R^{D88}$ |
| $L_{C266}$ | $R^{D4}$ | $R^{D89}$ |
| $L_{C267}$ | $R^{D4}$ | $R^{D93}$ |
| $L_{C268}$ | $R^{D4}$ | $R^{D116}$ |
| $L_{C269}$ | $R^{D4}$ | $R^{D117}$ |
| $L_{C270}$ | $R^{D4}$ | $R^{D118}$ |
| $L_{C271}$ | $R^{D4}$ | $R^{D119}$ |
| $L_{C272}$ | $R^{D4}$ | $R^{D120}$ |
| $L_{C273}$ | $R^{D4}$ | $R^{D133}$ |
| $L_{C274}$ | $R^{D4}$ | $R^{D134}$ |
| $L_{C275}$ | $R^{D4}$ | $R^{D135}$ |
| $L_{C276}$ | $R^{D4}$ | $R^{D136}$ |
| $L_{C277}$ | $R^{D4}$ | $R^{D143}$ |
| $L_{C278}$ | $R^{D4}$ | $R^{D144}$ |

-continued

| $L_{Cj}$ | $R^{201}$ | $R^{202}$ |
|---|---|---|
| $L_{C279}$ | $R^{D4}$ | $R^{D145}$ |
| $L_{C280}$ | $R^{D4}$ | $R^{D146}$ |
| $L_{C281}$ | $R^{D4}$ | $R^{D147}$ |
| $L_{C282}$ | $R^{D4}$ | $R^{D149}$ |
| $L_{C283}$ | $R^{D4}$ | $R^{D151}$ |
| $L_{C284}$ | $R^{D4}$ | $R^{D154}$ |
| $L_{C285}$ | $R^{D4}$ | $R^{D155}$ |
| $L_{C286}$ | $R^{D4}$ | $R^{D161}$ |
| $L_{C287}$ | $R^{D4}$ | $R^{D175}$ |
| $L_{C288}$ | $R^{D9}$ | $R^{D3}$ |
| $L_{C289}$ | $R^{D9}$ | $R^{D5}$ |
| $L_{C290}$ | $R^{D9}$ | $R^{D10}$ |
| $L_{C291}$ | $R^{D9}$ | $R^{D17}$ |
| $L_{C292}$ | $R^{D9}$ | $R^{D18}$ |
| $L_{C293}$ | $R^{D9}$ | $R^{D20}$ |
| $L_{C294}$ | $R^{D9}$ | $R^{D22}$ |
| $L_{C295}$ | $R^{D9}$ | $R^{D37}$ |
| $L_{C296}$ | $R^{D9}$ | $R^{D40}$ |
| $L_{C297}$ | $R^{D9}$ | $R^{D41}$ |
| $L_{C298}$ | $R^{D9}$ | $R^{D42}$ |
| $L_{C299}$ | $R^{D9}$ | $R^{D43}$ |
| $L_{C300}$ | $R^{D9}$ | $R^{D48}$ |
| $L_{C301}$ | $R^{D9}$ | $R^{D49}$ |
| $L_{C302}$ | $R^{D9}$ | $R^{D50}$ |
| $L_{C303}$ | $R^{D9}$ | $R^{D54}$ |
| $L_{C304}$ | $R^{D9}$ | $R^{D55}$ |
| $L_{C305}$ | $R^{D9}$ | $R^{D58}$ |
| $L_{C306}$ | $R^{D9}$ | $R^{D59}$ |
| $L_{C307}$ | $R^{D9}$ | $R^{D78}$ |
| $L_{C308}$ | $R^{D9}$ | $R^{D79}$ |
| $L_{C309}$ | $R^{D9}$ | $R^{D81}$ |
| $L_{C310}$ | $R^{D9}$ | $R^{D87}$ |
| $L_{C311}$ | $R^{D9}$ | $R^{D88}$ |
| $L_{C312}$ | $R^{D9}$ | $R^{D89}$ |
| $L_{C313}$ | $R^{D9}$ | $R^{D93}$ |
| $L_{C314}$ | $R^{D9}$ | $R^{D116}$ |
| $L_{C315}$ | $R^{D9}$ | $R^{D117}$ |
| $L_{C316}$ | $R^{D9}$ | $R^{D118}$ |
| $L_{C317}$ | $R^{D9}$ | $R^{D119}$ |
| $L_{C318}$ | $R^{D9}$ | $R^{D120}$ |
| $L_{C319}$ | $R^{D9}$ | $R^{D133}$ |
| $L_{C320}$ | $R^{D9}$ | $R^{D134}$ |
| $L_{C321}$ | $R^{D9}$ | $R^{D135}$ |
| $L_{C322}$ | $R^{D9}$ | $R^{D136}$ |
| $L_{C323}$ | $R^{D9}$ | $R^{D143}$ |
| $L_{C324}$ | $R^{D9}$ | $R^{D144}$ |
| $L_{C325}$ | $R^{D9}$ | $R^{D145}$ |
| $L_{C326}$ | $R^{D9}$ | $R^{D146}$ |
| $L_{C327}$ | $R^{D9}$ | $R^{D147}$ |
| $L_{C328}$ | $R^{D9}$ | $R^{D149}$ |
| $L_{C329}$ | $R^{D9}$ | $R^{D151}$ |
| $L_{C330}$ | $R^{D9}$ | $R^{D154}$ |
| $L_{C331}$ | $R^{D9}$ | $R^{D155}$ |
| $L_{C332}$ | $R^{D9}$ | $R^{D161}$ |
| $L_{C333}$ | $R^{D9}$ | $R^{D175}$ |
| $L_{C334}$ | $R^{D10}$ | $R^{D3}$ |
| $L_{C335}$ | $R^{D10}$ | $R^{D5}$ |
| $L_{C336}$ | $R^{D10}$ | $R^{D17}$ |
| $L_{C337}$ | $R^{D10}$ | $R^{D18}$ |
| $L_{C338}$ | $R^{D10}$ | $R^{D20}$ |
| $L_{C339}$ | $R^{D10}$ | $R^{D22}$ |
| $L_{C340}$ | $R^{D10}$ | $R^{D37}$ |
| $L_{C341}$ | $R^{D10}$ | $R^{D40}$ |
| $L_{C342}$ | $R^{D10}$ | $R^{D41}$ |
| $L_{C343}$ | $R^{D10}$ | $R^{D42}$ |
| $L_{C344}$ | $R^{D10}$ | $R^{D43}$ |
| $L_{C345}$ | $R^{D10}$ | $R^{D48}$ |
| $L_{C346}$ | $R^{D10}$ | $R^{D49}$ |
| $L_{C347}$ | $R^{D10}$ | $R^{D50}$ |
| $L_{C348}$ | $R^{D10}$ | $R^{D54}$ |
| $L_{C349}$ | $R^{D10}$ | $R^{D55}$ |
| $L_{C350}$ | $R^{D10}$ | $R^{D58}$ |
| $L_{C351}$ | $R^{D10}$ | $R^{D59}$ |
| $L_{C352}$ | $R^{D10}$ | $R^{D78}$ |
| $L_{C353}$ | $R^{D10}$ | $R^{D79}$ |
| $L_{C354}$ | $R^{D10}$ | $R^{D81}$ |
| $L_{C355}$ | $R^{D10}$ | $R^{D87}$ |

-continued

| $L_{Cj}$ | $R^{201}$ | $R^{202}$ |
|---|---|---|
| $L_{C356}$ | $R^{D10}$ | $R^{D88}$ |
| $L_{C357}$ | $R^{D10}$ | $R^{D89}$ |
| $L_{C358}$ | $R^{D10}$ | $R^{D93}$ |
| $L_{C359}$ | $R^{D10}$ | $R^{D116}$ |
| $L_{C360}$ | $R^{D10}$ | $R^{D117}$ |
| $L_{C361}$ | $R^{D10}$ | $R^{D118}$ |
| $L_{C362}$ | $R^{D10}$ | $R^{D119}$ |
| $L_{C363}$ | $R^{D10}$ | $R^{D120}$ |
| $L_{C364}$ | $R^{D10}$ | $R^{D133}$ |
| $L_{C365}$ | $R^{D10}$ | $R^{D134}$ |
| $L_{C366}$ | $R^{D10}$ | $R^{D135}$ |
| $L_{C367}$ | $R^{D10}$ | $R^{D136}$ |
| $L_{C368}$ | $R^{D10}$ | $R^{D143}$ |
| $L_{C369}$ | $R^{D10}$ | $R^{D144}$ |
| $L_{C370}$ | $R^{D10}$ | $R^{D145}$ |
| $L_{C371}$ | $R^{D10}$ | $R^{D146}$ |
| $L_{C372}$ | $R^{D10}$ | $R^{D147}$ |
| $L_{C373}$ | $R^{D10}$ | $R^{D149}$ |
| $L_{C374}$ | $R^{D10}$ | $R^{D151}$ |
| $L_{C375}$ | $R^{D10}$ | $R^{D154}$ |
| $L_{C376}$ | $R^{D10}$ | $R^{D155}$ |
| $L_{C377}$ | $R^{D10}$ | $R^{D161}$ |
| $L_{C378}$ | $R^{D10}$ | $R^{D175}$ |
| $L_{C379}$ | $R^{D17}$ | $R^{D3}$ |
| $L_{C380}$ | $R^{D17}$ | $R^{D5}$ |
| $L_{C381}$ | $R^{D17}$ | $R^{D18}$ |
| $L_{C382}$ | $R^{D17}$ | $R^{D20}$ |
| $L_{C383}$ | $R^{D17}$ | $R^{D22}$ |
| $L_{C384}$ | $R^{D17}$ | $R^{D37}$ |
| $L_{C385}$ | $R^{D17}$ | $R^{D40}$ |
| $L_{C386}$ | $R^{D17}$ | $R^{D41}$ |
| $L_{C387}$ | $R^{D17}$ | $R^{D42}$ |
| $L_{C388}$ | $R^{D17}$ | $R^{D43}$ |
| $L_{C389}$ | $R^{D17}$ | $R^{D48}$ |
| $L_{C390}$ | $R^{D17}$ | $R^{D49}$ |
| $L_{C391}$ | $R^{D17}$ | $R^{D50}$ |
| $L_{C392}$ | $R^{D17}$ | $R^{D54}$ |
| $L_{C393}$ | $R^{D17}$ | $R^{D55}$ |
| $L_{C394}$ | $R^{D17}$ | $R^{D58}$ |
| $L_{C395}$ | $R^{D17}$ | $R^{D59}$ |
| $L_{C396}$ | $R^{D17}$ | $R^{D78}$ |
| $L_{C397}$ | $R^{D17}$ | $R^{D79}$ |
| $L_{C398}$ | $R^{D17}$ | $R^{D81}$ |
| $L_{C399}$ | $R^{D17}$ | $R^{D87}$ |
| $L_{C400}$ | $R^{D17}$ | $R^{D88}$ |
| $L_{C401}$ | $R^{D17}$ | $R^{D89}$ |
| $L_{C402}$ | $R^{D17}$ | $R^{D93}$ |
| $L_{C403}$ | $R^{D17}$ | $R^{D116}$ |
| $L_{C404}$ | $R^{D17}$ | $R^{D117}$ |
| $L_{C405}$ | $R^{D17}$ | $R^{D118}$ |
| $L_{C406}$ | $R^{D17}$ | $R^{D119}$ |
| $L_{C407}$ | $R^{D17}$ | $R^{D120}$ |
| $L_{C408}$ | $R^{D17}$ | $R^{D133}$ |
| $L_{C409}$ | $R^{D17}$ | $R^{D134}$ |
| $L_{C410}$ | $R^{D17}$ | $R^{D135}$ |
| $L_{C411}$ | $R^{D17}$ | $R^{D136}$ |
| $L_{C412}$ | $R^{D17}$ | $R^{D143}$ |
| $L_{C413}$ | $R^{D17}$ | $R^{D144}$ |
| $L_{C414}$ | $R^{D17}$ | $R^{D145}$ |
| $L_{C415}$ | $R^{D17}$ | $R^{D146}$ |
| $L_{C416}$ | $R^{D17}$ | $R^{D147}$ |
| $L_{C417}$ | $R^{D17}$ | $R^{D149}$ |
| $L_{C418}$ | $R^{D17}$ | $R^{D151}$ |
| $L_{C419}$ | $R^{D17}$ | $R^{D154}$ |
| $L_{C420}$ | $R^{D17}$ | $R^{D155}$ |
| $L_{C421}$ | $R^{D17}$ | $R^{D161}$ |
| $L_{C422}$ | $R^{D17}$ | $R^{D175}$ |
| $L_{C423}$ | $R^{D50}$ | $R^{D3}$ |
| $L_{C424}$ | $R^{D50}$ | $R^{D5}$ |
| $L_{C425}$ | $R^{D50}$ | $R^{D18}$ |
| $L_{C426}$ | $R^{D50}$ | $R^{D20}$ |
| $L_{C427}$ | $R^{D50}$ | $R^{D22}$ |
| $L_{C428}$ | $R^{D50}$ | $R^{D37}$ |
| $L_{C429}$ | $R^{D50}$ | $R^{D40}$ |
| $L_{C430}$ | $R^{D50}$ | $R^{D41}$ |
| $L_{C431}$ | $R^{D50}$ | $R^{D42}$ |
| $L_{C432}$ | $R^{D50}$ | $R^{D43}$ |

-continued

| $L_{Cj}$ | $R^{201}$ | $R^{202}$ |
|---|---|---|
| $L_{C433}$ | $R^{D50}$ | $R^{D48}$ |
| $L_{C434}$ | $R^{D50}$ | $R^{D49}$ |
| $L_{C435}$ | $R^{D50}$ | $R^{D54}$ |
| $L_{C436}$ | $R^{D50}$ | $R^{D55}$ |
| $L_{C437}$ | $R^{D50}$ | $R^{D58}$ |
| $L_{C438}$ | $R^{D50}$ | $R^{D59}$ |
| $L_{C439}$ | $R^{D50}$ | $R^{D78}$ |
| $L_{C440}$ | $R^{D50}$ | $R^{D79}$ |
| $L_{C441}$ | $R^{D50}$ | $R^{D81}$ |
| $L_{C442}$ | $R^{D50}$ | $R^{D87}$ |
| $L_{C443}$ | $R^{D50}$ | $R^{D88}$ |
| $L_{C444}$ | $R^{D50}$ | $R^{D89}$ |
| $L_{C445}$ | $R^{D50}$ | $R^{D93}$ |
| $L_{C446}$ | $R^{D50}$ | $R^{D116}$ |
| $L_{C447}$ | $R^{D50}$ | $R^{D117}$ |
| $L_{C448}$ | $R^{D50}$ | $R^{D118}$ |
| $L_{C449}$ | $R^{D50}$ | $R^{D119}$ |
| $L_{C450}$ | $R^{D50}$ | $R^{D120}$ |
| $L_{C451}$ | $R^{D50}$ | $R^{D133}$ |
| $L_{C452}$ | $R^{D50}$ | $R^{D134}$ |
| $L_{C453}$ | $R^{D50}$ | $R^{D135}$ |
| $L_{C454}$ | $R^{D50}$ | $R^{D136}$ |
| $L_{C455}$ | $R^{D50}$ | $R^{D143}$ |
| $L_{C456}$ | $R^{D50}$ | $R^{D144}$ |
| $L_{C457}$ | $R^{D50}$ | $R^{D145}$ |
| $L_{C458}$ | $R^{D50}$ | $R^{D146}$ |
| $L_{C459}$ | $R^{D50}$ | $R^{D147}$ |
| $L_{C460}$ | $R^{D50}$ | $R^{D149}$ |
| $L_{C461}$ | $R^{D50}$ | $R^{D151}$ |
| $L_{C462}$ | $R^{D50}$ | $R^{D154}$ |
| $L_{C463}$ | $R^{D50}$ | $R^{D155}$ |
| $L_{C464}$ | $R^{D50}$ | $R^{D161}$ |
| $L_{C465}$ | $R^{D50}$ | $R^{D175}$ |
| $L_{C466}$ | $R^{D55}$ | $R^{D3}$ |
| $L_{C467}$ | $R^{D55}$ | $R^{D5}$ |
| $L_{C468}$ | $R^{D55}$ | $R^{D18}$ |
| $L_{C469}$ | $R^{D55}$ | $R^{D20}$ |
| $L_{C470}$ | $R^{D55}$ | $R^{D22}$ |
| $L_{C471}$ | $R^{D55}$ | $R^{D37}$ |
| $L_{C472}$ | $R^{D55}$ | $R^{D40}$ |
| $L_{C473}$ | $R^{D55}$ | $R^{D41}$ |
| $L_{C474}$ | $R^{D55}$ | $R^{D42}$ |
| $L_{C475}$ | $R^{D55}$ | $R^{D43}$ |
| $L_{C476}$ | $R^{D55}$ | $R^{D48}$ |
| $L_{C477}$ | $R^{D55}$ | $R^{D49}$ |
| $L_{C478}$ | $R^{D55}$ | $R^{D54}$ |
| $L_{C479}$ | $R^{D55}$ | $R^{D58}$ |
| $L_{C480}$ | $R^{D55}$ | $R^{D59}$ |
| $L_{C481}$ | $R^{D55}$ | $R^{D78}$ |
| $L_{C482}$ | $R^{D55}$ | $R^{D79}$ |
| $L_{C483}$ | $R^{D55}$ | $R^{D81}$ |
| $L_{C484}$ | $R^{D55}$ | $R^{D87}$ |
| $L_{C485}$ | $R^{D55}$ | $R^{D88}$ |
| $L_{C486}$ | $R^{D55}$ | $R^{D89}$ |
| $L_{C487}$ | $R^{D55}$ | $R^{D93}$ |
| $L_{C488}$ | $R^{D55}$ | $R^{D116}$ |
| $L_{C489}$ | $R^{D55}$ | $R^{D117}$ |
| $L_{C490}$ | $R^{D55}$ | $R^{D118}$ |
| $L_{C491}$ | $R^{D55}$ | $R^{D119}$ |
| $L_{C492}$ | $R^{D55}$ | $R^{D120}$ |
| $L_{C493}$ | $R^{D55}$ | $R^{D133}$ |
| $L_{C494}$ | $R^{D55}$ | $R^{D134}$ |
| $L_{C495}$ | $R^{D55}$ | $R^{D135}$ |
| $L_{C496}$ | $R^{D55}$ | $R^{D136}$ |
| $L_{C497}$ | $R^{D55}$ | $R^{D143}$ |
| $L_{C498}$ | $R^{D55}$ | $R^{D144}$ |
| $L_{C499}$ | $R^{D55}$ | $R^{D145}$ |
| $L_{C500}$ | $R^{D55}$ | $R^{D146}$ |
| $L_{C501}$ | $R^{D55}$ | $R^{D147}$ |
| $L_{C502}$ | $R^{D55}$ | $R^{D149}$ |
| $L_{C503}$ | $R^{D55}$ | $R^{D151}$ |
| $L_{C504}$ | $R^{D55}$ | $R^{D154}$ |
| $L_{C505}$ | $R^{D55}$ | $R^{D155}$ |
| $L_{C506}$ | $R^{D55}$ | $R^{D161}$ |
| $L_{C507}$ | $R^{D55}$ | $R^{D175}$ |
| $L_{C508}$ | $R^{D116}$ | $R^{D3}$ |
| $L_{C509}$ | $R^{D116}$ | $R^{D5}$ |

-continued

| $L_{Cj}$ | $R^{201}$ | $R^{202}$ |
|---|---|---|
| $L_{C510}$ | $R^{D116}$ | $R^{D17}$ |
| $L_{C511}$ | $R^{D116}$ | $R^{D18}$ |
| $L_{C512}$ | $R^{D116}$ | $R^{D20}$ |
| $L_{C513}$ | $R^{D116}$ | $R^{D22}$ |
| $L_{C514}$ | $R^{D116}$ | $R^{D37}$ |
| $L_{C515}$ | $R^{D116}$ | $R^{D40}$ |
| $L_{C516}$ | $R^{D116}$ | $R^{D41}$ |
| $L_{C517}$ | $R^{D116}$ | $R^{D42}$ |
| $L_{C518}$ | $R^{D116}$ | $R^{D43}$ |
| $L_{C519}$ | $R^{D116}$ | $R^{D48}$ |
| $L_{C520}$ | $R^{D116}$ | $R^{D49}$ |
| $L_{C521}$ | $R^{D116}$ | $R^{D54}$ |
| $L_{C522}$ | $R^{D116}$ | $R^{D58}$ |
| $L_{C523}$ | $R^{D116}$ | $R^{D59}$ |
| $L_{C524}$ | $R^{D116}$ | $R^{D78}$ |
| $L_{C525}$ | $R^{D116}$ | $R^{D79}$ |
| $L_{C526}$ | $R^{D116}$ | $R^{D81}$ |
| $L_{C527}$ | $R^{D116}$ | $R^{D87}$ |
| $L_{C528}$ | $R^{D116}$ | $R^{D88}$ |
| $L_{C529}$ | $R^{D116}$ | $R^{D89}$ |
| $L_{C530}$ | $R^{D116}$ | $R^{D93}$ |
| $L_{C531}$ | $R^{D116}$ | $R^{D117}$ |
| $L_{C532}$ | $R^{D116}$ | $R^{D118}$ |
| $L_{C533}$ | $R^{D116}$ | $R^{D119}$ |
| $L_{C534}$ | $R^{D116}$ | $R^{D120}$ |
| $L_{C535}$ | $R^{D116}$ | $R^{D133}$ |
| $L_{C536}$ | $R^{D116}$ | $R^{D134}$ |
| $L_{C537}$ | $R^{D116}$ | $R^{D135}$ |
| $L_{C538}$ | $R^{D116}$ | $R^{D136}$ |
| $L_{C539}$ | $R^{D116}$ | $R^{D143}$ |
| $L_{C540}$ | $R^{D116}$ | $R^{D144}$ |
| $L_{C541}$ | $R^{D116}$ | $R^{D145}$ |
| $L_{C542}$ | $R^{D116}$ | $R^{D146}$ |
| $L_{C543}$ | $R^{D116}$ | $R^{D147}$ |
| $L_{C544}$ | $R^{D116}$ | $R^{D149}$ |
| $L_{C545}$ | $R^{D116}$ | $R^{D151}$ |
| $L_{C546}$ | $R^{D116}$ | $R^{D154}$ |
| $L_{C547}$ | $R^{D116}$ | $R^{D155}$ |
| $L_{C548}$ | $R^{D116}$ | $R^{D161}$ |
| $L_{C549}$ | $R^{D116}$ | $R^{D175}$ |
| $L_{C550}$ | $R^{D143}$ | $R^{D3}$ |
| $L_{C551}$ | $R^{D143}$ | $R^{D5}$ |
| $L_{C552}$ | $R^{D143}$ | $R^{D17}$ |
| $L_{C553}$ | $R^{D143}$ | $R^{D18}$ |
| $L_{C554}$ | $R^{D143}$ | $R^{D20}$ |
| $L_{C555}$ | $R^{D143}$ | $R^{D22}$ |
| $L_{C556}$ | $R^{D143}$ | $R^{D37}$ |
| $L_{C557}$ | $R^{D143}$ | $R^{D40}$ |
| $L_{C558}$ | $R^{D143}$ | $R^{D41}$ |
| $L_{C559}$ | $R^{D143}$ | $R^{D42}$ |
| $L_{C560}$ | $R^{D143}$ | $R^{D43}$ |
| $L_{C561}$ | $R^{D143}$ | $R^{D48}$ |
| $L_{C562}$ | $R^{D143}$ | $R^{D49}$ |
| $L_{C563}$ | $R^{D143}$ | $R^{D54}$ |
| $L_{C564}$ | $R^{D143}$ | $R^{D58}$ |
| $L_{C565}$ | $R^{D143}$ | $R^{D59}$ |
| $L_{C566}$ | $R^{D143}$ | $R^{D78}$ |
| $L_{C567}$ | $R^{D143}$ | $R^{D79}$ |
| $L_{C568}$ | $R^{D143}$ | $R^{D81}$ |
| $L_{C569}$ | $R^{D143}$ | $R^{D87}$ |
| $L_{C570}$ | $R^{D143}$ | $R^{D88}$ |
| $L_{C571}$ | $R^{D143}$ | $R^{D89}$ |
| $L_{C572}$ | $R^{D143}$ | $R^{D93}$ |
| $L_{C573}$ | $R^{D143}$ | $R^{D116}$ |
| $L_{C574}$ | $R^{D143}$ | $R^{D117}$ |
| $L_{C575}$ | $R^{D143}$ | $R^{D118}$ |
| $L_{C576}$ | $R^{D143}$ | $R^{D119}$ |
| $L_{C577}$ | $R^{D143}$ | $R^{D120}$ |
| $L_{C578}$ | $R^{D143}$ | $R^{D133}$ |
| $L_{C579}$ | $R^{D143}$ | $R^{D134}$ |
| $L_{C580}$ | $R^{D143}$ | $R^{D135}$ |
| $L_{C581}$ | $R^{D143}$ | $R^{D136}$ |
| $L_{C582}$ | $R^{D143}$ | $R^{D144}$ |
| $L_{C583}$ | $R^{D143}$ | $R^{D145}$ |
| $L_{C584}$ | $R^{D143}$ | $R^{D146}$ |
| $L_{C585}$ | $R^{D143}$ | $R^{D147}$ |
| $L_{C586}$ | $R^{D143}$ | $R^{D149}$ |

-continued

| $L_{Cj}$ | $R^{201}$ | $R^{202}$ |
|---|---|---|
| $L_{C587}$ | $R^{D143}$ | $R^{D151}$ |
| $L_{C588}$ | $R^{D143}$ | $R^{D154}$ |
| $L_{C589}$ | $R^{D143}$ | $R^{D155}$ |
| $L_{C590}$ | $R^{D143}$ | $R^{D161}$ |
| $L_{C591}$ | $R^{D143}$ | $R^{D175}$ |
| $L_{C592}$ | $R^{D144}$ | $R^{D3}$ |
| $L_{C593}$ | $R^{D144}$ | $R^{D5}$ |
| $L_{C594}$ | $R^{D144}$ | $R^{D17}$ |
| $L_{C595}$ | $R^{D144}$ | $R^{D18}$ |
| $L_{C596}$ | $R^{D144}$ | $R^{D20}$ |
| $L_{C597}$ | $R^{D144}$ | $R^{D22}$ |
| $L_{C598}$ | $R^{D144}$ | $R^{D37}$ |
| $L_{C599}$ | $R^{D144}$ | $R^{D40}$ |
| $L_{C600}$ | $R^{D144}$ | $R^{D41}$ |
| $L_{C601}$ | $R^{D144}$ | $R^{D42}$ |
| $L_{C602}$ | $R^{D144}$ | $R^{D43}$ |
| $L_{C603}$ | $R^{D144}$ | $R^{D48}$ |
| $L_{C604}$ | $R^{D144}$ | $R^{D49}$ |
| $L_{C605}$ | $R^{D144}$ | $R^{D54}$ |
| $L_{C606}$ | $R^{D144}$ | $R^{D58}$ |
| $L_{C607}$ | $R^{D144}$ | $R^{D59}$ |
| $L_{C608}$ | $R^{D144}$ | $R^{D78}$ |
| $L_{C609}$ | $R^{D144}$ | $R^{D79}$ |
| $L_{C610}$ | $R^{D144}$ | $R^{D81}$ |
| $L_{C611}$ | $R^{D144}$ | $R^{D87}$ |
| $L_{C612}$ | $R^{D144}$ | $R^{D88}$ |
| $L_{C613}$ | $R^{D144}$ | $R^{D89}$ |
| $L_{C614}$ | $R^{D144}$ | $R^{D93}$ |
| $L_{C615}$ | $R^{D144}$ | $R^{D116}$ |
| $L_{C616}$ | $R^{D144}$ | $R^{D117}$ |
| $L_{C617}$ | $R^{D144}$ | $R^{D118}$ |
| $L_{C618}$ | $R^{D144}$ | $R^{D119}$ |
| $L_{C619}$ | $R^{D144}$ | $R^{D120}$ |
| $L_{C620}$ | $R^{D144}$ | $R^{D133}$ |
| $L_{C621}$ | $R^{D144}$ | $R^{D134}$ |
| $L_{C622}$ | $R^{D144}$ | $R^{D135}$ |
| $L_{C623}$ | $R^{D144}$ | $R^{D136}$ |
| $L_{C624}$ | $R^{D144}$ | $R^{D145}$ |
| $L_{C625}$ | $R^{D144}$ | $R^{D146}$ |
| $L_{C626}$ | $R^{D144}$ | $R^{D147}$ |
| $L_{C627}$ | $R^{D144}$ | $R^{D149}$ |
| $L_{C628}$ | $R^{D144}$ | $R^{D151}$ |
| $L_{C629}$ | $R^{D144}$ | $R^{D154}$ |
| $L_{C630}$ | $R^{D144}$ | $R^{D155}$ |
| $L_{C631}$ | $R^{D144}$ | $R^{D161}$ |
| $L_{C632}$ | $R^{D144}$ | $R^{D175}$ |
| $L_{C633}$ | $R^{D145}$ | $R^{D3}$ |
| $L_{C634}$ | $R^{D145}$ | $R^{D5}$ |
| $L_{C635}$ | $R^{D145}$ | $R^{D17}$ |
| $L_{C636}$ | $R^{D145}$ | $R^{D18}$ |
| $L_{C637}$ | $R^{D145}$ | $R^{D20}$ |
| $L_{C638}$ | $R^{D145}$ | $R^{D22}$ |
| $L_{C639}$ | $R^{D145}$ | $R^{D37}$ |
| $L_{C640}$ | $R^{D145}$ | $R^{D40}$ |
| $L_{C641}$ | $R^{D145}$ | $R^{D41}$ |
| $L_{C642}$ | $R^{D145}$ | $R^{D42}$ |
| $L_{C643}$ | $R^{D145}$ | $R^{D43}$ |
| $L_{C644}$ | $R^{D145}$ | $R^{D48}$ |
| $L_{C645}$ | $R^{D145}$ | $R^{D49}$ |
| $L_{C646}$ | $R^{D145}$ | $R^{D54}$ |
| $L_{C647}$ | $R^{D145}$ | $R^{D58}$ |
| $L_{C648}$ | $R^{D145}$ | $R^{D59}$ |
| $L_{C649}$ | $R^{D145}$ | $R^{D78}$ |
| $L_{C650}$ | $R^{D145}$ | $R^{D79}$ |
| $L_{C651}$ | $R^{D145}$ | $R^{D81}$ |
| $L_{C652}$ | $R^{D145}$ | $R^{D87}$ |
| $L_{C653}$ | $R^{D145}$ | $R^{D88}$ |
| $L_{C654}$ | $R^{D145}$ | $R^{D89}$ |
| $L_{C655}$ | $R^{D145}$ | $R^{D93}$ |
| $L_{C656}$ | $R^{D145}$ | $R^{D116}$ |
| $L_{C657}$ | $R^{D145}$ | $R^{D117}$ |
| $L_{C658}$ | $R^{D145}$ | $R^{D118}$ |
| $L_{C659}$ | $R^{D145}$ | $R^{D119}$ |
| $L_{C660}$ | $R^{D145}$ | $R^{D120}$ |
| $L_{C661}$ | $R^{D145}$ | $R^{D133}$ |
| $L_{C662}$ | $R^{D145}$ | $R^{D134}$ |
| $L_{C663}$ | $R^{D145}$ | $R^{D135}$ |

-continued

| $L_{Cj}$ | $R^{201}$ | $R^{202}$ |
|---|---|---|
| $L_{C664}$ | $R^{D145}$ | $R^{D136}$ |
| $L_{C665}$ | $R^{D145}$ | $R^{D146}$ |
| $L_{C666}$ | $R^{D145}$ | $R^{D147}$ |
| $L_{C667}$ | $R^{D145}$ | $R^{D149}$ |
| $L_{C668}$ | $R^{D145}$ | $R^{D151}$ |
| $L_{C669}$ | $R^{D145}$ | $R^{D154}$ |
| $L_{C670}$ | $R^{D145}$ | $R^{D155}$ |
| $L_{C671}$ | $R^{D145}$ | $R^{D161}$ |
| $L_{C672}$ | $R^{D145}$ | $R^{D175}$ |
| $L_{C673}$ | $R^{D146}$ | $R^{D3}$ |
| $L_{C674}$ | $R^{D146}$ | $R^{D5}$ |
| $L_{C675}$ | $R^{D146}$ | $R^{D17}$ |
| $L_{C676}$ | $R^{D146}$ | $R^{D18}$ |
| $L_{C677}$ | $R^{D146}$ | $R^{D20}$ |
| $L_{C678}$ | $R^{D146}$ | $R^{D22}$ |
| $L_{C679}$ | $R^{D146}$ | $R^{D37}$ |
| $L_{C680}$ | $R^{D146}$ | $R^{D40}$ |
| $L_{C681}$ | $R^{D146}$ | $R^{D41}$ |
| $L_{C682}$ | $R^{D146}$ | $R^{D42}$ |
| $L_{C683}$ | $R^{D146}$ | $R^{D43}$ |
| $L_{C684}$ | $R^{D146}$ | $R^{D48}$ |
| $L_{C685}$ | $R^{D146}$ | $R^{D49}$ |
| $L_{C686}$ | $R^{D146}$ | $R^{D54}$ |
| $L_{C687}$ | $R^{D146}$ | $R^{D58}$ |
| $L_{C688}$ | $R^{D146}$ | $R^{D59}$ |
| $L_{C689}$ | $R^{D146}$ | $R^{D78}$ |
| $L_{C690}$ | $R^{D146}$ | $R^{D79}$ |
| $L_{C691}$ | $R^{D146}$ | $R^{D81}$ |
| $L_{C692}$ | $R^{D146}$ | $R^{D87}$ |
| $L_{C693}$ | $R^{D146}$ | $R^{D88}$ |
| $L_{C694}$ | $R^{D146}$ | $R^{D89}$ |
| $L_{C695}$ | $R^{D146}$ | $R^{D93}$ |
| $L_{C696}$ | $R^{D146}$ | $R^{D117}$ |
| $L_{C697}$ | $R^{D146}$ | $R^{D118}$ |
| $L_{C698}$ | $R^{D146}$ | $R^{D119}$ |
| $L_{C699}$ | $R^{D146}$ | $R^{D120}$ |
| $L_{C700}$ | $R^{D146}$ | $R^{D133}$ |
| $L_{C701}$ | $R^{D146}$ | $R^{D134}$ |
| $L_{C702}$ | $R^{D146}$ | $R^{D135}$ |
| $L_{C703}$ | $R^{D146}$ | $R^{D136}$ |
| $L_{C704}$ | $R^{D146}$ | $R^{D146}$ |
| $L_{C705}$ | $R^{D146}$ | $R^{D147}$ |
| $L_{C706}$ | $R^{D146}$ | $R^{D149}$ |
| $L_{C707}$ | $R^{D146}$ | $R^{D151}$ |
| $L_{C708}$ | $R^{D146}$ | $R^{D154}$ |
| $L_{C709}$ | $R^{D146}$ | $R^{D155}$ |
| $L_{C710}$ | $R^{D146}$ | $R^{D161}$ |
| $L_{C711}$ | $R^{D146}$ | $R^{D175}$ |
| $L_{C712}$ | $R^{D133}$ | $R^{D3}$ |
| $L_{C713}$ | $R^{D133}$ | $R^{D5}$ |
| $L_{C714}$ | $R^{D133}$ | $R^{D3}$ |
| $L_{C715}$ | $R^{D133}$ | $R^{D18}$ |
| $L_{C716}$ | $R^{D133}$ | $R^{D20}$ |
| $L_{C717}$ | $R^{D133}$ | $R^{D22}$ |
| $L_{C718}$ | $R^{D133}$ | $R^{D37}$ |
| $L_{C719}$ | $R^{D133}$ | $R^{D40}$ |
| $L_{C720}$ | $R^{D133}$ | $R^{D41}$ |
| $L_{C721}$ | $R^{D133}$ | $R^{D42}$ |
| $L_{C722}$ | $R^{D133}$ | $R^{D43}$ |
| $L_{C723}$ | $R^{D133}$ | $R^{D48}$ |
| $L_{C724}$ | $R^{D133}$ | $R^{D49}$ |
| $L_{C725}$ | $R^{D133}$ | $R^{D54}$ |
| $L_{C726}$ | $R^{D133}$ | $R^{D58}$ |
| $L_{C727}$ | $R^{D133}$ | $R^{D59}$ |
| $L_{C728}$ | $R^{D133}$ | $R^{D78}$ |
| $L_{C729}$ | $R^{D133}$ | $R^{D79}$ |
| $L_{C730}$ | $R^{D133}$ | $R^{D81}$ |
| $L_{C731}$ | $R^{D133}$ | $R^{D87}$ |
| $L_{C732}$ | $R^{D133}$ | $R^{D88}$ |
| $L_{C733}$ | $R^{D133}$ | $R^{D89}$ |
| $L_{C734}$ | $R^{D133}$ | $R^{D93}$ |
| $L_{C735}$ | $R^{D133}$ | $R^{D117}$ |
| $L_{C736}$ | $R^{D133}$ | $R^{D118}$ |
| $L_{C737}$ | $R^{D133}$ | $R^{D119}$ |
| $L_{C738}$ | $R^{D133}$ | $R^{D120}$ |
| $L_{C739}$ | $R^{D133}$ | $R^{D133}$ |
| $L_{C740}$ | $R^{D133}$ | $R^{D134}$ |

-continued

| $L_{Cj}$ | $R^{201}$ | $R^{202}$ |
|---|---|---|
| $L_{C741}$ | $R^{D133}$ | $R^{D135}$ |
| $L_{C742}$ | $R^{D133}$ | $R^{D136}$ |
| $L_{C743}$ | $R^{D133}$ | $R^{D146}$ |
| $L_{C744}$ | $R^{D133}$ | $R^{D147}$ |
| $L_{C745}$ | $R^{D133}$ | $R^{D149}$ |
| $L_{C746}$ | $R^{D133}$ | $R^{D151}$ |
| $L_{C747}$ | $R^{D133}$ | $R^{D154}$ |
| $L_{C748}$ | $R^{D133}$ | $R^{D155}$ |
| $L_{C749}$ | $R^{D133}$ | $R^{D161}$ |
| $L_{C750}$ | $R^{D133}$ | $R^{D175}$ |
| $L_{C751}$ | $R^{D175}$ | $R^{D3}$ |
| $L_{C752}$ | $R^{D175}$ | $R^{D5}$ |
| $L_{C753}$ | $R^{D175}$ | $R^{D18}$ |
| $L_{C754}$ | $R^{D175}$ | $R^{D20}$ |
| $L_{C755}$ | $R^{D175}$ | $R^{D22}$ |
| $L_{C756}$ | $R^{D175}$ | $R^{D37}$ |
| $L_{C757}$ | $R^{D175}$ | $R^{D40}$ |
| $L_{C758}$ | $R^{D175}$ | $R^{D41}$ |
| $L_{C759}$ | $R^{D175}$ | $R^{D42}$ |
| $L_{C760}$ | $R^{D175}$ | $R^{D43}$ |
| $L_{C761}$ | $R^{D175}$ | $R^{D48}$ |
| $L_{C762}$ | $R^{D175}$ | $R^{D49}$ |
| $L_{C763}$ | $R^{D175}$ | $R^{D54}$ |
| $L_{C764}$ | $R^{D175}$ | $R^{D58}$ |
| $L_{C765}$ | $R^{D175}$ | $R^{D59}$ |
| $L_{C766}$ | $R^{D175}$ | $R^{D78}$ |
| $L_{C767}$ | $R^{D175}$ | $R^{D79}$ |
| $L_{C768}$ | $R^{D175}$ | $R^{D81}$ |
| $L_{C769}$ | $R^{D193}$ | $R^{D193}$ |
| $L_{C770}$ | $R^{D194}$ | $R^{D194}$ |
| $L_{C771}$ | $R^{D195}$ | $R^{D195}$ |
| $L_{C772}$ | $R^{D196}$ | $R^{D196}$ |
| $L_{C773}$ | $R^{D197}$ | $R^{D197}$ |
| $L_{C774}$ | $R^{D198}$ | $R^{D198}$ |
| $L_{C775}$ | $R^{D199}$ | $R^{D199}$ |
| $L_{C776}$ | $R^{D200}$ | $R^{D200}$ |
| $L_{C777}$ | $R^{D201}$ | $R^{D201}$ |
| $L_{C778}$ | $R^{D202}$ | $R^{D202}$ |
| $L_{C779}$ | $R^{D203}$ | $R^{D203}$ |
| $L_{C780}$ | $R^{D204}$ | $R^{D204}$ |
| $L_{C781}$ | $R^{D205}$ | $R^{D205}$ |
| $L_{C782}$ | $R^{D206}$ | $R^{D206}$ |
| $L_{C783}$ | $R^{D207}$ | $R^{D207}$ |
| $L_{C784}$ | $R^{D208}$ | $R^{D208}$ |
| $L_{C785}$ | $R^{D209}$ | $R^{D209}$ |
| $L_{C786}$ | $R^{D210}$ | $R^{D210}$ |
| $L_{C787}$ | $R^{D211}$ | $R^{D211}$ |
| $L_{C788}$ | $R^{D212}$ | $R^{D212}$ |
| $L_{C789}$ | $R^{D213}$ | $R^{D213}$ |
| $L_{C790}$ | $R^{D214}$ | $R^{D214}$ |
| $L_{C791}$ | $R^{D215}$ | $R^{D215}$ |
| $L_{C792}$ | $R^{D216}$ | $R^{D216}$ |
| $L_{C793}$ | $R^{D217}$ | $R^{D217}$ |
| $L_{C794}$ | $R^{D218}$ | $R^{D218}$ |
| $L_{C795}$ | $R^{D219}$ | $R^{D219}$ |
| $L_{C796}$ | $R^{D220}$ | $R^{D220}$ |
| $L_{C797}$ | $R^{D221}$ | $R^{D221}$ |
| $L_{C798}$ | $R^{D222}$ | $R^{D222}$ |
| $L_{C799}$ | $R^{D223}$ | $R^{D223}$ |
| $L_{C800}$ | $R^{D224}$ | $R^{D224}$ |
| $L_{C801}$ | $R^{D225}$ | $R^{D225}$ |
| $L_{C802}$ | $R^{D226}$ | $R^{D226}$ |
| $L_{C803}$ | $R^{D227}$ | $R^{D227}$ |
| $L_{C804}$ | $R^{D228}$ | $R^{D228}$ |
| $L_{C805}$ | $R^{D229}$ | $R^{D229}$ |
| $L_{C806}$ | $R^{D230}$ | $R^{D230}$ |
| $L_{C807}$ | $R^{D231}$ | $R^{D231}$ |
| $L_{C808}$ | $R^{D232}$ | $R^{D232}$ |
| $L_{C809}$ | $R^{D233}$ | $R^{D233}$ |
| $L_{C810}$ | $R^{D234}$ | $R^{D234}$ |
| $L_{C811}$ | $R^{D235}$ | $R^{D235}$ |
| $L_{C812}$ | $R^{D236}$ | $R^{D236}$ |
| $L_{C813}$ | $R^{D237}$ | $R^{D237}$ |
| $L_{C814}$ | $R^{D238}$ | $R^{D238}$ |
| $L_{C815}$ | $R^{D239}$ | $R^{D239}$ |
| $L_{C816}$ | $R^{D240}$ | $R^{D240}$ |
| $L_{C817}$ | $R^{D241}$ | $R^{D241}$ |

-continued

| $L_{Cj}$ | $R^{201}$ | $R^{202}$ |
|---|---|---|
| $L_{C818}$ | $R^{D242}$ | $R^{D242}$ |
| $L_{C819}$ | $R^{D243}$ | $R^{D243}$ |
| $L_{C820}$ | $R^{D244}$ | $R^{D244}$ |
| $L_{C821}$ | $R^{D245}$ | $R^{D245}$ |
| $L_{C822}$ | $R^{D246}$ | $R^{D246}$ |
| $L_{C823}$ | $R^{D17}$ | $R^{D193}$ |
| $L_{C824}$ | $R^{D17}$ | $R^{D194}$ |
| $L_{C825}$ | $R^{D17}$ | $R^{D195}$ |
| $L_{C826}$ | $R^{D17}$ | $R^{D196}$ |
| $L_{C827}$ | $R^{D17}$ | $R^{D197}$ |
| $L_{C828}$ | $R^{D17}$ | $R^{D198}$ |
| $L_{C829}$ | $R^{D17}$ | $R^{D199}$ |
| $L_{C830}$ | $R^{D17}$ | $R^{D200}$ |
| $L_{C831}$ | $R^{D17}$ | $R^{D201}$ |
| $L_{C832}$ | $R^{D17}$ | $R^{D202}$ |
| $L_{C833}$ | $R^{D17}$ | $R^{D203}$ |
| $L_{C834}$ | $R^{D17}$ | $R^{D204}$ |
| $L_{C835}$ | $R^{D17}$ | $R^{D205}$ |
| $L_{C836}$ | $R^{D17}$ | $R^{D206}$ |
| $L_{C837}$ | $R^{D17}$ | $R^{D207}$ |
| $L_{C838}$ | $R^{D17}$ | $R^{D208}$ |
| $L_{C839}$ | $R^{D17}$ | $R^{D209}$ |
| $L_{C840}$ | $R^{D17}$ | $R^{D210}$ |
| $L_{C841}$ | $R^{D17}$ | $R^{D211}$ |
| $L_{C842}$ | $R^{D17}$ | $R^{D212}$ |
| $L_{C843}$ | $R^{D17}$ | $R^{D213}$ |
| $L_{C844}$ | $R^{D17}$ | $R^{D214}$ |
| $L_{C845}$ | $R^{D17}$ | $R^{D215}$ |
| $L_{C846}$ | $R^{D17}$ | $R^{D216}$ |
| $L_{C847}$ | $R^{D17}$ | $R^{D217}$ |
| $L_{C848}$ | $R^{D17}$ | $R^{D218}$ |
| $L_{C849}$ | $R^{D17}$ | $R^{D219}$ |
| $L_{C850}$ | $R^{D17}$ | $R^{D220}$ |
| $L_{C851}$ | $R^{D17}$ | $R^{D221}$ |
| $L_{C852}$ | $R^{D17}$ | $R^{D222}$ |
| $L_{C853}$ | $R^{D17}$ | $R^{D223}$ |
| $L_{C854}$ | $R^{D17}$ | $R^{D224}$ |
| $L_{C855}$ | $R^{D17}$ | $R^{D225}$ |
| $L_{C856}$ | $R^{D17}$ | $R^{D226}$ |
| $L_{C857}$ | $R^{D17}$ | $R^{D227}$ |
| $L_{C858}$ | $R^{D17}$ | $R^{D228}$ |
| $L_{C859}$ | $R^{D17}$ | $R^{D229}$ |
| $L_{C860}$ | $R^{D17}$ | $R^{D230}$ |
| $L_{C861}$ | $R^{D17}$ | $R^{D231}$ |
| $L_{C862}$ | $R^{D17}$ | $R^{D232}$ |
| $L_{C863}$ | $R^{D17}$ | $R^{D233}$ |
| $L_{C864}$ | $R^{D17}$ | $R^{D234}$ |
| $L_{C865}$ | $R^{D17}$ | $R^{D235}$ |
| $L_{C866}$ | $R^{D17}$ | $R^{D236}$ |
| $L_{C867}$ | $R^{D17}$ | $R^{D237}$ |
| $L_{C868}$ | $R^{D17}$ | $R^{D238}$ |
| $L_{C869}$ | $R^{D17}$ | $R^{D239}$ |
| $L_{C870}$ | $R^{D17}$ | $R^{D240}$ |
| $L_{C871}$ | $R^{D17}$ | $R^{D241}$ |
| $L_{C872}$ | $R^{D17}$ | $R^{D242}$ |
| $L_{C873}$ | $R^{D17}$ | $R^{D243}$ |
| $L_{C874}$ | $R^{D17}$ | $R^{D244}$ |
| $L_{C875}$ | $R^{D17}$ | $R^{D245}$ |
| $L_{C876}$ | $R^{D17}$ | $R^{D246}$ |
| $L_{C877}$ | $R^{D17}$ | $R^{D193}$ |
| $L_{C878}$ | $R^{D1}$ | $R^{D194}$ |
| $L_{C879}$ | $R^{D1}$ | $R^{D195}$ |
| $L_{C880}$ | $R^{D1}$ | $R^{D196}$ |
| $L_{C881}$ | $R^{D1}$ | $R^{D197}$ |
| $L_{C882}$ | $R^{D1}$ | $R^{D198}$ |
| $L_{C883}$ | $R^{D1}$ | $R^{D199}$ |
| $L_{C884}$ | $R^{D1}$ | $R^{D200}$ |
| $L_{C885}$ | $R^{D1}$ | $R^{D201}$ |
| $L_{C886}$ | $R^{D1}$ | $R^{D202}$ |
| $L_{C887}$ | $R^{D1}$ | $R^{D203}$ |
| $L_{C888}$ | $R^{D1}$ | $R^{D204}$ |
| $L_{C889}$ | $R^{D1}$ | $R^{D205}$ |
| $L_{C890}$ | $R^{D1}$ | $R^{D206}$ |
| $L_{C891}$ | $R^{D1}$ | $R^{D207}$ |
| $L_{C892}$ | $R^{D1}$ | $R^{D208}$ |
| $L_{C893}$ | $R^{D1}$ | $R^{D209}$ |
| $L_{C894}$ | $R^{D1}$ | $R^{D210}$ |

-continued

| $L_{Cj}$ | $R^{201}$ | $R^{202}$ |
|---|---|---|
| $L_{C895}$ | $R^{D1}$ | $R^{D211}$ |
| $L_{C896}$ | $R^{D1}$ | $R^{D212}$ |
| $L_{C897}$ | $R^{D1}$ | $R^{D213}$ |
| $L_{C898}$ | $R^{D1}$ | $R^{D214}$ |
| $L_{C899}$ | $R^{D1}$ | $R^{D215}$ |
| $L_{C900}$ | $R^{D1}$ | $R^{D216}$ |
| $L_{C901}$ | $R^{D1}$ | $R^{D217}$ |
| $L_{C902}$ | $R^{D1}$ | $R^{D218}$ |
| $L_{C903}$ | $R^{D1}$ | $R^{D219}$ |
| $L_{C904}$ | $R^{D1}$ | $R^{D220}$ |
| $L_{C905}$ | $R^{D1}$ | $R^{D221}$ |
| $L_{C906}$ | $R^{D1}$ | $R^{D222}$ |
| $L_{C907}$ | $R^{D1}$ | $R^{D223}$ |
| $L_{C908}$ | $R^{D1}$ | $R^{D224}$ |
| $L_{C909}$ | $R^{D1}$ | $R^{D225}$ |
| $L_{C910}$ | $R^{D1}$ | $R^{D226}$ |
| $L_{C911}$ | $R^{D1}$ | $R^{D227}$ |
| $L_{C912}$ | $R^{D1}$ | $R^{D228}$ |
| $L_{C913}$ | $R^{D1}$ | $R^{D229}$ |
| $L_{C914}$ | $R^{D1}$ | $R^{D230}$ |
| $L_{C915}$ | $R^{D1}$ | $R^{D231}$ |
| $L_{C916}$ | $R^{D1}$ | $R^{D232}$ |
| $L_{C917}$ | $R^{D1}$ | $R^{D233}$ |
| $L_{C918}$ | $R^{D1}$ | $R^{D234}$ |
| $L_{C919}$ | $R^{D1}$ | $R^{D235}$ |
| $L_{C920}$ | $R^{D1}$ | $R^{D236}$ |
| $L_{C921}$ | $R^{D1}$ | $R^{D237}$ |
| $L_{C922}$ | $R^{D1}$ | $R^{D238}$ |
| $L_{C923}$ | $R^{D1}$ | $R^{D239}$ |
| $L_{C924}$ | $R^{D1}$ | $R^{D240}$ |
| $L_{C925}$ | $R^{D1}$ | $R^{D241}$ |
| $L_{C926}$ | $R^{D1}$ | $R^{D242}$ |
| $L_{C927}$ | $R^{D1}$ | $R^{D243}$ |
| $L_{C928}$ | $R^{D1}$ | $R^{D244}$ |
| $L_{C929}$ | $R^{D1}$ | $R^{D245}$ |
| $L_{C930}$ | $R^{D1}$ | $R^{D246}$ |
| $L_{C931}$ | $R^{D50}$ | $R^{D193}$ |
| $L_{C932}$ | $R^{D50}$ | $R^{D194}$ |
| $L_{C933}$ | $R^{D50}$ | $R^{D195}$ |
| $L_{C934}$ | $R^{D50}$ | $R^{D196}$ |
| $L_{C935}$ | $R^{D50}$ | $R^{D197}$ |
| $L_{C936}$ | $R^{D50}$ | $R^{D198}$ |
| $L_{C937}$ | $R^{D50}$ | $R^{D199}$ |
| $L_{C938}$ | $R^{D50}$ | $R^{D200}$ |
| $L_{C939}$ | $R^{D50}$ | $R^{D201}$ |
| $L_{C940}$ | $R^{D50}$ | $R^{D202}$ |
| $L_{C941}$ | $R^{D50}$ | $R^{D203}$ |
| $L_{C942}$ | $R^{D50}$ | $R^{D204}$ |
| $L_{C943}$ | $R^{D50}$ | $R^{D205}$ |
| $L_{C944}$ | $R^{D50}$ | $R^{D206}$ |
| $L_{C945}$ | $R^{D50}$ | $R^{D207}$ |
| $L_{C946}$ | $R^{D50}$ | $R^{D208}$ |
| $L_{C947}$ | $R^{D50}$ | $R^{D209}$ |
| $L_{C948}$ | $R^{D50}$ | $R^{D210}$ |
| $L_{C949}$ | $R^{D50}$ | $R^{D211}$ |
| $L_{C950}$ | $R^{D50}$ | $R^{D212}$ |
| $L_{C951}$ | $R^{D50}$ | $R^{D213}$ |
| $L_{C952}$ | $R^{D50}$ | $R^{D214}$ |
| $L_{C953}$ | $R^{D50}$ | $R^{D215}$ |
| $L_{C954}$ | $R^{D50}$ | $R^{D216}$ |
| $L_{C955}$ | $R^{D50}$ | $R^{D217}$ |
| $L_{C956}$ | $R^{D50}$ | $R^{D218}$ |
| $L_{C957}$ | $R^{D50}$ | $R^{D219}$ |
| $L_{C958}$ | $R^{D50}$ | $R^{D220}$ |
| $L_{C959}$ | $R^{D50}$ | $R^{D221}$ |
| $L_{C960}$ | $R^{D50}$ | $R^{D222}$ |
| $L_{C961}$ | $R^{D50}$ | $R^{D223}$ |
| $L_{C962}$ | $R^{D50}$ | $R^{D224}$ |
| $L_{C963}$ | $R^{D50}$ | $R^{D225}$ |
| $L_{C964}$ | $R^{D50}$ | $R^{D226}$ |
| $L_{C965}$ | $R^{D50}$ | $R^{D227}$ |
| $L_{C966}$ | $R^{D50}$ | $R^{D228}$ |
| $L_{C967}$ | $R^{D50}$ | $R^{D229}$ |
| $L_{C968}$ | $R^{D50}$ | $R^{D230}$ |
| $L_{C969}$ | $R^{D50}$ | $R^{D231}$ |
| $L_{C970}$ | $R^{D50}$ | $R^{D232}$ |
| $L_{C971}$ | $R^{D50}$ | $R^{D233}$ |

-continued

| $L_{Cj}$ | $R^{201}$ | $R^{202}$ |
|---|---|---|
| $L_{C972}$ | $R^{D50}$ | $R^{D234}$ |
| $L_{C973}$ | $R^{D50}$ | $R^{D235}$ |
| $L_{C974}$ | $R^{D50}$ | $R^{D236}$ |
| $L_{C975}$ | $R^{D50}$ | $R^{D237}$ |
| $L_{C976}$ | $R^{D50}$ | $R^{D238}$ |
| $L_{C977}$ | $R^{D50}$ | $R^{D239}$ |
| $L_{C978}$ | $R^{D50}$ | $R^{D240}$ |
| $L_{C979}$ | $R^{D50}$ | $R^{D241}$ |
| $L_{C980}$ | $R^{D50}$ | $R^{D242}$ |
| $L_{C981}$ | $R^{D50}$ | $R^{D243}$ |
| $L_{C982}$ | $R^{D50}$ | $R^{D244}$ |
| $L_{C983}$ | $R^{D50}$ | $R^{D245}$ |
| $L_{C984}$ | $R^{D50}$ | $R^{D246}$ |
| $L_{C985}$ | $R^{D143}$ | $R^{D193}$ |
| $L_{C986}$ | $R^{D4}$ | $R^{D194}$ |
| $L_{C987}$ | $R^{D4}$ | $R^{D195}$ |
| $L_{C988}$ | $R^{D4}$ | $R^{D196}$ |
| $L_{C989}$ | $R^{D4}$ | $R^{D197}$ |
| $L_{C990}$ | $R^{D4}$ | $R^{D198}$ |
| $L_{C991}$ | $R^{D4}$ | $R^{D199}$ |
| $L_{C992}$ | $R^{D4}$ | $R^{D200}$ |
| $L_{C993}$ | $R^{D4}$ | $R^{D201}$ |
| $L_{C994}$ | $R^{D4}$ | $R^{D202}$ |
| $L_{C995}$ | $R^{D4}$ | $R^{D203}$ |
| $L_{C996}$ | $R^{D4}$ | $R^{D204}$ |
| $L_{C997}$ | $R^{D4}$ | $R^{D205}$ |
| $L_{C998}$ | $R^{D4}$ | $R^{D206}$ |
| $L_{C999}$ | $R^{D4}$ | $R^{D207}$ |
| $L_{C1000}$ | $R^{D4}$ | $R^{D208}$ |
| $L_{C1001}$ | $R^{D4}$ | $R^{D209}$ |
| $L_{C1002}$ | $R^{D4}$ | $R^{D210}$ |
| $L_{C1003}$ | $R^{D4}$ | $R^{D211}$ |
| $L_{C1004}$ | $R^{D4}$ | $R^{D212}$ |
| $L_{C1005}$ | $R^{D4}$ | $R^{D213}$ |
| $L_{C1006}$ | $R^{D4}$ | $R^{D214}$ |
| $L_{C1007}$ | $R^{D4}$ | $R^{D215}$ |
| $L_{C1008}$ | $R^{D4}$ | $R^{D216}$ |
| $L_{C1009}$ | $R^{D4}$ | $R^{D217}$ |
| $L_{C1010}$ | $R^{D4}$ | $R^{D218}$ |
| $L_{C1011}$ | $R^{D4}$ | $R^{D219}$ |
| $L_{C1012}$ | $R^{D4}$ | $R^{D220}$ |
| $L_{C1013}$ | $R^{D4}$ | $R^{D221}$ |
| $L_{C1014}$ | $R^{D4}$ | $R^{D222}$ |
| $L_{C1015}$ | $R^{D4}$ | $R^{D223}$ |
| $L_{C1016}$ | $R^{D4}$ | $R^{D224}$ |
| $L_{C1017}$ | $R^{D4}$ | $R^{D225}$ |
| $L_{C1018}$ | $R^{D4}$ | $R^{D226}$ |
| $L_{C1019}$ | $R^{D4}$ | $R^{D227}$ |
| $L_{C1020}$ | $R^{D4}$ | $R^{D228}$ |
| $L_{C1021}$ | $R^{D4}$ | $R^{D229}$ |
| $L_{C1022}$ | $R^{D4}$ | $R^{D230}$ |
| $L_{C1023}$ | $R^{D4}$ | $R^{D231}$ |
| $L_{C1024}$ | $R^{D4}$ | $R^{D232}$ |
| $L_{C1025}$ | $R^{D4}$ | $R^{D233}$ |
| $L_{C1026}$ | $R^{D4}$ | $R^{D234}$ |
| $L_{C1027}$ | $R^{D4}$ | $R^{D235}$ |
| $L_{C1028}$ | $R^{D4}$ | $R^{D236}$ |
| $L_{C1029}$ | $R^{D4}$ | $R^{D237}$ |
| $L_{C1030}$ | $R^{D4}$ | $R^{D238}$ |
| $L_{C1031}$ | $R^{D4}$ | $R^{D239}$ |
| $L_{C1032}$ | $R^{D4}$ | $R^{D240}$ |
| $L_{C1033}$ | $R^{D4}$ | $R^{D241}$ |
| $L_{C1034}$ | $R^{D4}$ | $R^{D242}$ |
| $L_{C1035}$ | $R^{D4}$ | $R^{D243}$ |
| $L_{C1036}$ | $R^{D4}$ | $R^{D244}$ |
| $L_{C1037}$ | $R^{D4}$ | $R^{D245}$ |
| $L_{C1038}$ | $R^{D4}$ | $R^{D246}$ |
| $L_{C1039}$ | $R^{D145}$ | $R^{D193}$ |
| $L_{C1040}$ | $R^{D145}$ | $R^{D194}$ |
| $L_{C1041}$ | $R^{D145}$ | $R^{D195}$ |
| $L_{C1042}$ | $R^{D145}$ | $R^{D196}$ |
| $L_{C1043}$ | $R^{D145}$ | $R^{D197}$ |
| $L_{C1044}$ | $R^{D145}$ | $R^{D198}$ |
| $L_{C1045}$ | $R^{D145}$ | $R^{D199}$ |
| $L_{C1046}$ | $R^{D145}$ | $R^{D200}$ |
| $L_{C1047}$ | $R^{D145}$ | $R^{D201}$ |
| $L_{C1048}$ | $R^{D145}$ | $R^{D202}$ |

-continued

| $L_{Cj}$ | $R^{201}$ | $R^{202}$ |
|---|---|---|
| $L_{C1049}$ | $R^{D145}$ | $R^{D203}$ |
| $L_{C1050}$ | $R^{D145}$ | $R^{D204}$ |
| $L_{C1051}$ | $R^{D145}$ | $R^{D205}$ |
| $L_{C1052}$ | $R^{D145}$ | $R^{D206}$ |
| $L_{C1053}$ | $R^{D145}$ | $R^{D207}$ |
| $L_{C1054}$ | $R^{D145}$ | $R^{D208}$ |
| $L_{C1055}$ | $R^{D145}$ | $R^{D209}$ |
| $L_{C1056}$ | $R^{D145}$ | $R^{D210}$ |
| $L_{C1057}$ | $R^{D145}$ | $R^{D211}$ |
| $L_{C1058}$ | $R^{D145}$ | $R^{D212}$ |
| $L_{C1059}$ | $R^{D145}$ | $R^{D213}$ |
| $L_{C1060}$ | $R^{D145}$ | $R^{D214}$ |
| $L_{C1061}$ | $R^{D145}$ | $R^{D215}$ |
| $L_{C1062}$ | $R^{D145}$ | $R^{D216}$ |
| $L_{C1063}$ | $R^{D145}$ | $R^{D217}$ |
| $L_{C1064}$ | $R^{D145}$ | $R^{D218}$ |
| $L_{C1065}$ | $R^{D145}$ | $R^{D219}$ |
| $L_{C1066}$ | $R^{D145}$ | $R^{D220}$ |
| $L_{C1067}$ | $R^{D145}$ | $R^{D221}$ |
| $L_{C1068}$ | $R^{D145}$ | $R^{D222}$ |
| $L_{C1069}$ | $R^{D145}$ | $R^{D223}$ |
| $L_{C1070}$ | $R^{D145}$ | $R^{D224}$ |
| $L_{C1071}$ | $R^{D145}$ | $R^{D225}$ |
| $L_{C1072}$ | $R^{D145}$ | $R^{D226}$ |
| $L_{C1073}$ | $R^{D145}$ | $R^{D227}$ |
| $L_{C1074}$ | $R^{D145}$ | $R^{D228}$ |
| $L_{C1075}$ | $R^{D145}$ | $R^{D229}$ |
| $L_{C1076}$ | $R^{D145}$ | $R^{D230}$ |
| $L_{C1077}$ | $R^{D145}$ | $R^{D231}$ |
| $L_{C1078}$ | $R^{D145}$ | $R^{D232}$ |
| $L_{C1079}$ | $R^{D145}$ | $R^{D233}$ |
| $L_{C1080}$ | $R^{D145}$ | $R^{D234}$ |
| $L_{C1081}$ | $R^{D145}$ | $R^{D235}$ |
| $L_{C1082}$ | $R^{D145}$ | $R^{D236}$ |
| $L_{C1083}$ | $R^{D145}$ | $R^{D237}$ |
| $L_{C1084}$ | $R^{D145}$ | $R^{D238}$ |
| $L_{C1085}$ | $R^{D145}$ | $R^{D239}$ |
| $L_{C1086}$ | $R^{D145}$ | $R^{D240}$ |
| $L_{C1087}$ | $R^{D145}$ | $R^{D241}$ |
| $L_{C1088}$ | $R^{D145}$ | $R^{D242}$ |
| $L_{C1089}$ | $R^{D145}$ | $R^{D243}$ |
| $L_{C1090}$ | $R^{D145}$ | $R^{D244}$ |
| $L_{C1091}$ | $R^{D145}$ | $R^{D245}$ |
| $L_{C1092}$ | $R^{D145}$ | $R^{D246}$ |
| $L_{C1093}$ | $R^{D9}$ | $R^{D193}$ |
| $L_{C1094}$ | $R^{D9}$ | $R^{D194}$ |
| $L_{C1095}$ | $R^{D9}$ | $R^{D195}$ |
| $L_{C1096}$ | $R^{D9}$ | $R^{D196}$ |
| $L_{C1097}$ | $R^{D9}$ | $R^{D197}$ |
| $L_{C1098}$ | $R^{D9}$ | $R^{D198}$ |
| $L_{C1099}$ | $R^{D9}$ | $R^{D199}$ |
| $L_{C1100}$ | $R^{D9}$ | $R^{D200}$ |
| $L_{C1101}$ | $R^{D9}$ | $R^{D201}$ |
| $L_{C1102}$ | $R^{D9}$ | $R^{D202}$ |
| $L_{C1103}$ | $R^{D9}$ | $R^{D203}$ |
| $L_{C1104}$ | $R^{D9}$ | $R^{D204}$ |
| $L_{C1105}$ | $R^{D9}$ | $R^{D205}$ |
| $L_{C1106}$ | $R^{D9}$ | $R^{D206}$ |
| $L_{C1107}$ | $R^{D9}$ | $R^{D207}$ |
| $L_{C1108}$ | $R^{D9}$ | $R^{D208}$ |
| $L_{C1109}$ | $R^{D9}$ | $R^{D209}$ |
| $L_{C1110}$ | $R^{D9}$ | $R^{D210}$ |
| $L_{C1111}$ | $R^{D9}$ | $R^{D211}$ |
| $L_{C1112}$ | $R^{D9}$ | $R^{D212}$ |
| $L_{C1113}$ | $R^{D9}$ | $R^{D213}$ |
| $L_{C1114}$ | $R^{D9}$ | $R^{D214}$ |
| $L_{C1115}$ | $R^{D9}$ | $R^{D215}$ |
| $L_{C1116}$ | $R^{D9}$ | $R^{D216}$ |
| $L_{C1117}$ | $R^{D9}$ | $R^{D217}$ |
| $L_{C1118}$ | $R^{D9}$ | $R^{D218}$ |
| $L_{C1119}$ | $R^{D9}$ | $R^{D219}$ |
| $L_{C1120}$ | $R^{D9}$ | $R^{D220}$ |
| $L_{C1121}$ | $R^{D9}$ | $R^{D221}$ |
| $L_{C1122}$ | $R^{D9}$ | $R^{D222}$ |
| $L_{C1123}$ | $R^{D9}$ | $R^{D223}$ |
| $L_{C1124}$ | $R^{D9}$ | $R^{D224}$ |
| $L_{C1125}$ | $R^{D9}$ | $R^{D225}$ |

-continued

| $L_{Cj}$ | $R^{201}$ | $R^{202}$ |
|---|---|---|
| $L_{C1126}$ | $R^{D9}$ | $R^{D226}$ |
| $L_{C1127}$ | $R^{D9}$ | $R^{D227}$ |
| $L_{C1128}$ | $R^{D9}$ | $R^{D228}$ |
| $L_{C1129}$ | $R^{D9}$ | $R^{D229}$ |
| $L_{C1130}$ | $R^{D9}$ | $R^{D230}$ |
| $L_{C1131}$ | $R^{D9}$ | $R^{D231}$ |
| $L_{C1132}$ | $R^{D9}$ | $R^{D232}$ |
| $L_{C1133}$ | $R^{D9}$ | $R^{D233}$ |
| $L_{C1134}$ | $R^{D9}$ | $R^{D234}$ |
| $L_{C1135}$ | $R^{D9}$ | $R^{D235}$ |
| $L_{C1136}$ | $R^{D9}$ | $R^{D236}$ |
| $L_{C1137}$ | $R^{D9}$ | $R^{D237}$ |
| $L_{C1138}$ | $R^{D9}$ | $R^{D238}$ |
| $L_{C1139}$ | $R^{D9}$ | $R^{D239}$ |
| $L_{C1140}$ | $R^{D9}$ | $R^{D240}$ |
| $L_{C1141}$ | $R^{D9}$ | $R^{D241}$ |
| $L_{C1142}$ | $R^{D9}$ | $R^{D242}$ |
| $L_{C1143}$ | $R^{D9}$ | $R^{D243}$ |
| $L_{C1144}$ | $R^{D9}$ | $R^{D244}$ |
| $L_{C1145}$ | $R^{D9}$ | $R^{D245}$ |
| $L_{C1146}$ | $R^{D9}$ | $R^{D246}$ |
| $L_{C1147}$ | $R^{D168}$ | $R^{D193}$ |
| $L_{C1148}$ | $R^{D168}$ | $R^{D194}$ |
| $L_{C1149}$ | $R^{D168}$ | $R^{D195}$ |
| $L_{C1150}$ | $R^{D168}$ | $R^{D196}$ |
| $L_{C1151}$ | $R^{D168}$ | $R^{D197}$ |
| $L_{C1152}$ | $R^{D168}$ | $R^{D198}$ |
| $L_{C1153}$ | $R^{D168}$ | $R^{D199}$ |
| $L_{C1154}$ | $R^{D168}$ | $R^{D200}$ |
| $L_{C1155}$ | $R^{D168}$ | $R^{D201}$ |
| $L_{C1156}$ | $R^{D168}$ | $R^{D202}$ |
| $L_{C1157}$ | $R^{D168}$ | $R^{D203}$ |
| $L_{C1158}$ | $R^{D168}$ | $R^{D204}$ |
| $L_{C1159}$ | $R^{D168}$ | $R^{D205}$ |
| $L_{C1160}$ | $R^{D168}$ | $R^{D206}$ |
| $L_{C1161}$ | $R^{D168}$ | $R^{D207}$ |
| $L_{C1162}$ | $R^{D168}$ | $R^{D208}$ |
| $L_{C1163}$ | $R^{D168}$ | $R^{D209}$ |
| $L_{C1164}$ | $R^{D168}$ | $R^{D210}$ |
| $L_{C1165}$ | $R^{D168}$ | $R^{D211}$ |
| $L_{C1166}$ | $R^{D168}$ | $R^{D212}$ |
| $L_{C1167}$ | $R^{D168}$ | $R^{D213}$ |
| $L_{C1168}$ | $R^{D168}$ | $R^{D214}$ |
| $L_{C1169}$ | $R^{D168}$ | $R^{D215}$ |
| $L_{C1170}$ | $R^{D168}$ | $R^{D216}$ |
| $L_{C1171}$ | $R^{D168}$ | $R^{D217}$ |
| $L_{C1172}$ | $R^{D168}$ | $R^{D218}$ |
| $L_{C1173}$ | $R^{D168}$ | $R^{D219}$ |
| $L_{C1174}$ | $R^{D168}$ | $R^{D220}$ |
| $L_{C1175}$ | $R^{D168}$ | $R^{D221}$ |
| $L_{C1176}$ | $R^{D168}$ | $R^{D222}$ |
| $L_{C1177}$ | $R^{D168}$ | $R^{D223}$ |
| $L_{C1178}$ | $R^{D168}$ | $R^{D224}$ |
| $L_{C1179}$ | $R^{D168}$ | $R^{D225}$ |
| $L_{C1180}$ | $R^{D168}$ | $R^{D226}$ |
| $L_{C1181}$ | $R^{D168}$ | $R^{D227}$ |
| $L_{C1182}$ | $R^{D168}$ | $R^{D228}$ |
| $L_{C1183}$ | $R^{D168}$ | $R^{D229}$ |
| $L_{C1184}$ | $R^{D168}$ | $R^{D230}$ |
| $L_{C1185}$ | $R^{D168}$ | $R^{D231}$ |
| $L_{C1186}$ | $R^{D168}$ | $R^{D232}$ |
| $L_{C1187}$ | $R^{D168}$ | $R^{D233}$ |
| $L_{C1188}$ | $R^{D168}$ | $R^{D234}$ |
| $L_{C1189}$ | $R^{D168}$ | $R^{D235}$ |
| $L_{C1190}$ | $R^{D168}$ | $R^{D236}$ |
| $L_{C1191}$ | $R^{D168}$ | $R^{D237}$ |
| $L_{C1192}$ | $R^{D168}$ | $R^{D238}$ |
| $L_{C1193}$ | $R^{D168}$ | $R^{D239}$ |
| $L_{C1194}$ | $R^{D168}$ | $R^{D240}$ |
| $L_{C1195}$ | $R^{D168}$ | $R^{D241}$ |
| $L_{C1196}$ | $R^{D168}$ | $R^{D242}$ |
| $L_{C1197}$ | $R^{D168}$ | $R^{D243}$ |
| $L_{C1198}$ | $R^{D168}$ | $R^{D244}$ |
| $L_{C1199}$ | $R^{D168}$ | $R^{D245}$ |
| $L_{C1200}$ | $R^{D168}$ | $R^{D246}$ |
| $L_{C1201}$ | $R^{D10}$ | $R^{D193}$ |
| $L_{C1202}$ | $R^{D10}$ | $R^{D194}$ |

-continued

| $L_{Cj}$ | $R^{201}$ | $R^{202}$ |
|---|---|---|
| $L_{C1203}$ | $R^{D10}$ | $R^{D195}$ |
| $L_{C1204}$ | $R^{D10}$ | $R^{D196}$ |
| $L_{C1205}$ | $R^{D10}$ | $R^{D197}$ |
| $L_{C1206}$ | $R^{D10}$ | $R^{D198}$ |
| $L_{C1207}$ | $R^{D10}$ | $R^{D199}$ |
| $L_{C1208}$ | $R^{D10}$ | $R^{D200}$ |
| $L_{C1209}$ | $R^{D10}$ | $R^{D201}$ |
| $L_{C1210}$ | $R^{D10}$ | $R^{D202}$ |
| $L_{C1211}$ | $R^{D10}$ | $R^{D203}$ |
| $L_{C1212}$ | $R^{D10}$ | $R^{D204}$ |
| $L_{C1213}$ | $R^{D10}$ | $R^{D205}$ |
| $L_{C1214}$ | $R^{D10}$ | $R^{D206}$ |
| $L_{C1215}$ | $R^{D10}$ | $R^{D207}$ |
| $L_{C1216}$ | $R^{D10}$ | $R^{D208}$ |
| $L_{C1217}$ | $R^{D10}$ | $R^{D209}$ |
| $L_{C1218}$ | $R^{D10}$ | $R^{D210}$ |
| $L_{C1219}$ | $R^{D10}$ | $R^{D211}$ |
| $L_{C1220}$ | $R^{D10}$ | $R^{D212}$ |
| $L_{C1221}$ | $R^{D10}$ | $R^{D213}$ |
| $L_{C1222}$ | $R^{D10}$ | $R^{D214}$ |
| $L_{C1223}$ | $R^{D10}$ | $R^{D215}$ |
| $L_{C1224}$ | $R^{D10}$ | $R^{D216}$ |
| $L_{C1225}$ | $R^{D10}$ | $R^{D217}$ |
| $L_{C1226}$ | $R^{D10}$ | $R^{D218}$ |
| $L_{C1227}$ | $R^{D10}$ | $R^{D219}$ |
| $L_{C1228}$ | $R^{D10}$ | $R^{D220}$ |
| $L_{C1229}$ | $R^{D10}$ | $R^{D221}$ |
| $L_{C1230}$ | $R^{D10}$ | $R^{D222}$ |
| $L_{C1231}$ | $R^{D10}$ | $R^{D223}$ |
| $L_{C1232}$ | $R^{D10}$ | $R^{D224}$ |
| $L_{C1233}$ | $R^{D10}$ | $R^{D225}$ |
| $L_{C1234}$ | $R^{D10}$ | $R^{D226}$ |
| $L_{C1235}$ | $R^{D10}$ | $R^{D227}$ |
| $L_{C1236}$ | $R^{D10}$ | $R^{D228}$ |
| $L_{C1237}$ | $R^{D10}$ | $R^{D229}$ |
| $L_{C1238}$ | $R^{D10}$ | $R^{D230}$ |
| $L_{C1239}$ | $R^{D10}$ | $R^{D231}$ |
| $L_{C1240}$ | $R^{D10}$ | $R^{D232}$ |
| $L_{C1241}$ | $R^{D10}$ | $R^{D233}$ |
| $L_{C1242}$ | $R^{D10}$ | $R^{D234}$ |
| $L_{C1243}$ | $R^{D10}$ | $R^{D235}$ |
| $L_{C1244}$ | $R^{D10}$ | $R^{D236}$ |
| $L_{C1245}$ | $R^{D10}$ | $R^{D237}$ |
| $L_{C1246}$ | $R^{D10}$ | $R^{D238}$ |
| $L_{C1247}$ | $R^{D10}$ | $R^{D239}$ |
| $L_{C1248}$ | $R^{D10}$ | $R^{D240}$ |
| $L_{C1249}$ | $R^{D10}$ | $R^{D241}$ |
| $L_{C1250}$ | $R^{D10}$ | $R^{D242}$ |
| $L_{C1251}$ | $R^{D10}$ | $R^{D243}$ |
| $L_{C1252}$ | $R^{D10}$ | $R^{D244}$ |
| $L_{C1253}$ | $R^{D10}$ | $R^{D245}$ |
| $L_{C1254}$ | $R^{D10}$ | $R^{D246}$ |
| $L_{C1255}$ | $R^{D55}$ | $R^{D193}$ |
| $L_{C1256}$ | $R^{D55}$ | $R^{D194}$ |
| $L_{C1257}$ | $R^{D55}$ | $R^{D195}$ |
| $L_{C1258}$ | $R^{D55}$ | $R^{D196}$ |
| $L_{C1259}$ | $R^{D55}$ | $R^{D197}$ |
| $L_{C1260}$ | $R^{D55}$ | $R^{D198}$ |
| $L_{C1261}$ | $R^{D55}$ | $R^{D199}$ |
| $L_{C1262}$ | $R^{D55}$ | $R^{D200}$ |
| $L_{C1263}$ | $R^{D55}$ | $R^{D201}$ |
| $L_{C1264}$ | $R^{D55}$ | $R^{D202}$ |
| $L_{C1265}$ | $R^{D55}$ | $R^{D203}$ |
| $L_{C1266}$ | $R^{D55}$ | $R^{D204}$ |
| $L_{C1267}$ | $R^{D55}$ | $R^{D205}$ |
| $L_{C1268}$ | $R^{D55}$ | $R^{D206}$ |
| $L_{C1269}$ | $R^{D55}$ | $R^{D207}$ |
| $L_{C1270}$ | $R^{D55}$ | $R^{D208}$ |
| $L_{C1271}$ | $R^{D55}$ | $R^{D209}$ |
| $L_{C1272}$ | $R^{D55}$ | $R^{D210}$ |
| $L_{C1273}$ | $R^{D55}$ | $R^{D211}$ |
| $L_{C1274}$ | $R^{D55}$ | $R^{D212}$ |
| $L_{C1275}$ | $R^{D55}$ | $R^{D213}$ |
| $L_{C1276}$ | $R^{D55}$ | $R^{D214}$ |
| $L_{C1277}$ | $R^{D55}$ | $R^{D215}$ |
| $L_{C1278}$ | $R^{D55}$ | $R^{D216}$ |
| $L_{C1279}$ | $R^{D55}$ | $R^{D217}$ |

-continued

| $L_{Cj}$ | $R^{201}$ | $R^{202}$ |
|---|---|---|
| $L_{C1280}$ | $R^{D55}$ | $R^{D218}$ |
| $L_{C1281}$ | $R^{D55}$ | $R^{D219}$ |
| $L_{C1282}$ | $R^{D55}$ | $R^{D220}$ |
| $L_{C1283}$ | $R^{D55}$ | $R^{D221}$ |
| $L_{C1284}$ | $R^{D55}$ | $R^{D222}$ |
| $L_{C1285}$ | $R^{D55}$ | $R^{D223}$ |
| $L_{C1286}$ | $R^{D55}$ | $R^{D224}$ |
| $L_{C1287}$ | $R^{D55}$ | $R^{D225}$ |
| $L_{C1288}$ | $R^{D55}$ | $R^{D226}$ |
| $L_{C1289}$ | $R^{D55}$ | $R^{D227}$ |
| $L_{C1290}$ | $R^{D55}$ | $R^{D228}$ |
| $L_{C1291}$ | $R^{D55}$ | $R^{D229}$ |
| $L_{C1292}$ | $R^{D55}$ | $R^{D230}$ |
| $L_{C1293}$ | $R^{D55}$ | $R^{D231}$ |
| $L_{C1294}$ | $R^{D55}$ | $R^{D232}$ |
| $L_{C1295}$ | $R^{D55}$ | $R^{D233}$ |
| $L_{C1296}$ | $R^{D55}$ | $R^{D234}$ |
| $L_{C1297}$ | $R^{D55}$ | $R^{D235}$ |
| $L_{C1298}$ | $R^{D55}$ | $R^{D236}$ |
| $L_{C1299}$ | $R^{D55}$ | $R^{D237}$ |
| $L_{C1300}$ | $R^{D55}$ | $R^{D238}$ |
| $L_{C1301}$ | $R^{D55}$ | $R^{D239}$ |
| $L_{C1302}$ | $R^{D55}$ | $R^{D240}$ |
| $L_{C1303}$ | $R^{D55}$ | $R^{D241}$ |
| $L_{C1304}$ | $R^{D55}$ | $R^{D242}$ |
| $L_{C1305}$ | $R^{D55}$ | $R^{D243}$ |
| $L_{C1306}$ | $R^{D55}$ | $R^{D244}$ |
| $L_{C1307}$ | $R^{D55}$ | $R^{D245}$ |
| $L_{C1308}$ | $R^{D55}$ | $R^{D246}$ |
| $L_{C1309}$ | $R^{D37}$ | $R^{D193}$ |
| $L_{C1310}$ | $R^{D37}$ | $R^{D194}$ |
| $L_{C1311}$ | $R^{D37}$ | $R^{D195}$ |
| $L_{C1312}$ | $R^{D37}$ | $R^{D196}$ |
| $L_{C1313}$ | $R^{D37}$ | $R^{D197}$ |
| $L_{C1314}$ | $R^{D37}$ | $R^{D198}$ |
| $L_{C1315}$ | $R^{D37}$ | $R^{D199}$ |
| $L_{C1316}$ | $R^{D37}$ | $R^{D200}$ |
| $L_{C1317}$ | $R^{D37}$ | $R^{D201}$ |
| $L_{C1318}$ | $R^{D37}$ | $R^{D202}$ |
| $L_{C1319}$ | $R^{D37}$ | $R^{D203}$ |
| $L_{C1320}$ | $R^{D37}$ | $R^{D204}$ |
| $L_{C1321}$ | $R^{D37}$ | $R^{D205}$ |
| $L_{C1322}$ | $R^{D37}$ | $R^{D206}$ |
| $L_{C1323}$ | $R^{D37}$ | $R^{D207}$ |
| $L_{C1324}$ | $R^{D37}$ | $R^{D208}$ |
| $L_{C1325}$ | $R^{D37}$ | $R^{D209}$ |
| $L_{C1326}$ | $R^{D37}$ | $R^{D210}$ |
| $L_{C1327}$ | $R^{D37}$ | $R^{D211}$ |
| $L_{C1328}$ | $R^{D37}$ | $R^{D212}$ |
| $L_{C1329}$ | $R^{D37}$ | $R^{D213}$ |
| $L_{C1330}$ | $R^{D37}$ | $R^{D214}$ |
| $L_{C1331}$ | $R^{D37}$ | $R^{D215}$ |
| $L_{C1332}$ | $R^{D37}$ | $R^{D216}$ |
| $L_{C1333}$ | $R^{D37}$ | $R^{D217}$ |
| $L_{C1334}$ | $R^{D37}$ | $R^{D218}$ |
| $L_{C1335}$ | $R^{D37}$ | $R^{D219}$ |
| $L_{C1336}$ | $R^{D37}$ | $R^{D220}$ |
| $L_{C1337}$ | $R^{D37}$ | $R^{D221}$ |
| $L_{C1338}$ | $R^{D37}$ | $R^{D222}$ |
| $L_{C1339}$ | $R^{D37}$ | $R^{D223}$ |
| $L_{C1340}$ | $R^{D37}$ | $R^{D224}$ |
| $L_{C1341}$ | $R^{D37}$ | $R^{D225}$ |
| $L_{C1342}$ | $R^{D37}$ | $R^{D226}$ |
| $L_{C1343}$ | $R^{D37}$ | $R^{D227}$ |
| $L_{C1344}$ | $R^{D37}$ | $R^{D228}$ |
| $L_{C1345}$ | $R^{D37}$ | $R^{D229}$ |
| $L_{C1346}$ | $R^{D37}$ | $R^{D230}$ |
| $L_{C1347}$ | $R^{D37}$ | $R^{D231}$ |
| $L_{C1348}$ | $R^{D37}$ | $R^{D232}$ |
| $L_{C1349}$ | $R^{D37}$ | $R^{D233}$ |
| $L_{C1350}$ | $R^{D37}$ | $R^{D234}$ |
| $L_{C1351}$ | $R^{D37}$ | $R^{D235}$ |
| $L_{C1352}$ | $R^{D37}$ | $R^{D236}$ |
| $L_{C1353}$ | $R^{D37}$ | $R^{D237}$ |
| $L_{C1354}$ | $R^{D37}$ | $R^{D238}$ |
| $L_{C1355}$ | $R^{D37}$ | $R^{D239}$ |
| $L_{C1356}$ | $R^{D37}$ | $R^{D240}$ |

-continued

| $L_{Cj}$ | $R^{201}$ | $R^{202}$ |
|---|---|---|
| $L_{C1357}$ | $R^{D37}$ | $R^{D241}$ |
| $L_{C1358}$ | $R^{D37}$ | $R^{D242}$ |
| $L_{C1359}$ | $R^{D37}$ | $R^{D243}$ |
| $L_{C1360}$ | $R^{D37}$ | $R^{D244}$ |
| $L_{C1361}$ | $R^{D37}$ | $R^{D245}$ |
| $L_{C1362}$ | $R^{D37}$ | $R^{D246}$ |
| $L_{C1363}$ | $R^{D143}$ | $R^{D193}$ |
| $L_{C1364}$ | $R^{D143}$ | $R^{D194}$ |
| $L_{C1365}$ | $R^{D143}$ | $R^{D195}$ |
| $L_{C1366}$ | $R^{D143}$ | $R^{D196}$ |
| $L_{C1367}$ | $R^{D143}$ | $R^{D197}$ |
| $L_{C1368}$ | $R^{D143}$ | $R^{D198}$ |
| $L_{C1369}$ | $R^{D143}$ | $R^{D199}$ |
| $L_{C1370}$ | $R^{D143}$ | $R^{D200}$ |
| $L_{C1371}$ | $R^{D143}$ | $R^{D201}$ |
| $L_{C1372}$ | $R^{D143}$ | $R^{D202}$ |
| $L_{C1373}$ | $R^{D143}$ | $R^{D203}$ |
| $L_{C1374}$ | $R^{D143}$ | $R^{D204}$ |
| $L_{C1375}$ | $R^{D143}$ | $R^{D205}$ |
| $L_{C1376}$ | $R^{D143}$ | $R^{D206}$ |
| $L_{C1377}$ | $R^{D143}$ | $R^{D207}$ |
| $L_{C1378}$ | $R^{D143}$ | $R^{D208}$ |
| $L_{C1379}$ | $R^{D143}$ | $R^{D209}$ |
| $L_{C1380}$ | $R^{D143}$ | $R^{D210}$ |
| $L_{C1381}$ | $R^{D143}$ | $R^{D211}$ |
| $L_{C1382}$ | $R^{D143}$ | $R^{D212}$ |
| $L_{C1383}$ | $R^{D143}$ | $R^{D213}$ |
| $L_{C1384}$ | $R^{D143}$ | $R^{D214}$ |
| $L_{C1385}$ | $R^{D143}$ | $R^{D215}$ |
| $L_{C1386}$ | $R^{D143}$ | $R^{D216}$ |
| $L_{C1387}$ | $R^{D143}$ | $R^{D217}$ |
| $L_{C1388}$ | $R^{D143}$ | $R^{D218}$ |
| $L_{C1389}$ | $R^{D143}$ | $R^{D219}$ |
| $L_{C1390}$ | $R^{D143}$ | $R^{D220}$ |
| $L_{C1391}$ | $R^{D143}$ | $R^{D221}$ |
| $L_{C1392}$ | $R^{D143}$ | $R^{D222}$ |
| $L_{C1393}$ | $R^{D143}$ | $R^{D223}$ |
| $L_{C1394}$ | $R^{D143}$ | $R^{D224}$ |
| $L_{C1395}$ | $R^{D143}$ | $R^{D225}$ |
| $L_{C1396}$ | $R^{D143}$ | $R^{D226}$ |
| $L_{C1397}$ | $R^{D143}$ | $R^{D227}$ |
| $L_{C1398}$ | $R^{D143}$ | $R^{D228}$ |
| $L_{C1399}$ | $R^{D143}$ | $R^{D229}$ |
| $L_{C1400}$ | $R^{D143}$ | $R^{D230}$ |
| $L_{C1401}$ | $R^{D143}$ | $R^{D231}$ |
| $L_{C1402}$ | $R^{D143}$ | $R^{D232}$ |
| $L_{C1403}$ | $R^{D143}$ | $R^{D233}$ |
| $L_{C1404}$ | $R^{D143}$ | $R^{D234}$ |
| $L_{C1405}$ | $R^{D143}$ | $R^{D235}$ |
| $L_{C1406}$ | $R^{D143}$ | $R^{D236}$ |
| $L_{C1407}$ | $R^{D143}$ | $R^{D237}$ |
| $L_{C1408}$ | $R^{D143}$ | $R^{D238}$ |
| $L_{C1409}$ | $R^{D143}$ | $R^{D239}$ |
| $L_{C1410}$ | $R^{D143}$ | $R^{D240}$ |
| $L_{C1411}$ | $R^{D143}$ | $R^{D241}$ |
| $L_{C1412}$ | $R^{D143}$ | $R^{D242}$ |
| $L_{C1413}$ | $R^{D143}$ | $R^{D243}$ |
| $L_{C1414}$ | $R^{D143}$ | $R^{D244}$ |
| $L_{C1415}$ | $R^{D143}$ | $R^{D245}$ |
| $L_{C1416}$ | $R^{D143}$ | $R^{D246}$ |

wherein $R^{D1}$ to $R^{D246}$ have the structures as defined as follows:

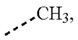
$R^{D1}$

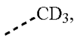
$R^{D2}$

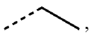
$R^{D3}$

-continued

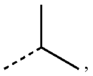
$R^{D4}$

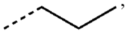
$R^{D5}$

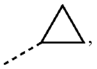
$R^{D6}$

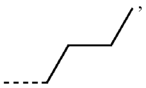
$R^{D7}$

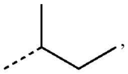
$R^{D8}$

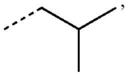
$R^{D9}$

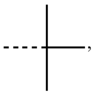
$R^{D10}$

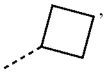
$R^{D11}$

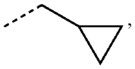
$R^{D12}$

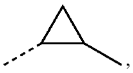
$R^{D13}$

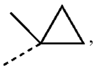
$R^{D14}$

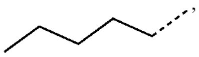
$R^{D15}$

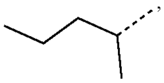
$R^{D16}$

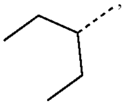
$R^{D17}$

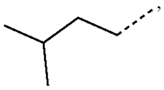
$R^{D18}$

-continued
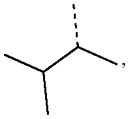
$R^{D19}$
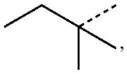
$R^{D20}$
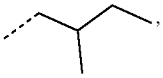
$R^{D21}$
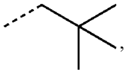
$R^{D22}$
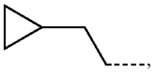
$R^{D23}$
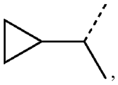
$R^{D24}$
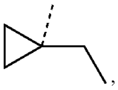
$R^{D25}$
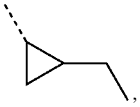
$R^{D26}$
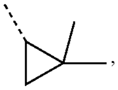
$R^{D27}$
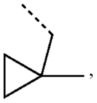
$R^{D28}$
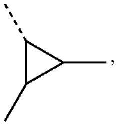
$R^{D29}$
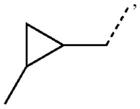
$R^{D30}$
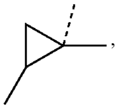
$R^{D31}$
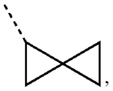
$R^{D32}$
-continued
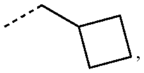
$R^{D33}$
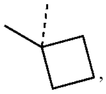
$R^{D34}$
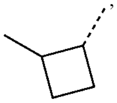
$R^{D35}$
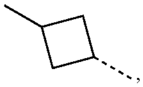
$R^{D36}$
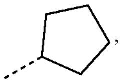
$R^{D37}$
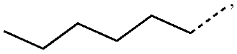
$R^{D38}$
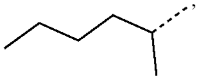
$R^{D39}$
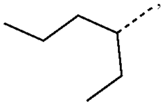
$R^{D40}$
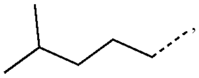
$R^{D41}$
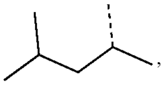
$R^{D42}$
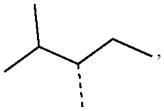
$R^{D43}$
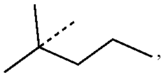
$R^{D44}$
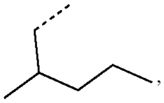
$R^{D45}$
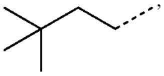
$R^{D46}$ -continued
$R^{D47}$
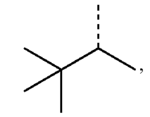
$R^{D48}$
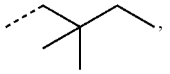
$R^{D49}$
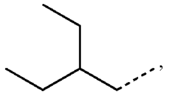
$R^{D50}$
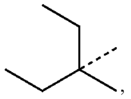
$R^{D51}$
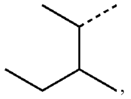
$R^{D52}$
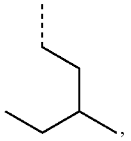
$R^{D53}$
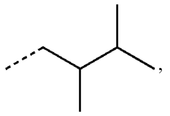
$R^{D54}$
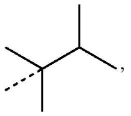
$R^{D55}$
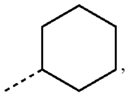
$R^{D56}$
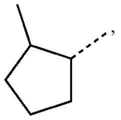
$R^{D57}$
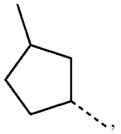
$R^{D58}$
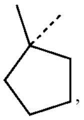
-continued
$R^{D59}$
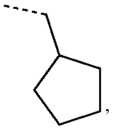
$R^{D60}$
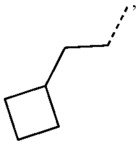
$R^{D61}$
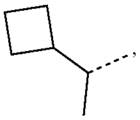
$R^{D62}$
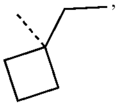
$R^{D63}$
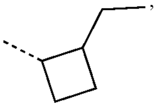
$R^{D64}$
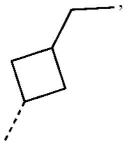
$R^{D65}$
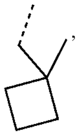
$R^{D66}$
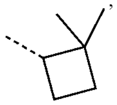
$R^{D67}$
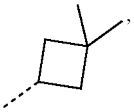
$R^{D68}$
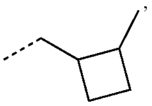
$R^{D69}$
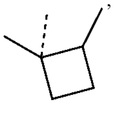

-continued
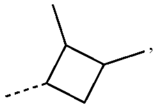
$R^{D70}$
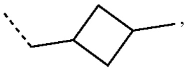
$R^{D71}$
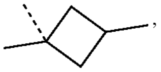
$R^{D72}$
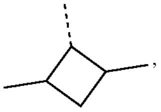
$R^{D73}$
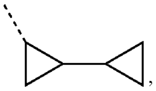
$R^{D74}$
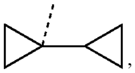
$R^{D75}$
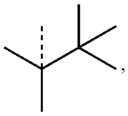
$R^{D76}$
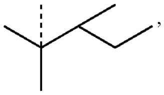
$R^{D77}$
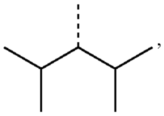
$R^{D78}$
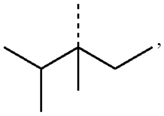
$R^{D79}$
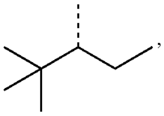
$R^{D80}$
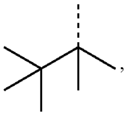
$R^{D81}$
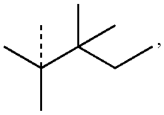
$R^{D82}$
-continued
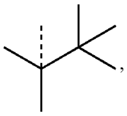
$R^{D83}$
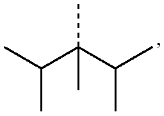
$R^{D84}$
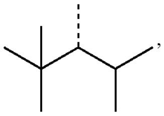
$R^{D85}$
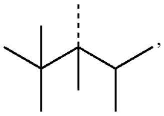
$R^{D86}$
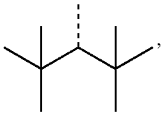
$R^{D87}$
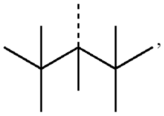
$R^{D88}$
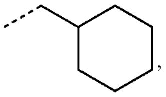
$R^{D89}$
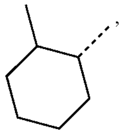
$R^{D90}$
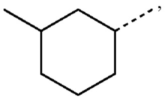
$R^{D91}$
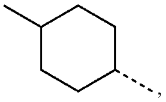
$R^{D92}$
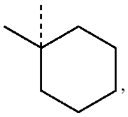
$R^{D93}$
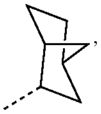
$R^{D94}$ -continued
$R^{D95}$
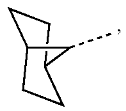
$R^{D96}$
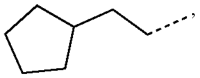
$R^{D97}$
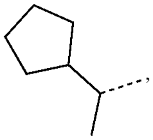
$R^{D98}$
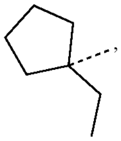
$R^{D99}$
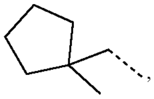
$R^{D100}$
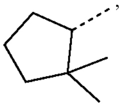
$R^{D101}$
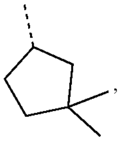
$R^{D102}$
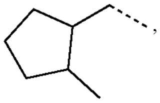
$R^{D103}$
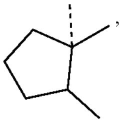
$R^{D104}$
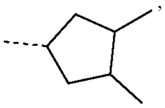
$R^{D105}$
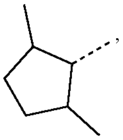
-continued
$R^{D106}$
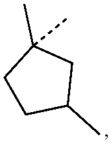
$R^{D107}$
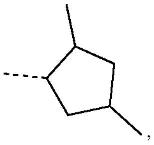
$R^{D108}$
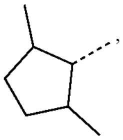
$R^{D109}$
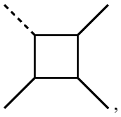
$R^{D110}$
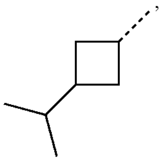
$R^{D111}$
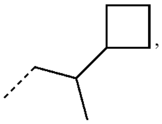
$R^{D112}$
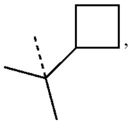
$R^{D113}$
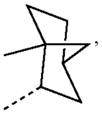
$R^{D114}$
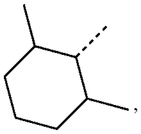
$R^{D115}$
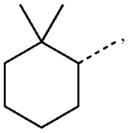

-continued
$R^{D116}$
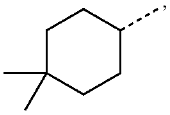
$R^{D117}$
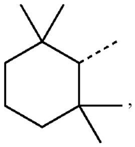
$R^{D118}$
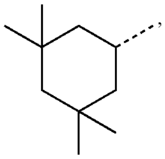
$R^{D119}$
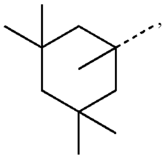
$R^{D120}$
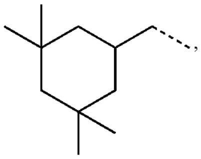
$R^{D121}$
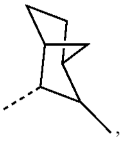
$R^{D122}$
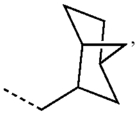
$R^{D123}$
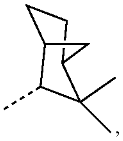
$R^{D124}$
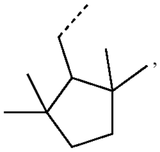
$R^{D125}$
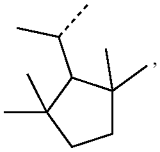
-continued
$R^{D126}$
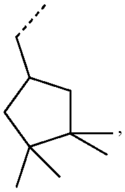
$R^{D127}$
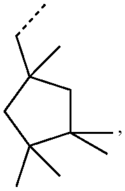
$R^{D128}$
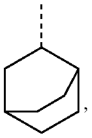
$R^{D129}$
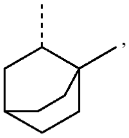
$R^{D130}$
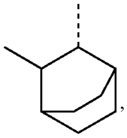
$R^{D131}$
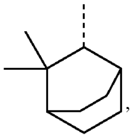
$R^{D132}$
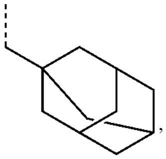
$R^{D133}$
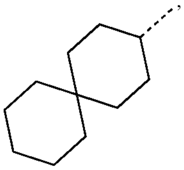
$R^{D134}$
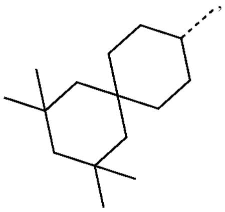

-continued
$R^{D135}$
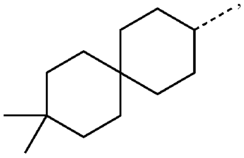
$R^{D136}$
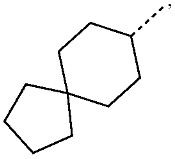
$R^{D137}$
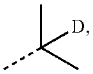
$R^{D138}$
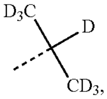
$R^{D139}$
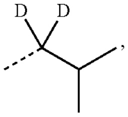
$R^{D140}$
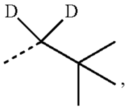
$R^{D141}$
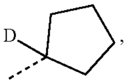
$R^{D142}$
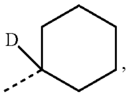
$R^{D143}$
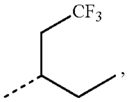
$R^{D144}$
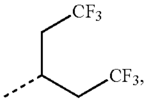
$R^{D145}$
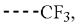
$R^{D146}$
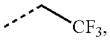
$R^{D147}$
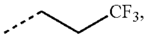
$R^{D148}$
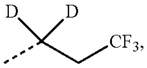
-continued
$R^{D149}$
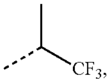
$R^{D150}$
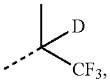
$R^{D151}$
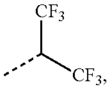
$R^{D152}$
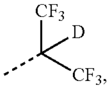
$R^{D153}$
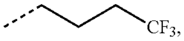
$R^{D154}$
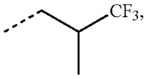
$R^{D155}$
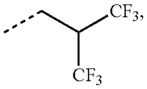
$R^{D156}$
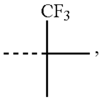
$R^{D157}$
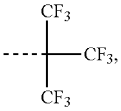
$R^{D158}$
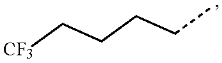
$R^{D159}$
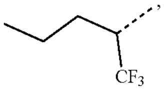
$R^{D160}$
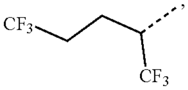
$R^{D161}$
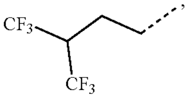
$R^{D162}$
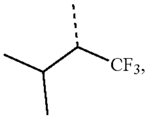

-continued
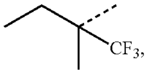
$R^{D163}$
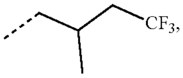
$R^{D164}$
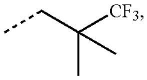
$R^{D165}$
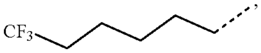
$R^{D166}$
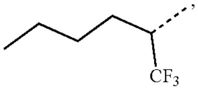
$R^{D167}$
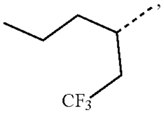
$R^{D168}$
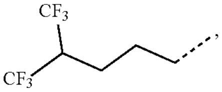
$R^{D169}$
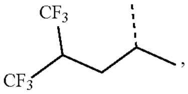
$R^{D170}$
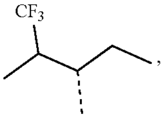
$R^{D171}$
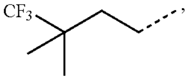
$R^{D172}$
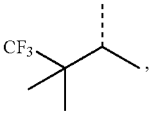
$R^{D173}$
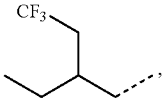
$R^{D174}$
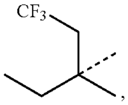
$R^{D175}$
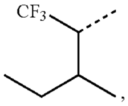
$R^{D176}$
-continued
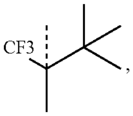
$R^{D177}$
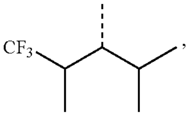
$R^{D178}$
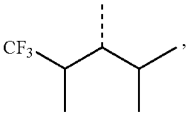
$R^{D179}$
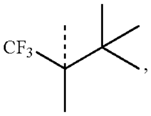
$R^{D180}$
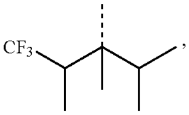
$R^{D181}$
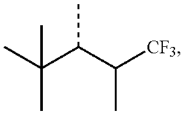
$R^{D182}$
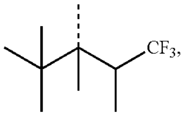
$R^{D183}$
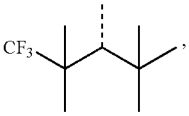
$R^{D184}$
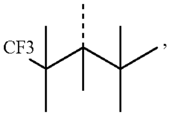
$R^{D185}$
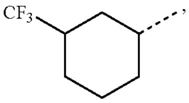
$R^{D186}$
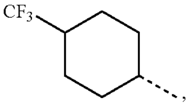
$R^{D187}$
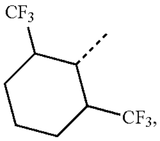
$R^{D188}$ -continued
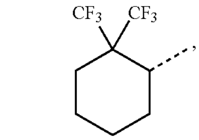
$R^{D189}$
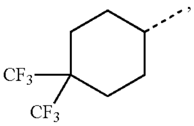
$R^{D190}$
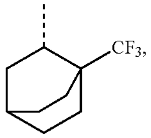
$R^{D191}$
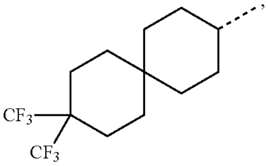
$R^{D192}$
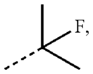
$R^{D193}$
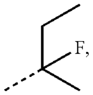
$R^{D194}$
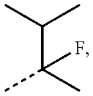
$R^{D195}$
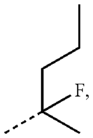
$R^{D196}$
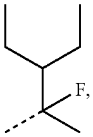
$R^{D197}$
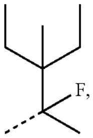
$R^{D198}$
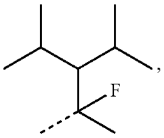
$R^{D199}$
-continued
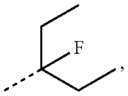
$R^{D200}$
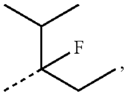
$R^{D201}$
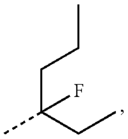
$R^{D202}$
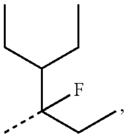
$R^{D203}$
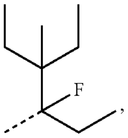
$R^{D204}$
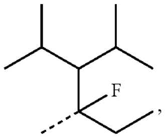
$R^{D205}$
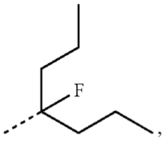
$R^{D206}$
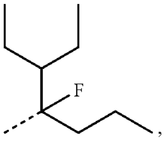
$R^{D207}$
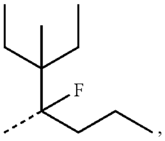
$R^{D208}$
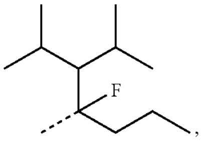
$R^{D209}$ -continued
$R^{D210}$
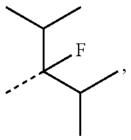
$R^{D211}$
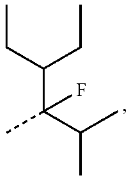
$R^{D212}$
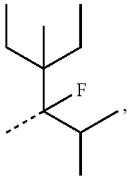
$R^{D213}$
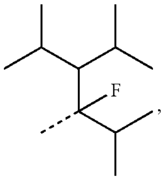
$R^{D214}$
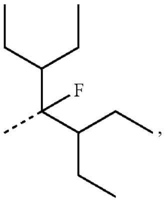
$R^{D215}$
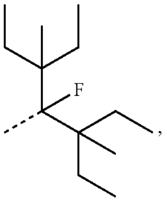
$R^{D216}$
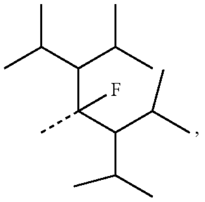
$R^{D217}$
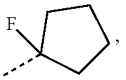
$R^{D218}$
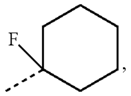
-continued
$R^{D219}$
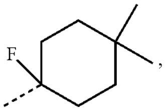
$R^{D220}$
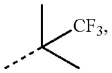
$R^{D221}$
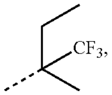
$R^{D222}$
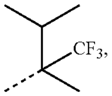
$R^{D223}$
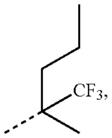
$R^{D224}$
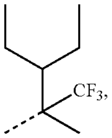
$R^{D225}$
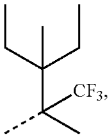
$R^{D226}$
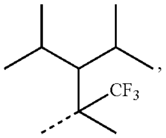
$R^{D227}$
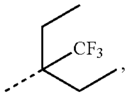
$R^{D228}$
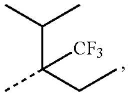
$R^{D229}$
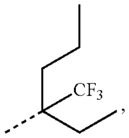
$R^{D230}$
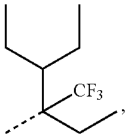

-continued
$R^{D231}$
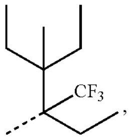
$R^{D232}$
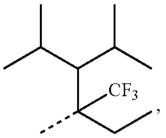
$R^{D233}$
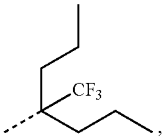
$R^{D234}$
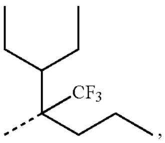
$R^{D235}$
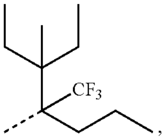
$R^{D236}$
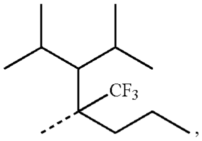
$R^{D237}$
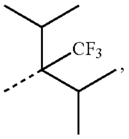
$R^{D238}$
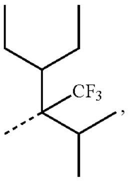
$R^{D239}$
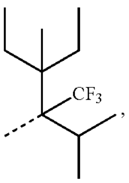
-continued
$R^{D240}$
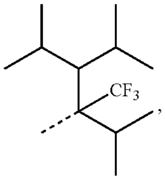
$R^{D241}$
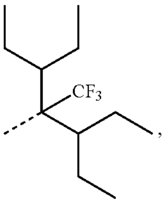
$R^{D242}$
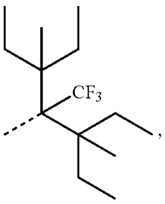
$R^{D243}$
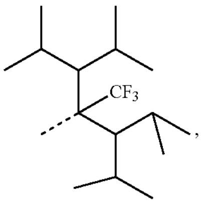
$R^{D244}$
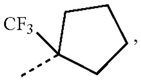
$R^{D245}$
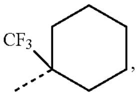
and
$R^{D246}$
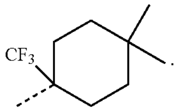
15. The compound of claim 12, wherein the compound is selected from the group consisting structures as defined as follows:
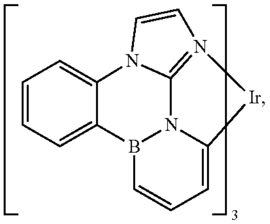
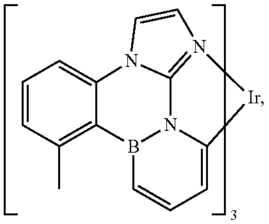

-continued
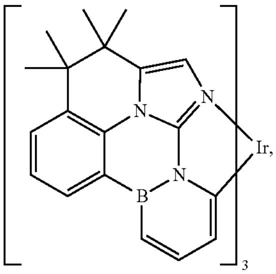
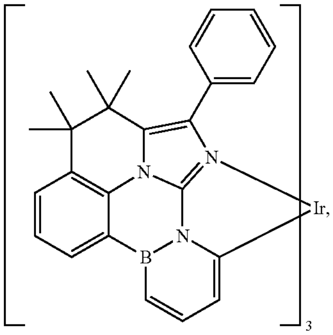
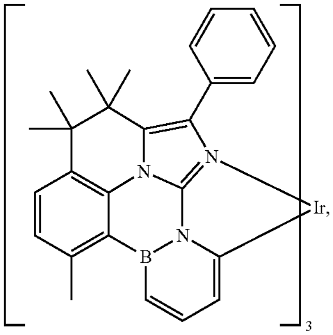
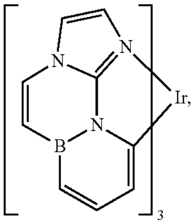
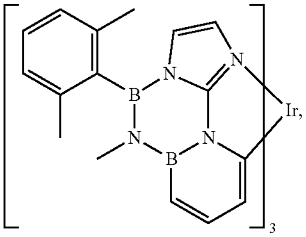
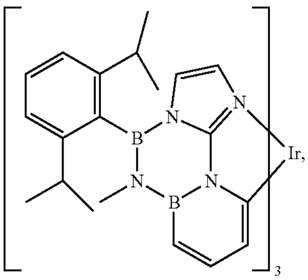
-continued
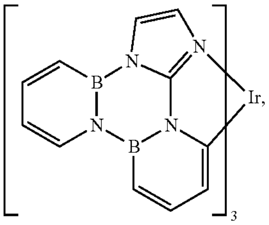
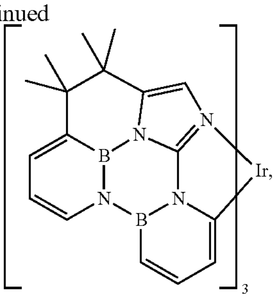
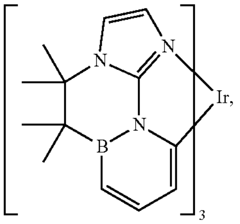
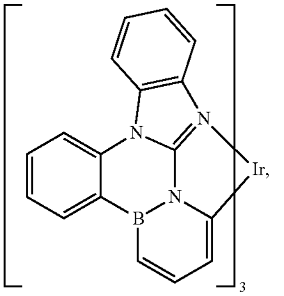
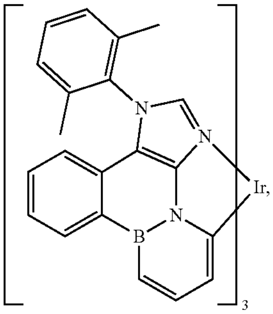
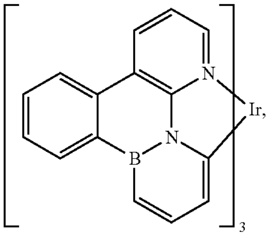
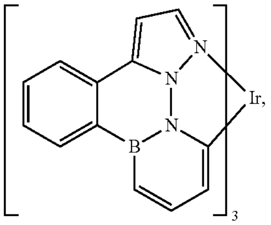
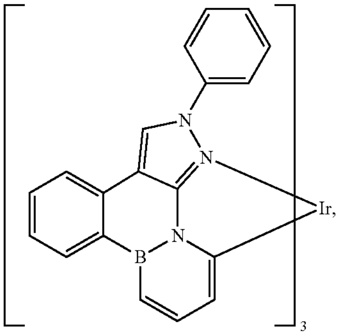
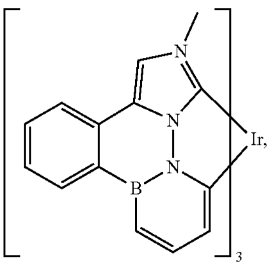
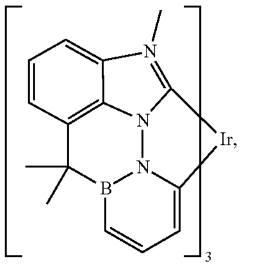

-continued
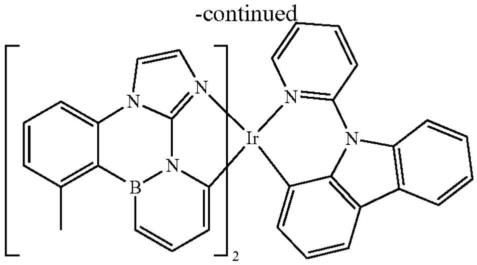
,
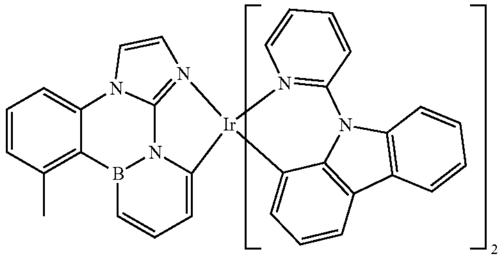
,
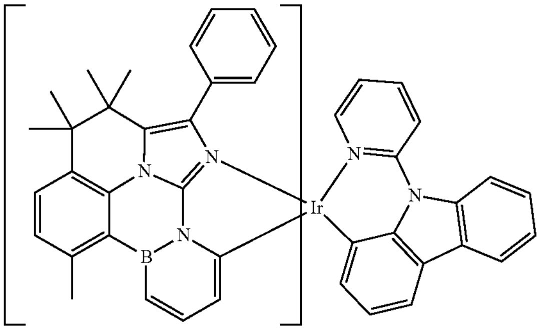
,
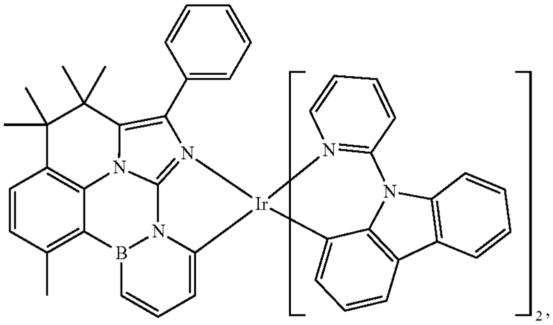
,
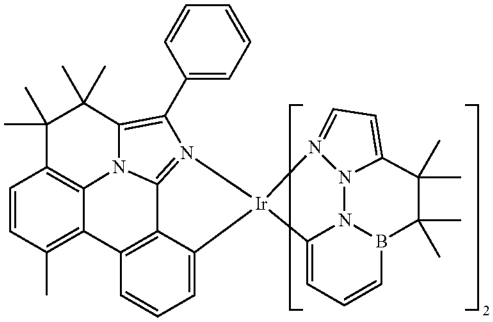
,
-continued
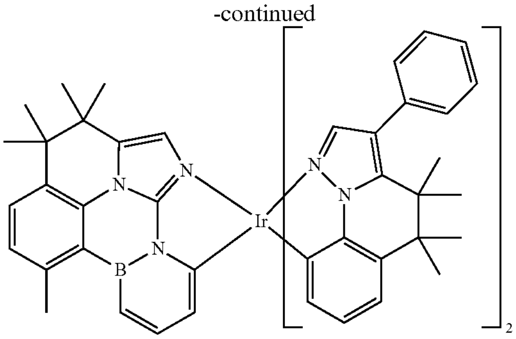
,
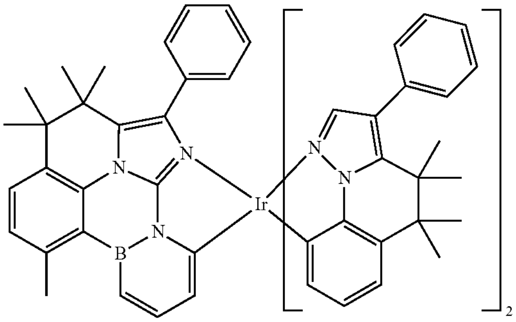
,
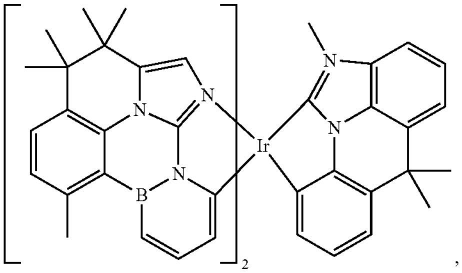
,
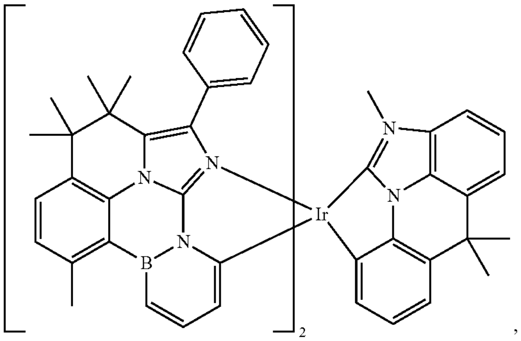
,
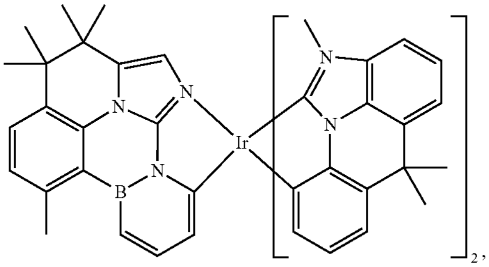
, and -continued

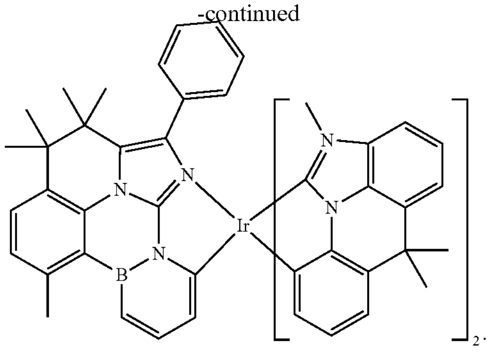

16. The compound of claim 12, wherein the compound has the Formula II:

Formula II

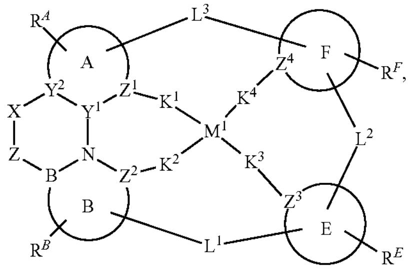

wherein:

$M^1$ is Pd or Pt;

moieties E and F are each independently monocyclic or polycyclic ring structure comprising 5-membered and/or 6-membered carbocyclic or heterocyclic rings;

$Z^3$ and $Z^4$ are each independently C or N;

$K^3$ and $K^4$ are each independently selected from the group consisting of a direct bond, O, and S, wherein at least two of them are direct bonds;

$L^1$, $L^2$, and $L^3$ are each independently selected from the group consisting of a single bond, absent a bond, O, S, CRR', SiRR', BR, and NR, wherein at least one of $L^1$ and $L^2$ is present;

$R^E$ and $R^F$ each independently represent zero, mono, or up to a maximum allowed number of substitutions to its associated ring;

each of R, R', $R^E$, and $R^F$ is independently a hydrogen or a substituent selected from the group consisting of the preferred general substituents as defined herein;

two adjacent $R^A$, $R^B$, $R^C$, $R^E$, and $R^F$ can be joined or fused together to form a ring where chemically feasible; and $K^1$, $K^2$, $Z^1$, $Z^2$, $Y^1$, $Y^2$, X, Z, $R^A$, $R^B$, ring A, and ring B are all defined the same as above.

17. An organic light emitting device (OLED) comprising:

an anode;

a cathode; and an organic layer disposed between the anode and the cathode, wherein the organic layer comprises a compound comprising a first ligand $L_A$ of Formula I:

Formula I

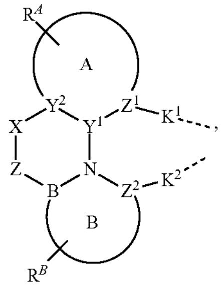

wherein ring A is a 5-membered or 6-membered carbocyclic or heterocyclic ring;

wherein ring B is a 5-membered or 6-membered heterocyclic ring;

wherein at least one of ring A and ring B is a 6-membered ring;

wherein $K^1$ and $K^2$ are each independently selected from the group consisting of a direct bond, O, and S;

wherein at least one of $K^1$ and $K^2$ is a direct bond;

wherein $Z^1$ and $Z^2$ are each independently C or N;

wherein $Z^1$ is C if $K^1$ is O or S;

wherein $Z^2$ is C if $K^2$ is O or S;

wherein $Y^1$ and $Y^2$ are each independently selected from the group consisting of C, N, and B;

wherein X and Z are each independently selected from the group consisting of CR, CRR', SiRR', GeRR', BR, BRR', N, NR, O, and S;

wherein $R^A$ and $R^B$ each independently represent mono to the maximum allowable substitution, or no substitution;

wherein each R, R', $R^A$ and $R^B$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, germyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof;

wherein $L_A$ is coordinated to a metal M through the indicated dashed lines;

wherein M may be coordinated to other ligands;

wherein $L_A$ may be joined with other ligands to comprise a tridentate, tetradentate, pentadentate, or hexadentate ligand; and wherein any two R, R', $R^A$ and $R^B$ may be joined or fused to form a ring.

18. The OLED of claim 17, wherein the organic layer further comprises a host, wherein host comprises at least one chemical moiety selected from the group consisting of triphenylene, carbazole, indolocarbazole, dibenzothiophene, dibenzofuran, dibenzoselenophene, 5λ2-benzo[d]benzo[4,5]imidazo[3,2-a]imidazole, 5,9-dioxa-13b-boranaphtho[3,2,1-de]anthracene, triazine, aza-triphenylene, aza-carbazole, aza-indolocarbazole, aza-dibenzothiophene, aza-dibenzofuran, aza-dibenzoselenophene, aza-5λ2-benzo[d]benzo[4,5]imidazo[3,2-a]imidazole, and aza-(5,9-dioxa-13b-boranaphtho[3,2,1-de]anthracene).

19. The OLED of claim 18, wherein the host is selected from the group consisting of the structures as defined as follows:

-continued
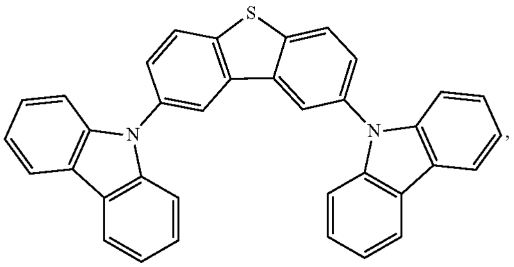
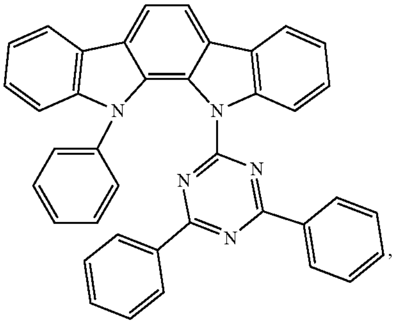
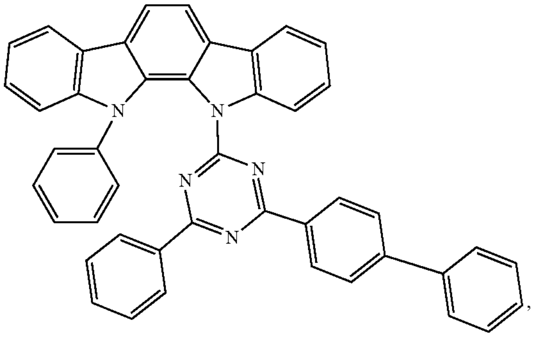
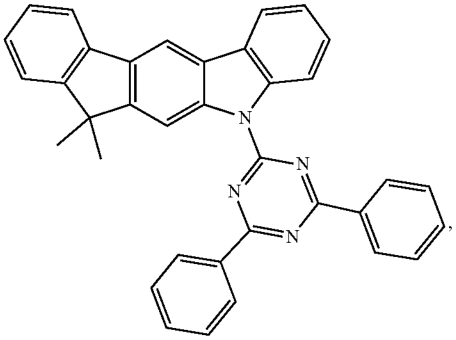
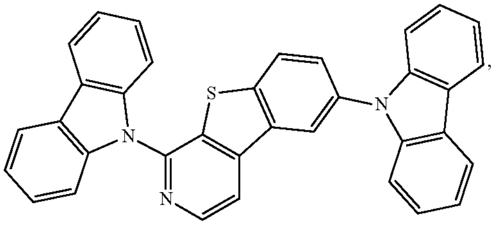
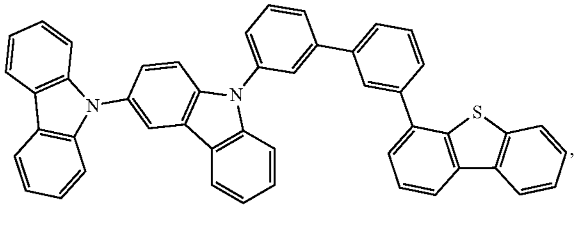
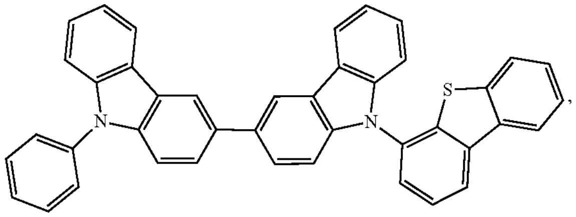
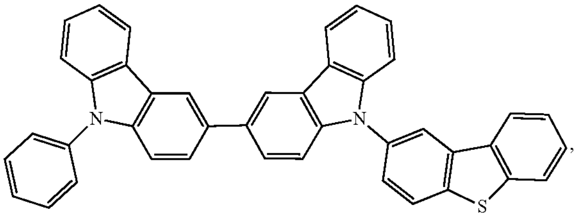
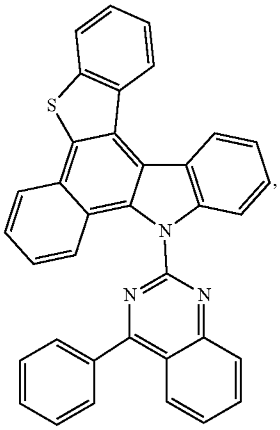
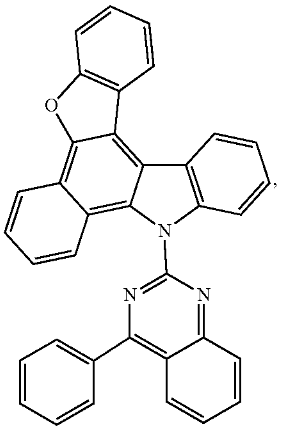
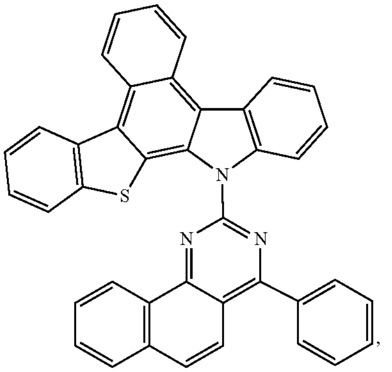
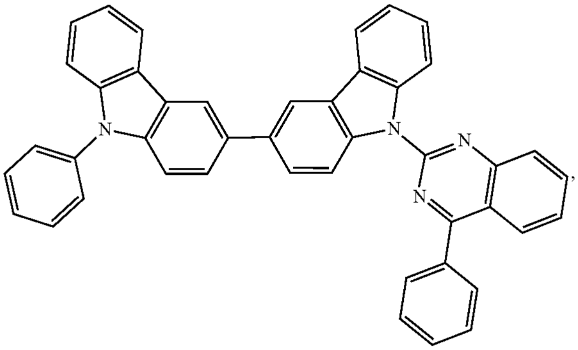

-continued
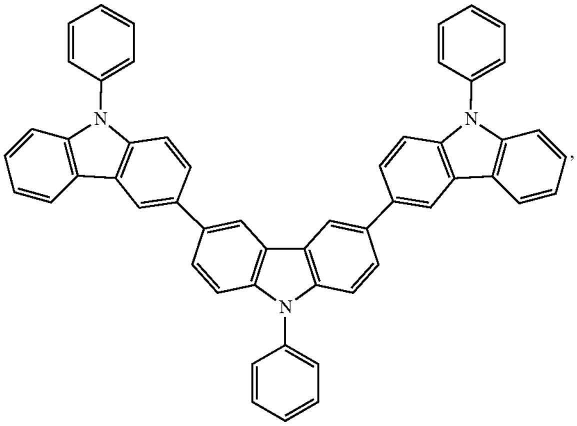
,
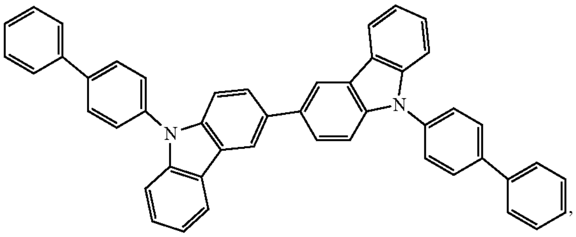
,
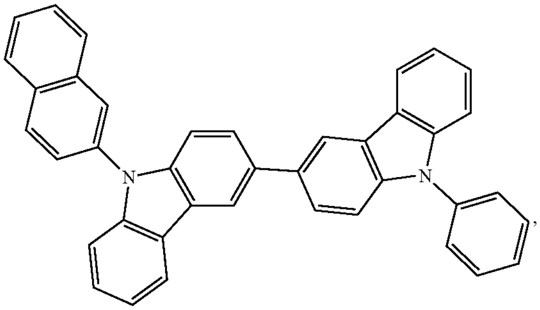
,
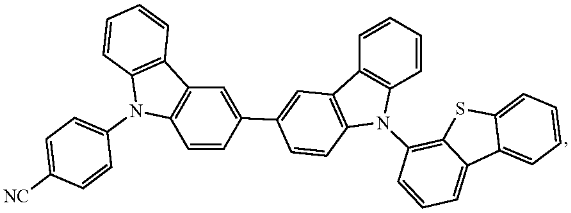
,
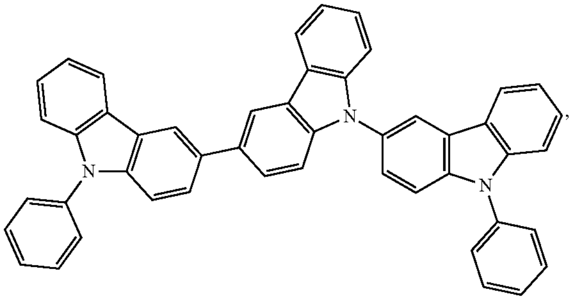
,
-continued
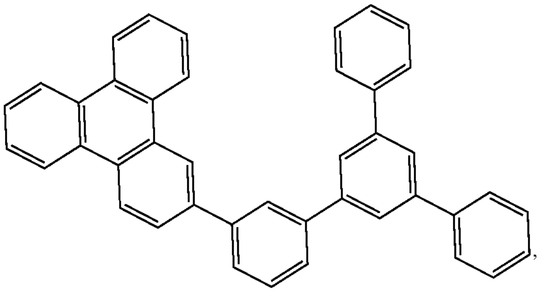
,
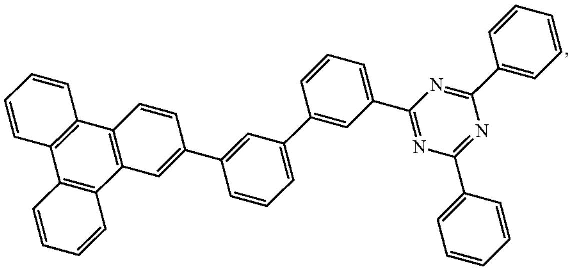
,
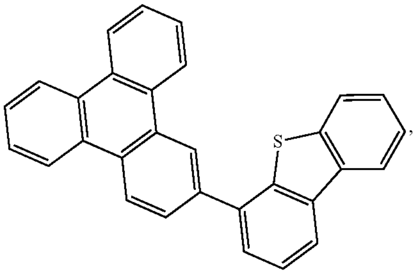
,
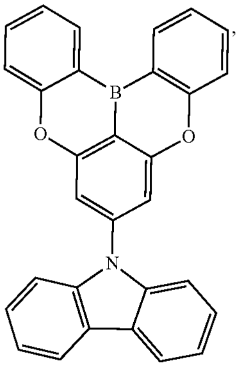
,
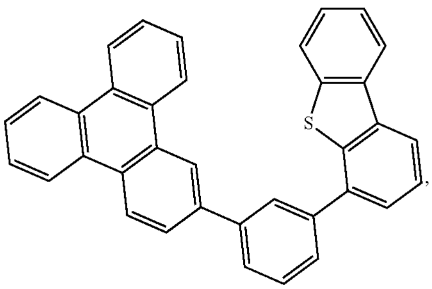
, -continued
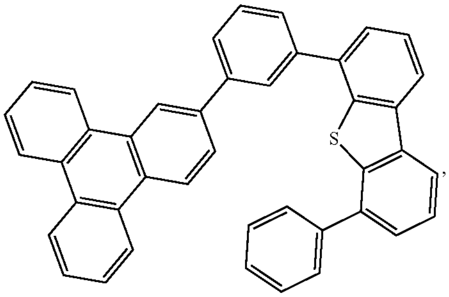
,
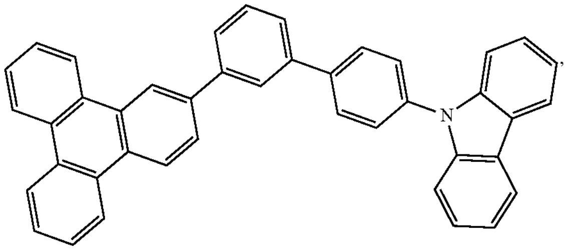
,
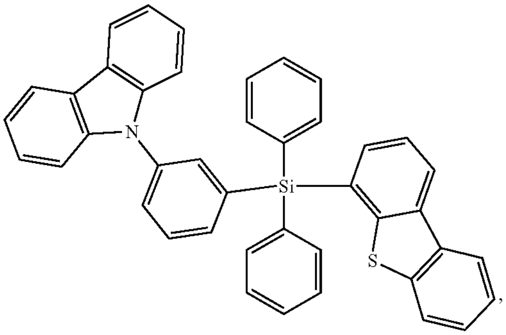
,
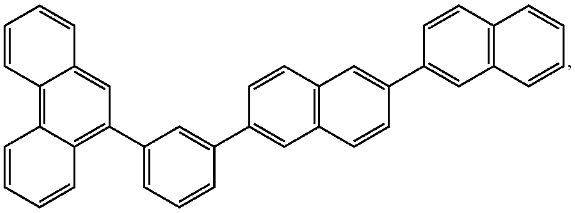
,
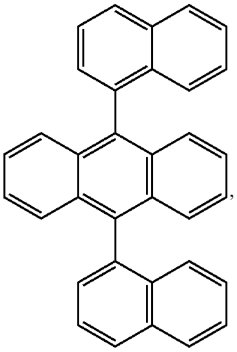
,
-continued
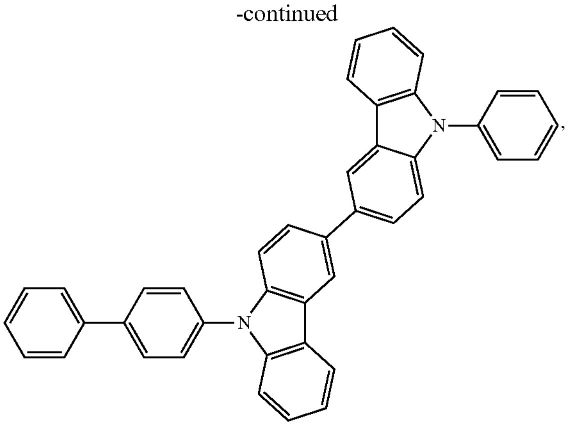
,
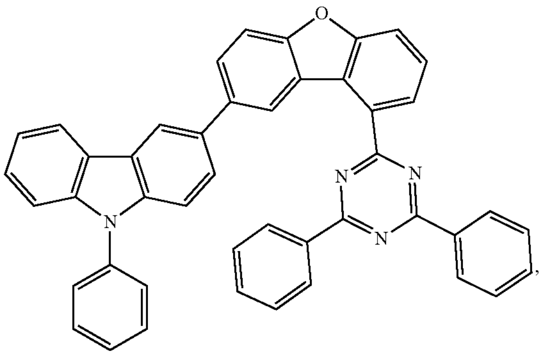
,
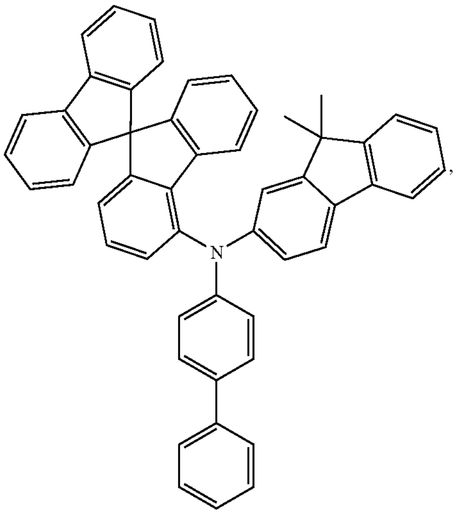
,
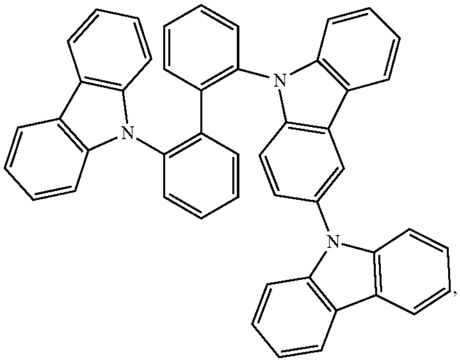
, -continued

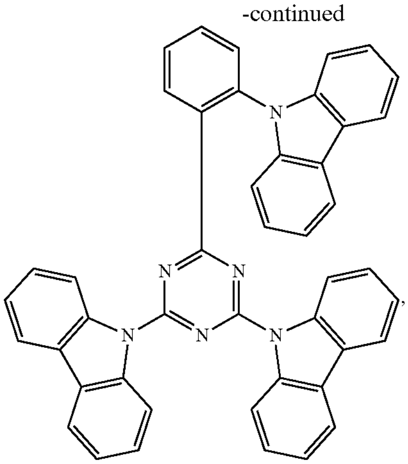

,

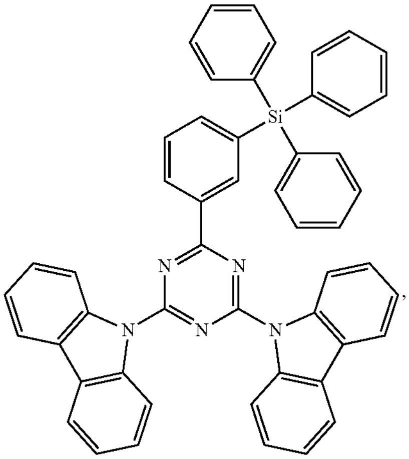

, and combinations thereof.

20. A consumer product comprising an organic light-emitting device (OLED) comprising:

an anode;

a cathode; and an organic layer disposed between the anode and the cathode, wherein the organic layer comprises a compound comprising a first ligand $L_A$ of Formula I:

Formula I

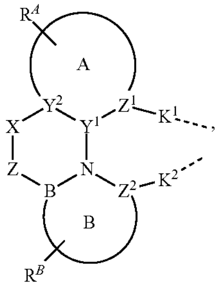

wherein ring A is a 5-membered or 6-membered carbocyclic or heterocyclic ring;

wherein ring B is a 5-membered or 6-membered heterocyclic ring;

wherein at least one of ring A and ring B is a 6-membered ring;

wherein $K^1$ and $K^2$ are each independently selected from the group consisting of a direct bond, O, and S;

wherein at least one of $K^1$ and $K^2$ is a direct bond;

wherein $Z^1$ and $Z^2$ are each independently C or N;

wherein $Z^1$ is C if $K^1$ is O or S;

wherein $Z^2$ is C if $K^2$ is O or S;

wherein $Y^1$ and $Y^2$ are each independently selected from the group consisting of C, N, and B;

wherein X and Z are each independently selected from the group consisting of CR, CRR', SiRR', GeRR', BR, BRR', N, NR, O, and S;

wherein $R^A$ and $R^B$ each independently represent mono to the maximum allowable substitution, or no substitution;

wherein each R, R', $R^A$ and $R^B$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, germyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof;

wherein $L_A$ is coordinated to a metal M through the indicated dashed lines;

wherein M may be coordinated to other ligands;

wherein $L_A$ may be joined with other ligands to comprise a tridentate, tetradentate, pentadentate, or hexadentate ligand; and wherein any two R, R', $R^A$ and $R^B$ may be joined or fused to form a ring.

* * * * *